United States Patent
Anthony et al.

(10) Patent No.: US 12,383,560 B2
(45) Date of Patent: *Aug. 12, 2025

(54) COMPOUNDS AND USES THEREOF

(71) Applicant: Foghorn Therapeutics Inc., Cambridge, MA (US)

(72) Inventors: Neville John Anthony, Northborough, MA (US); David Simon Millan, Stow, MA (US); Rishi G. Vaswani, Lexington, MA (US); Shawn E. R. Schiller, Haverhill, MA (US)

(73) Assignee: FOGHORN THERAPEUTICS INC., Cambridge, MA (US)

( * ) Notice: Subject to any disclaimer, the term of this patent is extended or adjusted under 35 U.S.C. 154(b) by 38 days.

This patent is subject to a terminal disclaimer.

(21) Appl. No.: 17/965,145

(22) Filed: Oct. 13, 2022

(65) Prior Publication Data

US 2023/0138480 A1 May 4, 2023

Related U.S. Application Data

(63) Continuation of application No. 16/965,822, filed as application No. PCT/US2019/015722 on Jan. 29, 2019, now Pat. No. 11,497,752.

(60) Provisional application No. 62/789,260, filed on Jan. 7, 2019, provisional application No. 62/770,431, filed on Nov. 21, 2018, provisional application No. 62/653,229, filed on Apr. 5, 2018, provisional application No. 62/623,907, filed on Jan. 30, 2018.

(51) Int. Cl.

| | |
|---|---|
| C07D 277/46 | (2006.01) |
| A61K 31/427 | (2006.01) |
| A61K 31/4409 | (2006.01) |
| A61K 31/4425 | (2006.01) |
| A61K 31/4439 | (2006.01) |
| A61K 31/4709 | (2006.01) |
| A61K 31/496 | (2006.01) |
| A61K 31/506 | (2006.01) |
| A61K 31/5377 | (2006.01) |
| A61K 31/541 | (2006.01) |
| A61K 45/06 | (2006.01) |
| A61P 35/04 | (2006.01) |
| C07D 417/04 | (2006.01) |
| C07D 417/10 | (2006.01) |
| C07D 417/14 | (2006.01) |

(52) U.S. Cl.
CPC .......... *A61K 31/541* (2013.01); *A61K 31/427* (2013.01); *A61K 31/4409* (2013.01); *A61K 31/4425* (2013.01); *A61K 31/4439* (2013.01); *A61K 31/4709* (2013.01); *A61K 31/496* (2013.01); *A61K 31/506* (2013.01); *A61K 31/5377* (2013.01); *A61K 45/06* (2013.01); *A61P 35/04* (2018.01); *C07D 277/46* (2013.01); *C07D 417/04* (2013.01); *C07D 417/10* (2013.01); *C07D 417/14* (2013.01)

(58) Field of Classification Search
CPC .. C07D 277/46; C07D 417/04; C07D 417/10; C07D 417/14; A61K 31/541; A61K 31/427; A61K 31/4409; A61K 31/4425
See application file for complete search history.

(56) References Cited

U.S. PATENT DOCUMENTS

| | | |
|---|---|---|
| 2,788,341 A | 4/1957 | Schwyzer et al. |
| 3,717,642 A | 2/1973 | Von Strandtmann |
| 4,109,496 A | 8/1978 | Allemann et al. |
| 4,650,796 A | 3/1987 | George et al. |
| 4,868,103 A | 9/1989 | Stavrianopoulos et al. |
| 5,223,409 A | 6/1993 | Ladner et al. |
| 5,225,422 A † | 7/1993 | Nagata |
| 5,283,317 A | 2/1994 | Saifer et al. |
| 5,631,169 A | 5/1997 | Lakowicz et al. |
| 5,677,158 A | 10/1997 | Zhou et al. |
| 5,801,030 A | 9/1998 | McVey et al. |
| 5,858,358 A | 1/1999 | June et al. |
| 5,883,223 A | 3/1999 | Gray |
| 6,180,612 B1 | 1/2001 | Hockensmith et al. |
| 6,309,634 B1 | 10/2001 | Bankiewicz et al. |
| 6,352,694 B1 | 3/2002 | June et al. |
| 6,551,786 B2 | 4/2003 | Manfredi |
| 6,683,058 B1 | 1/2004 | Tuszynski |
| 6,692,964 B1 | 2/2004 | June et al. |
| 6,716,662 B2 | 4/2004 | Akai |
| 6,797,514 B2 | 9/2004 | Berenson et al. |
| 6,867,041 B2 | 3/2005 | Berenson et al. |
| 6,887,466 B2 | 5/2005 | June et al. |
| 6,905,680 B2 | 6/2005 | June et al. |
| 6,905,681 B1 | 6/2005 | June et al. |
| 6,905,874 B2 | 6/2005 | Berenson et al. |
| 6,995,011 B2 | 2/2006 | Itoh et al. |

(Continued)

FOREIGN PATENT DOCUMENTS

| | | |
|---|---|---|
| CN | 103038231 A | 4/2013 |
| CN | 105473141 A | 4/2016 |

(Continued)

OTHER PUBLICATIONS

Extended European Search Report for European Application No. 19748410.8, dated Sep. 24, 2021 (10 pages).
International Preliminary Report on Patentability for International Application No. PCT/US2019/015722, issued Aug. 4, 2020 (6 pages).

(Continued)

*Primary Examiner* — Sikarl A Witherspoon
(74) *Attorney, Agent, or Firm* — Clark & Elbing LLP

(57) ABSTRACT

The present disclosure features compounds useful for the treatment of BAF complex-related disorders.

10 Claims, 3 Drawing Sheets

(56) References Cited

U.S. PATENT DOCUMENTS

| | | |
|---|---|---|
| 7,067,318 B2 | 6/2006 | June et al. |
| 7,144,575 B2 | 12/2006 | June et al. |
| 7,172,869 B2 | 2/2007 | June et al. |
| 7,175,843 B2 | 2/2007 | June et al. |
| 7,205,103 B2 | 4/2007 | Emerson |
| 7,232,566 B2 | 6/2007 | June et al. |
| 7,348,326 B2 | 3/2008 | DeSimone et al. |
| 7,572,631 B2 | 8/2009 | Berenson et al. |
| 8,324,367 B2 | 12/2012 | Kaemmerer et al. |
| 8,642,660 B2 | 2/2014 | Goldfarb |
| 8,697,359 B1 | 4/2014 | Zhang |
| 8,703,761 B2 | 4/2014 | Forster et al. |
| 8,771,945 B1 | 7/2014 | Zhang |
| 8,795,965 B2 | 8/2014 | Zhang |
| 8,865,406 B2 | 10/2014 | Zhang et al. |
| 8,946,268 B2 | 2/2015 | Lau et al. |
| 9,072,052 B2 | 6/2015 | Griffin et al. |
| 9,126,985 B2 | 9/2015 | Kley et al. |
| 9,353,051 B2 | 5/2016 | Byrd et al. |
| 9,403,843 B2 | 8/2016 | Thatcher et al. |
| 9,410,943 B2 | 8/2016 | Kadoch et al. |
| 9,546,206 B2 | 1/2017 | Ring et al. |
| 9,546,296 B2 | 1/2017 | Wang et al. |
| 9,636,323 B2 | 5/2017 | Lin et al. |
| 9,656,959 B2 | 5/2017 | Ni et al. |
| 9,694,084 B2 | 7/2017 | Bradner et al. |
| 9,708,338 B2 | 7/2017 | Yukimasa et al. |
| 9,708,348 B2 | 7/2017 | Castro et al. |
| 9,932,340 B2 | 4/2018 | Dai et al. |
| 10,105,420 B2 | 10/2018 | Kadoch et al. |
| 10,131,637 B2 | 11/2018 | Abdel-Meguid et al. |
| 10,207,998 B2 | 2/2019 | Derbyshire et al. |
| 10,239,888 B2 | 3/2019 | Bradner et al. |
| 10,266,850 B2 | 4/2019 | Doudna et al. |
| 10,464,925 B2 | 11/2019 | Bradner et al. |
| 10,472,376 B2 | 11/2019 | Yamamoto et al. |
| 10,646,575 B2 | 5/2020 | Phillips et al. |
| 10,660,968 B2 | 5/2020 | Phillips et al. |
| 10,669,253 B2 | 6/2020 | Bradner et al. |
| 10,849,982 B2 | 12/2020 | Phillips et al. |
| 10,905,768 B1 | 2/2021 | Phillips et al. |
| 10,976,320 B2 | 4/2021 | Dykhuizen et al. |
| 11,419,859 B2 | 8/2022 | Agresta |
| 11,485,732 B2 | 11/2022 | Vaswani et al. |
| 11,497,752 B2 | 11/2022 | Anthony et al. |
| 11,639,345 B2 | 5/2023 | Bloch et al. |
| 11,773,085 B2 | 10/2023 | Zhou et al. |
| 11,793,802 B2 | 10/2023 | Bearss et al. |
| 11,851,445 B2 | 12/2023 | Ruppel et al. |
| 11,865,114 B2 | 1/2024 | Ramachandra et al. |
| 2002/0037281 A1 | 3/2002 | Davidson et al. |
| 2003/0027335 A1 | 2/2003 | Ruley et al. |
| 2004/0216178 A1 | 10/2004 | Jones et al. |
| 2005/0079512 A1 | 4/2005 | Emerson et al. |
| 2005/0130919 A1 | 6/2005 | Xu et al. |
| 2006/0058255 A1 | 3/2006 | Chen et al. |
| 2007/0105181 A1 | 5/2007 | Pope et al. |
| 2008/0221157 A1 | 9/2008 | Chakravarty et al. |
| 2010/0048565 A1 | 2/2010 | Frenkel et al. |
| 2010/0197621 A1 | 8/2010 | Henry et al. |
| 2011/0003809 A1 | 1/2011 | Ahrendt |
| 2012/0034867 A1 | 2/2012 | Griffin et al. |
| 2012/0035244 A1 | 2/2012 | Chinnaiyan et al. |
| 2012/0308484 A1 | 12/2012 | Szalay et al. |
| 2014/0287931 A1 | 9/2014 | Bernards et al. |
| 2015/0045393 A1† | 2/2015 | Thatcher |
| 2015/0057169 A1 | 2/2015 | Siu et al. |
| 2015/0376139 A1 | 12/2015 | Abdel-Meguid et al. |
| 2016/0032402 A1 | 2/2016 | Jagani et al. |
| 2016/0130663 A1 | 5/2016 | Kohno et al. |
| 2016/0347708 A1 | 12/2016 | Ebright et al. |
| 2018/0086720 A1 | 3/2018 | Albrecht et al. |
| 2018/0140722 A1 | 5/2018 | Willis et al. |
| 2018/0258491 A1 | 9/2018 | Jagani et al. |
| 2018/0328913 A1 | 11/2018 | Kadoch et al. |
| 2020/0069669 A1 | 3/2020 | Grassian et al. |
| 2020/0206344 A1 | 7/2020 | Kadoch et al. |
| 2020/0261434 A1 | 8/2020 | Choe et al. |
| 2021/0038611 A1 | 2/2021 | Anthony et al. |
| 2021/0171958 A1 | 6/2021 | Chan et al. |
| 2021/0230154 A1 | 7/2021 | Vaswani et al. |
| 2021/0251988 A1 | 8/2021 | Zhou et al. |
| 2021/0260171 A1 | 8/2021 | Zhou et al. |
| 2021/0388040 A1 | 12/2021 | Kadoch et al. |
| 2022/0016083 A1 | 1/2022 | Centore et al. |
| 2022/0079940 A1 | 3/2022 | Centore et al. |
| 2022/0098190 A1 | 3/2022 | Ruppel et al. |
| 2022/0119378 A1 | 4/2022 | Anthony et al. |
| 2022/0396604 A1 | 12/2022 | Kadoch et al. |
| 2023/0035235 A1 | 2/2023 | Kadoch et al. |
| 2023/0079819 A1 | 3/2023 | Vaswani et al. |
| 2023/0121497 A1 | 4/2023 | Vaswani et al. |
| 2023/0129003 A1 | 4/2023 | Vaswani et al. |
| 2023/0145003 A1 | 5/2023 | Wilson et al. |
| 2023/0149414 A1 | 5/2023 | Anthony et al. |
| 2024/0101550 A1 | 3/2024 | Vaswani et al. |
| 2024/0158387 A1 | 5/2024 | Vaswani et al. |
| 2024/0189318 A1 | 6/2024 | Huang |

FOREIGN PATENT DOCUMENTS

| | | |
|---|---|---|
| CN | 104530013 B | 6/2016 |
| CN | 107531668 A | 1/2018 |
| EA | 202192101 A1 | 12/2021 |
| EP | 3018123 A1 | 5/2016 |
| JP | 2000-095767 A | 4/2000 |
| WO | WO-94/10300 A1 | 5/1994 |
| WO | WO-95/30761 A2 | 11/1995 |
| WO | WO-2000/024392 A1 | 5/2000 |
| WO | WO-00/59888 A1 | 10/2000 |
| WO | WO-00/59905 A1 | 10/2000 |
| WO | WO-2005/039643 A2 | 5/2005 |
| WO | WO-2005/112620 A2 | 12/2005 |
| WO | WO-2006/005941 A1 | 1/2006 |
| WO | WO-2006/051063 A1 | 5/2006 |
| WO | WO-2006/070806 A1 | 7/2006 |
| WO | WO-2008/022396 A1 | 2/2008 |
| WO | WO-2008/157500 A1 | 12/2008 |
| WO | WO-2009/086303 A2 | 7/2009 |
| WO | WO-2009/111277 A1 | 9/2009 |
| WO | WO-2010/007046 A2 | 1/2010 |
| WO | WO-2011/115998 A2 | 9/2011 |
| WO | WO-2011/132175 A2 | 10/2011 |
| WO | WO-2012/085650 A1 | 6/2012 |
| WO | WO-2013/116663 A1 | 8/2013 |
| WO | WO-2013/116682 A1 | 8/2013 |
| WO | WO-2014/150395 A1 | 9/2014 |
| WO | WO-2015/005473 A1 | 1/2015 |
| WO | WO-2015002230 A1 | 1/2015 |
| WO | WO-2015/103317 A1 | 7/2015 |
| WO | WO-2015/120320 A1 | 8/2015 |
| WO | WO-2015/121688 A1 | 8/2015 |
| WO | WO-2016/054491 A1 | 4/2016 |
| WO | WO-2016/138114 A1 | 9/2016 |
| WO | WO-2016/160718 A1 | 10/2016 |
| WO | WO-2016/207212 A1 | 12/2016 |
| WO | WO-2017/024318 A1 | 2/2017 |
| WO | WO-2017060470 A1 | 4/2017 |
| WO | WO-2017/087885 A1 | 5/2017 |
| WO | WO-2017/118734 A1 | 7/2017 |
| WO | WO-2017/158381 A1 | 9/2017 |
| WO | WO-2018/148443 A1 | 8/2018 |
| WO | WO-2018/160636 A1 | 9/2018 |
| WO | WO-2018/175324 A1 | 9/2018 |
| WO | WO-2019/038215 A1 | 2/2019 |
| WO | WO-2019/040098 A1 | 2/2019 |
| WO | WO-2019/138017 A1 | 7/2019 |
| WO | WO-2019/142192 A1 | 7/2019 |
| WO | WO-2019/152437 A1 | 8/2019 |
| WO | WO-2019/152440 A1 | 8/2019 |
| WO | WO-2019/226915 A1 | 11/2019 |
| WO | WO-2020/035779 A1 | 2/2020 |
| WO | WO-2020/081556 A2 | 4/2020 |
| WO | WO-2020/081588 A1 | 4/2020 |

(56) References Cited

FOREIGN PATENT DOCUMENTS

| | | |
|---|---|---|
| WO | WO-2020/106915 A1 | 5/2020 |
| WO | WO-2020/127685 A1 | 6/2020 |
| WO | WO-2020/160100 A1 | 8/2020 |
| WO | WO-2020/160180 A1 | 8/2020 |
| WO | WO-2021/081032 A1 | 4/2021 |
| WO | WO-2021/155262 A1 | 8/2021 |
| WO | WO-2021/155264 A1 | 8/2021 |
| WO | WO-2021/155316 A1 | 8/2021 |
| WO | WO-2021/155320 A1 | 8/2021 |
| WO | WO-2021/155321 A2 | 8/2021 |
| WO | WO-2021/183218 A1 | 9/2021 |
| WO | WO-2021/236080 A1 | 11/2021 |
| WO | WO-2022/192621 A1 | 9/2022 |
| WO | WO-2022/198043 A1 | 9/2022 |
| WO | WO-2023/009834 A2 | 2/2023 |
| WO | WO-2023/196560 A1 | 10/2023 |
| WO | WO-2023/196565 A1 | 10/2023 |
| WO | WO-2023/196567 A2 | 10/2023 |
| WO | WO-2024/024428 A1 | 2/2024 |
| WO | WO-2024/031875 A1 | 2/2024 |
| WO | WO-2024/086577 A1 | 4/2024 |
| WO | WO-2024/216136 A1 | 10/2024 |
| WO | WO-2024/216151 A1 | 10/2024 |

OTHER PUBLICATIONS

International Search Report and Written Opinion for International Application No. PCT/US19/15722, mailed May 31, 2019 (12 pages).
International Search Report and Written Opinion for International Patent Application No. PCT/US2019/062525, mailed Feb. 18, 2020 (14 pages).
Kadoch et al., "Reversible Disruption of mSWI/SNF (BAF) Complexes by the SS18-SSX Oncogenic Fusion in Synovial Sarcoma," available in PMC May 16, 2013, published in final edited form as: Cell. 153(1):71-85 (2013) (26 pages).
McBride et al., "Disruption of mammalian SWI/SNF and polycomb complexes in human sarcomas: mechanisms and therapeutic opportunities," J Pathol. 244(5): 638-649 (2018).
Papillon et al., "Discovery of Orally Active Inhibitors of Brahma Homolog (BRM)/SMARCA2 ATPase Activity for the Treatment of Brahma Related Gene 1 (BRG1)/SMARCA4-Mutant Cancers," J Med Chem. 61(22):10155-72 (2018).
PubChem, "Compound Summary for CID 108452511," <https://pubchem.ncbi.nlm.nih.gov/compound/108452511>, created Jan. 15, 2016, retrieved Jan. 4, 2021 (7 pages).
PubChem, "Compound Summary for CID 2955118," <https://pubchem.ncbi.nlm.nih.gov/compound/2955118>, created Jul. 29, 2005, retrieved Mar. 22, 2017 (13 pages).
PubChem, "Compound Summary for CID 7325930," <https://pubchem.ncbi.nlm.nih.gov/compound/7325930>, created Jul. 29, 2006, retrieved Mar. 22, 2017 (11 pages).
PubChem, "Compound Summary for CID 970466," <https://pubchem.ncbi.nlm.nih.gov/compound/970466>, created Jul. 9, 2005, retrieved Mar. 22, 2017 (11 pages).
Partial Supplementary European Search Report for European Patent Application No. 19887386.1, dated Jul. 20, 2022 (23 pages).
Tikdari et al., "Reaction of 2-Aminothiazoles with 5-Oxazolones," ChemInform. 18(47):Abstract 199 (1987) (1 page).
Vachtenheim et al., "SWI/SNF chromatin remodeling complex is critical for the expression of microphthalmia-associated transcription factor in melanoma cells," Biochemical and Biophysical Research Communications. 392(3):454-459 (2010).
Zvarec et al., "5-Benzylidenerhodanine and 5-benzylidene-2-4-thiazolidinedione based antibacterials," Bioorg Med Chem Lett. 22(8):2720-2 (2012).
U.S. Appl. No. 18/281,022-A1, Vaswani et al.
U.S. Appl. No. 18/282,279-A1, Huang, Liyue.
U.S. Appl. No. 18/373,518-A1, Vaswani et al.
"FLI1 gene," MedlinePlus, published May 1, 2012, <https://medlineplus.gov/genetics/> (3 pages).

Adam et al., International Application No. PCT/US2024/024407, filed Apr. 12, 2024 by applicant Foghorn Therapeutics Inc. (42 pages).
Adam et al., International Application No. PCT/US2024/024428, filed Apr. 12, 2024 by applicant Foghorn Therapeutics Inc. (40 pages).
Adamo et al., "The oncogene ERG: a key factor in prostate cancer," Oncogene 35(4):403-14 (Jan. 28, 2016).
Advani et al., "A Phase 1 study of imatinib mesylate in combination with cytarabine and daunorubicin for c-kit positive relapsed acute myeloid leukemia," Leuk Res. 34(12):1622-6 (Dec. 2010).
Alazawi, "Foghorn Therapeutics," Blackseed Bio, last updated Mar. 4, 2022, retrieved Jul. 24, 2023, from <https://blackseedbio.com/reports/fhtx#pipeline> (26 pages).
Anders et al., "HTSeq—a Python framework to work with high-throughput sequencing data," Bioinformatics 31(2):166-9 (Jan. 15, 2015).
Asangani et al., "Therapeutic targeting of BET bromodomain proteins in castration-resistant prostate cancer," available in PMC Dec. 12, 2014. Published in final edited form as: Nature. 510(7504):278-82 (2014) (44 pages).
Attard et al., "Duplication of the fusion of TMPRSS2 to ERG sequences identifies fatal human prostate cancer," available in PMC Feb. 24, 2009. Published in final edited form as: Oncogene. 27(3):253-63 (2008) (19 pages).
Basuyaux et al., "The Ets transcription factors interact with each other and with the c-Fos/c-Jun complex via distinct protein domains in a DNA-dependent and -independent manner," J Biol Chem. 272(42):26188-95 (1997).
Bendall et al., "Prevention of amino acid conversion in SILAC experiments with embryonic stem cells," Mol Cell Proteomics. 7(9):1587-97 (2008).
Berger et al., "Androgen-induced differentiation and tumorigenicity of human prostate epithelial cells," Cancer Res. 64(24):8867-75 (2004).
Boulay et al., "Cancer-Specific Retargeting of BAF Complexes by a Prion-like Domain," Cell 171(1):163-78 (Sep. 21, 2017) (36 pages).
Börno et al., "Genome-wide DNA methylation events in TMPRSS2-ERG fusion-negative prostate cancers implicate an EZH2-dependent mechanism with miR-26a hypermethylation," Cancer Discov. 2(11):1024-35 (2012).
Camuzeaux et al., "Imaging Erg and Jun transcription factor interaction in living cells using fluorescence resonance energy transfer analyses," Biochem Biophys Res Commun. 332(4):1107-14 (2005).
Cancer Genome Atlas Research Network, "The Molecular Taxonomy of Primary Prostate Cancer," Cell. 163(4):1011-25 (2015) (16 pages).
Carell et al., "A novel procedure for the synthesis of libraries containing small organic molecules," Angew Chem Int Ed Engl. 33(20):2059-2061 (1994).
Carell et al., "A Solution-Phase Screening Procedure for the Isolation of Active Compounds from a Library of Molecules," Angewandte Chemie International Edition in English. 33(20): 2061-2064 (1994).
Centore et al., "Abstract 1224: Discovery of novel BAF inhibitors for the treatment of transcription factor-driven cancers," Poster Presentations—Proffered abstracts, Cancer Research 81(13_Supplement):1224 (Jul. 1, 2021) (2 pages).
Chandler et al., "ARID1a-DNA interactions are required for promoter occupancy by SWI/SNF," Mol Cell Biol. 33(2):265-80 (Jan. 2013).
Chen et al., "ETS factors reprogram the androgen receptor cistrome and prime prostate tumorigenesis in response to PTEN loss," available in PMC Feb. 1, 2014. Published in final edited form as: Nat Med. 19(8):1023-9 (2013) (21 pages).
Chng et al., "A transcriptional repressor co-regulatory network governing androgen response in prostate cancers," EMBO J. 31(12):2810-23 (2012).
Cho et al., "An unnatural biopolymer," Science. 261(5126):1303-1305 (1993).
Cull et al., "Screening for receptor ligands using large libraries of peptides linked to the C terminus of the lac repressor," Proc Natl Acad Sci. 89(5):1865-1869. (1992).

(56) References Cited

OTHER PUBLICATIONS

Cwirla et al., "Peptides on phage: A vast library of peptides for identifying ligands," Proc Natl Acad Sci. 87:6378-6382 (1990).
Danziger et al., Automated site-directed drug design: a general algorithm for knowledge acquisition about hydrogen-bonding regions at protein surfaces, Proc R Soc Lond B Biol Sci. 236(1283): 101-113 (Mar. 1989) (14 pages).
Database Registry, RN 1004932-80-2, entered Feb. 21, 2008 (1 page).
Database Registry, RN 1175782-23-6, entered Aug. 26, 2009 (1 page).
Database Registry, RN 1315743-98-6, entered Aug. 11, 2011 (1 page).
Database Registry, RN 1323542-96-6, entered Aug. 26, 2011 (1 page).
Database Registry, RN 878254-76-3, entered Mar. 28, 2006 (1 page).
Delattre et al., "Gene fusion with an ETS DNA-binding domain caused by chromosome translocation in human tumours," Nature. 359(6391):162-5 (1992).
Demichelis et al., "TMPRSS2:ERG gene fusion associated with lethal prostate cancer in a watchful waiting cohort," Oncogene 26:4596-4599 (2007).
Devlin et al., "Random Peptide Libraries: a Source of Specific Protein Binding Molecules," Science. 249(4967):404-406 (1990).
DeWitt et al., "'Diversomers': an approach to nonpeptide, nonoligomeric chemical diversity," Proc Natl Acad Sci. 90(15):6909-6913 (1993).
Dobin et al., "STAR: ultrafast universal RNA-seq aligner," Bioinformatics. 29(1):15-21 (2013).
Dominguez et al. "Beyond editing: Repurposing CRISPR-Cas9 for Precision Genome Regulation and Interrogation," available in PMC Jun. 27, 2016, published in final edited form as: Nat Rev Mol Cell Biol. 17(1):5-15 (Jan. 2016) (24 pages).
Donaldson et al., "Solution structure of the ETS domain from murine Ets-1: a winged helix-turn-helix DNA binding motif," EMBO J. 15(1):125-34 (1996).
Erb et al., "Recursive deconvolution of combinatorial chemical libraries," Proc Natl Acad Sci. 91(24):11422-11426 (1994).
Extended European Search Report for European Application No. 19887386.1, dated Dec. 5, 2022 (18 pages).
Extended European Search Report for European Application No. 20749261.2, dated Oct. 18, 2022 (8 pages).
Extended European Search Report for European Application No. 21748261.1, dated Jan. 29, 2024 (17 pages).
Fadul et al., "EWS/FLI utilizes NKX2-2 to repress mesenchymal features of Ewing sarcoma," Genes Cancer 6(3-4):129-43 (Mar. 2015).
Fathi et al., "Differentiation syndrome with lower-intensity treatments for acute myeloid leukemia," Am J Hematol. 96(6):735-46 (Jun. 1, 2021) (13 Pages).
Felici et al., "Selection of antibody ligands from a large library of oligopeptides expressed on a multivalent exposition vector," J Mol Biol. 222(2):301-10 (1991).
Feng et al., "GFOLD: a generalized fold change for ranking differentially expressed genes from RNA-seq data," Bioinformatics. 28(21):2782-8 (2012).
Fodor et al., "Multiplexed biochemical assays with biological chips," Nature. 364:555-556 (1993).
Gaj et al. "ZFN, TALEN and CRISPR/Cas-based Methods for Genome Engineering," available in PMC Jul. 1, 2014, published in final edited form as: Trends Biotechnol. 31(7):397-405 (Jul. 2013) (20 pages).
Gallop et al., "Applications of Combinatorial Technologies to Drug Discovery. 1. Background and Peptide Combinatorial Libraries," J Med Chem 37(9):1233-51 (1994).
Gene Ontology Consortium, "Gene Ontology Consortium: going forward," Nucleic Acids Res. 43(Database issue):D1049-56 (2015).
Gingras et al., "Advances in protein complex analysis using mass spectrometry," J Physiol. 563(Pt 1):11-21 (Feb. 15, 2005).
Godwin et al., "Gemtuzumab ozogamicin in acute myeloid leukemia," Leukemia 31(9):1855-68 (Sep. 2017).
Grohar et al., "Ecteinascidin 743 interferes with the activity of EWS-FLI1 in Ewing sarcoma cells," Neoplasia 13(2):145-53 (Feb. 2011).
Helgeson et al., "Characterization of TMPRSS2:ETV5 and SLC45A3:ETV5 gene fusions in prostate cancer," Cancer Res. 68(1):73-80 (2008).
Herrero-Martín et al., "Stable interference of EWS-FLI1 in an Ewing sarcoma cell line impairs IGF- 1/IGF-1R signalling and reveals TOPK as a new target," Br J Cancer 101(1):80-90 (Jul. 7, 2009).
Ho et al., "An embryonic stem cell chromatin remodeling complex, esBAF, is essential for embryonic stem cell self-renewal and pluripotency," Proc Natl Acad Sci U S A. 106(13):5181-6 (2009).
Hohmann et al., "Sensitivity and engineered resistance of myeloid leukemia cells to BRD9 inhibition," Nat Chem Biol. 12(9): 672-679 (Sep. 2016) (12 pages).
Houghten et al., "The use of synthetic peptide combinatorial libraries for the identification of bioactive peptides," Biotechniques. 13(3):412-21 (1992).
Ichikawa et al., "An RNA-binding protein gene, TLS/FUS, is fused to ERG in human myeloid leukemia with t(16;21) chromosomal translocation," Cancer Res. 54(11):2865-8 (1994).
International Preliminary Report on Patentability for International Application No. PCT/US2016/062911 issued May 22, 2018 (13 pages).
International Preliminary Report on Patentability for International Application No. PCT/US2019/056312, mailed Apr. 29, 2021 (10 pages).
International Preliminary Report on Patentability for International Application No. PCT/US2020/033829, issued Nov. 17, 2022 (6 pages).
International Preliminary Report on Patentability for International Application No. PCT/US2022/019506, issued Sep. 12, 2023 (6 pages).
International Preliminary Report on Patentability for International Application No. PCT/US2022/020943, issued Sep. 12, 2023 (5 pages).
International Search Report and Written Opinion for International Application No. PCT/US18/000339 dated Jan. 28, 2019 (13 pages).
International Search Report and Written Opinion for International Application No. PCT/US19/56312, dated Jan. 14, 2020 (14 pages).
International Search Report and Written Opinion for International Application No. PCT/US19/56365 dated Jan. 30, 2020 (8 pages).
International Search Report and Written Opinion for International Application No. PCT/US2016/062911 dated Mar. 3, 2017 (16 pages).
International Search Report and Written Opinion for International Application No. PCT/US2020/015605, mailed Jun. 16, 2020 (15 pages).
International Search Report and Written Opinion for International Application No. PCT/US2020/015723, mailed Jul. 2, 2020 (15 pages).
International Search Report and Written Opinion for International Application No. PCT/US2020/033829, mailed Aug. 17, 2020 (14 pages).
International Search Report and Written Opinion for International Application No. PCT/US2022/019506, dated Jun. 7, 2022 (9 pages).
International Search Report and Written Opinion for International Application No. PCT/US2023/017839, mailed Sep. 6, 2023 (11 pages).
International Search Report and Written Opinion for International Application No. PCT/US2023/077088, mailed Mar. 4, 2024 (17 pages).
International Search Report and Written Opinion for International Application No. PCT/US2024/024407, mailed Jun. 24, 2024 (15 pages).
International Search Report and Written Opinion for International Application No. PCT/US2024/024428, mailed Jul. 16, 2024 (18 pages).

(56) References Cited

OTHER PUBLICATIONS

International Search Report and Written Opinion for International Application No. PCT/US21/15876, mailed on Apr. 7, 2021 (23 pages).
International Search Report and Written Opinion for International Application No. PCT/US21/15878, dated Jun. 4, 2021 (10 pages).
International Search Report and Written Opinion for International Application No. PCT/US23/17821, mailed Jun. 30, 2023 (9 pages).
International Search Report and Written Opinion for International Application No. PCT/US23/17829, mailed Aug. 23, 2023 (15 pages).
International Search Report and Written Opinion for PCT/US2022/020943, dated Jun. 14, 2022 (17 pages).
Kadoch et al., "Mammalian SWI/SNF chromatin remodeling complexes and cancer: Mechanistic insights gained from human genomics," Sci Adv. 1(5):e1500447 (2015) (17 pages).
Kadoch et al., "Proteomic and bioinformatic analysis of mammalian SWI/SNF complexes identifies extensive roles in human malignancy," Nat Genet. 45(6):592-601 (2013) (11 pages).
Karim et al., "The ETS-domain: a new DNA-binding motif that recognizes a purine-rich core DNA sequence," Genes Dev. 4(9):1451-3 (1990).
Kedage et al., "An Interaction with Ewing's Sarcoma Breakpoint Protein EWS Defines a Specific Oncogenic Mechanism of ETS Factors Rearranged in Prostate Cancer," Cell Rep. 17(5):1289-301 (Oct. 25, 2016) (14 pages).
Klezovitch et al., "A causal role for ERG in neoplastic transformation of prostate epithelium," Proc Natl Acad Sci U S A. 105(6):2105-10 (2008).
Kumar-Sinha et al., "Recurrent gene fusions in prostate cancer," available in PMC Jul. 16, 2009. Published in final edited form as: Nat Rev Cancer. 8(7):497-511 (2008) (29 pages).
Kunderfranco et al., "ETS transcription factors control transcription of EZH2 and epigenetic silencing of the tumor suppressor gene Nkx3.1 in prostate cancer," PLoS One. 5(5):e10547 (2010) (17 pages).
Lam et al., "A new type of synthetic peptide library for identifying ligand-binding activity," Nature. 354(6348):82-84 (1991).
Lam, "Application of combinatorial library methods in cancer research and drug discovery," Anticancer Drug Des. 12(3):145-67 (1997).
Langmead et al., "Fast gapped-read alignment with Bowtie 2," available in PMC Apr. 1, 2013. Published in final edited form as: Nat Methods. 9(4):357-9 (2012) (8 pages).
Link et al., "Targeting the BAF57 SWI/SNF subunit in prostate cancer: a novel platform to control androgen receptor activity," Cancer Res. 68(12):4551-8 (2008).
Love et al., "Moderated estimation of fold change and dispersion for RNA-seq data with DESeq2," Genome Biol. 15(12):550 (2014) (21 pages).
Lupien et al., "FoxA1 translates epigenetic signatures into enhancer-driven lineage-specific transcription," Cell. 132(6):958-70 (2008).
Machanick et al., "MEME-ChIP: motif analysis of large DNA datasets," Bioinformatics. 27(12):1696-7 (2011).
Mackereth et al., "Diversity in structure and function of the ETS family PNT domains," J Mol Biol. 342(4):1249-64 (2004).
Madura et al., "N-recognin/Ubc2 interactions in the N-end rule pathway," J Biol Chem. 268(16):12046-54 (1993).
Mélé et al., "The human transcriptome across tissues and individuals," available in PMC Aug. 24, 2015. Published in final edited form as: Science. 348(6235):660-5 (2015) (12 pages).
Michel et al., "Abstract PR15: BRD9 defines a novel mammalian SWI/SNF (BAF) complex configuration which supports proliferation in AML," Clin Cancer Res. 23(24_Suppl) Abstract PR15 (2017) (4 pages).
Mill et al., "RUNX1-targeted therapy for AML expressing somatic or germline mutation in RUNX1," Blood 134(1):59-73 (Jul. 4, 2019).
Mounir et al., "ERG signaling in prostate cancer is driven through PRMT5-dependent methylation of the Androgen Receptor," Elife. 5:e13964 (2016) (19 pages).
Nagaich et al., "Rapid periodic binding and displacement of the glucocorticoid receptor during chromatin remodeling," Mol Cell. 14(2):163-74 (2004).
Nam et al., "Expression of the TMPRSS2:ERG fusion gene predicts cancer recurrence after surgery for localised prostate cancer," Br J Cancer. 97(12):1690-5 (2007).
Ong et al., "A practical recipe for stable isotope labeling by amino acids in cell culture (SILAC)," Nat Protoc. 1(6):2650-60 (2006).
Partial Supplementary European Search Report for European Patent Application No. 20936213.6, dated Feb. 8, 2024 (20 pages).
Paulo et al., "FLI1 is a novel ETS transcription factor involved in gene fusions in prostate cancer," Genes Chromosomes Cancer. 51(3):240-9 (2012).
Petrovics et al., "Frequent overexpression of ETS-related gene-1 (ERG1) in prostate cancer transcriptome," Oncogene. 24(23):3847-52 (2005).
Piel et al., International Application No. PCT/US2024/031875, filed May 31, 2024 by applicant Foghorn Therapeutics Inc. (47 pages).
Pomerantz et al., "The androgen receptor cistrome is extensively reprogrammed in human prostate tumorigenesis," available in PMC May 1, 2016. Published in final edited form as: Nat Genet. 47(11):1346-51 (2015) (17 pages).
Prensner et al., "The long noncoding RNA SChLAP1 promotes aggressive prostate cancer and antagonizes the SWI/SNF complex," available in PMC May 1, 2014. Published in final edited form as: Nat Genet. 45(11):1392-8 (2013) (26 pages).
PubChem CID 117640569, "N-[2-[[4-(4-Methoxyphenyl)-1,3-thiazol-2-yl]amino]-2-oxoethyl]-1,3-thiazole-5-carboxamide," https://pubchem.ncbi.nlm.nih.gov/compound/117640569, created Feb. 23, 2016 (9 pages).
PubChem CID 56442706, "1-(4-Methoxyphenyl)-N-[2-oxo-2-[4-(1,2,4-triazol-1-yl)anilino]ethyl]pyrazole-3-carboxamide," https://pubchem.ncbi.nlm.nih.gov/compound/56442706, created Jan. 25, 2012 (8 pages).
PubChem CID 91946137, "N-[2-[(1-Ethylpyrazol-3-yl}amino]-2-oxoethyl]-1-methylpyrazole-3-carboxamide," https://pubchem.ncbi.nlm.nih.gov/compound/91946137, created Oct. 22, 2015 (8 pages).
PubChem Compound Summary for CID 155037309, dated Dec. 19, 2020 (9 pages).
PubChem Compound Summary for CID No. 136572628, "4-Chloro-N-[2-(cyclopentylamino)-2-oxoethyl]-5-nitro-1H-pyrazole-3-carboxamide," created Jan. 24, 2019, <https://pubchem.ncbi.nlm.nih.gov/compound/136572628>, (7 pages).
PubChem Compound Summary for CID No. 49726797, "N-Methyl-N-(2-oxo-2-((4-(pyridin-3-yl)thiazol-2-yl)amino)ethyl)-1H-indole-3-carboxamide," created Nov. 27, 2010, <https://pubchem.ncbi.nlm.nih.gov/compound/49726797>, (8 pages).
PubChem Compound Summary for CID No. 91945707, "N-[2-[(4,5-Dimethyl-1,3-thiazol-2-yl)amino]-2-oxoethyl]-1-methylpyrazole-3-carboxamide," created Oct. 22, 2015 <https://pubchem.ncbi.nlm.nih.gov/compound/91945707>, (8 pages).
PubChem Compound Summary for PubChem CID 49726798, "N-(2-((4-(Furan-2-yl)thiazol-2-yl)amino)-2-oxoethyl)-N-methyl-1H-indole-3-carboxamide," created Nov. 27, 2010 <https://pubchem.ncbi.nih.gov/compound/49726798> (8 pages).
PubChem Compound Summary for SID 172131678, dated Dec. 9, 2014 (8 pages).
Quinlan et al., "BEDTools: a flexible suite of utilities for comparing genomic features," Bioinformatics. 26(6):841-2 (2010).
Rago et al., "Exquisite Sensitivity to Dual BRG1/BRM ATPase Inhibitors Reveals Broad SWI/SNF Dependencies in Acute Myeloid Leukemia," Mol Cancer Res. 20(3):361-72 (Mar. 1, 2022).
Rajput et al., "Frequency of the TMPRSS2:ERG gene fusion is increased in moderate to poorly differentiated prostate cancers," J Clin Pathol. 60(11):1238-43 (2007).
Ramos et al., "Current Approaches in the Treatment of Relapsed and Refractory Acute Myeloid Leukemia," J Clin Med. 4(4):665-95 (Apr. 2015).

(56) References Cited

OTHER PUBLICATIONS

Rappsilber et al., "Protocol for micro-purification, enrichment, pre-fractionation and storage of peptides for proteomics using Stage Tips," Nat Protoc. 2(8):1896-906 (2007).
Riggi et al., "EWS-FLI1 utilizes divergent chromatin remodeling mechanisms to directly activate or repress enhancer elements in Ewing sarcoma," Cancer Cell 26(5):668-81 (Nov. 10, 2014).
Sankar et al., "Promiscuous partnerships in Ewing's sarcoma," Cancer Genet. 204(7):351-65 (Jul. 2011).
Schiefer et al., "Design, synthesis, and optimization of novel epoxide incorporating peptidomimetics as selective calpain inhibitors," J Med Chem. 56(15):6054-68 (Feb. 7, 2013).
Scott et al., "Searching for peptide ligands with an epitope library," Science. 249(4967):386-390 (1990).
Shen et al., "The SWI/SNF ATPase Brm is a gatekeeper of proliferative control in prostate cancer," Cancer Res. 68(24):10154-62 (Dec. 2008).
Shi et al., "Role of SWI/SNF in acute leukemia maintenance and enhancer-mediated Myc regulation," Genes Dev. 27(24):2648-62 (Dec. 2013).
Siegel et al., "Cancer statistics, 2015," CA Cancer J Clin. 65(1):5-29 (2015).
Simone, Part XIV: Oncology: Introduction, Textbook of Medicine, Bennett et al., 20(1), 1004-1010 (1997).
STN Registry Database, CAS RN 858073-83-3, Albany Molecular Research, Inc., entered Aug. 3, 2005 (1 page).
Subramanian et al., "Gene set enrichment analysis: a knowledge-based approach for interpreting genome-wide expression profiles," Proc Natl Acad Sci USA. 102(43):15545-50 (2005).
Sun et al., "TMPRSS2-ERG fusion, a common genomic alteration in prostate cancer activates C-MYC and abrogates prostate epithelial differentiation," available in PMC Oct. 4, 2020. Published in final edited form as: Oncogene. 27(40)5348-53 (2008) (12 pages).
Szabo et al., "Surface plasmon resonance and its use in biomolecular interaction analysis (BIA)," Curr Opin Struct Biol. 5(5):699-705 (1995).
Takigami et al., "Synthetic siRNA targeting the breakpoint of EWS/Fli-1 inhibits growth of Ewing sarcoma xenografts in a mouse model," Int J Cancer 128(1):216-26 (Jan. 1, 2011).
Tikdari et al., "Reaction of 2-Aminothiazoles with 5-Oxazolones," Indian Journal of Chemistry 26B:478-9 (May 1987).
Tomlins et al., "Recurrent fusion of TMPRSS2 and ETS transcription factor genes in prostate cancer," Science.310(5748):644-8 (2005).
Tomlins et al., "Role of the TMPRSS2-ERG gene fusion in prostate cancer," Neoplasia. 10(2):177-88 (2008) (21 pages).
Tomlins et al., "TMPRSS2:ETV4 gene fusions define a third molecular subtype of prostate cancer," Cancer Res. 66(7):3396-400 (2006).
Tsai et al. "Dimeric CRISPR RNA-guided FokI Nucleases for Highly Specific Genome Editing," available in PMC Dec. 1, 2014, published in final edited form as: Nat Biotechnol. 32(6):569-576 (Jun. 2014) (22 pages).
Tuoc et al., "Chromatin regulation by BAF170 controls cerebral cortical size and thickness," Dev Cell. 25(3):256-69 (May 2013).
Varambally et al., "The polycomb group protein EZH2 is involved in progression of prostate cancer," Nature. 419(6907):624-9 (2002).
Vela et al., "Discovery of Enhancers of the Secretion of Leukemia Inhibitory Factor for the Treatment of Multiple Sclerosis," J Biomol Screen. 21(5):437-45 (Jun. 2016).
Verger et al., "Identification of amino acid residues in the ETS transcription factor Erg that mediate Erg-Jun/Fos-DNA ternary complex formation," J Biol Chem. 276(20):17181-9 (2001).
Wahedy et al., "Facile Synthesis and In-Vitro Antimicrobial Activity of Some Novel 2-Hetroamido-5-Amino Benzimidazoles," Am J PharmTech Res. 3(2):868-82 (2013).
Wollenick et al., "Synthetic transactivation screening reveals ETV4 as broad coactivator of hypoxia-inducible factor signaling," Nucleic Acids Res. 40(5):1928-43 (2012).
Wu et al., "Targeting the chromatin remodeling enzyme BRG1 increases the efficacy of chemotherapy drugs in breast cancer cells," Oncotarget 7(19):27158-75 (May 10, 2016).
Yang et al., "EZH2, an epigenetic driver of prostate cancer," Protein Cell. 4(5):331-41 (2013).
Yildirim et al., "Mbd3/NURD complex regulates expression of 5-hydroxymethylcytosine marked genes in embryonic stem cells," Cell. 147(7):1498-510 (2011).
Yu et al., "An integrated network of androgen receptor, polycomb, and TMPRSS2-ERG gene fusions in prostate cancer progression," Cancer Cell. 17(5):443-54 (2010).
Yu et al., "Direct recruitment of polycomb repressive complex 1 to chromatin by core binding transcription factors," Mol Cell. 45(3):330-43 (2012).
Zervos et al., "Mxi1, a protein that specifically interacts with Max to bind Myc-Max recognition sites," Cell. 72(2):223-32 (1993).
Zhang et al., "Model-based analysis of ChIP-Seq (MACS)," Genome Biol. 9(9):R137 (2008) (9 pages).
Zong et al., "ETS family transcription factors collaborate with alternative signaling pathways to induce carcinoma from adult murine prostate cells," Proc Natl Acad Sci U S A. 106(30):12465-70 (Jul. 2009).
Zuckermann et al., "Discovery of Nanomolar Ligands for 7-Transmembrane G-Protein-Coupled Receptors from a Diverse N-(Substituted)glycine Peptoid Library," J Med Chem. 37(17):2678-2685 (1994).
CAS RN: 1223164-86-0; STN entry date: May 14, 2010; N-[2-[[4-(3-Fluoro-4-methoxyphenyl)-2-thiazolyl]amino]-2-oxoethyl]-2-methyl-3-furancarboxamide (1page).
CAS RN: 1300403-14-8; STN entry date May 25, 2011; 5-Methyl-N-[2-oxo-2-[ (5-phenyl-2-pyridinyl)amino]ethyl]-2-thiophenecarboxamide (1 page).
CAS RN: 924410-17-3; STN entry date: Mar. 2, 2007; 5-Methyl-N-[2-oxo-2-[ (4-phenyl-2-thiazolyl)amino]ethyl]-2-thiophenecarboxamide (1 page).
CAS RN: 924420-04-2; STN entry date: Mar. 2, 2007; 5-Methyl-N-[2-oxo-2-[[4-(4-pyridinyl)-2-thiazolyl]amino]ethyl]-2-thiophenecarboxamide (1 page).
Chattopadhyay et al., "Uveal melanoma: From diagnosis to treatment and the science in between," Cancer. 122(15):2299-2312 (26 pages) (Aug. 2016).
Database Registry, RN 1323331-37-8, entered Aug. 25, 2011 (1 page).
Database Registry, RN 1324163-01-0, entered Aug. 28, 2011 (1 page).
Database Registry, RN 1327304-26-6, entered Sep. 2, 2011 (1 page).
International Search Report and Written Opinion for International Patent Application No. PCT/US2024/031875, mailed Oct. 18, 2024 (15 pages).
"Compound Summary: N-[(S)-1-[[4-[6-[(2R,6S)-2,6-Dimethylmorpholino]-2-pyridyl]-2-thiazolyl]amino]-3-methoxy-1-oxo-2-propyl]-1-(methylsulfonyl)-1H-pyrrole-3-carboxamide," PubChem. CID: 156818027, <https://pubchem.ncbi.nlm.nih.gov/compound/156818027>, created Nov. 10, 2021, accessed Jan. 19, 2025 (9 pages).
"Form S-1 Registration Statement: Foghorn Therapeutics Inc.," as filed with the United States Securities and Exchange Commission on Oct. 2, 2020 (230 pages).
Collins et al., "Abstract 2122: The dual BRM/BRG1 (SMARCA2/4) inhibitor FHD-286 induces differentiation in preclinical models of AML," Cancer Res. 83(7_Supplement) (Apr. 2023) (5 pages).
Fiskus et al., "Pre-Clinical Efficacy of Targeting Baf Complexes through Inhibition of the Dual Atpases BRG1 and BRM By FHD-286 in Cellular Models of AML of Diverse Genetic Background," Blood. 140(Supplement 1):8819-20 (Nov. 2022) (15 pages).
Hentemann, "Abstract ND14: Pharmacological profile and anti-tumor properties of FHD-286: A novel BAF inhibitor for the treatment of transcription factor-driven cancers," Cancer Res. 82(12_Supplement): ND14 (Jun. 2022) (4 pages).
International Search Report and Written Opinion for International Patent Application No. PCT/US2024/050665, mailed Jan. 28, 2025 (15 pages).

(56) References Cited

OTHER PUBLICATIONS

International Search Report and Written Opinion for PCT/US2024/050660, mailed Nov. 26, 2024 (12 pages).
Selleck Chemicals, "Safety Data Sheet: FHD-286," <https://www.selleckchem.com/msds/MSDS_E1178.pdf>, revised May 1, 2014 (2 pages).
Coban, G., Kose, F. A., Kirmizibayrak, P. B., &Pabuccuoglu, V. (2015). Synthesis, biological activity screening and molecular modeling study of acylaminoacetamide derivatives. Medicinal Chemistry Research, 24(10), 3710-3729.†
STN Registry Database 931893-54-8, Date of publication: Apr. 23, 2007 923768-18-7, Date of publication: Feb. 28, 2007 932130-00-2, Date of publication: Apr. 24, 2007 1209112-42-4, Date of publication:Mar. 12, 2010 938283-11-5, Date of publication: Jun. 22, 2007 1049271-26-2, Date of publication: Sep. 14, 2008 1010893-05-6, Date of publication: Mar. 30, 2008 1586193-45-4, Date of publication: Apr. 17, 2014 1831899-24-1, Date of publication: Dec. 17, 2015 1827759-12-5, Date of publication: Dec. 13, 2015 1576383-94-2, Date of publication: Mar. 31, 2014 1839545-15-1, Date of publication: Dec. 31, 2015 1246047-75-5, Date of publication: Oct. 12, 2010 1351682-19-3, Date of publication: Dec. 22, 2011 1455783-72-8, Date of publication: Oct. 6, 2013 1401558-47-1, Date of publication: Oct. 22, 2012 923809-79-4, Date of publication: Feb. 28, 2007 1308280-67-2, Date of publication: Jun. 9, 2011 1081662-32-9, Date of publication: Dec. 8, 2008.†
Jones, P., Altamura, S., De Francesco, R., Paz, O. G., Kinzel, O., Mesiti, G., . . . Steinkuhler, C. A Novel Series of Potent and Selective Ketone Histone Deacetylase Inhibitors with Antitumor Activity in Vivo. J. Med. Chem. 2008, 51, 2350-2353.†
Pescatore, G., Kinzel, O., Attenni, B., Cecchetti, O., Fiore, F., Fonsi, M., . . . Jones, P. Optimization of a series of potent and selective ketone histone deacetylase inhibitors. Bioorganic &Medicinal Chemistry Letters, 18(20), 5528-5532.†
Triandafillidi, I., Bisticha, A., Voutyritsa, E., Galiatsatou, G., &Kokotos, C. G. (2015). tert-Butyl ester or benzylamide of the dipeptide Pro-Gly as organocatalysts for the asymmetric aldol reaction. Tetrahedron, 71(6), 932-940.†
Lei Zhang, Xiaojie Chen, Jun Liu, Qingzhang Zhu, Ying Leng, Xiaomin Luo, Huiliang Jiang, Hong Liu. Discovery of novel dual-action antidiabetic agents that inhibit glycogen phosphorylase and activate glucokinase. European Journal of Medicinal Chemistry 58 (2012) 624-639.†
Anne Décor, Chantal Grand-Maître, Oliver Hucke, Jeff O'Meara, Cyrille Kuhn, Léa Constantineau-Forget, Christian Brochu, Eric Malenfant, Megan Bertrand-Laperle, Josée Bordeleau, Elise Ghiro, Marc Pesant, Gulrez Fazal, Vida Gorys, Michael Little, Colette Boucher, Sylvain Bordeleau, Pascal Turcotte, Tim Guo, Michel Garneau, Catherine Spickler, Annick Gauthier. Design, synthesis and biological evaluation of novel aminothiazoles as antiviral compounds acting against human rhinovirus. Bioorganic &Medicinal Chemistry Letters 23 (2013) 3841-3847.†
Spickler, C., Lippens, J., Laberge, M.-K., Desmeules, S., Bellavance, É., Garneau, M., . . . Gauthier, A. (2013). Phosphatidylinositol 4-Kinase III Beta Is Essential for Replication of Human Rhinovirus and Its Inhibition Causes a Lethal Phenotype In Vivo. Antimicrobial Agents and Chemotherapy, 57(7), 3358-3368.†

† cited by third party

COMPOUNDS AND USES THEREOF

BACKGROUND

The invention relates to compounds useful for modulating BRG1- or BRM-associated factors (BAF) complexes. In particular, the invention relates to compounds useful for treatment of disorders associated with BAF complex function.

Chromatin regulation is essential for gene expression, and ATP-dependent chromatin remodeling is a mechanism by which such gene expression occurs. The human Switch/Sucrose Non-Fermentable (SWI/SNF) chromatin remodeling complex, also known as BAF complex, has two SWI2-like ATPases known as BRG1 (Brahma-related gene-1) and BRM (Brahma). The transcription activator BRG1, also known as ATP-dependent chromatin remodeler SMARCA4, is encoded by the SMARCA4 gene on chromosome 19. BRG1 is overexpressed in some cancer tumors and is needed for cancer cell proliferation. BRM, also known as probable global transcription activator SNF2L2 and/or ATP-dependent chromatin remodeler SMARCA2, is encoded by the SMARCA2 gene on chromosome 9 and has been shown to be essential for tumor cell growth in cells characterized by loss of BRG1 function mutations. Deactivation of BRG and/or BRM results in downstream effects in cells, including cell cycle arrest and tumor suppression.

SUMMARY

The present invention features compounds useful for modulating a BAF complex. In some embodiments, the compounds are useful for the treatment of disorders associated with an alteration in a BAF complex, e.g., a disorder associated with an alteration in one or both of the BRG1 and BRM proteins. The compounds of the invention, alone or in combination with other pharmaceutically active agents, can be used for treating such disorders.

Disclosed herein is a compound having the structure of Formula I:

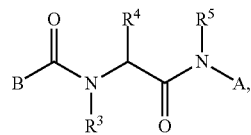

Formula I wherein
B is

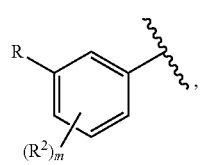

optionally substituted $C_2$-$C_9$ heteroaryl, or $C_2$-$C_9$ heterocyclyl;
m is 0, 1, 2, 3, or 4;
R is H,

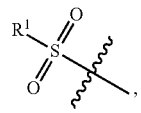

wherein $R^1$ is optionally substituted $C_1$-$C_3$ alkyl, optionally substituted $C_3$-$C_6$ cycloalkyl, optionally substituted $C_6$-$C_{10}$ aryl, optionally substituted $C_2$-$C_9$ heteroaryl, hydroxy, optionally substituted $C_1$-$C_6$ alkoxy, or —$NR^{1a}R^{1b}$, wherein each $R^{1a}$ and $R^{1b}$ is, independently, H or $CH_3$;

each $R^2$ is, independently, halo, optionally substituted $C_1$-$C_6$ alkyl, optionally substituted $C_1$-$C_6$ heteroalkyl, optionally substituted $C_3$-$C_{10}$ carbocyclyl, optionally substituted $C_1$-$C_6$ alkyl $C_3$-$C_{10}$ carbocyclyl, optionally substituted $C_1$-$C_6$ heteroalkyl $C_3$-$C_{10}$ carbocyclyl, optionally substituted $C_2$-$C_9$ heterocyclyl, optionally substituted $C_1$-$C_6$ alkyl $C_2$-$C_9$ heterocyclyl, optionally substituted $C_1$-$C_6$ heteroalkyl $C_2$-$C_9$ heterocyclyl, optionally substituted $C_6$-$C_{10}$ aryl, optionally substituted $C_1$-$C_6$ alkyl $C_6$-$C_{10}$ aryl, optionally substituted $C_1$-$C_6$ heteroalkyl $C_6$-$C_{10}$ aryl, optionally substituted $C_2$-$C_9$ heteroaryl, optionally substituted $C_1$-$C_6$ alkyl $C_2$-$C_9$ heteroaryl, optionally substituted $C_1$-$C_6$ heteroalkyl $C_2$-$C_9$ heteroaryl, optionally substituted $C_2$-$C_6$ alkenyl, optionally substituted $C_2$-$C_6$ heteroalkenyl, hydroxy, thiol, or optionally substituted amino;

each $R^3$ and $R^5$ is, independently, selected from the group consisting of H, optionally substituted $C_1$-$C_6$ alkyl, or optionally substituted $C_1$-$C_6$ heteroalkyl;

$R^4$ is hydrogen, optionally substituted $C_1$-$C_6$ alkyl, optionally substituted $C_1$-$C_6$ heteroalkyl, optionally substituted $C_3$-$C_{10}$ carbocyclyl, optionally substituted $C_1$-$C_6$ alkyl $C_3$-$C_{10}$ carbocyclyl, optionally substituted $C_1$-$C_6$ heteroalkyl $C_3$-$C_{10}$ carbocyclyl, optionally substituted $C_2$-$C_9$ heterocyclyl, optionally substituted $C_1$-$C_6$ alkyl $C_2$-$C_9$ heterocyclyl, optionally substituted $C_1$-$C_6$ heteroalkyl $C_2$-$C_9$ heterocyclyl, optionally substituted $C_6$-$C_{10}$ aryl, optionally substituted $C_1$-$C_6$ alkyl $C_6$-$C_{10}$ aryl, optionally substituted $C_1$-$C_6$ heteroalkyl $C_6$-$C_{10}$ aryl, optionally substituted $C_2$-$C_9$ heteroaryl, optionally substituted $C_1$-$C_6$ alkyl $C_2$-$C_9$ heteroaryl, or optionally substituted $C_1$-$C_6$ heteroalkyl $C_2$-$C_9$ heteroaryl; and A is

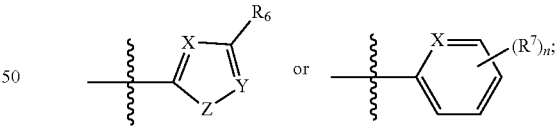

wherein X is N or $CR^X$, wherein $R^X$ is H, halo, optionally substituted $C_1$-$C_6$ alkyl, optionally substituted $C_1$-$C_6$ heteroalkyl, optionally substituted $C_3$-$C_{10}$ carbocyclyl, optionally substituted $C_2$-$C_9$ heterocyclyl, optionally substituted $C_6$-$C_{10}$ aryl, optionally substituted $C_2$-$C_9$ heteroaryl, optionally substituted $C_2$-$C_6$ alkenyl, or optionally substituted $C_2$-$C_6$ heteroalkenyl;

Y is N or CRY, wherein RY is H, halo, optionally substituted $C_1$-$C_6$ alkyl, optionally substituted $C_1$-$C_6$ heteroalkyl, optionally substituted $C_3$-$C_{10}$ carbocyclyl, optionally substituted $C_2$-$C_9$ heterocyclyl, optionally substituted $C_6$-$C_{10}$ aryl, optionally substituted $C_2$-$C_9$ heteroaryl, optionally substituted $C_2$-$C_6$ alkenyl, or optionally substituted $C_2$-$C_6$ heteroalkenyl;

Z is S, O, or NR$^Z$, wherein R$^Z$ is H, optionally substituted C$_1$-C$_6$ alkyl, or optionally substituted C$_1$-C$_6$ heteroalkyl;

R$^6$ and R$^7$ are, independently, H, halo, optionally substituted C$_1$-C$_6$ alkyl, optionally substituted C$_1$-C$_6$ heteroalkyl, optionally substituted C$_3$-C$_{10}$ carbocyclyl, optionally substituted C$_2$-C$_9$ heterocyclyl, optionally substituted C$_6$-C$_{10}$ aryl, optionally substituted C$_1$-C$_6$ alkyl optionally substituted C$_6$-C$_{10}$ aryl, optionally substituted C$_2$-C$_9$ heteroaryl, optionally substituted C$_2$-C$_6$ alkenyl, optionally substituted C$_2$-C$_6$ heteroalkenyl, or optionally substituted amino, or two R$^7$ combine with the carbons to which they are attached to form a 5- or 6-membered ring; and n is 1, 2, 3, or 4, or a pharmaceutically acceptable salt thereof,
wherein if B is

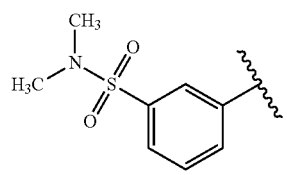 [SMILES: *c1cccc(S(=O)(=O)N(C)C)c1]

and R$^4$ is hydrogen then R$^6$ is H, halo, optionally substituted C$_1$-C$_6$ alkyl, optionally substituted C$_1$-C$_6$ heteroalkyl, optionally substituted C$_3$-C$_{10}$ carbocyclyl, optionally substituted C$_2$-C$_9$ heterocyclyl, optionally substituted C$_2$-C$_9$ heteroaryl, optionally substituted C$_2$-C$_6$ alkenyl, optionally substituted C$_2$-C$_6$ heteroalkenyl, optionally substituted amino, or C$_6$-C$_{10}$ aryl optionally substituted with one or more substituents selected from optionally substituted C$_1$-C$_6$ alkyl, optionally substituted C$_1$-C$_6$ heteroalkyl, optionally substituted C$_6$-C$_{10}$ aryl, optionally substituted C$_1$-C$_6$ acyl, and cyano, or two substituents combine with the carbons to which they are attached to form a 5- or 6-membered heterocycle.

In some embodiments, B is

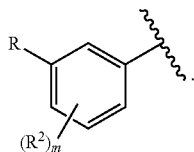

In some embodiments, R$^1$ is —NR$^{1a}$R$^{1b}$, wherein each R$^{1a}$ and R$^{1b}$ is, independently, H or CH$_3$.

In some embodiments, the compound of Formula I has the structure of Formula II:

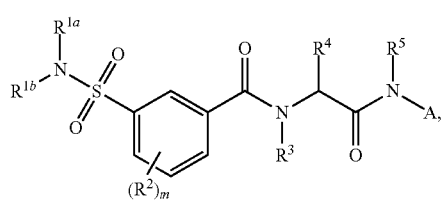

Formula II wherein R$^{1a}$ and R$^{1b}$ are, independently, H or CH$_3$, or a pharmaceutically acceptable salt thereof.

In some embodiments, m is 0.

In some embodiments, the compound of Formula II has the structure of Formula IIa:

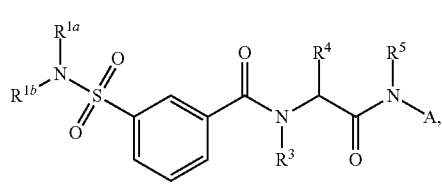

Formula IIa or a pharmaceutically acceptable salt thereof.

In some embodiments, the compound of Formula II has the structure of Formula IIb:

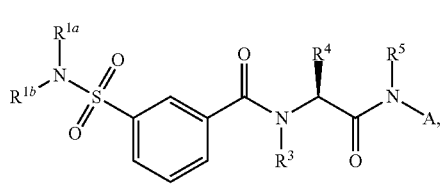

Formula IIb or a pharmaceutically acceptable salt thereof.

In some embodiments, A is

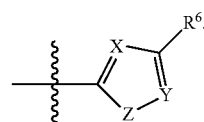

In some embodiments, the compound of Formula II has the structure of Formula IIc:

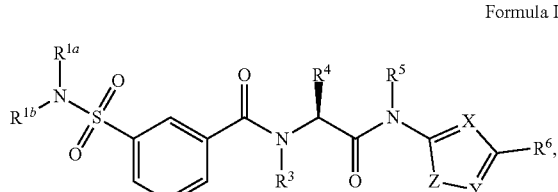

Formula IIc or a pharmaceutically acceptable salt thereof.

In some embodiments, the compound of Formula II has the structure of Formula IId:

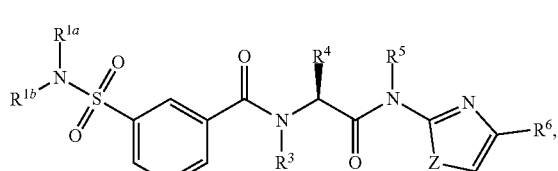

Formula IId or a pharmaceutically acceptable salt thereof.

In some embodiments, the compound of Formula II has the structure of Formula IIe:

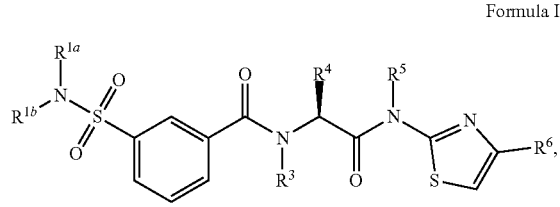

Formula IIe or a pharmaceutically acceptable salt thereof.

In some embodiments, the compound of Formula II has the structure of Formula IIf:

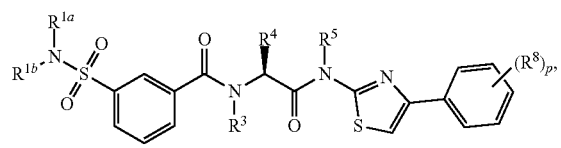

Formula IIf wherein p is 0, 1, 2, 3, 4, or 5; and each $R^8$ is, independently, optionally substituted $C_1$-$C_6$ alkyl, optionally substituted $C_1$-$C_6$ heteroalkyl, optionally substituted $C_1$-$C_6$ acyl, optionally substituted $C_6$-$C_{10}$ aryl, optionally substituted $C_2$-$C_9$ heteroaryl, cyano, hydroxy, thiol, or optionally substituted amino, or two $R^8$ combine with the carbons to which they are attached to form a 5- or 6-membered heterocycle, or a pharmaceutically acceptable salt thereof.

In some embodiments, p is 0.

In some embodiments, the compound of Formula II has the structure of Formula IIg:

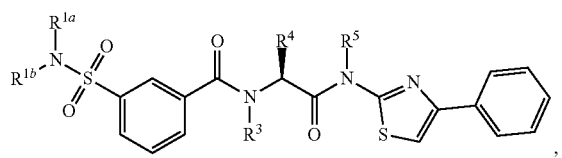

Formula IIg or a pharmaceutically acceptable salt thereof.

In some embodiments, A is

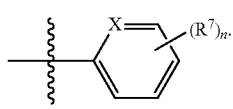

In some embodiments, the compound of Formula II has the structure of Formula IIh:

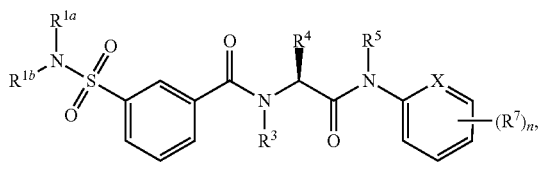

Formula IIh or a pharmaceutically acceptable salt thereof.

In some embodiments, n is 1. In some embodiments, A is

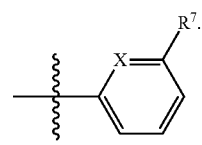

In some embodiments $R^7$ is

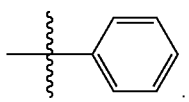

In some embodiments, n is 0.

In some embodiments, the compound of Formula II has the structure of Formula IIi:

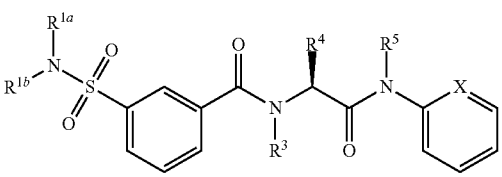

Formula IIi or a pharmaceutically acceptable salt thereof.

In some embodiments, X is N. In some embodiments, X is CH.

In some embodiments, each $R^{1a}$ and $R^{1b}$ is, independently, selected from the group consisting of H or $CH_3$. In some embodiments, both $R^{1a}$ and $R^{1b}$ are H. In some embodiments, both $R^{1a}$ and $R^{1b}$ are $CH_3$. In some embodiments, $R^{1a}$ is H and $R^{1b}$ is $CH_3$. In some embodiments, both $R^3$ and $R^5$ are H.

In some embodiments, $R^1$ is optionally substituted $C_1$-$C_3$ alkyl.

In some embodiments, the compound of Formula I has the structure of Formula III:

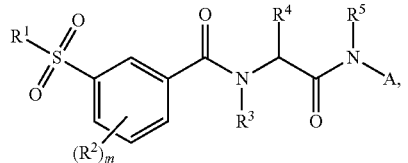

Formula III wherein $R^1$ is optionally substituted $C_1$-$C_3$ alkyl, or a pharmaceutically acceptable salt thereof.

In some embodiments, m is 0.

In some embodiments, the compound of Formula III has the structure of Formula IIIa:

Formula IIIa

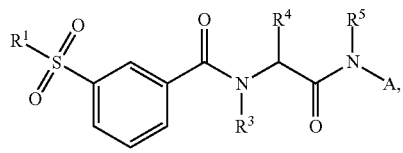

or a pharmaceutically acceptable salt thereof.

In some embodiments, the compound of Formula III has the structure of Formula IIIb:

Formula IIIb

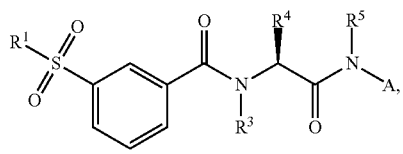

or a pharmaceutically acceptable salt thereof.

In some embodiments, A is Z

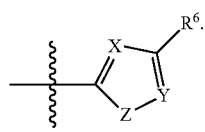

In some embodiments, the compound of Formula III has the structure of Formula IIIc:

Formula IIIc

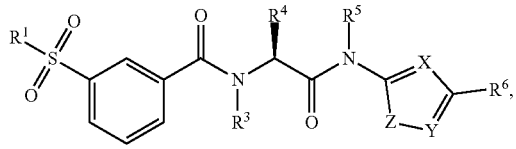

or a pharmaceutically acceptable salt thereof.

In some embodiments, the compound of Formula III has the structure of Formula IIId:

Formula IIId

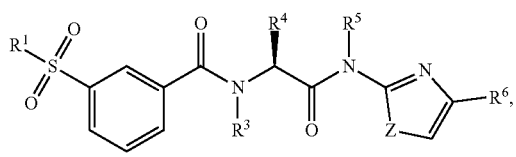

or a pharmaceutically acceptable salt thereof.

In some embodiments, the compound of Formula III has the structure of Formula IIIe:

Formula IIIe

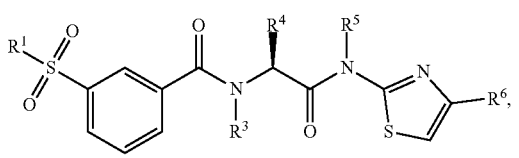

or a pharmaceutically acceptable salt thereof.

In some embodiments, the compound of Formula III has the structure of Formula IIIf:

Formula IIIf

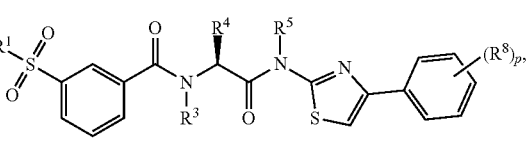

wherein p is 0, 1, 2, 3, 4, or 5; and each $R^8$ is, independently, optionally substituted $C_1$-$C_6$ alkyl, optionally substituted $C_1$-$C_6$ heteroalkyl, cyano, optionally substituted $C_1$-$C_6$ acyl, optionally substituted $C_6$-$C_{10}$ aryl, optionally substituted $C_2$-$C_9$ heteroaryl, hydroxy, thiol, or optionally substituted amino, or a pharmaceutically acceptable salt thereof.

In some embodiments, p is 0.

In some embodiments, the compound of Formula III has the structure of Formula IIIg:

Formula IIIg

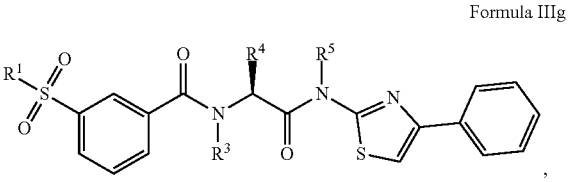

or a pharmaceutically acceptable salt thereof.

In some embodiments, A is

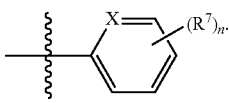

In some embodiments, the compound of Formula III has the structure of Formula IIIh:

Formula IIIh

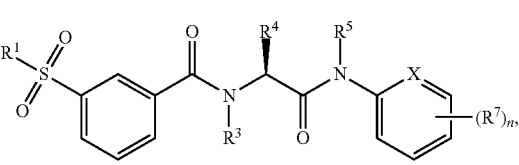

or a pharmaceutically acceptable salt thereof.

In some embodiments, n is 0.

In some embodiments, the compound of Formula III has the structure of Formula IIIi:

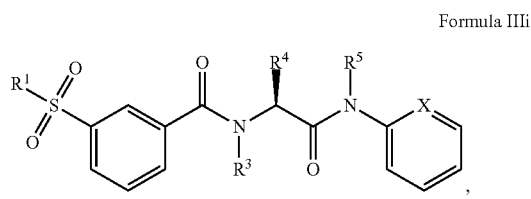

Formula IIIi or a pharmaceutically acceptable salt thereof.

In some embodiments, $R^1$ is $CH_3$, isopropyl, or cyclopropyl.

In some embodiments, B is optionally substituted $C_2$-$C_9$ heteroaryl or $C_2$-$C_9$ heterocyclyl. In some embodiments, B is

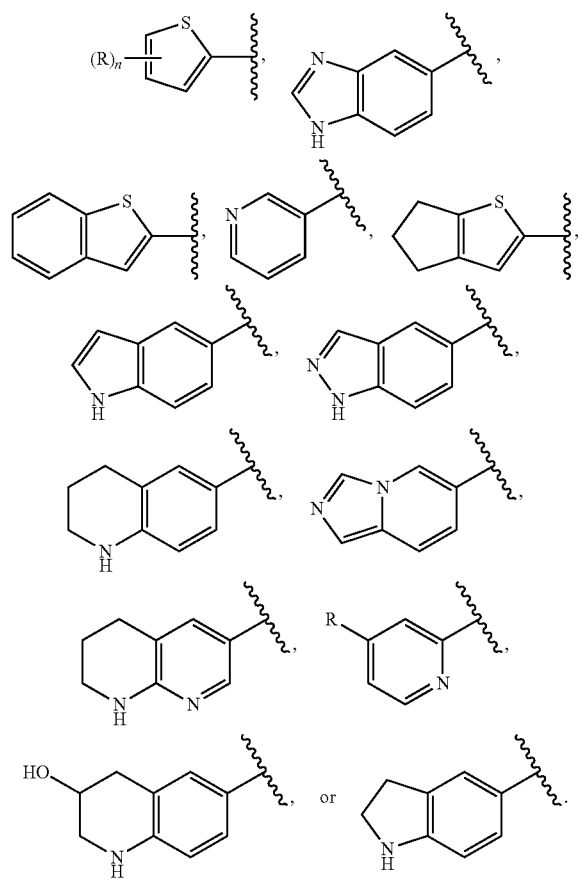

In some embodiments, both $R^3$ and $R^5$ are H.

In some embodiments, $R^4$ is hydrogen,

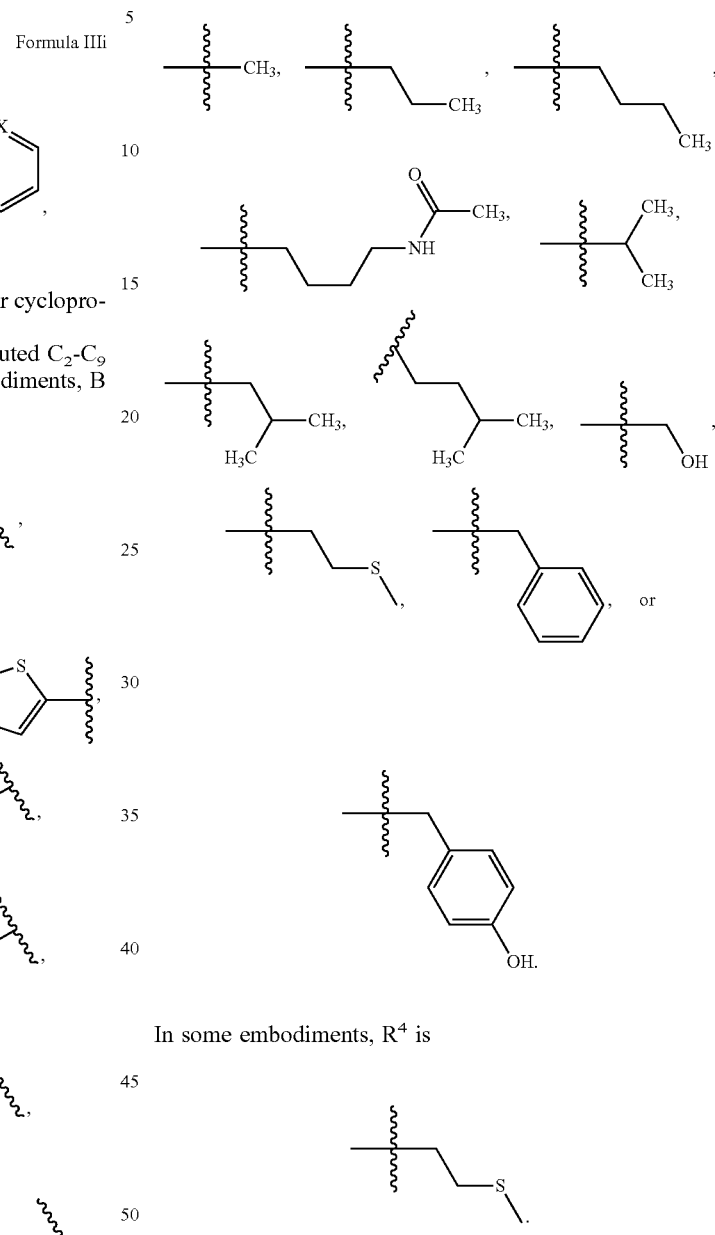

In some embodiments, $R^4$ is

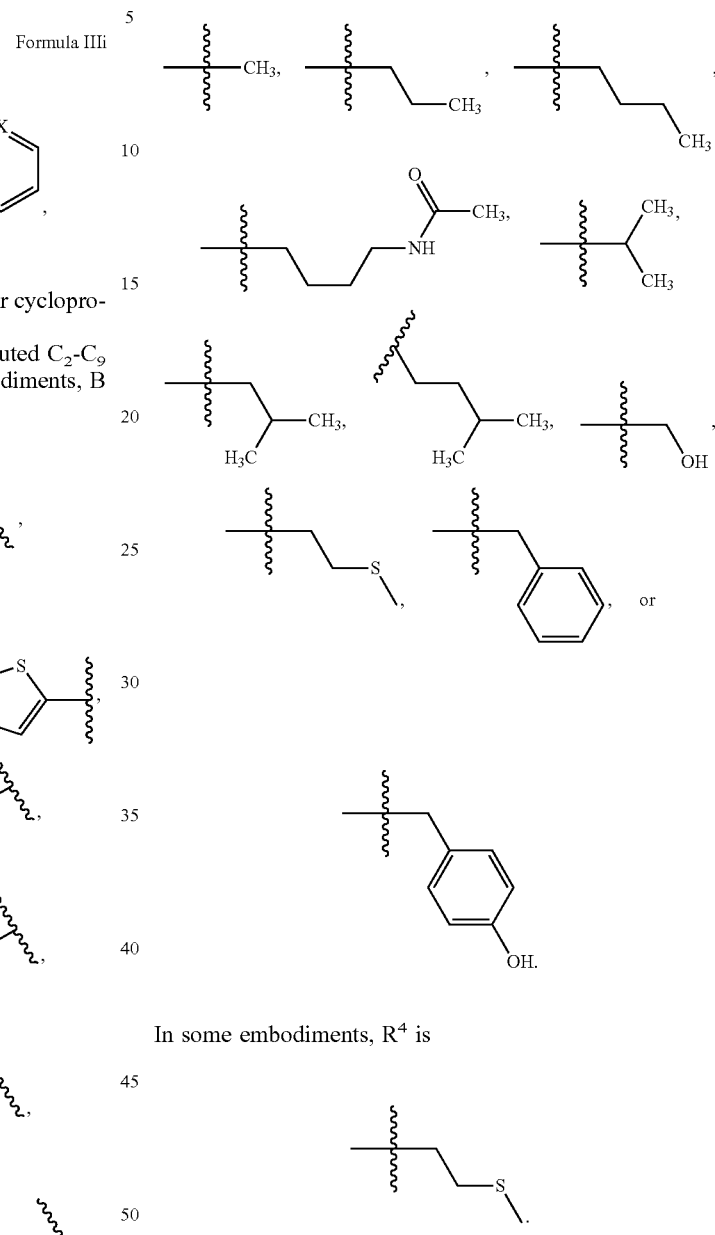

In some embodiments, $R^4$ is hydrogen.

In some embodiments, the compound is any one of compounds 1-40 or 88-105 in Table 1, or a pharmaceutically acceptable salt thereof.

TABLE 1

TABLE 1-continued

| | |
|---|---|
| (Structure: 3-methylsulfonyl-4-methylbenzoyl-(S)-methionine-N-(4-phenylthiazol-2-yl)amide) | 2 |
| (Structure: 3-methylsulfonylbenzoyl-(S)-methionine-N-(4-phenylthiazol-2-yl)amide) | 3 |
| (Structure: 3-(N,N-dimethylsulfamoyl)benzoyl-glycyl-N-[4-(3-(N-methylcarbamoyl)phenyl)thiazol-2-yl]amide) | 4 |
| (Structure: 3-(N,N-dimethylsulfamoyl)benzoyl-glycyl-N-[4-(3-(acetamidomethyl)phenyl)thiazol-2-yl]amide) | 5 |
| (Structure: 3-(isopropylsulfonyl)benzoyl-glycyl-N-(4-phenylthiazol-2-yl)amide) | 6 |
| (Structure: 3-(N,N-dimethylsulfamoyl)benzoyl-glycyl-N-[4-(3-bromophenyl)thiazol-2-yl]amide) | 7 |
| (Structure: 3-(N,N-dimethylsulfamoyl)benzoyl-glycyl-N-[4-(3-cyanophenyl)thiazol-2-yl]amide) | 8 |
| (Structure: 3-(N,N-dimethylsulfamoyl)benzoyl-glycyl-N-[4-(3-(methoxycarbonyl)phenyl)thiazol-2-yl]amide) | 9 |

TABLE 1-continued
| | |
|---|---|
| 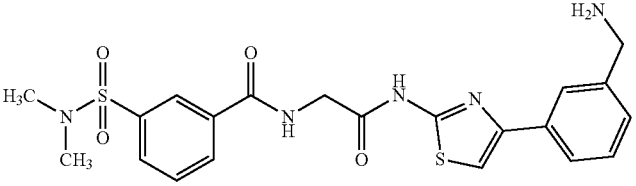 [SMILES: CN(C)S(=O)(=O)c1cccc(C(=O)NCC(=O)Nc2nc(-c3cccc(CN)c3)cs2)c1] | 10 |
| 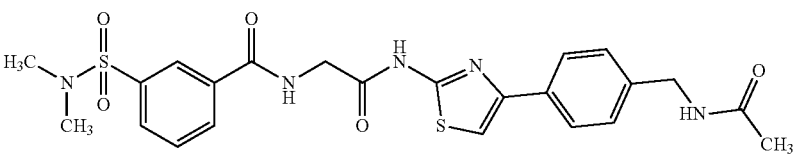 [SMILES: CC(=O)NCc1ccc(-c2csc(NC(=O)CNC(=O)c3cccc(S(=O)(=O)N(C)C)c3)n2)cc1] | 11 |
| 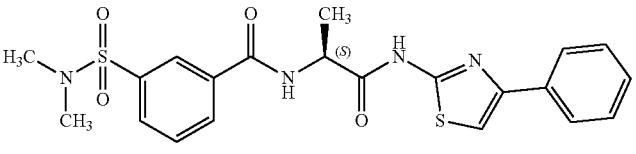 | 12 |
| 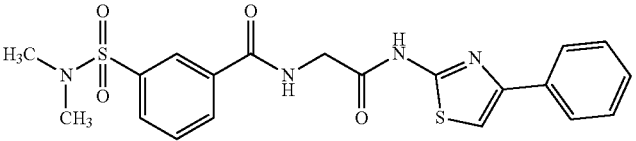 [SMILES: CN(C)S(=O)(=O)c1cccc(C(=O)NCC(=O)Nc2nc(-c3ccccc3)cs2)c1] | 13 |
| 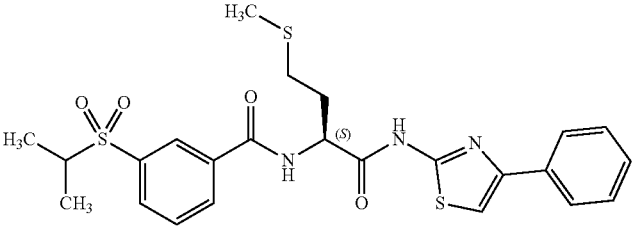 | 14 |
| 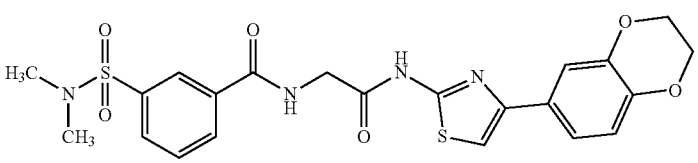 [SMILES: CN(C)S(=O)(=O)c1cccc(C(=O)NCC(=O)Nc2nc(-c3ccc4c(c3)OCCO4)cs2)c1] | 15 |
| 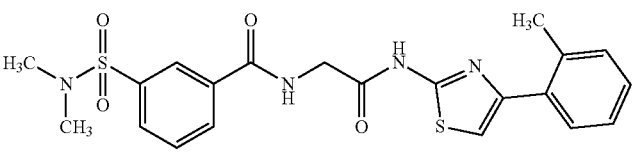 [SMILES: Cc1ccccc1-c1csc(NC(=O)CNC(=O)c2cccc(S(=O)(=O)N(C)C)c2)n1] | 16 |
| 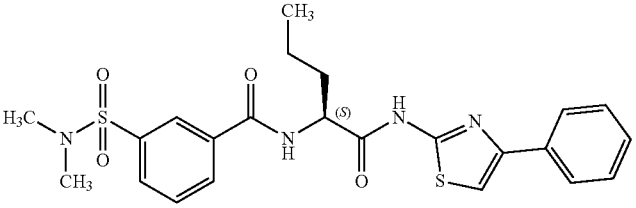 | 17 |
| 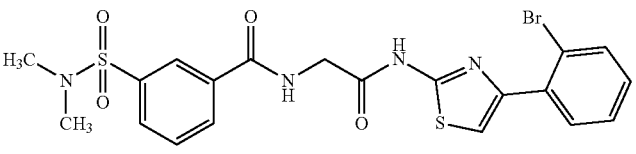 [SMILES: CN(C)S(=O)(=O)c1cccc(C(=O)NCC(=O)Nc2nc(-c3ccccc3Br)cs2)c1] | 18 |

TABLE 1-continued
| | |
|---|---|
| 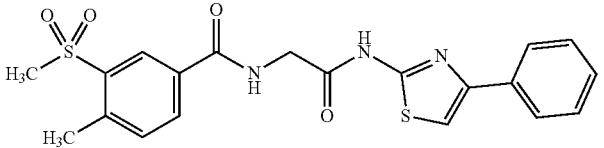 [SMILES: Cc1ccc(C(=O)NCC(=O)Nc2nc(-c3ccccc3)cs2)cc1S(C)(=O)=O] | 19 |
| 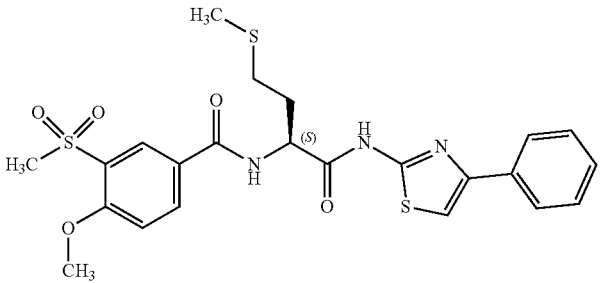 | 20 |
| 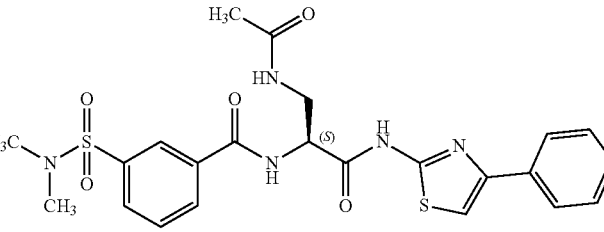 | 21 |
| 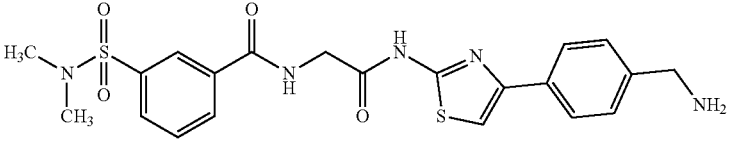 [SMILES: CN(C)S(=O)(=O)c1cccc(C(=O)NCC(=O)Nc2nc(-c3ccc(CN)cc3)cs2)c1] | 22 |
| 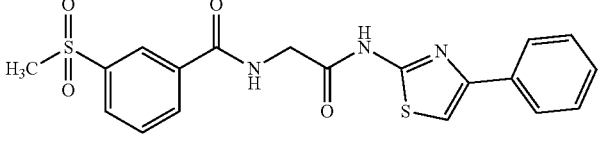 | 23 |
| 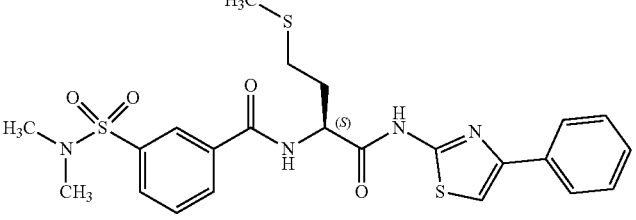 | 24 |
| 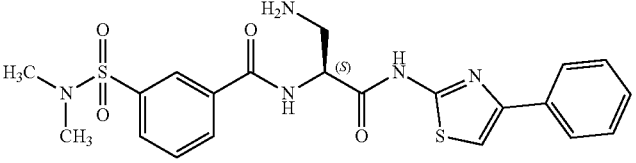 | 25 |
| 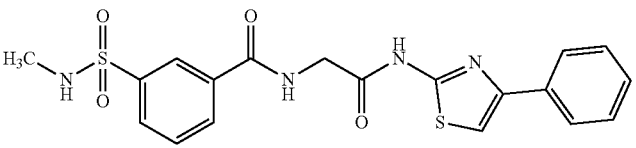 [SMILES: CNS(=O)(=O)c1cccc(C(=O)NCC(=O)Nc2nc(-c3ccccc3)cs2)c1] | 26 |

TABLE 1-continued

| Structure | # |
|---|---|
| (CH₃)₂NSO₂-C₆H₄-C(O)NH-CH₂-C(O)NH-thiazole-4-(2-cyanophenyl) | 27 |
| H₂NSO₂-C₆H₄-C(O)NH-CH₂-C(O)NH-thiazole-4-phenyl | 28 |
| (CH₃)₂NSO₂-C₆H₄-C(O)NH-CH₂-C(O)NH-thiazole-4-(2,6-dimethylphenyl) | 29 |
| (CH₃)₂NSO₂-C₆H₄-C(O)NH-CH₂-C(O)NH-(6-phenylpyridin-2-yl) | 30 |
| (CH₃)₂NSO₂-C₆H₄-C(O)NH-CH₂-C(O)NH-thiazole-4-(4-methylphenyl) | 31 |
| (CH₃)₂NSO₂-C₆H₄-C(O)NH-CH₂-C(O)NH-thiazole-4-(pyridin-2-yl) | 32 |
| (CH₃)₂NSO₂-C₆H₄-C(O)NH-CH₂-C(O)NH-thiazole-4-(3-carboxyphenyl) | 33 |
| (CH₃)₂NSO₂-C₆H₄-C(O)NH-CH₂-C(O)NH-thiazole-4-cyclohexyl | 34 |
| (CH₃)₂NSO₂-C₆H₄-C(O)NH-CH₂-C(O)NH-thiazole-4-isopropyl | 35 |

TABLE 1-continued
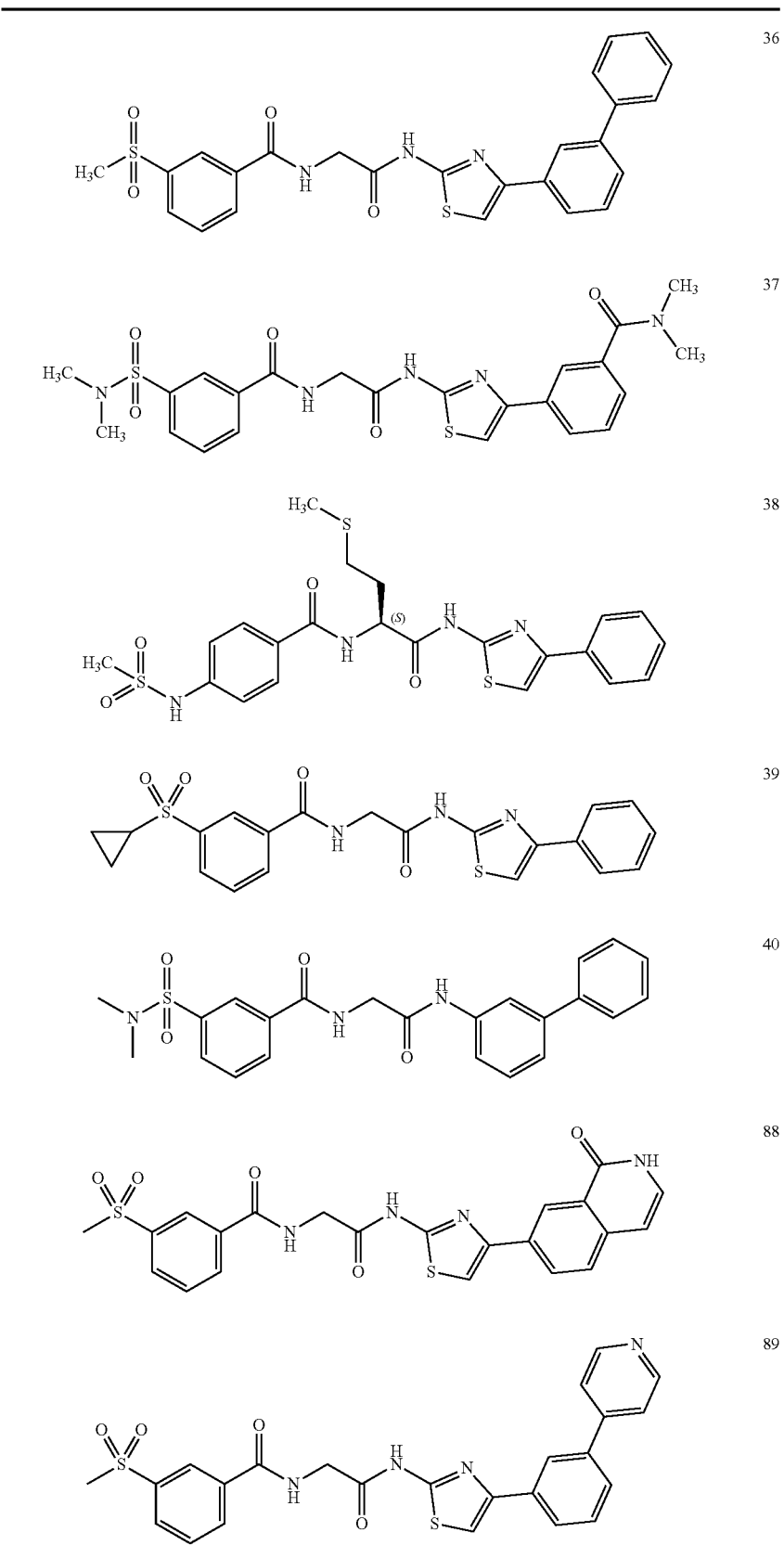

TABLE 1-continued
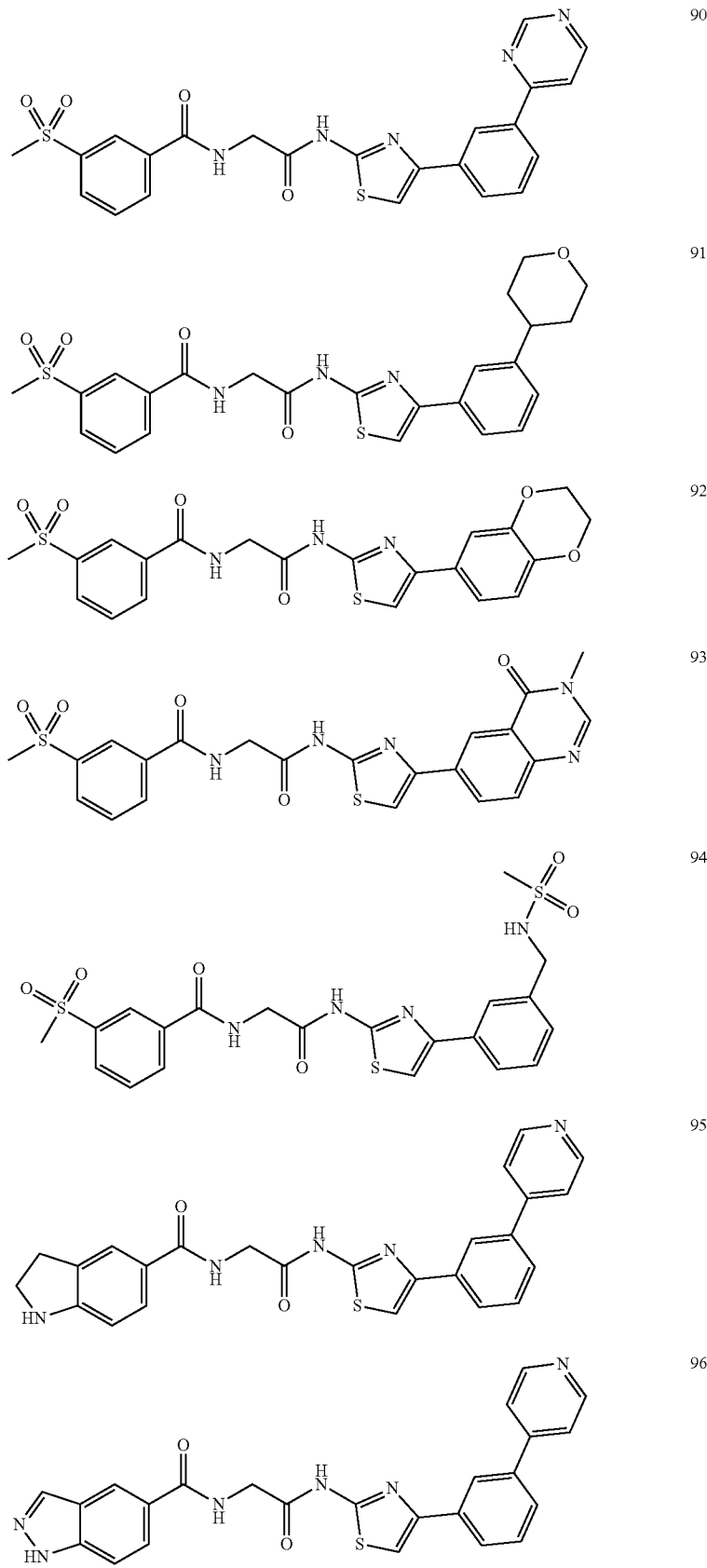

TABLE 1-continued
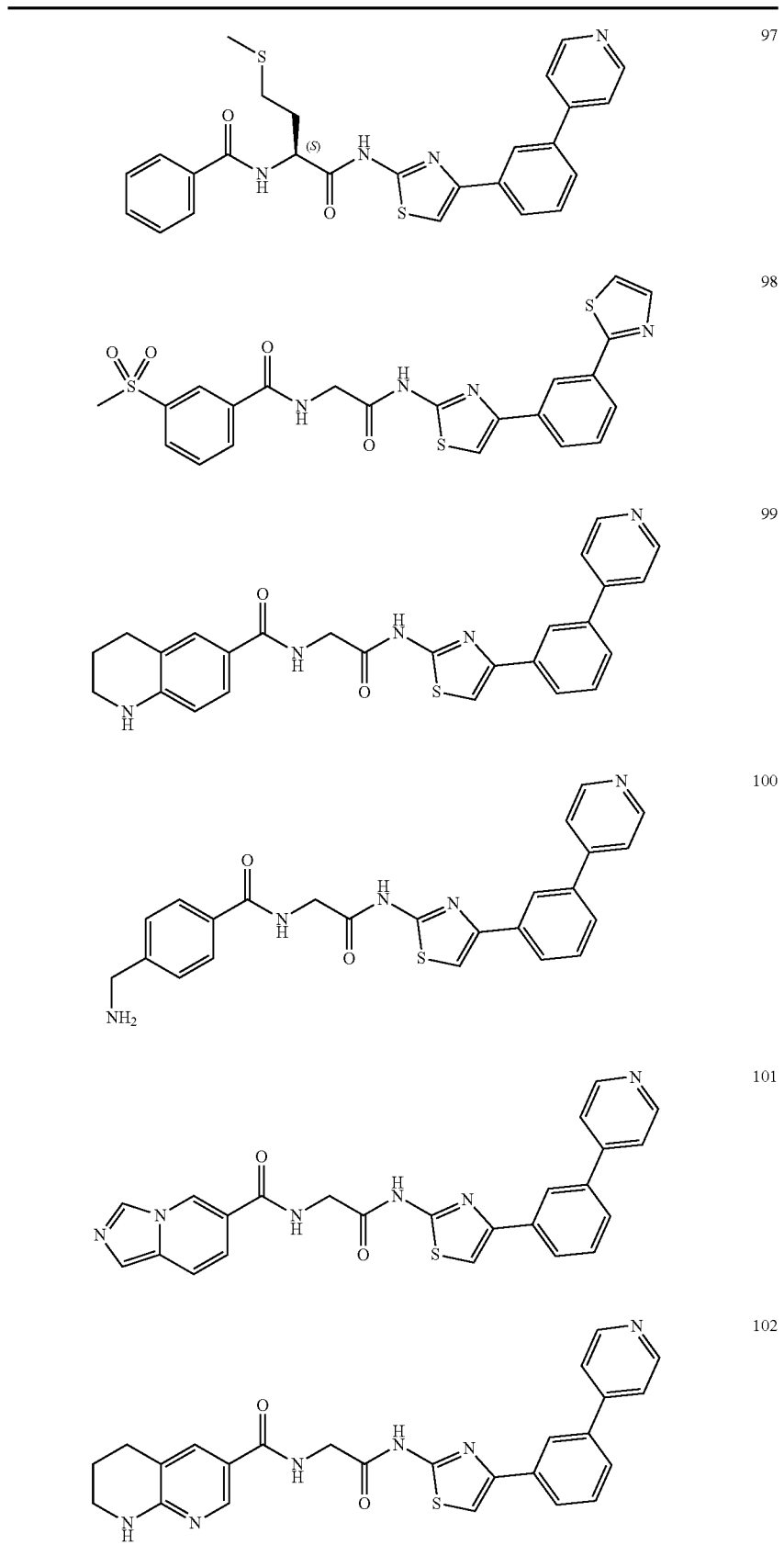

TABLE 1-continued

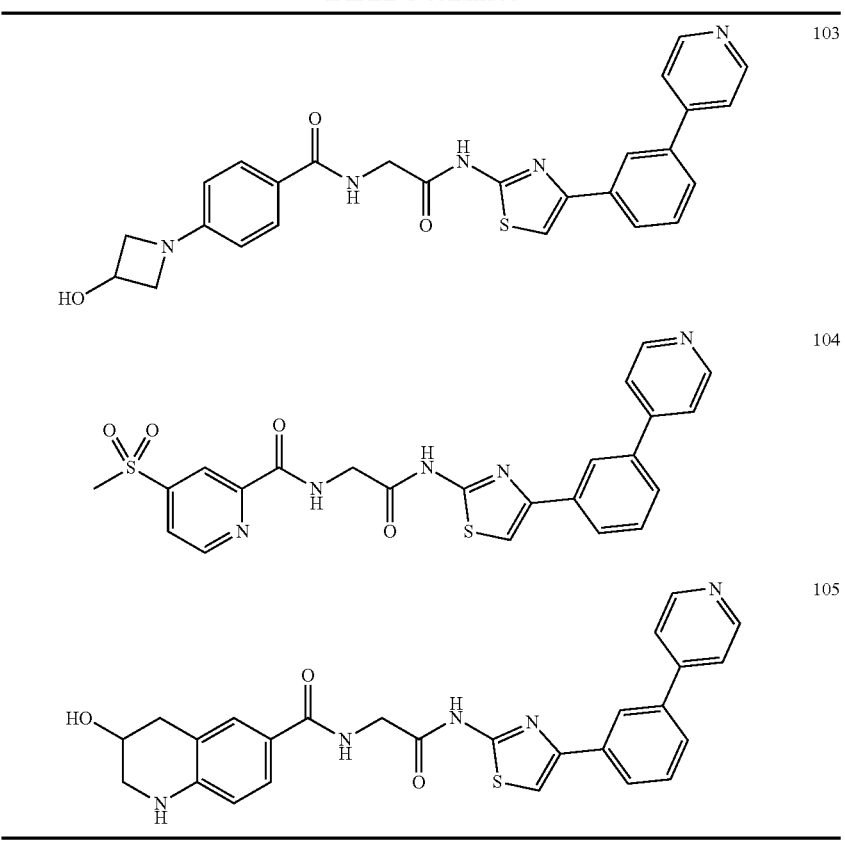

In another aspect, the invention features a compound having the structure of Formula IV:

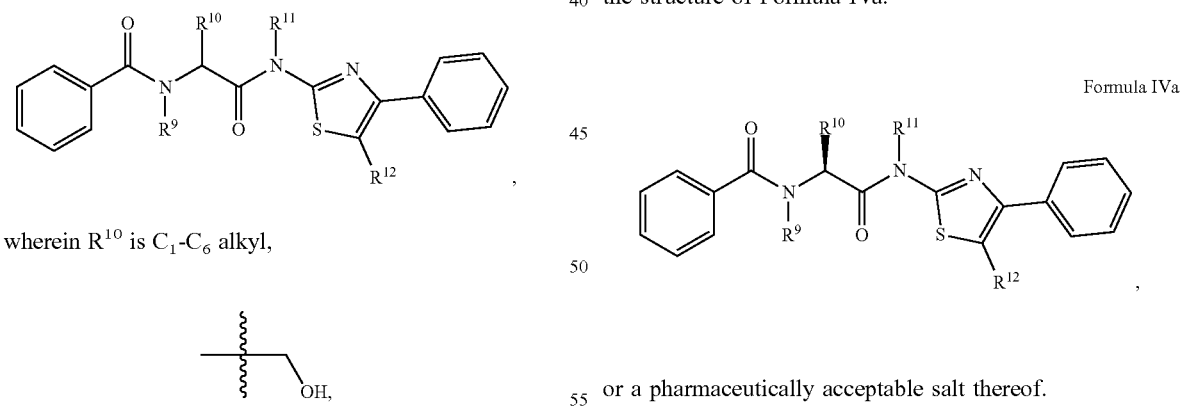

wherein $R^{10}$ is $C_1$-$C_6$ alkyl, optionally substituted $C_1$-$C_6$ aminoalkyl, optionally substituted $C_1$-$C_4$ alkyl $C_6$-$C_{10}$ aryl, optionally substituted $C_3$-$C_{10}$ carbocyclyl, optionally substituted $C_2$-$C_9$ heterocyclyl, or optionally substituted $C_2$-$C_9$ heteroaryl;

each $R^9$ and $R^{11}$ is, independently, selected from the group consisting of H, optionally substituted $C_1$-$C_6$ alkyl, or optionally substituted $C_1$-$C_6$ heteroalkyl; and $R^{12}$ is H, $C_2$-$C_6$ alkyl, optionally substituted $C_3$-$C_{10}$ carbocyclyl, optionally substituted $C_2$-$C_9$ heterocyclyl, optionally substituted $C_6$-$C_{10}$ aryl, optionally substituted $C_2$-$C_9$ heteroaryl, hydroxy, thiol, optionally substituted $C_1$-$C_6$ alkoxy, optionally substituted $C_1$-$C_6$ thioalkoxy, or optionally substituted amino, or a pharmaceutically acceptable salt thereof.

In some embodiments, the compound of Formula IV has the structure of Formula IVa:

Formula IVa or a pharmaceutically acceptable salt thereof.

In some embodiments, both $R^9$ and $R^{11}$ are H. In some embodiments, $R^{10}$ is

H,

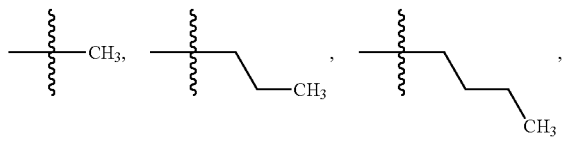

-continued
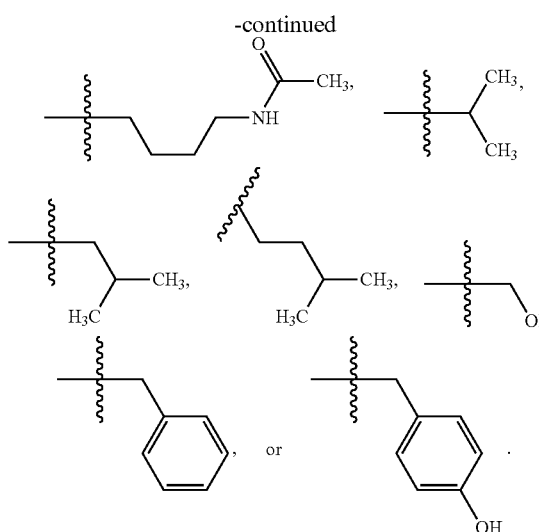
In some embodiments, the compound is any one of compounds 41-51 in Table 2 or a pharmaceutically acceptable salt thereof.
TABLE 2
| | |
|---|---|
| 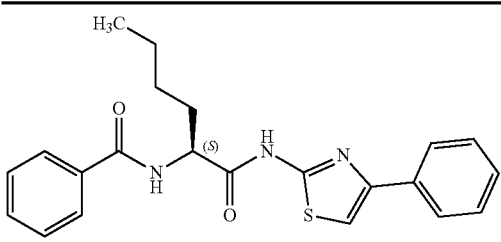 | 41 |
| 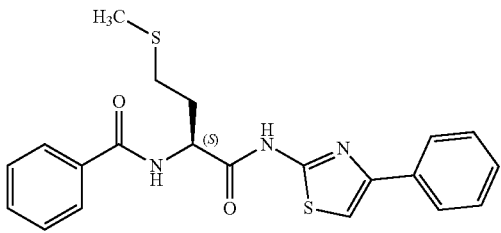 | 42 |
| 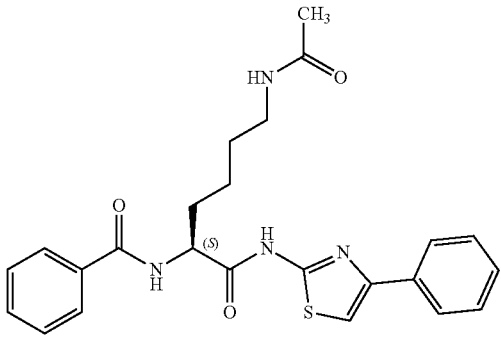 | 43 |
| 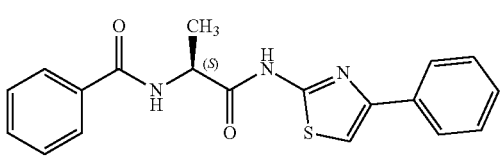 | 44 |
TABLE 2-continued
| | |
|---|---|
| 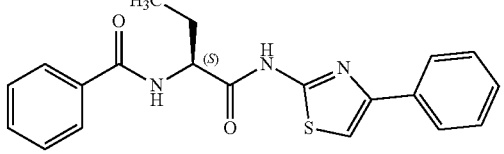 | 45 |
| 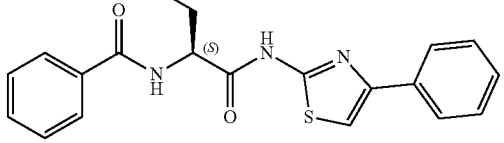 | 46 |
| 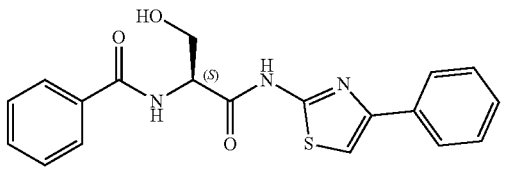 | 47 |
| 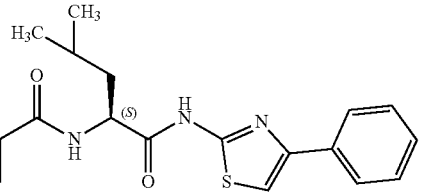 | 48 |
| 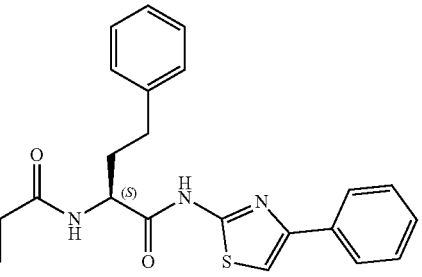 | 49 |
| 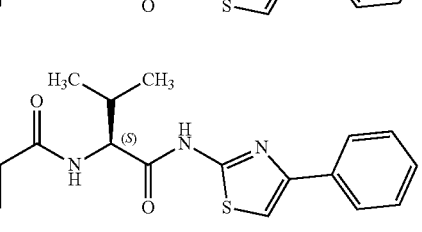 | 50 |
| 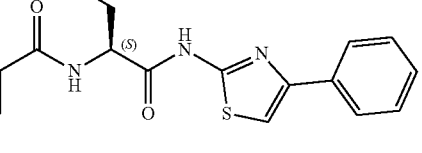 | 51 |

In another aspect, the invention features a compound having the structure of Formula V,

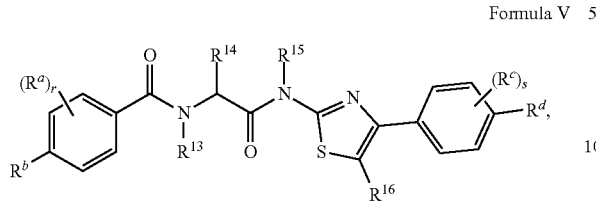

Formula V wherein $R^{14}$ is hydrogen, optionally substituted $C_1$-$C_6$ alkyl, optionally substituted $C_1$-$C_6$ heteroalkyl, optionally substituted $C_3$-$C_{10}$ carbocyclyl, optionally substituted $C_2$-$C_9$ heterocyclyl, optionally substituted $C_6$-$C_{10}$ aryl, or optionally substituted $C_2$-$C_9$ heteroaryl;

each $R^{13}$ and $R^{15}$ is, independently, selected from the group consisting of H, optionally substituted $C_1$-$C_6$ alkyl, or optionally substituted $C_1$-$C_6$ heteroalkyl;

$R^{16}$ is H or $C_1$-$C_6$ alkyl;

r is 0, 1, 2, 3, or 4;

$R^b$ is H, $C_1$-$C_6$ perfluoroalkyl, $C_2$-$C_6$ alkyl, optionally substituted $C_3$-$C_{10}$ carbocyclyl, optionally substituted $C_2$-$C_9$ heterocyclyl, optionally substituted $C_2$-$C_9$ heteroaryl, optionally substituted $C_2$-$C_6$ alkenyl, optionally substituted $C_2$-$C_6$ heteroalkenyl, optionally substituted acyl, hydroxy, thiol, nitrile, optionally substituted $C_1$-$C_6$ thioalkoxy, optionally substituted sulfone, optionally substituted sulfonamide, optionally substituted $C_1$-$C_6$ alkylamine, or optionally substituted amino;

each $R^a$ is, independently, $C_2$-$C_6$ alkyl, optionally substituted $C_1$-$C_6$ hydroxyalkyl, optionally substituted $C_1$-$C_6$ aminoalkyl, optionally substituted $C_3$-$C_{10}$ carbocyclyl, optionally substituted $C_2$-$C_9$ heterocyclyl, optionally substituted $C_6$-$C_{10}$ aryl, optionally substituted $C_2$-$C_9$ heteroaryl, optionally substituted $C_2$-$C_6$ alkenyl, optionally substituted $C_2$-$C_6$ heteroalkenyl, optionally substituted acyl, hydroxy, thiol, optionally substituted thioalkoxy, or optionally substituted amino;

s is 0, 1, 2, 3, or 4;

$R^d$ is H, optionally substituted $C_3$-$C_{10}$ carbocyclyl, optionally substituted $C_2$-$C_9$ heteroaryl, optionally substituted $C_2$-$C_6$ alkenyl, optionally substituted $C_2$-$C_6$ heteroalkenyl, optionally substituted acyl, hydroxy, thiol, or optionally substituted $C_1$-$C_6$ thioalkoxy, or $R^d$ and $R^c$ combine with the carbons to which they are attached to form a 5- or 6-membered heterocycle;

each $R^c$ is, independently, $C_2$-$C_6$ alkyl, optionally substituted $C_3$-$C_{10}$ carbocyclyl, optionally substituted $C_2$-$C_9$ heterocyclyl, optionally substituted $C_6$-$C_{10}$ aryl, optionally substituted $C_2$-$C_9$ heteroaryl, optionally substituted $C_2$-$C_6$ alkenyl, optionally substituted $C_2$-$C_6$ heteroalkenyl, optionally substituted acyl, hydroxy, thiol, optionally substituted $C_1$-$C_6$ thioalkoxy, or optionally substituted amino, or $R^d$ and $R^c$ combine with the carbons to which they are attached to form a 5- or 6-membered heterocycle;

if r is 0 then $R^{14}$ is hydrogen, optionally substituted $C_1$-$C_6$ heteroalkyl, optionally substituted $C_3$-$C_{10}$ carbocyclyl, optionally substituted $C_2$-$C_9$ heterocyclyl, optionally substituted $C_6$-$C_{10}$ aryl, or optionally substituted $C_2$-$C_9$ heteroaryl;

if $R^b$ is H, $R^d$ is H, and s is 0, then r is 1, 2, 3, or 4; and if $R^b$ is H, $R^d$ is H, and r is 0, then s is 1, 2, 3, or 4, or a pharmaceutically acceptable salt thereof.

In some embodiments, the compound of Formula V has the structure of Formula Va:

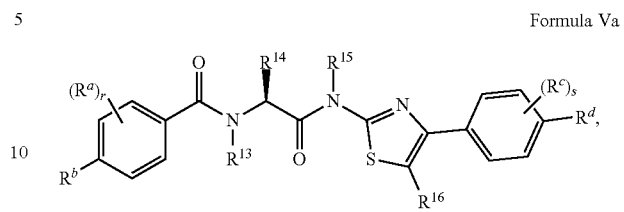

Formula Va or a pharmaceutically acceptable salt thereof.

In some embodiments, $R^{16}$ is H.

In some embodiments, the compound of Formula V has the structure of Formula Vb:

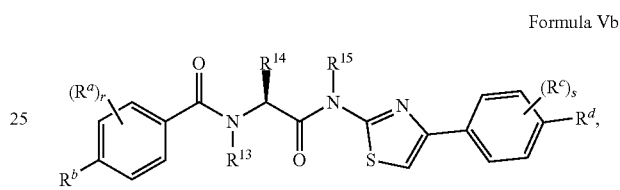

Formula Vb or a pharmaceutically acceptable salt thereof.

In some embodiments, $R^d$ is H and s is 0.

In some embodiments, the compound of Formula V has the structure of Formula Vc:

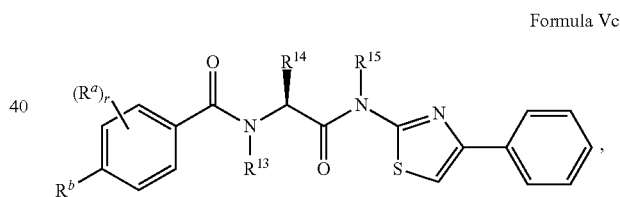

Formula Vc or a pharmaceutically acceptable salt thereof.

In some embodiments, $R^b$ is H. In some embodiments, r is 1.

In some embodiments the compound of Formula V has the structure of Formula Vd:

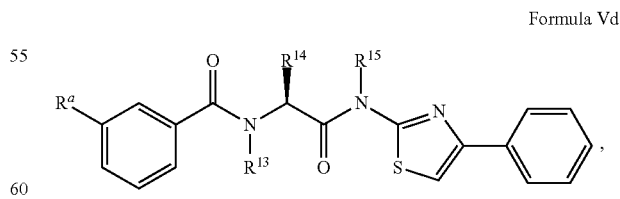

Formula Vd or a pharmaceutically acceptable salt thereof.

In some embodiments, $R^a$ is optionally substituted $C_1$-$C_6$ hydroxyalkyl, optionally substituted $C_1$-$C_6$ aminoalkyl, or optionally substituted acyl. In some embodiments, $R^a$ is —OH, —NH$_2$, —CH$_3$, —CF$_3$, —CH$_2$OH, —CH$_2$NH$_2$,

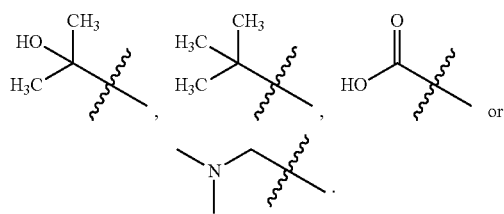

In some embodiments, $R^b$ is $C_2$-$C_6$ alkyl (e.g., methyl), optionally substituted sulfone (e.g., —$SO_2CH_3$), optionally substituted $C_1$-$C_6$ alkylamine (e.g., —$CH_2NH_2$, —$CH_2N(CH_3)_2$, or —$CH_2NHC(O)CH_3$), optionally substituted amino (e.g., —$NH_2$, —$NHCH_3$, or —$NHSO_2CH_3$), or optionally substituted acyl (e.g., —$C(O)NHCH_3$). In some embodiments, $R^b$ is —OH, —$CH_3$, —$OCH_3$, —$CF_3$, or —$CH_2OH$.

In some embodiments, the compound is any one of compounds 52-87 in Table 3 or a pharmaceutically acceptable salt thereof.

TABLE 3

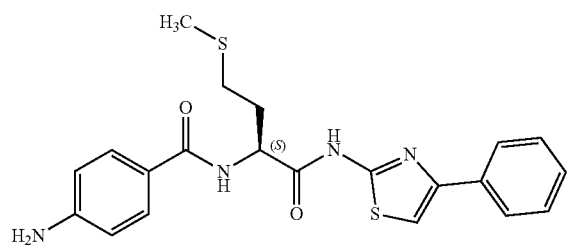

52

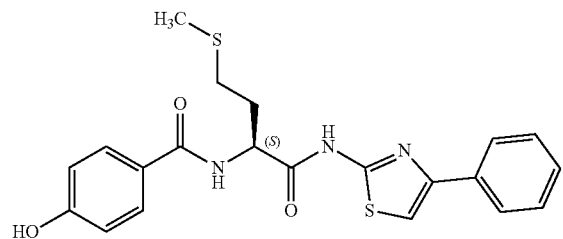

53

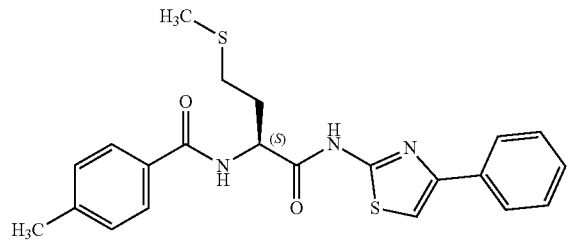

54

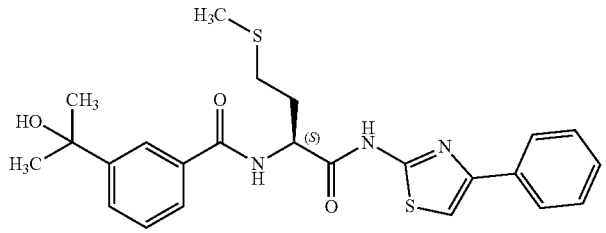

55

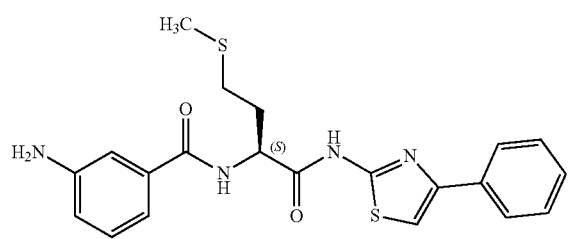

56

TABLE 3-continued
| | |
|---|---|
| 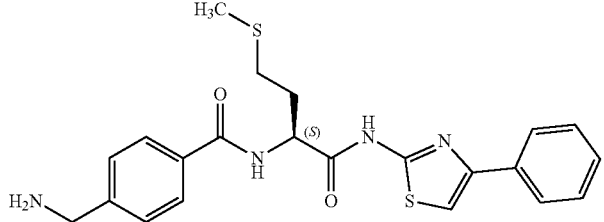 | 57 |
| 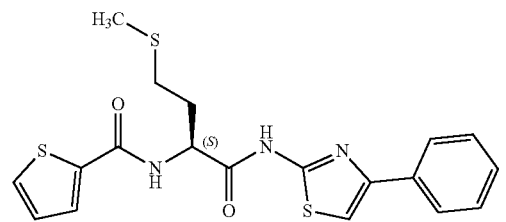 | 58 |
| 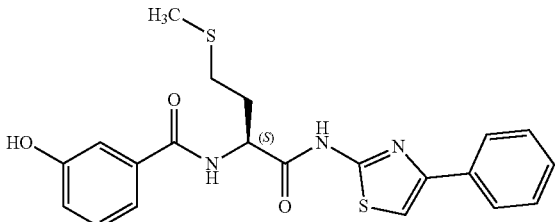 | 59 |
| 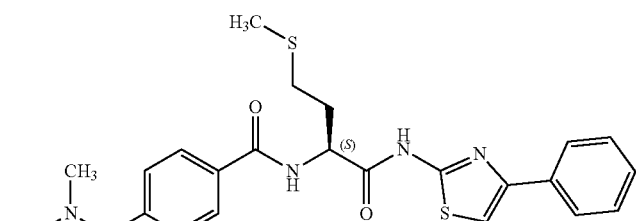 | 60 |
| 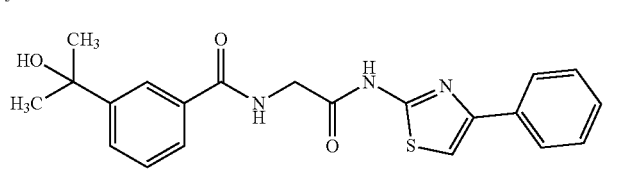 | 61 |
| 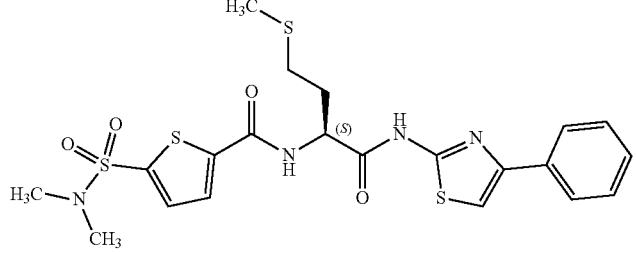 | 62 |
| 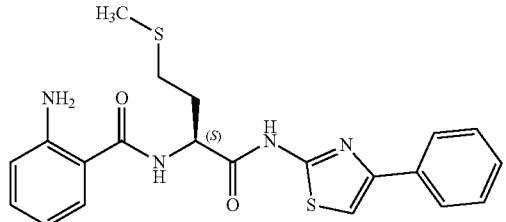 | 63 |

TABLE 3-continued
| | |
|---|---|
| 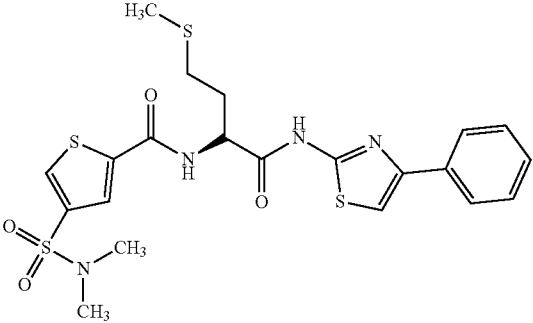 | 64 |
| 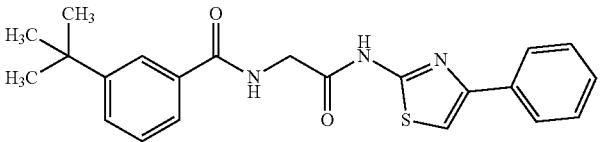 [SMILES: CC(C)(C)c1cccc(C(=O)NCC(=O)Nc2nc(-c3ccccc3)cs2)c1] | 65 |
| 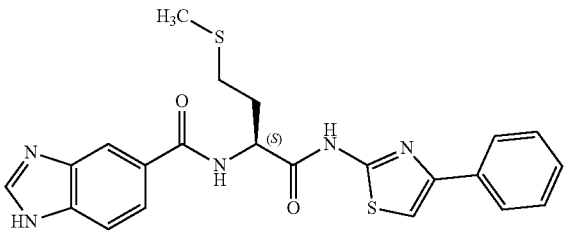 | 66 |
| 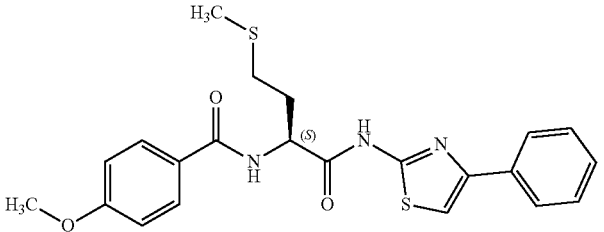 | 67 |
| 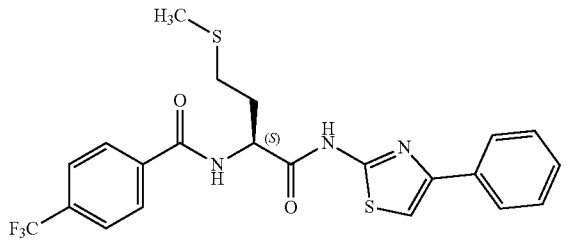 | 68 |
| 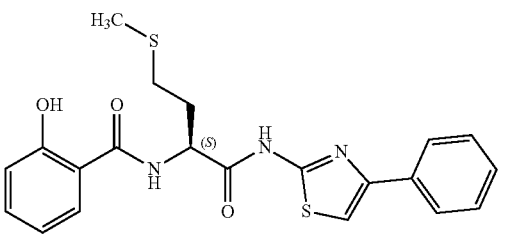 | 69 |

TABLE 3-continued
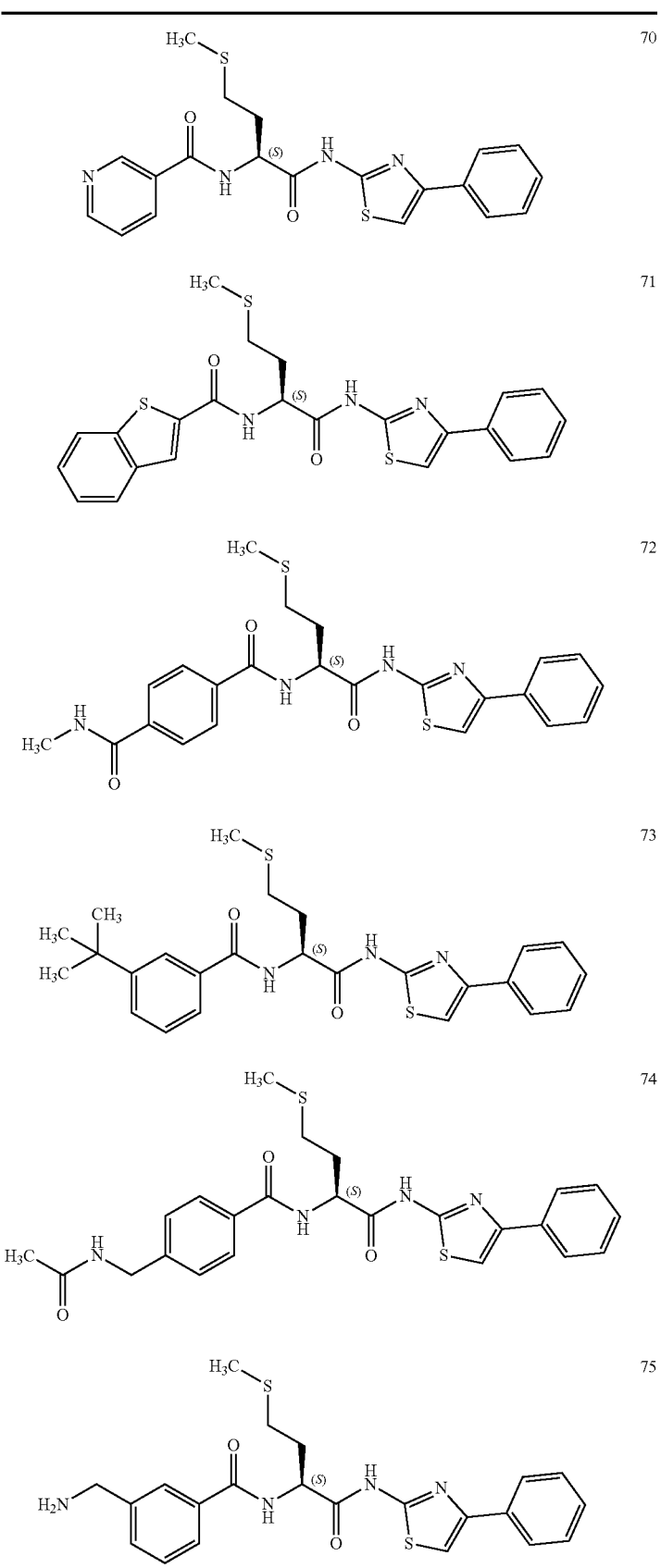

TABLE 3-continued
| | |
|---|---|
| 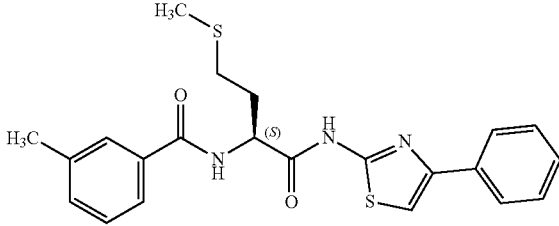 | 76 |
| 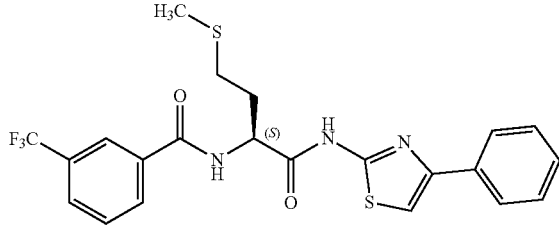 | 77 |
| 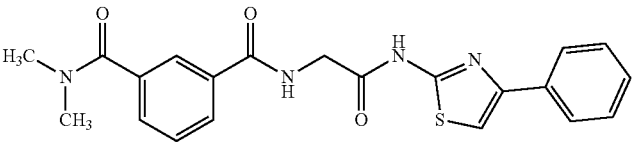 [SMILES: CN(C)C(=O)c1cccc(C(=O)NCC(=O)Nc2nc(-c3ccccc3)cs2)c1] | 78 |
| 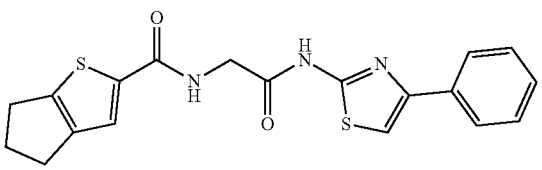 [SMILES: O=C(CNC(=O)c1cc2c(s1)CCC2)Nc1nc(-c2ccccc2)cs1] | 79 |
| 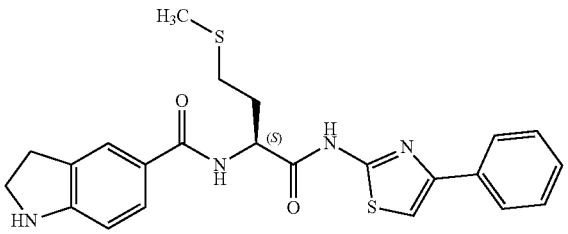 | 80 |
| 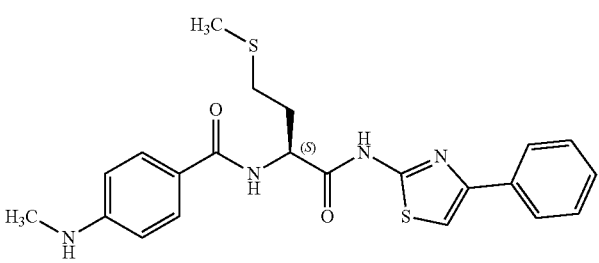 | 81 |
| 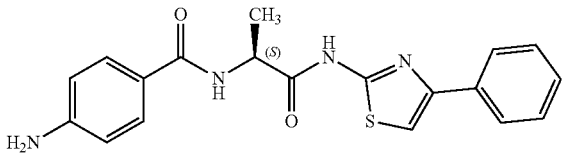 | 82 |

TABLE 3-continued

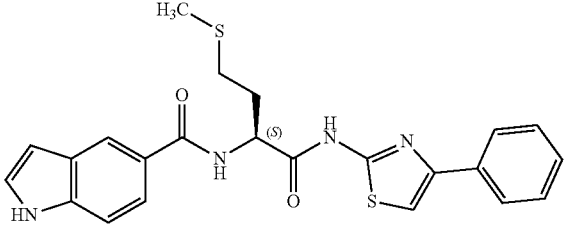
83

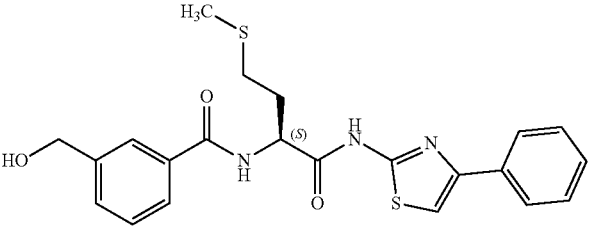
84

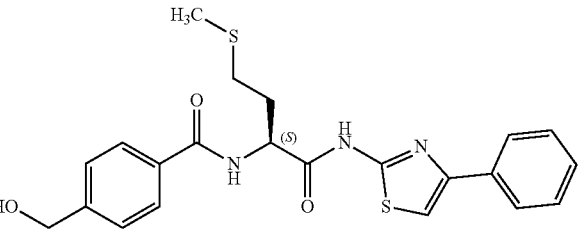
85

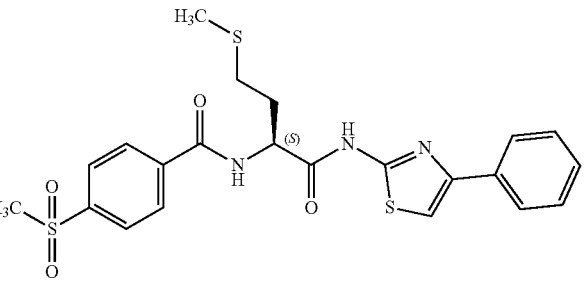
86

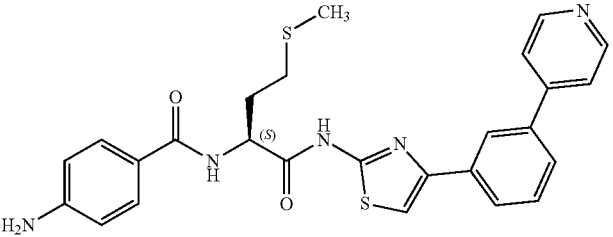
87

In another aspect, the invention features a compound of Formula VI having the structure:

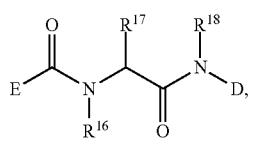

Formula VI wherein each $R^{16}$ and $R^{18}$ is, independently, selected from the group consisting of H, optionally substituted $C_1$-$C_6$ alkyl, or optionally substituted $C_1$-$C_6$ heteroalkyl;

$R^{17}$ is optionally substituted $C_1$-$C_6$ alkyl, optionally substituted $C_1$-$C_6$ heteroalkyl, optionally substituted $C_3$-$C_{10}$ carbocyclyl, optionally substituted $C_2$-$C_9$ heterocyclyl, optionally substituted $C_6$-$C_{10}$ aryl, or optionally substituted $C_2$-$C_9$ heteroaryl;

D is

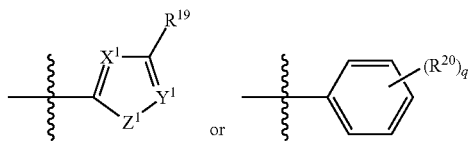

wherein $X^1$ is N or $CR^{X1}$, wherein $R^{X1}$ is H or optionally substituted $C_1$-$C_6$ alkyl;

$Y^1$ is N or $CR^{Y1}$, wherein $R^{Y1}$ is H, optionally substituted $C_1$-$C_6$ alkyl, optionally substituted $C_1$-$C_6$ heteroalkyl, optionally substituted $C_3$-$C_{10}$ carbocyclyl, optionally substituted $C_2$-$C_9$ heterocyclyl, optionally substituted $C_6$-$C_{10}$ aryl, optionally substituted $C_2$-$C_9$ heteroaryl, optionally substituted $C_2$-$C_6$ alkenyl, optionally substituted $C_2$-$C_6$ heteroalkenyl;

Z is S, O, $C(R^{Z1a})_2$, or $NR^{Z1b}$, wherein $R^{Z1a}$ is H, optionally substituted $C_1$-$C_6$ alkyl, optionally substituted $C_1$-$C_6$ heteroalkyl, optionally substituted $C_3$-$C_{10}$ carbocyclyl, optionally substituted $C_2$-$C_9$ heterocyclyl, optionally substituted $C_6$-$C_{10}$ aryl, optionally substituted $C_2$-$C_9$ heteroaryl, optionally substituted $C_2$-$C_6$ alkenyl, optionally substituted $C_2$-$C_6$ heteroalkenyl and $R^{Z1b}$ is H, optionally substituted $C_1$-$C_6$ alkyl, or optionally substituted $C_1$-$C_6$ heteroalkyl;

q is 0, 1, 2, 3, 4, or 5;

each $R^{19}$ is H, halo, optionally substituted $C_1$-$C_6$ alkyl, optionally substituted $C_1$-$C_6$ heteroalkyl, optionally substituted $C_3$-$C_{10}$ carbocyclyl, optionally substituted $C_2$-$C_9$ heterocyclyl, optionally substituted $C_6$-$C_{10}$ aryl, optionally substituted $C_2$-$C_9$ heteroaryl, optionally substituted $C_2$-$C_6$ alkenyl, optionally substituted $C_2$-$C_6$ heteroalkenyl, or optionally substituted amino;

each $R^{20}$ is, independently, halo, optionally substituted $C_1$-$C_6$ alkyl, optionally substituted $C_1$-$C_6$ heteroalkyl, optionally substituted $C_3$-$C_{10}$ carbocyclyl, optionally substituted $C_2$-$C_9$ heterocyclyl, optionally substituted $C_6$-$C_{10}$ aryl, optionally substituted $C_2$-$C_9$ heteroaryl, hydroxy, thiol, optionally substituted sulfone, optionally substituted sulfonamide, or optionally substituted amino; and E is

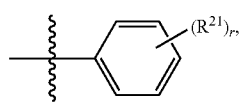

optionally substituted $C_2$-$C_9$ heteroaryl, or optionally substituted $C_2$-$C_9$ heterocyclyl, wherein r is 0, 1, 2, 3, 4, or 5; and each $R^{21}$ is independently halo, optionally substituted $C_1$-$C_6$ alkyl, optionally substituted $C_6$-$C_{10}$ aryl, optionally substituted $C_2$-$C_9$ heteroaryl, hydroxy, thiol, optionally substituted sulfone, optionally substituted sulfonamide, or optionally substituted amino, or a pharmaceutically acceptable salt thereof.

In another aspect, the invention features a compound having the structure of Formula VII:

Formula VII

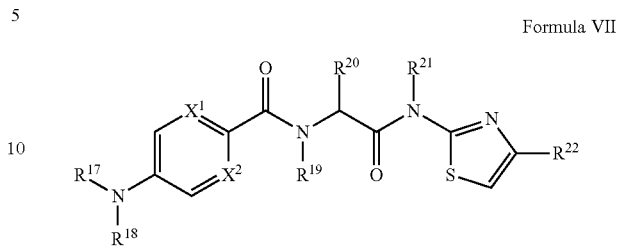

wherein $R^{17}$, $R^{18}$, $R^{19}$, and $R^{21}$ are, independently, H or optionally substituted $C_1$-$C_6$ alkyl;

$R^{20}$ is hydrogen, optionally substituted $C_1$-$C_6$ alkyl, or optionally substituted $C_1$-$C_6$ heteroalkyl;

$R^{22}$ is optionally substituted $C_6$-$C_{10}$ aryl, optionally substituted $C_2$-$C_9$ heterocyclyl, or optionally substituted $C_2$-$C_9$ heteroaryl; and $X^1$ and $X^2$ are, independently, N or CH, or a pharmaceutically acceptable salt thereof.

In some embodiments, $R^{19}$ is hydrogen. In some embodiments, $R^{21}$ is hydrogen.

In some embodiments, $X^1$ is N. In some embodiments, $X^1$ is CH. In some embodiments, $X^2$ is N.

In some embodiments, $X^2$ is CH.

In some embodiments, $R^{17}$ is hydrogen. In some embodiments, $R^{17}$ is optionally substituted $C_1$-$C_6$ alkyl (e.g., methyl).

In some embodiments, $R^{18}$ is optionally substituted $C_1$-$C_6$ alkyl (e.g., methyl).

In some embodiments, $R^{20}$ is hydrogen. In some embodiments, $R^{20}$ is optionally substituted $C_1$-$C_6$ heteroalkyl (e.g., $\begin{array}{c} \xi\text{-}CH_2CH_2\text{-}S\text{-}CH_3 \end{array}$, $\xi\text{-}CH_2\text{-}OH$, $\xi\text{-}CH_2CH_2\text{-}O\text{-}CH_3$, or $\xi\text{-}CH_2CH_2\text{-}N(CH_3)_2$).

In some embodiments, $R^{20}$ is optionally substituted $C_1$-$C_6$ alkyl (e.g., methyl).

In some embodiments, $R^{22}$ is optionally substituted $C_2$-$C_9$ heterocyclyl (e.g.,

)

wherein the dotted line represents an optional double bond; and R²³ is optionally substituted C₁-C₆ acyl or C₂-C₉ heteroaryl). In some embodiments, R²² is

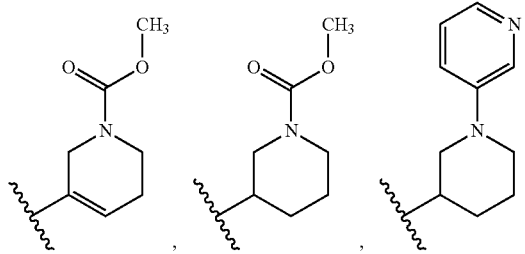

In some embodiments, R²² is optionally substituted C₂-C₉ heteroaryl (e.g., optionally substituted C₂-C₉ bicyclic heteroaryl such as

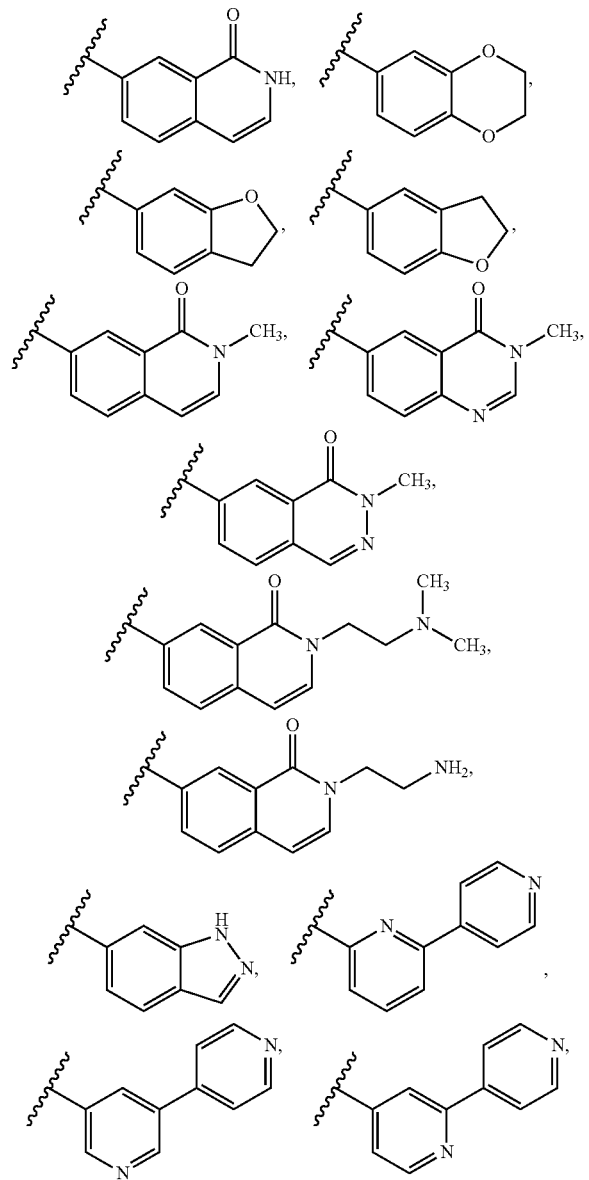

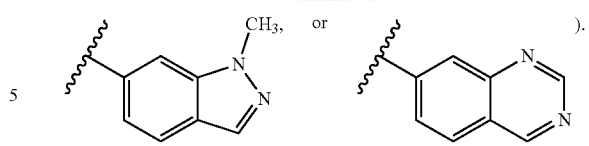

In some embodiments, R²² is optionally substituted C₆-C₁₀ aryl

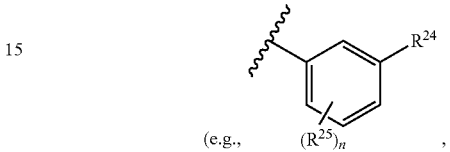

wherein n is 0, 1, 2, 3, or 4; R²⁴ is hydrogen, optionally substituted C₁-C₆ alkyl, optionally substituted C₁-C₆ heteroalkyl, optionally substituted C₃-C₈ carbocyclyl, optionally substituted C₆-C₁₀ aryl, optionally substituted C₂-C₉ heterocyclyl, optionally substituted C₂-C₉ heteroaryl; and R²⁵ is cyano, hydroxy, optionally substituted C₁-C₆ heteroalkyl, wherein if n is 0, then R²⁴ is optionally substituted C₁-C₆ alkyl, optionally substituted C₁-C₆ heteroalkyl, optionally substituted C₃-C₈ carbocyclyl, optionally substituted C₆-C₁₀ aryl, optionally substituted C₂-C₉ heterocyclyl, optionally substituted C₂-C₉ heteroaryl).

In some embodiments, n is 1. In some embodiments, at least one R²⁵ is cyano. In some embodiments, at least one R²⁵ is hydroxy. In some embodiments, at least one R²⁵ is optionally substituted C₁-C₆ heteroalkyl (i.e., methoxy or

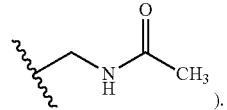 [SMILES: *CNC(C)=O]

).

In some embodiments, n is 0. In some embodiments, R²⁴ is hydrogen. In some embodiments, R²⁴ is optionally substituted C₁-C₆ heteroalkyl

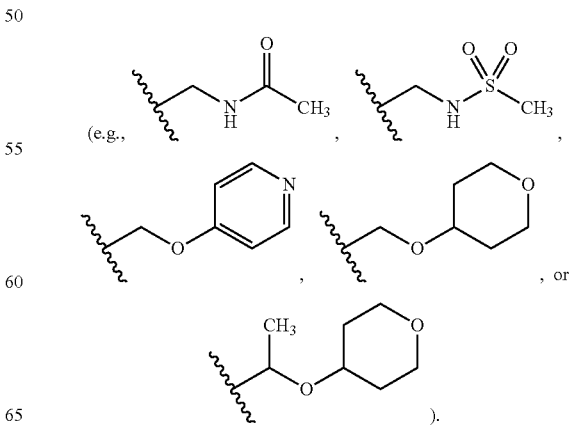

In some embodiments, $R^{24}$ is optionally substituted $C_1$-$C_6$ alkyl
(e.g., 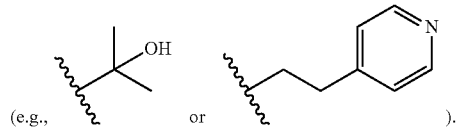 or ).
In some embodiments, $R^{24}$ is optionally substituted $C_3$-$C_8$ carbocyclyl
(e.g., 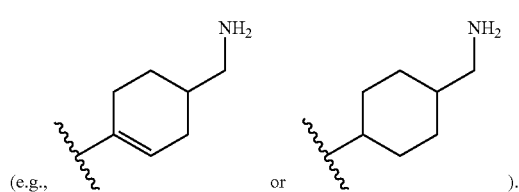 [SMILES: *C1=CCC(CN)CC1 ; *C1CCC(CN)CC1] or ).
In some embodiments, $R^{24}$ is optionally substituted $C_6$-$C_{10}$ aryl (e.g., phenyl, 4-aminomethyl-phenyl,
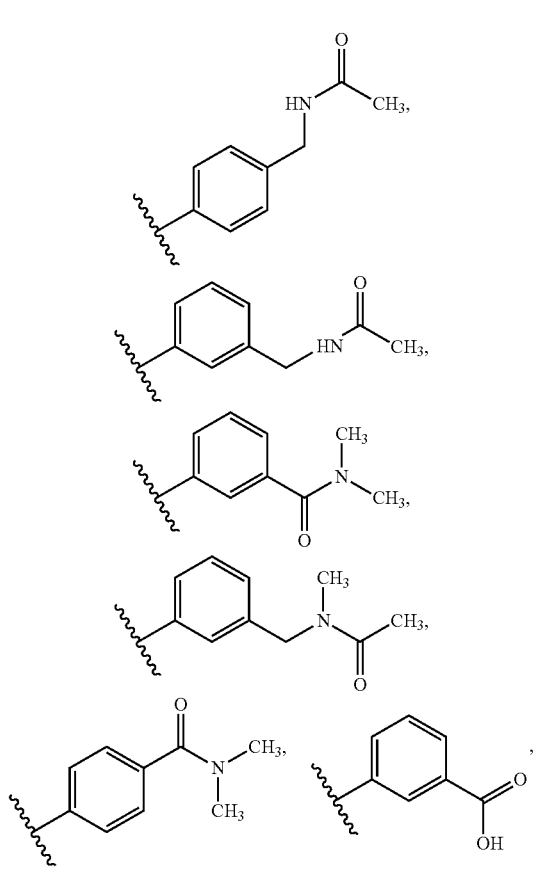
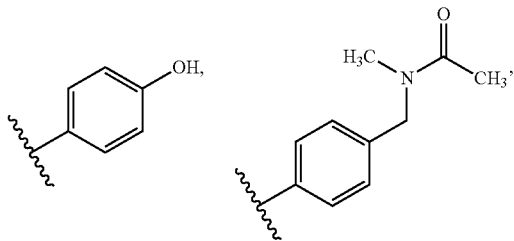
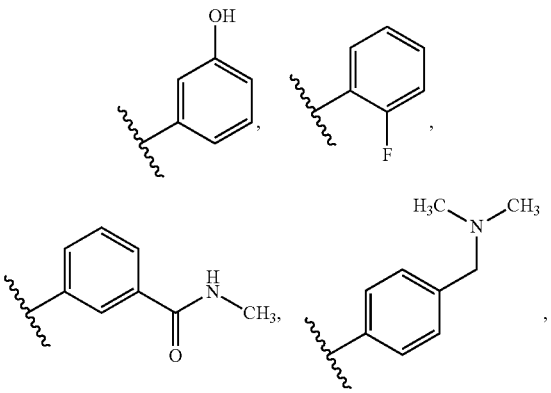
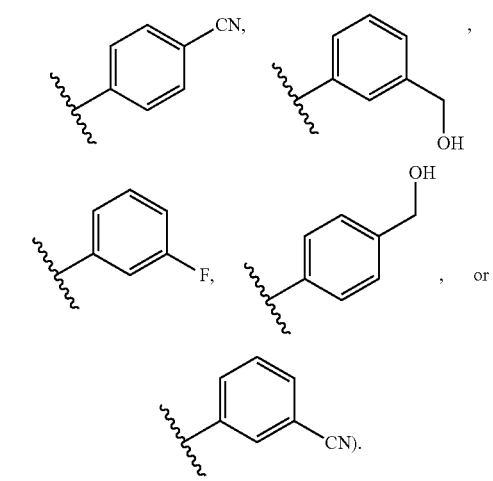
In some embodiments, $R^{24}$ is optionally substituted $C_2$-$C_9$ heterocyclyl
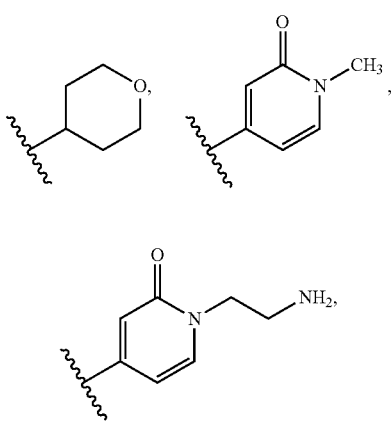

-continued
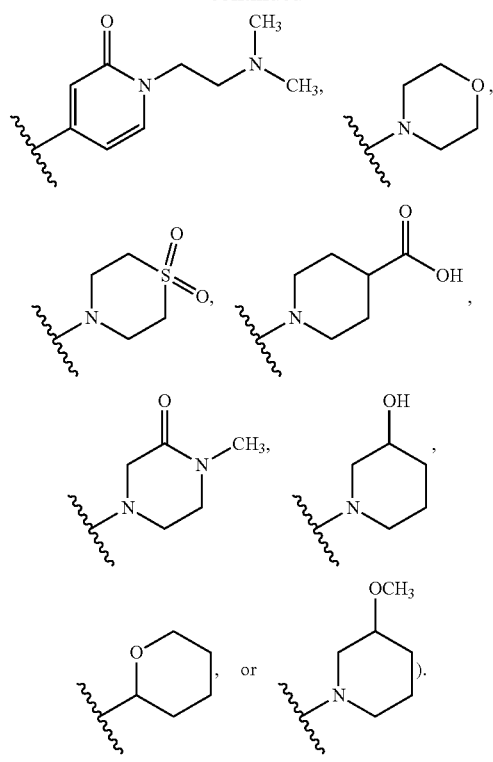
In some embodiments, $R^{24}$ is optionally substituted $C_2$-$C_9$ heteroaryl
(e.g.,
-continued
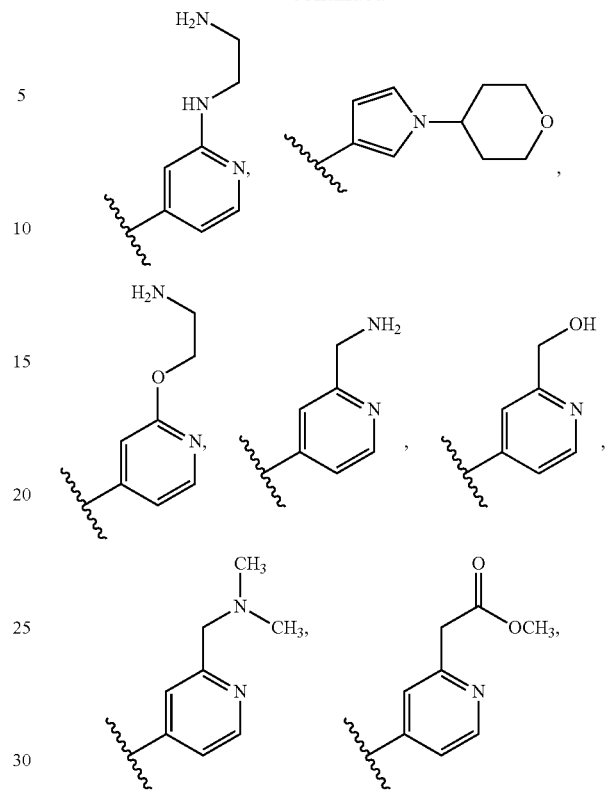
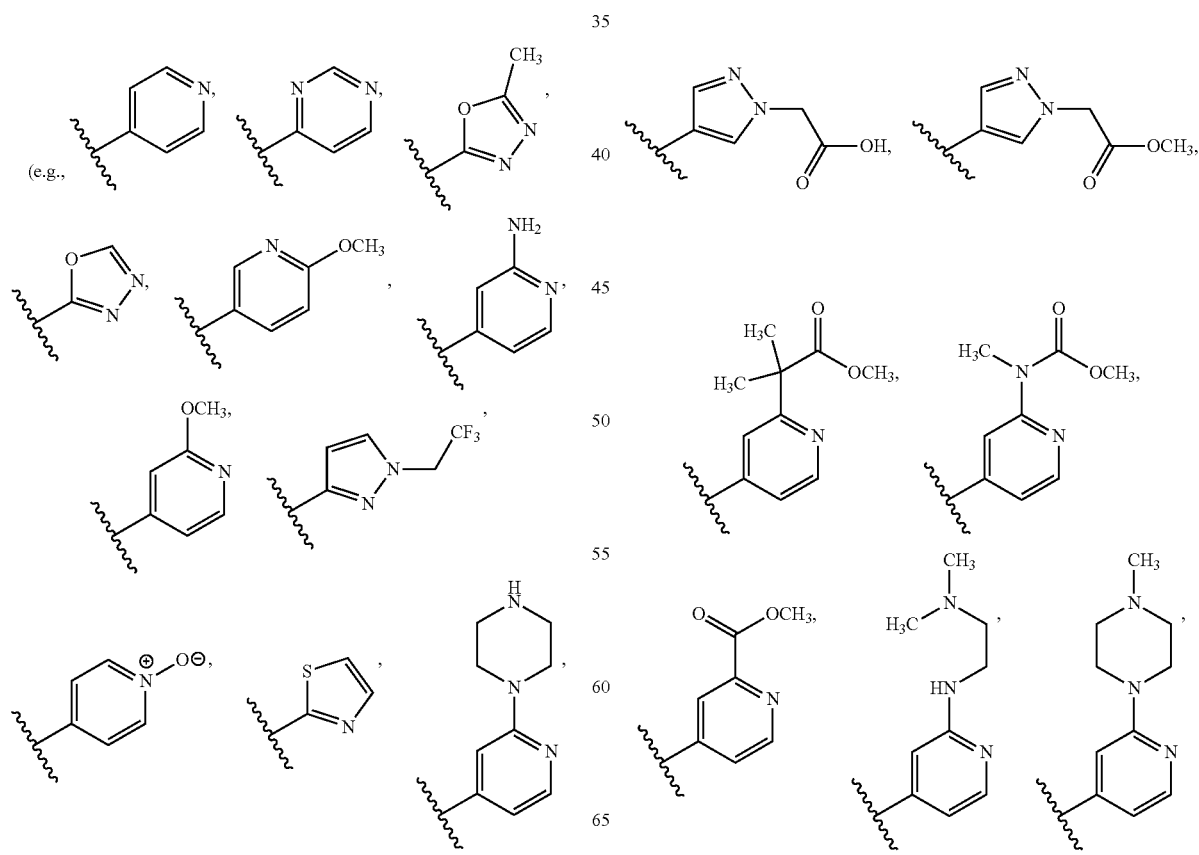

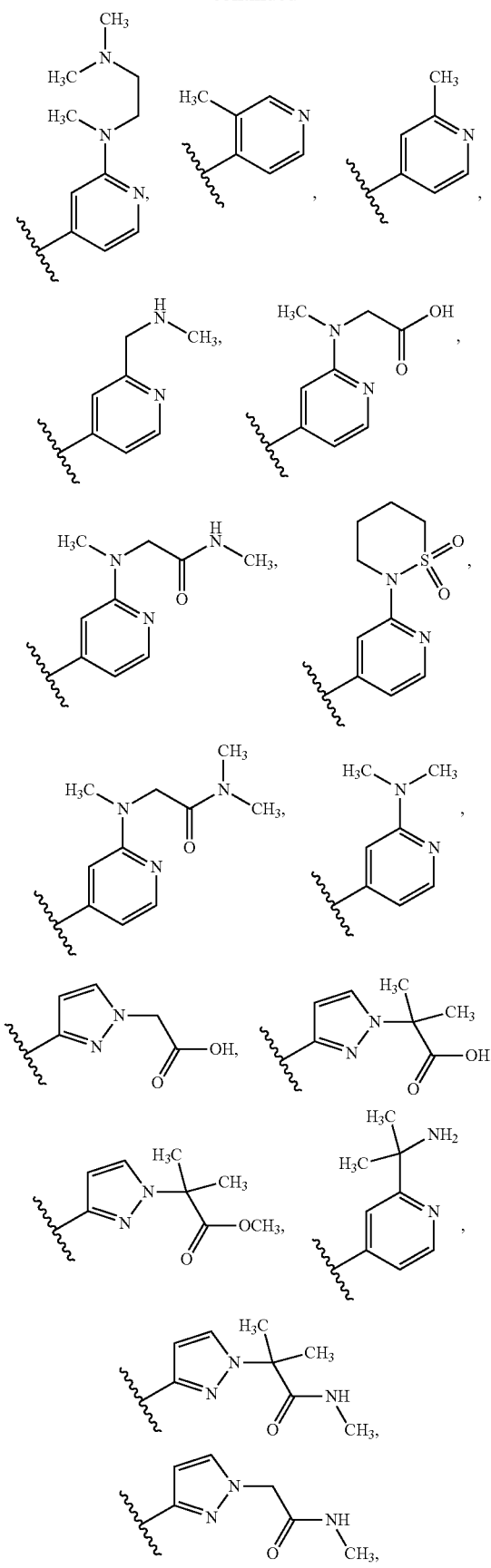
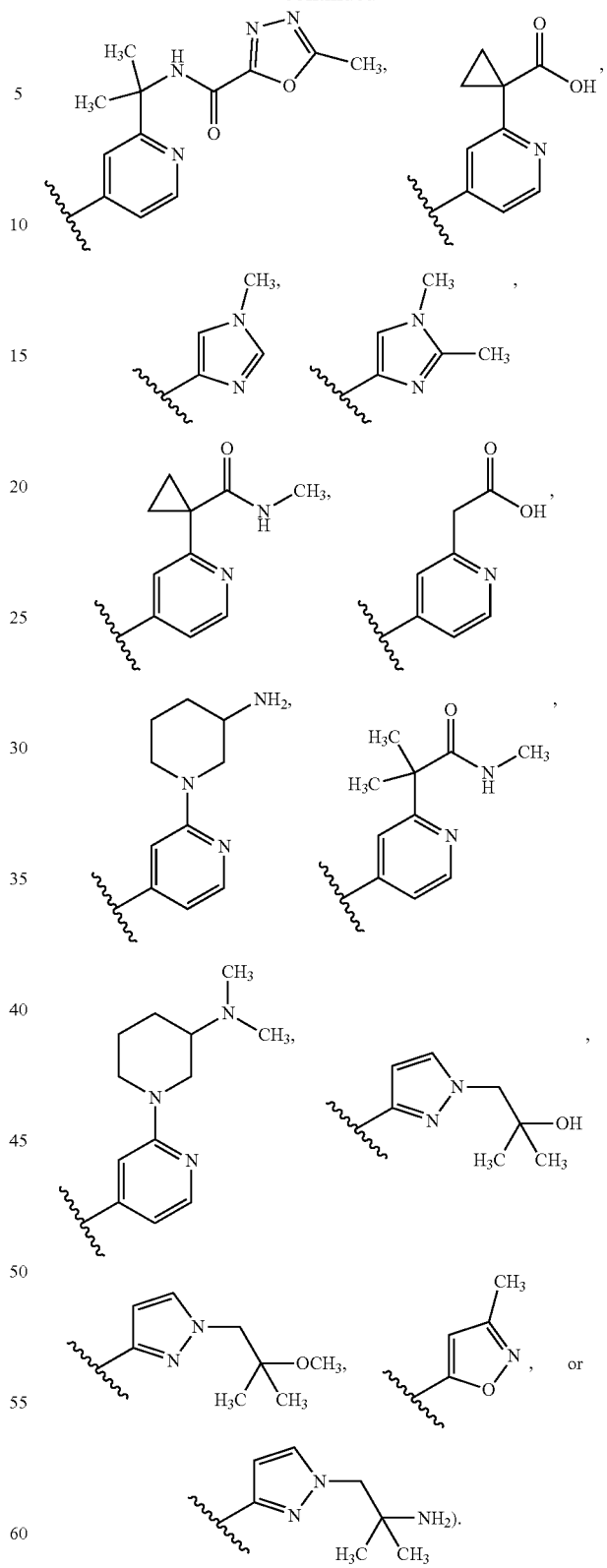
In some embodiments, the compound is any one of compounds 106-241 in Table 4 or a pharmaceutically acceptable salt thereof.

TABLE 4
| | |
|---|---|
| 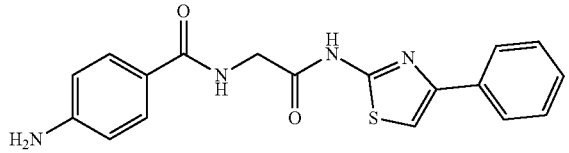 [SMILES: Nc1ccc(C(=O)NCC(=O)Nc2nc(-c3ccccc3)cs2)cc1] | 106 |
| 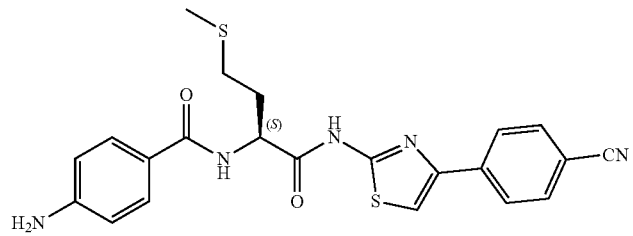 | 107 |
| 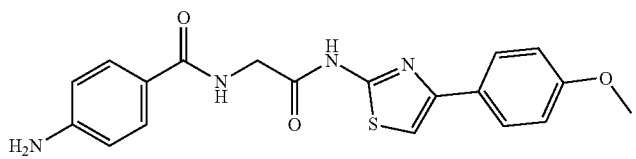 [SMILES: COc1ccc(-c2csc(NC(=O)CNC(=O)c3ccc(N)cc3)n2)cc1] | 108 |
| 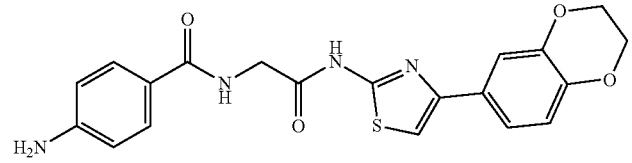 [SMILES: Nc1ccc(C(=O)NCC(=O)Nc2nc(-c3ccc4c(c3)OCCO4)cs2)cc1] | 109 |
| 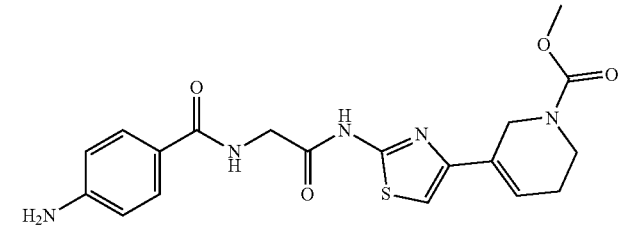 [SMILES: COC(=O)N1CCC=C(c2csc(NC(=O)CNC(=O)c3ccc(N)cc3)n2)C1] | 110 |
| 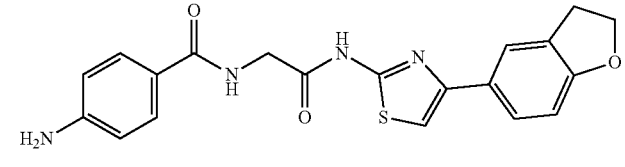 [SMILES: Nc1ccc(C(=O)NCC(=O)Nc2nc(-c3ccc4c(c3)CCO4)cs2)cc1] | 111 |
| 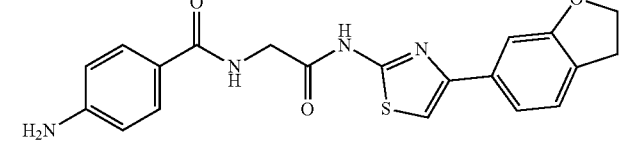 | 112 |
| 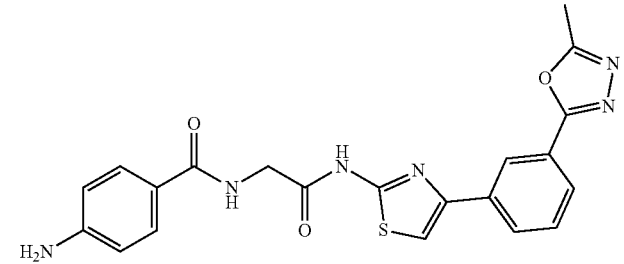 [SMILES: Cc1nnc(-c2cccc(-c3csc(NC(=O)CNC(=O)c4ccc(N)cc4)n3)c2)o1] | 113 |

TABLE 4-continued
| | |
|---|---|
| 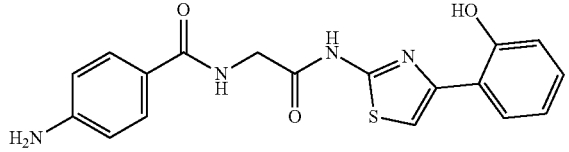 [SMILES: Nc1ccc(C(=O)NCC(=O)Nc2nc(-c3ccccc3O)cs2)cc1] | 114 |
| 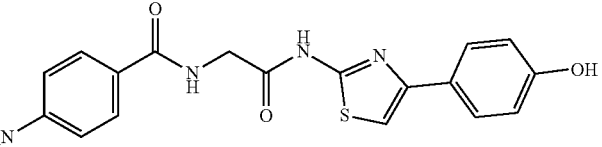 | 115 |
| 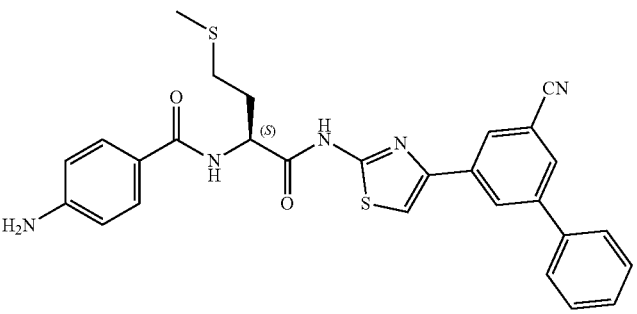 | 116 |
|  | 117 |
| 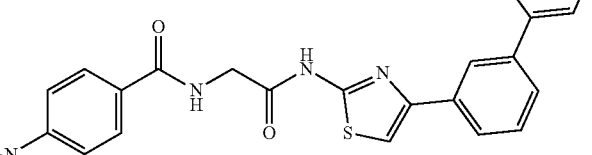 | 118 |
| 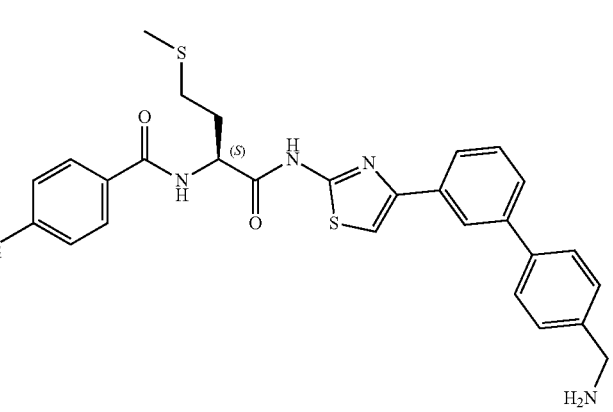 | 119 |

TABLE 4-continued
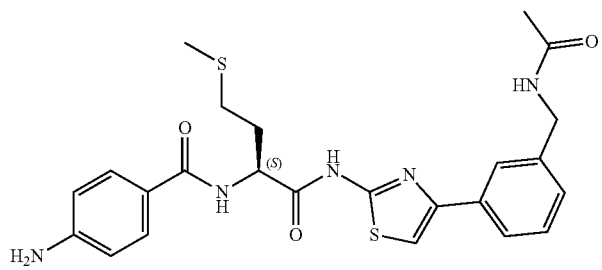
120
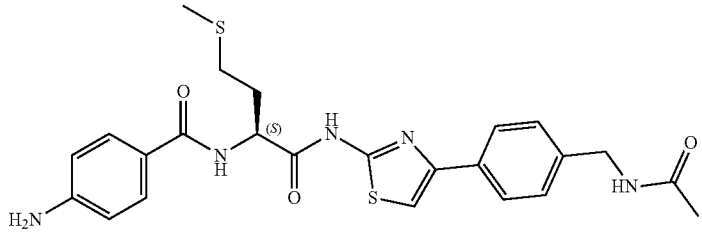
121
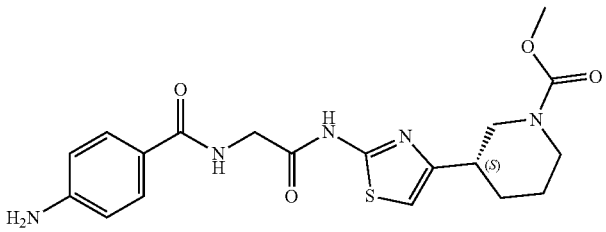
122
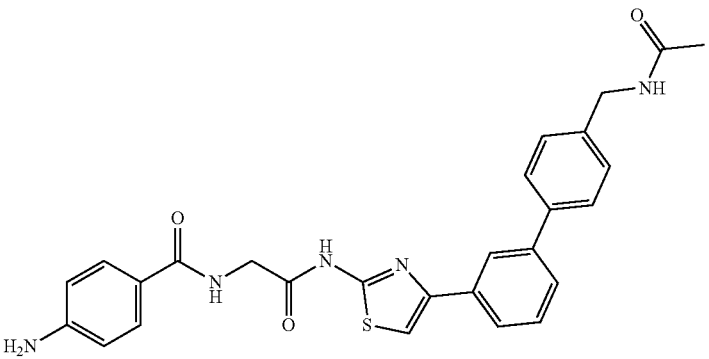 [SMILES: CC(=O)NCc1ccc(-c2cccc(-c3csc(NC(=O)CNC(=O)c4ccc(N)cc4)n3)c2)cc1]
123
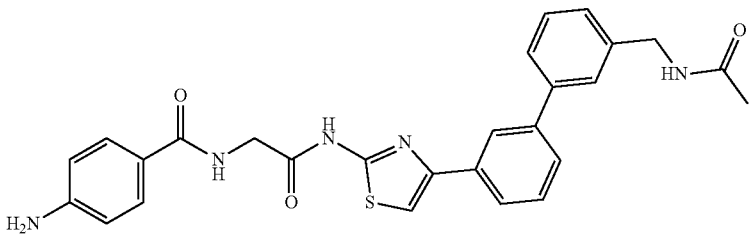 [SMILES: CC(=O)NCc1cccc(-c2cccc(-c3csc(NC(=O)CNC(=O)c4ccc(N)cc4)n3)c2)c1]
124
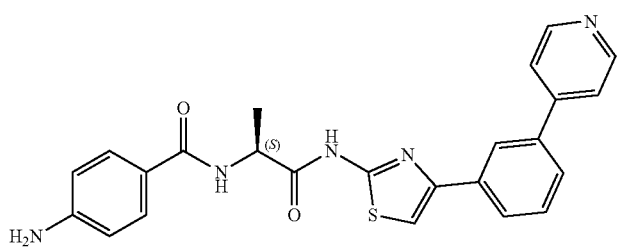
125

TABLE 4-continued
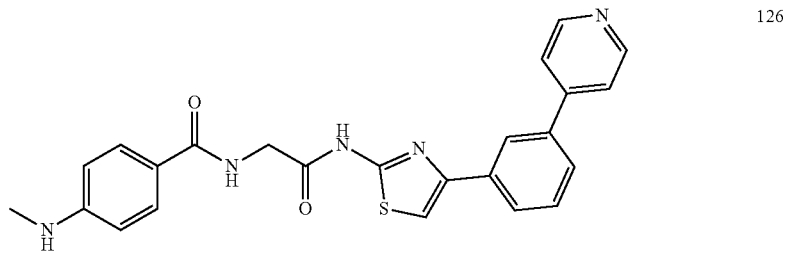 126
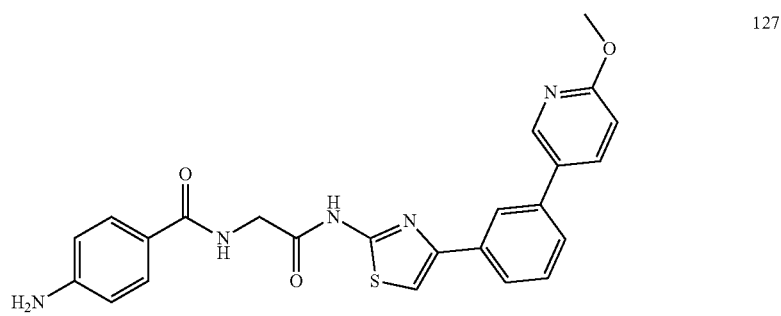 127
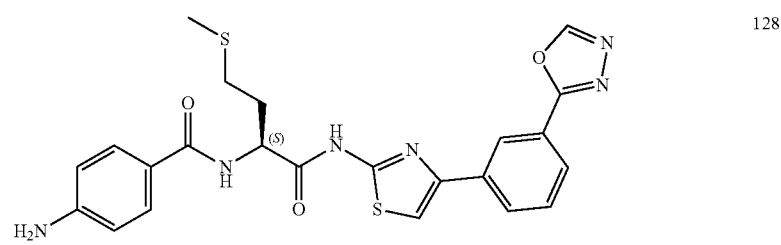 128
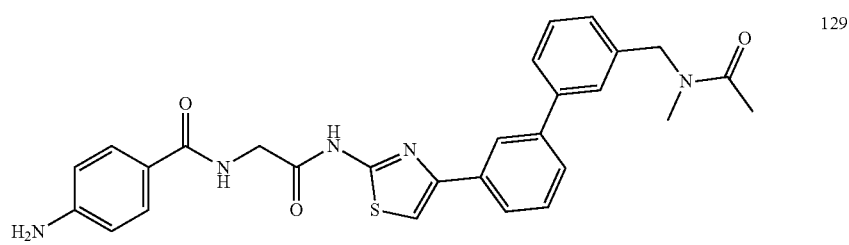 129
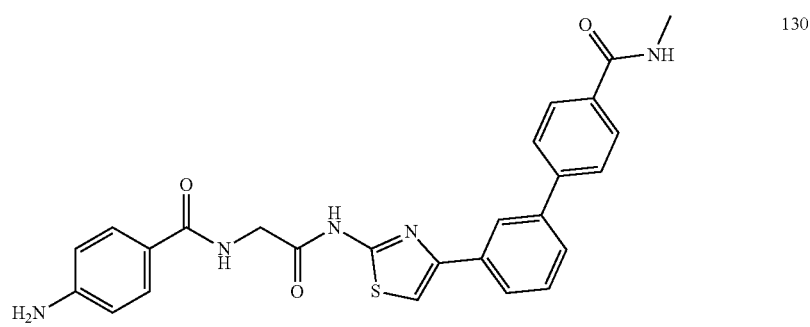 130
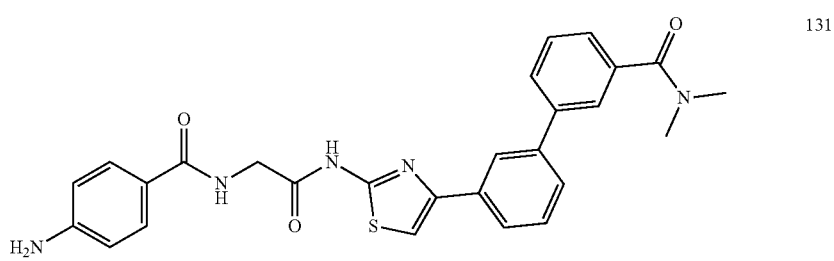 131

TABLE 4-continued
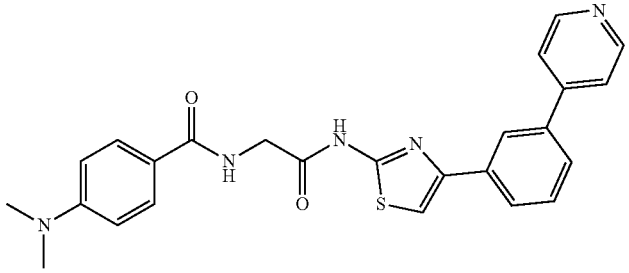 [SMILES: CN(C)c1ccc(C(=O)NCC(=O)Nc2nc(-c3cccc(-c4ccncc4)c3)cs2)cc1]
132
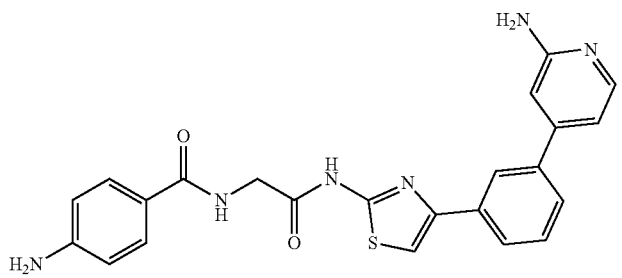 [SMILES: Nc1ccc(C(=O)NCC(=O)Nc2nc(-c3cccc(-c4ccnc(N)c4)c3)cs2)cc1]
133
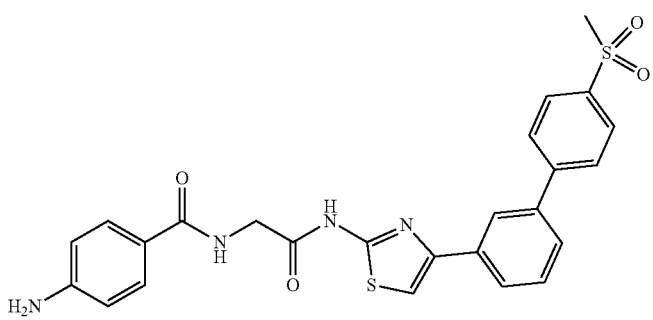 [SMILES: CS(=O)(=O)c1ccc(-c2cccc(-c3csc(NC(=O)CNC(=O)c4ccc(N)cc4)n3)c2)cc1]
134
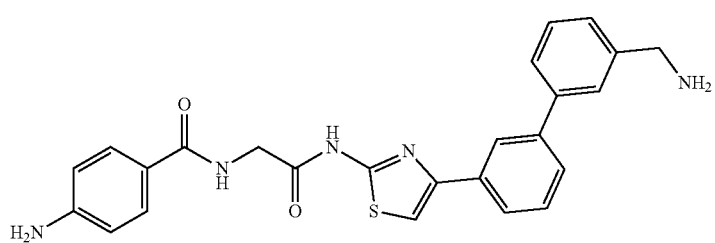 [SMILES: NCc1cccc(-c2cccc(-c3csc(NC(=O)CNC(=O)c4ccc(N)cc4)n3)c2)c1]
135
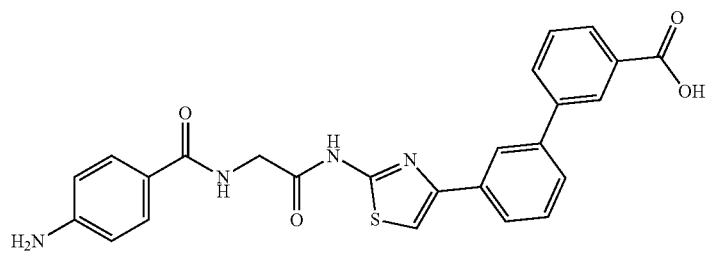 [SMILES: Nc1ccc(C(=O)NCC(=O)Nc2nc(-c3cccc(-c4cccc(C(=O)O)c4)c3)cs2)cc1]
136

TABLE 4-continued
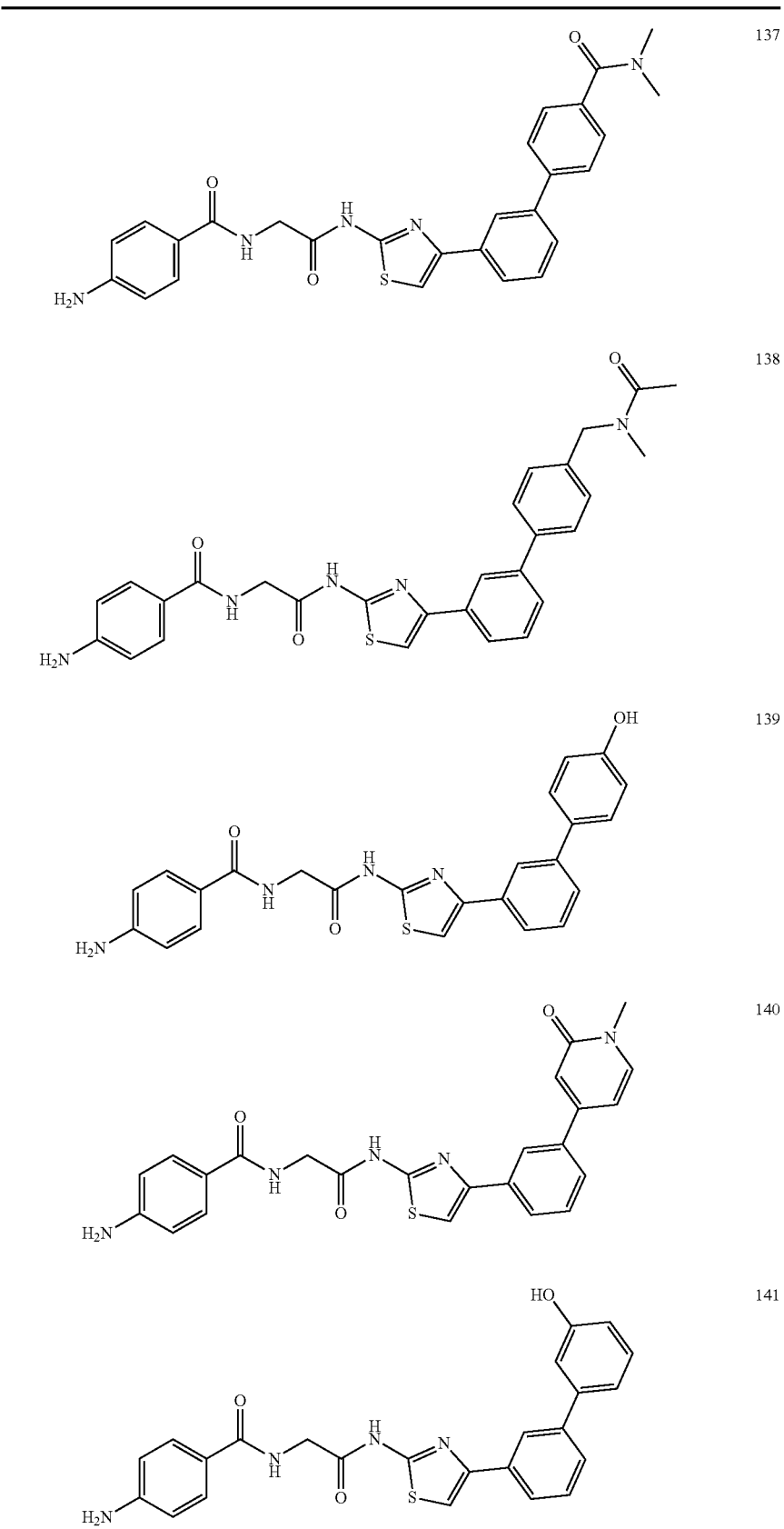

TABLE 4-continued
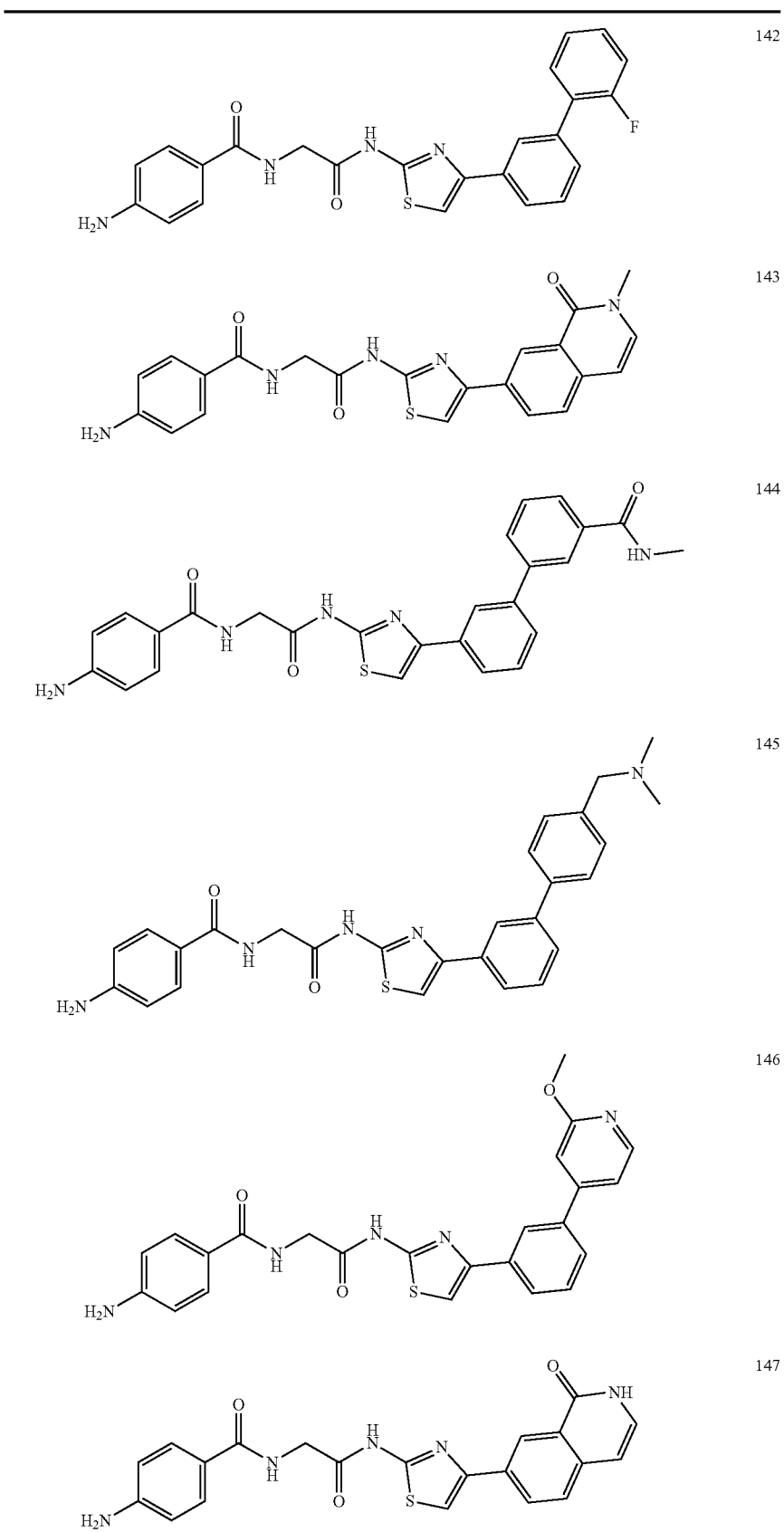

TABLE 4-continued
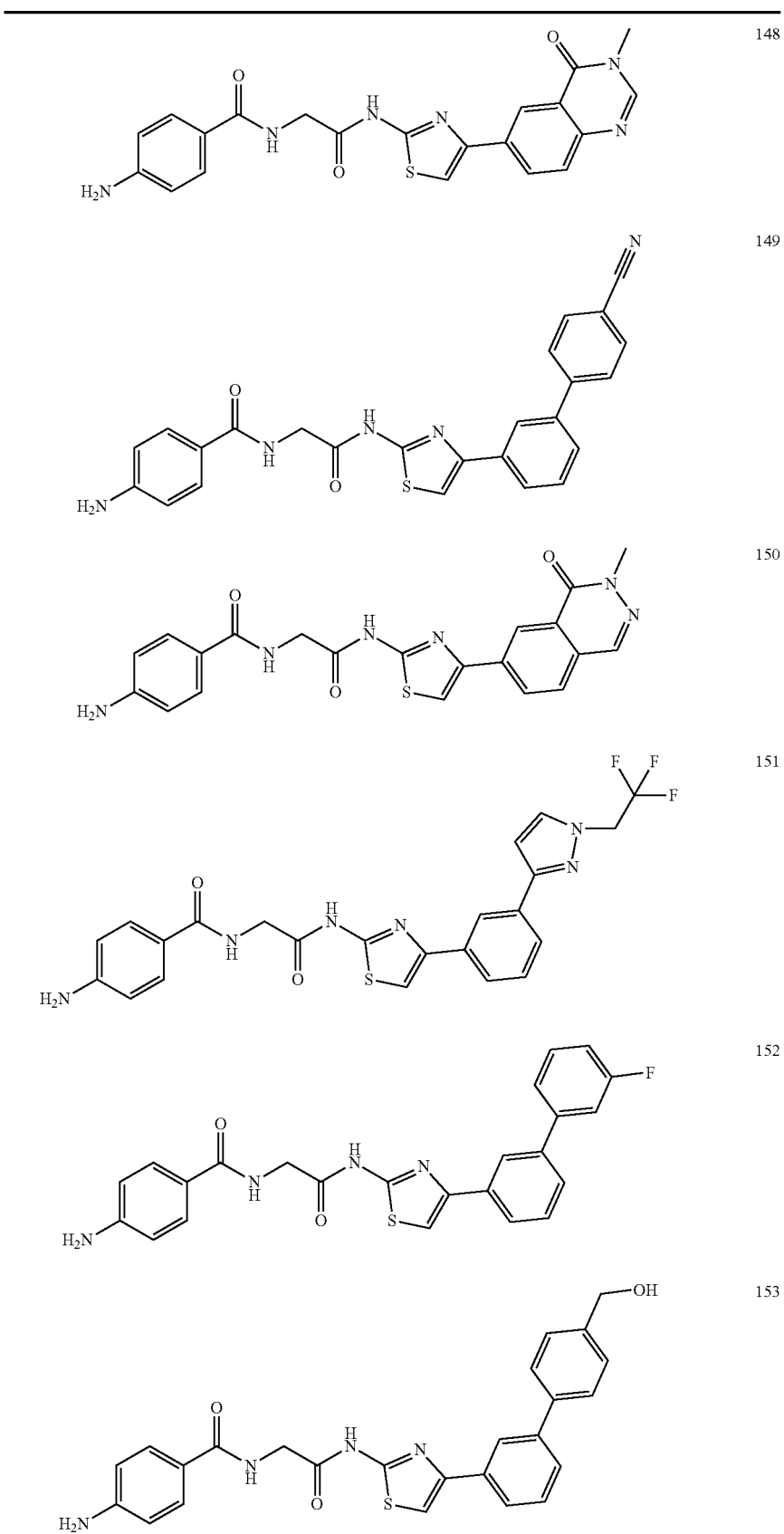

TABLE 4-continued
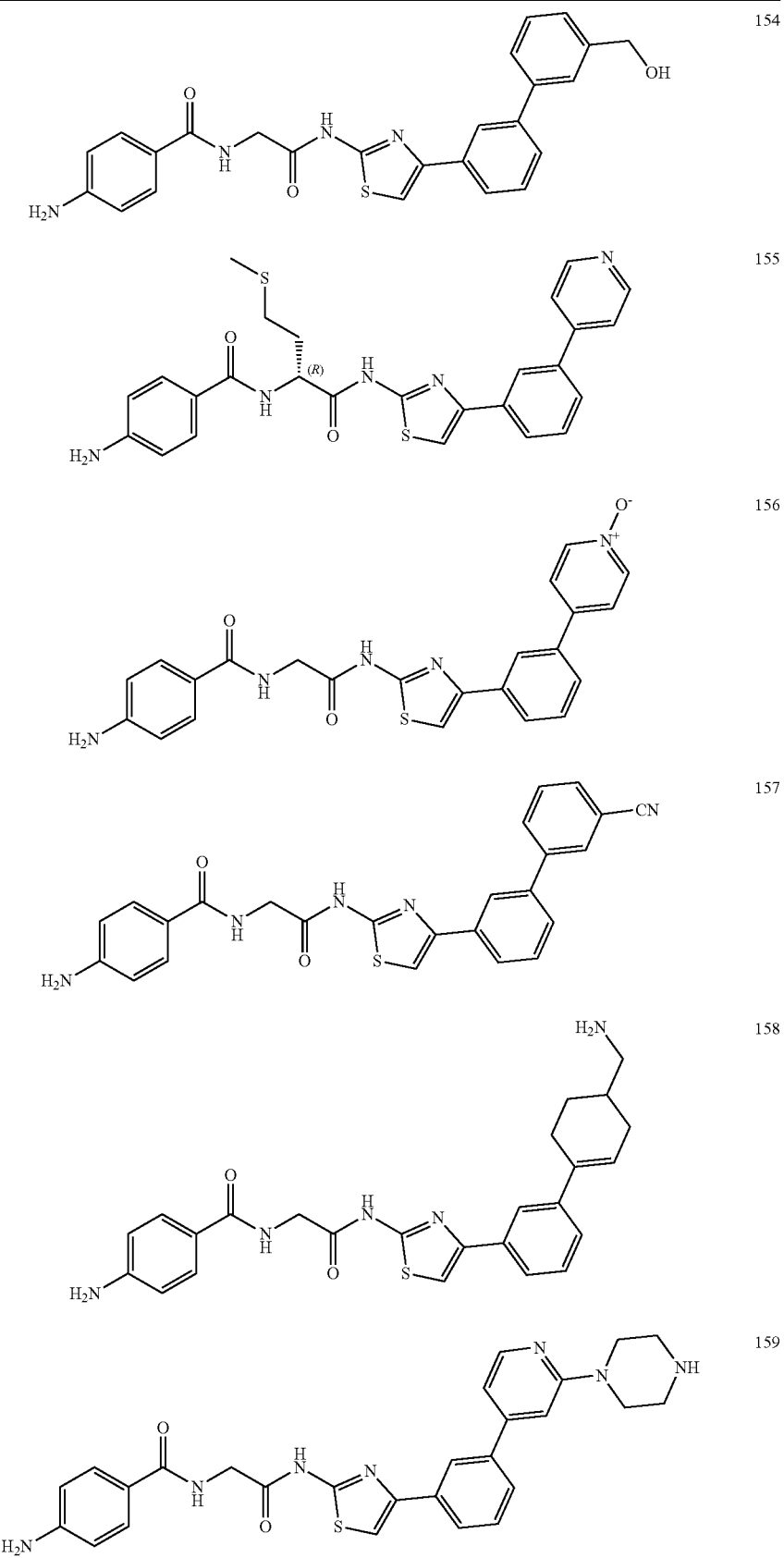

TABLE 4-continued
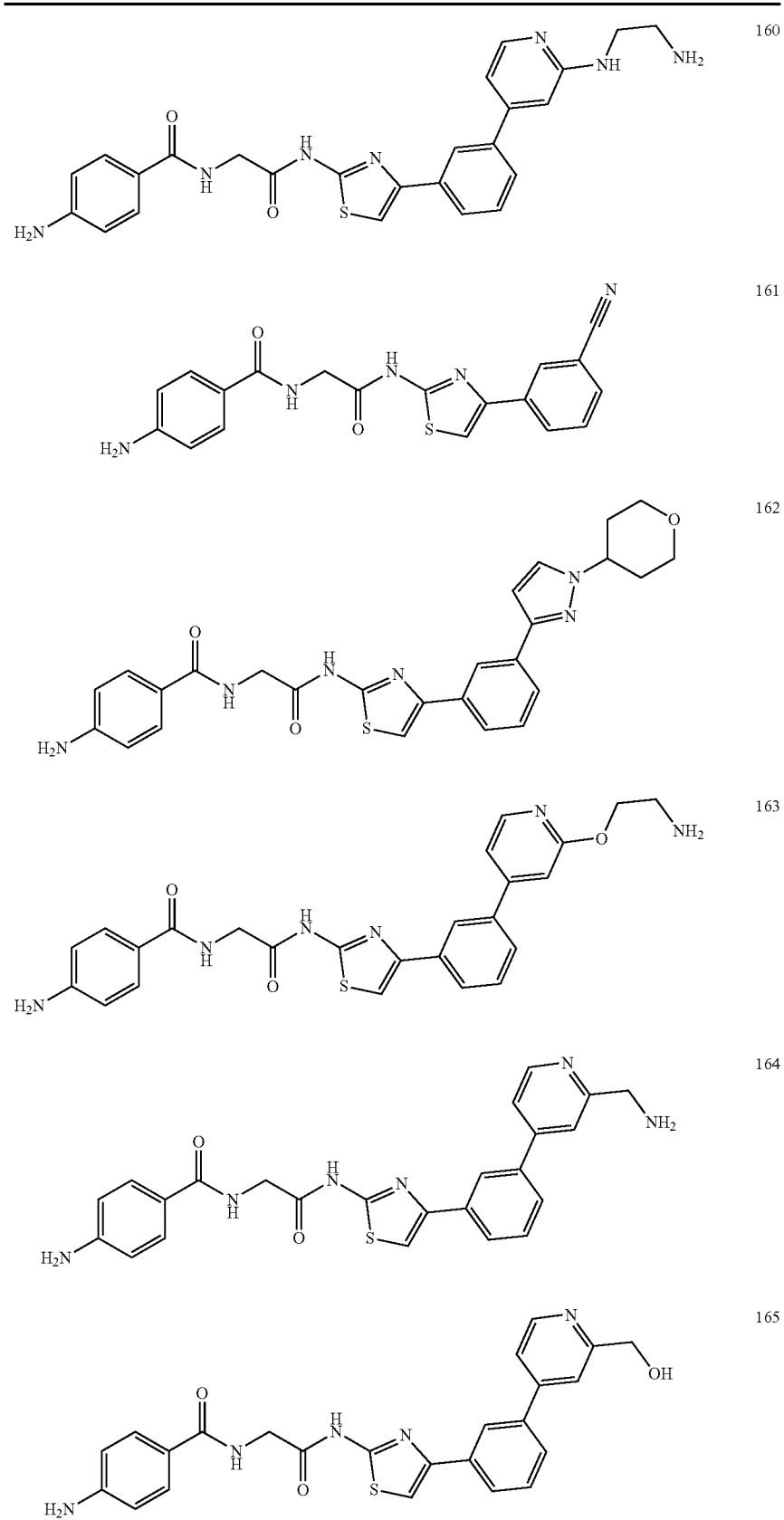

TABLE 4-continued
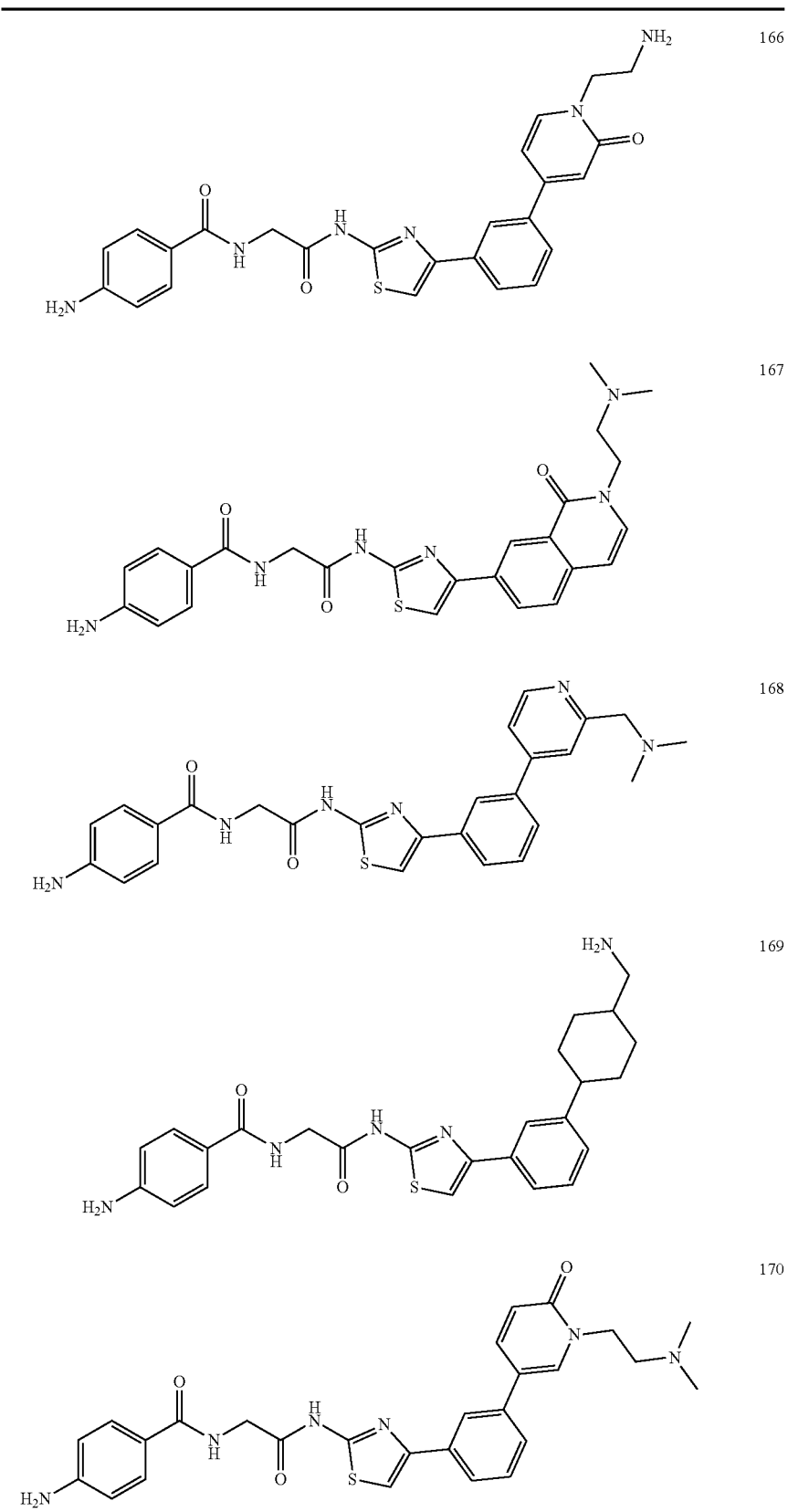

TABLE 4-continued
| | |
|---|---|
| 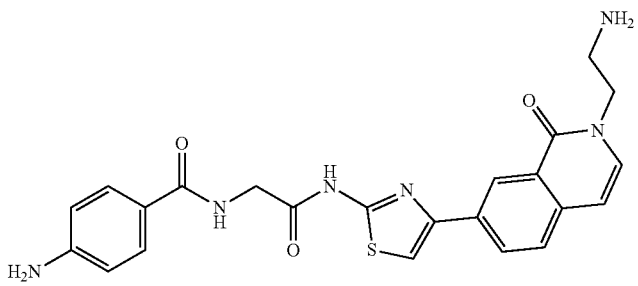 [SMILES: NCCn1ccc2ccc(-c3csc(NC(=O)CNC(=O)c4ccc(N)cc4)n3)cc2c1=O] | 171 |
| 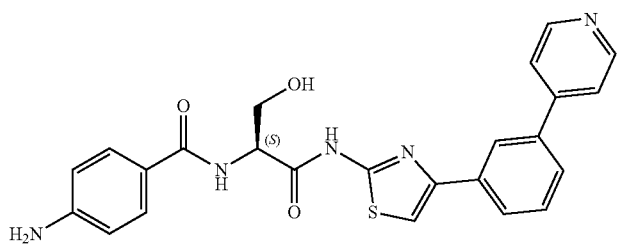 | 172 |
| 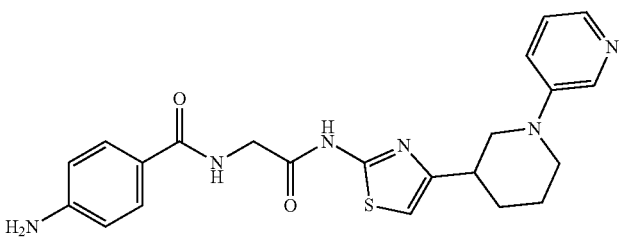 [SMILES: Nc1ccc(C(=O)NCC(=O)Nc2nc(C3CCCN(c4cccnc4)C3)cs2)cc1] | 173 |
| 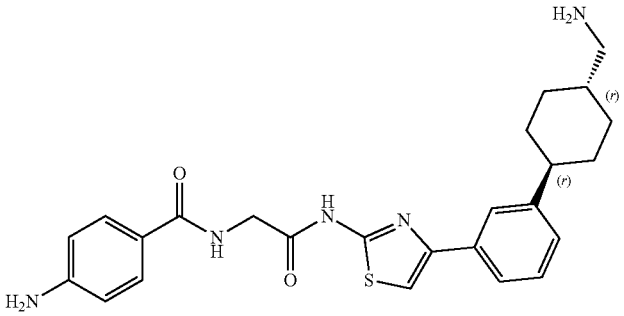 | 174 |
| 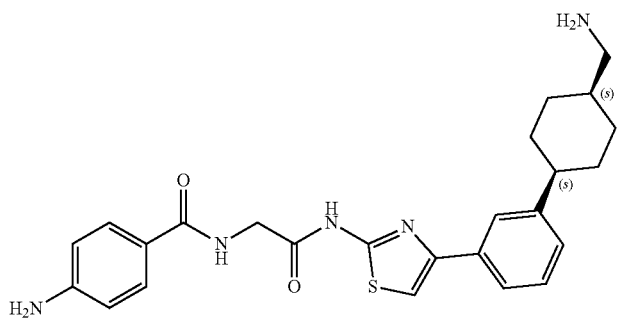 | 175 |

TABLE 4-continued
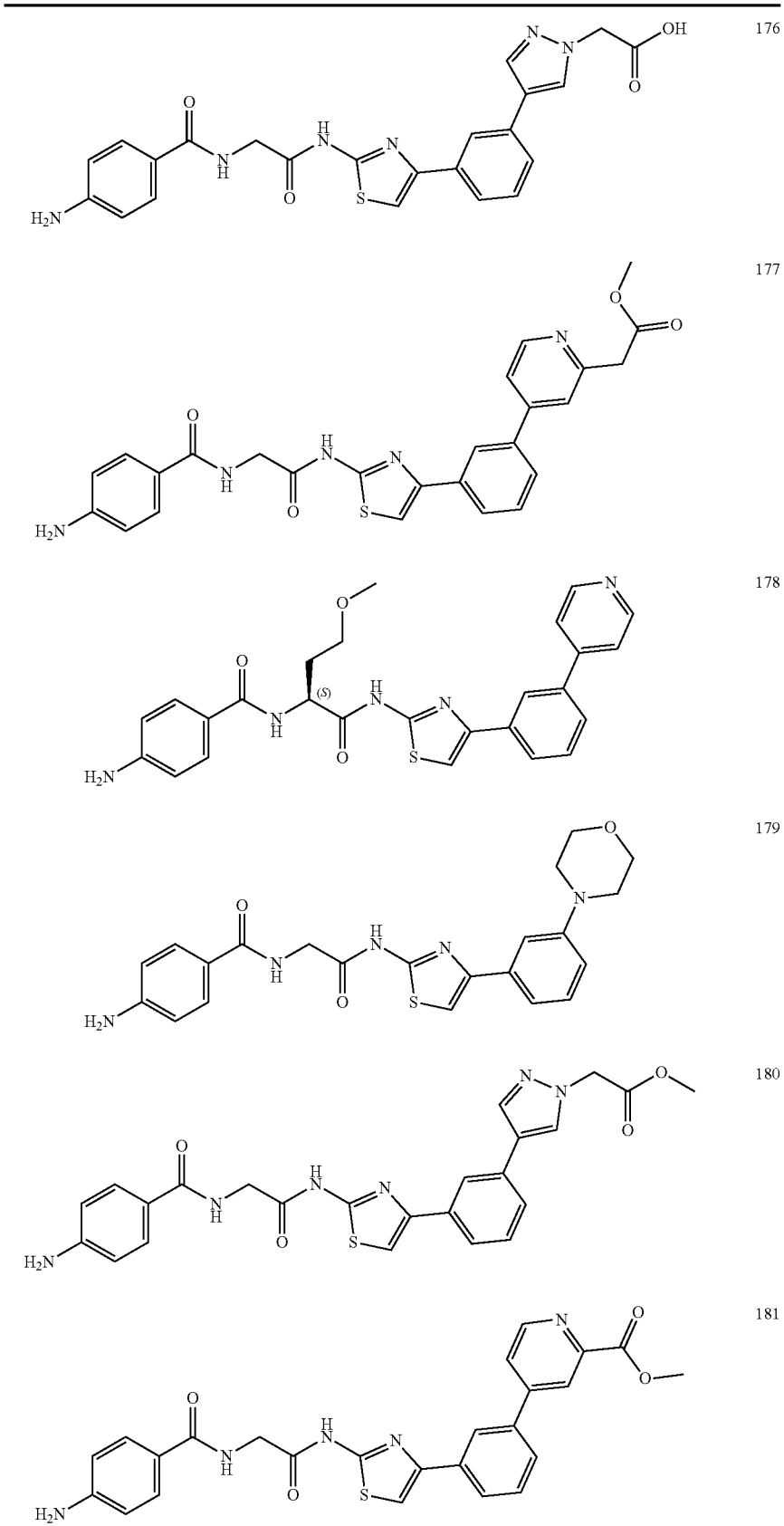

TABLE 4-continued
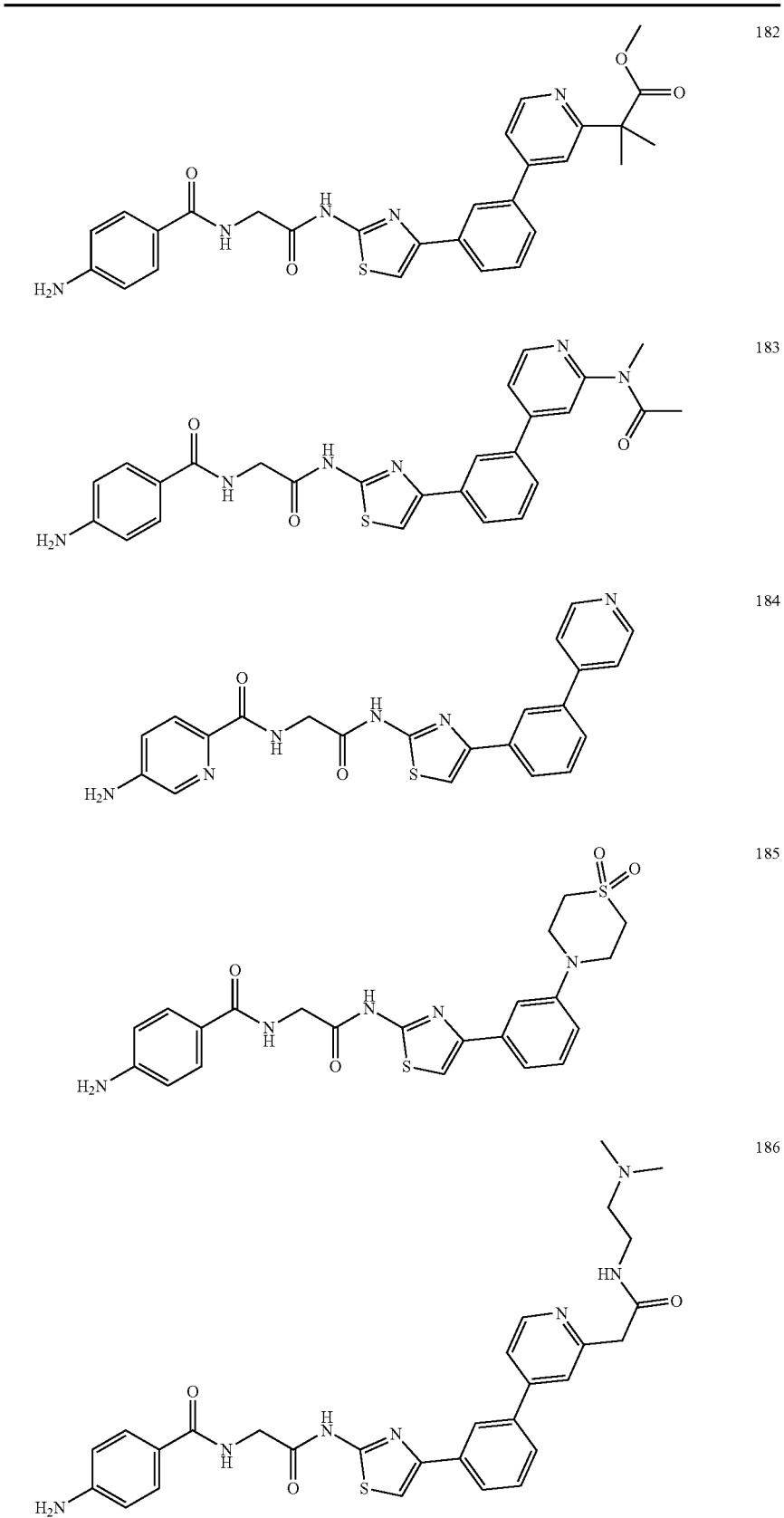

TABLE 4-continued
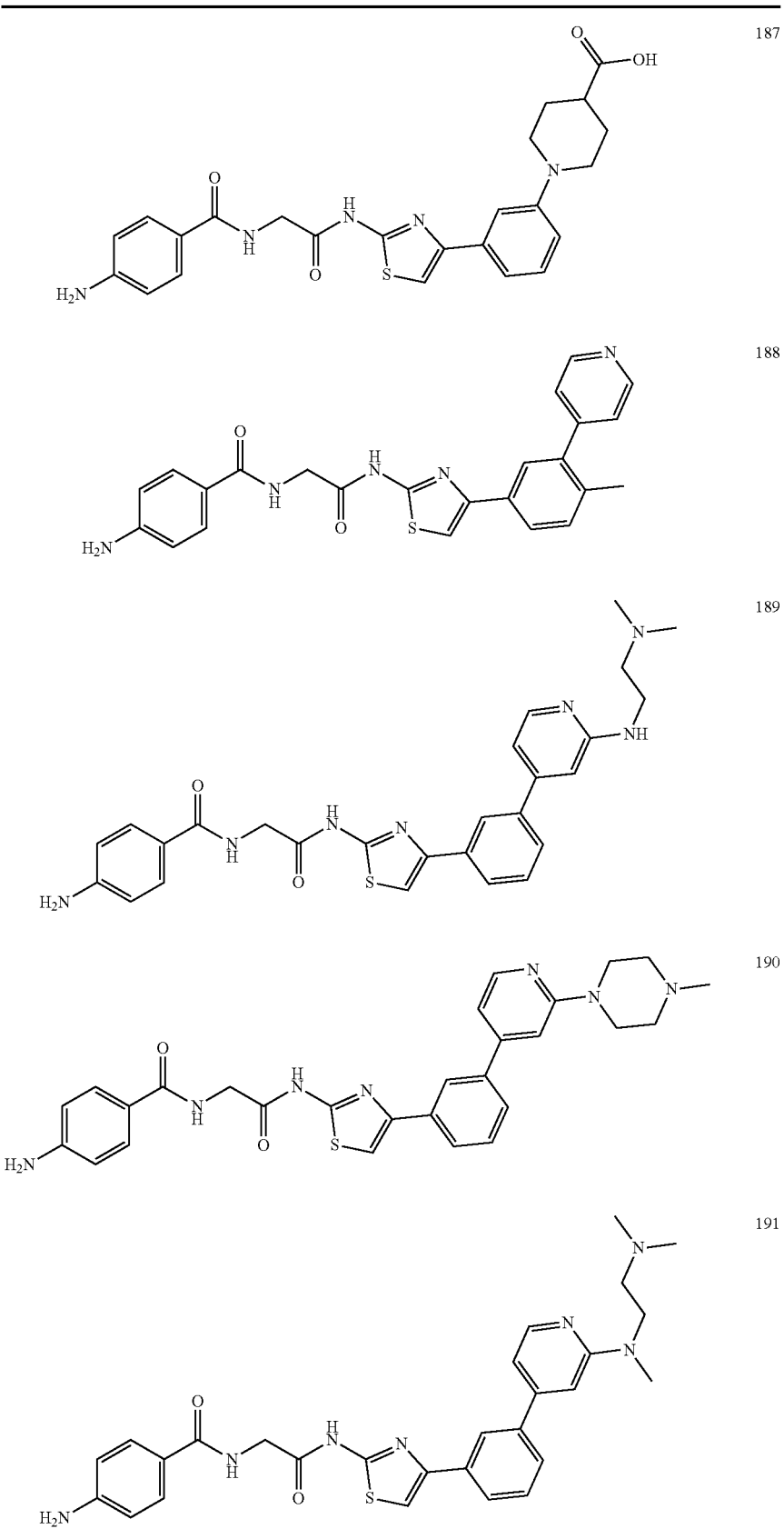

TABLE 4-continued
| | |
|---|---|
| 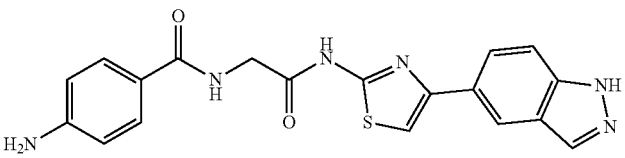 [SMILES: Nc1ccc(C(=O)NCC(=O)Nc2nc(-c3ccc4[nH]ncc4c3)cs2)cc1] | 192 |
| 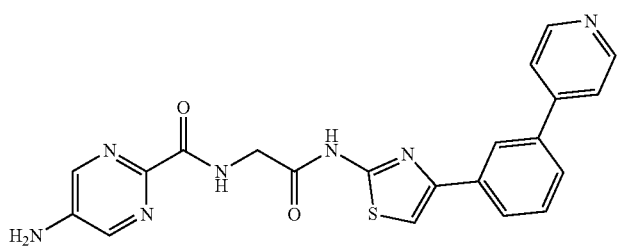 [SMILES: Nc1cnc(C(=O)NCC(=O)Nc2nc(-c3cccc(-c4ccncc4)c3)cs2)nc1] | 193 |
| 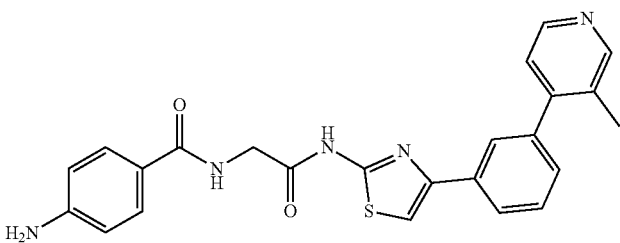 [SMILES: Cc1cnccc1-c1cccc(-c2csc(NC(=O)CNC(=O)c3ccc(N)cc3)n2)c1] | 194 |
| 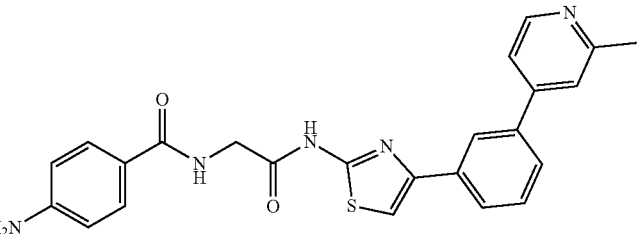 | 195 |
| 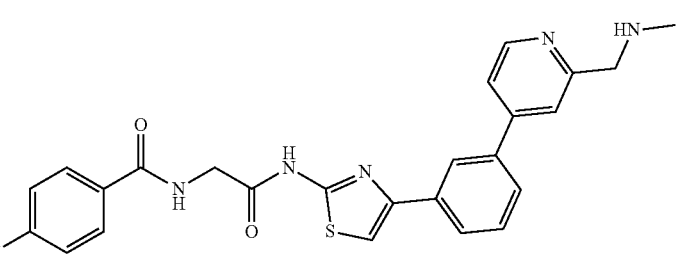 | 196 |
| 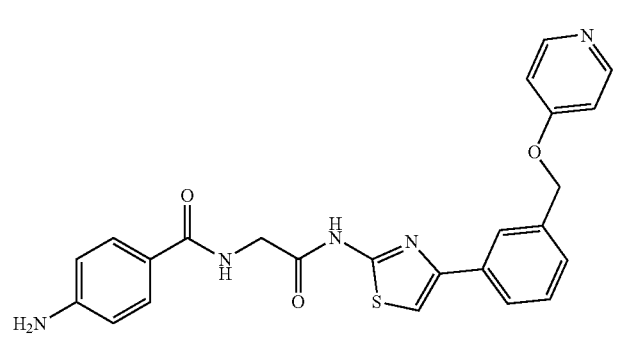 [SMILES: Nc1ccc(C(=O)NCC(=O)Nc2nc(-c3cccc(COc4ccncc4)c3)cs2)cc1] | 197 |

TABLE 4-continued
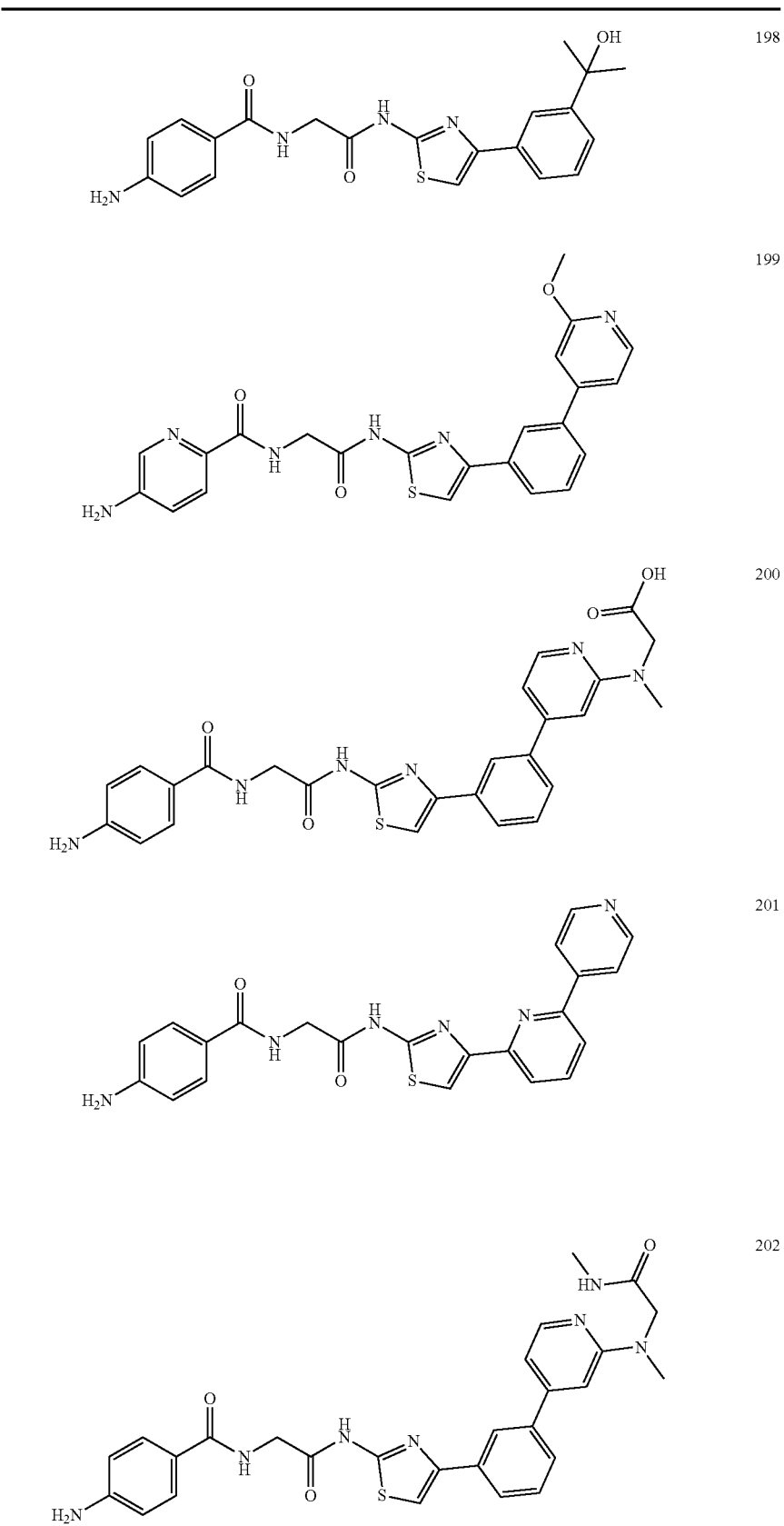

TABLE 4-continued
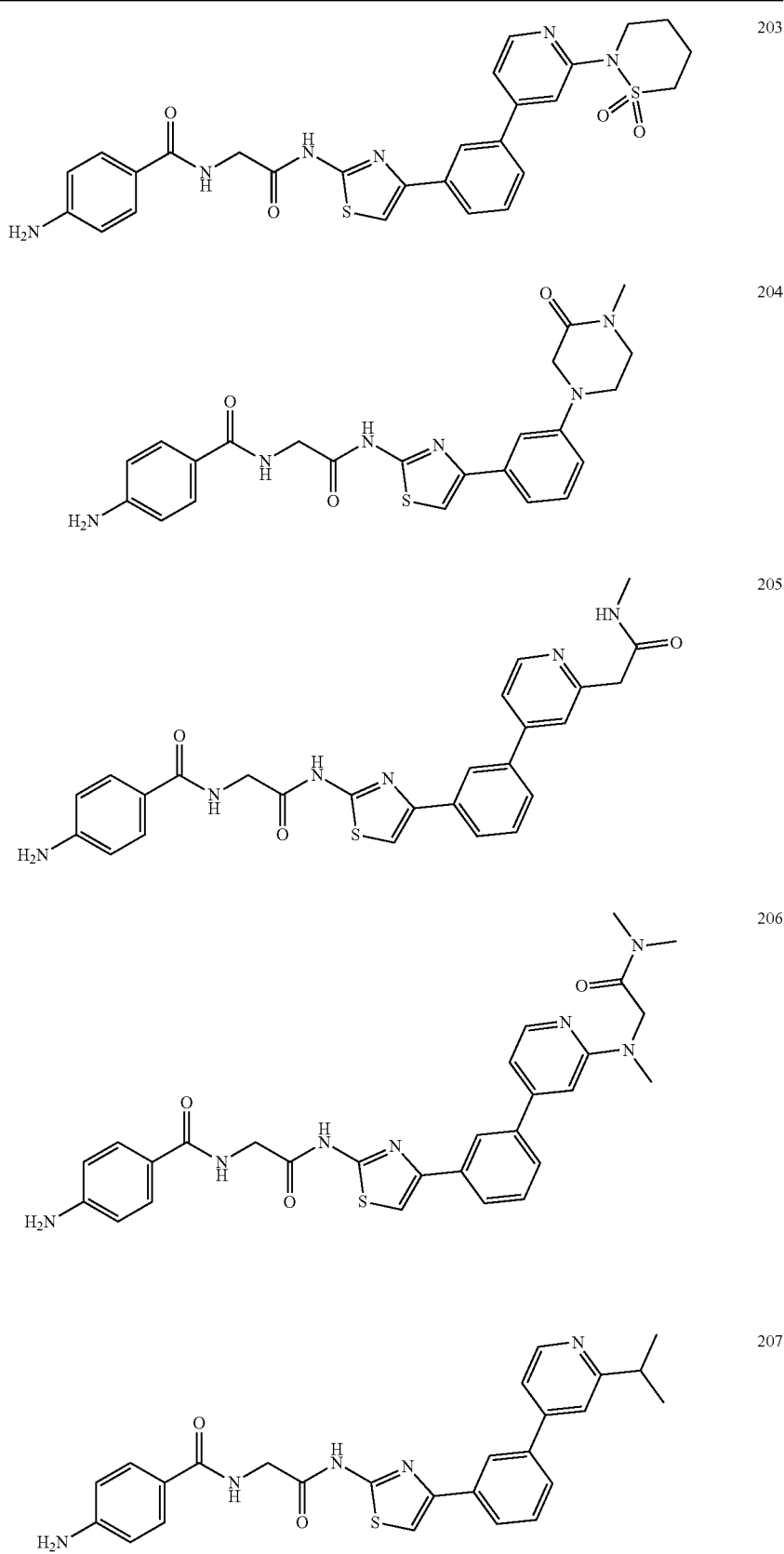

TABLE 4-continued
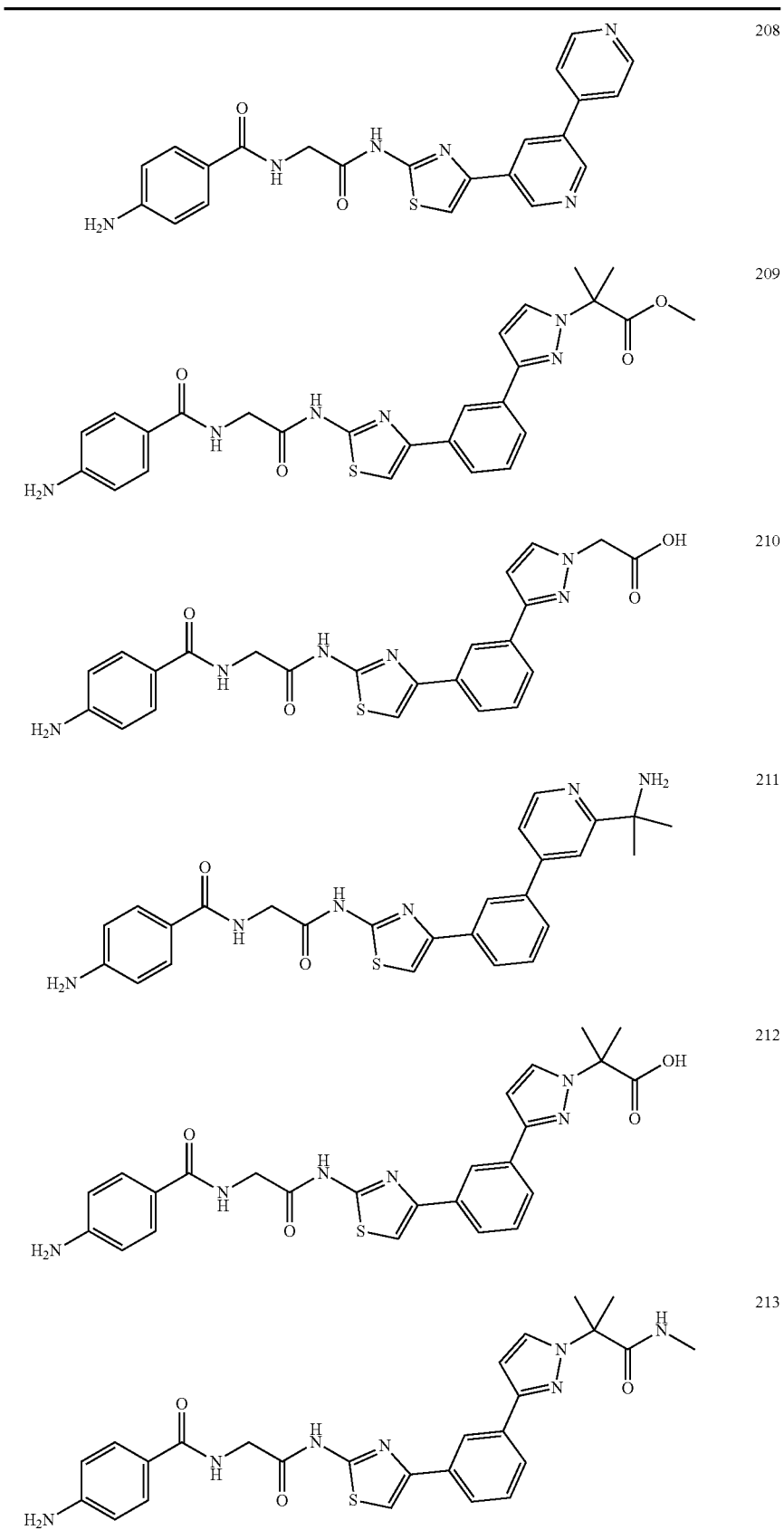

TABLE 4-continued
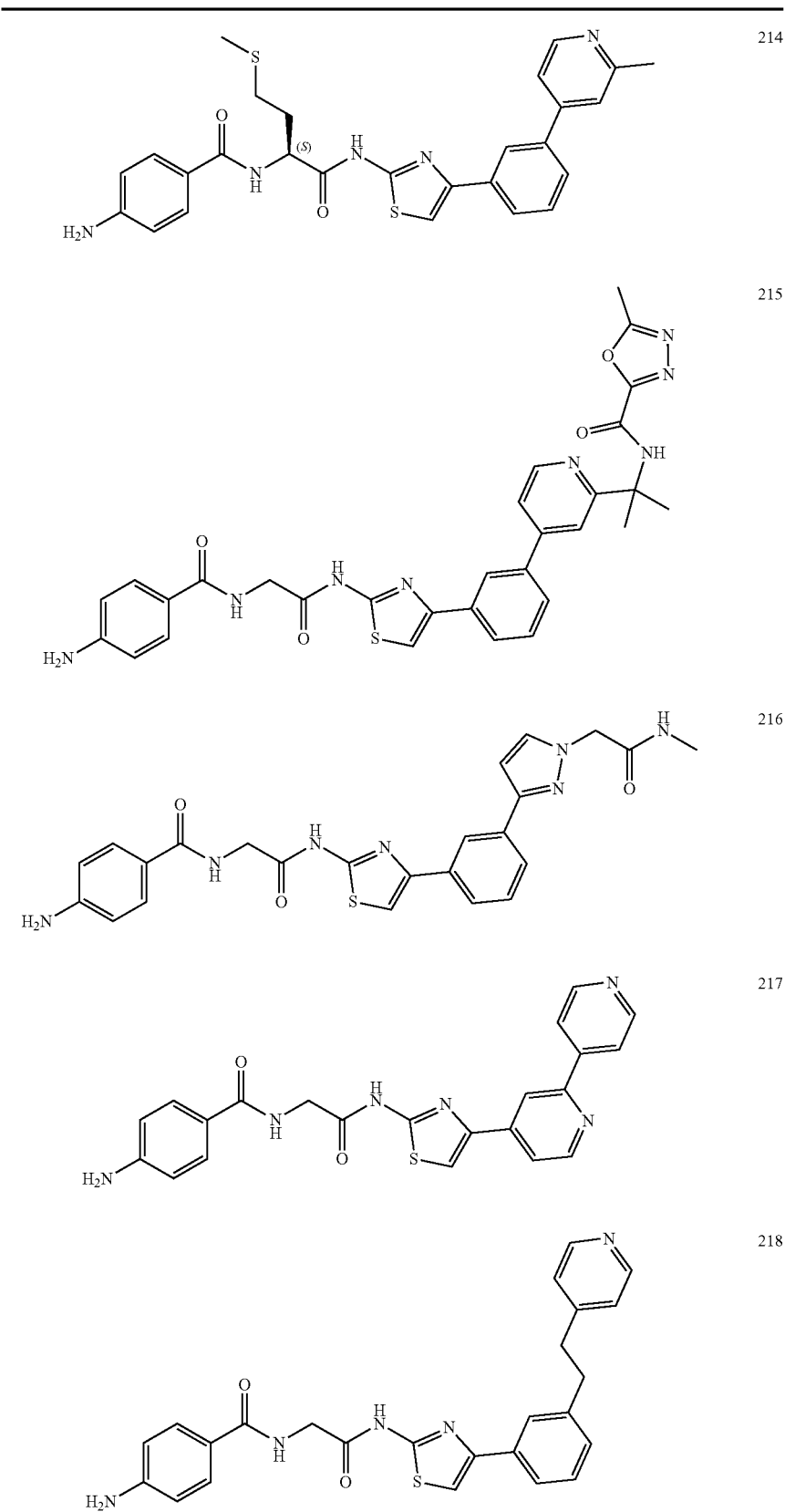
214
215
216
217
218

TABLE 4-continued
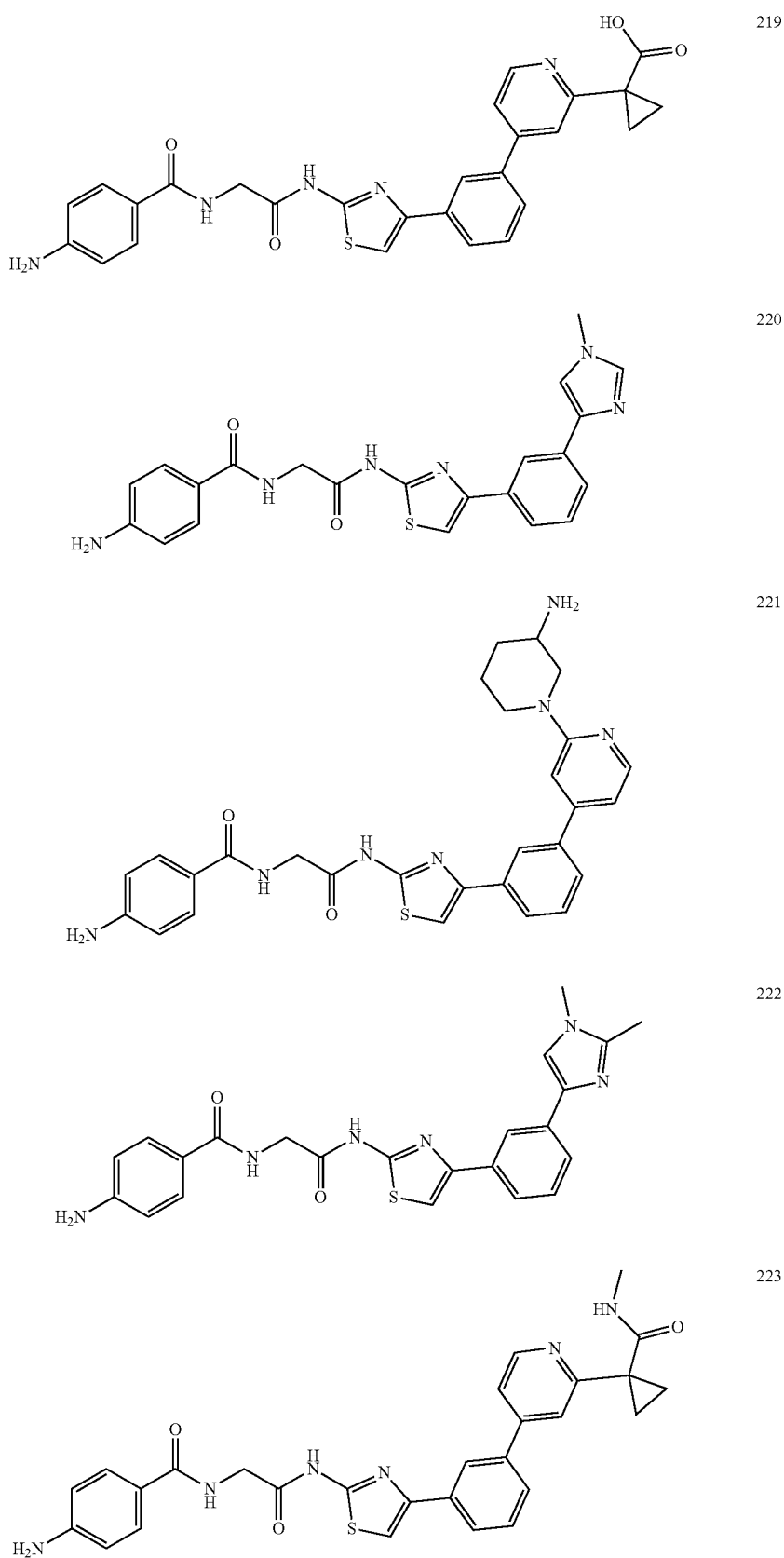

TABLE 4-continued
| | |
|---|---|
| 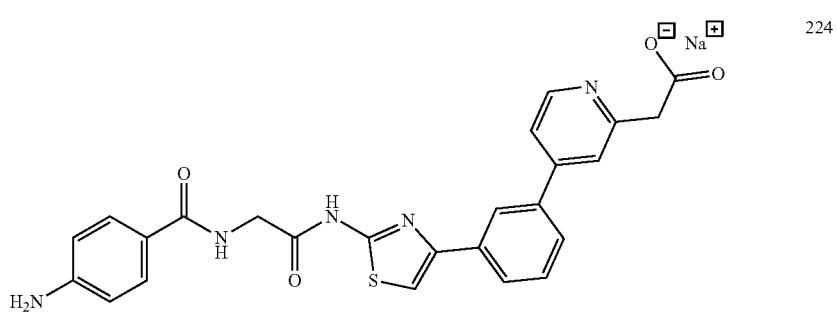 | 224 |
| 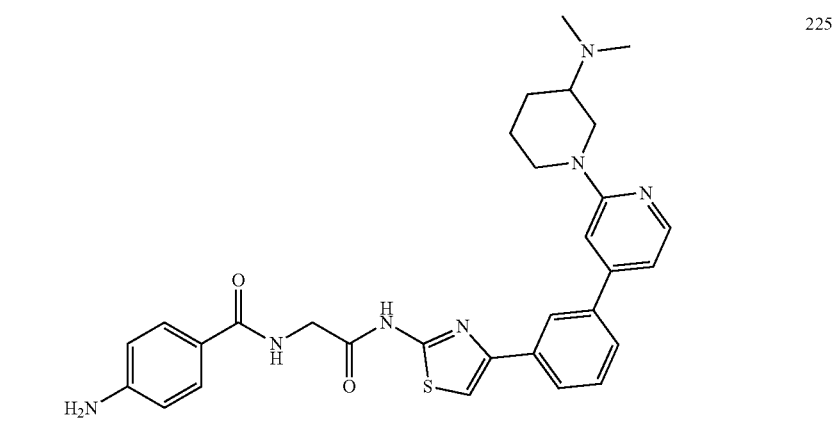 | 225 |
| 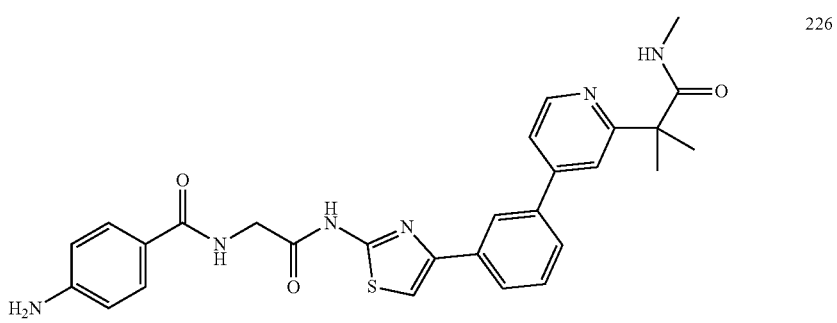 | 226 |
| 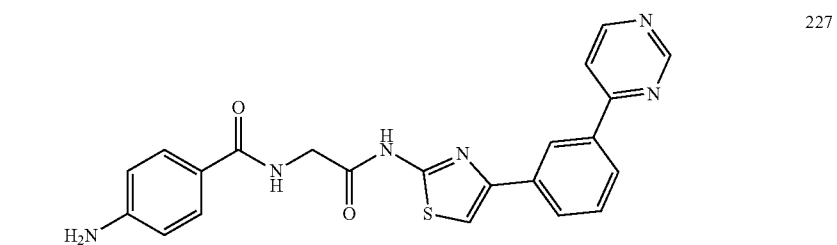 | 227 |
| 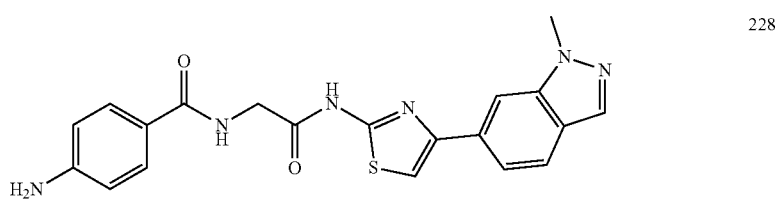 | 228 |

TABLE 4-continued
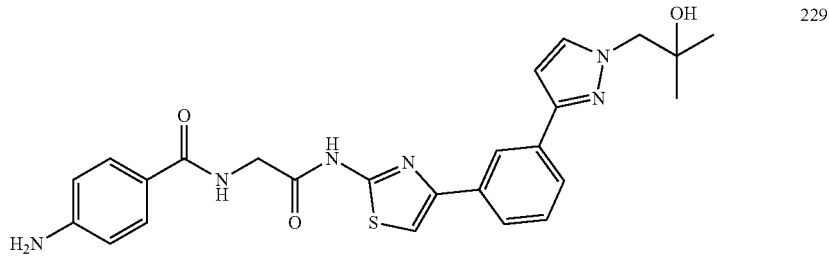
229
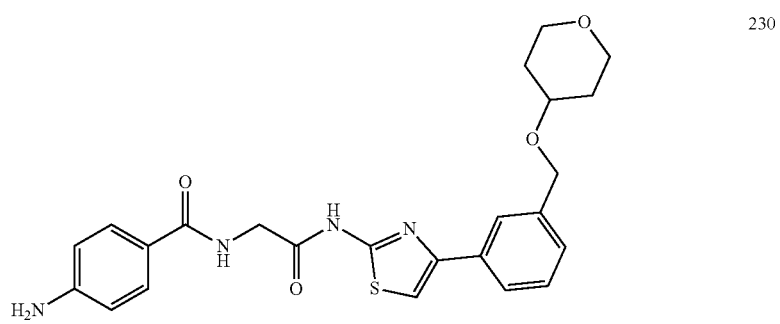
230
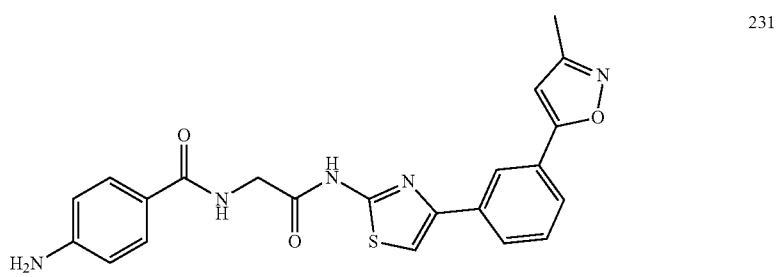
231
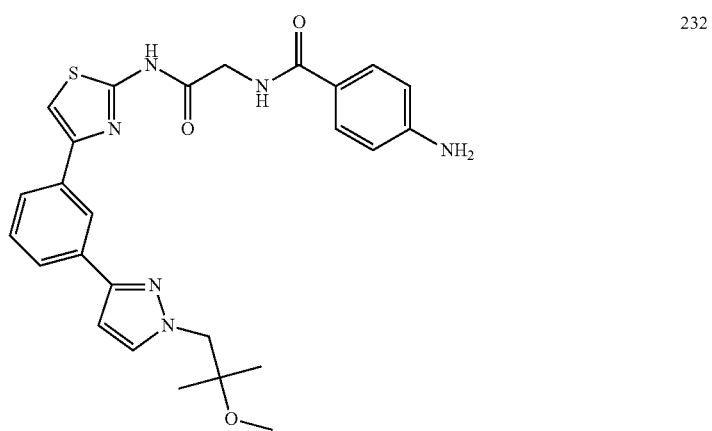
232

TABLE 4-continued
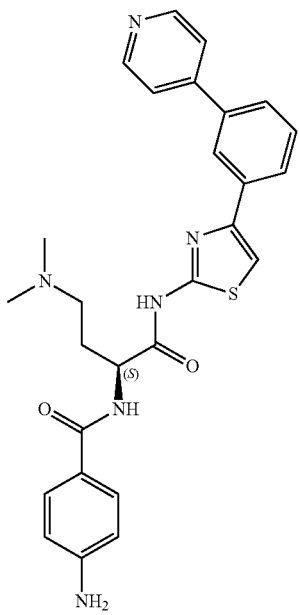 233
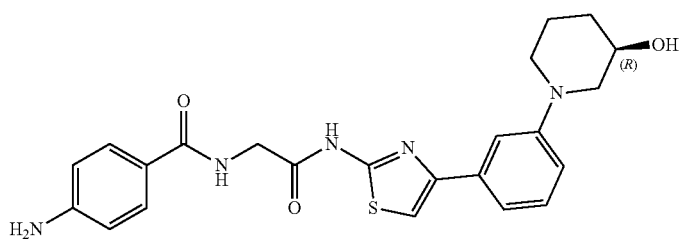 234
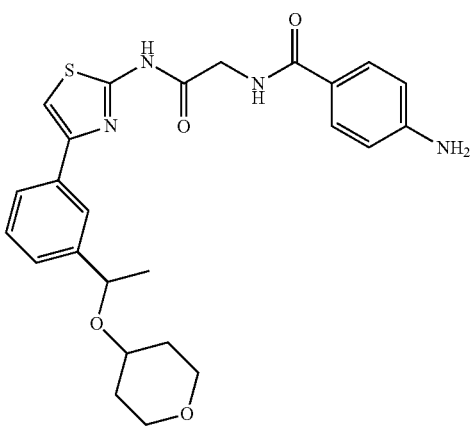 [SMILES: CC(OC1CCOCC1)c1cccc(-c2csc(NC(=O)CNC(=O)c3ccc(N)cc3)n2)c1] 235
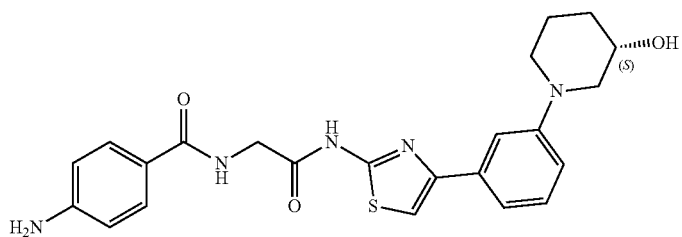 236

TABLE 4-continued
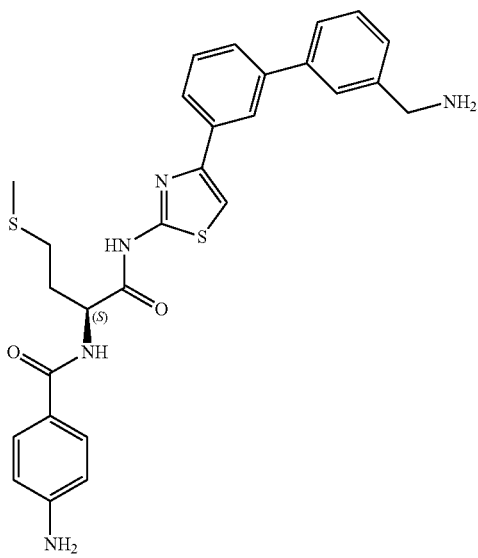 237
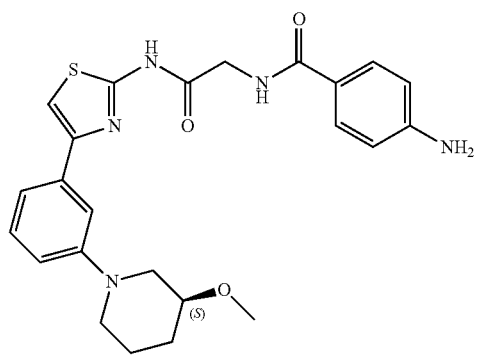 238
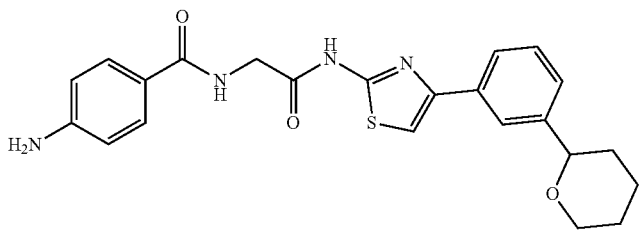 [SMILES: Nc1ccc(C(=O)NCC(=O)Nc2nc(-c3cccc(C4CCCCO4)c3)cs2)cc1] 239
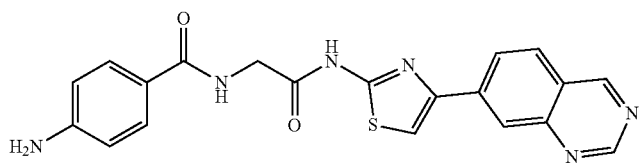 [SMILES: Nc1ccc(C(=O)NCC(=O)Nc2nc(-c3ccc4cncnc4c3)cs2)cc1] 240

TABLE 4-continued

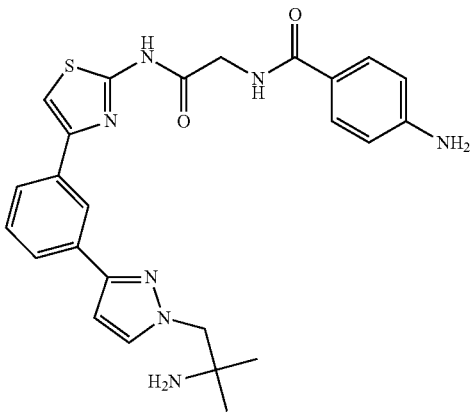 [SMILES: CC(C)(N)Cn1ccc(-c2cccc(-c3csc(NC(=O)CNC(=O)c4ccc(N)cc4)n3)c2)n1]

241

In another aspect, the invention features a pharmaceutical composition that includes any of the foregoing compounds and a pharmaceutically acceptable excipient.

In some embodiments, the pharmaceutical composition includes a compound of Formula I, Formula IV, Formula V, Formula VI, or Formula VII and a pharmaceutically acceptable excipient.

In some embodiments, the compound is any one of compounds 1-241 in Tables 1, 2, 3, and 4.

In another aspect, the invention features a method of decreasing the activity of a BAF complex in a cell, the method involving contacting the cell with an effective amount of any of the foregoing compounds or a pharmaceutical composition thereof.

In some embodiments, the cell is a cancer cell.

In another aspect, the invention features a method of treating a BAF complex-related disorder in a subject in need thereof, the method involving administering to the subject an effective amount of any of the foregoing compounds (e.g., a BRM/BRG1 dual inhibitor compound or a BRM-selective compound) or a pharmaceutical composition thereof.

In some embodiments, the BAF complex-related disorder is cancer.

In a further aspect, the invention features a method of inhibiting BRM, the method involving contacting a cell with an effective amount of any of the foregoing compounds (e.g., a BRM/BRG1 dual inhibitor compound or a BRM-selective compound) or a pharmaceutical composition thereof.

In some embodiments, the cell is a cancer cell.

In another aspect, the invention features a method of inhibiting BRG1, the method involving contacting the cell with an effective amount of any of the foregoing compounds or a pharmaceutical composition thereof.

In some embodiments, the cell is a cancer cell.

In a further aspect, the invention features a method of inhibiting BRM and BRG1, the method involving contacting the cell with an effective amount of any of the foregoing compounds or a pharmaceutical composition thereof.

In some embodiments, the cell is a cancer cell.

In another aspect, the invention features a method of treating a disorder related to a BRG1 loss of function mutation in a subject in need thereof, the method involving administering to the subject an effective amount of any of the foregoing compounds (e.g., a BRM/BRG1 dual inhibitor compound or a BRM-selective compound) or a pharmaceutical composition thereof.

In some embodiments, the disorder related to a BRG1 loss of function mutation is cancer. In other embodiments, the subject is determined to have a BRG1 loss of function disorder, for example, is determined to have a BRG1 loss of function cancer (for example, the cancer has been determined to include cancer cells with loss of BRG1 function).

In another aspect, the invention features a method of inducing apoptosis in a cell, the method involving contacting the cell with an effective amount of any of the foregoing compounds (e.g., a BRM/BRG1 dual inhibitor compound or a BRM-selective compound) or a pharmaceutical composition thereof.

In some embodiments, the cell is a cancer cell.

In a further aspect, the invention features a method of treating cancer in a subject in need thereof, the method including administering to the subject an effective amount of any of the foregoing compounds (e.g., a BRM/BRG1 dual inhibitor compound or a BRM-selective compound) or a pharmaceutical composition thereof.

In some embodiments of any of the foregoing methods, the cancer is non-small cell lung cancer, colorectal cancer, bladder cancer, cancer of unknown primary, glioma, breast cancer, melanoma, non-melanoma skin cancer, endometrial cancer, esophagogastric cancer, pancreatic cancer, hepatobiliary cancer, soft tissue sarcoma, ovarian cancer, head and neck cancer, renal cell carcinoma, bone cancer, non-Hodgkin lymphoma, small-cell lung cancer, prostate cancer, embryonal tumor, germ cell tumor, cervical cancer, thyroid cancer, salivary gland cancer, gastrointestinal neuroendocrine tumor, uterine sarcoma, gastrointestinal stromal tumor, CNS cancer, thymic tumor, Adrenocortical carcinoma, appendiceal cancer, small bowel cancer, or penile cancer.

In some embodiments of any of the foregoing methods, the cancer is non-small cell lung cancer, colorectal cancer, bladder cancer, cancer of unknown primary, glioma, breast cancer, melanoma, non-melanoma skin cancer, endometrial cancer, or penile cancer.

In some embodiments of any of the foregoing methods, the cancer is a drug resistant cancer or has failed to respond to a prior therapy (e.g., vemurafenib, dacarbazine, a CTLA4 inhibitor, a PD1 inhibitor, interferon therapy, a BRAF inhibitor, a MEK inhibitor, radiotherapy, temozolimide, irinotecan, a CAR-T therapy, herceptin, perjeta, tamoxifen, xeloda, docetaxol, platinum agents such as carboplatin, taxanes such as paclitaxel and docetaxel, ALK inhibitors, MET inihibitors, alimta, abraxane, Adriamycin®, gemcitabine, avastin, halaven, neratinib, a PARP inhibitor, ARN810, an mTOR inhibitor, topotecan, gemzar, a VEGFR2 inhibitor, a folate receptor antagonist, demcizumab, fosbretabulin, or a PDL1 inhibitor).

In some embodiments of any of the foregoing methods, the cancer has or has been determined to have BRG1 mutations. In some embodiments of any of the foregoing methods, the BRG1 mutations are homozygous. In some embodiments of any of the foregoing methods, the cancer does not have, or has been determined not to have, an epidermal growth factor receptor (EGFR) mutation. In some embodiments of any of the foregoing methods, the cancer does not have, or has been determined not to have, an anaplastic lymphoma kinase (ALK) driver mutation. In some embodiments of any of the foregoing methods, the cancer has, or has been determined to have, a KRAS mutation. In some embodiments of any of the foregoing methods, the BRG1 mutation is in the ATPase catalytic domain of the protein. In some embodiments of any of the foregoing methods, the BRG1 mutation is a deletion at the C-terminus of BRG1.

In another aspect, the disclosure provides a method treating a disorder related to BAF (e.g., cancer or viral infections) in a subject in need thereof. This method includes contacting a cell with an effective amount of any of the foregoing compounds (e.g., a BRM/BRG1 dual inhibitor compound or a BRM-selective compound), or pharmaceutically acceptable salts thereof, or any of the foregoing pharmaceutical compositions. In some embodiments, the disorder is a viral infection is an infection with a virus of the Retroviridae family such as the lentiviruses (e.g., Human immunodeficiency virus (HIV) and deltaretroviruses (e.g., human T cell leukemia virus I (HTLV-I), human T cell leukemia virus II (HTLV-II)), Hepadnaviridae family (e.g., hepatitis B virus (HBV)), Flaviviridae family (e.g., hepatitis C virus (HCV)), Adenoviridae family (e.g., Human Adenovirus), Herpesviridae family (e.g., Human cytomegalovirus (HCMV), Epstein-Barr virus, herpes simplex virus 1 (HSV-1), herpes simplex virus 2 (HSV-2), human herpesvirus 6 (HHV-6), Herpesvitus K*, CMV, varicella-zoster virus), Papillomaviridae family (e.g., Human Papillomavirus (HPV, HPV E1)), Parvoviridae family (e.g., Parvovirus B19), Polyomaviridae family (e.g., JC virus and BK virus), Paramyxoviridae family (e.g., Measles virus), Togaviridae family (e.g., Rubella virus). In some embodiments, the disorder is Coffin Siris, Neurofibromatosis (e.g., NF-1, NF-2, or Schwannomatosis), or Multiple Meningioma.

In another aspect, the disclosure provides a method for treating a viral infection in a subject in need thereof. This method includes administering to the subject an effective amount of any of the foregoing compounds (e.g., a BRM/BRG1 dual inhibitor compound or a BRM-selective compound), or pharmaceutically acceptable salts thereof, or any of the foregoing pharmaceutical compositions. In some embodiments, the viral infection is an infection with a virus of the Retroviridae family such as the lentiviruses (e.g., Human immunodeficiency virus (HIV) and deltaretroviruses (e.g., human T cell leukemia virus I (HTLV-I), human T cell leukemia virus II (HTLV-II)), Hepadnaviridae family (e.g., hepatitis B virus (HBV)), Flaviviridae family (e.g., hepatitis C virus (HCV)), Adenoviridae family (e.g., Human Adenovirus), Herpesviridae family (e.g., Human cytomegalovirus (HCMV), Epstein-Barr virus, herpes simplex virus 1 (HSV-1), herpes simplex virus 2 (HSV-2), human herpesvirus 6 (HHV-6), Herpesvitus K*, CMV, varicella-zoster virus), Papillomaviridae family (e.g., Human Papillomavirus (HPV, HPV E1)), Parvoviridae family (e.g., Parvovirus B19), Polyomaviridae family (e.g., JC virus and BK virus), Paramyxoviridae family (e.g., Measles virus), or Togaviridae family (e.g., Rubella virus).

In some embodiments of any of the foregoing aspects, the compound is a BRM-selective compound. In some embodiments, the BRM-selective compound inhibits the level and/or activity of BRM at least 10-fold greater than the compound inhibits the level and/or activity of BRG1 and/or the compound binds to BRM at least 10-fold greater than the compound binds to BRG1. For example, in some embodiments, a BRM-selective compound has an $IC_{50}$ or $IP_{50}$ that is at least 10-fold lower than the $IC_{50}$ or $IP_{50}$ against BRG1. In some embodiments of any of the foregoing aspects, the compound is a BRM/BRG1 dual inhibitor compound. In some embodiments, the BRM/BRG1 dual inhibitor compound has similar activity against both BRM and BRG1 (e.g., the activity of the compound against BRM and BRG1 with within 10-fold (e.g., less than 5-fold, less than 2-fold). In some embodiments, the activity of the BRM/BRG1 dual inhibitor compound is greater against BRM. In some embodiments, the activity of the BRM/BRG1 dual inhibitor compound is greater against BRG1. For example, in some embodiments, a BRM/BRG1 dual inhibitor compound has an $IC_{50}$ or $IP_{50}$ against BRM that is within 10-fold of the $IC_{50}$ or $IP_{50}$ against BRG1.

In another aspect, the invention features a method of treating melanoma, prostate cancer, breast cancer, bone cancer, renal cell carcinoma, or a hematologic cancer in a subject in need thereof, the method including administering to the subject an effective amount of any of the foregoing compounds or pharmaceutical compositions thereof.

In another aspect, the invention features a method of reducing tumor growth of melanoma, prostate cancer, breast cancer, bone cancer, renal cell carcinoma, or a hematologic cancer in a subject in need thereof, the method including administering to the subject an effective amount of any of the foregoing compounds or pharmaceutical compositions thereof.

In another aspect, the invention features a method of suppressing metastatic progression of melanoma, prostate cancer, breast cancer, bone cancer, renal cell carcinoma, or a hematologic cancer in a subject, the method including administering an effective amount of any of the foregoing compounds or pharmaceutical compositions thereof.

In another aspect, the invention features a method of suppressing metastatic colonization of melanoma, prostate cancer, breast cancer, bone cancer, renal cell carcinoma, or a hematologic cancer in a subject, the method including administering an effective amount of any of the foregoing compounds or pharmaceutical compositions thereof.

In another aspect, the invention features a method of reducing the level and/or activity of BRG1 and/or BRM in a melanoma, prostate cancer, breast cancer, bone cancer, renal cell carcinoma, or hematologic cancer cell, the method including contacting the cell with an effective amount of any of the foregoing compounds or pharmaceutical compositions thereof.

In some embodiments of any of the above aspects, the melanoma, prostate cancer, breast cancer, bone cancer, renal cell carcinoma, or hematologic cell is in a subject.

In some embodiments of any of the above aspects, the effective amount of the compound reduces the level and/or activity of BRG1 by at least 5% (e.g., 6%, 7%, 8%, 9%, 10%, 15%, 20%, 25%, 30%, 35%, 40%, 45%, 50%, 55%, 60%, 65%, 70%, 75%, 80%, 85%, 90%, or 95%) as compared to a reference. In some embodiments, the effective amount of the compound that reduces the level and/or activity of BRG1 by at least 50% (e.g., 55%, 60%, 65%, 70%, 75%, 80%, 85%, 90%, or 95%) as compared to a reference. In some embodiments, the effective amount of the compound that reduces the level and/or activity of BRG1 by at least 90% (e.g., 91%, 92%, 93%, 94%, 95%, 96%, 97%, 98%, or 99%).

In some embodiments, the effective amount of the compound reduces the level and/or activity of BRG1 by at least 5% (e.g., 6%, 7%, 8%, 9%, 10%, 15%, 20%, 25%, 30%, 35%, 40%, 45%, 50%, 55%, 60%, 65%, 70%, 75%, 80%, 85%, 90%, or 95%) as compared to a reference for at least 12 hours (e.g., 14 hours, 16 hours, 18 hours, 20 hours, 22 hours, 24 hours, 30 hours, 36 hours, 48 hours, 72 hours, or more). In some embodiments, the effective amount of the compound that reduces the level and/or activity of BRG1 by at least 5% (e.g., 6%, 7%, 8%, 9%, 10%, 15%, 20%, 25%, 30%, 35%, 40%, 45%, 50%, 55%, 60%, 65%, 70%, 75%, 80%, 85%, 90%, or 95%) as compared to a reference for at least 4 days (e.g., 5 days, 6 days, 7 days, 14 days, 28 days, or more).

In some embodiments of any of the above aspects, the effective amount of the compound reduces the level and/or activity of BRM by at least 5% (e.g., 6%, 7%, 8%, 9%, 10%, 15%, 20%, 25%, 30%, 35%, 40%, 45%, 50%, 55%, 60%, 65%, 70%, 75%, 80%, 85%, 90%, or 95%) as compared to a reference. In some embodiments, the effective amount of the compound that reduces the level and/or activity of BRM by at least 50% (e.g., 55%, 60%, 65%, 70%, 75%, 80%, 85%, 90%, or 95%) as compared to a reference.

In some embodiments, the effective amount of the compound that reduces the level and/or activity of BRM by at least 90% (e.g., 91%, 92%, 93%, 94%, 95%, 96%, 97%, 98%, or 99%). In some embodiments, the effective amount of the compound reduces the level and/or activity of BRM by at least 5% (e.g., 6%, 7%, 8%, 9%, 10%, 15%, 20%, 25%, 30%, 35%, 40%, 45%, 50%, 55%, 60%, 65%, 70%, 75%, 80%, 85%, 90%, or 95%) as compared to a reference for at least 12 hours (e.g., 14 hours, 16 hours, 18 hours, 20 hours, 22 hours, 24 hours, 30 hours, 36 hours, 48 hours, 72 hours, or more). In some embodiments, the effective amount of the compound that reduces the level and/or activity of BRM by at least 5% (e.g., 6%, 7%, 8%, 9%, 10%, 15%, 20%, 25%, 30%, 35%, 40%, 45%, 50%, 55%, 60%, 65%, 70%, 75%, 80%, 85%, 90%, or 95%) as compared to a reference for at least 4 days (e.g., 5 days, 6 days, 7 days, 14 days, 28 days, or more).

In some embodiments, the subject has cancer. In some embodiments, the cancer expresses BRG1 and/or BRM protein and/or the cell or subject has been identified as expressing BRG1 and/or BRM. In some embodiments, the cancer expresses BRG1 protein and/or the cell or subject has been identified as expressing BRG1. In some embodiments, the cancer expresses BRM protein and/or the cell or subject has been identified as expressing BRM. In some embodiments, the cancer is melanoma (e.g., uveal melanoma, mucosal melanoma, or cutaneous melanoma). In some embodiments, the cancer is prostate cancer. In some embodiments, the cancer is a hematologic cancer, e.g., multiple myeloma, large cell lymphoma, acute T-cell leukemia, acute myeloid leukemia, myelodysplastic syndrome, immunoglobulin A lambda myeloma, diffuse mixed histiocytic and lymphocytic lymphoma, B-cell lymphoma, acute lymphoblastic leukemia (e.g., T-cell acute lymphoblastic leukemia or B-cell acute lymphoblastic leukemia), diffuse large cell lymphoma, or non-Hodgkin's lymphoma. In some embodiments, the cancer is breast cancer (e.g., an ER positive breast cancer, an ER negative breast cancer, triple positive breast cancer, or triple negative breast cancer). In some embodiments, the cancer is a bone cancer (e.g., Ewing's sarcoma). In some embodiments, the cancer is a renal cell carcinoma (e.g., a Microphthalmia Transcription Factor (MITF) family translocation renal cell carcinoma (tRCC)). In some embodiments, the cancer is metastatic (e.g., the cancer has spread to the liver). The metastatic cancer can include cells exhibiting migration and/or invasion of migrating cells and/or include cells exhibiting endothelial recruitment and/or angiogenesis. In other embodiments, the migrating cancer is a cell migration cancer. In still other embodiments, the cell migration cancer is a non-metastatic cell migration cancer. The metastatic cancer can be a cancer spread via seeding the surface of the peritoneal, pleural, pericardial, or subarachnoid spaces. Alternatively, the metastatic cancer can be a cancer spread via the lymphatic system, or a cancer spread hematogenously. In some embodiments, the effective amount of an agent that reduces the level and/or activity of BRG1 and/or BRM is an amount effective to inhibit metastatic colonization of the cancer to the liver.

In some embodiments the cancer harbors a mutation in GNAQ. In some embodiments the cancer harbors a mutation in GNA11. In some embodiments the cancer harbors a mutation in PLCB4. In some embodiments the cancer harbors a mutation in CYSLTR2. In some embodiments the cancer harbors a mutation in BAP1. In some embodiments the cancer harbors a mutation in SF3B1. In some embodiments the cancer harbors a mutation in EIF1AX. In some embodiments the cancer harbors a TFE3 translocation. In some embodiments the cancer harbors a TFEB translocation. In some embodiments the cancer harbors a M/TF translocation. In some embodiments the cancer harbors an EZH2 mutation. In some embodiments the cancer harbors a SUZ12 mutation. In some embodiments the cancer harbors an EED mutation.

In some embodiments, the method further includes administering to the subject or contacting the cell with an anticancer therapy, e.g., a chemotherapeutic or cytotoxic agent, immunotherapy, surgery, radiotherapy, thermotherapy, or photocoagulation. In some embodiments, the anticancer therapy is a chemotherapeutic or cytotoxic agent, e.g., an antimetabolite, antimitotic, antitumor antibiotic, asparagine-specific enzyme, bisphosphonates, antineoplastic, alkylating agent, DNA-Repair enzyme inhibitor, histone deacetylase inhibitor, corticosteroid, demethylating agent, immunomodulatory, janus-associated kinase inhibitor, phosphinositide 3-kinase inhibitor, proteasome inhibitor, or tyrosine kinase inhibitor.

In some embodiments, the compound of the invention is used in combination with another anti-cancer therapy used for the treatment of uveal melanoma such as surgery, a MEK inhibitor, and/or a PKC inhibitor. For example, in some embodiments, the method further comprises performing surgery prior to, subsequent to, or at the same time as administration of the compound of the invention. In some embodiments, the method further comprises administration of a MEK inhibitor and/or a PKC inhibitor prior to, subsequent to, or at the same time as administration of the compound of the invention.

In some embodiments, the anticancer therapy and the compound of the invention are administered within 28 days of each other and each in an amount that together are effective to treat the subject.

In some embodiments, the subject or cancer has and/or has been identified as having a BRG1 loss of function mutation. In some embodiments, the subject or cancer has and/or has been identified as having a BRM loss of function mutation.

In some embodiments, the cancer is resistant to one or more chemotherapeutic or cytotoxic agents (e.g., the cancer has been determined to be resistant to chemotherapeutic or cytotoxic agents such as by genetic markers, or is likely to be resistant, to chemotherapeutic or cytotoxic agents such as a cancer that has failed to respond to a chemotherapeutic or cytotoxic agent). In some embodiments, the cancer has failed to respond to one or more chemotherapeutic or cytotoxic agents. In some embodiments, the cancer is resistant or has failed to respond to dacarbazine, temozolomide, cisplatin, treosulfan, fotemustine, IMCgp100, a CTLA-4 inhibitor (e.g., ipilimumab), a PD-1 inhibitor (e.g., Nivolumab or pembrolizumab), a PD-L1 inhibitor (e.g., atezolizumab, avelumab, or durvalumab), a mitogen-activated protein kinase (MEK) inhibitor (e.g., selumetinib, binimetinib, or tametinib), and/or a protein kinase C (PKC) inhibitor (e.g., sotrastaurin or IDE196).

In some embodiments, the cancer is resistant to or failed to respond to a previously administered therapeutic used for the treatment of uveal melanoma such as a MEK inhibitor or PKC inhibitor. For example, in some embodiments, the cancer is resistant to or failed to respond to a mitogen-activated protein kinase (MEK) inhibitor (e.g., selumetinib, binimetinib, or tametinib), and/or a protein kinase C (PKC) inhibitor (e.g., sotrastaurin or IDE196).

Chemical Terms

The terminology employed herein is for the purpose of describing particular embodiments and is not intended to be limiting.

For any of the following chemical definitions, a number following an atomic symbol indicates that total number of atoms of that element that are present in a particular chemical moiety. As will be understood, other atoms, such as H atoms, or substituent groups, as described herein, may be present, as necessary, to satisfy the valences of the atoms. For example, an unsubstituted $C_2$ alkyl group has the formula —$CH_2CH_3$. When used with the groups defined herein, a reference to the number of carbon atoms includes the divalent carbon in acetal and ketal groups but does not include the carbonyl carbon in acyl, ester, carbonate, or carbamate groups. A reference to the number of oxygen, nitrogen, or sulfur atoms in a heteroaryl group only includes those atoms that form a part of a heterocyclic ring.

The term "acyl," as used herein, represents a H or an alkyl group that is attached to a parent molecular group through a carbonyl group, as defined herein, and is exemplified by formyl (i.e., a carboxyaldehyde group), acetyl, trifluoroacetyl, propionyl, and butanoyl. Exemplary unsubstituted acyl groups include from 1 to 6, from 1 to 11, or from 1 to 21 carbons.

The term "alkyl," as used herein, refers to a branched or straight-chain monovalent saturated aliphatic hydrocarbon radical of 1 to 20 carbon atoms (e.g., 1 to 16 carbon atoms, 1 to 10 carbon atoms, 1 to 6 carbon atoms, or 1 to 3 carbon atoms).

An alkylene is a divalent alkyl group. The term "alkenyl," as used herein, alone or in combination with other groups, refers to a straight chain or branched hydrocarbon residue having a carbon-carbon double bond and having 2 to 20 carbon atoms (e.g., 2 to 16 carbon atoms, 2 to 10 carbon atoms, 2 to 6 carbon atoms, or 2 carbon atoms).

The term "alkynyl," as used herein, alone or in combination with other groups, refers to a straight chain or branched hydrocarbon residue having a carbon-carbon triple bond and having 2 to 20 carbon atoms (e.g., 2 to 16 carbon atoms, 2 to 10 carbon atoms, 2 to 6 carbon atoms, or 2 carbon atoms).

The term "amino," as used herein, represents —$N(R^{N1})_2$, wherein each $R^{N1}$ is, independently, H, OH, $NO_2$, $N(R^{N2})_2$, $SO_2OR^{N2}$, $SO_2R^{N2}$, $SOR^{N2}$, an N-protecting group, alkyl, alkoxy, aryl, arylalkyl, cycloalkyl, acyl (e.g., acetyl, trifluoroacetyl, or others described herein), wherein each of these recited $R^{N1}$ groups can be optionally substituted; or two $R^{N1}$ combine to form an alkylene or heteroalkylene, and wherein each $R^{N2}$ is, independently, H, alkyl, or aryl. The amino groups of the invention can be an unsubstituted amino (i.e., —$NH_2$) or a substituted amino (i.e., —$N(R^{N1})_2$).

The term "aryl," as used herein, refers to an aromatic mono- or polycarbocyclic radical of 6 to 12 carbon atoms having at least one aromatic ring. Examples of such groups include, but are not limited to, phenyl, naphthyl, 1,2,3,4-tetrahydronaphthyl, 1,2-dihydronaphthyl, indanyl, and 1H-indenyl.

The term "arylalkyl," as used herein, represents an alkyl group substituted with an aryl group. Exemplary unsubstituted arylalkyl groups are from 7 to 30 carbons (e.g., from 7 to 16 or from 7 to 20 carbons, such as $C_1$-$C_6$ alkyl $C_6$-$C_{10}$ aryl, $C_1$-$C_{10}$ alkyl $C_6$-$C_{10}$ aryl, or $C_1$-$C_{20}$ alkyl $C_6$-$C_{10}$ aryl), such as, benzyl and phenethyl. In some embodiments, the alkyl and the aryl each can be further substituted with 1, 2, 3, or 4 substituent groups as defined herein for the respective groups.

The term "azido," as used herein, represents a —$N_3$ group.

The term "bridged polycycloalkyl," as used herein, refers to a bridged polycyclic group of 5 to 20 carbons, containing from 1 to 3 bridges.

The term "cyano," as used herein, represents a —CN group.

The term "carbocyclyl," as used herein, refers to a non-aromatic $C_3$-$C_{12}$ monocyclic, bicyclic, or tricyclic structure in which the rings are formed by carbon atoms. Carbocyclyl structures include cycloalkyl groups and unsaturated carbocyclyl radicals.

The term "cycloalkyl," as used herein, refers to a saturated, non-aromatic, and monovalent mono- or polycarbocyclic radical of 3 to 10, preferably 3 to 6 carbon atoms. This term is further exemplified by radicals such as cyclopropyl, cyclobutyl, cyclopentyl, cyclohexyl, cycloheptyl, norbornyl, and adamantyl.

The term "halo," as used herein, means a fluorine (fluoro), chlorine (chloro), bromine (bromo), or iodine (iodo) radical.

The term "heteroalkyl," as used herein, refers to an alkyl group, as defined herein, in which one or more of the constituent carbon atoms have been replaced by nitrogen, oxygen, or sulfur. In some embodiments, the heteroalkyl group can be further substituted with 1, 2, 3, or 4 substituent groups as described herein for alkyl groups. Examples of heteroalkyl groups are an "alkoxy" which, as used herein, refers alkyl-O— (e.g., methoxy and ethoxy). A heteroalkylene is a divalent heteroalkyl group. The term "heteroalkenyl," as used herein, refers to an alkenyl group, as defined herein, in which one or more of the constituent carbon atoms have been replaced by nitrogen, oxygen, or sulfur. In some embodiments, the heteroalkenyl group can be further substituted with 1, 2, 3, or 4 substituent groups as described herein for alkenyl groups. Examples of heteroalkenyl groups are an "alkenoxy" which, as used herein, refers alkenyl-O—. A heteroalkenylene is a divalent heteroalkenyl group. The term "heteroalkynyl," as used herein, refers to an alkynyl group, as defined herein, in which one or more of the constituent carbon atoms have been replaced by nitrogen, oxygen, or sulfur. In some embodiments, the heteroalkynyl group can be further substituted with 1, 2, 3, or 4 substituent groups as described herein for alkynyl groups. Examples of heteroalkynyl groups are an "alkynoxy" which, as used herein, refers alkynyl-O—. A heteroalkynylene is a divalent heteroalkynyl group.

The term "heteroaryl," as used herein, refers to an aromatic mono- or polycyclic radical of 5 to 12 atoms having at least one aromatic ring containing 1, 2, or 3 ring atoms selected from nitrogen, oxygen, and sulfur, with the remaining ring atoms being carbon. One or two ring carbon atoms of the heteroaryl group may be replaced with a carbonyl group. Examples of heteroaryl groups are pyridyl, pyrazoyl, benzooxazolyl, benzoimidazolyl, benzothiazolyl, imidazolyl, oxaxolyl, and thiazolyl.

The term "heteroarylalkyl," as used herein, represents an alkyl group substituted with a heteroaryl group. Exemplary unsubstituted heteroarylalkyl groups are from 7 to 30 carbons (e.g., from 7 to 16 or from 7 to 20 carbons, such as $C_1$-$C_6$ alkyl $C_2$-$C_9$ heteroaryl, $C_1$-$C_{10}$ alkyl $C_2$-$C_9$ heteroaryl, or $C_1$-$C_{20}$ alkyl $C_2$-$C_9$ heteroaryl). In some embodiments, the alkyl and the heteroaryl each can be further substituted with 1, 2, 3, or 4 substituent groups as defined herein for the respective groups.

The term "heterocyclyl," as used herein, refers a mono- or polycyclic radical having 3 to 12 atoms having at least one ring containing 1, 2, 3, or 4 ring atoms selected from N, O or S, wherein no ring is aromatic. Examples of heterocyclyl groups include, but are not limited to, morpholinyl, thiomorpholinyl, furyl, piperazinyl, piperidinyl, pyranyl, pyrrolidinyl, tetrahydropyranyl, tetrahydrofuranyl, and 1,3-dioxanyl.

The term "heterocyclylalkyl," as used herein, represents an alkyl group substituted with a heterocyclyl group. Exemplary unsubstituted heterocyclylalkyl groups are from 7 to 30 carbons (e.g., from 7 to 16 or from 7 to 20 carbons, such as $C_1$-$C_6$ alkyl $C_2$-$C_9$ heterocyclyl, $C_1$-$C_{10}$ alkyl $C_2$-$C_9$ heterocyclyl, or $C_1$-$C_{20}$ alkyl $C_2$-$C_9$ heterocyclyl). In some embodiments, the alkyl and the heterocyclyl each can be further substituted with 1, 2, 3, or 4 substituent groups as defined herein for the respective groups.

The term "hydroxyalkyl," as used herein, represents alkyl group substituted with an —OH group.

The term "hydroxyl," as used herein, represents an —OH group.

The term "N-protecting group," as used herein, represents those groups intended to protect an amino group against undesirable reactions during synthetic procedures. Commonly used N-protecting groups are disclosed in Greene, "Protective Groups in Organic Synthesis," 3rd Edition (John Wiley & Sons, New York, 1999). N-protecting groups include, but are not limited to, acyl, aryloyl, or carbamyl groups such as formyl, acetyl, propionyl, pivaloyl, t-butylacetyl, 2-chloroacetyl, 2-bromoacetyl, trifluoroacetyl, trichloroacetyl, phthalyl, o-nitrophenoxyacetyl, α-chlorobutyryl, benzoyl, 4-chlorobenzoyl, 4-bromobenzoyl, 4-nitrobenzoyl, and chiral auxiliaries such as protected or unprotected D, L, or D, L-amino acids such as alanine, leucine, and phenylalanine; sulfonyl-containing groups such as benzenesulfonyl, and p-toluenesulfonyl; carbamate forming groups such as benzyloxycarbonyl, p-chlorobenzyloxycarbonyl, p-methoxybenzyloxycarbonyl, p-nitrobenzyloxycarbonyl, 2-nitrobenzyloxycarbonyl, p-bromobenzyloxycarbonyl, 3,4-dimethoxybenzyloxycarbonyl, 3,5-dimethoxybenzyloxycarbonyl, 2,4-dimethoxybenzyloxycarbonyl, 4-methoxybenzyloxycarbonyl, 2-nitro-4,5-dimethoxybenzyloxycarbonyl, 3,4,5-trimethoxybenzyloxycarbonyl, 1-(p-biphenylyl)-1-methylethoxycarbonyl, α,α-dimethyl-3,5-dimethoxybenzyloxycarbonyl, benzhydryloxy carbonyl, t-butyloxycarbonyl, diisopropylmethoxycarbonyl, isopropyloxycarbonyl, ethoxycarbonyl, methoxycarbonyl, allyloxycarbonyl, 2,2,2-trichloroethoxycarbonyl, phenoxycarbonyl, 4-nitrophenoxy carbonyl, fluorenyl-9-methoxycarbonyl, cyclopentyloxycarbonyl, adamantyloxycarbonyl, cyclohexyloxycarbonyl, and phenylthiocarbonyl, arylalkyl groups such as benzyl, triphenylmethyl, and benzyloxymethyl, and silyl groups, such as trimethylsilyl. Preferred N-protecting groups are alloc, formyl, acetyl, benzoyl, pivaloyl, t-butylacetyl, alanyl, phenylsulfonyl, benzyl, t-butyloxycarbonyl (Boc), and benzyloxycarbonyl (Cbz).

The term "nitro," as used herein, represents an —NO$_2$ group.

The term "thiol," as used herein, represents an —SH group.

The alkyl, alkenyl, alkynyl, heteroalkyl, heteroalkenyl, heteroalkynyl, carbocyclyl (e.g., cycloalkyl), aryl, heteroaryl, and heterocyclyl groups may be substituted or unsubstituted. When substituted, there will generally be 1 to 4 substituents present, unless otherwise specified. Substituents include, for example: alkyl (e.g., unsubstituted and substituted, where the substituents include any group described herein, e.g., aryl, halo, hydroxy), aryl (e.g., substituted and unsubstituted phenyl), carbocyclyl (e.g., substituted and unsubstituted cycloalkyl), halo (e.g., fluoro), hydroxyl, heteroalkyl (e.g., substituted and unsubstituted methoxy, ethoxy, or thioalkoxy), heteroaryl, heterocyclyl, amino (e.g., NH$_2$ or mono- or dialkyl amino), azido, cyano, nitro, or thiol. Aryl, carbocyclyl (e.g., cycloalkyl), heteroaryl, and heterocyclyl groups may also be substituted with alkyl (unsubstituted and substituted such as arylalkyl (e.g., substituted and unsubstituted benzyl)).

Compounds of the invention can have one or more asymmetric carbon atoms and can exist in the form of optically pure enantiomers, mixtures of enantiomers such as, for example, racemates, optically pure diastereoisomers, mixtures of diastereoisomers, diastereoisomeric racemates, or mixtures of diastereoisomeric racemates. The optically active forms can be obtained for example by resolution of the racemates, by asymmetric synthesis or asymmetric chromatography (chromatography with a chiral adsorbents or eluant). That is, certain of the disclosed compounds may exist in various stereoisomeric forms. Stereoisomers are compounds that differ only in their spatial arrangement. Enantiomers are pairs of stereoisomers whose mirror images are not superimposable, most commonly because they contain an asymmetrically substituted carbon atom that acts as a chiral center. "Enantiomer" means one of a pair of molecules that are mirror images of each other and are not superimposable. Diastereomers are stereoisomers that are not related as mirror images, most commonly because they contain two or more asymmetrically substituted carbon atoms and represent the configuration of substituents around one or more chiral carbon atoms. Enantiomers of a compound can be prepared, for example, by separating an enantiomer from a racemate using one or more well-known techniques and methods, such as, for example, chiral chromatography and separation methods based thereon. The appropriate technique and/or method for separating an enantiomer of a compound described herein from a racemic mixture can be readily determined by those of skill in the art. "Racemate" or "racemic mixture" means a compound containing two enantiomers, wherein such mixtures exhibit no optical activity; i.e., they do not rotate the plane of polarized light. "Geometric isomer" means isomers that differ in the orientation of substituent atoms in relationship to a carbon-carbon double bond, to a cycloalkyl ring, or to a bridged bicyclic system. Atoms (other than H) on each side of a carbon-carbon double bond may be in an E (substituents are on opposite sides of the carbon-carbon double bond) or Z (substituents are oriented on the same side) configuration. "R," "S," "S*," "R*," "E," "Z," "cis," and "trans," indicate configurations relative to the core molecule. Certain of the disclosed compounds may exist in atropisomeric forms. Atropisomers are stereoisomers resulting from hindered rotation about single bonds where the steric strain barrier to rotation is high enough to allow for the isolation of the conformers. The compounds of the invention may be prepared as individual isomers by either isomer-specific synthesis or resolved from an isomeric mixture. Conventional resolution techniques include forming the salt of a free base of each isomer of an isomeric pair using an optically active acid (followed by fractional crystallization and regeneration of the free base), forming the salt of the acid form of each isomer of an isomeric pair using an optically active amine (followed by fractional crystallization and regeneration of the free acid), forming an ester or amide 35 of each of the isomers of an isomeric pair using an optically pure acid, amine or alcohol (followed by chromatographic separation and removal of the chiral auxiliary), or resolving an isomeric mixture of either a starting material or a final product using various well known chromatographic methods. When the stereochemistry of a disclosed compound is named or depicted by structure, the named or depicted stereoisomer is at least 60%, 70%, 80%, 90%, 99%, or 99.9% by weight relative to the other stereoisomers. When a single enantiomer is named or depicted by structure, the depicted or named enantiomer is at least 60%, 70%, 80%, 90%, 99%, or 99.9% by weight optically pure. When a single diastereomer is named or depicted by structure, the depicted or named diastereomer is at least 60%, 70%, 80%, 90%, 99%, or 99.9% by weight pure. Percent optical purity is the ratio of the weight of the enantiomer or over the weight of the enantiomer plus the weight of its optical isomer. Diastereomeric purity by weight is the ratio of the weight of one diastereomer or over the weight of all the diastereomers. When the stereochemistry of a disclosed compound is named or depicted by structure, the named or depicted stereoisomer is at least 60%, 70%, 80%, 90%, 99%, or 99.9% by mole fraction pure relative to the other stereoisomers. When a single enantiomer is named or depicted by structure, the depicted or named enantiomer is at least 60%, 70%, 80%, 90%, 99%, or 99.9% by mole fraction pure. When a single diastereomer is named or depicted by structure, the depicted or named diastereomer is at least 60%, 70%, 80%, 90%, 99%, or 99.9% by mole fraction pure. Percent purity by mole fraction is the ratio of the moles of the enantiomer or over the moles of the enantiomer plus the moles of its optical isomer. Similarly, percent purity by moles fraction is the ratio of the moles of the diastereomer or over the moles of the diastereomer plus the moles of its isomer. When a disclosed compound is named or depicted by structure without indicating the stereochemistry, and the compound has at least one chiral center, it is to be understood that the name or structure encompasses either enantiomer of the compound free from the corresponding optical isomer, a racemic mixture of the compound, or mixtures enriched in one enantiomer relative to its corresponding optical isomer. When a disclosed compound is named or depicted by structure without indicating the stereochemistry and has two or more chiral centers, it is to be understood that the name or structure encompasses a diastereomer free of other diastereomers, a number of diastereomers free from other diastereomeric pairs, mixtures of diastereomers, mixtures of diastereomeric pairs, mixtures of diastereomers in which one diastereomer is enriched relative to the other diastereomer(s), or mixtures of diastereomers in which one or more diastereomer is enriched relative to the other diastereomers. The invention embraces all of these forms.

Unless otherwise defined, all technical and scientific terms used herein have the same meaning as commonly understood by one of ordinary skill in the art to which this invention belongs. Methods and materials are described herein for use in the present disclosure; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Definitions

In this application, unless otherwise clear from context, (i) the term "a" may be understood to mean "at least one"; (ii) the term "or" may be understood to mean "and/or"; and (iii) the terms "comprising" and "including" may be understood to encompass itemized components or steps whether presented by themselves or together with one or more additional components or steps.

As used herein, the terms "about" and "approximately" refer to a value that is within 10% above or below the value being described. For example, the term "about 5 nM" indicates a range of from 4.5 to 5.5 nM.

As used herein, the term "administration" refers to the administration of a composition (e.g., a compound or a preparation that includes a compound as described herein) to a subject or system. Administration to an animal subject (e.g., to a human) may be by any appropriate route. For example, in some embodiments, administration may be bronchial (including by bronchial instillation), buccal, enteral, interdermal, intra-arterial, intradermal, intragastric, intramedullary, intramuscular, intranasal, intraperitoneal, intrathecal, intratumoral, intravenous, intraventricular, mucosal, nasal, oral, rectal, subcutaneous, sublingual, topical, tracheal (including by intratracheal instillation), transdermal, vaginal, and vitreal.

As used herein, the term "BAF complex" refers to the BRG1- or HRBM-associated factors complex in a human cell.

As used herein, the term "BAF complex-related disorder" refers to a disorder that is caused or affected by the level of activity of a BAF complex.

As used herein, the term "BRG1 loss of function mutation" refers to a mutation in BRG1 that leads to the protein having diminished activity (e.g., at least 1% reduction in BRG1 activity, for example 2%, 5%, 10%, 25%, 50%, or 100% reduction in BRG1 activity). Exemplary BRG1 loss of function mutations include, but are not limited to, a homozygous BRG1 mutation and a deletion at the C-terminus of BRG1.

As used herein, the term "BRG1 loss of function disorder" refers to a disorder (e.g., cancer) that exhibits a reduction in BRG1 activity (e.g., at least 1% reduction in BRG1 activity, for example 2%, 5%, 10%, 25%, 50%, or 100% reduction in BRG1 activity).

As used herein, the term "BRM-selective compound," refers to a compound that has greater activity against BRM than against BRG1 (e.g., the compound inhibits the level and/or activity of BRM at least 2-fold (e.g, at least 5-fold, at least 10-fold, at least 20-fold, at least 50-fold, at least 100-fold) greater than the compound inhibits the level and/or activity of BRG1 and/or the compound binds to BRM at least 2-fold (e.g., at least 5-fold, at least 10-fold, at least 20-fold, at least 50-fold, at least 100-fold) greater than the compound binds to BRG1). For example, in some embodiments, a BRM-selective compound has an $IC_{50}$ or $IP_{50}$ that is at least 2-fold (e.g, at least 5-fold, at least 10-fold, at least 20-fold, at least 50-fold, at least 100-fold) lower than the $IC_{50}$ or $IP_{50}$ against BRG1.

As used herein, the term "BRM/BRG1 dual inhibitor compound" refers to a compound that has activity against both BRM and BRG1. In some embodiments, a BRM/BRG1 dual inhibitor compound has similar activity against both BRM and BRG1 (e.g., the activity of the compound against BRM and BRG1 is within 10-fold (e.g., less than 5-fold, less than 2-fold)). For example, in some embodiments, a BRM/BRG1 dual inhibitor compound has an $IC_{50}$ or $IP_{50}$ against BRM that is within 10-fold of the $IC_{50}$ or $IP_{50}$ against BRG1.

The term "cancer" refers to a condition caused by the proliferation of malignant neoplastic cells, such as tumors, neoplasms, carcinomas, sarcomas, leukemias, and lymphomas.

As used herein, a "combination therapy" or "administered in combination" means that two (or more) different agents or treatments are administered to a subject as part of a defined treatment regimen for a particular disease or condition. The treatment regimen defines the doses and periodicity of administration of each agent such that the effects of the separate agents on the subject overlap. In some embodiments, the delivery of the two or more agents is simultaneous or concurrent and the agents may be co-formulated. In some embodiments, the two or more agents are not co-formulated and are administered in a sequential manner as part of a prescribed regimen. In some embodiments, administration of two or more agents or treatments in combination is such that the reduction in a symptom, or other parameter related to the disorder is greater than what would be observed with one agent or treatment delivered alone or in the absence of the other. The effect of the two treatments can be partially additive, wholly additive, or greater than additive (e.g., synergistic). Sequential or substantially simultaneous administration of each therapeutic agent can be effected by any appropriate route including, but not limited to, oral routes, intravenous routes, intramuscular routes, and direct absorption through mucous membrane tissues. The therapeutic agents can be administered by the same route or by different routes. For example, a first therapeutic agent of the combination may be administered by intravenous injection while a second therapeutic agent of the combination may be administered orally.

By "determining the level" of a protein or RNA is meant the detection of a protein or an RNA, by methods known in the art, either directly or indirectly. "Directly determining" means performing a process (e.g., performing an assay or test on a sample or "analyzing a sample" as that term is defined herein) to obtain the physical entity or value. "Indirectly determining" refers to receiving the physical entity or value from another party or source (e.g., a third party laboratory that directly acquired the physical entity or value). Methods to measure protein level generally include, but are not limited to, western blotting, immunoblotting, enzyme-linked immunosorbent assay (ELISA), radioimmunoassay (RIA), immunoprecipitation, immunofluorescence, surface plasmon resonance, chemiluminescence, fluorescent polarization, phosphorescence, immunohistochemical analysis, matrix-assisted laser desorption/ionization time-of-flight (MALDI-TOF) mass spectrometry, liquid chromatography (LC)-mass spectrometry, microcytometry, microscopy, fluorescence activated cell sorting (FACS), and flow cytometry, as well as assays based on a property of a protein including, but not limited to, enzymatic activity or interaction with other protein partners. Methods to measure RNA levels are known in the art and include, but are not limited to, quantitative polymerase chain reaction (qPCR) and Northern blot analyses.

By a "decreased level" or an "increased level" of a protein or RNA is meant a decrease or increase, respectively, in a protein or RNA level, as compared to a reference (e.g., a decrease or an increase by about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, about 100%, about 150%, about 200%, about 300%, about 400%, about 500%, or more; a decrease or an increase of more than about 10%, about 15%, about 20%, about 50%, about 75%, about 100%, or about 200%, as compared to a reference; a decrease or an increase by less than about 0.01-fold, about 0.02-fold, about 0.1-fold, about 0.3-fold, about 0.5-fold, about 0.8-fold, or less; or an increase by more than about 1.2-fold, about 1.4-fold, about 1.5-fold, about 1.8-fold, about 2.0-fold, about 3.0-fold, about 3.5-fold, about 4.5-fold, about 5.0-fold, about 10-fold, about 15-fold, about 20-fold, about 30-fold, about 40-fold, about 50-fold, about 100-fold, about 1000-fold, or more). A level of a protein may be expressed in mass/vol (e.g., g/dL, mg/mL, μg/mL, ng/mL) or percentage relative to total protein in a sample.

By "decreasing the activity of a BAF complex" is meant decreasing the level of an activity related to a BAF complex, or a related downstream effect. A non-limiting example of decreasing an activity of a BAF complex is Sox2 activation. The activity level of a BAF complex may be measured using any method known in the art, e.g., the methods described in Kadoch et al. Cell, 2013, 153, 71-85, the methods of which are herein incorporated by reference.

As used herein, the term "inhibiting BRM" refers to blocking or reducing the level or activity of the ATPase catalytic binding domain or the bromodomain of the protein. BRM inhibition may be determined using methods known in the art, e.g., a BRM ATPase assay, a Nano DSF assay, or a BRM Luciferase cell assay.

The term "pharmaceutical composition," as used herein, represents a composition containing a compound described herein formulated with a pharmaceutically acceptable excipient and appropriate for administration to a mammal, for example a human. Typically, a pharmaceutical composition is manufactured or sold with the approval of a governmental regulatory agency as part of a therapeutic regimen for the treatment of disease in a mammal. Pharmaceutical compositions can be formulated, for example, for oral administration in unit dosage form (e.g., a tablet, capsule, caplet, gelcap, or syrup); for topical administration (e.g., as a cream, gel, lotion, or ointment); for intravenous administration (e.g., as a sterile solution free of particulate emboli and in a solvent system suitable for intravenous use); or in any other pharmaceutically acceptable formulation.

A "pharmaceutically acceptable excipient," as used herein, refers to any ingredient other than the compounds described herein (for example, a vehicle capable of suspending or dissolving the active compound) and having the properties of being substantially nontoxic and non-inflammatory in a patient. Excipients may include, for example:

antiadherents, antioxidants, binders, coatings, compression aids, disintegrants, dyes (colors), emollients, emulsifiers, fillers (diluents), film formers or coatings, flavors, fragrances, glidants (flow enhancers), lubricants, preservatives, printing inks, sorbents, suspensing or dispersing agents, sweeteners, and waters of hydration. Exemplary excipients include, but are not limited to: butylated hydroxytoluene (BHT), calcium carbonate, calcium phosphate (dibasic), calcium stearate, croscarmellose, crosslinked polyvinyl pyrrolidone, citric acid, crospovidone, cysteine, ethylcellulose, gelatin, hydroxypropyl cellulose, hydroxypropyl methylcellulose, lactose, magnesium stearate, maltitol, mannitol, methionine, methylcellulose, methyl paraben, microcrystalline cellulose, polyethylene glycol, polyvinyl pyrrolidone, povidone, pregelatinized starch, propyl paraben, retinyl palmitate, shellac, silicon dioxide, sodium carboxymethyl cellulose, sodium citrate, sodium starch glycolate, sorbitol, starch (corn), stearic acid, sucrose, talc, titanium dioxide, vitamin A, vitamin E, vitamin C, and xylitol.

As used herein, the term "pharmaceutically acceptable salt" means any pharmaceutically acceptable salt of a compound, for example, any compound of Formula I, Formula IV, Formula V, Formula VI, or Formula VII. Pharmaceutically acceptable salts of any of the compounds described herein may include those that are within the scope of sound medical judgment, suitable for use in contact with the tissues of humans and animals without undue toxicity, irritation, allergic response and are commensurate with a reasonable benefit/risk ratio. Pharmaceutically acceptable salts are well known in the art. For example, pharmaceutically acceptable salts are described in: Berge et al., J. Pharmaceutical Sciences 66:1-19, 1977 and in Pharmaceutical Salts: Properties, Selection, and Use, (Eds. P. H. Stahl and C. G. Wermuth), Wiley-VCH, 2008. The salts can be prepared in situ during the final isolation and purification of the compounds described herein or separately by reacting a free base group with a suitable organic acid.

The compounds of the invention may have ionizable groups so as to be capable of preparation as pharmaceutically acceptable salts. These salts may be acid addition salts involving inorganic or organic acids or the salts may, in the case of acidic forms of the compounds of the invention be prepared from inorganic or organic bases. Frequently, the compounds are prepared or used as pharmaceutically acceptable salts prepared as addition products of pharmaceutically acceptable acids or bases. Suitable pharmaceutically acceptable acids and bases and methods for preparation of the appropriate salts are well-known in the art. Salts may be prepared from pharmaceutically acceptable non-toxic acids and bases including inorganic and organic acids and bases. Representative acid addition salts include acetate, adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, fumarate, glucoheptonate, glycerophosphate, hemisulfate, heptonate, hexanoate, hydrobromide, hydrochloride, hydroiodide, 2-hydroxyethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, toluenesulfonate, undecanoate, and valerate salts. Representative alkali or alkaline earth metal salts include sodium, lithium, potassium, calcium, and magnesium, as well as nontoxic ammonium, quaternary ammonium, and amine cations, including, but not limited to ammonium, tetramethylammonium, tetraethylammonium, methylamine, dimethylamine, trimethylamine, triethylamine, and ethylamine.

By a "reference" is meant any useful reference used to compare protein or RNA levels. The reference can be any sample, standard, standard curve, or level that is used for comparison purposes. The reference can be a normal reference sample or a reference standard or level. A "reference sample" can be, for example, a control, e.g., a predetermined negative control value such as a "normal control" or a prior sample taken from the same subject; a sample from a normal healthy subject, such as a normal cell or normal tissue; a sample (e.g., a cell or tissue) from a subject not having a disease; a sample from a subject that is diagnosed with a disease, but not yet treated with a compound of the invention; a sample from a subject that has been treated by a compound of the invention; or a sample of a purified protein or RNA (e.g., any described herein) at a known normal concentration. By "reference standard or level" is meant a value or number derived from a reference sample. A "normal control value" is a pre-determined value indicative of non-disease state, e.g., a value expected in a healthy control subject. Typically, a normal control value is expressed as a range ("between X and Y"), a high threshold ("no higher than X"), or a low threshold ("no lower than X"). A subject having a measured value within the normal control value for a particular biomarker is typically referred to as "within normal limits" for that biomarker. A normal reference standard or level can be a value or number derived from a normal subject not having a disease or disorder (e.g., cancer); a subject that has been treated with a compound of the invention. In preferred embodiments, the reference sample, standard, or level is matched to the sample subject sample by at least one of the following criteria: age, weight, sex, disease stage, and overall health. A standard curve of levels of a purified protein or RNA, e.g., any described herein, within the normal reference range can also be used as a reference.

As used herein, the term "subject" refers to any organism to which a composition in accordance with the invention may be administered, e.g., for experimental, diagnostic, prophylactic, and/or therapeutic purposes. Typical subjects include any animal (e.g., mammals such as mice, rats, rabbits, non-human primates, and humans). A subject may seek or be in need of treatment, require treatment, be receiving treatment, be receiving treatment in the future, or be a human or animal who is under care by a trained professional for a particular disease or condition.

As used herein, the terms "treat," "treated," or "treating" mean therapeutic treatment or any measures whose object is to slow down (lessen) an undesired physiological condition, disorder, or disease, or obtain beneficial or desired clinical results. Beneficial or desired clinical results include, but are not limited to, alleviation of symptoms; diminishment of the extent of a condition, disorder, or disease; stabilized (i.e., not worsening) state of condition, disorder, or disease; delay in onset or slowing of condition, disorder, or disease progression; amelioration of the condition, disorder, or disease state or remission (whether partial or total); an amelioration of at least one measurable physical parameter, not necessarily discernible by the patient; or enhancement or improvement of condition, disorder, or disease. Treatment includes eliciting a clinically significant response without excessive levels of side effects. Treatment also includes prolonging survival as compared to expected survival if not receiving treatment. Compounds of the invention may also be used to "prophylactically treat" or "prevent" a disorder, for example, in a subject at increased risk of developing the disorder.

As used herein, the terms "variant" and "derivative" are used interchangeably and refer to naturally-occurring, synthetic, and semi-synthetic analogues of a compound, peptide, protein, or other substance described herein. A variant or derivative of a compound, peptide, protein, or other substance described herein may retain or improve upon the biological activity of the original material.

The details of one or more embodiments of the invention are set forth in the description below. Other features, objects, and advantages of the invention will be apparent from the description and from the claims.

DETAILED DESCRIPTION

Figure 1:
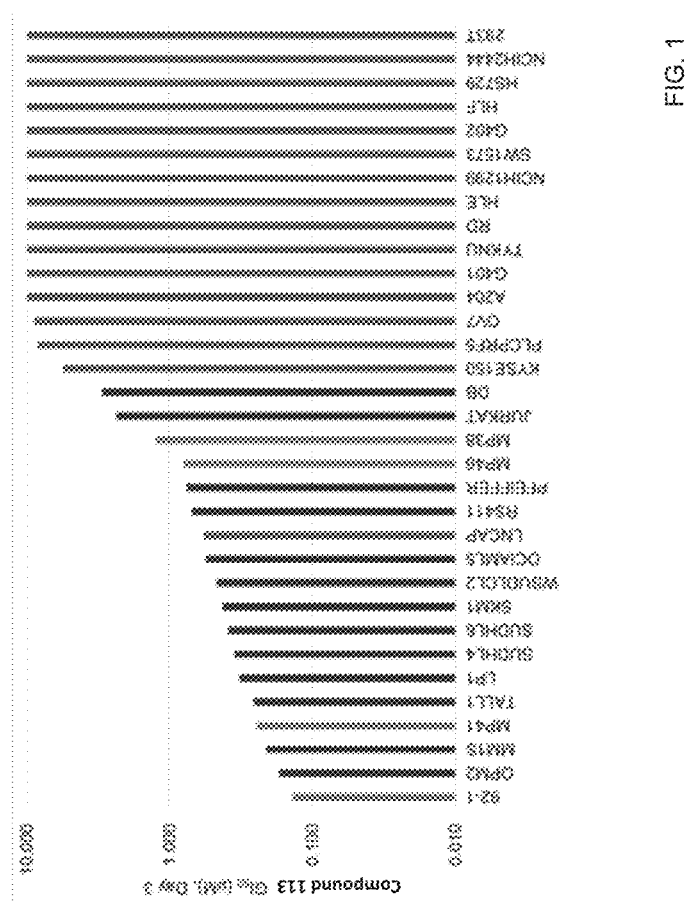
FIG. 1 is a graph illustrating inhibition of cell proliferation of several cancer cell lines by a BRG1/BRM inhibitor (Compound 87).

The present disclosure features compounds useful for the inhibition of BRG1 and/or BRM. These compounds may be used to modulate the activity of a BAF complex, for example, for the treatment of a BAF-related disorder, such as cancer. Exemplary compounds described herein include compounds having a structure according to Formula I, Formula IV, Formula V, or Formula VII:

Formula I
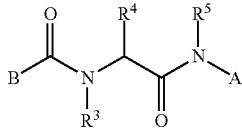

Formula IV
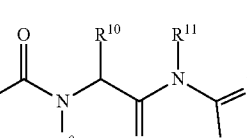

Formula V
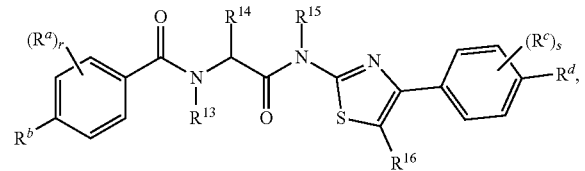

Formula VII
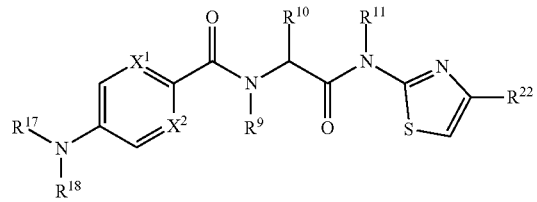

or a pharmaceutically acceptable salt thereof.

In some embodiments, the compound, or pharmaceutically acceptable salt thereof, has the structure of any one of compounds 1-241 in Tables 1, 2, 3, and 4.

Other embodiments, as well as exemplary methods for the synthesis of production of these compounds, are described herein.

Pharmaceutical Uses

The compounds described herein are useful in the methods of the invention and, while not bound by theory, are believed to exert their ability to modulate the level, status, and/or activity of a BAF complex, i.e., by inhibiting the activity of the BRG1 and/or BRM proteins within the BAF complex in a mammal. BAF complex-related disorders include, but are not limited to, BRG1 loss of function mutation-related disorders.

An aspect of the present invention relates to methods of treating disorders related to BRG1 loss of function mutations such as cancer (e.g., non-small cell lung cancer, colorectal cancer, bladder cancer, cancer of unknown primary, glioma, breast cancer, melanoma, non-melanoma skin cancer, endometrial cancer, or penile cancer) in a subject in need thereof. Another aspect of the invention relates to methods of treating cancer by administering a compound that selectively inhibits BRM. For example, the compound that selectively inhibits BRM is a compound as described herein. In some embodiments, the compound is administered in an amount and for a time effective to result in one or more (e.g., two or more, three or more, four or more) of: (a) reduced tumor size, (b) reduced rate of tumor growth, (c) increased tumor cell death (d) reduced tumor progression, (e) reduced number of metastases, (f) reduced rate of metastasis, (g) decreased tumor recurrence (h) increased survival of subject, (i) increased progression free survival of subject.

Treating cancer can result in a reduction in size or volume of a tumor. For example, after treatment, tumor size is reduced by 5% or greater (e.g., 10%, 20%, 30%, 40%, 50%, 60%, 70%, 80%, 90%, or greater) relative to its size prior to treatment. Size of a tumor may be measured by any reproducible means of measurement. For example, the size of a tumor may be measured as a diameter of the tumor.

Treating cancer may further result in a decrease in number of tumors. For example, after treatment, tumor number is reduced by 5% or greater (e.g., 10%, 20%, 30%, 40%, 50%, 60%, 70%, 80%, 90%, or greater) relative to number prior to treatment. Number of tumors may be measured by any reproducible means of measurement, e.g., the number of tumors may be measured by counting tumors visible to the naked eye or at a specified magnification (e.g., 2×, 3×, 4×, 5×, 10×, or 50×).

Treating cancer can result in a decrease in number of metastatic nodules in other tissues or organs distant from the primary tumor site. For example, after treatment, the number of metastatic nodules is reduced by 5% or greater (e.g., 10%, 20%, 30%, 40%, 50%, 60%, 70%, 80%, 90% or greater)

relative to number prior to treatment. The number of metastatic nodules may be measured by any reproducible means of measurement. For example, the number of metastatic nodules may be measured by counting metastatic nodules visible to the naked eye or at a specified magnification (e.g., 2×, 10×, or 50×).

Treating cancer can result in an increase in average survival time of a population of subjects treated according to the present invention in comparison to a population of untreated subjects. For example, the average survival time is increased by more than 30 days (more than 60 days, 90 days, or 120 days). An increase in average survival time of a population may be measured by any reproducible means. An increase in average survival time of a population may be measured, for example, by calculating for a population the average length of survival following initiation of treatment with the compound of the invention. An increase in average survival time of a population may also be measured, for example, by calculating for a population the average length of survival following completion of a first round of treatment with a pharmaceutically acceptable salt of the invention.

Treating cancer can also result in a decrease in the mortality rate of a population of treated subjects in comparison to an untreated population. For example, the mortality rate is decreased by more than 2% (e.g., more than 5%, 10%, or 25%). A decrease in the mortality rate of a population of treated subjects may be measured by any reproducible means, for example, by calculating for a population the average number of disease-related deaths per unit time following initiation of treatment with a pharmaceutically acceptable salt of the invention. A decrease in the mortality rate of a population may also be measured, for example, by calculating for a population the average number of disease-related deaths per unit time following completion of a first round of treatment with a pharmaceutically acceptable salt of the invention.

Exemplary cancers that may be treated by the invention include, but are not limited to, non-small cell lung cancer, small-cell lung cancer, colorectal cancer, bladder cancer, glioma, breast cancer, melanoma, non-melanoma skin cancer, endometrial cancer, esophagogastric cancer, pancreatic cancer, hepatobiliary cancer, soft tissue sarcoma, ovarian cancer, head and neck cancer, renal cell carcinoma, bone cancer, non-hodgkin lymphoma, prostate cancer, embryonal tumor, germ cell tumor, cervical cancer, thyroid cancer, salivary gland cancer, gastrointestinal neuroendocrine tumor, uterine sarcoma, gastrointestinal stromal tumor, CNS cancer, thymic tumor, Adrenocortical carcinoma, appendiceal cancer, small bowel cancer and penile cancer.

Combination Formulations and Uses Thereof

The compounds of the invention can be combined with one or more therapeutic agents. In particular, the therapeutic agent can be one that treats or prophylactically treats any cancer described herein.

Combination Therapies

A compound of the invention can be used alone or in combination with an additional therapeutic agent, e.g., other agents that treat cancer or symptoms associated therewith, or in combination with other types of treatment to treat cancer. In combination treatments, the dosages of one or more of the therapeutic compounds may be reduced from standard dosages when administered alone. For example, doses may be determined empirically from drug combinations and permutations or may be deduced by isobolographic analysis (e.g., Black et al., Neurology 65:S3-S6, 2005). In this case, dosages of the compounds when combined should provide a therapeutic effect.

In some embodiments, the second therapeutic agent is a chemotherapeutic agent (e.g., a cytotoxic agent or other chemical compound useful in the treatment of cancer). These include alkylating agents, antimetabolites, folic acid analogs, pyrimidine analogs, purine analogs and related inhibitors, vinca alkaloids, epipodopyyllotoxins, antibiotics, L-Asparaginase, topoisomerase inhibitors, interferons, platinum coordination complexes, anthracenedione substituted urea, methyl hydrazine derivatives, adrenocortical suppressant, adrenocorticosteroides, progestins, estrogens, antiestrogen, androgens, antiandrogen, and gonadotropin-releasing hormone analog. Also included is 5-fluorouracil (5-FU), leucovorin (LV), irenotecan, oxaliplatin, capecitabine, paclitaxel and doxetaxel. Non-limiting examples of chemotherapeutic agents include alkylating agents such as thiotepa and cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gammaII and calicheamicin omegaII (see, e.g., Agnew, Chem. Intl. Ed Engl. 33:183-186 (1994)); dynemicin, including dynemicin A; bisphosphonates, such as clodronate; an esperamicin; as well as neocarzinostatin chromophore and related chromoprotein enediyne antiobiotic chromophores), aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, Adriamycin® (doxorubicin, including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elfomithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK® polysaccharide complex (JHS Natural Products, Eugene, Oreg.); razoxane; rhizoxin; sizofuran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., Taxol® paclitaxel (Bristol-Myers Squibb Oncology, Princeton, N.J.), ABraxane®, cremophor-free, albumin-engineered nanoparticle formulation of paclitaxel (American Pharmaceutical Partners, Schaumberg, Ill.), and Taxotere® doxetaxel (Rhone-Poulenc Rorer, Antony, France); chlorambucil; Gemzar® gemcitabine; 6-thioguanine; mercaptopurine; methotrexate; platinum coordination complexes such as cisplatin, oxaliplatin and carboplatin; vinblastine; platinum; etoposide (VP-16); ifosfamide; mitoxantrone; vincristine; Navelbine® vinorelbine; novantrone; teniposide; edatrexate; daunomycin; aminopterin; xeloda; ibandronate; irinotecan (e.g., CPT-11); topoisomerase inhibitor RFS 2000; difluoromethylornithine (DMFO); retinoids such as retinoic acid; capecitabine; and pharmaceutically acceptable salts, acids or derivatives of any of the above. Two or more chemotherapeutic agents can be used in a cocktail to be administered in combination with the first therapeutic agent described herein. Suitable dosing regimens of combination chemotherapies are known in the art and described in, for example, Saltz et al. (1999) Proc ASCO 18:233a and Douillard et al. (2000) Lancet 355:1041-7.

In some embodiments, the second therapeutic agent is a therapeutic agent which is a biologic such a cytokine (e.g., interferon or an interleukin (e.g., IL-2)) used in cancer treatment. In some embodiments the biologic is an anti-angiogenic agent, such as an anti-VEGF agent, e.g., bevacizumab (Avastin®). In some embodiments the biologic is an immunoglobulin-based biologic, e.g., a monoclonal antibody (e.g., a humanized antibody, a fully human antibody, an Fc fusion protein or a functional fragment thereof) that agonizes a target to stimulate an anti-cancer response, or antagonizes an antigen important for cancer. Such agents include Rituxan (Rituximab); Zenapax (Daclizumab); Simulect (Basiliximab); Synagis (Palivizumab); Remicade (Infliximab); Herceptin (Trastuzumab); Mylotarg (Gemtuzumab ozogamicin); Campath (Alemtuzumab); Zevalin (Ibritumomab tiuxetan); Humira (Adalimumab); Xolair (Omalizumab); Bexxar (Tositumomab-1-131); Raptiva (Efalizumab); Erbitux (Cetuximab); Avastin (Bevacizumab); Tysabri (Natalizumab); Actemra (Tocilizumab); Vectibix (Panitumumab); Lucentis (Ranibizumab); Soliris (Eculizumab); Cimzia (Certolizumab pegol); Simponi (Golimumab); Ilaris (Canakinumab); Stelara (Ustekinumab); Arzerra (Ofatumumab); Prolia (Denosumab); Numax (Motavizumab); ABThrax (Raxibacumab); Benlysta (Belimumab); Yervoy (Ipilimumab); Adcetris (Brentuximab Vedotin); Perjeta (Pertuzumab); Kadcyla (Ado-trastuzumab emtansine); and Gazyva (Obinutuzumab). Also included are antibody-drug conjugates.

The second agent may be a therapeutic agent which is a non-drug treatment. For example, the second therapeutic agent is radiation therapy, cryotherapy, hyperthermia and/or surgical excision of tumor tissue.

The second agent may be a checkpoint inhibitor. In one embodiment, the inhibitor of checkpoint is an inhibitory antibody (e.g., a monospecific antibody such as a monoclonal antibody). The antibody may be, e.g., humanized or fully human. In some embodiments, the inhibitor of checkpoint is a fusion protein, e.g., an Fc-receptor fusion protein. In some embodiments, the inhibitor of checkpoint is an agent, such as an antibody, that interacts with a checkpoint protein. In some embodiments, the inhibitor of checkpoint is an agent, such as an antibody, that interacts with the ligand of a checkpoint protein. In some embodiments, the inhibitor of checkpoint is an inhibitor (e.g., an inhibitory antibody or small molecule inhibitor) of CTLA-4 (e.g., an anti-CTLA4 antibody such as ipilimumab/Yervoy or tremelimumab). In some embodiments, the inhibitor of checkpoint is an inhibitor (e.g., an inhibitory antibody or small molecule inhibitor) of PD-1 (e.g., nivolumab/Opdivo®; pembrolizumab/Keytruda®; pidilizumab/CT-011). In some embodiments, the inhibitor of checkpoint is an inhibitor (e.g., an inhibitory antibody or small molecule inhibitor) of PDL1 (e.g., MPDL3280A/RG7446; MEDI4736; MSB0010718C; BMS 936559). In some embodiments, the inhibitor of checkpoint is an inhibitor (e.g., an inhibitory antibody or Fc fusion or small molecule inhibitor) of PDL2 (e.g., a PDL2/Ig fusion protein such as AMP 224). In some embodiments, the inhibitor of checkpoint is an inhibitor (e.g., an inhibitory antibody or small molecule inhibitor) of B7-H3 (e.g., MGA271), B7-H4, BTLA, HVEM, TIM3, GAL9, LAG3, VISTA, KIR, 2B4, CD160, CGEN-15049, CHK 1, CHK2, A2aR, B-7 family ligands, or a combination thereof.

In any of the combination embodiments described herein, the first and second therapeutic agents are administered simultaneously or sequentially, in either order. The first therapeutic agent may be administered immediately, up to 1 hour, up to 2 hours, up to 3 hours, up to 4 hours, up to 5 hours, up to 6 hours, up to 7 hours, up to, 8 hours, up to 9 hours, up to 10 hours, up to 11 hours, up to 12 hours, up to 13 hours, 14 hours, up to hours 16, up to 17 hours, up 18 hours, up to 19 hours up to 20 hours, up to 21 hours, up to 22 hours, up to 23 hours up to 24 hours or up to 1-7, 1-14, 1-21 or 1-30 days before or after the second therapeutic agent Pharmaceutical Compositions The compounds of the invention are preferably formulated into pharmaceutical compositions for administration to a mammal, preferably, a human, in a biologically compatible form suitable for administration in vivo. Accordingly, in an aspect, the present invention provides a pharmaceutical composition comprising a compound of the invention in admixture with a suitable diluent, carrier, or excipient.

The compounds of the invention may be used in the form of the free base, in the form of salts, solvates, and as prodrugs. All forms are within the scope of the invention. In accordance with the methods of the invention, the described compounds or salts, solvates, or prodrugs thereof may be administered to a patient in a variety of forms depending on the selected route of administration, as will be understood by those skilled in the art. The compounds of the invention may be administered, for example, by oral, parenteral, buccal, sublingual, nasal, rectal, patch, pump, or transdermal administration and the pharmaceutical compositions formulated accordingly. Parenteral administration includes intravenous, intraperitoneal, subcutaneous, intramuscular, transepithelial, nasal, intrapulmonary, intrathecal, rectal, and topical modes of administration. Parenteral administration may be by continuous infusion over a selected period of time.

A compound of the invention may be orally administered, for example, with an inert diluent or with an assimilable edible carrier, or it may be enclosed in hard or soft shell gelatin capsules, or it may be compressed into tablets, or it may be incorporated directly with the food of the diet. For oral therapeutic administration, a compound of the invention may be incorporated with an excipient and used in the form of ingestible tablets, buccal tablets, troches, capsules, elixirs, suspensions, syrups, and wafers. A compound of the invention may also be administered parenterally. Solutions of a compound of the invention can be prepared in water suitably mixed with a surfactant, such as hydroxypropylcellulose. Dispersions can also be prepared in glycerol, liquid polyethylene glycols, DMSO, and mixtures thereof with or without alcohol, and in oils. Under ordinary conditions of storage and use, these preparations may contain a preservative to prevent the growth of microorganisms. Conventional procedures and ingredients for the selection and preparation of suitable formulations are described, for example, in Remington's Pharmaceutical Sciences (2003, 20th ed.) and in The United States Pharmacopeia: The National Formulary (USP 24 NF19), published in 1999. The pharmaceutical forms suitable for injectable use include sterile aqueous solutions or dispersions and sterile powders for the extemporaneous preparation of sterile injectable solutions or dispersions. In all cases the form must be sterile and must be fluid to the extent that may be easily administered via syringe. Compositions for nasal administration may conveniently be formulated as aerosols, drops, gels, and powders. Aerosol formulations typically include a solution or fine suspension of the active substance in a physiologically acceptable aqueous or non-aqueous solvent and are usually presented in single or multidose quantities in sterile form in a sealed container, which can take the form of a cartridge or refill for use with an atomizing device. Alternatively, the sealed container may be a unitary dispensing device, such as a single dose nasal inhaler or an aerosol dispenser fitted with a metering valve which is intended for disposal after use. Where the dosage form comprises an aerosol dispenser, it will contain a propellant, which can be a compressed gas, such as compressed air or an organic propellant, such as fluorochlorohydrocarbon. The aerosol dosage forms can also take the form of a pump-atomizer. Compositions suitable for buccal or sublingual administration include tablets, lozenges, and pastilles, where the active ingredient is formulated with a carrier, such as sugar, acacia, tragacanth, gelatin, and glycerine. Compositions for rectal administration are conveniently in the form of suppositories containing a conventional suppository base, such as cocoa butter. A compound described herein may be administered intratumorally, for example, as an intratumoral injection. Intratumoral injection is injection directly into the tumor vasculature and is specifically contemplated for discrete, solid, accessible tumors. Local, regional, or systemic administration also may be appropriate. A compound described herein may advantageously be contacted by administering an injection or multiple injections to the tumor, spaced for example, at approximately, 1 cm intervals. In the case of surgical intervention, the present invention may be used preoperatively, such as to render an inoperable tumor subject to resection. Continuous administration also may be applied where appropriate, for example, by implanting a catheter into a tumor or into tumor vasculature.

The compounds of the invention may be administered to an animal, e.g., a human, alone or in combination with pharmaceutically acceptable carriers, as noted herein, the proportion of which is determined by the solubility and chemical nature of the compound, chosen route of administration, and standard pharmaceutical practice.

Dosages

The dosage of the compounds of the invention, and/or compositions comprising a compound of the invention, can vary depending on many factors, such as the pharmacodynamic properties of the compound; the mode of administration; the age, health, and weight of the recipient; the nature and extent of the symptoms; the frequency of the treatment, and the type of concurrent treatment, if any; and the clearance rate of the compound in the animal to be treated. One of skill in the art can determine the appropriate dosage based on the above factors. The compounds of the invention may be administered initially in a suitable dosage that may be adjusted as required, depending on the clinical response. In general, satisfactory results may be obtained when the compounds of the invention are administered to a human at a daily dosage of, for example, between 0.05 mg and 3000 mg (measured as the solid form). Dose ranges include, for example, between 10-1000 mg (e.g., 50-800 mg). In some embodiments, 50, 100, 150, 200, 250, 300, 350, 400, 450, 500, 550, 600, 650, 700, 750, 800, 850, 900, 950, or 1000 mg of the compound is administered.

Alternatively, the dosage amount can be calculated using the body weight of the patient. For example, the dose of a compound, or pharmaceutical composition thereof, administered to a patient may range from 0.1-50 mg/kg (e.g., 0.25-25 mg/kg). In exemplary, non-limiting embodiments, the dose may range from 0.5-5.0 mg/kg (e.g., 0.5, 1.0, 1.5, 2.0, 2.5, 3.0, 3.5, 4.0, 4.5, or 5.0 mg/kg) or from 5.0-20 mg/kg (e.g., 5.5, 6.0, 6.5, 7.0, 7.5, 8.0, 8.5, 9.0, 9.5, 10, 11, 12, 13, 14, 15, 16, 17, 18, 19, or 20 mg/kg).

EXAMPLES

Example 1. Preparation of 3-(dimethylsulfamoyl)-N-[2-oxo-2-[(4-phenylthiazol-2-yl)amino]ethyl]benzamide (compound 13)

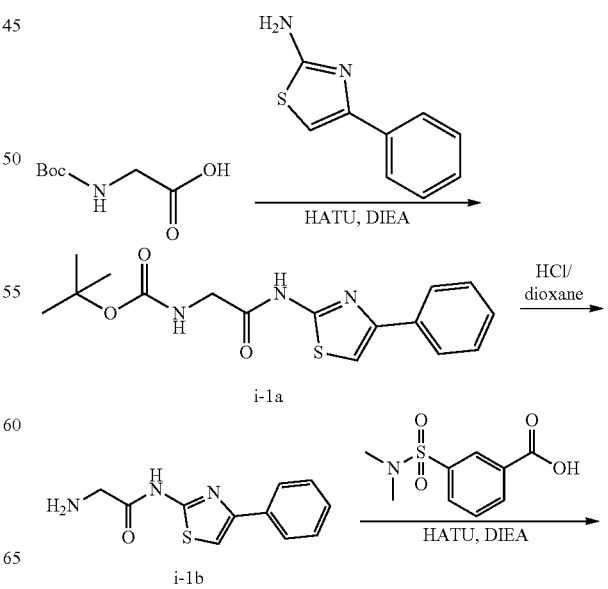

-continued

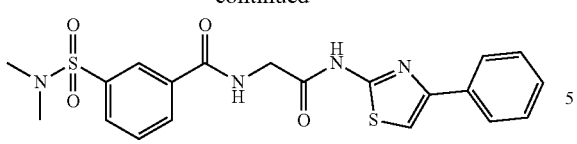

13

Step 1: Preparation of tert-butyl N-[2-oxo-2-[(4-phenylthiazol-2-yl)amino]ethyl]carbamate (i-1a)

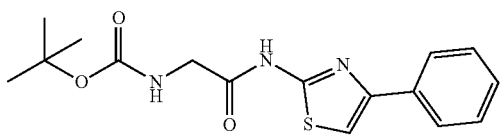

i-1a

To a solution of 2-(tert-butoxycarbonylamino)acetic acid (1 g, 5.71 mmol) in dimethylformamide (DMF) (20 mL) was added 1-[Bis(dimethylamino)methylene]-1H-1,2,3-triazolo[4,5-b]pyridinium 3-oxide hexafluorophosphate (HATU) (2.39 g, 6.28 mmol) and N-Ethyl-N-(propan-2-yl)propan-2-amine (DIPEA) (2.21 g, 17.13 mmol). The solution was stirred for 10 minutes and then 4-phenylthiazol-2-amine (1.01 g, 5.71 mmol) was added. The solution was stirred at 30° C. for 12 hrs. The reaction solution was poured into water (200 mL) and then extracted with EtOAc (200 mL). The organic layer was washed with aqueous citric acid (100 mL*5), brine (200 mL) and then dried over Na₂SO₄. The solution was concentrated in vacuum. The residue was purified through column chromatography (SiO2, PE/EtOAc=20/1~3/1) to give intermediate i-1a as a yellow solid.

¹H NMR (400 MHz, CDCl3) δ=10.08 (brs, 1H), 7.83-7.81 (m, 2H), 7.45-7.41 (m, 2H), 7.36-7.34 (m, 1H), 7.28 (s, 1H), 7.17 (s, 1H), 4.04 (s, 2H), 1.51 (s, 9H) ppm.

LCMS (ESI) m/z: [M+H]⁺=333.9.

Step 2: Preparation of 2-amino-N-(4-phenylthiazol-2-yl)acetamide hydrochloride salt (i-1b)

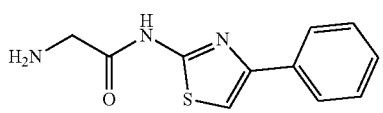

i-1b

To a solution of intermediate i-1a (100 mg, 284.94 μmol) in dioxane (5 mL) was added HCl/dioxane (4 M, 5 mL), then the solution was stirred at 30° C. for 1 hr. The reaction solution was concentrated in vacuum to give intermediate i-1b (HCl salt) as a white solid, which was used for the next step directly.

LCMS (ESI) m/z: [M+H]⁺=233.9.

Step 3: Preparation of 3-(dimethylsulfamoyl)-N-[2-oxo-2-[(4-phenylthiazol-2-yl)amino]ethyl]benzamide (compound 13)

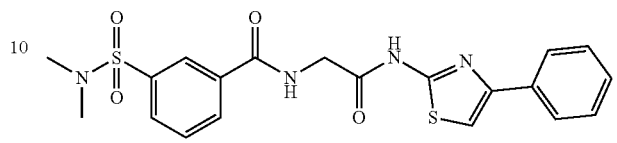

13

To a solution of 3-(dimethylsulfamoyl)benzoic acid (75.72 mg, 330.31 μmol) in DCM (10 mL) was added HATU (125.59 mg, 330.31 μmol) and DIPEA (155.24 mg, 1.20 mmol). The solution was stirred for 10 min and then intermediate i-1b (81 mg, 300.28 μmol) was added. The solution was stirred at 30° C. for 12 hr. The reaction solution was poured into water (50 mL) and extracted with EtOAc (100 mL). The organic layer was washed with brine (50 mL), dried (Na₂SO₄) and concentrated in vacuum. To the residue was added MeOH (20 mL) and stirred for 20 min, a white solid was formed. The solid was filtered and dried in vacuum to give compound 13 as a white solid.

LCMS (ESI) m/z: [M+H]⁺=444.9.

¹H NMR (400 MHz, DMSO-d6) δ=12.49 (s, 1H), 9.32 (t, J=5.6 Hz, 1H), 8.27-8.25 (m, 2H), 7.96-7.90 (m, 3H), 7.81-7.80 (m, 1H), 7.64 (s, 1H), 7.46-7.42 (m, 2H), 7.33-7.30 (m, 1H), 4.23 (d, J=5.6 Hz, 2H), 2.65 (s, 6H) ppm.

Example 2. Preparation of Compound (S)—N-(4-(methylthio)-1-oxo-1-((4-phenylthiazol-2-yl)amino)butan-2-yl)benzamide (compound 42)

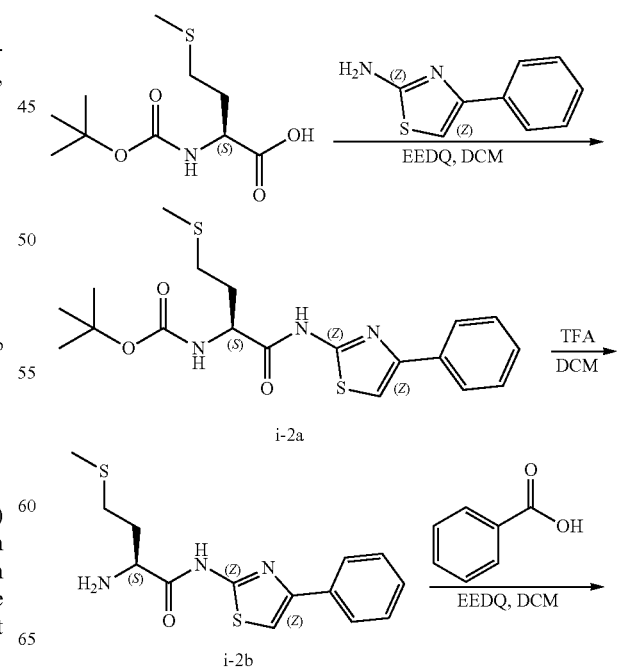

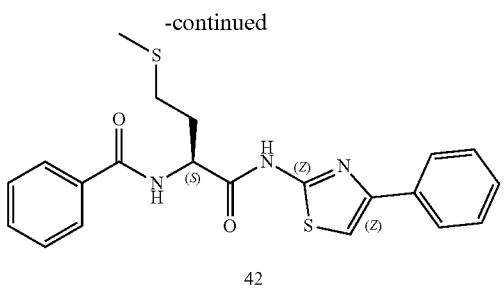

42

Step 1: Preparation of (S)-tert-butyl (4-(methylthio)-1-oxo-1-((4-phenylthiazol-2-yl)amino)butan-2-yl)carbamate (intermediate i-2a)

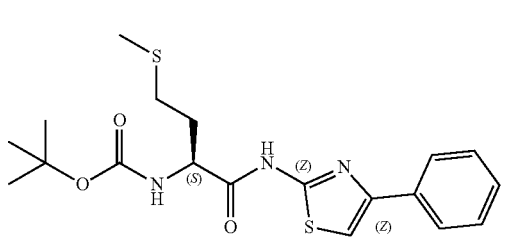

i-2a

To a solution of (2S)-2-(tert-butoxycarbonylamino)-4-methylsulfanyl-butanoic acid (1 g, 4.01 mmol) in DCM (20 mL) was added 2-ethoxy-1-ethoxycarbonyl-1,2-dihydroquinoline (EEDQ) (1.24 g, 5.01 mmol) and then 4-phenylthiazol-2-amine (589.05 mg, 3.34 mmol) was added. The mixture was stirred at 28° C. for 3 hr. The reaction mixture was diluted with EtOAc (400 mL). The organic layer was washed with brine (40 mL), dried over $Na_2SO_4$, filtered and concentrated under reduced pressure to give a residue. The residue was purified by column chromatography ($SiO_2$, Petroleum ether/Ethyl acetate=50/1 to 8/1) to give intermediate i-2a as a white solid.

1H NMR (400 MHz, METHANOL-d4) δ 7.89 (d, J=7.6 Hz, 2H), 7.43-7.35 (m, 3H), 7.30-7.27 (m, 1H), 4.41-4.32 (m, 1H), 2.62-2.55 (m, 2H), 2.20-2.11 (m, 4H), 2.00-1.94 (m, 1H), 1.46-1.39 (m, 9H) ppm.

LCMS (ESI) m/z: $[M+H]^+$=408.2.

Step 2: Preparation of (S)-2-amino-4-(methylthio)-N-(4-phenylthiazol-2-yl)butanamide trifluoroacetate salt (intermediate i-2b)

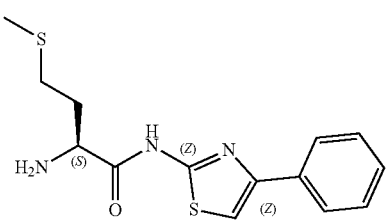

To a solution of intermediate i-2a (200 mg, 490.74 μmol) in DCM (5 mL) was added TFA (0.25 mL). The mixture was stirred at 28° C. for 2 hr. To the reaction solution was added a.q $NaHCO_3$ to adjust pH to 7 and then extracted with EtOAc (100 mL*2). The combined organic layers were washed with brine (20 mL), dried over $Na_2SO_4$, filtered and concentrated under reduced pressure to give a residue.

The residue was purified by prep-HPLC (TFA condition; column: Phenomenex Synergi C18 150*25*10 μm; mobile phase: [water (0.1% TFA)-ACN]; B %: 15%-45%, 12 min) and lyophilized to give the TFA salt of intermediate i-2b as a white solid.

1H NMR (400 MHz, METHANOL-d4) δ 7.91-7.89 (m, 2H), 7.46 (s, 1H), 7.42-7.38 (m, 2H), 7.32-7.31 (m, 1H), 4.27-4.23 (m, 1H), 2.67-2.63 (m, 2H), 2.33-2.22 (m, 2H), 2.14 (s, 3H) ppm.

LCMS (ESI) m/z: $[M+H]^+$=308.1.

Step 3: Preparation of (S)—N-(4-(methylthio)-1-oxo-1-((4-phenylthiazol-2-yl)amino)butan-2-yl)benzamide (compound 42)

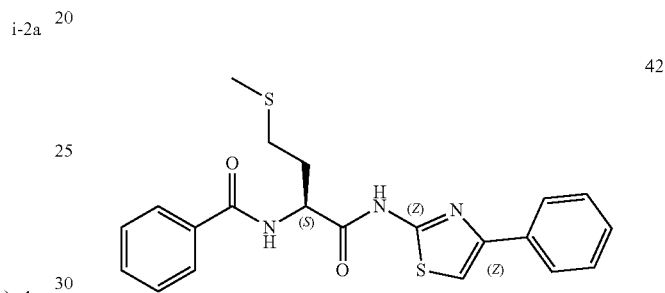

42

To a solution of benzoic acid (43.70 mg, 357.80 μmol) in DCM (2 mL) was added EEDQ (120.66 mg, 487.91 μmol) and then intermediate i-2b (100 mg, 325.27 μmol) was added. The mixture was stirred at 28° C. for 3 hr. The reaction mixture was diluted with EA (150 mL), washed with 10% aqueous citric acid (50 mL*4), dried over $Na_2SO_4$, filtered and concentrated under reduced pressure to give a residue. The residue was purified by prep-HPLC (TFA condition; column: Phenomenex Synergi C18 150*25*10 μm; mobile phase: [water (0.1% TFA)-ACN]; B %: 45%-75%, 13 min) and lyophilized to give compound 42 as a white solid.

1H NMR (400 MHz, METHANOL-d4) δ 7.91-7.88 (m, 4H), 7.60-7.51 (m, 1H), 7.50-7.48 (m, 2H), 7.38-7.36 (m, 3H), 7.29-7.27 (m, 1H), 4.93-4.89 (m, 1H), 2.70-2.63 (m, 2H), 2.28-2.21 (m, 2H), 2.13 (s, 3H) ppm.

LCMS (ESI) m/z: $[M+H]^+$=412.2.

Chiral HPLC: AD-3S_3_40_3ML_12MIN_T35.M, 4.866 min.

Example 3. Preparation of (S)-3-(N,N-dimethylsulfamoyl)-N-(4-(methylthio)-1-oxo-1-((4-phenylthiazol-2-yl)amino)butan-2-yl)benzamide (compound 24)

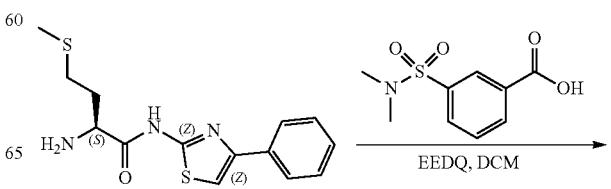

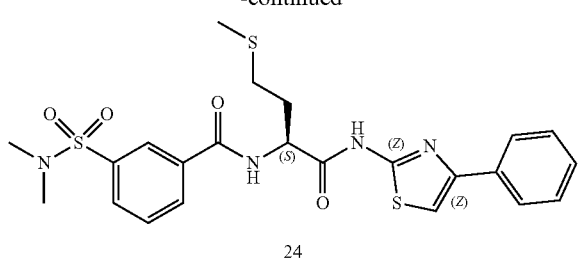

24

To a solution of 3-(dimethylsulfamoyl)benzoic acid (59.66 mg, 260.22 μmol) in DCM (2 mL) was added EEDQ (96.52 mg, 390.33 μmol) and then (2S)-2-amino-4-methyl-sulfanyl-N-(4-phenylthiazol-2-yl)butanamide (80 mg, 260.22 μmol) was added. The mixture was stirred at 28° C. for 2 hr. The reaction mixture was diluted with EtOAc (150 mL). The organic layer was washed with brine (50 mL), dried over Na₂SO₄, filtered and concentrated under reduced pressure to give a residue. The residue was purified by column chromatography (SiO2, Petroleum ether/Ethyl acetate=50/1 to 1:1) and lyophilized to give compound 24 as a white solid.

1H NMR (400 MHz, DMSO-d6) δ 12.55 (s, 1H), 9.10 (d, J=6.8 Hz, 1H), 8.28-8.26 (m, 2H), 7.92-7.89 (m, 3H), 7.80-7.76 (m, 1H), 7.64 (s, 1H), 7.45-7.41 (m, 2H), 7.36-7.30 (m, 1H), 4.83-4.76 (m, 1H), 2.65 (s, 6H), 2.61-2.55 (m, 2H), 2.21-2.16 (m, 2H), 2.10 (s, 3H) ppm.

LCMS (ESI) m/z: [M+H]⁺=519.2.

Example 4. Preparation of (S)-3-(N,N-dimethylsulfamoyl)-N-(1-oxo-1-((4-phenylthiazol-2-yl)amino)propan-2-yl)benzamide (compound 12)

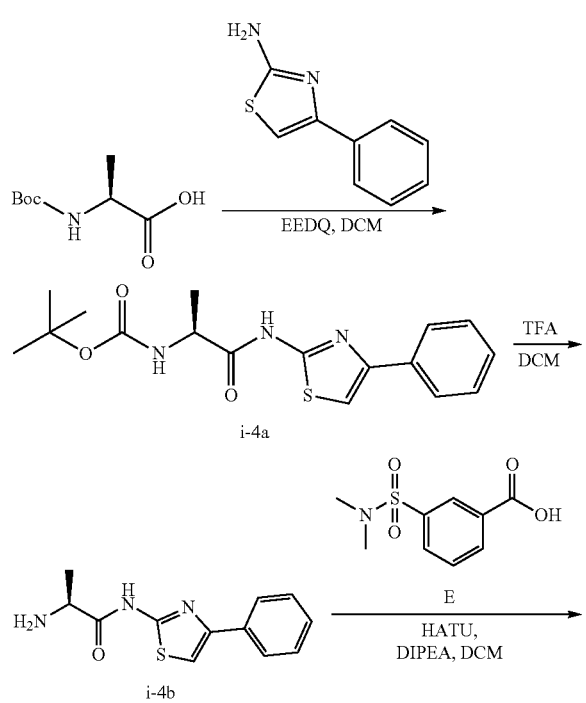

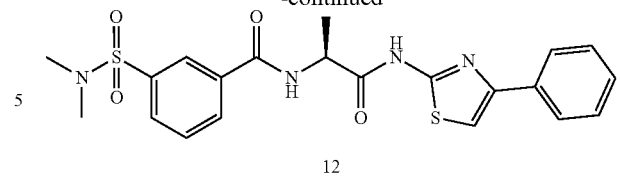

12

Step 1: Preparation of (S)-tert-butyl (1-oxo-1-((4-phenylthiazol-2-yl)amino)propan-2-yl)carbamate (intermediate 4a)

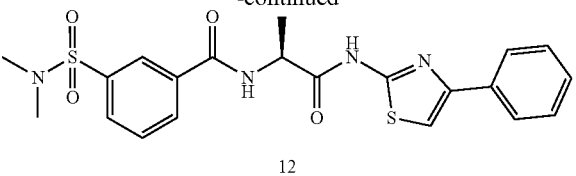

i-4a

To a solution of (2S)-2-(tert-butoxycarbonylamino)propanoic acid (200 mg, 1.06 mmol) in THF (5 mL) was added EEDQ (392.09 mg, 1.59 mmol), then 4-phenylthiazol-2-amine (186.29 mg, 1.06 mmol) was added to the mixture. The mixture was stirred at 25° C. for 12 hr. Citric acid (10%) 80 mL (40*2) was added and the reaction mixture was extracted with EtOAc (100 mL*2). The combined organic layers were washed with brine (20 mL), dried over Na₂SO₄, filtered and concentrated under reduced pressure to give a residue. The residue was purified by column chromatography (SiO₂, Petroleum ether/Ethyl acetate=50/1 to 5:1) to give intermediate i-4a as a white solid. ¹HNMR (400 MHz, DMSO-d6) δ 12.29 (s, 1H), 7.96-7.84 (m, 2H), 7.63 (s, 1H), 7.49-7.39 (m, 2H), 7.35-7.30 (m, 1H), 7.25 (d, J=6.8 Hz, 1H), 4.31-4.20 (m, 1H), 1.38 (s, 7H), 1.28 (d, J=7.2 Hz, 4H) ppm.

LCMS (ESI) m/z: [M+H]⁺=347.9.

SFC HPLC: AD-3-MeOH(DEA)-5-40-3 mL-35T.I, 1.584 min.

Step 2: Preparation of (S)-2-amino-N-(4-phenylthiazol-2-yl)propanamide (intermediate i-4b)

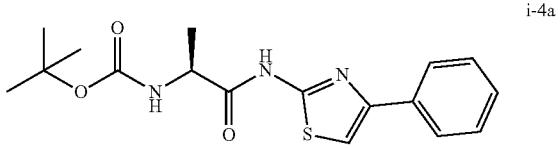 [SMILES: C[C@H](NC(=O)OC(C)(C)C)C(=O)Nc1nc(-c2ccccc2)cs1]

i-4b

To a solution of intermediate i-4a (300 mg, 863.48 μmol) in DCM (5 mL) was added TFA (0.5 mL). The mixture was stirred at 25° C. for 2 hr. The reaction solution was poured into water (20 mL) and adjusted pH to 7 with NaHCO₃. The reaction mixture was extracted with EA (100 mL*2). The combined organic layers were washed with brine (40 mL), dried over Na₂SO₄, filtered and concentrated under reduced pressure to give intermediate i-4b as a white solid which was used to the next step without further purification.

¹HNMR (400 MHz, DMSO-d6) δ 7.93-7.87 (m, 2H), 7.60 (s, 1H), 7.46-7.39 (m, 2H), 7.35-7.28 (m, 1H), 5.46 (s, 2H), 3.59-3.57 (m, 1H), 3.33 (s, 3H), 1.23 (d, J=6.8 Hz, 3H) ppm.

LCMS (ESI) m/z: [M+H]⁺=248.0.

SFC HPLC: OD-3-MeOH(DEA)-5-40-3 mL-35T.I, 1.708 min.

Step 3: Preparation of (S)-3-(N,N-dimethylsulfamoyl)-N-(1-oxo-1-((4-phenylthiazol-2-yl)amino)propan-2-yl)benzamide (compound 12)

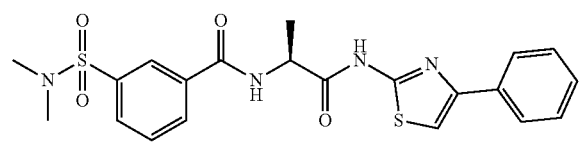

12

To a solution of 3-(dimethylsulfamoyl)benzoic acid (92.70 mg, 404.34 μmol) in DCM (3 mL) was added HATU (169.12 mg, 444.78 μmol) and DIPEA (156.77 mg, 1.21 mmol, 211.29 μL), then intermediate i-4b (100 mg, 404.34 μmol) was added to the mixture. The mixture was stirred at 25° C. for 2 hr. The reaction mixture was concentrated under reduced pressure to give a solid. To the solid was added MeOH (80 mL) and stirred for 10 min and then filtered, the solid was collected by filtration and dried in vacuum to give compound 12 as a white solid.

¹HNMR (400 MHz, DMSO-d6) δ 12.48 (s, 1H), 9.13 (d, J=6.4 Hz, 1H), 8.30-8.23 (m, 2H), 7.92-7.89 (m, 3H), 7.80-7.76 (m, 1H), 7.64 (s, 1H), 7.46-7.41 (m, 2H), 7.36-7.29 (m, 1H), 4.76-4.69 (m, 1H), 2.65 (s, 6H), 1.49 (d, J=7.2 Hz, 3H) ppm.

LCMS (ESI) m/z: [M+H]⁺=459.0.

SFC HPLC: OD-3-EtOH(DEA)-5-40-3 mL-35T.Ic, 2.455 min.

Example 5. Preparation of 3-(dimethylsulfamoyl)-N-[2-oxo-2-(3-phenyl anilino)ethyl]benzamide (compound 40)

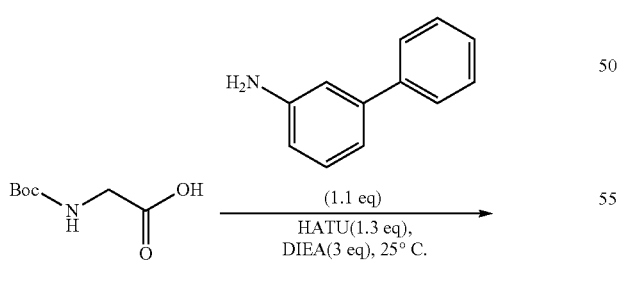

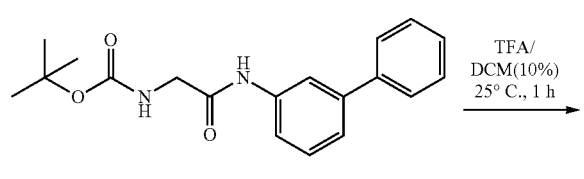

i-5a

Step 1: Preparation of tert-butyl N-[2-oxo-2-(3-phenylanilino)ethyl] carbamate (intermediate i-5a)

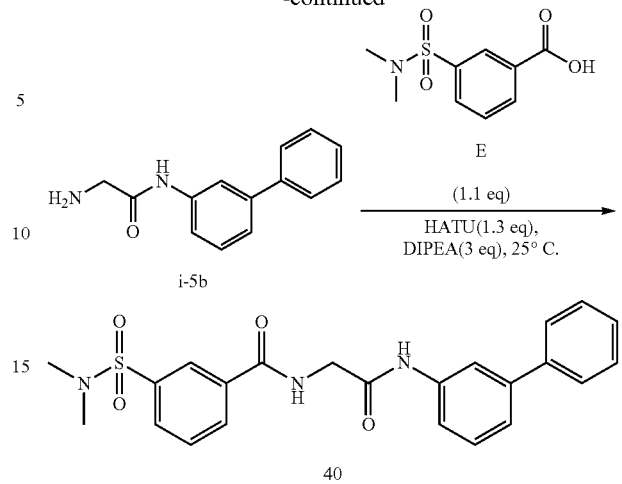

To a solution of 2-(tert-butoxycarbonylamino)acetic acid (113.87 mg, 650.03 μmol) in DCM (3 mL) was added DIPEA (229.12 mg, 1.77 mmol) and HATU (337.04 mg, 886.41 μmol). The mixture was stirred at 25° C. for 10 min. 3-phenylaniline (100.00 mg, 590.94 μmol) was added and the mixture was stirred at 25° C. for 2 hr. The reaction mixture was quenched by addition water (10 mL), and then extracted with ethyl acetate (10 mL*2). The combined organic layers were washed with water (10 mL*2), dried over Na₂SO₄, filtered and concentrated under reduced pressure to give a crude product. To the residue was added a solvent (EA:PE=1:5, v/v, 10 mL) and stirred for 10 min then filtered, the solid was dried in vacuum to give Intermediate i-5a as a pale yellow solid.

LCMS (ESI) m/z: [M+Na]⁺=349.2.

Step 2: Preparation of 2-amino-N-(3-phenylphenyl)acetamide (intermediate i-5b) trifluoroacetate salt

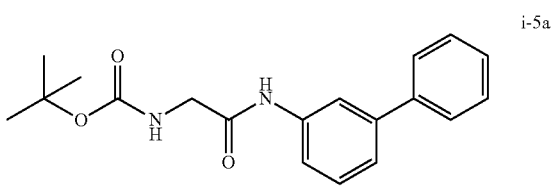 [SMILES: CC(C)(C)OC(=O)NCC(=O)Nc1cccc(-c2ccccc2)c1]

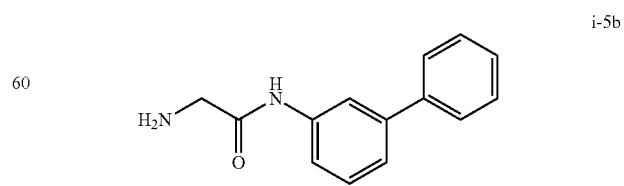

To a solution of Intermediate i-5a (70.11 mg, 201.48 μmol) in DCM (3 mL) was added TFA (150.00 μL). The mixture was stirred at 25° C. for 1 hr. The reaction mixture was concentrated to dryness to give a residue, which was slurried with methyl t-butyl ether (5 mL) and the solid collected by filtration, and dried in vacuum to afford intermediate i-5b (TFA salt) as a light yellow solid, which was used in next step without further purification.

LCMS (ESI) m/z: [M+H]⁺=227.2.

Step 3: Preparation of 3-(dimethylsulfamoyl)-N-[2-oxo-2-(3-phenyl anilino)ethyl]benzamide (compound 40)

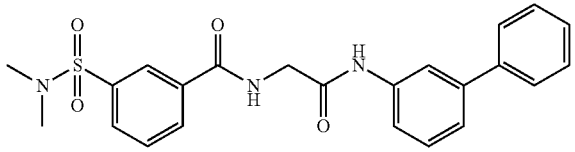

40

To a solution of 3-(dimethylsulfamoyl)benzoic acid (45.59 mg, 198.87 μmol) in DCM (3 mL) was added DIPEA (77.11 mg, 596.62 μmol) and HATU (113.43 mg, 298.31 μmol). The mixture was stirred at 25° C. for 10 min and then intermediate i-5b was added and the mixture was stirred at 25° C. for 2 hr. The reaction mixture was concentrated in vacuo to give a residue. To the residue was added a mixture of methanol:water=1:1, v/v, (4 mL) and stirred for 10 min, then filtered, the filter cake was washed with methanol (2 mL) and then lyophilized to give compound 40 as a white solid.

¹H NMR (400 MHz, DMSO-d6) δ 10.22 (s, 1H), 9.24 (m, 1H), 8.19-8.32 (m, 2H), 7.90-8.00 (m, 2H), 7.73-7.86 (m, 1H), 7.56-7.65 (m, 3H), 7.32-7.51 (m, 5H), 4.14 (m, 2H), 2.63-2.68 (m, 6H) ppm; LCMS (ESI) m/z: [M+H]+=438.2.

Example 6. Preparation of 3-(methylsulfamoyl)-N-[2-oxo-2-[(4-phenyl thiazol-2-yl)amino]ethyl]benzamide (compound 26)

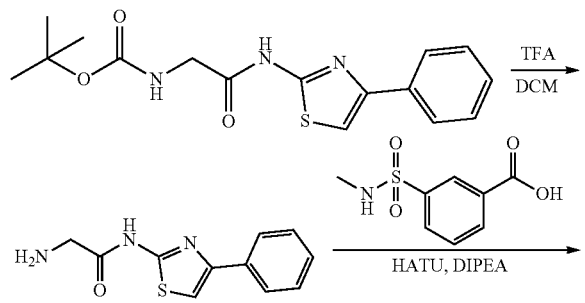

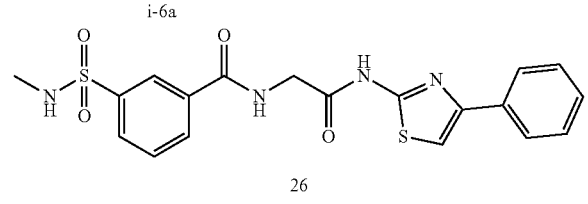

26

Step 1: Preparation of 2-amino-N-(4-phenylthiazol-2-yl)acetamide (intermediate 6a) trifluoroacetate salt

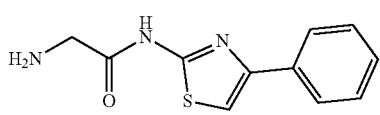

i-6a

To a solution of tert-butyl N-[2-oxo-2-[(4-phenylthiazol-2-yl)amino]ethyl]carbamate (500 mg, 1.50 mmol) in DCM (3 mL) was added TFA (2.22 mL). The mixture was stirred at 25° C. for 1 h. The reaction mixture was evaporated to dryness. To the residue was added MTBE/PE=(2/1, 30 mL) and stirred for 10 min, then filtered to give a solid which was dried in vacuum to give intermediate i-6a (TFA salt) as a yellow solid.

LCMS (ESI) m/z: [M+H]⁺=234.2.

Step 2: Preparation of 3-(methylsulfamoyl)-N-[2-oxo-2-[(4-phenylthiazol-2-yl)amino]ethyl]benzamide (compound 26)

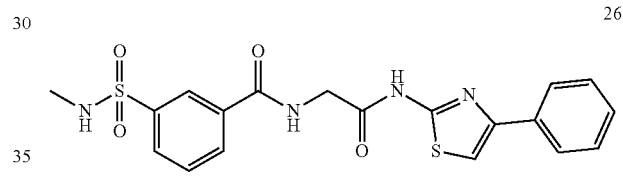

26

To a mixture of 3-(methylsulfamoyl)benzoic acid (46.13 mg, 214.33 μmol) in DCM (2 mL) was added HATU (89.64 mg, 235.75 μmol) and DIPEA (138.5 mg, 1.07 mmol) at 25° C. The mixture was stirred at 25° C. for 10 min and then intermediate 6a (50 mg, 143.96 μmol) was added and stirred for 1 h. The reaction mixture was evaporated to dryness to give the crude product. To the residue was added MeOH (30 mL) and stirred for 10 min, then filtered and the filter cake was washed with MeOH (30 mL). The solid was dried in vacuo to give compound 26 as a white solid.

¹HNMR (400 MHz, DMSO-d6) δ=12.47 (brs, 1H), 9.25-9.23 (m, 1H), 8.31 (s, 1H), 8.16 (d, J=7.9 Hz, 1H), 7.96 (d, J=7.8 Hz, 1H), 7.90 (m, 2H), 7.76-7.74 (m, 1H), 7.64 (s, 1H), 7.00-7.58 (m, 1H), 7.46-7.40 (m, 2H), 7.32-7.29 (m, 1H), 4.23 (d, J=5.6 Hz, 2H), 2.43 (m, 3H) ppm; LCMS (ESI) m/z: [M+H]⁺=431.1.

Example 7. Preparation of Compound N-(2-oxo-2-((4-phenylthiazol-2-yl) amino)ethyl)-3-sulfamoyl-benzamide (compound 28)

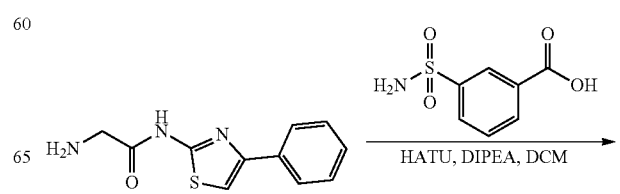

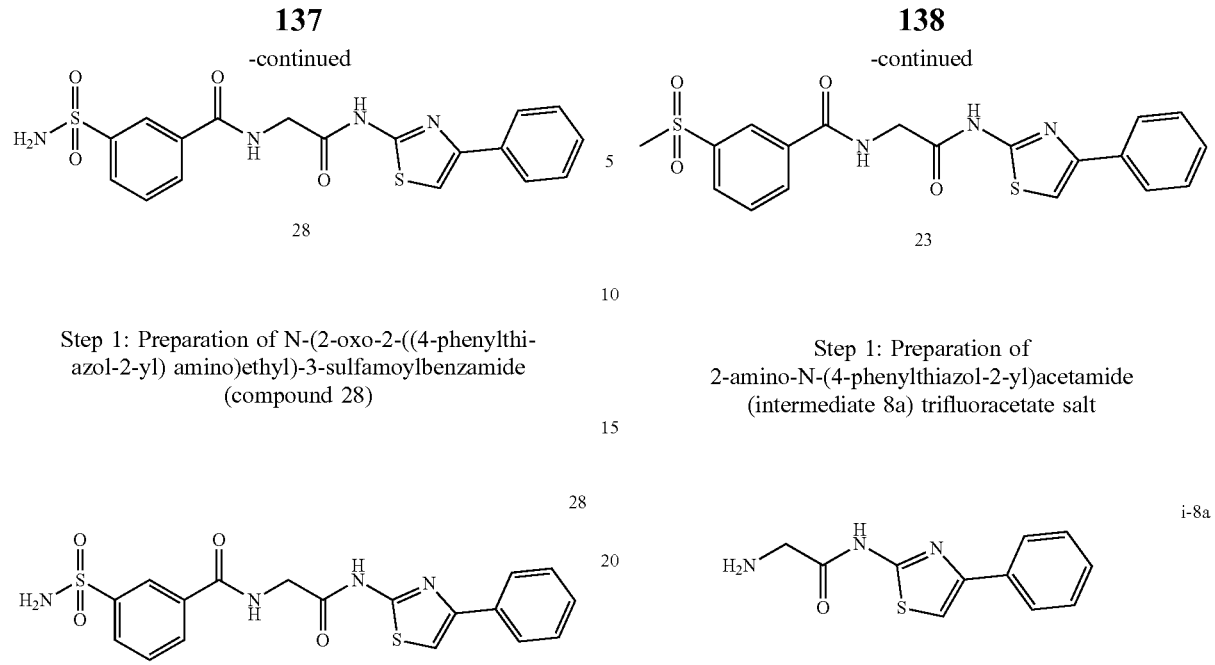

Step 1: Preparation of N-(2-oxo-2-((4-phenylthiazol-2-yl) amino)ethyl)-3-sulfamoylbenzamide (compound 28)

To a solution of 2-amino-N-(4-phenylthiazol-2-yl)acetamide (50 mg, 143.96 μmol) in DCM (2.0 mL) was added 3-sulfamoylbenzoic acid (28.97 mg, 143.96 μmol) and DIPEA (74.42 mg, 575.85 μmol, 100.30 μL). Then HATU (54.74 mg, 143.96 μmol) was added to the reaction. The mixture was stirred at 25° C. for 2 hr. Water (80.0 mL) was added and the reaction mixture was extracted with EtOAc (80.0 mL). The combined organic layers were washed with brine (20.0 mL), dried over $Na_2SO_4$, filtered and concentrated under reduced pressure to give a residue. To the residue was added DCM (80.0 mL) and then stirred for 10 min. The solid was filtered and dried in vacuum to give compound 28 as an off-white solid.

$^1$HNMR (400 MHz, DMSO-d6) δ=12.47 (s, 1H), 9.21-9.18 (m, 1H), 8.37 (s, 1H), 8.12 (d, J=7.6 Hz, 1H), 8.01 (d, J=8.0 Hz, 1H), 7.91-7.90 (m, 2H), 7.74-7.72 (m, 1H), 7.64 (s, 1H), 7.48-7.42 (m, 4H), 7.33-7.30 (m, 1H), 4.23 (d, J=5.6 Hz, 2H) ppm.

LCMS (ESI) m/z: [M-t-Bu]$^+$=417.2.

Example 8. Preparation of 3-methylsulfonyl-N-[2-oxo-2-[(4-phenylthiazol-2-yl)amino]ethyl]benzamide (compound 23)

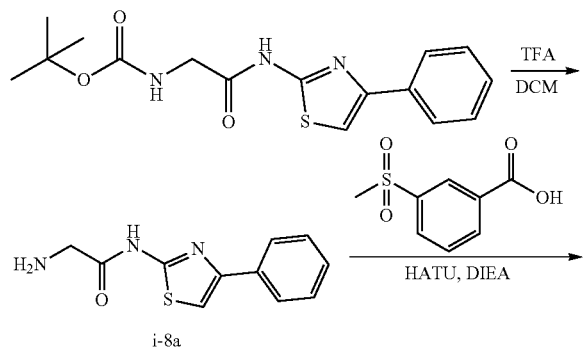

Step 1: Preparation of 2-amino-N-(4-phenylthiazol-2-yl)acetamide (intermediate 8a) trifluoracetate salt To a solution of tert-butyl N-[2-oxo-2-[(4-phenylthiazol-2-yl)amino]ethyl]carbamate (500 mg, 1.50 mmol) in DCM (3 mL) was added TFA (2.22 mL). The mixture was stirred at 25° C. for 1 hr. The reaction mixture was evaporated to dryness. To the residue was added MTBE/PE=(2/1, 30 mL) and stirred for 10 min then filtered to give a solid which was dried in vacuum to give intermediate i-8a (TFA salt) as a yellow solid.

LCMS (ESI) m/z: [M+H]$^+$=234.2.

Step 2: Preparation of 3-methylsulfonyl-N-[2-oxo-2-[(4-phenylthiazol-2-yl)amino]ethyl]benzamide (compound 23)

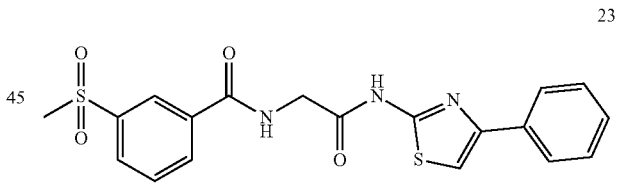

To a solution of 3-methylsulfonylbenzoic acid (42.91 mg, 214.32 μmol) in DCM (2 mL) were added HATU (89.64 mg, 235.75 μmol) and DIPEA (138.5 mg, 1.07 mmol) at 25° C. The mixture was stirred for 10 min and then intermediate i-8a (50 mg, 143.96 μmol) was added and the mixture was stirred at 25° C. for 1 hr. The reaction mixture was evaporated to dryness. To the residue was added 30 mL MeOH and stirred for 10 min, a white solid formed, the solid was filtered off and dried in vacuum to give compound 23 as an off-white solid.

$^1$H NMR (400 MHz, DMSO-d6) δ 12.44 (br s, 1H), 9.26-9.25 (m, 1H), 8.44 (s, 1H), 8.23 (d, J=7.6 Hz, 1H), 8.10 (d, J=7.6 Hz, 1H), 7.91-7.89 (m, 2H), 7.80-7.78 (m, 1H), 7.63 (s, 1H), 7.45-7.41 (m, 2H), 7.32-7.30 (m, 1H), 4.24 (d, J=6.0 Hz, 2H), 3.27 (s, 3H) ppm.

LCMS (ESI) m/z: [M+H]$^+$=416.1.

Example 9. Preparation of 3-(dimethylsulfamoyl)-N-[2-oxo-2-[[4-(2-pyridyl)thiazol-2-yl]amino]ethyl]benzamide (compound 32)

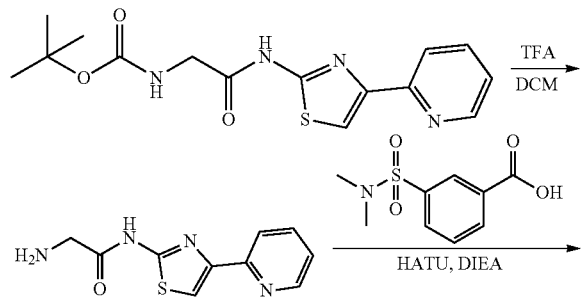

Step 1: Preparation of 2-amino-N-[4-(2-pyridyl)thiazol-2-yl]acetamide (intermediate 9a) trifluoroacetate salt To a solution of tert-butyl N-[2-oxo-2-[[4-(2-pyridyl)thiazol-2-yl]amino]ethyl]carbamate (250 mg, 665.39 μmol) in DCM (2 mL) was added TFA (1.10 mL). The mixture was stirred at 25° C. for 1 h. The reaction mixture was evaporated to dryness. To the residue was added MTBE/PE=(2/1, 30 mL) and stirred for 10 min then filtered. The solid was dried in vacuum to give intermediate i-9a (TFA salt) as a yellow solid.

LCMS (ESI) m/z: [M+H]$^+$=234.9.

Step 2: Preparation of 3-(dimethylsulfamoyl)-N-[2-oxo-2-[[4-(2-pyridyl)thiazol-2-yl]amino]ethyl]benzamide (compound 32)

To a mixture of 3-(dimethylsulfamoyl)benzoic acid (98.73 mg, 430.66 μmol) in DCM (2 mL) was added HATU (180.13 mg, 473.73 μmol) and DIPEA (278.30 mg, 2.15 mmol) at 25° C. The mixture was stirred at 25° C. for 10 min, then intermediate 9a (150 mg, 430.66 μmol) was added and stirred for 1 h. The reaction mixture was evaporated to dryness. To the residue was added MeOH (30 mL) and stirred for 10 min, then filtered and the filter cake was washed with MeOH (30 mL). The filter cake was evaporated to dryness to give compound 32 as an off-white solid.

$^1$HNMR (400 MHz, DMSO-d6) δ=12.49 (br s, 1H), 9.30-9.28 (m, 1H), 8.60 (d, J=4.0 Hz, 1H), 8.27-8.21 (m, 2H), 7.98-7.92 (m, 2H), 7.92-7.86 (m, 1H), 7.85-7.80 (m, 2H), 7.36-7.32 (m, 1H), 4.24 (d, J=5.6 Hz, 2H), 2.66 (s, 6H) ppm; LCMS (ESI) m/z: [M+H]$^+$=446.2.

Example 10. Preparation of Compound N-[(1S)-1-[(4-phenylthiazol-2-yl)carbamoyl]propyl]benzamide (compound 45)

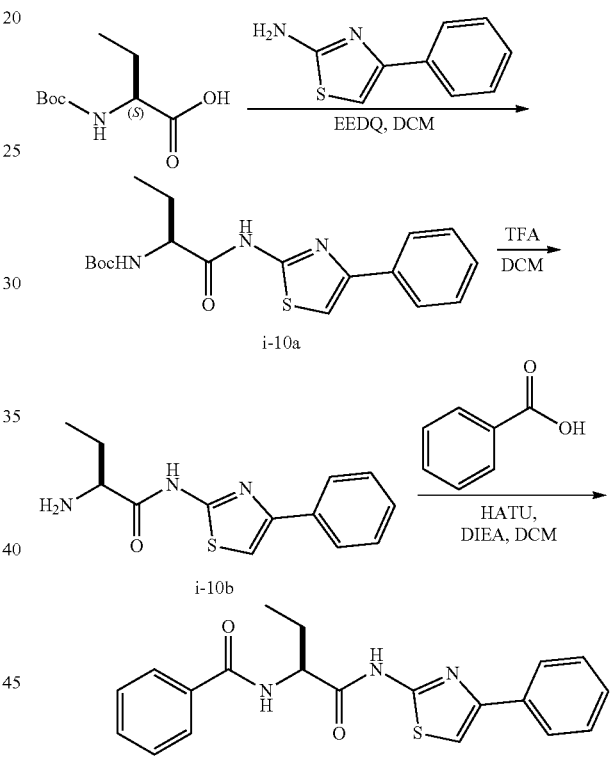

Step 1: Preparation of tert-butyl N-[(1S)-1-[(4-phenylthiazol-2-yl)carbamoyl]propyl]carbamate (intermediate i-10a)

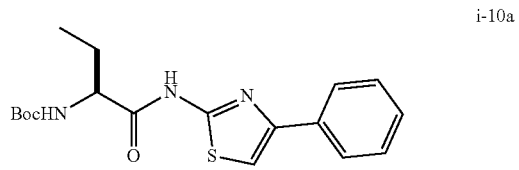 [SMILES: CC[C@H](NC(=O)OC(C)(C)C)C(=O)Nc1nc(-c2ccccc2)cs1]

To a solution of (2S)-2-(tert-butoxycarbonylamino)butanoic acid (200.0 mg, 984.08 μmol) in DCM (5.0 mL) were added EEDQ (331.85 mg, 1.34 mmol) and 4-phenylthiazol-2-amine (157.67 mg, 894.62 µmol) in one portion at 20° C. under $N_2$. The mixture was stirred at 20° C. for 8 hours. The reaction mixture was diluted with EtOAc (50.0 mL), and washed with citric acid (10%) (50.0 mL*3). The organic phase was washed with saturated brine (20.0 mL*3) and dried over $Na_2SO_4$, filtered and concentrated under reduced pressure to give a residue. The residue was purified by column chromatography ($SiO_2$, Petroleum ether/Ethyl acetate=20/1) to give intermediate i-10a as a white solid.

$^1$H NMR (400 MHz, CDCl3) δ 9.90 (br s, 1H), 7.94-7.77 (m, 2H), 7.50-7.38 (m, 2H), 7.37-7.31 (m, 1H), 7.15 (s, 1H), 5.10 (br s, 1H), 4.36 (br s, 1H), 1.50 (s, 9H), 1.40-1.22 (m, 2H), 1.07-0.97 (m, 3H) ppm.

LCMS (ESI) m/z: [M+H]$^+$=362.2.

Step 2: Preparation of (2S)-2-amino-N-(4-phenylthiazol-2-yl)butanamide (intermediate i-10b) trifluoroacetate salt

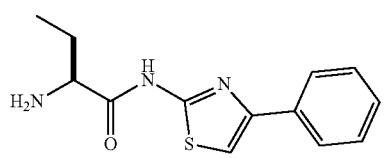

i-10b

To a solution of intermediate i-10a (300.00 mg, 829.97 µmol) in DCM (10.0 mL) was added TFA (1.08 mL) in one portion at 20° C. under $N_2$. The mixture was stirred at 20° C. for 2 hours. The reaction mixture was concentrated under reduced pressure to give intermediate i-10b (TFA salt) as a white solid, which was used in the next step without further purification.

LCMS (ESI) m/z: [M+H]$^+$=262.2.

Step 3: Preparation of N-[(1 S)-1-[(4-phenylthiazol-2-yl)carbamoyl]propyl]benzamide (compound 45)

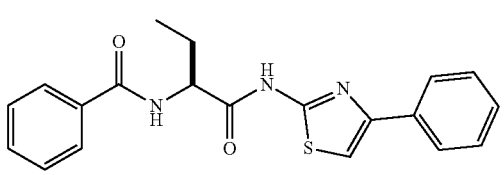

45

To a mixture of HATU (73.95 mg, 194.48 µmol) and benzoic acid (17.42 mg, 142.62 µmol) in DCM (10.0 mL) was added DIPEA (67.03 mg, 518.62 µmol) in one portion at 20° C. under $N_2$. The mixture was stirred at 20° C. for 10 min. Then intermediate i-10b (50.0 mg, 191.32 µmol) was added and the mixture was stirred at 20° C. for 2 hours. The reaction mixture was concentrated under reduced pressure to give a residue. The residue was purified by prep-HPLC (TFA condition; column: Boston pH-lex 150*25 10 µm; mobile phase: [water (0.1% TFA)-ACN]; B %: 47%-77%, 10 min) and lyophilized to give compound 45 as a white solid.

$^1$H NMR (400 MHz, CDCl$_3$) δ=8.00 (d, J=7.2 Hz, 2H), 7.84 (d, J=7.6 Hz, 2H), 7.64-7.54 (m, 1H), 7.53-7.46 (m, 2H), 7.46-7.40 (m, 2H), 7.40-7.33 (m, 1H), 7.17 (s, 1H), 7.00 (br d, J=8.0 Hz, 1H), 5.18-5.12 (m, 1H), 2.22-2.17 (m, 1H), 2.05-1.97 (m, 1H), 1.14-1.11 (m, 3H) ppm.

LCMS (ESI) m/z: [M+H]$^+$=366.0.

Chiral HPLC: Amycoat-MeOH(DEA)-40-3 mL-35T, 1.417 min.

Example 11. Preparation of N-[(1S)-1-(hydroxymethyl)-2-oxo-2-[(4-phenylthiazol-2-yl)amino]ethyl] benzamide (compound 47)

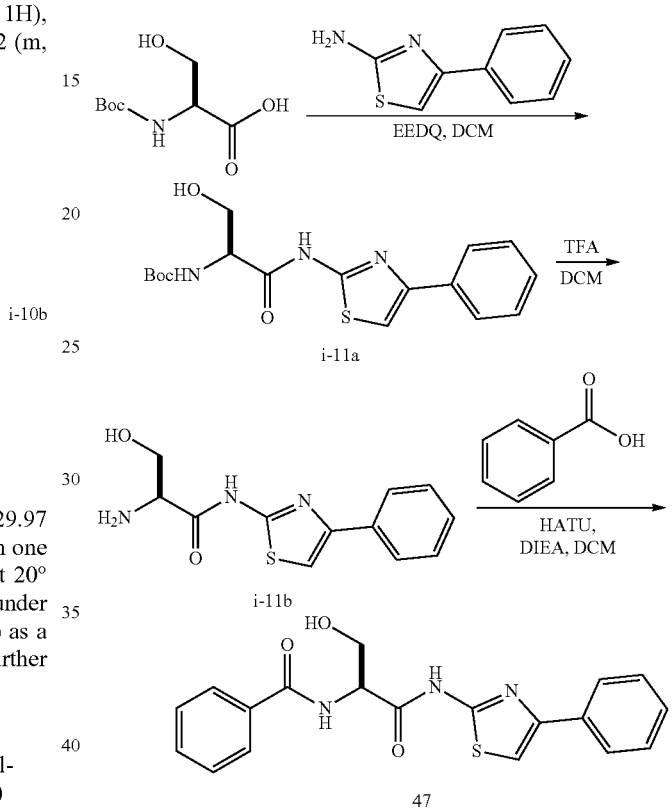

47

Step 1: Preparation of tert-butyl N-[(1S)-1-(hydroxymethyl)-2-oxo-2-[(4-phenylthiazol-2-yl)amino]ethyl]carbamate (intermediate i-11a)

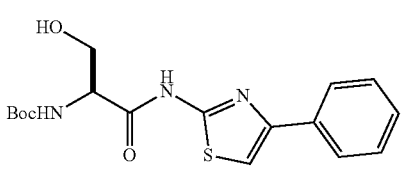

i-11a

To a mixture of (2S)-2-(tert-butoxycarbonylamino)-3-hydroxy-propanoic acid (200.0 mg, 974.62 µmol) in DCM (5.0 mL) was added EEDQ (328.66 mg, 1.33 mmol) and 4-phenylthiazol-2-amine (156.15 mg, 886.02 µmol) in one portion at 20° C. under $N_2$. The mixture was stirred at 20° C. for 3 hours. The reaction mixture was diluted with EtOAc (50.0 mL), and washed with citric acid (10%) (50.0 mL*3). The organic phase was washed with brine (20.0 mL*3) and dried over Na$_2$SO$_4$, filtered and concentrated under reduced pressure to give a residue. The residue was purified by column chromatography (SiO$_2$, Petroleum ether/Ethyl acetate=5/1 to 2:1) to give intermediate i-11a as colorless oil.

LCMS (ESI) m/z: [M+H]$^+$=364.2.

Step 2: Preparation of ((2S)-2-amino-3-hydroxy-N-(4-phenylthiazol-2-yl)propanamide (intermediate i-11b) trifluoroacetate salt

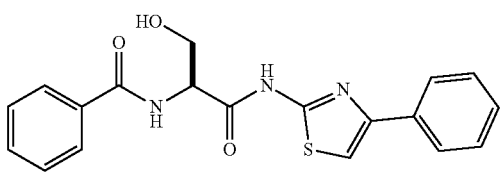

i-11b

To a mixture of intermediate i-11a (130.00 mg, 182.07 μmol) in DCM (10.0 mL) was added trifluoroacetic acid (1.0 mL) in one portion at 20° C. under N$_2$. The mixture was stirred at 20° C. for 2 hours. The reaction mixture was concentrated under reduced pressure to give intermediate i-11b (TFA salt) as a white solid and which was used in the next step without further purification.

LCMS (ESI) m/z: [M+H]$^+$=264.2.

Step 3: Preparation of N-[(1 S)-1-(hydroxymethyl)-2-oxo-2-[(4-phenylthiazol-2-yl)amino]ethyl]benzamide (compound 47)

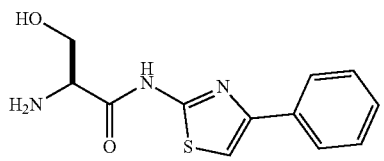

47

To a mixture of HATU (47.91 mg, 126.00 μmol) and benzoic acid (11.29 mg, 92.48 μmol) in DCM (2.0 mL) was added DIPEA (43.43 mg, 336.04 μmol) in one portion at 20° C. under N$_2$, and the mixture was stirred at 20° C. for 10 min. Then intermediate i-11b (50.0 mg, 132.51 μmol) was added and the mixture was stirred at 20° C. for 2 hours. The reaction mixture was concentrated under reduced pressure to give a residue. The residue was purified by prep-HPLC (TFA condition; column: Phenomenex Synergi C18 150*25*10 μm; mobile phase: [water (0.1% TFA)-ACN]; B %: 35%-65%, 9 min) and lyophilized to give the compound 47 as a white solid.

$^1$H NMR (400 MHz, CDCl$_3$) δ=7.93 (d, J=8.0 Hz, 2H), 7.84 (d, J=8.0 Hz, 2H), 7.63-7.57 (m, 1H), 7.52-7.37 (m, 5H), 7.18 (s, 1H), 5.02-4.99 (m, 1H), 4.47-4.43 (m, 1H), 3.96-3.92 (m, 1H) ppm.

LCMS (ESI) m/z: [M+H]$^+$=368.0.

Chiral HPLC: Amycoat-MeOH(DEA)-40-7 min-3 mL, 2.042 min.

Example 12. Preparation of N-[(1S)-2-methyl-1-[(4-phenylthiazol-2-yl)carbamoyl]propyl]benzamide (compound 50)

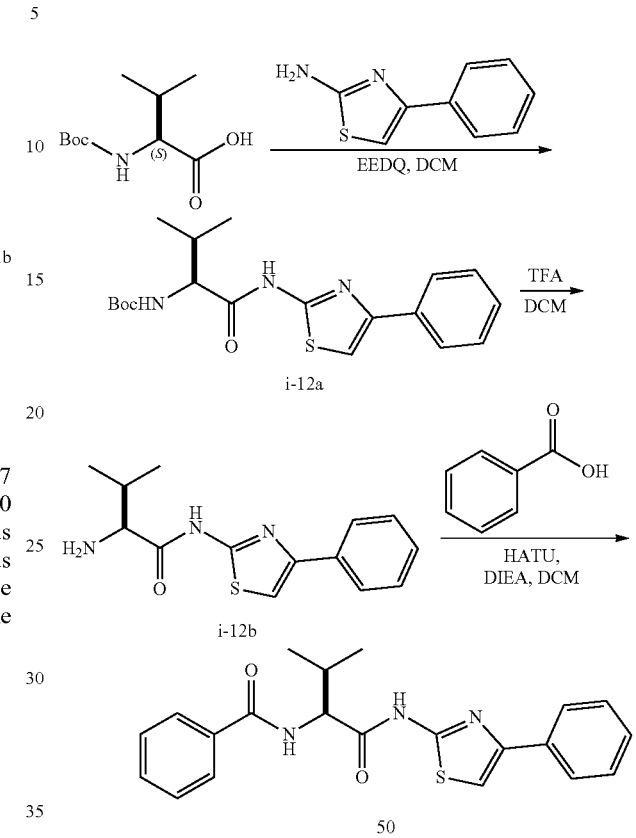

50

Step 1: Preparation of tert-butylN-[(1S)-2-methyl-1-[(4-phenylthiazol-2-yl)carbamoyl]propyl]carbamate (intermediate i-12a)

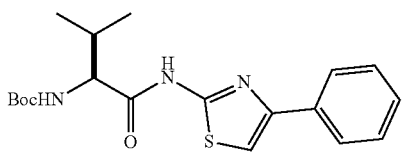

i-12a

To a solution of (2S)-2-(tert-butoxycarbonylamino)-3-methyl-butanoic acid (200.0 mg, 920.55 μmol) in DCM (5.0 mL) were added EEDQ (310.42 mg, 1.26 mmol) and 4-phenylthiazol-2-amine (147.49 mg, 836.86 μmol) in one portion at 20° C. under N$_2$. The mixture was stirred at 20° C. for 8 hours. The reaction mixture was diluted with EtOAc (50.0 mL), and washed with citric acid (10%) (50.0 mL*3). The combined organic layers were washed with saturated brine (20.0 mL*3), dried over Na$_2$SO$_4$, filtered and concentrated under reduced pressure to give a residue. The residue was purified by column chromatography (SiO$_2$, Petroleum ether/Ethyl acetate=20/1) to give intermediate i-12a as a colorless oil.

LCMS (ESI) m/z: [M+H]$^+$=376.2.

Step 2: Preparation of (2S)-2-amino-3-methyl-N-(4-phenylthiazol-2-yl)butanamide (intermediate i-12b) trifluoroacetate salt

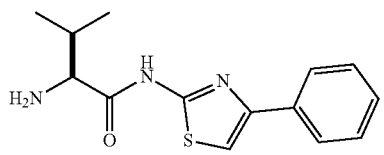

i-12b

To a mixture of Intermediate i-12a (300.00 mg, 629.59 µmol) in DCM (10.0 mL) was added trifluoroacetic acid (1.0 mL) in one portion at 20° C. under N₂. The mixture was stirred at 20° C. for 2 hours. The reaction mixture was concentrated under reduced pressure to give intermediate i-12b (TFA salt) as a white solid which was used into next step without purification.

LCMS (ESI) m/z: [M+H]$^+$=276.2.

Step 3: Preparation of N-[(1 S)-2-methyl-1-[(4-phenylthiazol-2-yl)carbamoyl]propyl]benzamide (compound 50)

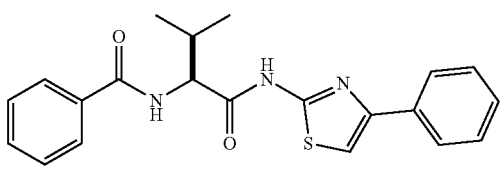

50

To a mixture of HATU (61.81 mg, 162.56 µmol) and benzoic acid (14.56 mg, 119.23 µmol) in DCM (2.0 mL) was added DIPEA (56.03 mg, 433.53 µmol) in one portion at 20° C. under N₂. The mixture was stirred at 20° C. for 10 min. Then intermediate i-12b (50.0 mg, 128.41 µmol) was added and the mixture was stirred at 20° C. for 2 hours. The reaction mixture was concentrated under reduced pressure to give a residue. The residue was purified by prep-HPLC (TFA condition; column: Boston pH-lex 150*25 10 µm; mobile phase: [water (0.1% TFA)-ACN]; B %:50%-80%, 10 min) and lyophilized to give compound 50 as a white solid.

¹H NMR (400 MHz, CDCl3) δ 10.52 (br s, 1H), 7.99 (d, J=8.0 Hz, 2H), 7.81 (d, J=8.0 Hz, 2H), 7.61-7.54 (m, 1H), 7.52-7.45 (m, 2H), 7.43-7.36 (m, 2H), 7.36-7.29 (m, 1H), 7.16 (s, 1H), 6.91 (d, J=8.0 Hz, 1H), 5.24-5.09 (m, 1H), 2.46-2.38 (m, 1H), 1.16-1.13 (m, 6H).

LCMS (ESI) m/z: [M+H]$^+$=380.0.

Chiral HPLC: Cellucoat-MeOH(DEA)-5-40-3 mL-35, 1.981 min.

Example 13. Preparation of Compound N-[(1S)-1-[(4-phenylthiazol-2-yl)carbamoyl]butyl]benzamide (compound 51)

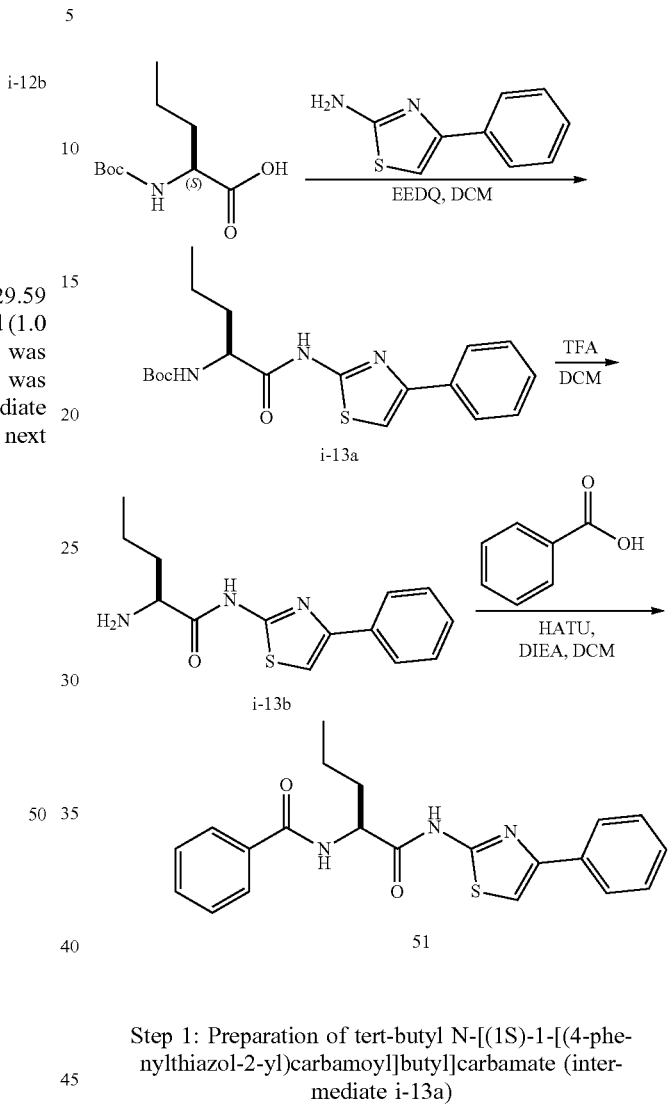

Step 1: Preparation of tert-butyl N-[(1S)-1-[(4-phenylthiazol-2-yl)carbamoyl]butyl]carbamate (intermediate i-13a)

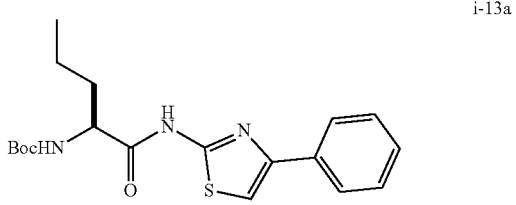 [SMILES: CCC[C@H](NC(=O)OC(C)(C)C)C(=O)Nc1nc(-c2ccccc2)cs1]

i-13a

To a mixture of (2S)-2-(tert-butoxycarbonylamino)pentanoic acid (200.0 mg, 920.55 µmol) in DCM (5.0 mL) was added EEDQ (310.42 mg, 1.26 mmol) and 4-phenylthiazol-2-amine (147.49 mg, 836.86 µmol) in one portion at 20° C. under N₂. The mixture was stirred at 20° C. for 8 hours. The reaction mixture was diluted with EtOAC (50.0 mL), and washed with citric acid (10%) (50.0 mL*3). The combined organic layers were washed with saturated brine (20.0 mL*3), dried over Na₂SO₄, filtered and concentrated under reduced pressure to give a residue. The residue was purified by column chromatography (SiO$_2$, Petroleum ether/Ethyl acetate=20/1) to give intermediate i-13a as colorless oil.

LCMS (ESI) m/z: [M+H]$^+$=376.3.

Step 2: Preparation of (2S)-2-amino-3-methyl-N-(4-phenylthiazol-2-yl)butanamide (intermediate i-13b) trifluoroacetate salt

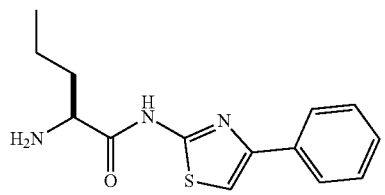

i-13b

To a mixture of Intermediate i-13a (300.00 mg, 661.55 μmol) in DCM (10.0 mL) was added trifluoroacetic acid (937.48 μL) in one portion at 20° C. under N$_2$. The mixture was stirred at 20° C. for 2 hours. The reaction mixture was concentrated under reduced pressure to give intermediate i-13b (TFA salt) as a white solid, which was used into the next step without further purification.

LCMS (ESI) m/z: [M+H]$^+$=276.2.

Step 3: Preparation of N-[(1 S)-1-[(4-phenylthiazol-2-yl)carbamoyl]butyl]benzamide (compound 40)

51

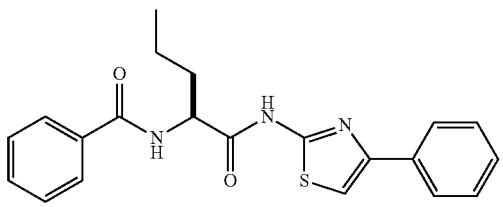

To a mixture of HATU (51.26 mg, 134.83 μmol) and benzoic acid (15.09 mg, 123.59 μmol) in DCM (2.0 mL) was added DIPEA (58.08 mg, 449.42 μmol) in one portion at 20° C. under N$_2$. The mixture was stirred at 20° C. for 10 min. Then intermediate i-13b (50.0 mg, 181.57 μmol, TFA salt) was added and the mixture was stirred at 20° C. for 2 hours. The reaction mixture was concentrated under reduced pressure to give a residue. The residue was purified by prep-HPLC (TFA condition; column: Boston pH-lex 150*25 10 μm; mobile phase: [water (0.1% TFA)-ACN]; B %: 50%-80%, 10 min) and lyophilized to give compound 51 as a white solid.

$^1$H NMR (400 MHz, CDCl3) δ 7.95-7.93 (m, 2H), 7.78-7.76 (m, 2H), 7.58-7.51 (m, 1H), 7.48-7.41 (m, 5H), 7.12 (s, 1H), 7.08-6.99 (m, 1H), 5.04-4.99 (m, 1H), 2.09-2.03 (m, 1H), 1.95-1.92 (m, 1H), 1.56-1.50 (m, 2H), 1.04-1.00 (m, 3H) ppm.

LCMS (ESI) m/z: [M+H]$^+$=380.0.

Chiral HPLC: Cellucoat-MeOH(DEA)-5-40-3 mL-3, 2.141 min.

Example 14. Preparation of N-[(1S)-3-methyl-1-[(4-phenylthiazol-2-yl)carbamoyl]butyl]benzamide (compound 48)

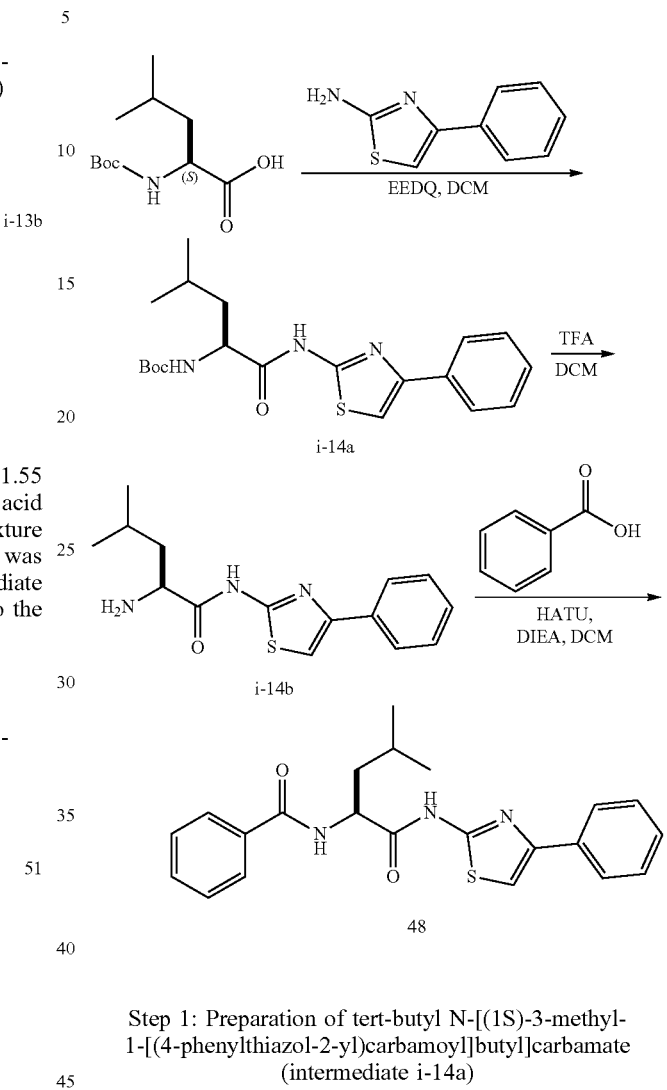

Step 1: Preparation of tert-butyl N-[(1S)-3-methyl-1-[(4-phenylthiazol-2-yl)carbamoyl]butyl]carbamate (intermediate i-14a)

i-14a

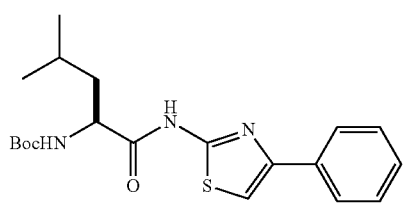

To a mixture of (2S)-2-(tert-butoxycarbonylamino)-4-methyl-pentanoic acid;hydrate (200.00 mg, 802.24 μmol) in DCM (5.0 mL) was added EEDQ (270.53 mg, 1.09 mmol) and 4-phenylthiazol-2-amine (128.53 mg, 729.31 μmol) in one portion at 20° C. under N$_2$. The mixture was stirred at 20° C. for 3 hours. The reaction mixture was diluted with EA (50.0 mL), and washed with citric acid (10%) (50.0 mL*3). The organic phase was washed with saturated brine (20.0 mL*3) and dried over Na$_2$SO$_4$, filtered and concentrated under reduced pressure to give a residue. The residue was purified by column chromatography (SiO2, Petroleum ether/Ethyl acetate=20/1) to give intermediate i-14a as colorless oil.

LCMS (ESI) m/z: [M+H]$^+$=390.3.

Step 2: Preparation of (2S)-2-amino-3-methyl-N-(4-phenylthiazol-2-yl)butanamide (intermediate i-14b) trifluoroacetate salt

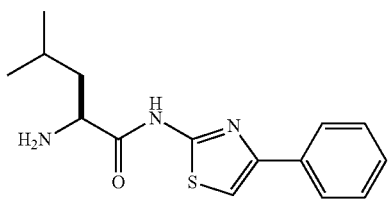

i-14b

To a solution of intermediate i-14a (170.00 mg, 392.80 μmol) in DCM (10.0 mL) was added trifluoroacetic acid (742.95 μL) in one portion at 20° C. under N$_2$. The mixture was stirred at 20° C. for 2 hours. The reaction mixture was concentrated under reduced pressure to give intermediate i-14b (TFA salt) as a white solid, which was used into the next step without further purification.

LCMS (ESI) m/z: [M+H]$^+$=290.2.

Step 3: Preparation of N-[(1 S)-3-methyl-1-[(4-phenylthiazol-2-yl)carbamoyl]butyl]benzamide (compound 48)

48

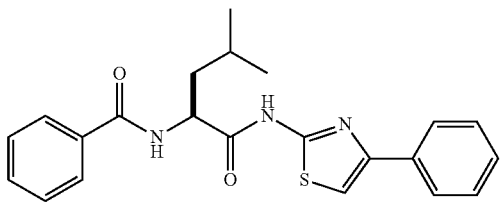

To a mixture of HATU (69.13 mg, 181.81 μmol) and benzoic acid (16.28 mg, 133.31 μmol,) in DCM (2.0 mL) was added DIPEA (62.66 mg, 484.82 μmol) in one portion at 20° C. under N$_2$. The mixture was stirred at 20° C. for 10 min. Then intermediate i-14b (50.0 mg, 172.77 μmol TFA salt) was added and the mixture was stirred at 20° C. for 2 hours. The reaction mixture was concentrated under reduced pressure to give a residue. The residue was purified by prep-HPLC (TFA condition; column: Boston pH-lex 150*25 10 μm; mobile phase: [water (0.1% TFA)-ACN]; B %: 53%-83%, 10 min) to give compound 48 as a white solid.

$^1$H NMR (400 MHz, CDCl3) δ 10.19 (br s, 1H), 7.92-7.87 (m, 2H), 7.86-7.81 (m, 2H), 7.61-7.55 (m, 1H), 7.52-7.46 (m, 2H), 7.45-7.38 (m, 2H), 7.37-7.30 (m, 1H), 7.16 (s, 1H), 6.59 (br d, J=8.0 Hz, 1H), 5.10-5.00 (m, 1H), 2.02-1.98 (m, 1H), 1.84-1.79 (m, 2H), 1.05-1.02 (m, 6H) ppm.

LCMS (ESI) m/z: [M+H]$^+$=394.1.

Chiral HPLC: Cellucoat-MeOH(DEA)-5-40-3 mL-3, 1.875 min.

Example 15. Preparation of (1S)-3-methyl-1-[(4-phenylthiazol-2-yl)carbamoyl]butyl]benzamide (compound 41)

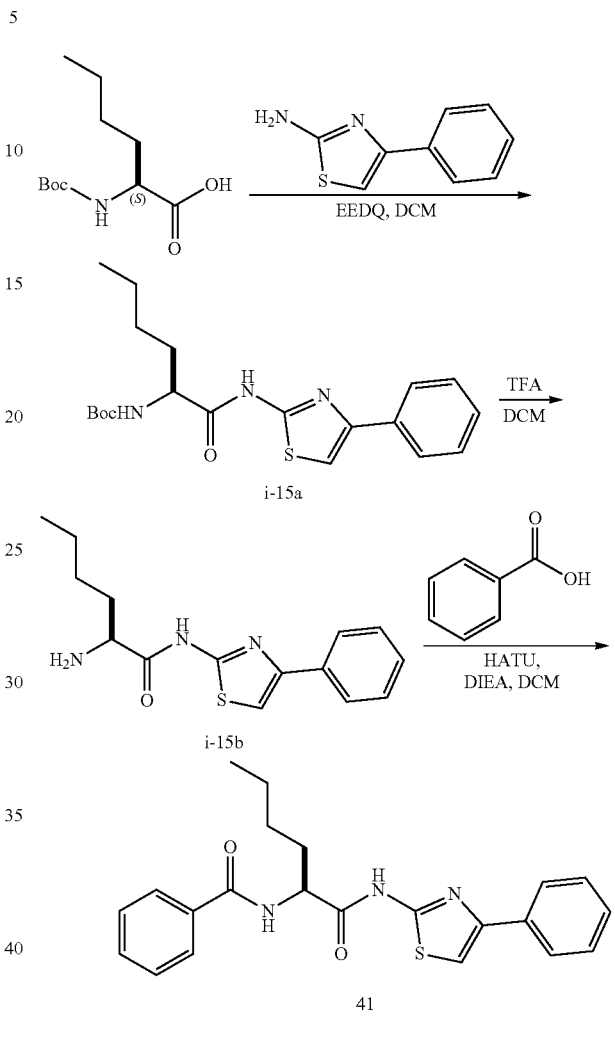

41

Step 1: Preparation of tert-butyl N-[(1S)-1-[(4-phenylthiazol-2-yl)carbamoyl]pentyl]carbamate (intermediate i-15a)

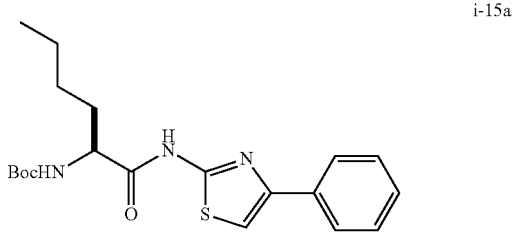 [SMILES: CCCC[C@H](NC(=O)OC(C)(C)C)C(=O)Nc1nc(-c2ccccc2)cs1]

i-15a

To a solution of (2S)-2-(tert-butoxycarbonylamino) hexanoic acid (200.0 mg, 864.72 μmol) in DCM (5.0 mL) were added EEDQ (291.60 mg, 1.18 mmol) and 4-phenylthiazol-2-amine (138.54 mg, 786.11 μmol) in one portion at 20° C. under N$_2$. The mixture was stirred at 20° C. for 8 hours. The reaction mixture was diluted with EtOAc (50.0 mL) and washed with citric acid (10%) (50.0 mL*3). The organic phase was washed with saturated brine (20.0 mL*3) and dried over Na$_2$SO$_4$, filtered and concentrated under reduced pressure to give a residue. The residue was purified by column chromatography (SiO$_2$, Petroleum ether/Ethyl acetate=20/1). Intermediate i-15a was obtained as a white solid.

LCMS (ESI) m/z: [M+H]$^+$=390.3.

Step 2: Preparation of (2S)-2-amino-N-(4-phenylthiazol-2-yl)hexanamide (intermediate i-15b)

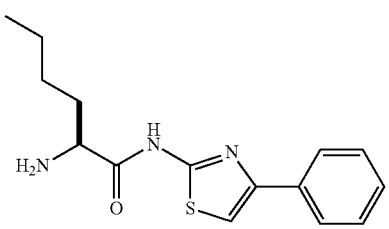

i-15b

To a mixture of Intermediate i-15a (230.00 mg, 590.48 µmol) in DCM (10.0 mL) was added trifluoroacetic acid (1.03 mL) in one portion at 20° C. under N$_2$. The mixture was stirred at 20° C. for 2 hours. The reaction mixture was concentrated under reduced pressure to give intermediate i-15b (TFA salt) as a white solid, which was used in the next step without further purification.

LCMS (ESI) m/z: [M+H]$^+$=290.2.

Step 3: Preparation of N-[(1 S)-3-methyl-1-[(4-phenylthiazol-2-yl)carbamoyl]butyl]benzamide (compound 41)

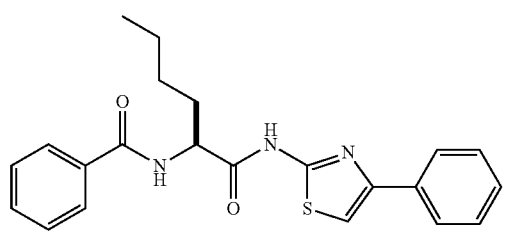

41

To a mixture of HATU (67.32 mg, 177.05 µmol) and benzoic acid (15.86 mg, 129.84 µmol,) in DCM (5.0 mL) was added DIPEA (61.02 mg, 472.15 µmol) in one portion at 20° C. under N$_2$. The mixture was stirred at 20° C. for 10 min. Then Intermediate i-15b (50.0 mg, 123.94 µmol) was added and the mixture was stirred at 20° C. for 2 hours. The reaction mixture was concentrated under reduced pressure to give a residue. The residue was purified by prep-HPLC (TFA condition; column: Boston pH-lex 150*25 10 µm; mobile phase: [water (0.1% TFA)-ACN]; B %: 53%-83%, 10 min) and lyophilized to give compound 41 as a white solid.

$^1$H NMR (400 MHz, CDCl3) δ 7.98-7.96 (m, 2H), 7.83-7.81 (m, 2H), 7.62-7.55 (m, 1H), 7.53-7.42 (m, 4H), 7.41-7.35 (m, 1H), 7.15 (s, 1H), 7.04-6.95 (m, 1H), 5.13-5.08 (m, 1H), 2.15-2.11 (m, 1H), 1.98-1.94 (m, 1H), 1.51-1.41 (m, 4H), 0.96-0.92 (m, 3H) ppm.

LCMS (ESI) m/z: [M+H]$^+$=394.0.

Chiral HPLC: Amycoat-MeOH(DEA)-40-3 mL-35T, 1.431 min.

Example 16. Preparation of Compound N-[(1S)-3-phenyl-1-[(4-phenylthiazol-2-)carbamoyl]propyl]benzamide (compound 49)

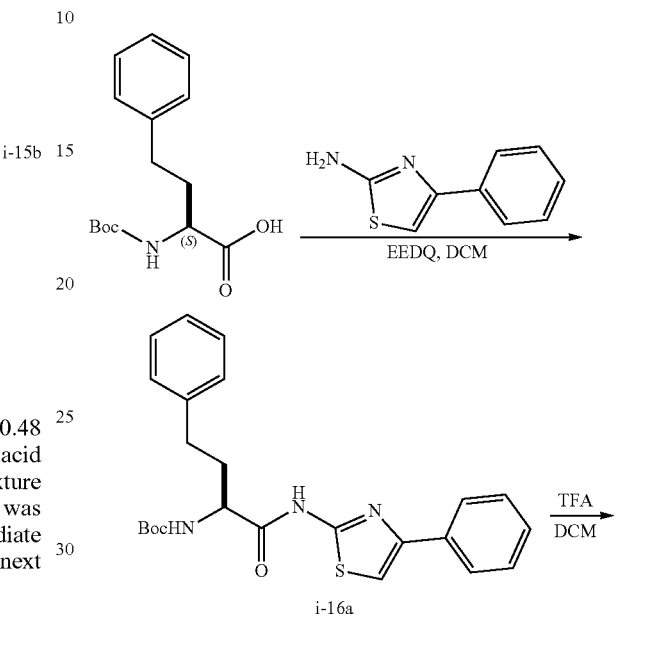

i-16a

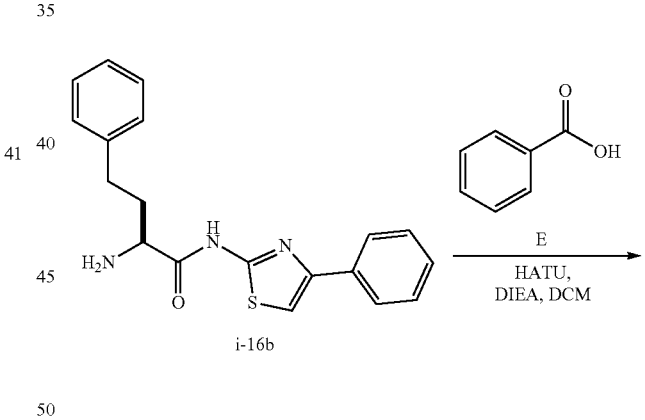

i-16b

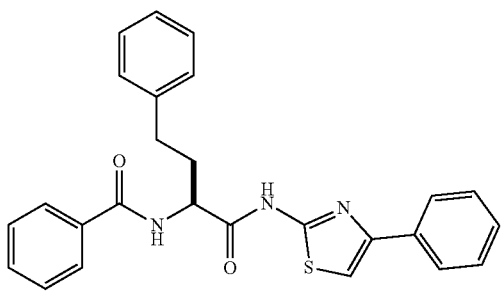

49

Step 1: Preparation of tert-butyl N-[(1S)-3-phenyl-1-[(4-phenylthiazol-2-yl)carbamoyl]propyl]carbamate (intermediate i-16a)

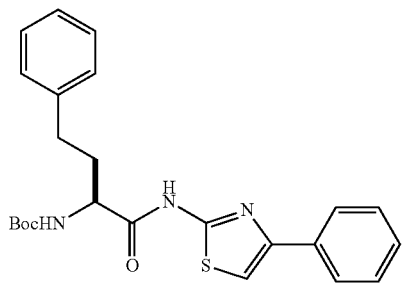

i-16a

To a mixture of 4-phenylthiazol-2-amine (114.71 mg, 650.91 μmol) in DCM (5 mL) was added EEDQ (241.44 mg, 976.36 μmol) and (2S)-2-(tert-butoxycarbonylamino)-4-phenyl-butanoic acid (200.0 mg, 716.00 μmol) in one portion at 20° C. under $N_2$. The mixture was stirred at 20° C. for 8 hours. The reaction mixture was diluted with EtOAc (50.0 mL), and washed with citric acid (10%) (50.0 mL*3). The organic phase was washed with saturated brine (20.0 mL*3) and dried over $Na_2SO_4$, filtered and concentrated under reduced pressure to give a residue. The residue was purified by column chromatography ($SiO_2$, Petroleum ether/Ethyl acetate=10/1). Intermediate i-16a was obtained as a white solid.

LCMS (ESI) m/z: $[M+H]^+$=438.3.

Step 2: Preparation of (2S)-2-amino-4-phenyl-N-(4-phenylthiazol-2-yl)butanamide (intermediate i-16b)

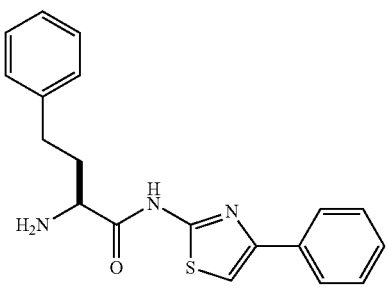

i-16b

To a mixture of Intermediate i-16a (270.00 mg, 569.67 μmol) in DCM (10.0 mL) was added trifluoroacetic acid (923.19 μL) in one portion at 20° C. under $N_2$. The mixture was stirred at 20° C. for 1 hour. The reaction mixture was concentrated under reduced pressure to give intermediate i-16b (TFA salt) as yellow oil, which was used in the next step without further purification.

LCMS (ESI) m/z: $[M+H]^+$=338.2.

Step 3: Preparation of N-[(1 S)-3-phenyl-1-[(4-phenylthiazol-2-yl)carbamoyl]propyl]benzamide (compound 49)

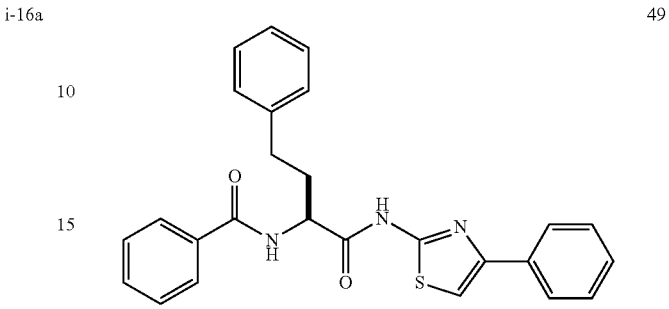

49

To a mixture of HATU (57.62 mg, 151.54 μmol) and benzoic acid (13.57 mg, 111.13 μmol) in DCM (2.0 mL) was added DIPEA (52.23 mg, 404.11 μmol) in one portion at 20° C. under $N_2$. The mixture was stirred at 20° C. for 10 min. Then intermediate i-16b (50.0 mg, 110.75 μmol) was added and the mixture was stirred at 20° C. for 2 hours. The reaction mixture was concentrated under reduced pressure to give a residue. The residue was triturated in MeOH (10.0 mL), the solid was collected by filtration and dried in vacuum to give compound 49 as a white solid.

$^1$H NMR (400 MHz, DMSO-d6) δ=12.54 (s, 1H), 8.85 (d, J=7.2 Hz, 1H), 8.02-7.95 (m, 4H), 7.69 (s, 1H), 7.67-7.61 (m, 1H), 7.61-7.54 (m, 2H), 7.53-7.46 (m, 2H), 7.42-7.29 (m, 5H), 7.28-7.22 (m, 1H), 4.80-4.74 (m, 1H), 2.87-2.75 (m, 1H), 2.55-2.45 (m, 1H), 2.23-2.19 (m, 2H).

LCMS (ESI) m/z: $[M+H]^+$=442.1.

Chiral HPLC: Amycoat-MeOH(DEA)-40-7 min-3 mL, 3.118 min.

Example 17. Preparation of Compound 3-(dimethylsulfamoyl)-N-[2-[[4-(o-tolyl)thiazol-2-yl]amino]-2-oxo-ethyl]benzamide (compound 16)

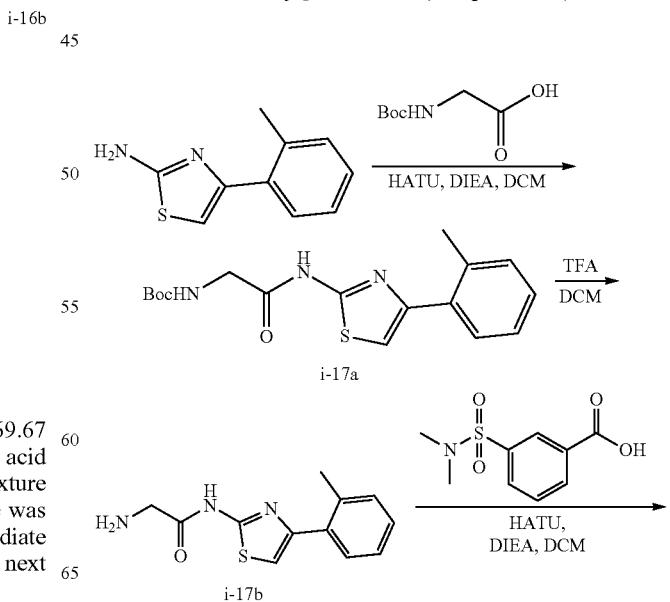

-continued

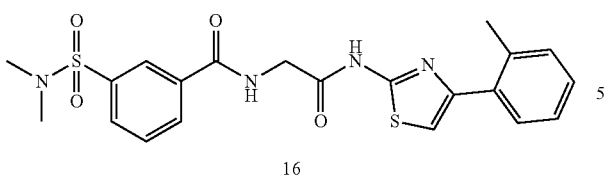

16

Step 1: Preparation of tert-butyl (2-oxo-2-((4-(o-tolyl)thiazol-2-yl)amino)ethyl)carbamate (intermediate i-17a)

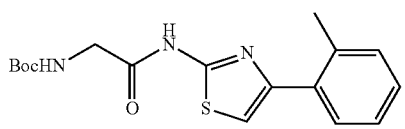

i-17a

To a solution of 2-(tert-butoxycarbonylamino)acetic acid (184.15 mg, 1.05 mmol) in DCM (2.0 mL) was added DIEA (407.57 mg, 3.15 mmol) and HATU (439.65 mg, 1.16 mmol). After 0.5 hr, 4-(o-tolyl)thiazol-2-amine (200.0 mg, 1.05 mmol) was added and the mixture was stirred at 20° C. for 1.5 hr. The reaction mixture was poured into water (10.0 mL) and extracted with EtOAc (10.0 mL*3). The combined organic layers were washed with brine (10.0 mL), dried over $Na_2SO_4$, filtered and concentrated. The crude product was triturated with MTBE (10.0 mL). The solid was collected by filtration and dried in vacuo to give intermediate i-17a as white solid.

$^1$H NMR (400 MHz, $CDCl_3$) δ 10.53-10.01 (m, 1H), 7.51 (s, 1H), 7.32-7.30 (m, 6H), 6.94 (s, 1H), 5.01 (br s, 1H), 3.87 (br s, 2H), 2.41 (s, 3H), 1.46 (s, 9H) ppm LCMS (ESI) m/z: [M+H]$^+$=348.1

Step 2: Preparation of 2-amino-N-(4-(o-tolyl)thiazol-2-yl)acetamide (intermediate i-17b)

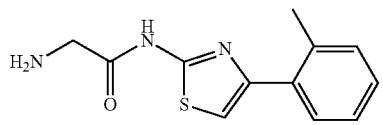

i-17b

To a solution of intermediate i-17a (210 mg, 604.44 μmol) in DCM (2.1 mL) was added TFA (0.3 mL) at 20° C. The mixture was stirred at 20° C. for 16 hr. The reaction mixture was poured into sat.$NaHCO_3$ (10.0 mL) and extracted with EtOAc (20.0 mL*3). The combined organic extracts were washed with brine (20.0 mL), dried over $Na_2SO_4$, filtered and concentrated. The residue was purified by column chromatography ($SiO_2$, PE:EA=10:1 to 8:1 to 5:1) to give intermediate i-17b as brown oil.

LCMS (ESI) m/z: [M+H]$^+$=248.1

Step 3: Preparation of -(dimethylsulfamoyl)-N-[2-[[4-(o-tolyl)thiazol-2-yl]amino]-2-oxo-ethyl]benzamide (compound 16)

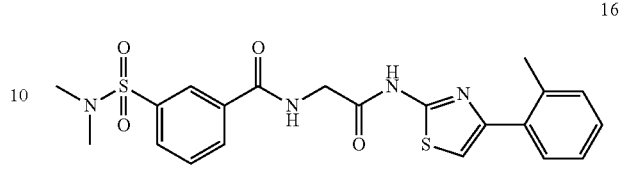

16

To a solution of 3-(dimethylsulfamoyl)benzoic acid (111.24 mg, 485.21 μmol) in DCM (2.0 mL) was added HATU (202.94 mg, 533.73 μmol) and DIEA (188.13 mg, 1.46 mmol). The mixture was stirred at 20° C. for 0.5 hr. Intermediate D (120.0 mg, 485.21 μmol) was added and the mixture was stirred at 20° C. for 1.5 hr. The reaction mixture was poured into water (10.0 mL) and extracted with EtOAc (10.0 mL*3). The combined organic extract were washed with brine (10.0 mL), dried over $Na_2SO_4$, filtered and concentrated. The crude product was triturated with MeOH (10.0 mL). The solid was collected by filtration and dried in vacuo to give compound 16 as white solid.

$^1$H NMR (400 MHz, DMSO-d6) δ 12.40 (s, 1H), 9.31-9.28 (m, 1H), 8.26-8.22 (m, 2H), 7.95-7.93 (m, 1H), 7.82-7.80 (m, 1H), 7.59-7.57 (m, 1H), 7.27-7.25 (m, 4H), 4.22 (d, J=5.6 Hz, 2H), 2.65 (s, 6H), 2.43 (s, 3H) ppm LCMS (ESI) m/z: [M+H]$^+$=459.0

Example 18. Preparation of Compound 3-(dimethylsulfamoyl)-N-[2-[[4-(m-tolyl)thiazol-2-yl]amino]-2-oxo-ethyl]benzamide (compound 1)

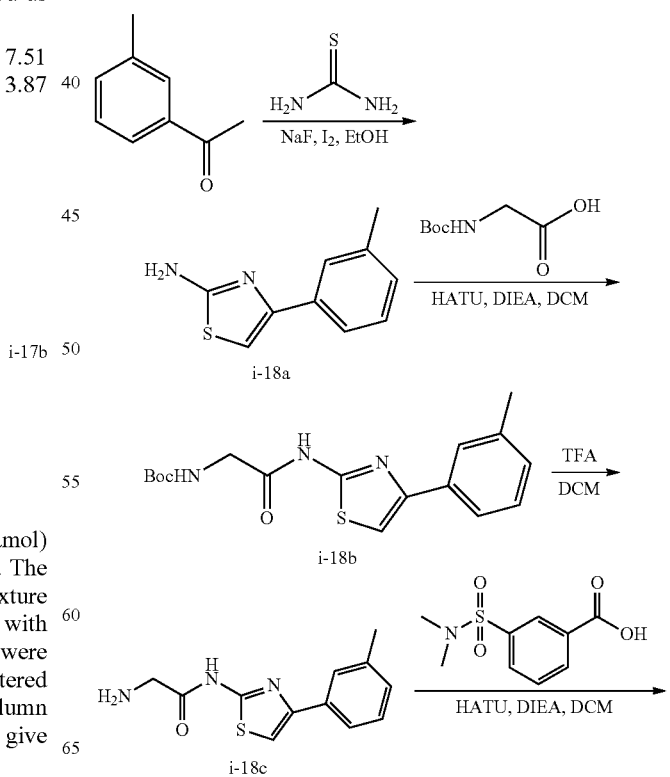

-continued

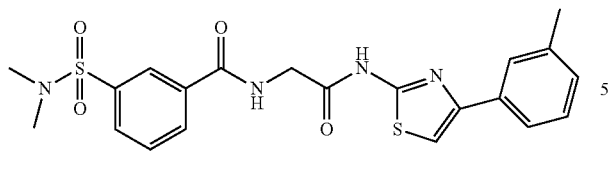

Step 1: Preparation of 4-(m-tolyl)thiazol-2-amine (intermediate i-18a)

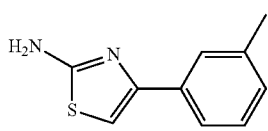

To a mixture of 1-(m-tolyl)ethanone (100.0 mg, 745.30 µmol), thiourea (85.10 mg, 1.12 mmol,) and 12 (189.16 mg, 745.30 µmol) in EtOH (1.0 mL) was added NaF (10 mg, 238.16 µmol). The mixture was stirred at 20° C. for 3 hr. The reaction mixture was poured into water (8.0 mL) and extracted with EtOAc (10.0 mL*3). The combined organic layers were washed with brine (10.0 mL), dried over Na$_2$SO$_4$, filtered and concentrated in vacuum to give intermediate i-18a as green oil which was used directly in the next step.

LCMS (ESI) m/z: [M+H]$^+$=191.1

Step 2: Preparation of tert-butyl (2-oxo-2-((4-(m-tolyl)thiazol-2-yl)amino)ethyl)carbamate (intermediate i-18b)

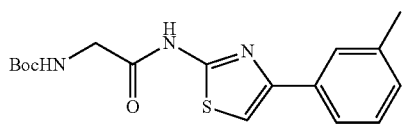

To a solution of 2-(tert-butoxycarbonylamino)acetic acid (138.11 mg, 788.38 µmol) in DCM (2.0 mL) were added DIEA (305.68 mg, 2.37 mmol) and HATU (329.74 mg, 867.22 µmol) at 20° C. The mixture was stirred at 20° C. for 0.5 hr. Intermediate i-18a (150.0 mg, 788.38 µmol) was added and the mixture was stirred at 20° C. for 1.5 hr. The reaction mixture was poured into water (10.0 mL) and extracted with EtOAc (10.0 mL*3). The combined organic extracts were washed with brine (10.0 mL), dried over Na$_2$SO$_4$, filtered and concentrated to give intermediate i-18b as brown oil, which was used directly in the next step.

LCMS (ESI) m/z: [M+H]$^+$=348.1

Step 3: Preparation of 2-amino-N-(4-(m-tolyl)thiazol-2-yl)acetamide (intermediate i-18c)

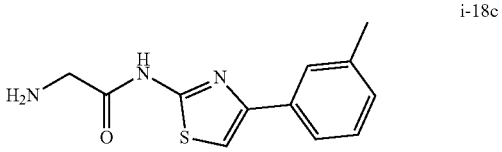 [SMILES: Cc1cccc(-c2csc(NC(=O)CN)n2)c1]

To a solution of intermediate i-18b (75 mg, 215.87 µmol) in DCM (1.0 mL) was added TFA (0.25 mL) at 20° C. The mixture was stirred at 20° C. for 2 hr. The reaction mixture was poured into sat.Na$_2$CO$_3$ (10.0 mL) and extracted with EtOAc (10.0 mL*3). The combined organic extracts were washed with brine (10.0 mL), dried over Na$_2$SO$_4$, filtered and concentrated. The residue was purified by prep-HPLC (column: Phenomenex Synergi C18 150*25*10 µm; mobile phase: [water (0.1% TFA)-ACN]; B %: 15%-45%, 9 min) to give a fraction. Then the fraction was concentrated in vacuo, then poured into sat.Na$_2$CO$_3$ (15.0 mL) and extracted with EtOAc (20.0 mL*3). The combined organic extracts were washed with brine (10.0 mL), dried over Na$_2$SO$_4$, filtered and concentrated to give intermediate i-18c as yellow oil.

LCMS (ESI) m/z: [M+H]$^+$=248.1

Step 4: Preparation of 3-(dimethylsulfamoyl)-N-[2-[[4-(m-tolyl)thiazol-2-yl]amino]-2-oxo-ethyl]benzamide (compound 1)

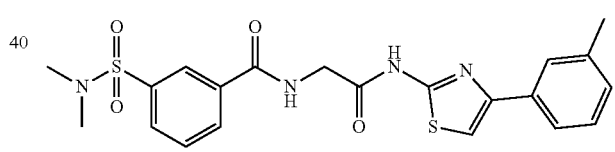

To a solution of 3-(dimethylsulfamoyl)benzoic acid (46.35 mg, 202.17 µmol) in DCM (1.0 mL) were added HATU (84.56 mg, 222.39 µmol) and DIEA (78.39 mg, 606.51 µmol) at 20° C. The mixture was stirred at 20° C. for 0.5 hr. Then intermediate i-18c (50.0 mg, 202.17 µmol) was added and the mixture was stirred at 20° C. for 1.5 hr. The reaction mixture was poured into water (5.0 mL) and extracted with EtOAc (10.0 mL*3). The combined organic extracts were washed with brine (10.0 mL), dried over Na$_2$SO$_4$, filtered and concentrated. The residue was purified by prep-HPLC (column: Phenomenex Synergi C18 150*25*10 µm; mobile phase: [water (0.1% TFA)-ACN]; B %: 42%-72%, 9 min) and lyophilized to give compound 1 as white solid.

1H NMR (400 MHz, DMSO-d6) δ=12.45 (s, 1H), 9.30-9.27 (m, 1H), 8.26-8.22 (m, 2H), 7.94 (d, J=7.6 Hz, 1H), 7.82-7.77 (m, 1H), 7.73-7.65 (m, 2H), 7.60 (s, 1H), 7.32-7.30 (m, 1H), 7.14 (d, J=7.6 Hz, 1H), 4.23 (d, J=5.6 Hz, 2H), 2.65 (s, 6H), 2.35 (s, 3H) ppm LCMS (ESI) m/z: [M+H]$^+$=459.0

Example 19. Preparation of 3-(dimethylsulfamoyl)-N-[2-oxo-2-[[4-(p-tolyl)thiazol-2-yl]amino]ethyl]benzamide (compound 31)

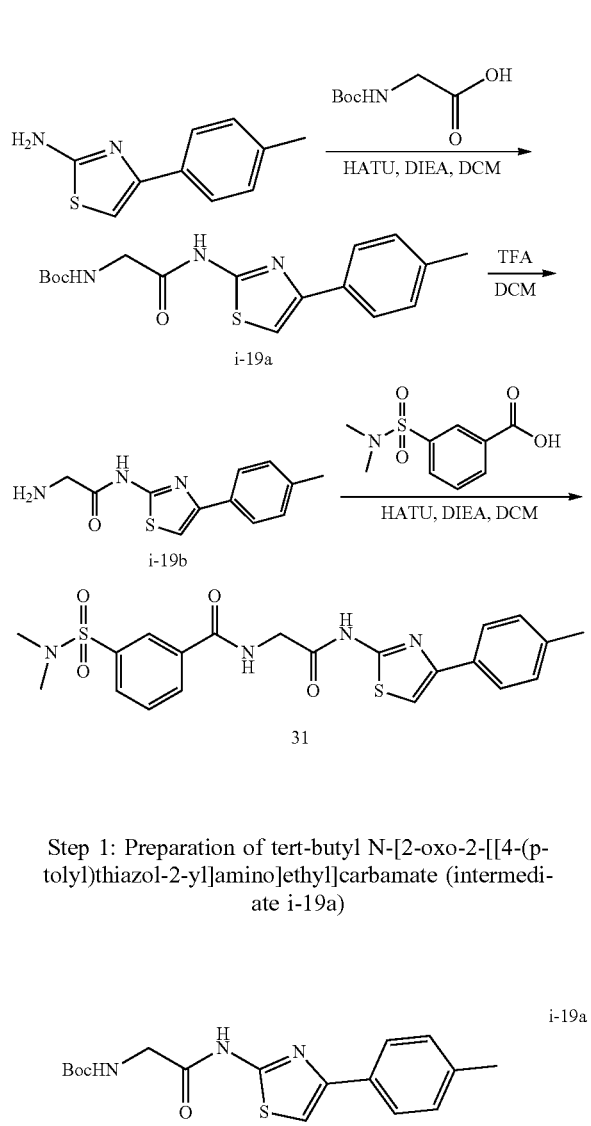

Step 1: Preparation of tert-butyl N-[2-oxo-2-[[4-(p-tolyl)thiazol-2-yl]amino]ethyl]carbamate (intermediate i-19a)

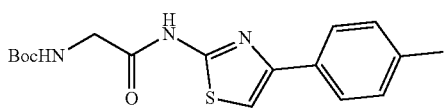

To a solution of 2-(tert-butoxycarbonylamino)acetic acid (184.15 mg, 1.05 mmol) in DCM (2.0 mL) was added DIEA (407.57 mg, 3.15 mmol) and HATU (439.65 mg, 1.16 mmol). After 0.5 hr, 4-(o-tolyl)thiazol-2-amine (200.0 mg, 1.05 mmol) was added the mixture and stirred at 20° C. for 1.5 hr. The reaction mixture was poured into water (10.0 mL) and extracted with EtOAc (10.0 mL*3). The combined organic extracts were washed with brine (10.0 mL), dried over $Na_2SO_4$, filtered and concentrated. The crude product was triturated with MTBE (10.0 mL). The solid was collected by filtration and dried in vacuo to give intermediate i-19a as a white solid.

1H NMR (400 MHz, CDCl3) δ 9.75 (br s, 1H), 7.71 (d, J=8.0 Hz, 2H), 7.23 (d, J=8.0 Hz, 2H), 7.11 (s, 1H), 5.22-5.03 (m, 1H), 4.20-3.94 (m, 2H), 2.39 (s, 3H), 1.50 (s, 9H).

LCMS (ESI) m/z: $[M+H]^+$=348.1

Step 2: Preparation of 2-amino-N-[4-(p-tolyl)thiazol-2-yl]acetamide (i-19b)

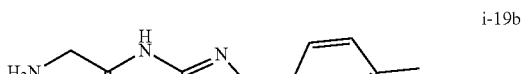

To a solution of intermediate i-19a (210 mg, 604.44 μmol) in DCM (2.1 mL) was added TFA (0.3 mL) at 20° C. The mixture was stirred at 20° C. for 16 hr. The reaction mixture was poured into sat.$Na_2CO_3$ (10.0 mL) and extracted with EtOAc (20.0 mL*3). The combined organic extracts were washed with brine (20.0 mL), dried over $Na_2SO_4$, filtered and concentrated. The crude product was triturated with MTBE (10.0 mL). The solid was collected by filtration and dried in vacuum to give intermediate i-19b as a white solid.

LCMS (ESI) m/z: $[M+H]^+$=248.1

Step 3: Preparation of 3-(dimethylsulfamoyl)-N-[2-oxo-2-[[4-(p-tolyl)thiazol-2-yl]amino]ethyl]benzamide (compound 31)

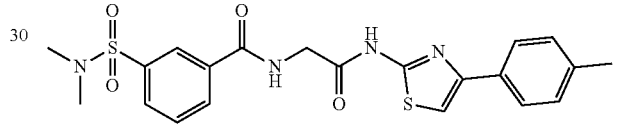

To a solution of 3-(dimethylsulfamoyl)benzoic acid (139 mg, 606.32 μmol) in DCM (2.0 mL) were added DIEA (235.09 mg, 1.82 mmol) and HATU (253.59 mg, 666.95 μmol), the mixture was stirred at 20° C. for 0.5 hr. Then intermediate D (150.00 mg, 606.51 μmol) was added at 20° C. and the mixture was stirred at 20° C. for 1.5 hr. The reaction mixture was poured into water (10.0 mL) and extracted with EtOAc (10.0 mL*3). The combined organic extracts were washed with brine (10.0 mL), dried over $Na_2SO_4$, filtered and concentrated. The crude product was triturated with MTBE (10.0 mL). The solid was collected by filtration and dried in vacuo to give compound 31 as a white solid.

1H NMR (400 MHz, DMSO-d6) δ=12.45 (s, 1H), 9.30-9.27 (m, 1H), 8.26-8.22 (m, 2H), 7.94 (d, J=8.0 Hz, 1H), 7.82-7.77 (m, 3H), 7.56 (s, 1H), 7.24 (d, J=8.0 Hz, 2H), 4.23 (d, J=5.6 Hz, 2H), 2.65 (s, 6H), 2.32 (s, 3H) ppm LCMS (ESI) m/z: $[M+H]^+$=459.0

Example 20. Preparation of N-[2-[[4-(2,6-dimethylphenyl)thiazol-2-yl]amino]-2-oxo-ethyl]-3-(dimethylsulfamoyl)benzamide (compound 29)

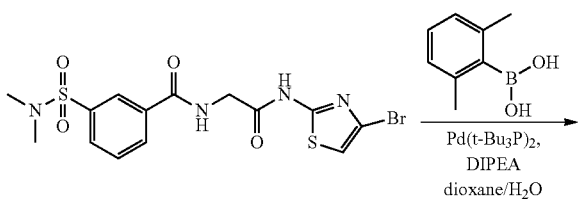

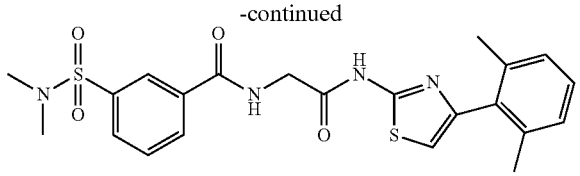

29

To a solution of N-[2-[(4-bromothiazol-2-yl)amino]-2-oxo-ethyl]-3-(dimethylsulfamoyl)benzamide (50 mg, 111.78 μmol) and (2,6-dimethylphenyl)boronic acid (50.29 mg, 335.33 μmol) in dioxane (2 mL) and H$_2$O (0.1 mL) was added DIPEA (28.89 mg, 223.55 μmol), then Pd(t-Bu$_3$P)$_2$ (28.56 mg, 55.89 μmol) was added. The reaction mixture was degassed three times and then stirred at 100° C. for 12 hr. The reaction solution was diluted with EtOAc (100 mL) and then washed with aq. NaHCO$_3$ (100 mL) and brine (100 mL), the organic layer was dried over Na$_2$SO$_4$ and then concentrated in vacuum. The residue was purified through Prep-HPLC (combiflash, CH$_3$CN/H$_2$O: 5-95%, NH$_3$OH) to give compound 29 as a pink solid.

$^1$HNMR (400 MHz, MeOD) δ=8.34 (s, 1H), 8.23 (d, J=7.2 Hz, 1H), 8.01 (d, J=8.0 Hz, 1H), 7.80-7.76 (m, 1H), 7.20-7.16 (m, 1H), 7.11-7.09 (m, 2H), 6.91 (s, 1H), 4.36 (s, 2H), 2.76 (s, 6H), 2.12 (s, 6H) ppm.

LCMS (ESI) m/z: [M+H]$^+$=473.3.

Example 21. Preparation of Compound N-[2-oxo-2-[(4-phenylthiazol-2-yl)amino]ethyl]-5,6-dihydro-4H-cyclopenta[b]thiophene-2-carboxamide (compound 79)

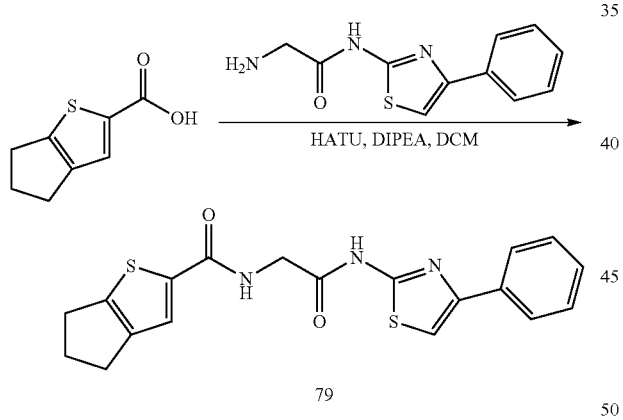

79

To a solution of 5,6-dihydro-4H-cyclopenta[b]thiophene-2-carboxylic acid (30.0 mg, 178.35 μmol), HATU (67.81 mg, 178.35 μmol) and DIPEA (83.82 mg, 648.53 μmol, 112.96 μL) in DCM (0.5 mL) was added 2-amino-N-(4-phenylthiazol-2-yl)acetamide (56.31 mg, 162.13 μmol, TFA salt). The mixture was stirred at 20° C. for 2 h. The reaction mixture was concentrated under reduced pressure to give a residue. The residue was triturated with MeOH (10.0 mL), the solid was collected by filtration and dried in vacuum to give compound 79 as a white solid 1H NMR (400 MHz, DMSO-d$_6$) δ=12.41 (s, 1H), 8.79-8.76 (m, 1H), 7.91 (d, J=7.2 Hz, 2H), 7.64-7.58 (m, 2H), 7.46-7.42 (m, 2H), 7.37-7.30 (m, 1H), 4.15 (d, J=6.0 Hz, 2H), 2.90-2.87 (m, 2H), 2.78-2.69 (m, 2H), 2.41-2.37 (m, 2H) ppm.

LCMS (ESI) m/z: [M+H]$^+$=384.0.

Example 22. Preparation of Compound N-[(1S)-4-methyl-1-[(4-phenylthiazol-2-yl)carbamoyl]pentyl]benzamide (compound 46)

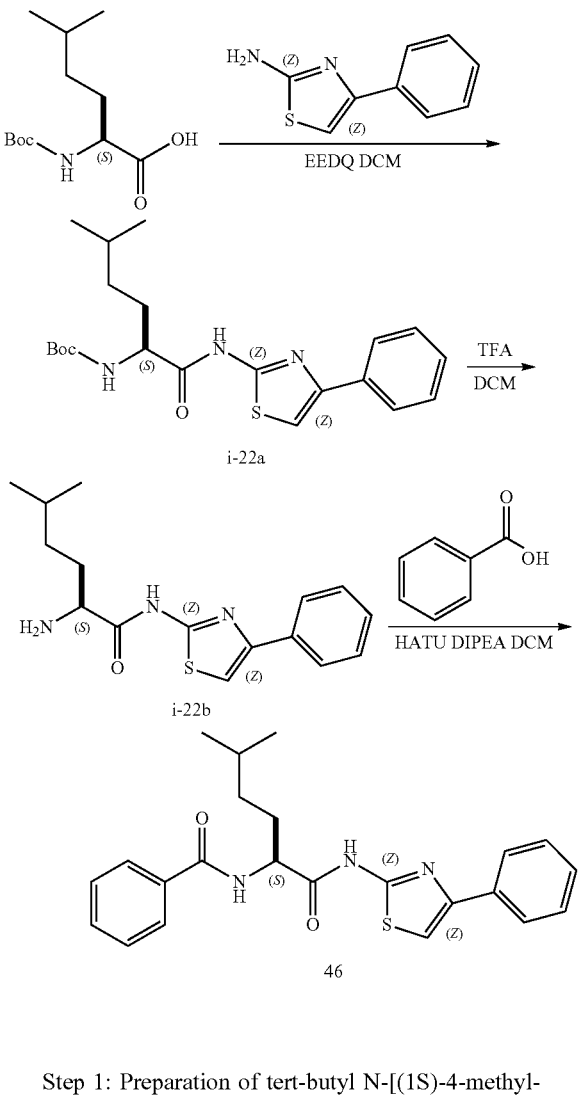

Step 1: Preparation of tert-butyl N-[(1S)-4-methyl-1-[(4-phenylthiazol-2-yl)carbamoyl]pentyl]carbamate (intermediate i-22a)

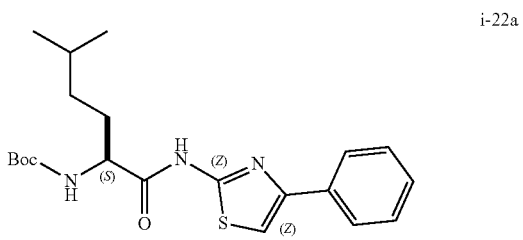

i-22a

To a solution of (2S)-2-(tert-butoxycarbonylamino)-5-methyl-hexanoic acid (153.11 mg, 624.15 μmol) and EEDQ (210.47 mg, 851.12 μmol) in DCM (2.0 mL) was added 4-phenylthiazol-2-amine (100.0 mg, 567.41 μmol), the mixture was stirred at 20° C. for 12 hr. The reaction mixture was concentrated under reduced pressure to give a residue. The residue was purified by column chromatography (SiO$_2$, Petroleum ether/Ethyl acetate=10:1 to 2:1) to give intermediate i-22a as a white solid.

1H NMR (400 MHz, DMSO-d6) δ=12.33 (s, 1H), 7.91 (d, J=7.2 Hz, 2H), 7.63 (s, 1H), 7.49-7.40 (m, 2H), 7.37-7.28 (m, 1H), 7.20 (d, J=7.6 Hz, 1H), 4.31-4.11 (m, 1H), 2.50-2.06 (m, 5H), 1.73-1.56 (m, 2H), 1.55-1.45 (m, 1H), 1.39 (s, 7H), 1.27 (s, 2H), 0.86-0.84 (m, 6H) ppm.

LCMS (ESI) m/z: [M+H]$^+$=404.2.

Step 2: Preparation of (2S)-2-amino-5-methyl-N-(4-phenylthiazol-2-yl)hexanamide (intermediate i-22b) trifluoroacetate salt

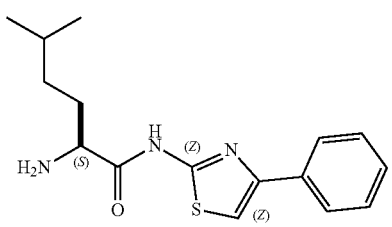

i-22b

To a solution of intermediate i-22a (150.0 mg, 371.71 μmol) in DCM (1.0 mL) was added TFA (0.1 mL, 1.35 mmol), the mixture was stirred at 20° C. for 12 hr. The reaction mixture was concentrated under reduced pressure to give intermediate i-22b (TFA salt) as a white solid, which was used in the next step directly.

LCMS (ESI) m/z: [M+H]$^+$=304.2.

Step 3: Preparation of N-[(1 S)-4-methyl-1-[(4-phenylthiazol-2-yl)carbamoyl]pentyl]benzamide (compound 46)

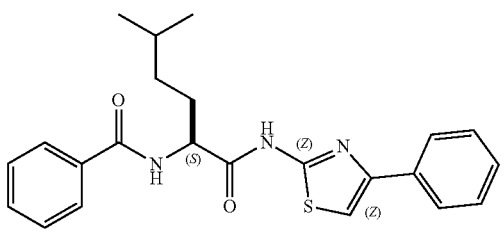

46

To a solution of benzoic acid (16.09 mg, 131.75 μmol, 20.11 μL), HATU (50.10 mg, 131.75 μmol) and DIPEA (61.92 mg, 479.11 μmol) in DCM (1.0 mL) was added intermediate i-22b (50.0 mg, 119.78 μmol, TFA salt), the mixture was stirred at 30° C. for 2 hr. The reaction mixture was concentrated under reduced pressure to give a residue. The residue was purified by prep-HPLC (column: Phenomenex Synergi C18 150*25*10 μm; mobile phase: [water (0.1% TFA)-ACN]; B %: 58%-88%, 9 min) and lyophilized to give compound 46 as a white solid.

1H NMR (400 MHz, DMSO-d6) δ 12.46 (s, 1H), 8.68 (d, J=7.2 Hz, 1H), 7.93-7.90 (m, 4H), 7.63 (s, 1H), 7.60-7.54 (m, 1H), 7.53-7.47 (m, 2H), 7.44-7.42 (m, 2H), 7.37-7.28 (m, 1H), 4.67-4.61 (m, 1H), 1.87-1.83 (m, 2H), 1.59-1.56 (m, 1H), 1.48-1.32 (m, 1H), 1.31-1.15 (m, 1H), 0.90-0.88 (m, 6H) ppm.

LCMS (ESI) m/z: [M+H]$^+$=408.2

Chiral HPLC: Cellucoat-MeOH(DEA)-5-40-3 mL-35T.Icm, 1.982 min.

Example 23. Preparation of compound 3-(dimethylsulfamoyl)-N-[(1S)-1-[(4-phenylthiazol-2-yl)carbamoyl]butyl]benzamide (compound 17)

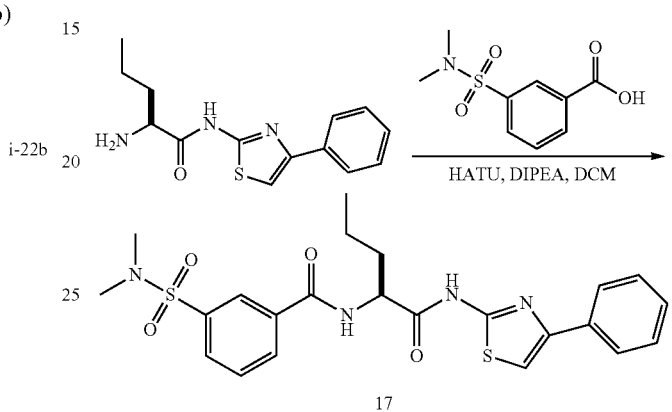

17

To a mixture of HATU (36.25 mg, 95.35 μmol) and 3-(dimethylsulfamoyl)benzoic acid (20.04 mg, 87.40 μmol) in DCM (2.0 mL) was added DIPEA (41.07 mg, 317.82 μmol) in one portion at 20° C. under N$_2$. The mixture was stirred at 20° C. for 10 min. Then (2S)-2-amino-N-(4-phenylthiazol-2-yl)pentanamide (50.0 mg, 128.41 μmol, TFA salt) was added and the mixture was stirred at 20° C. for 2 hours. The reaction mixture was concentrated under reduced pressure to give a residue. The residue was purified by prep-HPLC (TFA condition; column: Boston pH-lex 150*25 10 μm; mobile phase: [water (0.1% TFA)-ACN]; B %: 57%-76%, 8 min) and lyophilized to give compound 17 as a white solid.

$^1$H NMR (400 MHz, DMSO-d6) δ 12.52 (s, 1H), 9.05 (d, J=7.6 Hz, 1H), 8.29-8.27 (m, 2H), 7.93-7.90 (m, 3H), 7.81-7.79 (m, 1H), 7.64 (s, 1H), 7.54-7.39 (m, 2H), 7.38-7.27 (m, 1H), 4.76-4.70 (m, 1H), 2.68-2.65 (m, 6H), 1.86-1.83 (m, 2H), 1.58-1.31 (m, 2H), 0.96-0.92 (m, 3H) ppm.

LCMS (ESI) m/z: [M+H]$^+$=487.1.

Chiral HPLC: Amycoat-MeOH(DEA)-40-7 min-3 mL, 2.022 min.

Example 24. Preparation of compound N-[(1S)-1-methyl-2-oxo-2-[(4-phenylthiazol-2-yl)amino]ethyl]benzamide (compound 44)

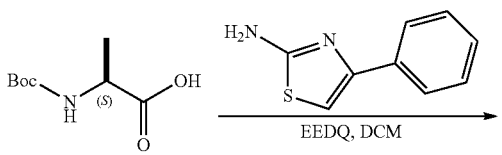

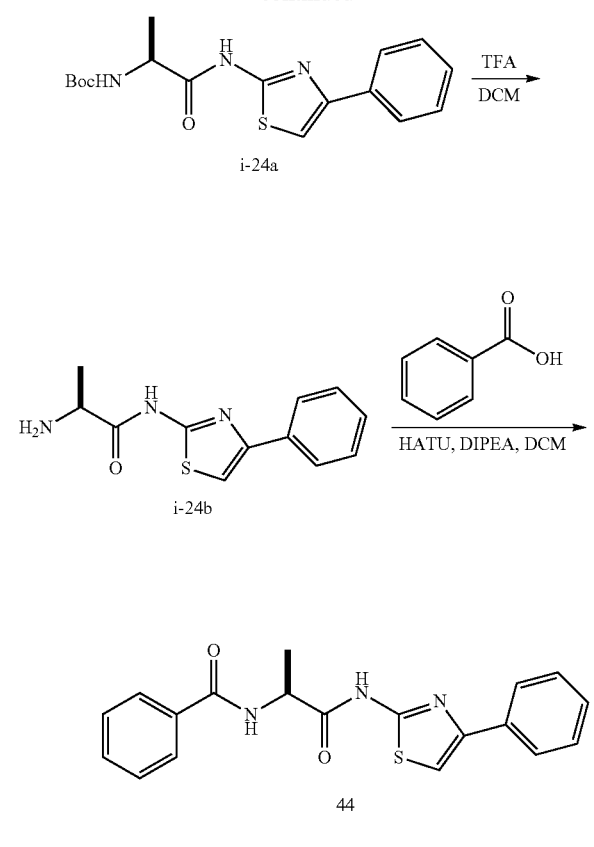

Step 1: Preparation of tert-butyl N-[(1S)-1-methyl-2-oxo-2-[(4-phenylthiazol-2-yl)amino]ethyl]carbamate (intermediate i-24a)

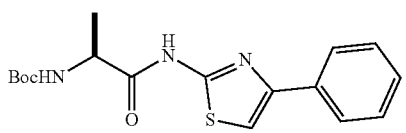

To a solution of (2S)-2-(tert-butoxycarbonylamino)propanoic acid (2.0 g, 10.57 mmol) in DCM (20.0 mL) were added EEDQ (3.56 g, 14.41 mmol) and 4-phenylthiazol-2-amine (1.69 g, 9.61 mmol) in one portion at 20° C. under $N_2$. The mixture was stirred at 20° C. for 8 hours. The reaction mixture was diluted with EtOAc (50.0 mL), and washed with citric acid (10%) (50.0 mL*3). The organic phase was washed with brine (50.0 mL*3) and dried over $Na_2SO_4$, filtered and concentrated under reduced pressure to give a residue. The residue was purified by column chromatography ($SiO_2$, Petroleum ether/Ethyl acetate=10/1 to 3/1) to give intermediate i-24a as a white solid.

$^1$H NMR (400 MHz, DMSO-$d_6$) δ=12.30 (s, 1H), 7.90 (d, J=8.0 Hz, 2H), 7.63 (s, 1H), 7.45-7.41 (m, 2H), 7.36-7.30 (m, 1H), 7.26 (d, J=8.0 Hz, 1H), 4.31-4.24 (m, 1H), 1.38-1.28 (m, 12H) ppm.

LCMS (ESI) m/z: [M+H]$^+$=348.2.

Step 2: Preparation of (2S)-2-amino-N-(4-phenylthiazol-2-yl)propanamide (intermediate i-24b) trifluoroacetate salt

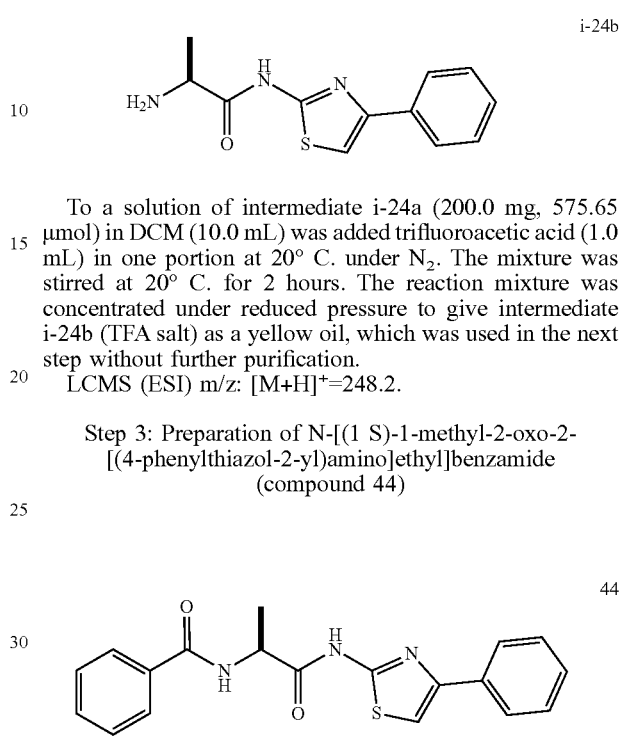

To a solution of intermediate i-24a (200.0 mg, 575.65 μmol) in DCM (10.0 mL) was added trifluoroacetic acid (1.0 mL) in one portion at 20° C. under $N_2$. The mixture was stirred at 20° C. for 2 hours. The reaction mixture was concentrated under reduced pressure to give intermediate i-24b (TFA salt) as a yellow oil, which was used in the next step without further purification.

LCMS (ESI) m/z: [M+H]$^+$=248.2.

Step 3: Preparation of N-[(1S)-1-methyl-2-oxo-2-[(4-phenylthiazol-2-yl)amino]ethyl]benzamide (compound 44)

To benzoic acid (37.18 mg, 304.42 μmol) in DCM (5.0 mL) was added DIPEA (143.07 mg, 1.11 mmol) and HATU (157.84 mg, 415.12 μmol) in one portion at 20° C. under $N_2$, and the mixture was stirred at 20° C. for 10 min. Then intermediate i-24b (100.0 mg, 276.75 μmol) was added and the mixture was stirred at 20° C. for 2 hours. The reaction mixture was concentrated under reduced pressure to give a residue. The residue was purified by prep-HPLC (TFA condition; column: Boston pH-lex 150*25 10 μm; mobile phase: [water (0.1% TFA)-ACN]; B %: 52%-72%, 8 min) and lyophilized to give compound 44 as a white solid.

$^1$H NMR (400 MHz, DMSO-d6) δ 12.38 (br s, 1H), 8.75 (d, J=8.0 Hz, 1H), 7.94-7.90 (m, 4H), 7.64 (s, 1H), 7.60-7.54 (m, 1H), 7.53-7.47 (m, 2H), 7.47-7.41 (m, 2H), 7.37-7.29 (m, 1H), 4.74-4.67 (m, 1H), 1.48 (d, J=8.0 Hz, 3H) ppm.

LCMS (ESI) m/z: [M+H]$^+$=352.3.

Chiral HPLC: Cellucoat-MeOH(DEA)-5-40-3 mL-35T.Icm, 2.262 min.

Example 25. Preparation of (S)-3-methyl-N-(4-(methylthio)-1-oxo-1-((4-phenylthiazol-2-yl) amino)butan-2-yl)benzamide (compound 76)

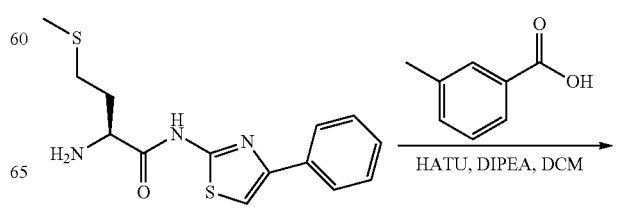

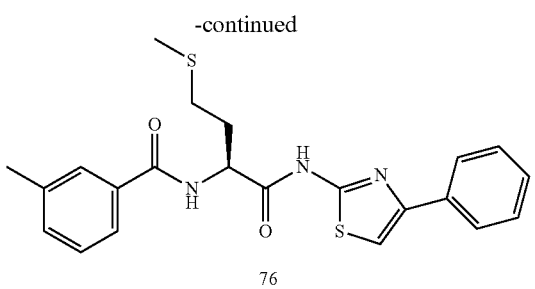

76

To a solution of 3-methylbenzoic acid (17.77 mg, 130.54 μmol) in DCM (1 mL) was added HATU (74.45 mg, 195.81 μmol) and DIPEA (50.61 mg, 391.61 μmol), then (2S)-2-amino-4-methylsulfanyl-N-(4-phenylthiazol-2-yl)butanamide (40.13 mg, 130.54 μmol) was added. The mixture was stirred at 25° C. for 2 hr. The reaction mixture was concentrated under reduced pressure. The residue was purified by prep-HPLC (TFA condition; column: Phenomenex Synergi C18 150*25*10 μm; mobile phase: [water(0.1% TFA)-ACN]; B %: 55%-85%, 9 min) and lyophilized to give compound 76 as a white solid.

1H NMR (400 MHz, METHANOL-d4) δ 7.90 (d, J=7.2 Hz, 2H), 7.73-7.70 (m, 2H), 7.42-7.34 (m, 5H), 7.30-7.27 (m, 1H), 4.93-4.89 (m, 1H), 2.71-2.60 (m, 2H), 2.42 (s, 3H), 2.30-2.17 (m, 2H), 2.14 (s, 3H) ppm.

LCMS (ESI) m/z: [M+H]$^+$=426.0.

SFC HPLC: OD-3_5CM_MEOH(DEA)_5_40_3ML_T3, 2.236 min.

Example 26. Preparation of Compound (S)-4-methyl-N-(4-(methylthio)-1-oxo-1-((4-phenylthiazol-2-yl) amino)butan-2-yl)benzamide (compound 54)

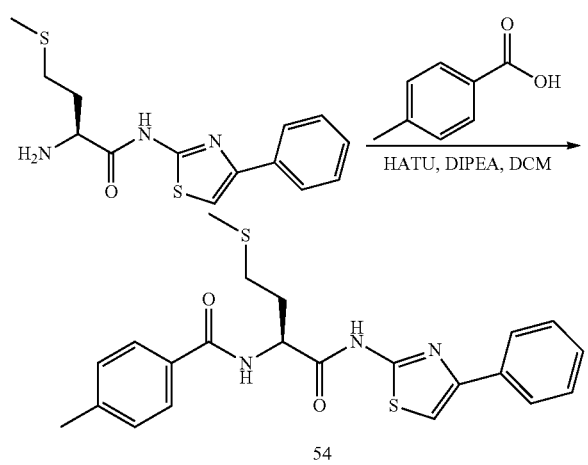

54

To a solution of 4-methylbenzoic acid (17.77 mg, 130.54 μmol) in DCM (1 mL) was added HATU (74.45 mg, 195.81 μmol,) and DIPEA (50.61 mg, 391.62 μmol), and then (2S)-2-amino-4-methylsulfanyl-N-(4-phenylthiazol-2-yl) butanamide (40.13 mg, 130.54 μmol) was added. The mixture was stirred at 25° C. for 2 hr. The reaction mixture was concentrated under reduced pressure. The residue was purified by prep-HPLC (TFA condition; column: Phenomenex Synergi C18 150*25*10 μm; mobile phase: [water(0.1% TFA)-ACN]; B %: 55%-85%, 9 min) to give compound 54 as a white solid.

$^1$HNMR (400 MHz, METHANOL-d4) δ 7.90 (d, J=7.2 Hz, 2H), 7.81 (d, J=8.0 Hz, 2H), 7.42-7.36 (m, 3H), 7.33-7.28 (m, 3H), 4.93-4.89 (m, 1H), 2.75-2.62 (m, 2H), 2.41 (s, 3H), 2.30-2.21 (m, 2H), 2.14 (s, 3H) ppm.

LCMS (ESI) m/z: [M+H]$^+$=426.0.

Chiral HPLC: OD-3_5CM_MEOH(DEA) _40_3ML_T35.M, 1.673 min.

Example 27. Preparation of (S)-3-(methylsulfonyl)-N-(4-(methylthio)-1-oxo-1-((4-phenylthiazol-2-yl) amino)butan-2-yl)benzamide (compound 3)

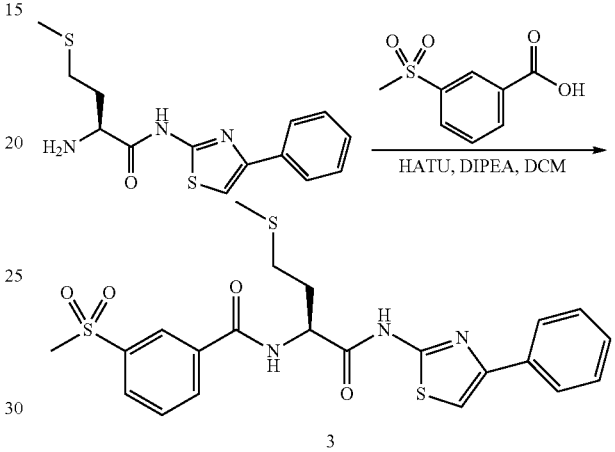

3

To a solution of 3-methylsulfonylbenzoic acid (19.00 mg, 94.91 μmol) in DCM (2 mL) was added HATU (54.13 mg, 142.36 μmol) and DIPEA (49.07 mg, 379.64 μmol), then (2S)-2-amino-4-methylsulfanyl-N-(4-phenylthiazol-2-yl) butanamide (40 mg, 94.91 μmol) was added. The mixture was stirred at 10° C. for 2 hr. The reaction mixture was concentrated under reduced pressure. The residue was purified by prep-HPLC (TFA condition; column: Phenomenex Synergi C18 150*25*10 μm; mobile phase: [water(0.1% TFA)-ACN]; B %: 48%-78%, 9 min) to give compound 3 as a white solid.

$^1$HNMR (400 MHz, METHANOL-d4) δ 8.50 (s, 1H), 8.24 (d, J=8.0 Hz, 1H), 8.16 (d, J=8.0 Hz, 1H), 7.91-7.88 (m, 2H) 7.79-7.77 (m, 1H), 7.42-7.36 (m, 3H), 7.31-7.30 (m, 1H), 4.96-4.92 (m, 1H), 3.18 (s, 3H), 2.77-2.66 (m, 2H), 2.36-2.20 (m, 2H), 2.15 (s, 3H) ppm.

LCMS (ESI) m/z: [M+H]$^+$=490.0.

Example 28. Preparation of 3-(tert-butyl)-N-(2-oxo-2-((4-phenylthiazol-2-yl)amino)ethyl)benzamide (compound 65)

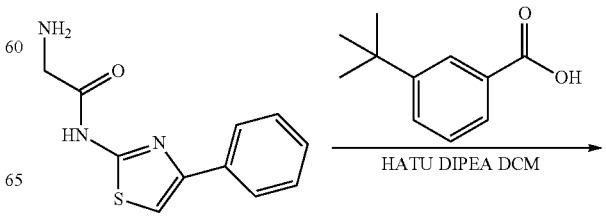

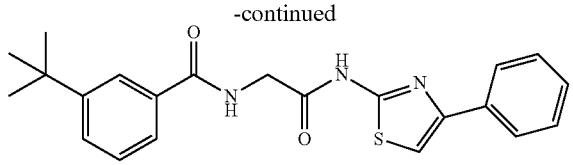

To a solution of 3-tert-butylbenzoic acid (25.66 mg, 143.96 μmol) in DCM (1 mL) was added HATU (82.11 mg, 215.94 μmol), DIPEA (93.03 mg, 719.81 μmol, 125.38 μL). The reaction mixture was stirred at 25° C. for 0.5 hrs, then 2-amino-N-(4-phenylthiazol-2-yl)acetamide (50 mg, 143.96 μmol) was added. The reaction mixture was stirred at 25° C. for 2 hr. The reaction mixture was diluted with MeCN (2 mL) and a white precipitate formed. The precipitate was filtered off and lyophilized to afford compound 65 as a white solid.

LCMS (ESI) m/z: [M+H]$^+$=394.3.

$^1$H NMR (400 MHz, DMSO-d6) δ=12.44 (s, 1H), 8.96-8.94 (m, 1H), 7.94-7.90 (m, 3H), 7.73 (d, J=8.0 Hz, 1H), 7.64 (s, 1H), 7.60 (br d, J=8.4 Hz, 1H), 7.47-7.42 (m, 3H), 7.34-7.31 (m, 1H), 4.21 (d, J=5.6 Hz, 2H), 1.33 (s, 9H) ppm.

Example 29. Preparation of 3-(2-hydroxypropan-2-yl)-N-(2-oxo-2-((4-phenylthiazol-2-yl)amino)ethyl) benzamide (compound 61)

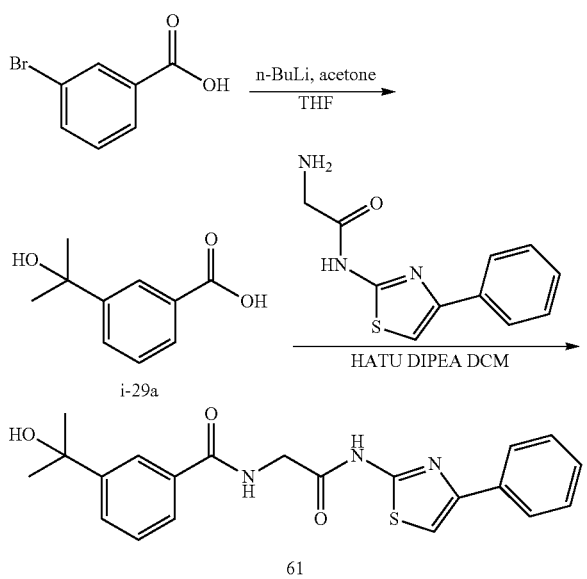

Step 1: Preparation of 3-(2-hydroxypropan-2-yl)benzoic acid (intermediate i-29a)

To a solution of 3-bromobenzoic acid (500 mg, 2.49 mmol) in THF (10 mL) was added n-BuLi (2 mL, 4.97 mmol, 2.5 M) at −65° C. under N$_2$. The reaction mixture was stirred at −65° C. for 10 min, then acetone (365 μL 4.97 mmol) was added at −65° C. The reaction mixture was warmed to 25° C. gradually and then stirred at room temperature for 50 min. The reaction mixture was poured into 20 mL saturated aqueous ammonium chloride. The mixture was adjusted to pH=4 with 2 M HCl. Then the mixture was extracted with EtOAc (30 mL×5). The combined organic extracts were washed with brine, dried over anhydrous sodium sulfate, filtered and concentrated to give residue. To the residue was added MeCN to afford a precipitate. The precipitate was filtered off and dried in vacuum to afford intermediate i-29a as a white solid.

$^1$H NMR (400 MHz, DMSO-d6) δ=8.09 (m, 1H), 7.80-7.76 (m, 1H), 7.72-7.67 (m, 1H), 7.43 (m, 1H), 5.15 (br s, 1H), 1.44 (s, 6H) ppm.

LCMS (ESI) m/z: [M−H$_2$O+H]$^+$=163.1.

Step 2: Preparation of 3-(2-hydroxypropan-2-yl)-N-(2-oxo-2-((4-phenylthiazol-2-yl)amino)ethyl)benzamide (compound 61)

To a solution of intermediate i-29a (25.94 mg, 143.96 μmol) in DCM (1 mL) were added HATU (82.11 mg, 215.94 μmol) and DIPEA (93.03 mg, 719.80 μmol). The reaction mixture was stirred at 25° C. for 0.5 hr, Then 2-amino-N-(4-phenylthiazol-2-yl)acetamide (50 mg, 143.96 μmol, TFA salt) was added. The reaction mixture was stirred at 25° C. for 2 hr. The reaction mixture was diluted with MeCN (2 mL) and a white precipitate formed. The precipitate was filtered off and lyophilized to afford compound 61 as a white solid.

LCMS (ESI) m/z: [M+H]$^+$=396.3.

$^1$H NMR (400 MHz, DMSO-d6) δ=8.93-8.90 (m, 1H), 8.01 (s, 1H), 7.90 (d, J=7.6 Hz, 2H), 7.73 (d, J=8.0 Hz, 1H), 7.65 (d, J=8.0 Hz, 1H), 7.63 (s, 1H), 7.45-7.40 (m, 3H), 7.35-7.30 (m, 1H), 5.14 (s, 1H), 4.19 (d, J=5.6 Hz, 2H), 1.46 (s, 6H) ppm.

Example 30. Preparation of (S)-3-(tert-butyl)-N-(4-(methylthio)-1-oxo-1-((4-phenylthiazol-2-yl)amino)butan-2-yl)benzamide (compound 73)

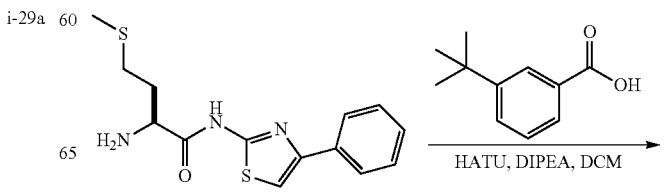

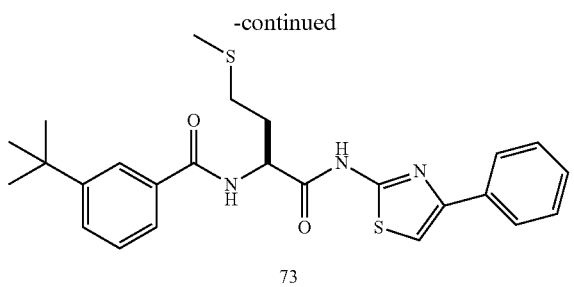

73

To a solution of 3-tert-butylbenzoic acid (21.14 mg, 118.64 µmol), DIPEA (82.66 µL) in DCM (0.5 mL) was added HATU (67.66 mg, 177.96 µmol) at 0° C. After addition, the mixture was stirred at this temperature for 15 min, and then (2S)-2-amino-4-methylsulfanyl-N-(4-phenylthiazol-2-yl) butanamide (50 mg, 118.64 µmol) was added at 0° C. The resulting mixture was stirred at 20° C. for 2 hr. The reaction mixture was diluted with water (1 mL) and extracted with DCM (2*1 mL). The combined organic extracts were washed with brine (2 mL), dried over anhydrous Na$_2$SO$_4$, filtered and concentrated under reduced pressure to give the residue. The residue was purified by prep-HPLC (combiflash, CH$_3$CN/H$_2$O, 5-95%, FA condition) to give compound 73 as a white solid.

LCMS (ESI) m/z: [M+H]$^+$=468.3.

$^1$H NMR (400 MHz, DMSO-d6) δ=12.62-12.30 (br s, 1H), 8.73 (d, J=7.2 Hz, 1H), 7.91-7.89 (m, 3H), 7.76 (d, J=8.0 Hz, 1H), 7.63 (s, 1H), 7.62-7.57 (m, 1H), 7.43-7.41 (m, 3H), 7.35-7.30 (m, 1H), 4.79-4.74 (m, 1H), 2.66-2.50 (m, 2H), 2.14-2.12 (m, 2H), 2.10 (s, 3H), 1.32 (s, 9H) ppm.

Example 31. Preparation of (S)-3-(2-hydroxypropan-2-yl)-N-(4-(methylthio)-1-oxo-1-((4-phenylthiazol-2-yl)amino)butan-2-yl)benzamide (compound 55)

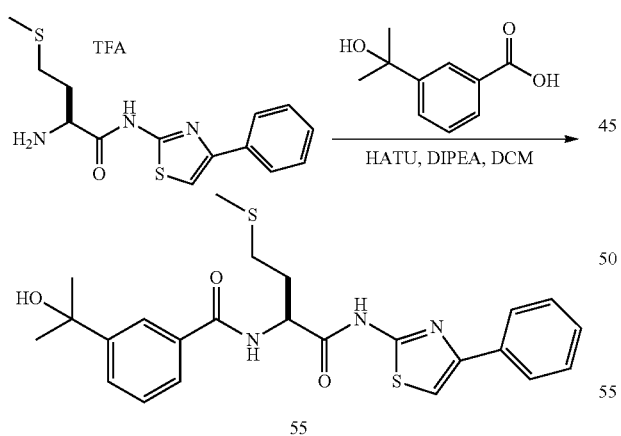

55

To a solution of 3-(1-hydroxy-1-methyl-ethyl) benzoic acid (21.38 mg, 118.64 µmol), DIPEA (82.66 µL) in DCM (0.5 mL) was added HATU (67.66 mg, 177.96 µmol) at 0° C. The mixture was stirred at this temperature for 15 min, and then (2S)-2-amino-4-methylsulfanyl-N-(4-phenylthiazol-2-yl)butanamide (50 mg, 118.64 µmol) was added at 0° C. The resulting mixture was stirred at 20° C. for 12 hr. The reaction mixture was diluted with water (1 mL) and extracted with DCM (2*1 mL). The combined organic extracts were washed with brine (2 mL), dried over anhydrous Na$_2$SO$_4$, filtered and concentrated under reduced pressure to give the residue. The residue was purified by reverse phase-HPLC (FA condition) to give compound 55 as a white solid.

$^1$H NMR (400 MHz, DMSO-d6) δ=12.48 (s, 1H), 8.71 (br d, J=7.2 Hz, 1H), 8.00 (s, 1H), 7.90 (d, J=7.6 Hz, 2H), 7.77 (d, J=8.0 Hz, 1H), 7.65-7.62 (m, 2H), 7.45-7.41 (m, 3H), 7.33-7.32 (m, 1H), 5.11 (s, 1H), 4.78-4.77 (m, 1H), 2.66-2.56 (m, 2H), 2.16-2.12 (m, 2H), 2.10 (s, 3H), 1.45 (s, 6H) ppm.

LCMS (ESI) m/z: [M+H]$^+$=470.1.

Example 32. Preparation of 4-methyl-N-[(1S)-3-methylsulfanyl-1-[(4-phenylthiazol-2-yl)carbamoyl]propyl]-3-methylsulfonyl-benzamide (compound 2)

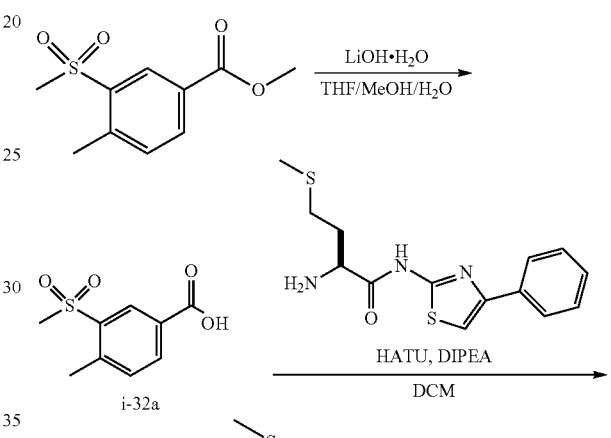

2

Step 1: Preparation 4-methyl-3-methylsulfonyl-benzoic acid (intermediate i-32a)

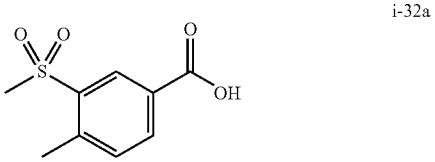

i-32a

To a mixture of methyl 4-methyl-3-methylsulfonyl-benzoate (100 mg, 438.09 µmol) in THF (1 mL), MeOH (1 mL) and H$_2$O (0.5 mL) was added LiOH·H$_2$O (55.15 mg, 1.31 mmol) and the mixture was stirred at 30° C. for 2 hr. Water (20 mL) was added and pH adjusted to 4 with 2N HCl and then the mixture was extracted with EtOAc (20 mL*2). The combined organic phase was washed with brine, dried over anhydrous Na$_2$SO$_4$, filtered and concentrated under vacuum to give intermediate i-32a as a white solid which was used in the next step without further purification.

LCMS (ESI) m/z: [M+H]$^+$=215.2.

Step 2: Preparation of 4-methyl-N-[(1S)-3-methyl-sulfanyl-1-[(4-phenylthiazol-2-yl)carbamoyl]propyl]-3-methylsulfonyl-benzamide (compound 2)

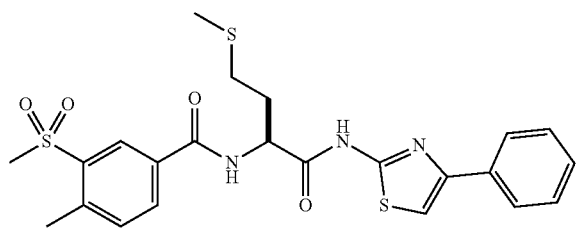

2

To a mixture of intermediate i-32a (20.33 mg, 94.91 µmol) in DCM (1 mL) was added HATU (43.30 mg, 113.89 µmol) and DIEA (36.80 mg, 284.73 µmol) and the mixture was stirred at 15° C. for 5 min. Then (2S)-2-amino-4-methylsulfanyl-N-(4-phenylthiazol-2-yl)butanamide (40 mg, 94.91 µmol, TFA salt) was added and the mixture was stirred at 15° C. for 16 hr. The solvent was removed under reduced pressure and then the residue was purified through Prep.HPLC (column: Phenomenex Synergi C18 150*25*10 µm; mobile phase: [water(0.1% TFA)-ACN]; B %: 42%-72%, 9 min), and lyophilized to give compound 2 as a white solid $^1$H NMR (400 MHz, MeOD) δ=8.53 (d, J=1.6 Hz, 1H), 8.11-8.09 (m, 1H), 7.91-7.89 (m, 2H), 7.57 (d, J=8.0, 1H), 7.40-7.37 (m, 3H), 7.31-7.27 (m, 1H), 4.93-4.91 (m, 1H), 3.19 (s, 3H), 2.77 (s, 3H), 2.72-2.61 (m, 2H), 2.33-2.18 (m, 2H), 2.14 (s, 3H) ppm.

LCMS (ESI) m/z: [M+H]$^+$=504.2.

Example 33. Preparation of methyl 3-[2-[[2-[[3-(dimethylsulfamoyl)benzoyl]amino]acetyl]amino]thiazol-4-yl]benzoate (compound 9)

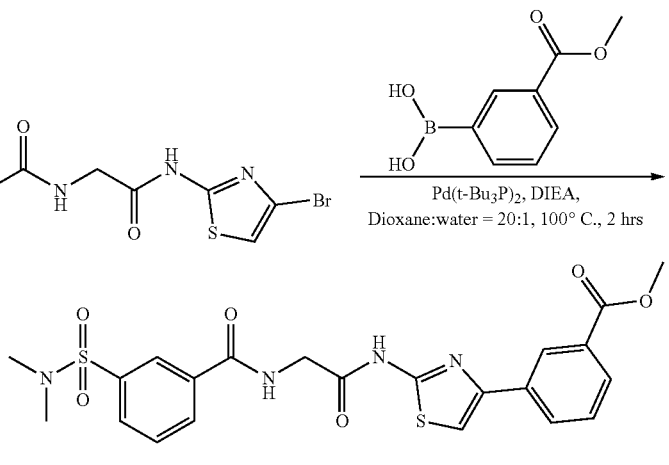

9

To a solution of N-[2-[(4-bromothiazol-2-yl)amino]-2-oxo-ethyl]-3-(dimethylsulfamoyl) benzamide (30 mg, 67.07 µmol) and (3-methoxycarbonylphenyl)boronic acid (36.21 mg, 201.21 µmol) in 1,4-dioxane (3 mL) and H$_2$O (0.2 mL) were added Pd(t-Bu$_3$P)$_2$ (17.14 mg, 33.53 µmol) and DIEA (43.34 mg, 335.35 µmol, 58.41 µL) under N$_2$. The mixture was stirred at 100° C. for 2 hrs then poured into H$_2$O (20 mL) and extracted with EtOAc (5 mL*3). The combined organic extracts were washed with H$_2$O (5 mL*2) and brine (5 mL*1), dried over Na$_2$SO$_4$, filtered and concentrated under vacuum. The residue was purified through Prep-HPLC (column: Phenomenex Gemini 150*25 mm*10 µm; mobile phase: [water(0.04% NH$_3$H2O+10 mM NH$_4$HCO3)-ACN]; B %: 36%-66%, 10 min) and lyophilized to compound 9 as a white solid.

$^1$H NMR (400 MHz, DMSO-d$_6$) δ 12.58 (s, 1H), 9.33-9.31 (m, 1H), 8.56 (s, 1H), 8.27-8.24 (m, 2H), 8.18 (d, J=8.0 Hz, 1H), 7.94-7.91 (m, 2H), 7.83-7.81 (m, 2H), 7.62-7.60 (m, 1H), 4.25 (d, J=5.6 Hz, 2H), 3.89 (s, 3H), 2.66 (s, 6H) ppm LCMS (ESI) m/z: [M+H]$^+$=503.3.

Example 34. Preparation of 3-[2-[[2-[[3-(dimethyl-sulfamoyl)benzoyl]amino]acetyl]amino]thiazol-4-yl]-N-methyl-benzamide (compound 4)

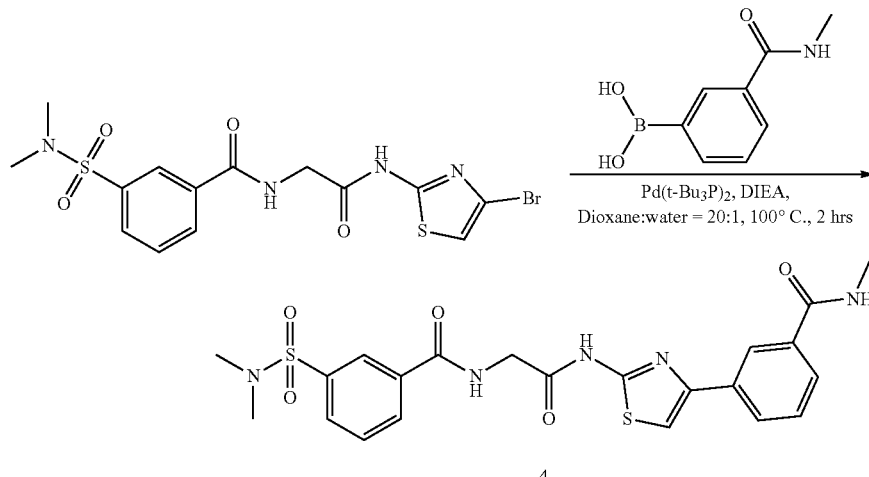

To a solution of N-[2-[(4-bromothiazol-2-yl)amino]-2-oxo-ethyl]-3-(dimethylsulfamoyl) benzamide (30 mg, 67.07 μmol) and [3-(methylcarbamoyl)phenyl]boronic acid (36.01 mg, 201.21 μmol) in 1,4-dioxane (3 mL) and H₂O (0.15 mL) were added Pd(t-Bu₃P)₂ (17.14 mg, 33.53 μmol) and DIEA (43.34 mg, 335.35 μmol, 58.41 μL) under N₂. The mixture was stirred at 100° C. for 2 hrs then poured into H2/(20 mL) and extracted with EtOAC (5 mL*3). The combined organic layers were washed with H₂O (5 mL*2) and brine (5 mL), dried over Na₂SO₄, filtered and concentrated under vacuum. The residue was purified by Prep-HPLC (column: Phenomenex Synergi C18 150*25*10 μm; mobile phase: [water (0.1% TFA)-ACN]; B %: 35%-65%, 9 min) and lyophilized to give compound 4 as a white solid.

$^1$H NMR (400 MHz, DMSO-d₆) δ=12.55 (s, 1H), 9.33-9.30 (m, 1H), 8.52 (s, 1H), 8.40 (s, 1H), 8.27-8.24 (m, 2H), 8.02 (d, J=7.6 Hz, 1H), 7.94 (d, J=7.6 Hz, 1H), 7.81-7.76 (m, 3H), 7.53-7.51 (m, 1H), 4.25 (d, J=5.6 Hz, 2H), 2.81 (d, J=4.4 Hz, 3H), 2.66 (s, 6H), ppm.

LCMS (ESI) m/z: [M+H]⁺=502.3.

Example 35. Preparation of N-[2-[[4-(2-bromophenyl)thiazol-2-yl]amino]-2-oxo-ethyl]-3-(dimethylsulfamoyl)benzamide (compound 18)

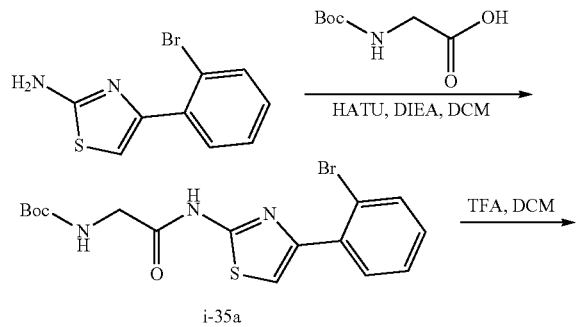

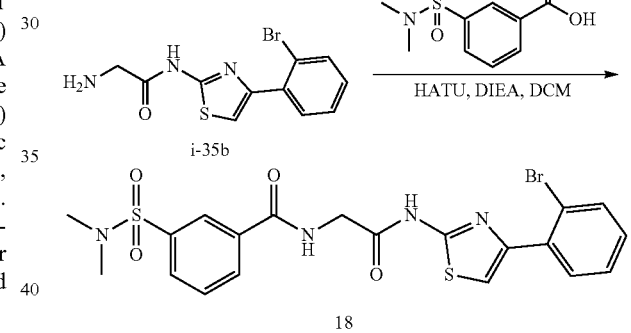

Step 1: Preparation of tert-butyl N-[2-[[4-(2-bromophenyl)thiazol-2-yl] amino]-2-oxo-ethyl]carbamate (intermediate i-35a)

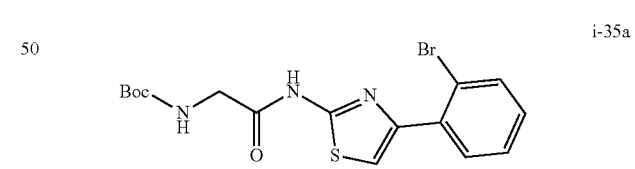

To a solution of 2-(tert-butoxycarbonylamino)acetic acid (82.40 mg, 470.34 μmol) in DCM (10 mL) were added HATU (223.55 mg, 587.93 μmol) and DIEA (151.97 mg, 1.18 mmol) and the mixture was stirred at 30° C. for 30 min. Then 4-(2-bromophenyl) thiazol-2-amine (100 mg, 391.95 μmol) was added. The mixture was stirred at 30° C. for another 12 hrs and then diluted with DCM (50.0 mL) and washed with H₂O (10.0 mL*3) and brine (10.0 mL*2), then dried over Na₂SO₄, filtered and concentrated under vacuum to give intermediate i-35a as yellow oil which was used in the next step directly.

LCMS (ESI) m/z: [M+H]⁺=412.3.

Step 2: Preparation of 2-amino-N-[4-(2-bromophenyl)thiazol-2-yl]acetamide (intermediate i-35b) trifluoroacetate salt

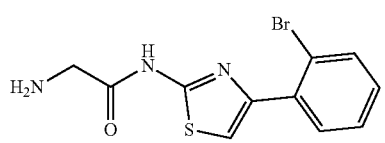
i-35b

To a solution of intermediate i-35a (150 mg, 363.81 μmol) in DCM (5.0 mL) was added TFA (1.0 mL). The solution was stirred at 30° C. for 2 hr. Then the mixture was diluted with DCM (20.0 mL) and concentrated under vacuum. This operation was repeated three times. The residue was washed by MTBE (5.0 mL*2) and dried in vacuum to give intermediate i-35b (TFA salt) as yellow oil which was used in the next step directly.

LCMS (ESI) m/z: [M+H]$^+$=312.3

Step 3: Preparation of N-[2-[[4-(2-bromophenyl)thiazol-2-yl]amino]-2-oxo-ethyl]-3-(dimethylsulfamoyl)benzamide (compound 18)

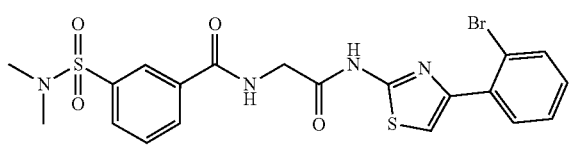
18

To a solution of 3-(dimethylsulfamoyl)benzoic acid (96.82 mg, 422.33 μmol) in DMF (3.0 mL) were added HATU (401.46 mg, 1.06 mmol) and DIEA (227.43 mg, 1.76 mmol, 306.51 μL) and the mixture was stirred at 30° C. for 30 min. Then intermediate i-35b (150 mg, 351.94 μmol) was added. The mixture was stirred at 30° C. for 16 hrs, then poured into H$_2$O (30.0 mL) and extracted with EtOAc (5.0 mL*3). The combined organic extracts were washed with H$_2$O (5.0 mL*2) and brine (5.0 mL), then dried over Na$_2$SO$_4$, filtered and concentrated under vacuum. The residue was purified by Prep-HPLC (column: Phenomenex Synergi C18 150*25*10 μm; mobile phase: [water(0.1% TFA)-ACN]; B %: 42%-72%, 9 min) and lyophilized to give compound 18 as a light yellow solid.

$^1$H NMR (400 MHz, DMSO-d6) δ=12.51 (s, 1H), 9.34-9.31 (m, 1H), 8.27-8.23 (m, 2H), 7.94 (d, J=8.0 Hz, 1H), 7.83-7.81 (m, 1H), 7.75-7.69 (m, 2H), 7.54 (s, 1H), 7.48-7.46 (m, 1H), 7.32-7.30 (m, 1H), 4.24 (d, J=5.6 Hz, 2H), 2.66 (s, 6H) ppm LCMS (ESI) m/z: [M+H]$^+$=525.0.

Example 36. Preparation of (N-[2-[[4-(3-bromophenyl)thiazol-2-yl]amino]-2-oxo-ethyl]-3-(dimethylsulfamoyl)benzamide (compound 7)

Step 1: Preparation of tert-butyl N-[2-[[4-(3-bromophenyl)thiazol-2-yl] amino]-2-oxo-ethyl]carbamate (intermediate i-36a)

To a solution of 2-(tert-butoxycarbonylamino)acetic acid (82.40 mg, 470.34 μmol) in DCM (10 mL) were added HATU (223.55 mg, 587.93 μmol) and DIEA (151.97 mg, 1.18 mmol, 204.81 μL) and the mixture was stirred at 30° C. for 30 min. Then 4-(3-bromophenyl)thiazol-2-amine (100.00 mg, 391.95 μmol) was added. The mixture was stirred at 30° C. for another 12 hrs then diluted with DCM (50.0 mL). The solution was washed with H$_2$O (10.0 mL*3) and brine (10 mL*2), then dried over Na$_2$SO$_4$, filtered and concentrated under vacuum to give intermediate i-36a as yellow oil which was used directly in the next step.

LCMS (ESI) m/z: [M+H]$^+$=412.3

Step 2: Preparation of 2-amino-N-[4-(3-bromophenyl)thiazol-2-yl]acetamide (intermediate i-36b) trifluoroacetate salt

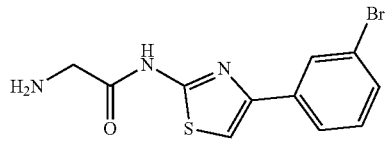

i-36b

To a solution of intermediate i-36a (150.00 mg, 363.81 μmol) in DCM (5 mL) was added TFA (1 mL), the solution was stirred at 30° C. for 2 hrs. Then the mixture was diluted with DCM (20.0 mL) and concentrated in vacuum. This operation was repeated three times. The residue was washed by MTBE (5.0 mL*2) and dried in vacuum to give intermediate i-36b (TFA salt) as yellow oil which was used directly in the next step.

LCMS (ESI) m/z: [M+H]$^+$=312.3

Step 3: Preparation of (N-[2-[[4-(3-bromophenyl)thiazol-2-yl]amino]-2-oxo-ethyl]-3-(dimethylsulfamoyl)benzamide (compound 7)

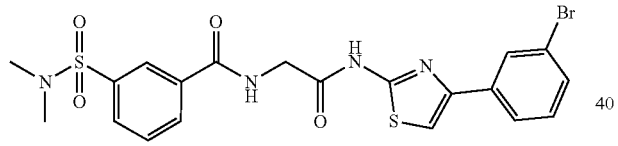

7

To a solution of 3-(dimethylsulfamoyl)benzoic acid (96.82 mg, 422.33 μmol) in DMF (3.0 mL) were added HATU (401.46 mg, 1.06 mmol) and DIEA (227.43 mg, 1.76 mmol, 306.51 μL) and the mixture was stirred at 30° C. for 30 min. Then intermediate i-36b (150 mg, 351.94 μmol) was added. The mixture was stirred at 30° C. for 16 hrs then poured into H$_2$O (30.0 mL) and extracted with EtOAc (5.0 mL*3). The combined organic extracts were washed with H$_2$O (5.0 mL*2) and brine (5 mL), then dried over Na$_2$SO$_4$, filtered and concentrated under vacuum. The residue was purified by Pre-HPLC (column: Phenomenex Synergi C18 150*25*10 μm; mobile phase: [water(0.1% TFA)-ACN]; B %: 42%-72%, 9 min) and lyophilized to give compound 7 as a pink solid.

$^1$H NMR (400 MHz, DMSO-d6) δ=12.51 (s, 1H), 9.33-9.30 (m, 1H), 8.27-8.23 (m, 2H), 8.11 (s, 1H), 7.94-7.91 (m, 2H), 7.82-7.80 (m, 2H), 7.43-7.42 (m, 1H), 7.41-7.40 (m, 1H), 4.24 (d, J=5.6 Hz, 2H), 2.66 (s, 6H) ppm LCMS (ESI) m/z: [M+H]$^+$=523.2.

Example 37. Preparation of Compound (S)—N-(4-(methylthio)-1-oxo-1-((4-phenylthiazol-2-yl)amino)butan-2-yl)nicotinamide (compound 70)

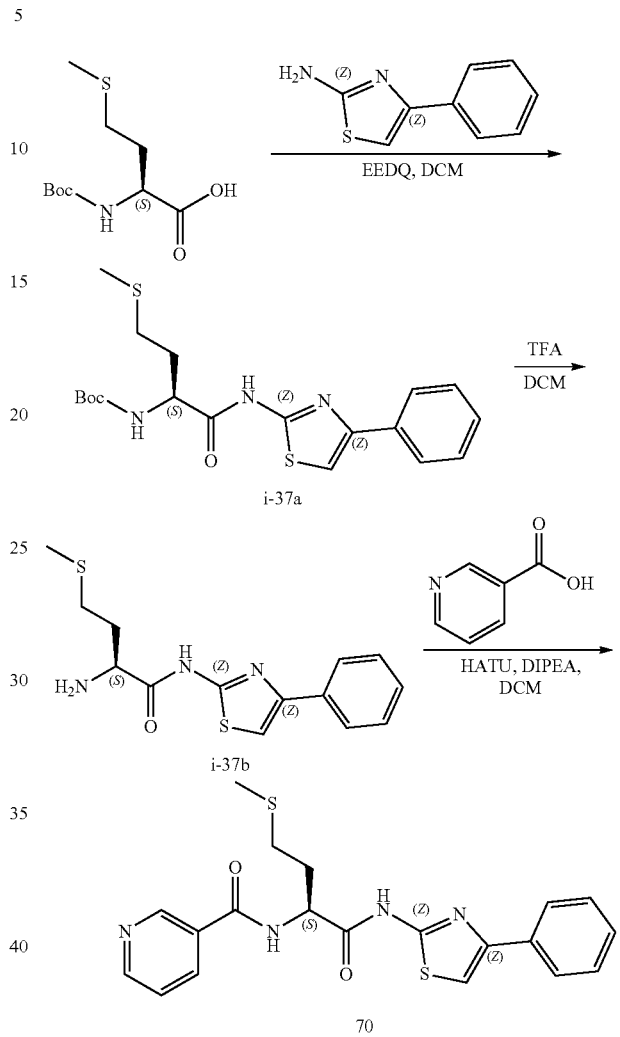

Step 1: Preparation of (S)-tert-butyl (4-(methylthio)-1-oxo-1-((4-phenylthiazol-2-yl)amino)butan-2-yl)carbamate (intermediate i-37a)

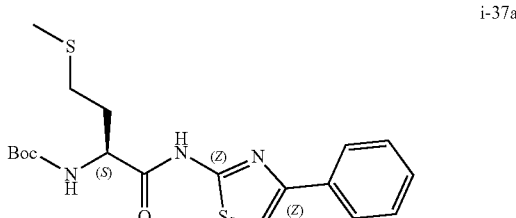

i-37a

To a solution of (2S)-2-(tert-butoxycarbonylamino)-4-methylsulfanyl-butanoic acid (5.0 g, 20.05 mmol) in DCM (20.0 mL) was added EEDQ (6.20 g, 25.07 mmol), then 4-phenylthiazol-2-amine (2.95 g, 16.71 mmol) was added to the mixture. The mixture was stirred at 25° C. for 3 hr. 10% of Citric acid (800.0 mL) was added and the reaction mixture was extracted with EtOAc (200 mL). The combined organic extracts were washed with brine (100 mL), dried over Na$_2$SO$_4$, filtered and concentrated under reduced pressure to give a residue. The residue was purified by column chromatography (SiO$_2$, Petroleum ether/Ethyl acetate=50/1 to 8:1) to give intermediate i-37a as a white solid.

LCMS (ESI) m/z: [M+H]$^+$=408.0.

SFC HPLC: Amycoat-MeOH(DEA)-5-40-3 mL-35, 2.284 min.

Step 2: Preparation of (S)-2-amino-4-(methylthio)-N-(4-phenylthiazol-2-yl) butanamide (intermediate i-37b) trifluoroacetate salt

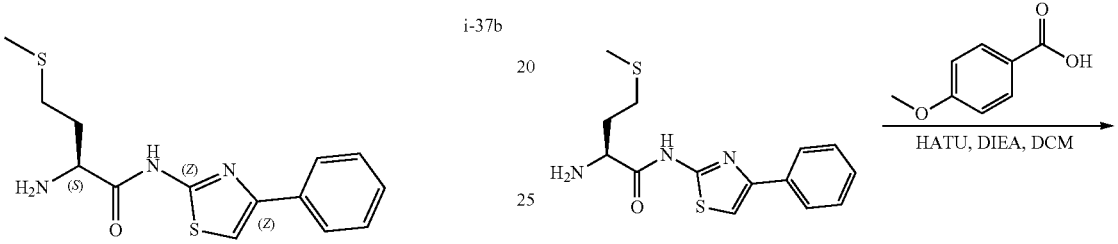

To a solution of intermediate i-37a (5.8 g, 14.23 mmol) in DCM (20.0 mL) was added TFA (4.0 mL). The mixture was stirred at 10° C. for 2 hr. The reaction mixture was concentrated under reduced pressure. The crude product intermediate i-37b (TFA salt) was lyophilized and obtained as a white solid.

This material was used in the next step without further purification

LCMS (ESI) m/z: [M+H]$^+$=307.9.

SFC HPLC: Cellucoat-MeOH(DEA)-10-12 min-3, 8.970 min.

Step 3: Preparation of (S)—N-(4-(methylthio)-1-oxo-1-((4-phenylthiazol-2-yl)amino)butan-2-yl)nicotinamide (compound 70)

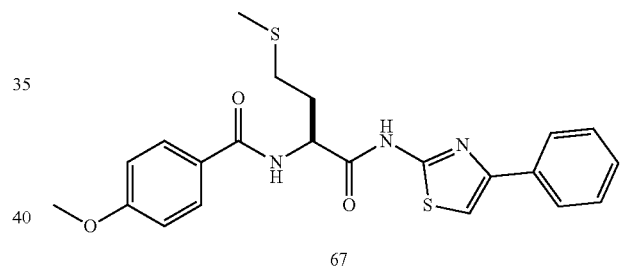

To a solution of nicotinic acid (14.61 mg, 118.64 μmol) in DCM (2 mL) was added HATU (67.66 mg, 177.95 μmol) and DIPEA (61.33 mg, 474.54 μmol, 82.66 μL), then intermediate i-37b (50 mg, 118.64 μmol) was added. The mixture was stirred at 10° C. for 2 hr. The reaction mixture was concentrated under reduced pressure. The residue was purified by prep-HPLC (Phenomenex Gemini 150*25 mm*10 μm; mobile phase: [water(10 mM NH4HCO3)-ACN]; B %: 45%-75%, 10 min) and lyophilized to give compound 70 as a white solid.

1H NMR (400 MHz, METHANOL-d4) δ 9.06 (m, 1H), 8.72-8.71 (m, 1H), 8.33-8.31 (m, 1H), 7.91-7.89 (m, 2H), 7.58-7.55 (m, 1H), 7.40-7.38 (m, 3H), 7.37-7.30 (m, 1H), 4.94-4.91 (m, 1H), 2.75-2.65 (m, 2H), 2.31-2.29 (m, 2H), 2.14 (s, 3H) ppm.

LCMS (ESI) m/z: [M+H]$^+$=413.1.

Chiral HPLC: Cellucoat-MeOH(DEA)-5-40-3 mL-35T.Icm, 2.269 min.

Example 38. Preparation of 4-methoxy-N-[(1S)-3-methylsulfanyl-1-[(4-phenylthiazol-2-yl)carbamoyl]propyl]benzamide (compound 67)

To a solution of 4-methoxybenzoic acid (21.66 mg, 142.36 μmol) in DCM (2.0 mL) was added HATU (90.22 mg, 237.27 μmol) and DIEA (76.66 mg, 593.18 μmol, 103.32 μL). The mixture was stirred at 30° C. for 30 min. Then (2S)-2-amino-4-methylsulfanyl-N-(4-phenylthiazol-2-yl) butanamide (50 mg, 118.64 μmol) was added. The mixture was stirred at 30° C. for another 2 hrs. The reaction solution was diluted with DCM (20.0 mL) and washed with (5.0 mL*3) and brine (5 mL), dried over Na$_2$SO$_4$, filtered and concentrated under vacuum. The residue was purified by Pre-HPLC (column: Phenomenex Synergi C18 150*25*10 μm; mobile phase: [water(0.1% TFA)-ACN]; B %: 45%-75%, 9 min) and lyophilized to give compound 67 as a white solid.

$^1$HNMR (400 MHz, METHANOL-d4) δ 7.92-7.90 (m, 4H), 7.42-7.38 (m, 3H), 7.33-7.29 (m, 1H), 7.03 (d, J=9.2 Hz, 2H), 4.94-4.91 (m, 1H), 3.88 (s, 3H), 2.75-2.65 (m, 2H), 2.36-2.15 (m, 2H), 2.14 (s, 3H) ppm.

LCMS (ESI) m/z: [M+H]$^+$=442.1.

Example 39. Preparation of 2-hydroxy-N-[(1S)-3-methylsulfanyl-1-[(4-phenylthiazol-2-yl)carbamoyl]propyl]benzamide (compound 69)

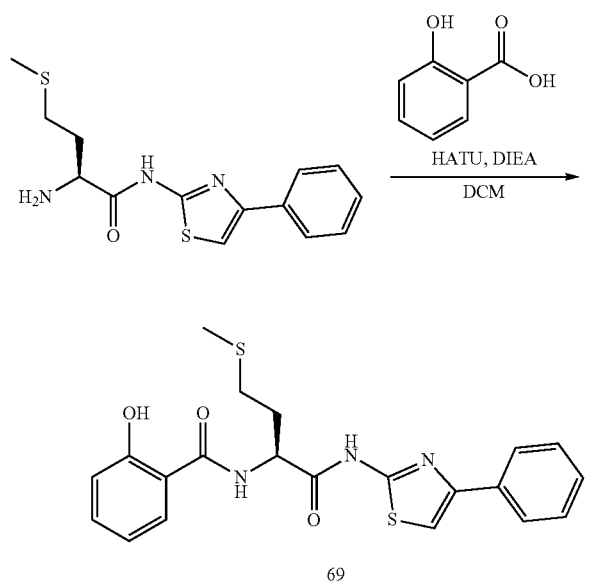 [SMILES: CSCC[C@H](N)C(=O)Nc1nc(-c2ccccc2)cs1 ; O=C(O)c1ccccc1O ; CSCC[C@H](NC(=O)c1ccccc1O)C(=O)Nc1nc(-c2ccccc2)cs1]

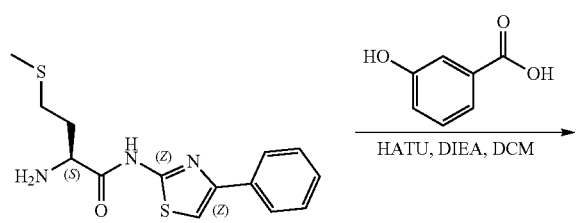

To a mixture of (2S)-2-amino-4-methylsulfanyl-N-(4-phenylthiazol-2-yl)butanamide (50 mg, 118.64 µmol) and 2-hydroxybenzoic acid (16.39 mg, 118.64 µmol) in DCM (1 mL) was added DIPEA (61.33 mg, 474.54 µmol). The mixture was stirred at 30° C. for 15 min, then HATU (67.66 mg, 177.95 µmol) was added and stirred at 30° C. for 2 hours. The reaction mixture was evaporated to dryness to give the crude product. The residue was purified by prep-HPLC (column: Phenomenex Synergi C18 150*25*10 µm; mobile phase: [water(0.1% TFA)-ACN]; B %: 51%-71%, 12 min) and lyophilized to give compound 69 as a white solid.

$^1$H NMR (400 MHz, MeOD-d$_4$) δ=7.92-7.89 (m, 3H), 7.43-7.37 (m, 4H), 7.31-7.28 (m, 1H), 6.96-6.92 (m, 2H), 4.98-4.94 (m, 1H), 2.72-2.60 (m, 2H), 2.35-2.27 (m, 1H), 2.25-2.17 (m, 1H), 2.13 (s, 3H) ppm.

LCMS (ESI) m/z: [M+H]$^+$=428.1.

Chiral HPLC: OD-3_5CM_MEOH (DEA)_40_3ML_T35.M, 0.822 min.

Example 40. Preparation of Compound (S)-3-hydroxy-N-(4-(methylthio)-1-oxo-1-((4-phenylthiazol-2-yl)amino)butan-2-yl)benzamide (compound 59)

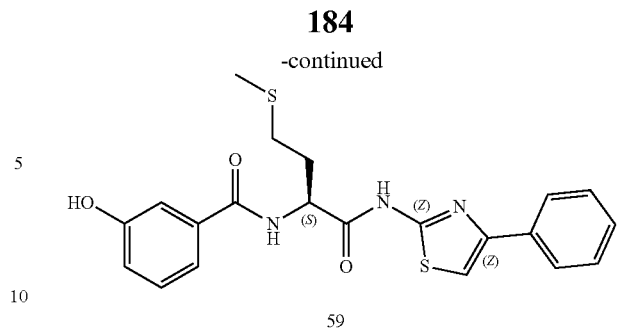

To a solution of 3-hydroxybenzoic acid (16.39 mg, 118.64 µmol, 9.94 µL) and (2S)-2-amino-4-methylsulfanyl-N-(4-phenylthiazol-2-yl)butanamide (50 mg, 118.64 µmol) in DCM (2.0 mL) was added DIPEA (61.33 mg, 474.56 µmol), then HATU (67.66 mg, 177.96 µmol) was added. The mixture was stirred at 10° C. for 2 hr. The reaction mixture was concentrated under reduced pressure. The residue was purified by prep-HPLC (TFA condition; column: column: Phenomenex Synergi C18 150*25*10 µm; mobile phase: [water(0.1% TFA)-ACN]; B %: 45%-75%, 9 min) and lyophilized to give compound 59 as a white solid.

$^1$HNMR (400 MHz, METHANOL-d4) δ=7.90-7.88 (m, 2H) 7.38-7.34 (m, 4H), 7.30-7.27 (m, 3H), 6.98-6.95 (m, 1H), 4.90-4.87 (m, 1H), 2.69-2.62 (m, 2H), 2.26-2.20 (m, 2H), 2.13 (s, 3H) ppm LCMS (ESI) m/z: [M+H]$^+$=428.1.

Chiral HPLC: AS-3_5CM_MEOH (DEA)_40_3ML_5MIN_T35.M, 1.341 min.

Example 41. Preparation of 4-hydroxy-N-[(1S)-3-methylsulfanyl-1-[(4-phenylthiazol-2-yl)carbamoyl]propyl]benzamide (compound 53)

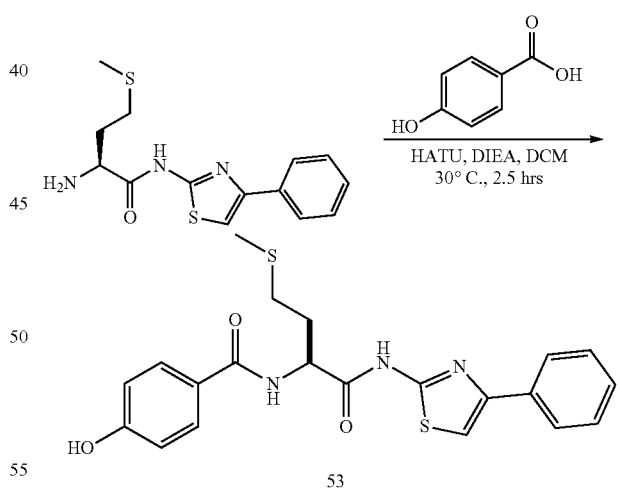

To a solution of 4-hydroxybenzoic acid (16.39 mg, 118.64 µmol) and (2S)-2-amino-4-methyl sulfanyl-N-(4-phenylthiazol-2-yl)butanamide (50 mg, 118.64 µmol) in DCM (2.0 mL) were added DIEA (76.66 mg, 593.18 µmol, 103.32 µL) and HATU (90.22 mg, 237.27 µmol). The mixture was stirred at 30° C. for 2.5 hrs. The reaction was diluted with DCM (20.0 mL) and washed with water (5.0 mL*3) and brine (5.0 mL), dried over Na$_2$SO$_4$, filtered and concentrated under vacuum to give crude product. The crude product was purified by Pre-HPLC (column: Boston pH-lex 150*25 10

μm; mobile phase: [water(0.1% TFA)-ACN]; B %: 48%-68%, 8 min) and lyophilized to give compound 53 as a yellow solid.

$^1$H NMR (400 MHz, METHANOL-d4) δ=7.91 (d, J=8.4 Hz, 2H), 7.82 (d, J=8.4 Hz, 2H), 7.42-7.38 (m, 3H), 7.32-7.30 (m, 1H), 6.87-6.85 (m, 2H), 4.90-4.86 (m, 1H), 2.72-2.64 (m, 2H), 2.28-2.21 (m, 2H), 2.15 (s, 3H) ppm.

LCMS (ESI) m/z: [M+H]$^+$=428.3.

Example 42. Preparation of 2-amino-N-[(1S)-3-methylsulfanyl-1-[(4-phenylthiazol-2-yl)carbamoyl]propyl]benzamide (compound 63)

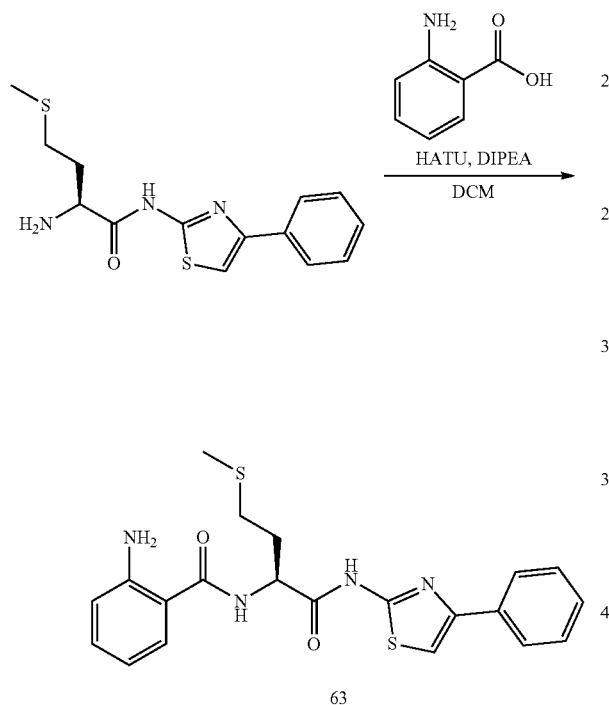

63

To a mixture of 2-aminobenzoic acid (16.27 mg, 118.64 μmol) and (2S)-2-amino-4-methyl sulfanyl-N-(4-phenylthiazol-2-yl)butanamide (50 mg, 118.64 μmol) in DCM (1 mL) was added DIPEA (61.33 mg, 474.54 μmol). The mixture was stirred at 30° C. for 15 min, then HATU (67.66 mg, 177.95 μmol) was added and stirred at 30° C. for 2 hours. The reaction mixture was evaporated to dryness to give the crude product. The residue was purified by prep-HPLC (column: Boston pH-lex 150*25 10 μm; mobile phase: [water(0.1% TFA)-ACN]; B %: 55%-75%, 8 min) and lyophilized to give compound 63 (TFA salt) as a white solid.

$^1$H NMR (400 MHz, MeOD-d$_4$) δ=7.91-7.89 (m, 2H), 7.71-7.69 (m, 1H), 7.41-7.37 (m, 3H), 7.35-7.28 (m, 2H), 6.93-6.86 (m, 2H), 4.91-4.87 (m, 1H), 2.75-2.61 (m, 2H), 2.33-2.26 (m, 1H), 2.25-2.16 (m, 1H), 2.15 (s, 3H) ppm; LCMS (ESI) m/z: [M+H]$^+$=427.3.

Chiral HPLC: Cellucoat-MeOH(DEA)-40-3 mL-35T.1 cm, 1.540 min.

Example 43. Preparation of Compound (S)-3-amino-N-(4-(methylthio)-1-oxo-1-((4-phenylthiazol-2-yl)amino)butan-2-yl)benzamide (compound 56)

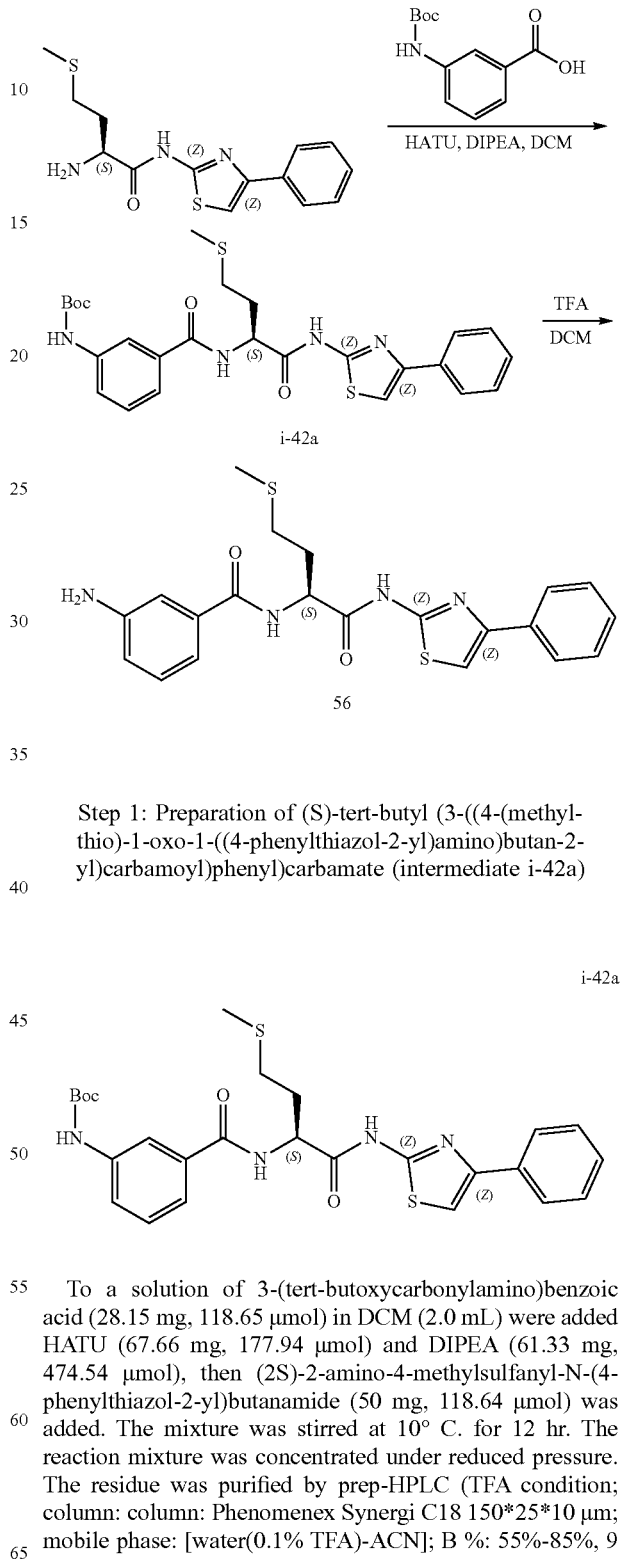

Step 1: Preparation of (S)-tert-butyl (3-((4-(methylthio)-1-oxo-1-((4-phenylthiazol-2-yl)amino)butan-2-yl)carbamoyl)phenyl)carbamate (intermediate i-42a)

To a solution of 3-(tert-butoxycarbonylamino)benzoic acid (28.15 mg, 118.65 μmol) in DCM (2.0 mL) were added HATU (67.66 mg, 177.94 μmol) and DIPEA (61.33 mg, 474.54 μmol), then (2S)-2-amino-4-methylsulfanyl-N-(4-phenylthiazol-2-yl)butanamide (50 mg, 118.64 μmol) was added. The mixture was stirred at 10° C. for 12 hr. The reaction mixture was concentrated under reduced pressure. The residue was purified by prep-HPLC (TFA condition; column: column: Phenomenex Synergi C18 150*25*10 μm; mobile phase: [water(0.1% TFA)-ACN]; B %: 55%-85%, 9 min) to give intermediate i-42a as a white solid.

LCMS (ESI) m/z: [M+H]$^+$=527.1.

Step 2: Preparation of (S)-3-amino-N-(4-(methyl-thio)-1-oxo-1-((4-phenylthiazol-2-yl)amino)butan-2-yl)benzamide (compound 56) trifluoroacetate salt

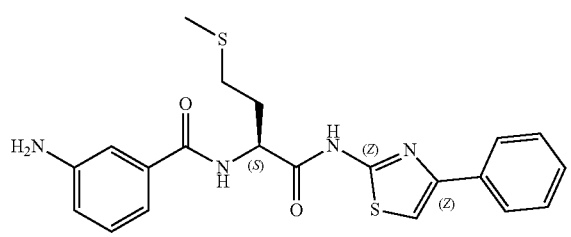

56

To a solution of intermediate i-42a (20 mg, 37.97 μmol) in DCM (2.0 mL) was added TFA (1.0 mL). The mixture was stirred at 10° C. for 2 hr. The reaction mixture was concentrated under reduced pressure. The residue was purified by prep-HPLC (TFA condition; column: Phenomenex Synergi C18 150*25*10 μm; mobile phase: [water(0.1% TFA)-ACN]; B %: 35%-65%, 9 min) and lyophilized to give compound 56 (TFA salt) as a white solid.

1H NMR (400 MHz, METHANOL-d4) δ=7.90-7.88 (m, 2H), 7.84-7.83 (m, 1H), 7.72-7.71 (m, 1H), 7.57-7.55 (m, 1H), 7.40-7.36 (m, 4H), 7.31-7.279 (m, 1H), 4.93-4.91 (m, 1H), 2.70-2.64 (m, 2H), 2.30-2.20 (m, 2H), 2.14 (s, 3H) ppm.

LCMS (ESI) m/z: [M+H]$^+$=427.1.

Example 44. Preparation of 4-amino-N-[(1S)-3-methylsulfanyl-1-[(4-phenylthiazol-2-yl)carbamoyl]propyl]benzamide (compound 52)

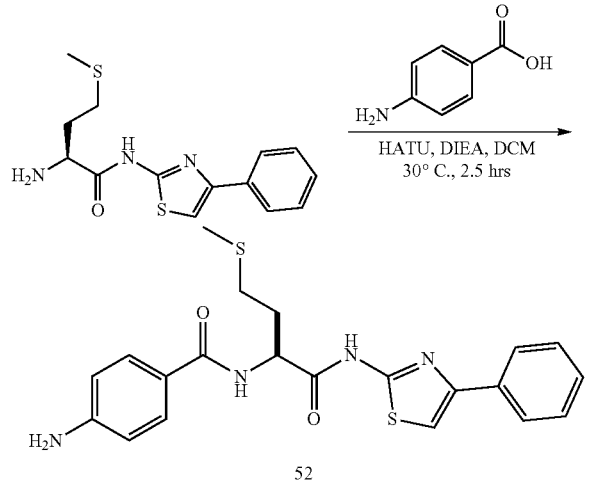

52

To a solution of 4-aminobenzoic acid (19.52 mg, 142.36 μmol) in DCM (2 mL) were added HATU (90.22 mg, 237.27 μmol) and DIEA (76.66 mg, 593.18 μmol, 103.32 μL) and the mixture was stirred at 30° C. for 30 min. Then (2S)-2-amino-4-methylsulfanyl-N-(4-phenylthiazol-2-yl) butanamide (50 mg, 118.64 μmol) was added. The mixture was stirred at 30° C. for another 2 hrs then diluted with DCM (20.0 mL). The organic layer was washed with (5.0 mL*3) and brine (5 mL), dried over Na$_2$SO$_4$, filtered and concentrated under vacuum. The residue was purified by Pre-HPLC (column: Phenomenex Synergi C18 150*25*10 μm; mobile phase: [water(0.225% FA)-ACN]; B %: 40%-70%, 9 min) and lyophilized to give compound 52 (TFA salt) as a white solid.

$^1$H NMR (400 MHz, METHANOL-d4) δ 7.92-7.89 (m, 2H), 7.76-7.74 (m, 2H), 7.42-7.38 (m, 3H), 7.33-7.31 (m, 1H), 6.80 (d, J=8.8 Hz, 2H), 4.94-4.88 (m, 1H), 2.71-2.64 (m, 2H), 2.28-2.21 (m, 2H), 2.15 (s, 3H) ppm.

LCMS (ESI) m/z: [M+H]$^+$=427.1.

Example 45. Preparation of (S)—N-(3-amino-1-oxo-1-((4-phenylthiazol-2-yl)amino)propan-2-yl)-3-(N,N-dimethylsulfamoyl)benzamide (compound 25)

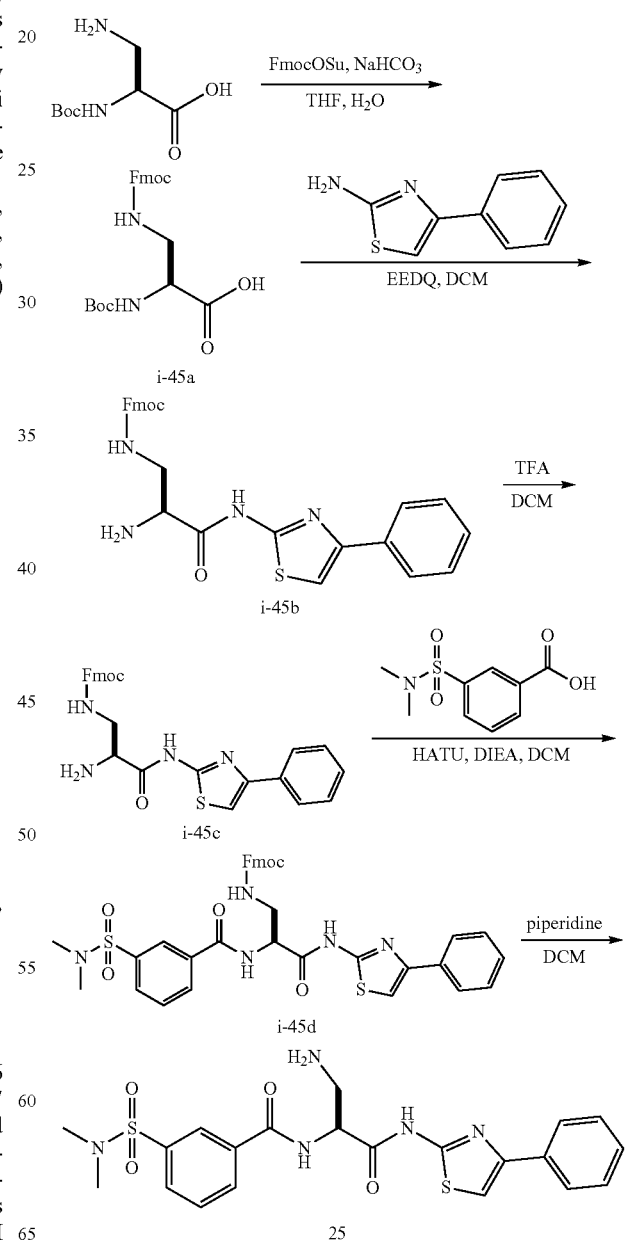

25

Step 1: Preparation of (S)-3-((((9H-fluoren-9-yl)methoxy)carbonyl)amino)-2-((tert-butoxycarbonyl)amino)propanoic acid (intermediate i-45a)

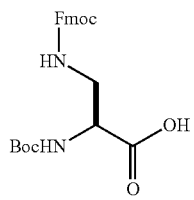

To a solution of (2S)-3-amino-2-(tert-butoxycarbonylamino)propanoic acid (1.0 g, 4.90 mmol) in THF (10.0 mL) and water (10.0 mL) were added FmocOSu (1.82 g, 5.39 mmol) and NaHCO₃ (822.69 mg, 9.79 mmol). The mixture was stirred at 20° C. for 3 hours. The reaction mixture was adjusted to pH 4 with citric acid solution. The solution was extracted with EtOAc (10.0 mL*3). The organic layer was washed with brine (20.0 mL), dried over Na₂SO₄ and filtered. The filtrate was concentrated to give a residue. The residue was triturated with MTBE (10.0 mL). The solution was filtered and the filter cake was dried under vacuum to give intermediate i-45a as a white solid.

LCMS (ESI) m/z: [M+Na]⁺=449.3

Step 2: Preparation of (S)-(9H-fluoren-9-yl)methyl tert-butyl (3-oxo-3-((4-phenylthiazol-2-yl)amino)propane-1,2-diyl)dicarbamate (intermediate i-45b)

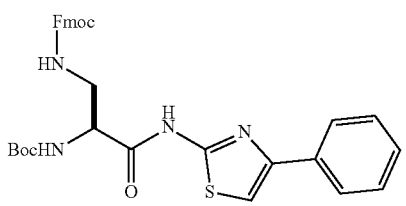

To a solution of intermediate i-45a (1.8 g, 4.22 mmol) in DCM (18.0 mL) were added EEDQ (1.57 g, 6.33 mmol) and 4-phenylthiazol-2-amine (743.86 mg, 4.22 mmol). The reaction mixture was stirred at 20° C. for 12 hours and then poured into water (20.0 mL). The solution was extracted with EtOAc (20.0 mL*3). The combine organic layers were washed with brine (50.0 mL), dried over Na₂SO₄ and filtered. The filtrate was concentrated to give a residue. The residue was purified by column chromatography (SiO₂, PE:EA=100:1-50:1-10:1-5:1-2:1) to give intermediate i-45b as a yellow solid.

LCMS (ESI) m/z: [M+H]⁺=585.4

Chiral HPLC: Cellucoat-MeOH(DEA)-40-7MIN-3ML, 3.031 min.

Step 3: Preparation of (S)-(9H-fluoren-9-yl)methyl (2-amino-3-oxo-3-((4-phenylthiazol-2-yl)amino)propyl)carbamate (intermediate i-45c)

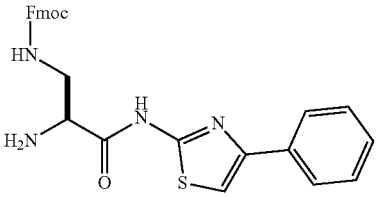

To a solution of intermediate i-45b (2.5 g, 4.28 mmol) in DCM (25.0 mL) was added TFA (4.0 mL). The reaction mixture was stirred at 20° C. for 1.5 hours. The reaction mixture was concentrated to give a residue. The residue was triturated with PE (10.0 mL). Then the mixture was filtered and the solid was dried in vacuum to give intermediate i-45c (TFA salt) as a white solid.

LCMS (ESI) m/z: [M+Na]⁺=507.3

Chiral HPLC: OJ-3-MeOH(DEA)-60-7MIN-3ML-35T, 5.436 min

Step 4: Preparation of (S)-(9H-fluoren-9-yl)methyl (2-(3-(N,N-dimethylsulfamoyl)benzamido)-3-oxo-3-((4-phenylthiazol-2-yl)amino)propyl)carbamate (intermediate i-45c)

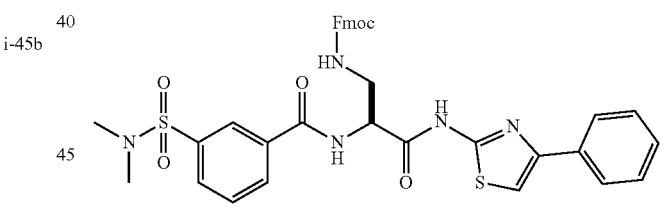

To a solution of 3-(dimethylsulfamoyl)benzoic acid (38.30 mg, 167.06 μmol) in DCM (1.0 mL) were added HATU (69.87 mg, 183.76 μmol), DIEA (64.77 mg, 501.18 μmol, 87.30 μL) and intermediate i-45b (100 mg, 167.06 μmol). The reaction mixture was stirred at 20° C. for 12 hours and then poured into water (2.0 mL). The solution was extracted with EtOAc (2.0 mL*3). The combined organic extracts were washed with brine (5.0 mL), dried over Na₂SO₄ and filtered. The filtrate was concentrated to give a residue. The residue was purified by column chromatography (SiO₂, PE/EA=50/1-1/1) to give intermediate i-45c as a white solid.

LCMS (ESI) m/z: [M+H]⁺=696.0

Chiral HPLC: OJ-3-MeOH(DEA)-60-7MIN-3ML-35T, 5.276 min.

Step 5: Preparation of (S)—N-(3-amino-1-oxo-1-((4-phenylthiazol-2-yl)amino)propan-2-yl)-3-(N,N-dimethylsulfamoyl)benzamide (compound 25) formate salt

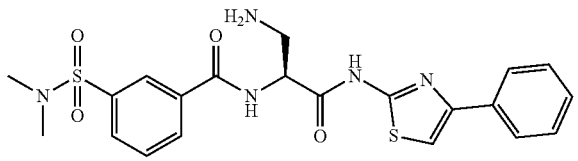

To a solution of intermediate i-45c (100.0 mg, 140.84 μmol) in DCM (1.0 mL) was added piperidine (98.00 μL). The solution was stirred at 20° C. for 2 hours. The mixture was poured into water (2.0 mL), extracted with EtOAc (2.0 mL*3). The combined organic extracts were washed with brine (3.0 mL), dried over Na$_2$SO$_4$ and filtered. The filtrate was concentrated to give a residue. The residue was purified by Prep-HPLC (column: Phenomenex Synergi C18 150*25*10 μm; mobile phase: [water (0.225% FA)-ACN]; B %: 17%-37%, 7 min) and lyophilized to give compound 25 (FA salt) as a white solid.

$^1$H NMR (400 MHz, DMSO-d6) δ=8.30-8.28 (m, 2H), 8.23-8.22 (m, 2H), 7.96-7.89 (m, 3H), 7.81 (d, J=8.0 Hz, 1H), 7.63 (s, 1H), 7.45-7.43 (m, 2H), 7.41-7.32 (m, 1H), 4.74 (s, 1H), 3.11 (s, 2H), 2.66 (s, 6H) ppm LCMS (ESI) m/z: [M+H]$^+$=474.3

Chiral HPLC: OJ-3-MeOH (DEA)-40-7MIN-3ML-35T, 2.956 min.

Chiral HPLC: AD-3_5CM_MEOH (DEA)_40_3ML_8MIN_T35.M

Example 46. Preparation of (S)—N-(3-acetamido-1-oxo-1-((4-phenylthiazol-2-yl)amino)propan-2-yl)-3-(N,N-dimethylsulfamoyl)benzamide (compound 21)

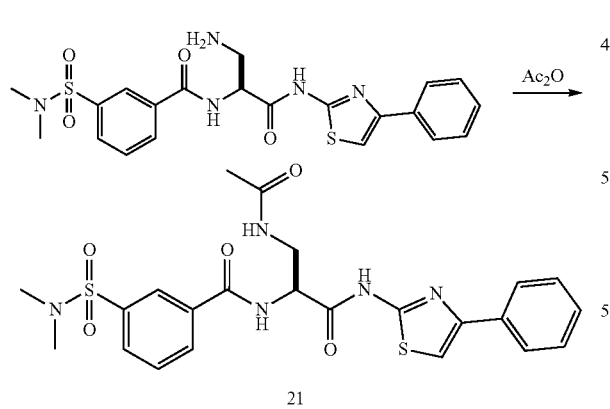

The solution of N-[(1S)-1-(aminomethyl)-2-oxo-2-[(4-phenylthiazol-2-yl)amino]ethyl]-3-(dimethylsulfamoyl)benzamide (20.0 mg, 38.49 μmol) in AC$_2$O (0.2 mL) was stirred at 20° C. for 2 hrs. Then the reaction mixture was poured into water (2.0 mL) and extracted with EtOAc (2.0 mL*3). The combined organic extracts were washed with brine (5.0 mL), dried over Na$_2$SO$_4$ and filtered. The filtrate was concentrated to give a residue. The residue was lyophilized to give compound 21 (51.86% ee) as a white solid.

1H NMR (400 MHz, DMSO-d6) δ=12.54 (s, 1H), 9.12 (d, J=6.8 Hz, 1H), 8.23-8.22 (m, 3H), 7.95 (d, J=7.6 Hz, 1H), 7.89 (d, J=7.2 Hz, 2H), 7.81 (s, 1H), 7.65 (s, 1H), 7.44-7.42 (m, 2H), 7.40-7.31 (m, 1H), 4.72 (d, J=6.0 Hz, 1H), 3.62 (m, 2H), 2.65 (s, 6H), 1.83 (s, 3H) ppm LCMS (ESI) m/z: [M+H]$^+$=516.4

Chiral HPLC: Amycoat-MeOH(DEA)-40-5MIN-3ML-35T, 1.514 min and 3.407 min.

Example 47. Preparation of N-(2-((4-(2-cyanophenyl)thiazol-2-yl)amino)-2-oxoethyl)-3-(N,N-dimethylsulfamoyl)benzamide (compound 27)

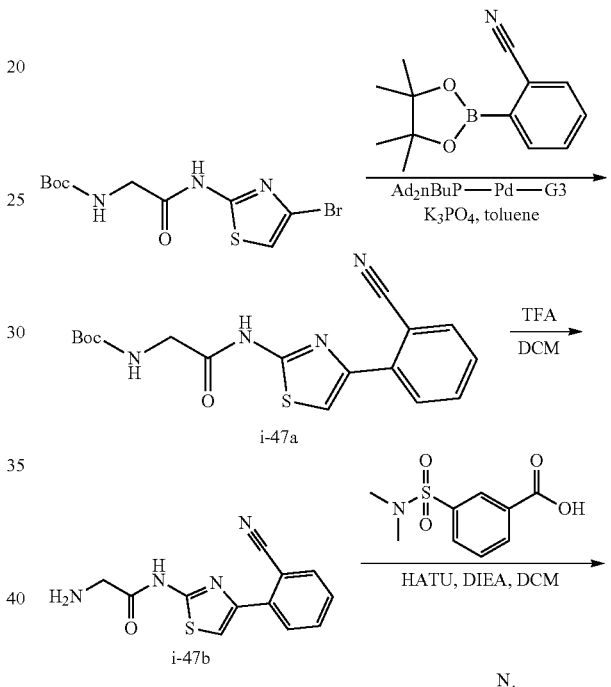

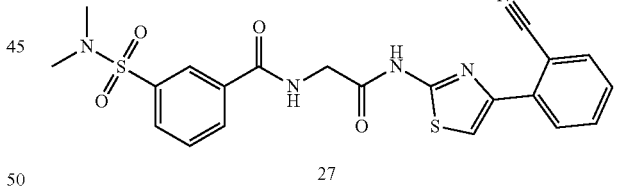

Step 1: Preparation tert-butyl (2-((4-(2-cyanophenyl)thiazol-2-yl)amino)-2-oxoethyl)carbamate (intermediate i-47a)

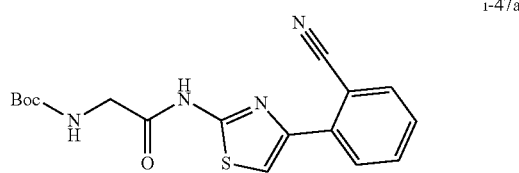 [SMILES: CC(C)(C)OC(=O)NCC(=O)Nc1nc(-c2ccccc2C#N)cs1]

To a solution of tert-butyl N-[2-[(4-bromothiazol-2-yl)amino]-2-oxo-ethyl]carbamate (200.0 mg, 558.65 μmol) in toluene (3.0 mL) were added 2-(4,4,5,5-tetramethyl-1,3,2-dioxaborolan-2-yl) benzonitrile (383.93 mg, 1.68 mmol), Ad2nBuP-Pd-G3 (406.85 mg, 558.65 μmol) and $K_3PO_4$ (177.87 mg, 837.97 μmol) under $N_2$. The reaction mixture was stirred at 60° C. for 12 hr. The reaction mixture was concentrated to give a residue. The residue was purified by column chromatography ($SiO_2$, PE/EA=50/1-1/1) to give intermediate i-47a as a brown solid.

LCMS (ESI) m/z: $[M+H]^+$=359.2

Step 2: Preparation 2-amino-N-(4-(2-cyanophenyl)thiazol-2-yl)acetamide (intermediate i-47b)

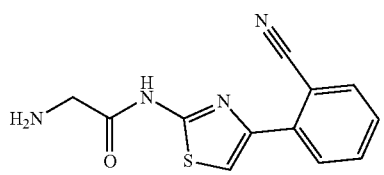 [SMILES: N#Cc1ccccc1-c1csc(NC(=O)CN)n1]

To a solution of intermediate i-47a (230 mg, 628.88 μmol) in DCM (2.5 mL) was added TFA (0.25 mL). The mixture was stirred at 30° C. for 2 hr. The reaction mixture was concentrated to give intermediate i-47b (TFA salt) as a yellow solid which was used for next step directly.

LCMS (ESI) m/z: $[M+Na]^+$=281.2

Step 3: Preparation of N-(2-((4-(2-cyanophenyl)thiazol-2-yl)amino)-2-oxoethyl)-3-(N,N-dimethylsulfamoyl)benzamide (compound 27)

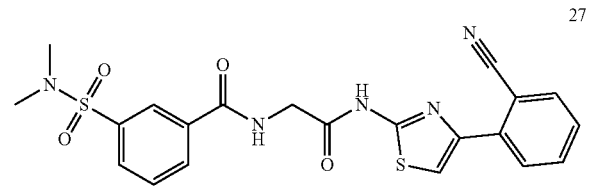 [SMILES: CN(C)S(=O)(=O)c1cccc(C(=O)NCC(=O)Nc2nc(-c3ccccc3C#N)cs2)c1]

To a solution of 3-(dimethylsulfamoyl)benzoic acid (81.41 mg, 355.13 μmol) in DCM (2.0 mL) were added HATU (162.04 mg, 426.15 μmol), DIEA (183.59 mg, 1.42 mmol) and intermediate i-47b (110.0 mg, 355.13 μmol). The reaction mixture was stirred at 30° C. for 12 hr. The reaction mixture was poured into water (5.0 mL). Then the solution was extracted with EtOAc (5.0 mL*3). The combined organic extracts were washed with brine (10.0 mL), dried over $Na_2SO_4$ and filtered. The filtrate was concentrated to give a residue. The residue was purified by Pre-HPLC (column: Phenomenex Synergi C18 150*25*10 μm; mobile phase: [water (0.225% FA)-ACN]; B %: 37%-57%, 7 min) and lyophilized to give compound 27 as a white solid.

1H NMR (400 MHz, DMSO-d6) δ=12.43 (br s, 1H), 9.32 (m, 1H), 8.26-8.25 (m, 2H), 7.97-7.92 (m, 3H), 7.80-7.79 (m, 3H), 7.56 (m, 1H), 4.26 (d, J=5.6 Hz, 2H), 2.65 (s, 6H) ppm LCMS (ESI) m/z: $[M+H]^+$=470.2

Example 48. Preparation of N-[2-[[4-[3-(aminomethyl)phenyl]thiazol-2-yl]amino]-2-oxo-ethyl]-3-(dimethylsulfamoyl)benzamide (compound 10)

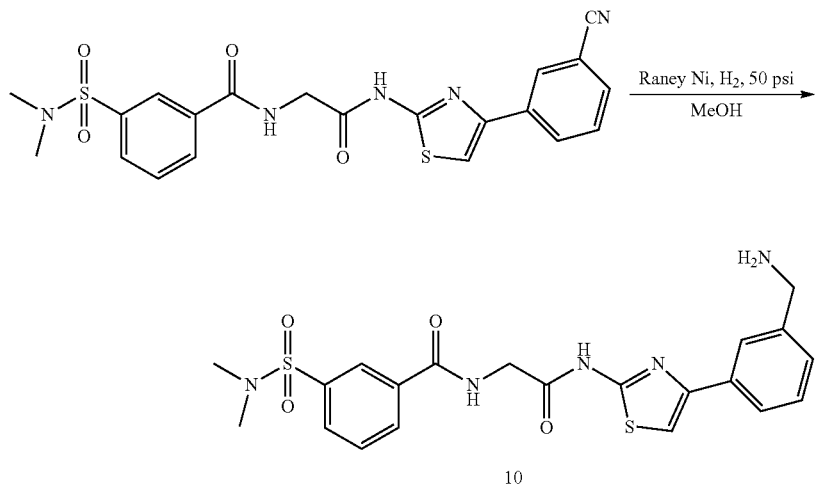 [SMILES: "MeOH" ; CN(C)S(=O)(=O)c1cccc(C(=O)NCC(=O)Nc2nc(-c3cccc(C#N)c3)cs2)c1 ; CN(C)S(=O)(=O)c1cccc(C(=O)NCC(=O)Nc2nc(-c3cccc(CN)c3)cs2)c1]

To a solution of N-[2-[[4-(3-cyanophenyl)thiazol-2-yl]amino]-2-oxo-ethyl]-3-(dimethylsulfamoyl) benzamide (100.0 mg, 212.98 μmol) in MeOH (4.0 mL) was added Raney-Ni (99.99 mg, 1.17 mmol) under $N_2$. The mixture was stirred under $H_2$ (50 psi) at 15° C. for 16 hours. The mixture was filtered and the filtrate was concentrated under vacuum to give residue. The residue was purified by prep-HPLC (TFA condition; column: Phenomenex Synergi C18 150*25*10 μm; mobile phase: [water (0.1% TFA)-ACN]; B %: 15%-45%, 9 min) and lyophilized to give compound 10 (TFA salt) as a white solid.

$^1$H NMR (400 MHz, DMSO-$d_6$) δ=12.48 (s, 1H), 9.34-9.31 (m, 1H), 8.27-8.18 (m, 5H), 7.97-7.91 (m, 3H), 7.83-7.79 (m, 1H), 7.62 (s, 1H), 7.53-7.49 (m, 1H), 7.42 (d, J=7.6, 1H), 4.24 (d, J=5.6 Hz, 2H), 4.08 (m, 2H), 2.66 (m, 6H) ppm.

LCMS (ESI) m/z: $[M+H]^+$=474.2

Example 49. Preparation of N-[2-[[4-(3-cyanophenyl)thiazol-2-yl]amino]-2-oxo-ethyl]-3-(dimethylsulfamoyl)benzamide (compound 8)

Step 1: Preparation of 2 3-(2-aminothiazol-4-yl)benzonitrile (intermediate i-49a)

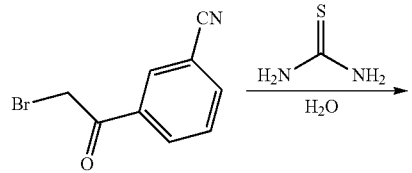

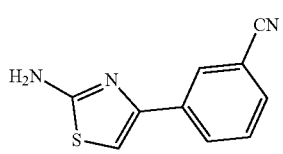

i-49a

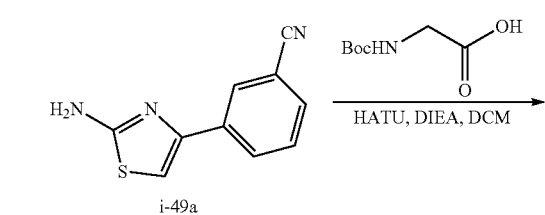

To a solution of 3-(2-bromoacetyl)benzonitrile (200.00 mg, 892.64 μmol) in H₂O (5.0 mL) was added thiourea (74.74 mg, 981.91 μmol). The mixture was stirred at 25° C. for 1.5 hr. The reaction mixture was diluted with water (10.0 mL) and extracted with EtOAC (35.0 mL*3). The combined organic extracts were washed with brine (20.0 mL*2), dried over Na₂SO₄, filtered and concentrated under reduced pressure to give intermediate i-49a as a yellow solid.

LCMS (ESI) m/z: [M+H]⁺=202.1.

Step 2: Preparation of tert-butyl N-[2-[[4-(3-cyanophenyl)thiazol-2-yl]amino]-2-oxo-ethyl]carbamate (intermediate i-49b)

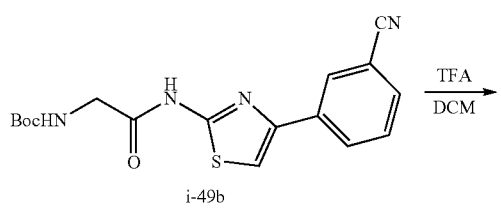

i-49b

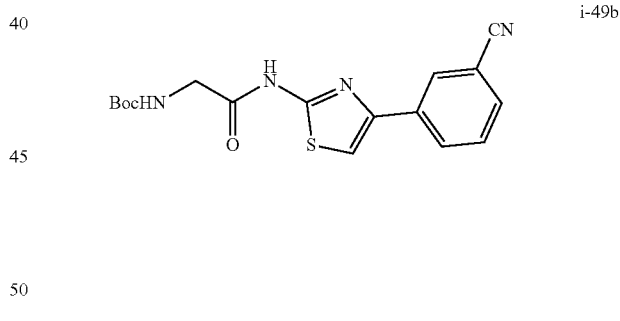

i-49b

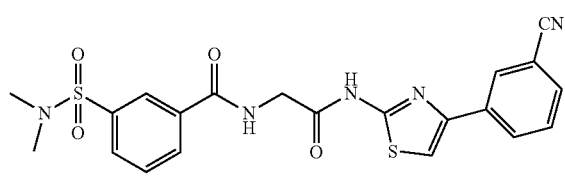

8

To a solution of 2-(tert-butoxycarbonylamino)acetic acid (129.27 mg, 737.90 μmol) in DCM (8.0 mL) were added HATU (280.57 mg, 737.90 μmol), DIEA (260.09 mg, 2.01 mmol, 350.52 μL) and intermediate i-49a (135.0 mg, 670.82 μmol). The mixture was stirred at 25° C. for 12 hr. The reaction mixture was diluted with water (10.0 mL) and extracted with EtOAc (20.0 mL*3). The combined organic extracts were washed with brine (20.0 mL*2), dried over Na₂SO₄, filtered and concentrated under reduced pressure to give a residue. The residue was purified by Prep-HPLC (TFA condition; column: Boston pH-lex 150*25 10 μm; mobile phase: [water (0.1% TFA)-ACN]; B %: 40%-70%, 10 min) and lyophilized to give intermediate i-49b as a white solid.

LCMS (ESI) m/z: [M+H]⁺=359.4

Step 3: Preparation of 2-amino-N-[4-(3-cyanophenyl)thiazol-2-yl]acetamide (intermediate i-49c)

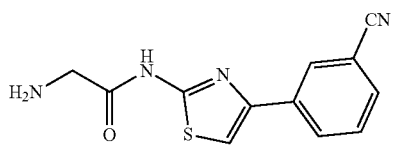

i-49c

To a solution of intermediate i-49b (93.0 mg, 259.48 μmol) in DCM (1.0 mL) was added TFA (0.1 mL). The mixture was stirred at 25° C. for 1.5 hr. The mixture was concentrated under reduced pressure to give intermediate i-49c (TFA salt) as brown oil which was used in the next step without further purification.

LCMS (ESI) m/z: [M+H]$^+$=259.1.

Step 4: Preparation of N-[2-[[4-(3-cyanophenyl)thiazol-2-yl]amino]-2-oxo-ethyl]-3-(dimethylsulfamoyl)benzamide (compound 8)

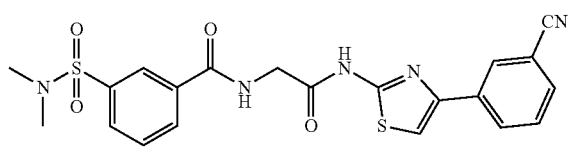

8

To a solution of 3-(dimethylsulfamoyl)benzoic acid (75.74 mg, 330.36 μmol) in DCM (2.0 mL) were added HATU (138.17 mg, 363.40 μmol), DIEA (170.79 mg, 1.32 mmol, 230.17 μL) and intermediate F (123.0 mg, 330.36 μmol. The mixture was stirred at 25° C. for 12 hr. The reaction mixture was diluted with water (10.0 mL) and extracted with EtOAc (30.0 mL*3). The combined organic extracts were washed with brine (20.0 mL*2), dried over Na$_2$SO$_4$, filtered and concentrated under reduced pressure to give a residue. The residue was purified by prep-HPLC (TFA condition; column: Phenomenex Synergi C18 150*25*10 μm; mobile phase: [water (0.1% TFA)-ACN]; B %: 35%-65%, 9 min) and lyophilized to give compound 8 as a white solid.

$^1$HNMR (400 MHz, DMSO-d6) δ 12.53 (s, 1H), 9.34-9.31 (m, 1H), 8.33 (s, 1H), 8.26-8.22 (m, 3H), 7.94 (d, J=8.0 Hz, 1H), 7.88 (s, 1H), 7.82-7.78 (m, 2H), 7.68-7.64 (m, 1H), 4.24 (d, J=5.6 Hz, 2H), 2.65 (s, 6H).

LCMS (ESI) m/z: [M+H]$^+$=470.0.

Example 50. Preparation of N-[2-[[4-[3-(acetamidomethyl)phenyl]thiazol-2-yl]amino]-2-oxo-ethyl]-3-(dimethylsulfamoyl)benzamide (compound 5)

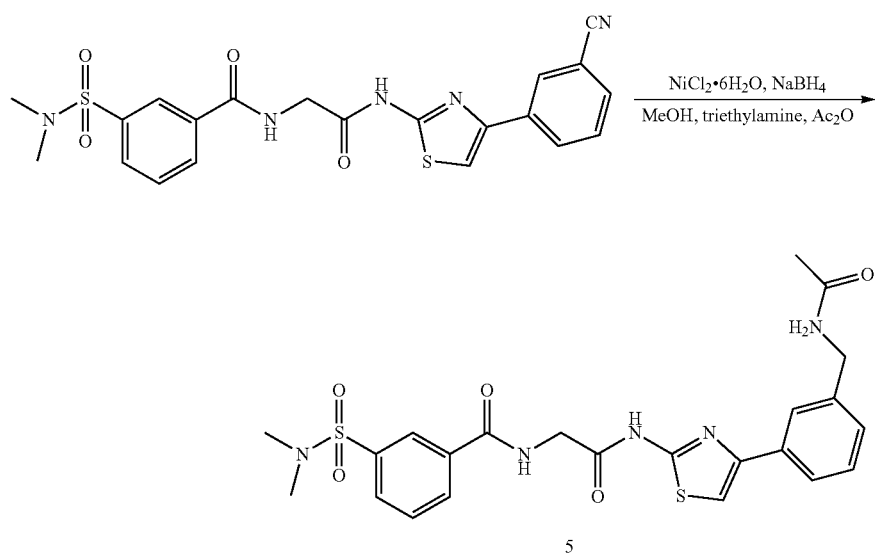

5

To a solution of N-[2-[[4-(3-cyanophenyl)thiazol-2-yl]amino]-2-oxo-ethyl]-3-(dimethylsulfamoyl) benzamide (100 mg, 212.98 μmol) in MeOH (2.0 mL) were added NiCl$_2$.6H$_2$O (126.56 mg, 532.44 μmol) and NaBH$_4$ (80.57 mg, 2.13 mmol), the mixture was stirred at 25° C. for 2 hr, then Ac$_2$O (21.74 mg, 212.98 μmol) and TEA (43.10 mg, 425.95 μmol) were added into the mixture. The mixture was stirred at 25° C. for another 2 hr and then concentrated under vacuum to give a residue. The residue was diluted with water (20.0 mL) and extracted with EtOAc (15.0 mL*2). The combined organic extracts were washed with brine (5.0 mL*2), dried over Na$_2$SO$_4$, filtered and concentrated under reduced pressure to give a residue. The residue was purified by prep-HPLC (TFA condition; column: Phenomenex Synergi C18 150*25*10 μm; mobile phase: [water (0.1% TFA)-ACN]; B %: 30%-53%, 7 min) and lyophilized to give compound 5 as a white solid.

$^1$H NMR (400 MHz, DMSO-d6) δ 12.52 (s, 1H), 9.31-9.29 (m, 1H), 8.37-8.36 (m, 1H), 8.26-8.23 (m, 2H), 7.94 (d, J=8.0 Hz, 1H), 7.82-7.76 (m, 3H), 7.61 (s, 1H), 7.39-7.36 (m, 1H), 7.21 (d, J=7.6 Hz, 1H), 4.29 (d, J=5.6 Hz, 2H), 4.23 (d, J=5.6 Hz, 2H), 2.65 (s, 6H), 1.88 (s, 3H) ppm.

LCMS (ESI) m/z: [M+H]$^+$=516.3.

Example 51. Preparation of N-[2-[[4-[4-(aminomethyl)phenyl]thiazol-2-yl]amino]-2-oxo-ethyl]-3-(dimethylsulfamoyl)benzamide (compound 22)

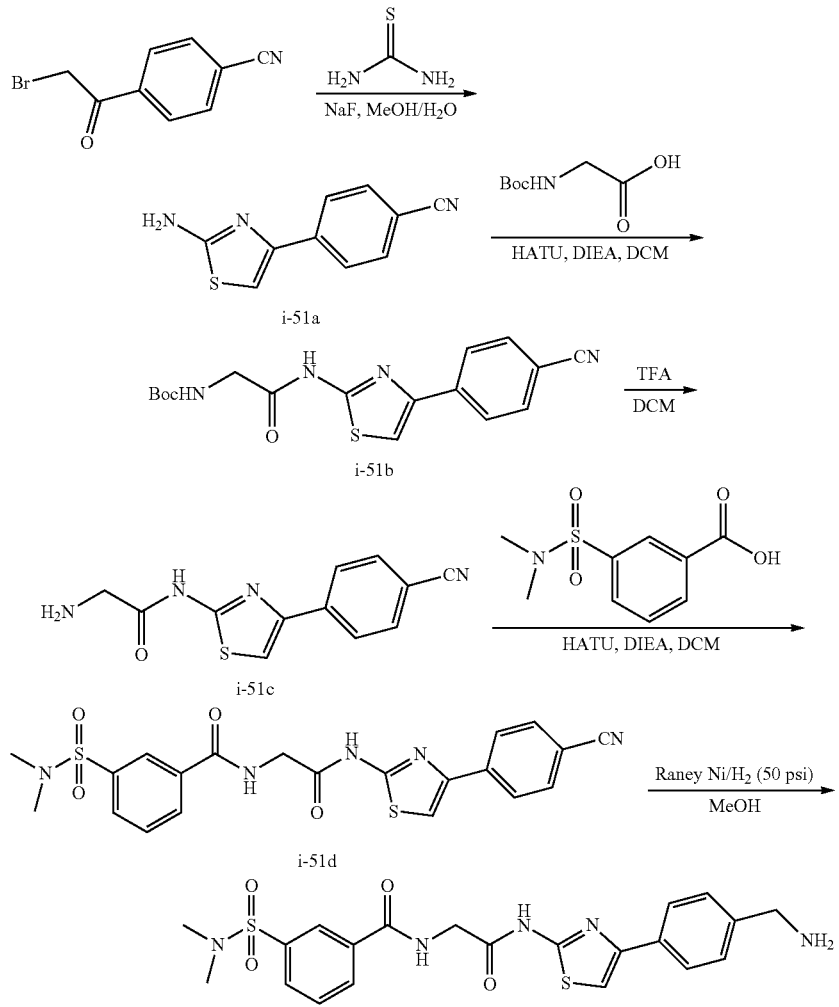

Step 1: Preparation of 4-(2-aminothiazol-4-yl)benzonitrile (intermediate i-51a)

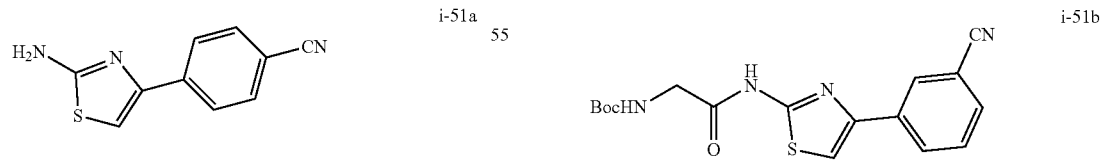

To a mixture of 4-(2-bromoacetyl)benzonitrile (500 mg, 2.23 mmol, 79.78 µL) and NaF (0.1 g, 2.38 mmol) in H$_2$O (8.0 mL) and MeOH (8.0 mL) was added thiourea (186.86 mg, 2.45 mmol). The mixture was stirred at 25° C. for 30 min and then diluted with water (10.0 mL) and extracted with EtOAc (35.0 mL*3). The combined organic extracts were washed with sat.NaHCO$_3$ (20.0 mL*2), dried over Na$_2$SO$_4$, filtered and concentrated under reduced pressure to give intermediate i-51a as a yellow solid.
$^1$H NMR (400 MHz, DMSO-d6) δ=7.97-7.95 (m, 2H), 7.82-7.80 (m, 2H), 7.32 (s, 1H), 7.19 (s, 2H) ppm.

Step 2: Preparation of tert-butyl N-[2-[[4-(4-cyanophenyl)thiazol-2-yl]amino]-2-oxo-ethyl]carbamate (intermediate i-51b)

To a solution of 2-(tert-butoxycarbonylamino)acetic acid (287.26 mg, 1.64 mmol) in pyridine (6 mL) were added EDCI (1.43 g, 7.45 mmol) and intermediate i-51a (300.0 mg, 1.49 mmol), and the mixture was stirred at 25° C. for 48 hr. The reaction mixture was diluted with water (15.0 mL) and extracted with EtOAc (30.0 mL*3). The combined organic extracts were washed with brine (20.0 mL*2), dried over Na₂SO₄, filtered and concentrated under reduced pressure to give a residue. The residue was purified by Prep-HPLC (TFA condition; column: Phenomenex Synergi C18 150*25*10 μm; mobile phase: [water (0.1% TFA)-ACN]; B %: 38%-68%, 9 min) and lyophilized to give intermediate i-51b as a white solid.

LCMS (ESI) m/z: [M+H]⁺=359.2.

Step 3: Preparation of 2-amino-N-[4-(4-cyanophenyl)thiazol-2-yl]acetamide (intermediate i-51c)

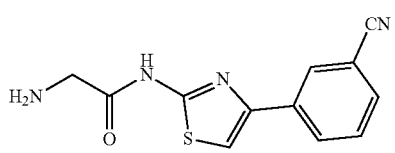

To a solution of intermediate i-51b (250 mg, 697.52 μmol) in DCM (2.0 mL) was added TFA (0.2 mL) and stirred at 25° C. for 4 hrs. The mixture was concentrated under reduced pressure to give intermediate i-51c (TFA salt) as a brown solid, which was used in the next step without further purification.

LCMS (ESI) m/z: [M+H]⁺=259.1.

Step 4: Preparation of N-[2-[[4-(4-cyanophenyl)thiazol-2-yl]amino]-2-oxo-ethyl]-3-(dimethylsulfamoyl)benzamide (intermediate i-51d)

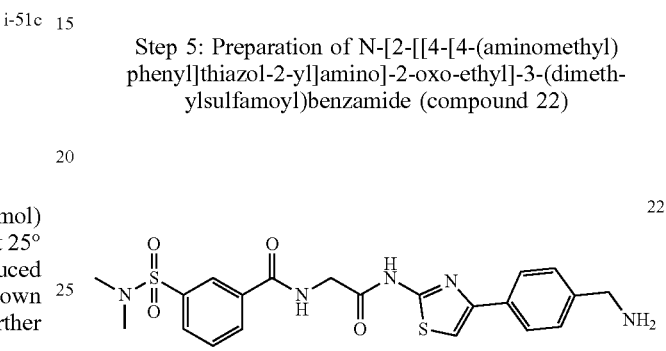

To a solution of 3-(dimethylsulfamoyl)benzoic acid (244.08 mg, 1.06 mmol) in DCM (5.0 mL) were added HATU (404.82 mg, 1.06 mmol), DIEA (500.36 mg, 3.87 mmol, 674.34 μL) and intermediate i-51c (250.0 mg, 967.87 μmol. The mixture was stirred at 25° C. for 24 hr. The reaction mixture was diluted with water (10.0 mL) and extracted with EtOAc (15.0 mL*3). The combined organic extracts were washed with brine (10.0 mL*2), dried over Na₂SO₄, filtered and concentrated under reduced pressure to give a residue. The residue was purified by prep-HPLC (TFA condition; column: Phenomenex Synergi C18 150*25*10 μm; mobile phase: [water (0.1% TFA)-ACN]; B %: 45%-75%, 9 min) and lyophilized to give intermediate i-51d as a white solid.

1H NMR (400 MHz, DMSO-d6) δ 12.27 (s, 1H), 9.33-9.30 (m, 1H), 8.26-8.23 (m, 2H), 8.08 (d, J=8.4 Hz, 2H), 7.95-7.89 (m, 4H), 7.82-7.78 (m, 1H), 4.24 (d, J=5.6 Hz, 2H), 2.65 (s, 6H) ppm.

LCMS (ESI) m/z: [M+H]⁺=469.2.

Step 5: Preparation of N-[2-[[4-[4-(aminomethyl)phenyl]thiazol-2-yl]amino]-2-oxo-ethyl]-3-(dimethylsulfamoyl)benzamide (compound 22)

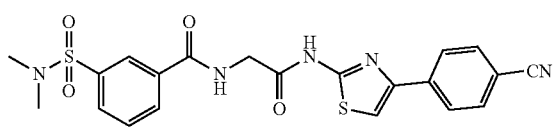

To a solution of intermediate i-51d (200.0 mg, 425.95 μmol) in MeOH (1.0 mL) was added Raney-Ni (200.00 mg, 2.33 mmol) under N₂. The mixture was stirred under H2 (50 psi) at 15° C. for 16 hours. The mixture was filtered and the filtrate was concentrated under vacuum. The residue was purified by prep-HPLC (Base column: Phenomenex Gemini 150*25 mm*10 μm; mobile phase: [water (0.05% ammonia hydroxide v/v)-ACN]; B %: 28%-58%, 11.5 min) and lyophilized to give compound 22 as a white solid.

¹H NMR (400 MHz, DMSO-d6) δ 9.16 (s, 1H), 8.26-8.23 (m, 2H), 7.93 (d, J=7.6 Hz, 1H), 7.82-7.77 (m, 3H), 7.43 (s, 1H), 7.35 (d, J=7.6, 2H), 4.15 (m, 2H), 3.72 (s, 2H), 2.65 (s, 6H) ppm.

LCMS (ESI) m/z: [M+H]⁺=474.3.

Example 52. Preparation of N-[2-[[4-[4-(acetamidomethyl)phenyl]thiazol-2-yl]amino]-2-oxo-ethyl]-3-(dimethylsulfamoyl)benzamide (compound 11)

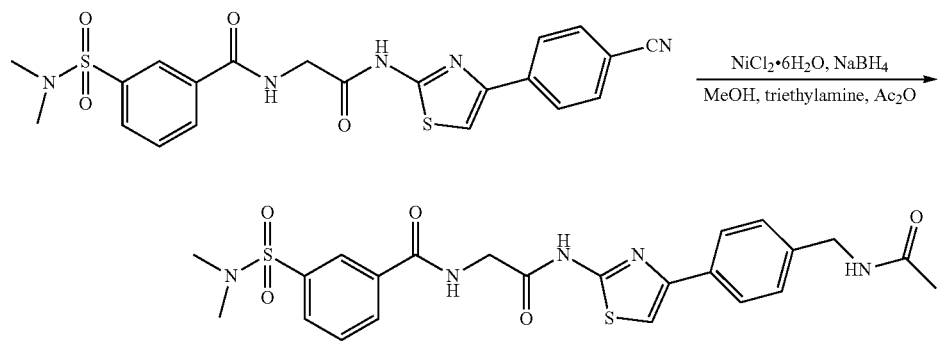

To a solution of N-[2-[[4-(4-cyanophenyl)thiazol-2-yl]amino]-2-oxo-ethyl]-3-(dimethylsulfamoyl) benzamide (100.00 mg, 212.98 μmol) in MeOH (2.0 mL) were added NiCl₂.6H₂O (126.56 mg, 532.44 μmol) and NaBH₄ (80.57 mg, 2.13 mmol), the mixture was stirred at 25° C. for 2 hr, then Ac₂O (21.74 mg, 212.98 μmol, 19.94 μL) and TEA (43.10 mg, 425.95 μmol, 59.29 μL) were added. The mixture was stirred at 25° C. for another 2 hr and then concentrated under vacuum to give a residue. The residue was diluted with water (20.0 mL) and extracted with EtOAc (15.0 mL*2). The combined organic extracts were washed with brine (5.0 mL*2), dried over anhydrous sodium sulfate, filtered and concentrated under reduced pressure to give a residue. The residue was purified by prep-HPLC (TFA condition; column: Phenomenex Synergi C18 150*25*10 μm; mobile phase: [water (0.1% TFA)-ACN]; B %: 30%-53%, 7 min) and lyophilized to give compound 11 as a white solid.

¹H NMR (400 MHz, DMSO-d6) δ=12.49 (s, 1H), 9.32-9.29 (m, 1H), 8.38-8.35 (m, 1H), 8.27-8.23 (m, 2H), 7.95 (d, J=8.0 Hz, 1H), 7.86-7.79 (m, 3H), 7.60 (s, 1H), 7.31 (d, J=8.4 Hz, 2H), 4.27 (d, J=5.6 Hz, 2H), 4.23 (d, J=5.6 Hz, 2H), 2.66 (s, 6H), 1.88 (s, 3H) ppm.

LCMS (ESI) m/z: [M+H]⁺=516.3.

Example 53. Preparation of (S)—N-(6-acetamido-1-oxo-1-((4-phenylthiazol-2-yl)amino)hexan-2-yl)benzamide (compound 43)

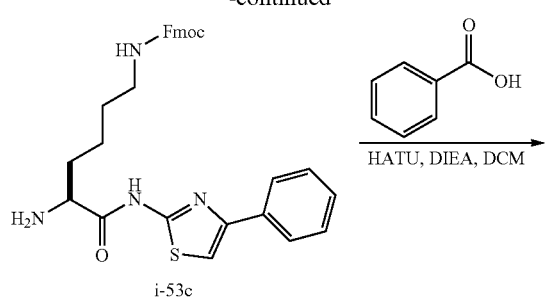

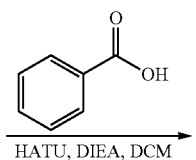

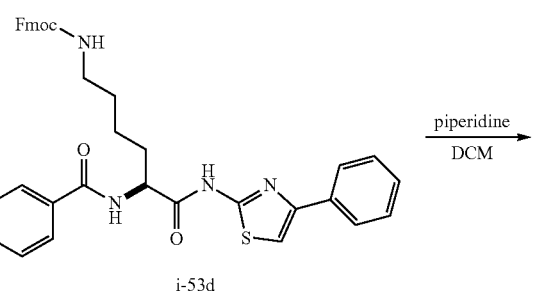

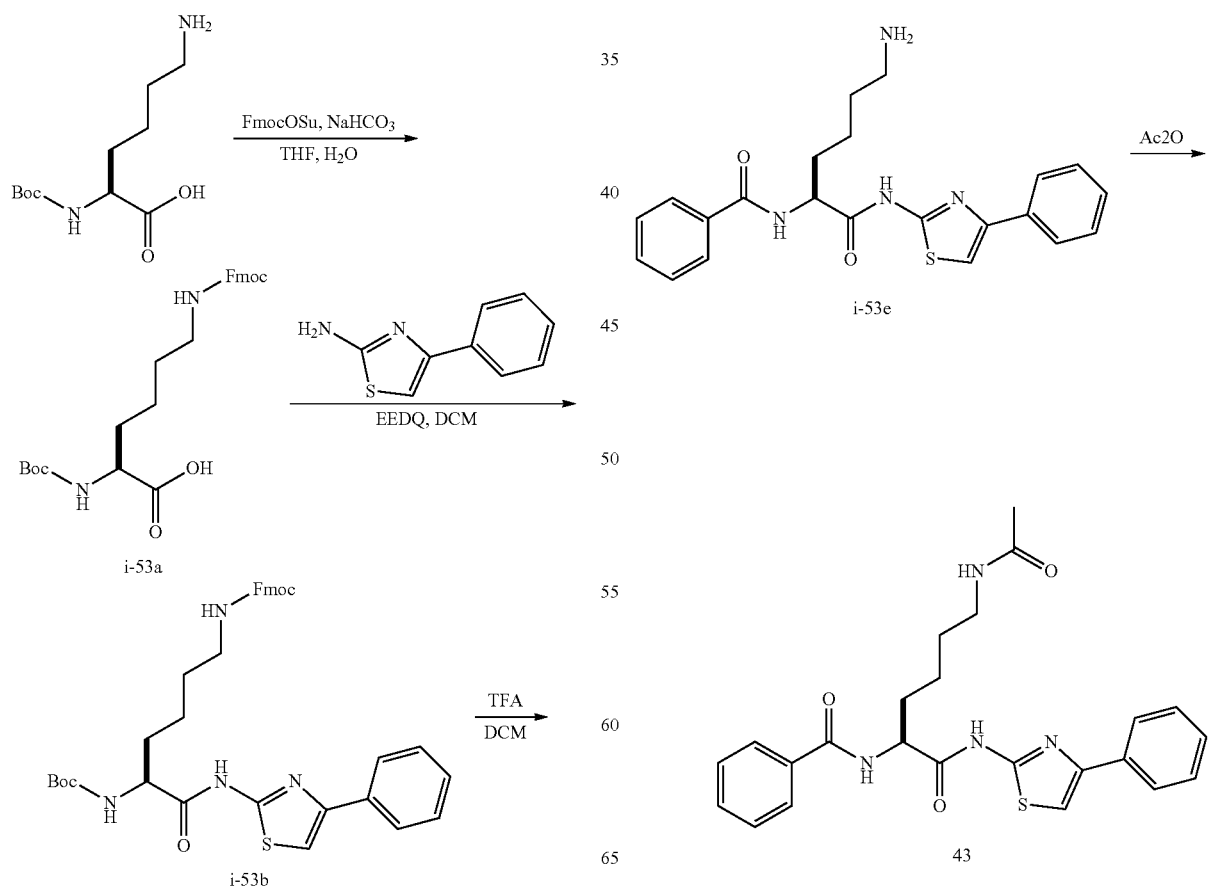

Step 1: Preparation of (S)-6-((((9H-fluoren-9-yl)methoxy)carbonyl)amino)-2-((tert-butoxycarbonyl)amino)hexanoic acid (intermediate i-53a)

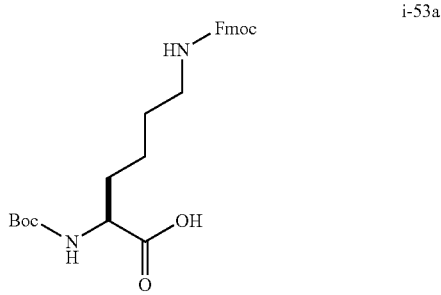

i-53a

To a solution of (2S)-6-amino-2-(tert-butoxycarbonylamino)hexanoic acid (1 g, 4.06 mmol) in THF (10.0 mL) was added a solution of NaHCO$_3$ (682.14 mg, 8.12 mmol) in water (10.0 mL) and FmocOSu (1.51 g, 4.47 mmol). The reaction mixture was stirred at 20° C. for 3 hrs. The reaction mixture was poured into water (10.0 mL). The solution was adjusted to pH4 with saturated citric acid solution. The mixture was extracted with EtOAc (15 mL*3). The combined organic extracts were washed with brine (20.0 mL), dried over Na$_2$SO$_4$ and filtered. The filtrate was concentrated to give intermediate i-53a as a white solid. The compound was used directly in the next step.

LCMS (ESI) m/z: [M+Na]$^+$=491.4

Step 2: Preparation of (S)-(9H-fluoren-9-yl)methyl-tert-butyl (6-oxo-6-((4-phenylthiazol-2-yl)amino)hexane-1,5-diyl)dicarbamate (intermediate i-53b)

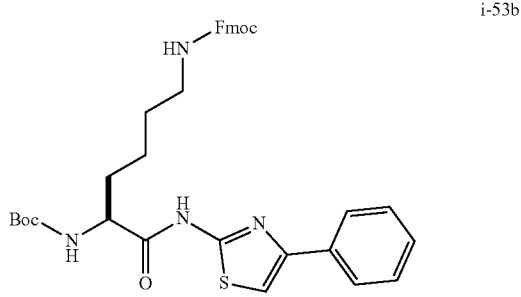

i-53b

To a solution of intermediate i-53a (500 mg, 977.50 μmol) in DCM (5.0 mL) was added EEDQ (362.59 mg, 1.47 mmol) and 4-phenylthiazol-2-amine (172.27 mg, 977.50 μmol). The reaction mixture was stirred at 20° C. for 18 hr. The reaction mixture was poured into water (10.0 mL). The solution was extracted with EtOAc (10.0 mL*3). The combined organic extracts were washed with brine (20.0 mL), dried over Na$_2$SO$_4$ and filtered. The filtrate was concentrated to give a residue. The residue was purified by column chromatography (SiO$_2$, Petroleum ether/Ethyl acetate=100:1 to 1:1) to give intermediate i-53b as a yellow oil.

LCMS (ESI) m/z: [M+H]$^+$=627.5

Step 3: Preparation of (S)-(9H-fluoren-9-yl)methyl (5-amino-6-oxo-6-((4-phenylthiazol-2-yl)amino)hexyl)carbamate (intermediate i-53c)

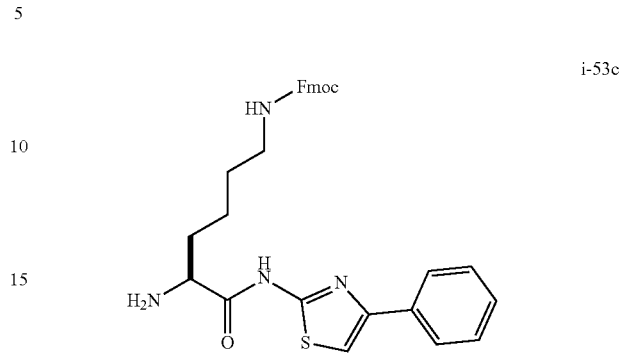

i-53c

To a solution of intermediate i-53b (440 mg, 586.68 μmol) in DCM (5.0 mL) was added TFA (417.85 μL). The reaction mixture was stirred at 20° C. for 2 hrs. The reaction mixture was adjusted to pH 8 with saturated NaHCO$_3$ solution. The solution was extracted with EtOAc (5.0 mL*3). The combined organic extracts were washed with brine (10.0 mL), dried over Na$_2$SO$_4$ and filtered. The filtrate was concentrated to give a residue. The residue was triturated with MTBE (10.0 mL). The solution was filtered. The filter cake was dried in vacuum to give intermediate i-53c as a white solid.

LCMS (ESI) m/z: [M+Na]$^+$=549.4.

Chiral HPLC: AS-3-MeOH (DEA)-5-40-3ML-35T, 2.386 min.

Step 4: Preparation of (S)-(9H-fluoren-9-yl)methyl (5-benzamido-6-oxo-6-((4-phenylthiazol-2-yl)amino)hexyl)carbamate (intermediate i-53d)

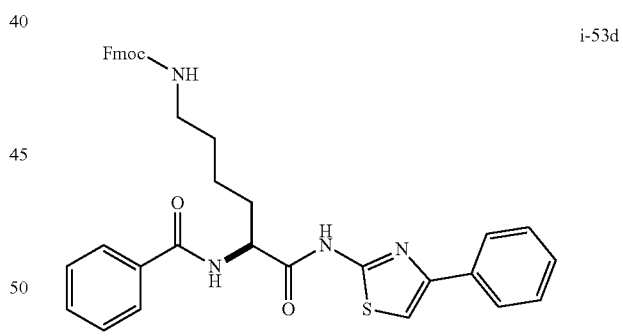

i-53d

To a solution of benzoic acid (41.68 mg, 341.33 μmol, 52.10 μL) in DCM (2.0 mL) was added HATU (142.76 mg, 375.46 μmol), DIEA (176.46 mg, 1.37 mmol) and intermediate i-53c (190 mg, 341.33 μmol). The reaction mixture was stirred at 20° C. for 3 hr. The reaction mixture was poured into water (2.0 mL). The solution was extracted with EtOAc (2.0 mL*3). The combined organic extracts were washed with brine (5.0 mL), dried over Na$_2$SO$_4$ and filtered. The filtrate was concentrated to give a residue. The residue was purified by flash silica gel chromatography (PE:EA=50:1-10:1-3:1-1:1) to give intermediate i-53d as a white solid.

LCMS (ESI) m/z: [M+H]$^+$=631.4.

Chiral HPLC: OJ-3-MeOH(DEA)-60-7MIN-3ML-35T, 3.881 min.

Step 5: Preparation of (S)—N-(6-amino-1-oxo-1-((4-phenylthiazol-2-yl)amino)hexan-2-yl)benzamide (intermediate i-53e)

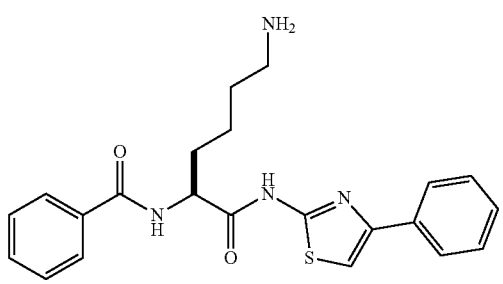

To a solution of intermediate i-53d (120 mg, 179.50 μmol) in DCM (1.2 mL) was added piperidine (120.00 μL). The solution was stirred at 20° C. for 2 hr. The mixture was poured into water (2.0 mL). The reaction mixture was diluted with saturated NaHCO$_3$ solution (5 mL) and extracted with EtOAc (2.0 mL*3). The combined organic extracts were washed with brine (5.0 mL), dried over Na$_2$SO$_4$ and filtered. The filtrate was concentrated to give a residue. The residue was purified by prep-HPLC (column: Phenomenex Synergi C18 150*25*10 μm; mobile phase: [water(0.225% FA)-ACN]; B %: 17%-37%, 7 min) to give intermediate i-53e (FA salt) as a white solid.

1H NMR (400 MHz, DMSO-d6) δ 8.73 (d, J=6.8 Hz, 1H), 8.42 (s, 1H), 7.93-7.89 (m, 4H), 7.62 (s, 1H), 7.58-7.54 (m, 1H), 7.50-7.47 (m, 2H), 7.44-7.40 (m, 2H), 7.33-7.30 (m, 1H), 4.67-4.63 (m, 1H), 2.73 (s, 2H), 1.85 (d, J=6.4 Hz, 2H), 1.53-1.40 (m, 4H) ppm.

LCMS (ESI) m/z: [M+H]$^+$=409.3.
Chiral HPLC: OD-RH_0-60_1ML.M, 8.037 min.

Step 6: Preparation of (S)—N-(6-acetamido-1-oxo-1-((4-phenylthiazol-2-yl)amino)hexan-2-yl)benzamide (compound 43)

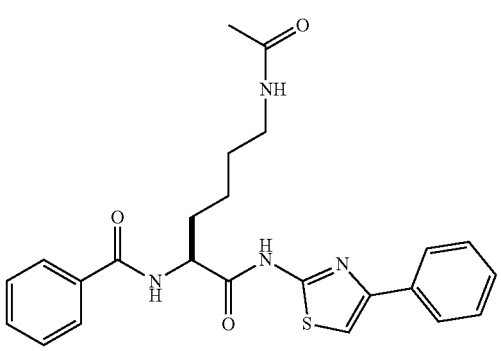

A solution of intermediate i-53e (13 mg, 31.82 μmol) in Ac$_2$O (0.2 mL) was stirred at 30° C. for 2 hr. The reaction mixture was filtered to give a filter cake. The filter cake was washed with MTBE (2.0 mL) and dried in vacuo to give a solid. The solid was poured into water (2.0 mL) and the solution was lyophilized to give compound 43 as a white solid.

$^1$H NMR (400 MHz, DMSO-d6) δ 12.46 (br s, 1H), 8.67 (d, J=7.2 Hz, 1H), 7.94-7.90 (m, 4H), 7.84 (s, 1H), 7.64 (s, 1H), 7.57-7.51 (m, 1H), 7.53-7.47 (m, 2H), 7.49-7.44 (m, 2H), 7.44-7.42 (m, 1H), 4.67-4.62 (m, 1H), 3.04 (m, 2H), 1.85 (m, 2H), 1.78 (s, 3H), 1.44-1.35 (m, 4H) ppm.

LCMS (ESI) m/z: [M+H]$^+$=451.3.
Chiral HPLC: Cellucoat-MeOH(DEA)-40-3ML-35T, 0.767 min.

Example 54. Preparation of 3-(isopropylsulfonyl)-N-(2-oxo-2-((4-phenylthiazol-2-yl)amino)ethyl)benzamide (compound 6)

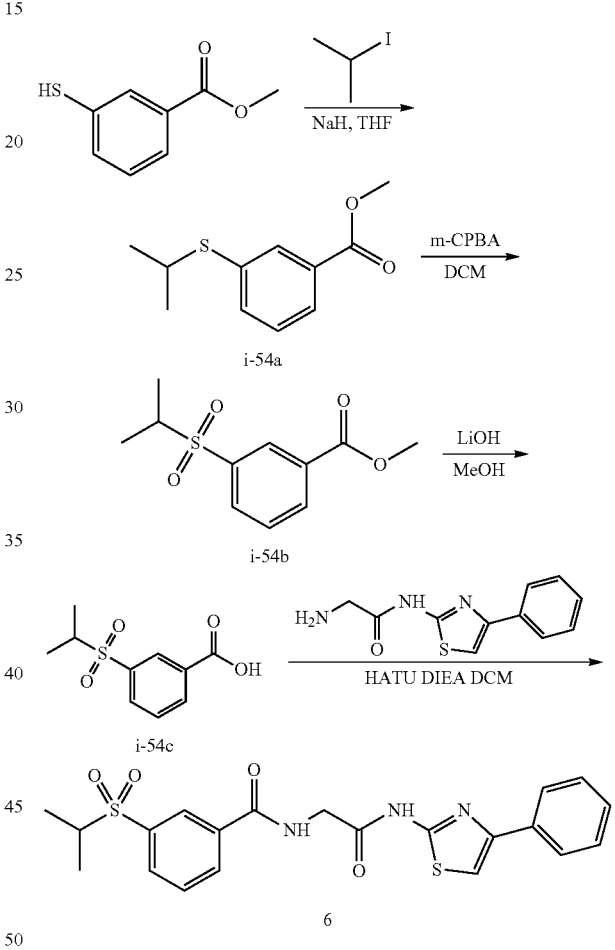

Step 1: Preparation of methyl 3-(isopropylthio)benzoate (intermediate i-54a)

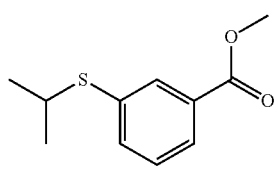

To a solution of methyl 3-sulfanylbenzoate (200.0 mg, 1.19 mmol) in THF (2.0 mL) was added 2-iodopropane (303.17 mg, 1.78 mmol). Then NaH (57.07 mg, 1.43 mmol, 60% purity) was added in small portions over 5 min. The reaction mixture was stirred at 20° C. for 1 hr and then poured into 1N HCl (6 mL). The solution was extracted with EtOAc (5.0 mL*3). The combined organic extracts were washed with brine (10.0 mL), dried over Na$_2$SO$_4$ and filtered. The filtrate was concentrated to give a residue. The residue was purified by column chromatography (SiO$_2$, PE/EA=100/1-1/1) to give intermediate i-54a as yellow oil.

LCMS (ESI) m/z: [M+H]$^+$=211.3.

Step 2: Preparation of methyl 3-(isopropylsulfonyl)benzoate (intermediate i-54b)

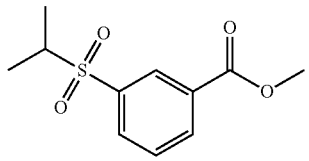

i-54b

To a solution of intermediate i-54a (200.0 mg, 883.15 µmol) in DCM (2.0 mL) was added m-CPBA (320.04 mg, 1.58 mmol, 85% purity). The mixture was stirred at 20° C. for 1 hr and then poured into saturated a.q NaHCO$_3$ (30.0 mL). The solution was extracted with EtOAc (20.0 mL*3). The combined organic extracts were washed with brine (50.0 mL), dried over Na$_2$SO$_4$ and filtered. The filtrate was concentrated to give intermediate i-54b as a white solid, which was used directly in the next step.

LCMS (ESI) m/z: [M+H]$^+$=243.3.

Step 3: Preparation of 3-(isopropylsulfonyl)benzoic acid (intermediate i-54c)

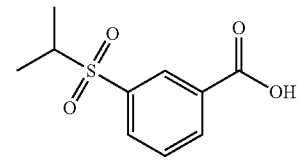

i-54c

To a solution of intermediate i-54b (300.0 mg, 1.24 mmol) in dioxane (3.0 mL) and water (2.0 mL) was added LiOH (59.30 mg, 2.48 mmol). The reaction mixture was stirred at 20° C. for 1 hr and then adjusted pH 6 with saturated citric acid solution. Then the solution was extracted with EtOAc (10.0 mL*3). The combined organic extracts were washed with brine (20.0 mL), dried over Na$_2$SO$_4$ and filtered. The filtrate was concentrated to give a residue. The residue was purified with column chromatography (SiO$_2$, PE:EA=50:1-20:1-10:1-3:1) to give intermediate i-54c as a white solid.

$^1$H NMR (400 MHz, DMSO-d6) δ 13.58 (s, 1H), 8.31-8.27 (m, 2H), 8.11-8.03 (m, 1H), 7.82 (d, J=7.6 Hz, 1H), 3.53-3.45 (m, 1H), 1.16 (d, J=6.8 Hz, 6H) ppm.

LCMS (ESI) m/z: [M+H]$^+$=229.2.

Step 4: Preparation of 3-(isopropylsulfonyl)-N-(2-oxo-2-((4-phenylthiazol-2-yl)amino)ethyl)benzamide (compound 6)

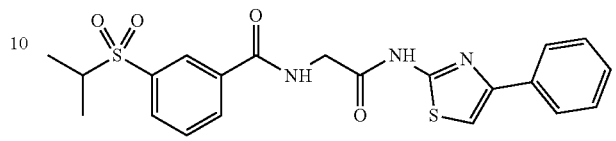

6

To a solution of intermediate i-54c (30.0 mg, 129.42 µmol) in DCM (0.3 mL) were added HATU (59.05 mg, 155.30 µmol), DIEA (66.90 mg, 517.66 µmol) and 2-amino-N-(4-phenylthiazol-2-yl)acetamide (30.19 mg, 86.93 µmol). The reaction mixture was stirred at 30° C. for 12 hr and then poured into water (2.0 mL). The solution was extracted with EtOAc (2.0 mL*3). The combined organic extracts were washed with brine (5.0 mL), dried over Na$_2$SO$_4$ and filtered. The filtrate was concentrated to give a residue. To the residue was added MeOH (0.5 mL) and stirred for 5 min, then filtered. The solid was lyophilized to give compound 6 as a white solid.

$^1$H NMR (400 MHz, DMSO-d6) δ 12.49 (s, 1H), 9.31-9.28 (m, 1H), 8.38 (s, 1H), 8.27 (d, J=8.0 Hz, 1H), 8.05 (d, J=7.6 Hz, 1H), 7.90 (d, J=7.2 Hz, 2H), 7.84-7.80 (m, 1H), 7.65 (s, 1H), 7.45-7.43 (m, 2H), 7.41-7.32 (m, 1H), 4.24 (d, J=5.6 Hz, 2H), 3.54-3.47 (m, 1H), 1.18 (d, J=6.8 Hz, 6H) ppm.

LCMS (ESI) m/z: [M+H]$^+$=444.3.

Example 55. Preparation of 3-(dimethylsulfamoyl)-N-[2-oxo-2-[(6-phenyl-2-pyridyl)amino]ethyl]benzamide (Compound 41)

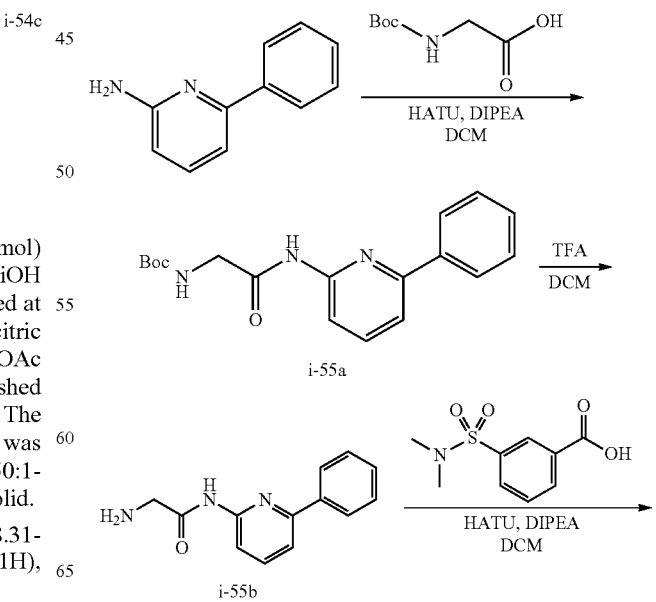

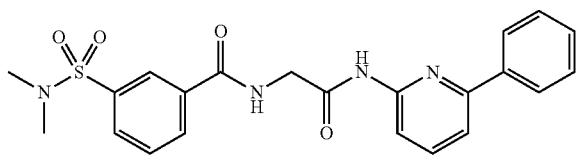

41

Step 1: Preparation of tert-butyl N-[2-oxo-2-[(6-phenyl-2-pyridyl)amino]ethyl]carbamate (intermediate i-55a)

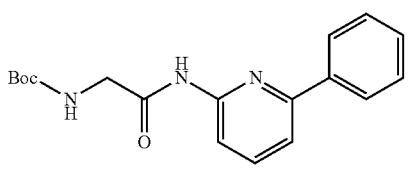

i-55a

To a solution of 2-(tert-butoxycarbonylamino)acetic acid (113.21 mg, 646.26 μmol), DIPEA (303.73 mg, 2.35 mmol) and HATU (245.73 mg, 646.26 μmol) in DCM (2.0 mL) was added 6-phenylpyridin-2-amine (100.0 mg, 587.51 μmol), and the mixture was stirred at 20° C. for 2 hr. The reaction mixture was concentrated under reduced pressure to give a residue. The residue was purified by column chromatography (SiO2, Petroleum ether/Ethyl acetate=5:1 to 2:1) to give intermediate i-55a as a light yellow oil.

$^1$H NMR (400 MHz, CDCl$_3$) δ 8.48 (s, 1H), 8.14 (d, J=8 Hz, 1H), 7.96 (d, J=7.2 Hz, 2H), 7.82-7.78 (m, 1H), 7.52-7.45 (m, 4H), 5.22-5.21 (m, 1H), 4.03 (s, 2H), 1.52 (s, 9H) ppm.

LCMS (ESI) m/z: [M+H]$^+$=328.0.

Step 2: Preparation of 2-amino-N-(6-phenyl-2-pyridyl)acetamide (intermediate i-55b)

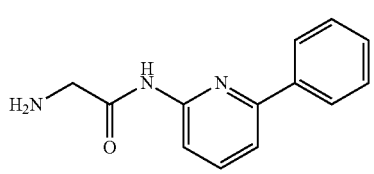

i-55b

To a solution of Intermediate i-55a (130 mg, 381.21 μmol) in DCM (2.0 mL) was added TFA (192.00 g L) and the mixture was stirred at 20° C. for 12 hr. The reaction mixture was concentrated under reduced pressure to give a residue. The residue was triturated with MTBE (5 mL), the solid was collected by filtration and dried in vacuo to give Intermediate i-55b (TFA salt) as a white solid.

LCMS (ESI) m/z: [M+H]$^+$=228.0.

Step 3: Preparation of 3-(dimethylsulfamoyl)-N-[2-oxo-2-[(6-phenyl-2-pyridyl)amino]ethyl]benzamide (compound 41) trifluoroacetate salt

41

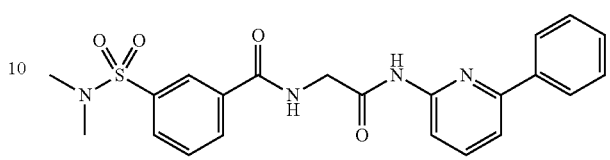

To a solution of 3-(dimethylsulfamoyl)benzoic acid (36.58 mg, 159.54 μmol), HATU (60.66 mg, 159.54 μmol) and DIPEA (74.98 mg, 580.16 μmol) in DCM (1.0 mL) was added Intermediate i-55b (50.0 mg, 145.04 μmol) and the mixture was stirred at 25° C. for 2 hr. The reaction mixture was concentrated under reduced pressure to give a residue. The residue was purified by prep-HPLC (column: Phenomenex Synergi C18 150*25*10 μm; mobile phase: [water (0.1% TFA)-ACN]; B %: 35%-65%, 9 min) and lyophilized to give compound 41 (TFA salt) as a white solid.

$^1$H NMR (400 MHz, DMSO-d6) δ 10.68 (s, 1H), 9.24-9.21 (m, 1H), 8.27-8.26 (m, 2H), 8.10-8.08 (m, 2H), 8.02 (d, J=8.0 Hz, 1H), 7.96-7.93 (m, 1H), 7.90-7.88 (m, 1H), 7.82-7.78 (m, 1H), 7.69 (d, J=8.0 Hz, 1H), 7.51-7.46 (m, 3H), 4.23 (d, J=6.0 Hz, 2H), 2.68-2.66 (m, 6H) ppm.

LCMS (ESI) m/z: [M+H]$^+$=439.0.

Example 56. Preparation of N-[(1S)-3-methylsulfanyl-1-[(4-phenylthiazol-2-yl)carbamoyl]propyl]thiophene-2-carboxamide (compound 58)

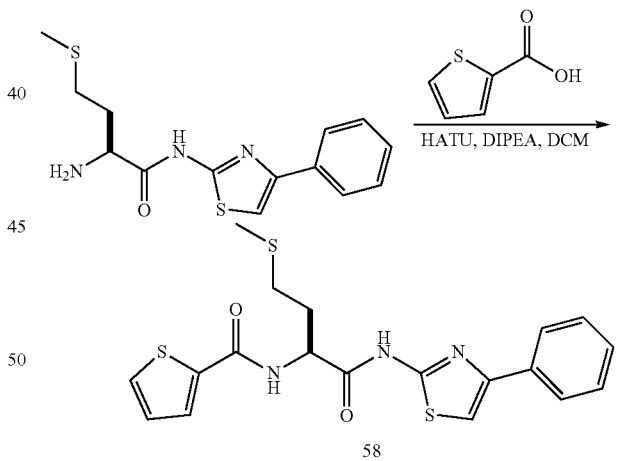

58

To a solution of thiophene-2-carboxylic acid (22.93 mg, 178.90 μmol), HATU (68.02 mg, 178.90 μmol) and DIPEA (84.08 mg, 650.55 μmol) in DCM (1.0 mL) was added (2S)-2-amino-4-methylsulfanyl-N-(4-phenylthiazol-2-yl)butanamide (50.00 mg, 162.64 μmol) and the mixture was stirred at 20° C. for 2 hr.

The reaction mixture was concentrated under reduced pressure to give a residue. The residue was purified by prep-HPLC (column: Phenomenex Synergi C18 150*25*10 μm; mobile phase: [water (0.1% TFA)-ACN]; B %: 50%-80%, 9 min) and lyophilized to give compound 58 as a white solid.

$^1$H NMR (400 MHz, CDCl$_3$) δ=7.69 (d, J=7.2 Hz, 2H), 7.62-7.61 (m, 1H), 7.48 (d, J=4.8 Hz, 1H), 7.40-7.36 (m, 2H), 7.34-7.30 (m, 1H), 7.26-7.24 (d, J=8.0 Hz, 1H), 7.07 (s, 1H), 7.06-7.03 (m, 1H), 5.00-4.95 (m, 1H), 2.68-2.63 (m, 2H), 2.29-2.20 (m, 2H), 2.10 (s, 3H) ppm.

LCMS (ESI) m/z: [M+H]$^+$=418.0

Chiral HPLC: Amycoat-MeOH(DEA)-40-7 min-3 mL-35T, 3.772 min.

Example 57. Preparation of (S)—N-(4-(methylthio)-1-oxo-1-((4-phenylthiazol-2-yl)amino)butan-2-yl)benzo[b]thiophene-2-carboxamide (compound 71)

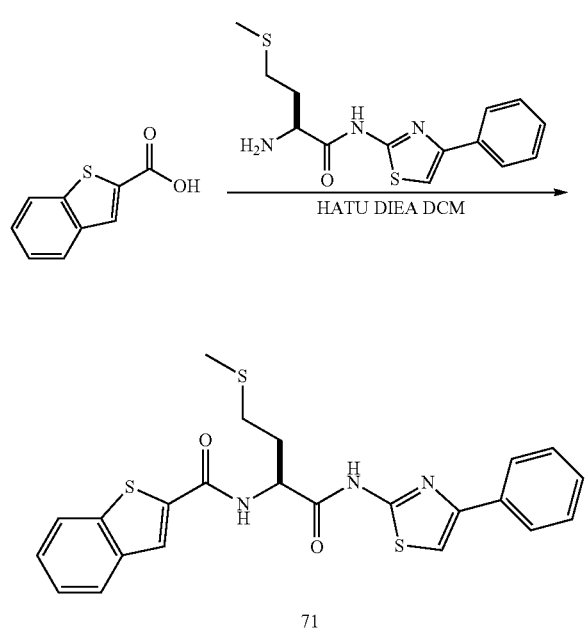

To a solution of benzothiophene-2-carboxylic acid (50.0 mg, 280.57 μmol, 47.17 μL) in DCM (1.0 mL) were added HATU (128.02 mg, 336.69 μmol), DIEA (108.79 mg, 841.71 μmol) and (2S)-2-amino-4-methylsulfanyl-N-(4-phenylthiazol-2-yl)butanamide (118.25 mg, 280.57 μmol). The reaction mixture was stirred at 20° C. for 12 hr. Then the reaction mixture was poured into water (2.0 mL), extracted with EtOAc (2.0 mL*3). The combined organic extracts were washed with brine (5.0 mL), dried over Na$_2$SO$_4$, filtered and concentrated under vacuum to give a residue. The residue was purified by prep-HPLC (column: Phenomenex Synergi C18 150*25*10 μm; mobile phase: [water(0.1% TFA)-ACN]; B %: 52%-82%, 9 min) and lyophilized to give compound 71 as a white solid.

$^1$H NMR (400 MHz, DMSO-d6) δ=12.58 (s, 1H), 9.08 (d, J=7.2 Hz, 1H), 8.31 (s, 1H), 8.03-7.92 (m, 2H), 7.91 (d, J=7.2 Hz, 2H), 7.66 (s, 1H), 7.48-7.43 (m, 4H), 7.41-7.33 (m, 1H), 4.79-4.74 (m, 1H), 2.68-2.66 (m, 1H), 2.59-2.54 (m, 1H), 2.16-2.11 (m, 5H) ppm.

LCMS (ESI) m/z: [M+H]$^+$=468.3.

Chiral HPLC: Cellucoat-MeOH+CAN(DEA)-40-7MIN-3ML-35T, 5.321 min.

Example 58. Preparation of 5-(dimethylsulfamoyl)-N-[(1S)-3-methylsulfanyl-1-[(4-phenylthiazol-2-yl)carbamoyl]propyl]thiophene-2-carboxamide (compound 62)

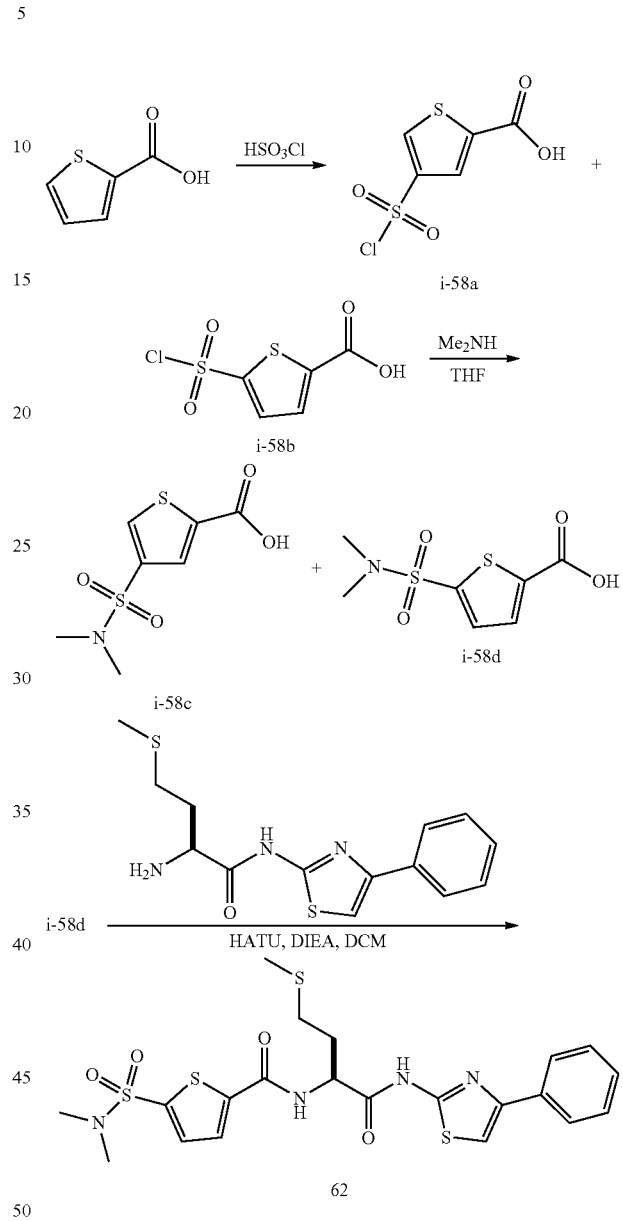

Step 1: Preparation of 4-chlorosulfonylthiophene-2-carboxylic acid (intermediate i-58a) and 5-chlorosulfonylthiophene-2-carboxylic acid (intermediate i-58b)

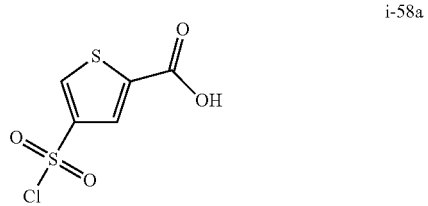

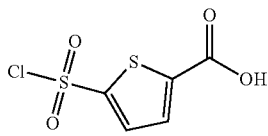
i-58b

Thiophene-2-carboxylic acid (300.0 mg, 2.34 mmol) was added to sulfurochloridic acid (1.36 g, 11.71 mmol) and the mixture was stirred at 100° C. for 1 hr. The reaction mixture was carefully added dropwise to ice water (30.0 mL) and stirred for 5 minutes. The precipitate was filtered and dried in vacuo to give a mixture of i-58a and i-58b as a white solid, which was used in the next step without further purification.

$^1$H NMR (400 MHz, DMSO-d6) δ 7.81 (d, J=1.6 Hz, 2H), 7.60 (d, J=1.6 Hz, 2H), 7.51 (d, J=4 Hz, 1H), 7.13 (d, J=4 Hz, 1H) ppm.

Step 2: Preparation of 4-(dimethylsulfamoyl)thiophene-2-carboxylicacid (intermediate i-58c) and 5-(dimethylsulfamoyl)thiophene-2-carboxylic acid (intermediate i-58d)

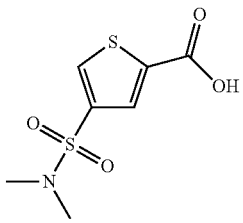
i-58c

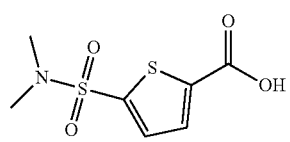
i-58d

To a mixture of i-58a and i-58b (260.0 mg, crude) in THF (2.0 mL) was added N-methylmethanamine (2.29 mL, 4.59 mmol, 2.0 M in THF) at 0° C., the mixture was stirred at 25° C. for 2 hr. The reaction mixture was concentrated under reduced pressure to give a residue. The residue was purified by prep-HPLC (column: Phenomenex Synergi C18 150*25*10 μm; mobile phase: [water(0.1% TFA)-ACN]; B %: 18%-40%, 12 min) and lyophilized to give intermediate i-58c as a white solid and intermediate i-58d as a white solid.

Intermediate i-58c:
$^1$H NMR (400 MHz, DMSO-d6) δ 8.51 (d, J=1.6 Hz, 1H), 7.78 (d, J=1.6 Hz, 1H), 2.73-2.66 (m, 7H) ppm.
LCMS (ESI) m/z: [M+H]$^+$=236.0.

Intermediate i-58d:
$^1$H NMR (400 MHz, DMSO-d6) δ 7.82 (d, J=4.0 Hz, 1H), 7.66 (d, J=4.0 Hz, 1H), 2.70-2.67 (m, 6H) ppm.
LCMS (ESI) m/z: [M+H]$^+$=236.0.

Step 3: Preparation of 5-(dimethylsulfamoyl)-N-[(1S)-3-methylsulfanyl-1-[(4-phenylthiazol-2-yl)carbamoyl]propyl]thiophene-2-carboxamide (compound 62)

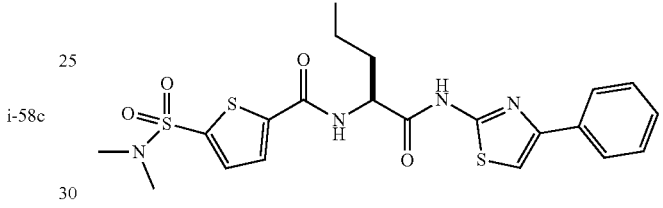
62

To a solution of intermediate i-58d (40.0 mg, 170.01 μmol), DIPEA (87.89 mg, 680.04 μmol) and HATU (71.11 mg, 187.01 μmol) in DCM (1.0 mL) was added (2S)-2-amino-4-methylsulfanyl-N-(4-phenylthiazol-2-yl)butanamide (78.82 mg, 187.01 μmol) and the mixture was stirred at 30° C. for 2 hr. The reaction mixture was concentrated under reduced pressure to give a residue. The residue was purified by prep-HPLC (column: Phenomenex Synergi C18 150*25*10 μm; mobile phase: [water (0.1% TFA)-ACN]; B %: 43%-73%, 10 min) and lyophilized to give compound 62 as a white solid.

$^1$H NMR (400 MHz, DMSO-d6) δ=12.61 (s, 1H), 9.15 (d, J=7.6 Hz, 1H), 8.07 (d, J=4.0 Hz, 1H), 7.92-7.90 (m, 2H), 7.71 (d, J=4.0 Hz, 1H), 7.66 (s, 1H), 7.46-7.42 (m, 2H), 7.35-7.31 (m, 1H), 4.78-4.67 (m, 1H), 2.69 (s, 6H), 2.65-2.56 (m, 2H), 2.17-2.07 (m, 5H) ppm.
LCMS (ESI) m/z: [M+H]$^+$=525.1.

Example 59. Preparation of N-(2-((4-(2,3-dihydrobenzo[b][1,4]dioxin-6-yl)thiazol-2-yl)amino)-2-oxoethyl)-3-(N,N-dimethylsulfamoyl)benzamide (compound 15)

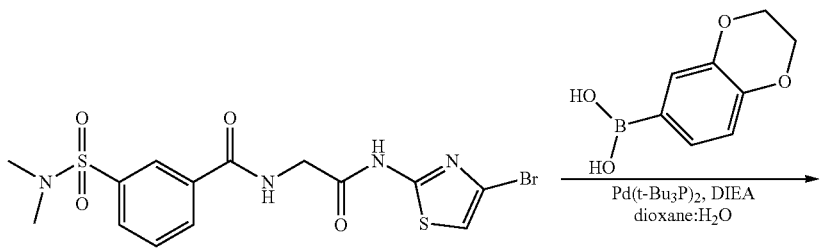

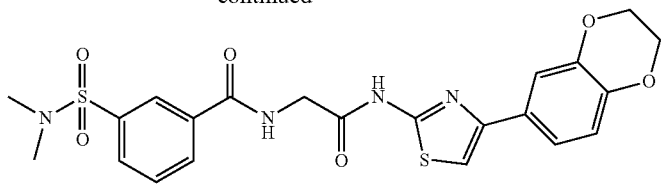

15

To a solution of N-[2-[(4-bromothiazol-2-yl)amino]-2-oxo-ethyl]-3-(dimethylsulfamoyl) benzamide (30.0 mg, 67.07 μmol) and 2,3-dihydro-1,4-benzodioxin-6-ylboronic acid (36.21 mg, 201.20 μmol) in dioxane (2.0 mL) and H₂O (0.2 mL) were added DIEA (43.34 mg, 335.33 μmol) and palladium;tritert-butylphosphane (17.14 mg, 33.53 μmol) under N₂. The mixture was stirred at 100 C for 2 hr. The reaction mixture was filtered. The filtrate was concentrated to give a residue. The residue was purified by Prep-HPLC (column: Boston pH-lex 150*25 10 μm; mobile phase: [water (0.1% TFA)-ACN]; B %: 39%-59%, 8 min) and lyophilized to give compound 15 as a white solid.

1H NMR (400 MHz, DMSO-d6) δ=12.42 (s, 1H), 9.30-9.28 (m, 1H), 8.26-8.22 (m, 2H), 7.93 (d, J=7.6 Hz, 1H), 7.82-7.80 (m, 1H), 7.48 (s, 1H), 7.39-7.35 (m, 2H), 6.89 (d, J=8.0 Hz, 1H), 4.27 (s, 4H), 4.22 (d, J=6.0 Hz, 2H), 2.65 (s, 6H) ppm.

LCMS (ESI) m/z: [M+H]⁺=503.3.

Example 60. Preparation of (S)-3-(isopropylsulfonyl)-N-(4-(methylthio)-1-oxo-1-((4-phenylthiazol-2-yl)amino)butan-2-yl)benzamide (compound 14)

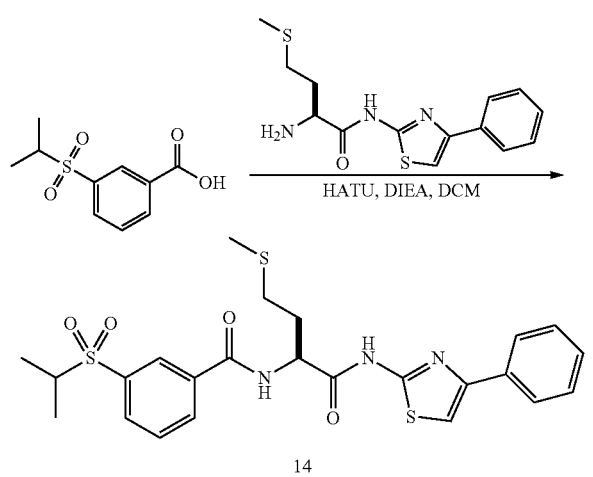

14

To a solution of 3-(isopropylsulfonyl)benzoic acid (30.0 mg, 129.42 μmol) in DCM (0.3 mL) were added HATU (59.05 mg, 155.30 μmol), DIEA (66.90 mg, 517.66 μmol) and (2S)-2-amino-4-methylsulfanyl-N-(4-phenylthiazol-2-yl)butanamide (54.54 mg, 129.42 μmol). The reaction mixture was stirred at 30° C. for 12 hr. Then the reaction mixture was poured into water (2.0 mL), extracted with EtOAc (2.0 mL*3). The combined organic extracts were washed with brine (5.0 mL), dried over Na₂SO₄ and filtered. The filtrate was concentrated to give a residue. The residue was purified by Pre-HPLC(column: Phenomenex Synergi C18 150*25*10 μm; mobile phase: [water(0.1% TFA)-ACN]; B %: 45%-75%, 9 min) and lyophilized to give compound 14 as a white solid.

1H NMR (400 MHz, DMSO-d6) δ=12.59 (s, 1H), 9.12 (d, J=7.2 Hz, 1H), 8.39 (s, 1H), 8.30 (d, J=8.0 Hz, 1H), 8.05 (d, J=7.6 Hz, 1H), 7.91 (d, J=7.2 Hz, 2H), 7.83-7.79 (m, 1H), 7.66 (s, 1H), 7.45-7.41 (m, 2H), 7.34-7.30 (m, 1H), 4.82-4.77 (m, 1H), 3.51 (s, 1H), 2.64-2.55 (m, 2H), 2.16-2.09 (m, 2H), 2.10 (s, 3H), 1.18-1.16 (m, 6H) ppm.

LCMS (ESI) m/z: [M+H]⁺=518.3

Chiral HPLC: Cellucoat-MeOH(DEA)-40-3ML-35T, 1.119 min.

Example 61 Preparation of N-[(1S)-3-methylsulfanyl-1-[(4-phenylthiazol-2-yl)carbamoyl]propyl]-3-(trifluoromethyl)benzamide (compound 77)

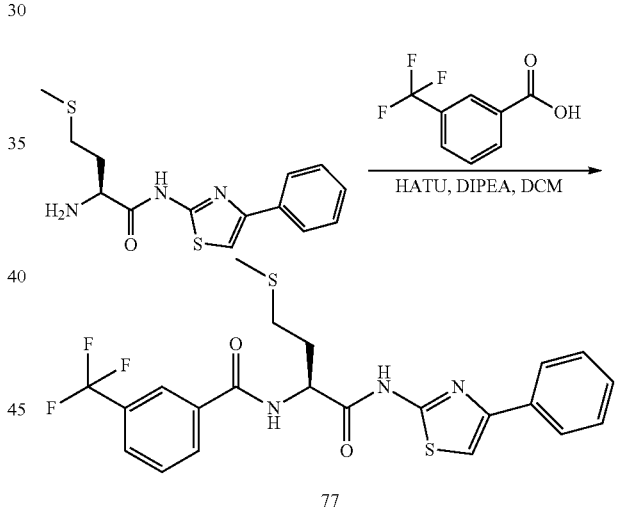

77

To a solution of 3-(trifluoromethyl)benzoic acid (22.55 mg, 118.64 μmol) in DCM (3 mL) was added DIPEA (46.00 mg, 355.91 μmol) and HATU (49.62 mg, 130.50 μmol). The mixture was stirred at 30° C. for 10 min. (2S)-2-amino-4-methylsulfanyl-N-(4-phenylthiazol-2-yl)butanamide (50 mg, 118.64 μmol) was added and the reaction mixture was stirred at 30° C. for 2 hr. The reaction mixture was concentrated to dryness to give a residue. The residue was purified by prep-HPLC (column: Phenomenex Synergi C18 150*25*10 μm; mobile phase: [water(0.1% TFA)-ACN]; B %: 53%-80%, 12 min) and lyophilized to afford compound 77 (97.3% ee value) as a white solid.

¹H NMR (400 MHz, METHANOL-d4) δ 8.27 (m, 1H) 8.20 (d, J=8.0 Hz, 1H), 7.93-7.89 (m, 3H), 7.73 (m, 1H), 7.42-7.39 (m, 3H), 7.34-7.28 (m, 1H), 4.97-4.95 (m, 1H), 2.73-2.66 (m, 2H), 2.30-2.24 (m, 2H), 2.16 (s, 3H) ppm.

LCMS (ESI) m/z: [M+H]+=480.1.

Chiral SFC: OD-3_5CM_MEOH(DEA)_40_3ML_5MIN_T35.M., 0.601 min.

Example 62. Preparation of N-[(1S)-3-methylsulfanyl-1-[(4-phenylthiazol-2-yl)carbamoyl]propyl]-4-(trifluoromethyl)benzamide (compound 68)

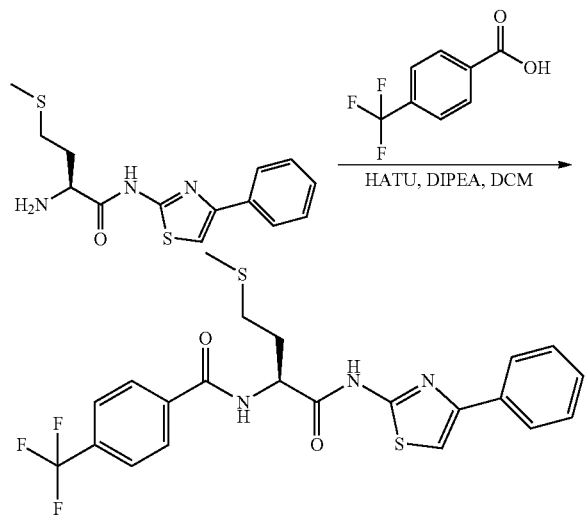

68

To a solution of 4-(trifluoromethyl)benzoic acid (22.55 mg, 118.64 µmol) in DCM (3 mL) was added DIPEA (46.00 mg, 355.91 µmol) and HATU (49.62 mg, 130.50 µmol). The mixture was stirred at 30° C. for 10 min. (2S)-2-amino-4-methylsulfanyl-N-(4-phenylthiazol-2-yl)butanamide (50 mg, 118.64 µmol) was added and the reaction mixture was stirred at 30° C. for 2 hr. The reaction mixture was concentrated to dryness to give a residue. The residue was purified by prep-HPLC (column: Phenomenex Synergi C18 150*25*10 µm; mobile phase: [water(0.1% TFA)-ACN]; B %: 65%-85%, 8 min) and lyophilized to afford compound 68 as a white solid.

$^1$HNMR (400 MHz, METHANOL-d4) δ 8.09 (d, J=8.0 Hz, 1H), 7.92 (d, J=7.2 Hz, 1H), 7.83 (d, J=8.4 Hz, 2H), 7.42-7.39 (m, 3H), 7.33-7.31 (m, 1H), 4.97-4.94 (m, 1H), 2.73-2.66 (m, 2H), 2.33-2.24 (m, 2H), 2.16 (s, 3H) ppm.

LCMS (ESI) m/z: [M+H]+=480.1.

Chiral SFC: Cellucoat-MeOH(DEA)-40-7 min-3 mL-35T, 0.937 min.

Example 63. Preparation of N₄-methyl-N₁-[(1S)-3-methylsulfanyl-1-[(4-phenylthiazol-2-yl)carbamoyl]propyl]terephthalamide (compound 72)

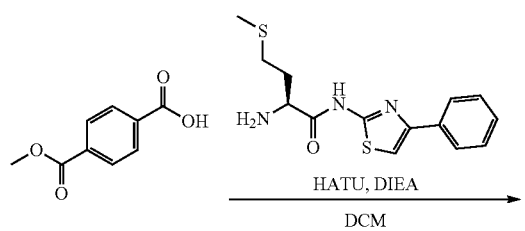

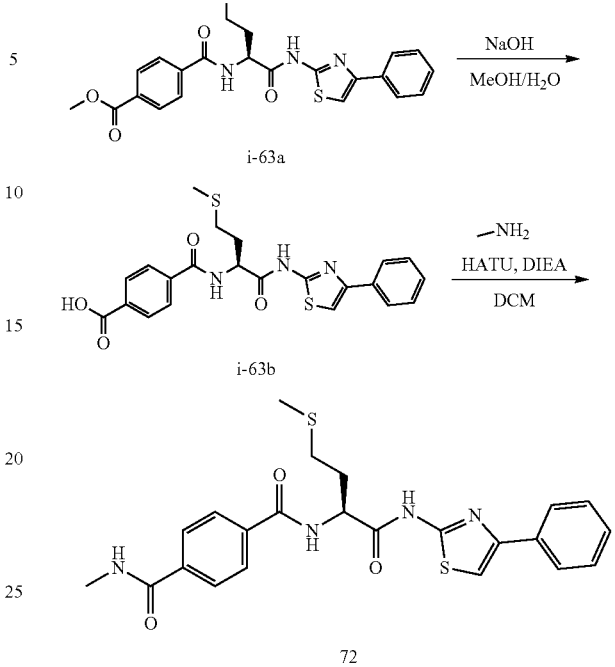

72

Step 1: Preparation of methyl 4-[[(1S)-3-methylsulfanyl-1-[(4-phenylthiazol-2-yl)carbamoyl]propyl]carbamoyl]benzoate (intermediate i-63a)

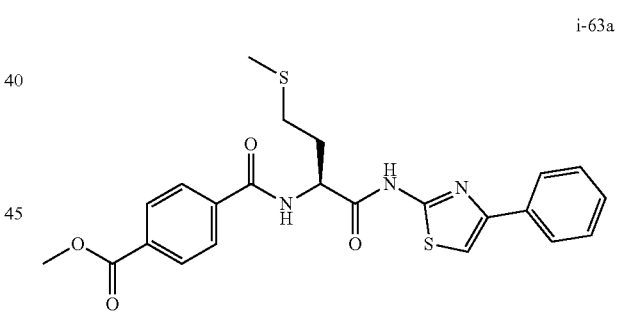

i-63a

To a solution of 4-methoxycarbonylbenzoic acid (85.49 mg, 474.54 µmol) in DCM (5 mL) were added DIPEA (183.99 mg, 1.42 mmol) and HATU (198.48 mg, 522.00 µmol). The mixture was stirred at 30° C. for 10 min. (2S)-2-amino-4-methylsulfanyl-N-(4-phenylthiazol-2-yl)butanamide (200 mg, 474.54 µmol) was added and the reaction mixture was stirred at 30° C. for 2 hr. The reaction mixture was quenched by addition water (10 mL) and extracted with ethyl acetate (10 mL×2). The combined organic extracts were washed with water (10 mL), dried over Na₂SO₄, filtered and concentrated under reduced pressure to give intermediate i-63a as colorless oil, which was used in next step without further purification.

LCMS (ESI) m/z: [M+H]⁺=470.3.

Step 2: Preparation of 4-[[(1S)-3-methylsulfanyl-1-[(4-phenylthiazol-2-yl) carbamoyl]propyl]carbamoyl]benzoic acid (intermediate i-63b)

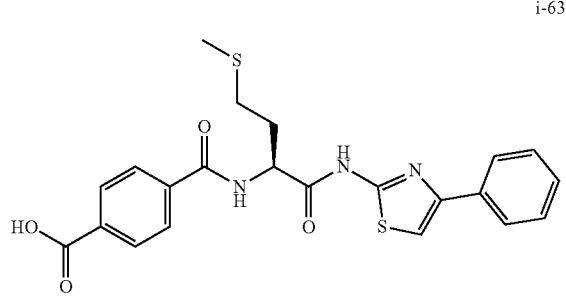

i-63b

To a solution of intermediate i-63a (258.82 mg, 468.50 μmol) in MeOH (2.0 mL) and H₂O (2.0 mL) was added NaOH (36.39 mg, 909.75 μmol). The mixture was stirred at 30° C. for 18 hr. The reaction mixture was concentrated in vacuo. The pH of the residue was adjusted to pH 4 with 20% HCl solution. A white precipitate was formed and the mixture was filtered. The filtration cake was washed with water (4.0 mL) and concentrated to dryness to give intermediate i-63b as an off-white solid.

LCMS (ESI) m/z: [M+H]⁺=456.3.

Step 3: Preparation of N₄-methyl-N₁-[(1S)-3-methylsulfanyl-1-[(4-phenylthiazol-2-yl)carbamoyl]propyl]terephthalamide (compound 72)

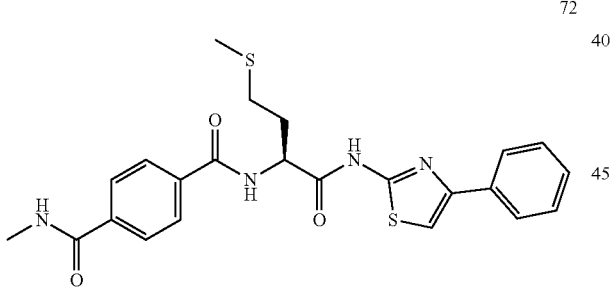

72

To a solution of intermediate i-63b (40 mg, 81.66 μmol) in DCM (3 mL) was added HATU (36.15 mg, 95.07 μmol) and DIPEA (20.48 mg, 158.46 μmol). The mixture was stirred at 30° C. for 10 min. methanamine (2 M, 396.05 μL) was added and the reaction mixture was stirred at 30° C. for 3 hr. The reaction mixture was concentrated to dryness to give a residue. The residue was purified by prep-HPLC (column: Boston pH-lex 150*25 10 μm; mobile phase: [water(0.1% TFA)-ACN]; B %: 50%-70%, 8 min) and lyophilized to afford compound 72 as a white solid.

¹H NMR (400 MHz, METHANOL-d4) δ 8.00 (d, J=8.4 Hz, 2H), 7.94-7.91 (m, 4H), 7.42-7.39 (m, 3H), 7.33-7.29 (m, 1H), 4.97-4.94 (m, 1H), 2.95 (s, 3H), 2.73-2.66 (m, 2H), 2.33-2.24 (m, 2H), 2.16 (s, 3H) ppm.

LCMS (ESI) m/z: [M+H]+=469.3.

Example 64. Preparation of (S)-tert-butyl 3-((4-(methylthio)-1-oxo-1-((4-phenylthiazol-2-yl)amino)butan-2-yl)carbamoyl)benzylcarbamate (compound 75)

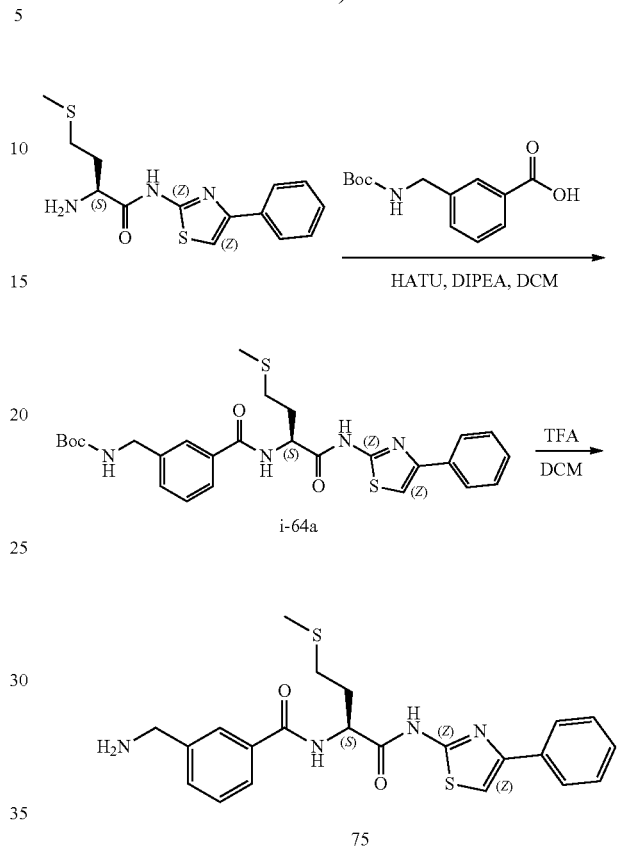

Step 1: Preparation of (S)-tert-butyl 3-((4-(methylthio)-1-oxo-1-((4-phenylthiazol-2-yl)amino)butan-2-yl)carbamoyl)benzylcarbamate (intermediate i-64a)

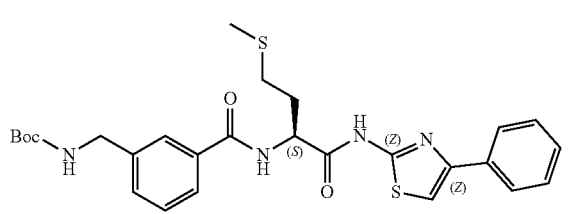

i-64a

To a solution of 3-[(tert-butoxycarbonylamino)methyl]benzoic acid (29.81 mg, 118.64 μmol) in DCM (2 mL) were added HATU (67.66 mg, 177.96 μmol) and DIPEA (61.33 mg, 474.56 μmol), then (2S)-2-amino-4-methylsulfanyl-N-(4-phenylthiazol-2-yl)butanamide (50 mg, 118.64 μmol) was added. The mixture was stirred at 10° C. for 12 hr. The reaction mixture was concentrated under reduced pressure.

The residue was purified by prep-TLC (SiO2, PE:EA=1:1) to give intermediate i-64a as a white solid.

LCMS (ESI) m/z: [M+H]⁺=541.1.

Step 2: Preparation of (S)-tert-butyl 3-((4-(methylthio)-1-oxo-1-((4-phenylthiazol-2-yl)amino)butan-2-yl)carbamoyl)benzylcarbamate (compound 75) trifluoroacetate salt

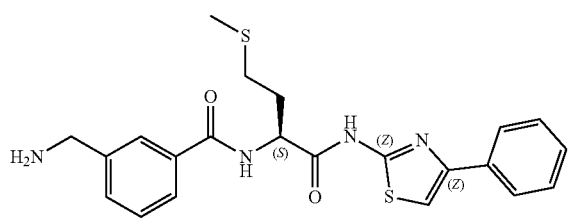

75

To a solution of intermediate i-64a (50 mg, 76.37 µmol) in DCM (2.0 mL) was added TFA (1.0 mL). The mixture was stirred at 12° C. for 2 hr. The reaction mixture was concentrated under reduced pressure to remove DCM. The residue was purified by prep-HPLC (TFA condition; column: Phenomenex Synergi C18 150*25*10 µm; mobile phase: [water (0.1% TFA)-ACN]; B %: 25%-55%, 9 min) and lyophilized to give compound 75 (TFA salt) as a white solid.

1H NMR (400 MHz, METHANOL-d4) δ=7.99-7.97 (m, 2H), 7.91-7.89 (m, 2H), 7.66-7.64 (m, 1H), 7.61-7.59 (m, 1H), 7.41-7.36 (m, 3H), 7.31-7.29 (m, 1H), 4.95-4.91 (m, 1H), 4.19 (s, 2H), 2.72-2.65 (m, 2H), 2.30-2.20 (m, 2H), 2.15 (s, 3H) ppm.

LCMS (ESI) m/z: [M+H]$^+$=441.0.

Example 65. Preparation of 4-(aminomethyl)-N-[3-methylsulfanyl-1-[(4-phenylthiazol-2-yl)carbamoyl]propyl]benzamide (compound 57)

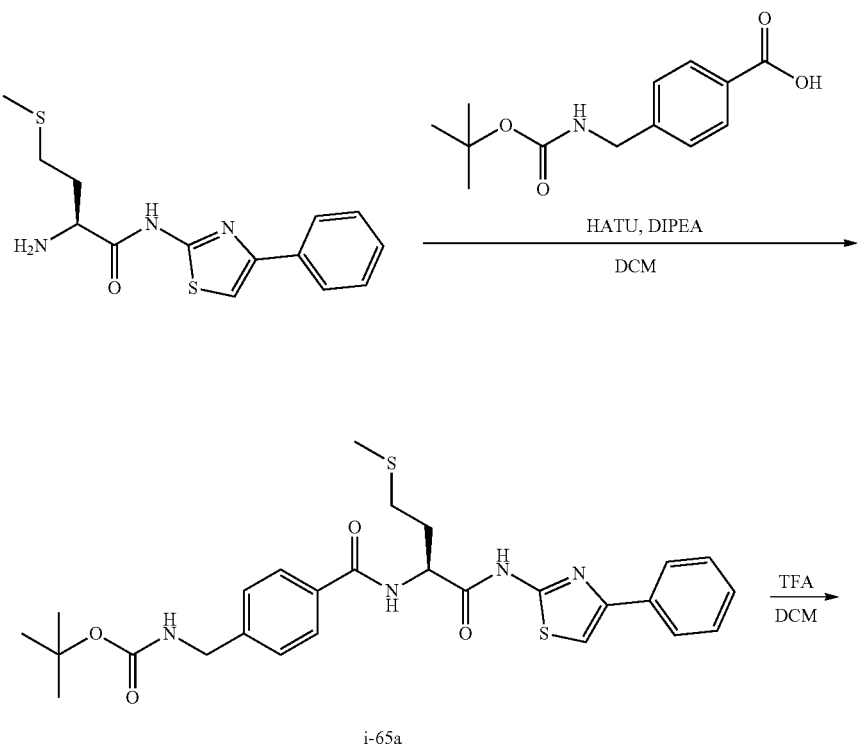

i-65a

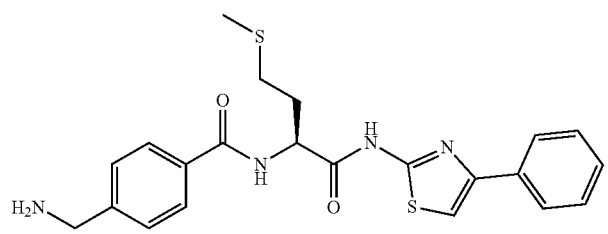

57

Step 1: Preparation of tert-butylN-[[4-[[(1S)-3-methylsulfanyl-1-[(4-phenylthiazol-2-yl)carbamoyl]propyl]carbamoyl]phenyl]methyl]carbamate (intermediate i-65a)

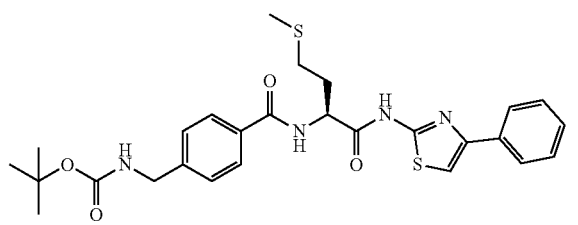

i-65a

To a mixture of 4-[(tert-butoxycarbonylamino)methyl]benzoic acid (89.43 mg, 355.91 μmol) in DCM (1 mL) was added HATU (202.99 mg, 533.86 μmol) and DIPEA (247.97 μL, 1.42 mmol). The mixture was stirred at 30° C. for 15 min, then (2S)-2-amino-4-methylsulfanyl-N-(4-phenylthiazol-2-yl)butanamide (150 mg, 355.91 μmol) was added and stirred at 30° C. for 16 hours. The reaction mixture was evaporated to dryness to give the crude product. The residue was purified by prep-HPLC (column: Boston pH-lex 150*25 10 μm; mobile phase: [water(0.1% TFA)-ACN]; B %: 59%-79%, 8 min) and lyophilized to give intermediate i-65a as a white solid.

$^{1}$H NMR (400 MHz, MeOD-d$_4$) δ=7.91-7.86 (m, 4H), 7.41-7.37 (m, 5H), 7.31-7.28 (m, 1H), 4.92 (brd, J=5.2 Hz, 1H), 4.30 (s, 2H), 2.74-2.60 (m, 2H), 2.33-2.17 (m, 2H), 2.14 (s, 3H), 1.46 (s, 9H) ppm.

LCMS (ESI) m/z: [M+H]$^{+}$=541.3.

Step 2: Preparation of 4-(aminomethyl)-N-[3-methylsulfanyl-1-[(4-phenylthiazol-2-yl)carbamoyl]propyl]benzamide trifluoroacetate salt (compound 57)

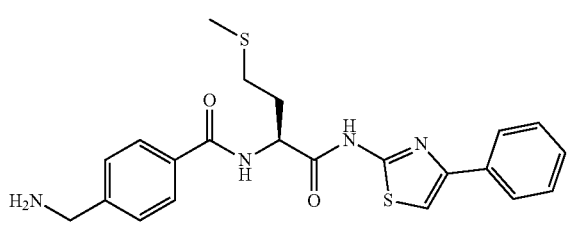

57

To a solution of intermediate i-65a (150.00 mg, 277.42 μmol) in DCM (1 mL) was added TFA (205.40 μL). The mixture was stirred at 30° C. for 2 hours. The reaction mixture was evaporated to dryness to give the crude product. The residue was purified by prep-HPLC (column: Phenomenex Synergi C18 150*25*10 μm; mobile phase: [water (0.1% TFA)-ACN]; B %: 18%-48%, 12 min) and lyophilized to give compound 57 (TFA salt) as a white solid.

$^{1}$H NMR (400 MHz, MeOD-d$_4$) δ=8.00 (d, J=8.4 Hz, 2H), 7.91-7.89 (m, 2H), 7.58 (d, J=8.4 Hz, 2H), 7.41-7.37 (m, 3H), 7.32-7.28 (m, 1H), 4.94-4.91 (m, 1H), 4.20 (s, 2H), 2.71-2.64 (m, 2H), 2.31-2.22 (m, 2H), 2.14 (s, 3H) ppm.

LCMS (ESI) m/z: [M+H]$^{+}$=441.2.

Example 66. Preparation of 4-[(dimethylamino)methyl]-N-[(1S)-3-methylsulfanyl-1-[(4-phenylthiazol-2-yl)carbamoyl]propyl]benzamide (compound 60)

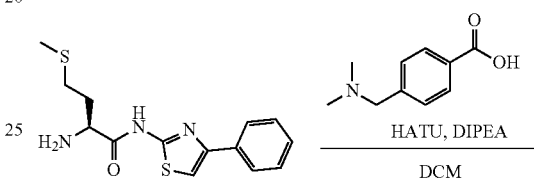

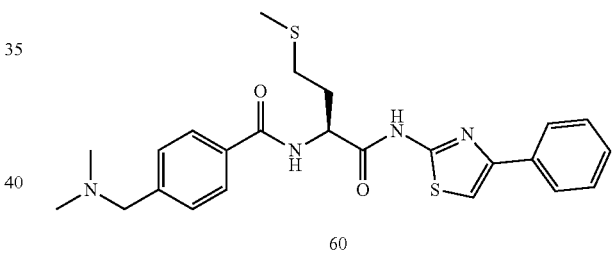

60

To a mixture of 4-[(dimethylamino)methyl]benzoic acid; hydrochloride (25.59 mg, 118.64 μmol) in DCM (1 mL) was added HATU (67.66 mg, 177.96 μmol) and DIPEA (82.66 μL, 474.56 μmol). The mixture was stirred at 30° C. for 15 min, then (2S)-2-amino-4-methylsulfanyl-N-(4-phenylthiazol-2-yl)butanamide (50 mg, 118.64 μmol) was added and stirred at 30° C. for 2 hours. The reaction mixture was evaporated to dryness. The residue was purified by prep-HPLC (column: Phenomenex Synergi C18 150*25*10 μm; mobile phase: [water(0.1% TFA)-ACN]; B %: 25%-55%, 9 min) and lyophilized to give compound 60 as an off-white solid.

$^{1}$H NMR (400 MHz, MeOD-d$_4$) δ=8.03 (d, J=8.0 Hz, 2H), 7.90 (d, J=8.0 Hz, 2H), 7.63 (d, J=8.4 Hz, 2H), 7.40-7.36 (m, 3H), 7.31-7.29 (m, 1H), 4.95-4.91 (m, 1H), 4.39 (s, 2H), 2.88 (s, 6H), 2.71-2.64 (m, 2H), 2.29-2.19 (m, 2H), 2.14 (s, 3H) ppm.

LCMS (ESI) m/z: [M+H]$^{+}$=469.1.

Example 67. Preparation of 4-(acetamidomethyl)-N-[3-methylsulfanyl-1-[(4-phenylthiazol-2-yl)carbamoyl]propyl]benzamide (compound 74)

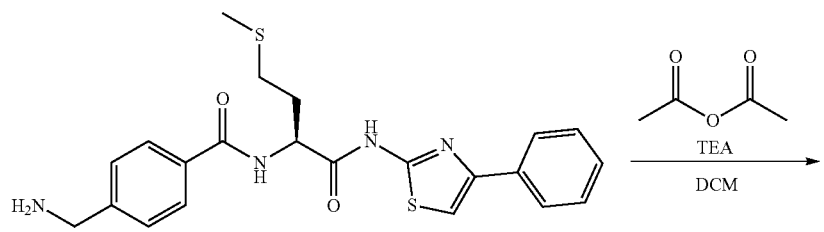

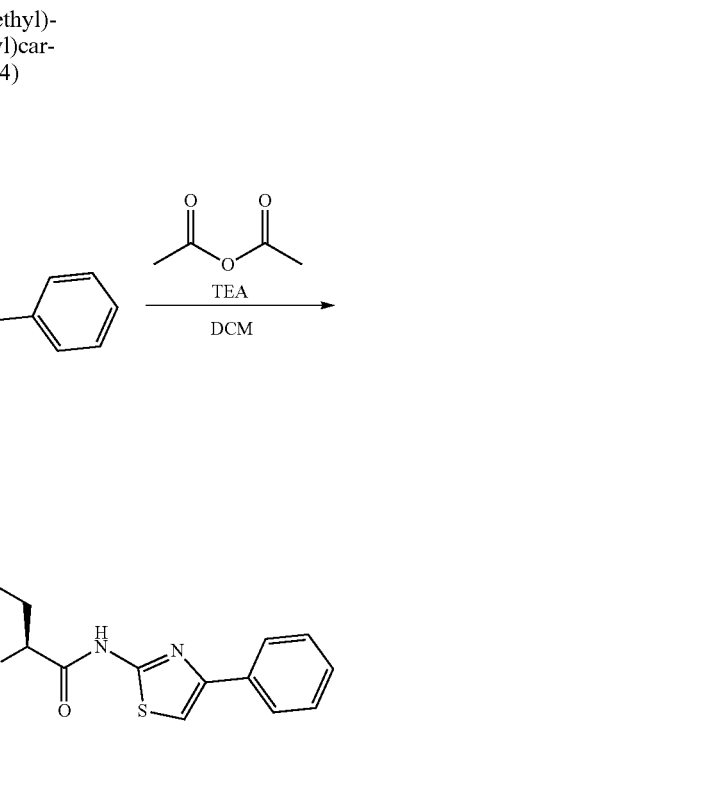

74

To a solution of 4-(aminomethyl)-N-[3-methylsulfanyl-1-[(4-phenylthiazol-2-yl)carbamoyl]propyl]benzamide (50 mg, 90.15 µmol, TFA salt) in DCM (1 mL) was added TEA (62.74 µL, 450.77 µmol) followed by Ac$_2$O (21.11 µL, 225.39 µmol) at 0° C. The mixture was stirred at 30° C. for 1 hour. The reaction mixture was evaporated to dryness. The residue was purified by prep-HPLC (column: Xtimate C18 150*25 mm*5 µm; mobile phase: [water (0.05% ammonia hydroxide v/v)-ACN]; B %: 30%-60%, 12 min) and lyophilized to give compound 74 as an off-white solid.

$^1$H NMR (400 MHz, MeOD-d$_4$) δ=7.90-7.87 (m, 4H), 7.41-7.36 (m, 5H), 7.31-7.27 (m, 1H), 4.92-4.90 (m, 1H), 4.43 (s, 2H), 2.73-2.60 (m, 2H), 2.27-2.21 (m, 2H), 2.13 (s, 3H), 2.01 (s, 3H) ppm.

LCMS (ESI) m/z: [M+H]$^+$=483.3.

Example 68. Preparation of Compound N-[(1S)-3-methylsulfanyl-1-[(4-phenylthiazol-2-yl)carbamoyl]propyl]-4-methylsulfonyl-benzamide (compound 68)

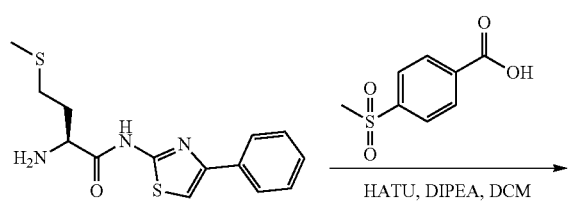

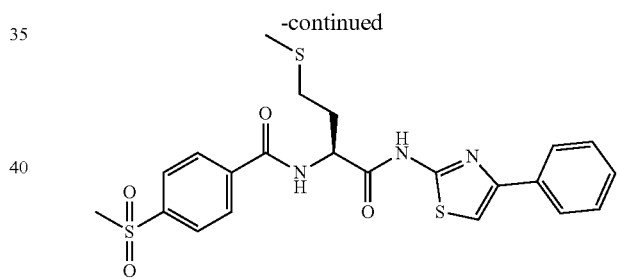

68

To a solution of 4-methylsulfonylbenzoic acid (23.75 mg, 118.64 µmol) in DCM (3 mL) was added DIPEA (46.00 mg, 355.91 µmol) and HATU (49.62 mg, 130.50 µmol). The mixture was stirred at 30° C. for 10 min. (2S)-2-amino-4-methylsulfanyl-N-(4-phenylthiazol-2-yl)butanamide (50 mg, 118.64 µmol) was added and the reaction mixture was stirred at 30° C. for 2 hr. The reaction mixture was concentrated to dryness to give a residue. The residue was purified by prep-HPLC (column: Phenomenex Synergi C18 150*25*10 µm; mobile phase: [water(0.1% TFA)-ACN]; B %: 45%-69%, 12 min) and lyophilized to afford compound 68 as a white solid.

1H NMR (400 MHz, METHANOL-d4) δ=8.19-8.05 (m, 4H), 7.92 (d, J=7.2 Hz, 2H), 7.42-7.39 (m, 3H), 7.33-7.31 (m, 1H), 4.97-4.94 (m, 1H), 3.19 (s, 3H), 2.73-2.66 (m, 2H), 2.33-2.24 (m, 2H), 2.16 (s, 3H) ppm.

LCMS (ESI) m/z: [M+H]+=490.1.

Example 69. Preparation of 4-methoxy-N-[(1S)-3-methylsulfanyl-1-[(4-phenylthiazol-2-yl)carbamoyl]propyl]-3-methylsulfonyl-benzamide (compound 20)

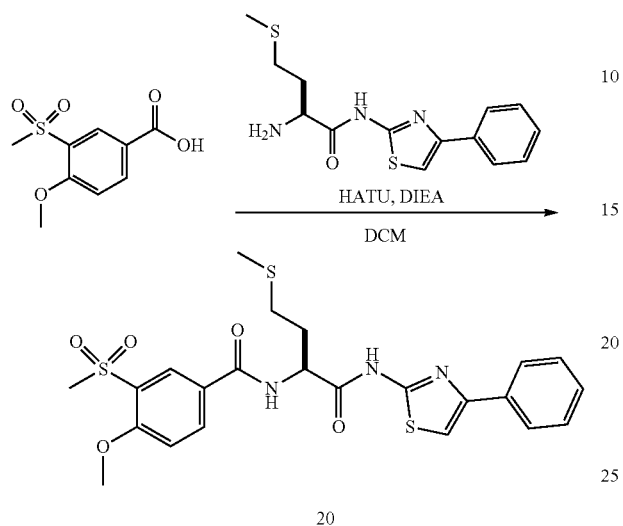

To a solution of 4-methoxy-3-methylsulfonyl-benzoic acid (21.85 mg, 94.91 µmol) in DCM (1 mL) was added HATU (43.30 mg, 113.89 µmol) and DIEA (36.80 mg, 284.73 µmol) and the mixture was stirred at 15° C. for 5 min. Then (2S)-2-amino-4-methylsulfanyl-N-(4-phenylthiazol-2-yl) butanamide (40 mg, 94.91 µmol) was added and the mixture was stirred at 15° C. for 1 hr. The solvent was removed under reduced pressure and the residue was purified by Prep.HPLC (column: Phenomenex Synergi C18 150*25*10 µm; mobile phase: [water(0.1% TFA)-ACN]; B %:42%-72%, 9 min) and lyophilized to give compound 20 as a white solid.

$^1$H NMR (400 MHz, MeOD) δ=8.49 (d, J=2.4, 1H), 8.26-8.23 (m, 1H), 7.90-7.88 (m, 2H), 7.40-7.36 (m, 4H), 7.31-7.27 (m, 1H), 4.92-4.91 (m, 1H), 4.08 (s, 3H), 3.26 (s, 3H), 2.73-2.60 (m, 2H), 2.34-2.17 (m, 2H), 2.14 (s, 3H) ppm.

LCMS (ESI) m/z: [M+H]$^+$=520.1.

Example 70. Preparation of 4-methyl-3-(methylsulfonyl)-N-(2-oxo-2-((4-phenylthiazol-2-yl)amino)ethyl)benzamide (compound 19)

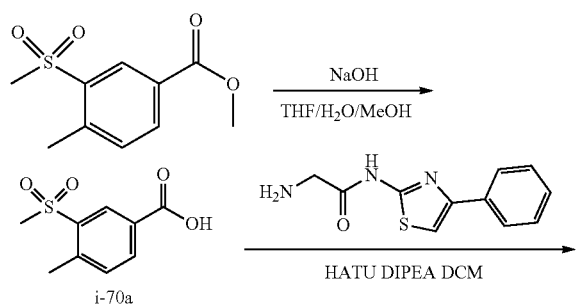

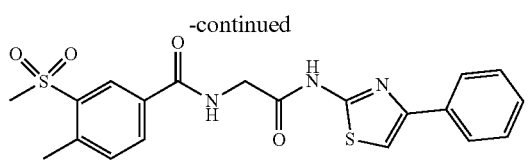

Step 1: Preparation of 4-methyl-3-(methylsulfonyl)benzoic acid (intermediate i-70a)

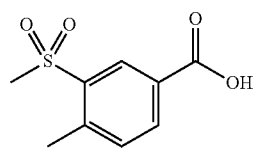

NaOH (13.14 mg, 328.57 µmol) was dissolved in H$_2$O (1 mL) and then added into solution of methyl 4-methyl-3-methylsulfonyl-benzoate (50 mg, 219.04 µmol) in THF (0.5 mL) and MeOH (0.2 mL). The reaction mixture was stirred at 30° C. for 17 hr. The reaction mixture was diluted with water (3 mL) then washed by EtOAc (5 mL). The water layer was adjusted to pH=3 with 2 M aq. HCl, then extracted by EtOAc (5 mL*3). The combined organic extracts were washed with brine, dried over anhydrous sodium sulfate, filtered and concentrated to give intermediate i-70a as a white solid.

LCMS (ESI) m/z: [M+H]+=215.0.

Step 2: Preparation of 4-methyl-3-(methylsulfonyl)-N-(2-oxo-2-((4-phenylthiazol-2-yl)amino)ethyl)benzamide (compound 19)

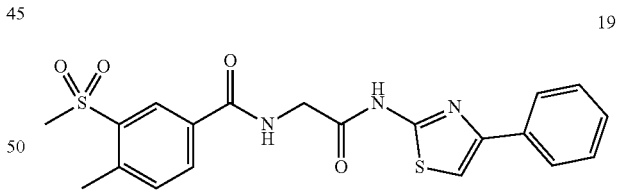

To a solution of intermediate i-70a (25 mg, 116.69 µmol) in DCM (1 mL) were added HATU (66.56 mg, 175.04 µmol) and DIPEA (75.41 mg, 583.46 µmol) and then 2-amino-N-(4-phenylthiazol-2-yl)acetamide (40.53 mg, 116.69 µmol) was added. A precipitate was formed after stirring at 30° C. for 2 hr. The precipitate was collected by filtration and lyophilized to afford compound 19 as a white solid.

$^1$H NMR (400 MHz, DMSO-d6) δ=12.09-10.54 (br s, 1H), 9.20-9.19 (m, 1H), 8.44 (s, 1H), 8.13-7.10 (m, 1H), 7.91-7.89 (m, 2H), 7.63-7.60 (m, 2H), 7.45-7.40 (m, 2H), 7.35-7.32 (m, 1H), 4.22 (d, J=5.6 Hz, 2H), 3.27 (s, 3H), 2.71 (s, 3H) ppm.

LCMS (ESI) m/z: [M+H]$^+$=430.3.

Example 71. Preparation of Compound 4-(dimethylsulfamoyl)-N-[(1S)-3-methylsulfanyl-1-[(4-phenylthiazol-2-yl) carbamoyl]propyl]thiophene-2-carboxamide (compound 64)

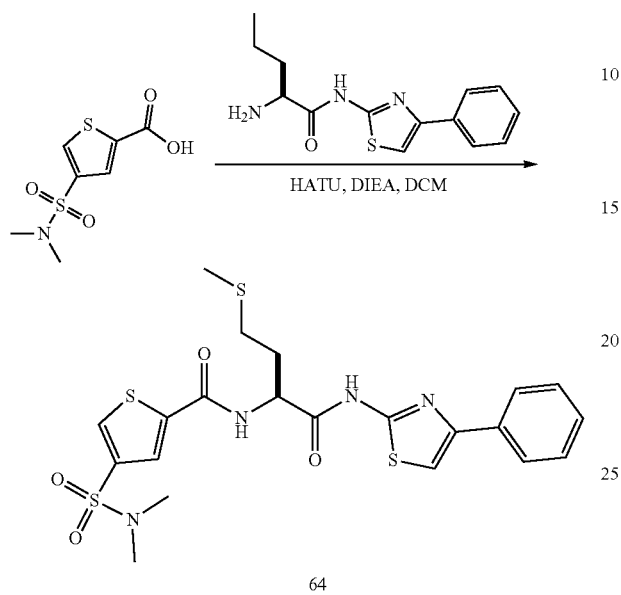

To a solution of 4-(dimethylsulfamoyl)thiophene-2-carboxylic acid (40.00 mg, 170.01 μmol), DIPEA (87.89 mg, 680.04 μmol, 118.45 μL) and HATU (71.11 mg, 187.01 μmol) in DCM (1.0 mL) was added (2S)-2-amino-4-methylsulfanyl-N-(4-phenylthiazol-2-yl)butanamide (78.82 mg, 187.01 μmol) and the mixture was stirred at 30° C. for 2 hr. The reaction mixture was concentrated under reduced pressure to give a residue. The residue was purified by prep-HPLC (column: Phenomenex Synergi C18 150*25*10 μm; mobile phase: [water (0.1% TFA)-ACN]; B %: 45%-75%, 10 min) and lyophilized to give compound 64 as a white solid.

1H NMR (400 MHz, DMSO-d6) δ=12.60 (s, 1H), 9.09 (d, J=7.2 Hz, 1H), 8.46 (d, J=1.6 Hz, 1H), 8.27 (d, J=1.6 Hz, 1H), 7.92-7.90 (m, 2H), 7.67 (s, 1H), 7.46-7.42 (m, 2H), 7.35-7.33 (m, 1H), 4.77-4.73 (m, 1H), 2.73-2.67 (m, 6H), 2.66-2.53 (m, 2H), 2.10-2.03 (m, 5H) ppm.

LCMS (ESI) m/z: [M+H]$^+$=525.0

Example 72. Preparation of 3-cyclopropylsulfonyl-N-[2-oxo-2-[(4-phenylthiazol-2-yl)amino]ethyl]benzamide (compound 39)

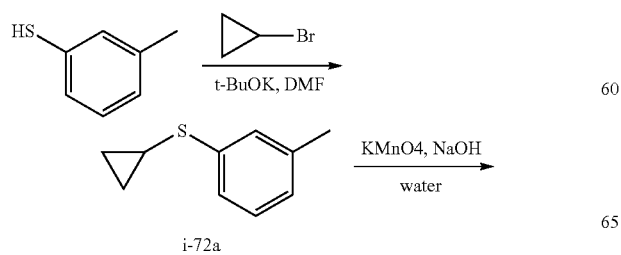

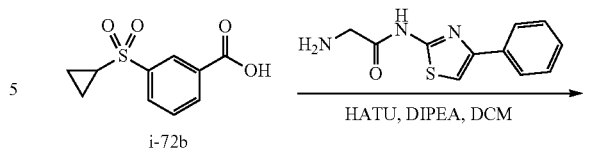

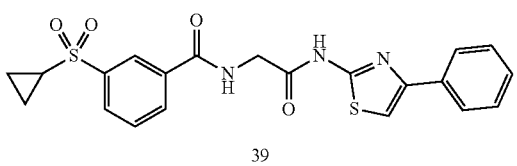

Step 1: Preparation of 1-cyclopropylsulfanyl-3-methyl-benzene (intermediate i-72a)

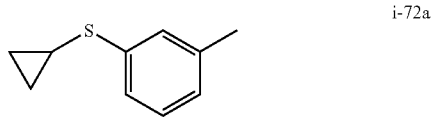

A mixture of 3-methylbenzenethiol (100.0 mg, 805.13 μmol), bromocyclopropane (292.21 mg, 2.42 mmol) and t-BuOK (99.38 mg, 885.65 μmol,) in DMSO (0.5 mL) was stirred at 100° C. for 12 hr. The reaction mixture was diluted with water (2.0 mL) and extracted with EtOAc (2.0 mL*3). The combined organic extracts were dried over Na$_2$SO$_4$, filtered and concentrated under reduced pressure to give a residue. The residue was purified by column chromatography (SiO$_2$, Petroleum ether) to give intermediate i-72a as colorless oil.

$^1$H NMR (400 MHz, CDCl$_3$) δ=7.18 (s, 1H), 7.10 (d, J=4.0 Hz, 3H), 6.88-6.86 (m, 1H), 2.29-2.25 (m, 3H), 2.14-2.09 (m, 1H), 1.01-0.96 (m, 2H), 0.63-0.60 (m, 2H) ppm.

Step 2: Preparation of 3-cyclopropylsulfonylbenzoic acid (intermediate i-72b)

To a solution of intermediate i-72a (60.0 mg, 365.26 μmol) and KMnO₄ (230.89 mg, 1.46 mmol) in water (1.0 mL) was added NaOH (7.30 mg, 182.63 μmol). The mixture was stirred at 100° C. for 16 hr. The reaction mixture was poured into sat. Na₂SO₃ (20.0 mL), then 1 N HCl (20.0 mL) was added to the mixture and extracted with EtOAc (20.0 mL*3). The combined organic extracts were washed with brine (20.0 mL), dried over Na₂SO₄, filtered and concentrated under reduced pressure to give the intermediate i-72b as yellow oil.

¹H NMR (400 MHz, DMSO-d6) δ=8.35 (s, 1H), 8.26 (d, J=7.6 Hz, 1H), 8.13 (d, J=7.6 Hz, 1H), 7.82-7.78 (m, 1H), 2.99-2.93 (m, 1H), 1.17-1.06 (m, 4H) ppm.

LCMS (ESI) m/z: [M+H]⁺=227.0 vacuum to give a white solid. Then the solid was suspended in water (3.0 mL) and lyophilized to give compound 39 as a white solid.

¹H NMR (400 MHz, DMSO-d6) δ=12.46 (s, 1H), 9.27 (m, 1H), 8.42 (s, 1H), 8.25 (d, J=8.0 Hz, 1H), 8.10 (d, J=8.4 Hz, 1H), 7.92-7.90 (m, 2H), 7.81-7.79 (m, 1H), 7.64 (s, 1H), 7.44-7.42 (m, 2H), 7.33-7.31 (m, 1H), 4.24 (d, J=5.6 Hz, 2H), 2.95-2.90 (m, 1H), 1.19-1.07 (m, 4H) ppm.

LCMS (ESI) m/z: [M+H]⁺=442.3.

Example 73. Preparation of 3-[2-[[2-[[3-(dimethyl-sulfamoyl)benzoyl]amino]acetyl]amino]thiazol-4-yl]-N,N-dimethyl-benzamide (compound 37)

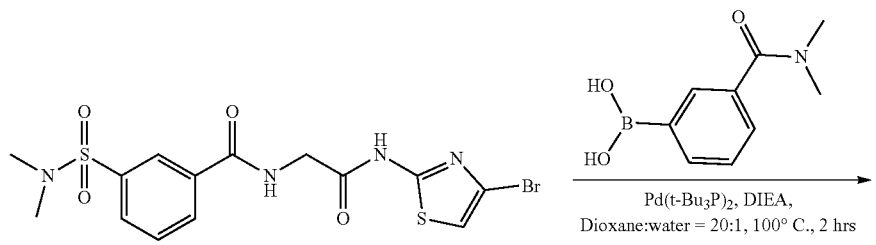

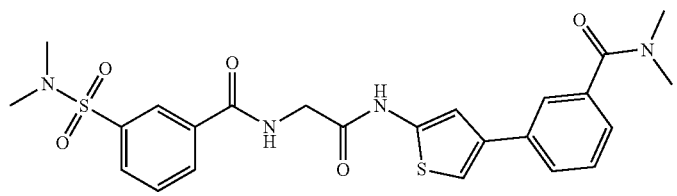

37

Step 3: Preparation of 3-cyclopropylsulfonyl-N-[2-oxo-2-[(4-phenylthiazol-2-yl)amino]ethyl]benzamide (compound 39)

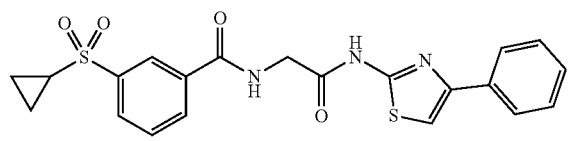

39

To a solution of intermediate i-72b (30.0 mg, 132.60 μmol), HATU (60.50 mg, 159.12 μmol) and DIPEA (68.55 mg, 530.39 μmol,) in DCM (1.0 mL) was added 2-amino-N-(4-phenylthiazol-2-yl) acetamide (50.66 mg, 145.86 μmol). Then the mixture was stirred at 30° C. for 4 hr. The reaction mixture was concentrated under reduced pressure to give a residue. The residue was triturated with MeOH (4.0 mL), the solid was collected by filtration and dried in To a solution of N-[2-[(4-bromothiazol-2-yl)amino]-2-oxo-ethyl]-3-(dimethylsulfamoyl) benzamide (50.0 mg, 111.78 μmol) and [3-(dimethylcarbamoyl)phenyl]boronic acid (64.72 mg, 335.33 μmol) in dioxane (3.0 mL) and H₂O (0.3 mL) were added Pd(t-Bu₃P)₂ (28.56 mg, 55.89 μmol) and DIEA (72.23 mg, 558.88 μmol, 97.34 μL) under N₂. The mixture was stirred at 100° C. for 2 hrs. The solution was cooled to 30° C. and a solid formed. The mixture was filtered to give the crude product as a solid. The crude product was dissolved in MeOH (1.0 mL) and DMSO (1.0 mL), purified by Pre-HPLC(column: Phenomenex Synergi C18 150*25*10 μm; mobile phase: [water(0.1% TFA)-ACN]; B %: 30%-60%, 9 min) and lyophilized to give compound 37 as a white solid.

¹H NMR (400 MHz, DMSO-d6) δ=12.47 (s, 1H), 9.30-9.29 (m, 1H), 8.27-8.23 (m, 2H), 7.98-7.93 (m, 3H), 7.81-7.75 (m, 2H), 7.50-7.52 (m, 1H), 7.34 (d, J=7.60 Hz, 1H), 4.25 (d, J=5.6 Hz, 2H), 3.01-2.94 (m, 6H), 2.66 (s, 6H) ppm.

LCMS (ESI) m/z: [M+H]⁺=516.0.

Example 74. Preparation of 3-methylsulfonyl-N-[2-oxo-2-[[4-(3-phenylphenyl)thiazol-2-yl]amino]ethyl]benzamide (compound 36)

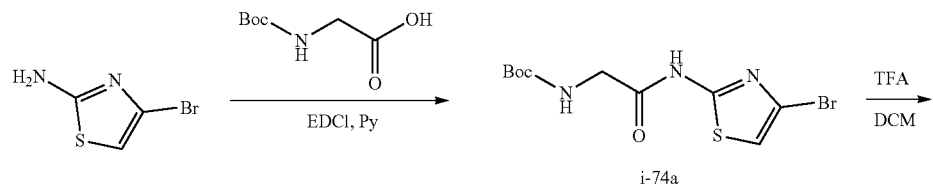

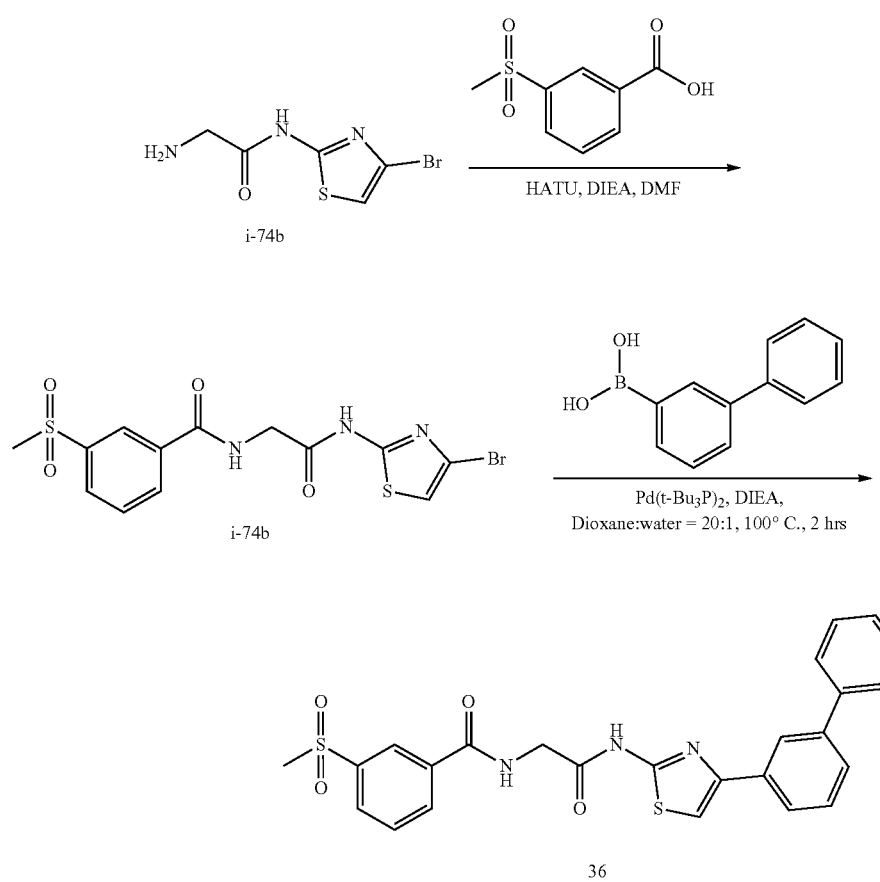

Step 1: Preparation of tert-butyl N-[2-[(4-bromothiazol-2-yl)amino]-2-oxo-ethyl]carbamate (intermediate i-74a)

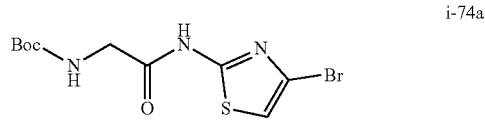 [SMILES: CC(C)(C)OC(=O)NCC(=O)Nc1nc(Br)cs1]

To a solution of 4-bromothiazol-2-amine (3.0 g, 16.76 mmol) and 2-(tert-butoxycarbonylamino) acetic acid (4.40 g, 25.13 mmol) in pyridine (30.0 mL) was added EDCI (16.06 g, 83.78 mmol). The mixture was stirred at 15° C. for 16 hr. The reaction mixture was then concentrated under reduced pressure. The residue was diluted with 0.5N HCl (100.0 mL) and extracted with EtOAc (50 mL*3). The combined organic extracts were washed with NaHCO₃ (50.0 mL) and brine (50.0 mL), dried over Na₂SO₄, filtered and concentrated under reduced pressure to give a residue. The residue was purified by column chromatography (SiO₂, Petroleum ether/Ethyl acetate=7/1 to 3:1) to give intermediate i-74a as a white solid.

LCMS (ESI) m/z: [M+Na]⁺=358.1

Step 2: Preparation of 2-amino-N-(4-bromothiazol-2-yl)acetamide (intermediate i-74b)

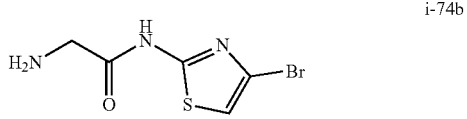 [SMILES: NCC(=O)Nc1nc(Br)cs1]

A mixture of intermediate i-74a (300 mg, 892.31 µmol) in DCM (5.0 mL) and TFA (1.0 mL) was stirred at 30° C. for 2 hrs. The mixture was diluted with DCM (20.0 mL) and concentrated under vacuum.

This operation was repeated three times. The residue was washed with MTBE (5 mL*2) to give intermediate i-74b (TFA salt) as yellow oil which was used directly in the next step.

LCMS (ESI) m/z: [M+Na]⁺=236.1

Step 3: Preparation of N-[2-[(4-bromothiazol-2-yl)amino]-2-oxo-ethyl]-3-methylsulfonyl-benzamide (intermediate i-74c)

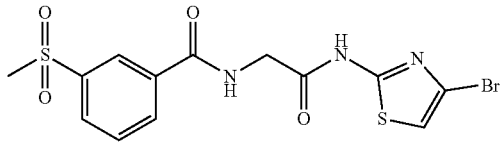

i-74c

To a solution of 3-methylsulfonylbenzoic acid (171.55 mg, 856.87 µmol) in DMF (10.0 mL) were added HATU (977.42 mg, 2.57 mmol) and DIEA (553.72 mg, 4.28 mmol). The mixture was stirred at 30° C. for 30 min. Then intermediate i-74b (300.0 mg, 856.87 µmol) was added and the mixture was stirred at 30° C. for another 2 hrs. The mixture was poured into H₂O (100.0 mL) and extracted with EtOAc (10.0 mL*3). The combined organic layers were washed with H₂O (5.0 mL*3) and brine (5.0 mL*2), then dried over Na₂SO₄, filtered and concentrated under reduced pressure. The residue was purified by Pre-HPLC(column: Phenomenex Synergi C18 150*25*10 µm; mobile phase: [water (0.1% TFA)-ACN]; B %: 32%-62%, 9 min) and lyophilized to give intermediate i-74c as a light yellow solid.

LCMS (ESI) m/z: [⁸¹BrM+H]⁺=419.9.

Step 4: Preparation of 3-methylsulfonyl-N-[2-oxo-2-[[4-(3-phenylphenyl)thiazol-2-yl]amino]ethyl]benzamide (compound 36)

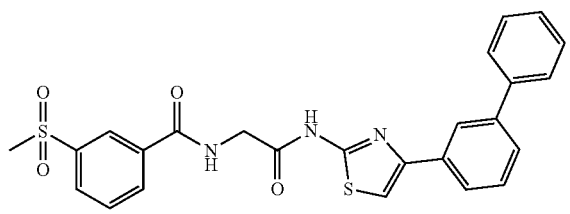

36

To a solution of intermediate i-74c (60.0 mg, 143.44 µmol) and (3-phenylphenyl)boronic acid (85.22 mg, 430.33 µmol) in dioxane (3.0 mL) and H₂O (0.15 mL) were added Pd(t-Bu₃P)₂ (36.65 mg, 71.72 µmol) and DIEA (92.69 mg, 717.21 µmol, 124.92 µL). The mixture was stirred at 100° C. for 2 hrs. The mixture was cooled to 30° C. and a solid formed. The mixture was filtered to give crude product as yellow solid, which was dissolved in MeOH (1.0 mL) and DMSO (1.0 mL) and purified by Pre-HPLC(column: Phenomenex Synergi C18 150*25*10 µm; mobile phase: [water (0.1% TFA)-ACN]; B %: 45%-75%, 9 min) and lyophilized to give compound 36 as a white solid.

¹H NMR (400 MHz, DMSO-d6) δ=12.49 (s, 1H), 9.27-9.25 (m, 1H), 8.46 (s, 1H), 8.25-8.21 (m, 2H), 8.13 (d, J=7.80 Hz, 1H), 7.90 (d, J=7.80 Hz, 1H), 7.81-7.79 (m, 2H), 7.73-7.71 (m, 2H), 7.65-7.60 (m, 1H), 7.54-7.49 (m, 3H), 7.48-7.40 (m, 1H), 4.25 (d, J=5.6 Hz, 2H), 3.29 (s, 3H) ppm LCMS (ESI) m/z: [M+H]⁺=492.0.

Example 75. Preparation of 4-(methanesulfonamido)-N-[(1S)-3-methylsulfanyl-1-[(4-phenylthiazol-2-yl)carbamoyl]propyl]benzamide (compound 38)

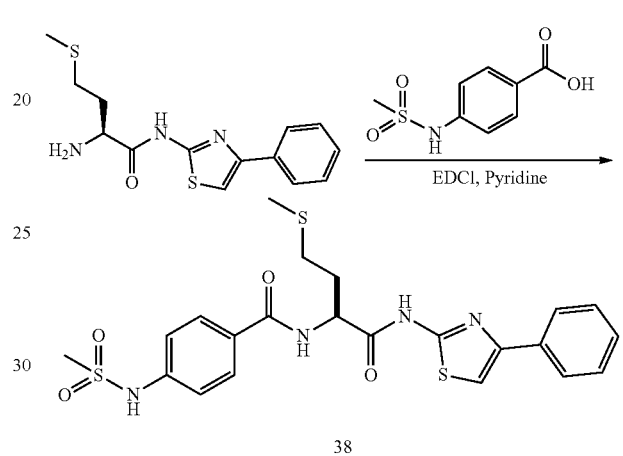

38

To a mixture of (2S)-2-amino-4-methylsulfanyl-N-(4-phenylthiazol-2-yl)butanamide (50.0 mg, 118.64 µmol) and 4-(methanesulfonamido)benzoic acid (30.64 mg, 142.36 µmol) in pyridine (1 mL) was added EDCI (68.23 mg, 355.91 µmol). The mixture was stirred at 30° C. for 2 h. The reaction mixture was concentrated under reduced pressure to give a residue. The residue was purified by Prep-HPLC (column: Boston Green ODS 150*30 5µ; mobile phase: [water (0.1% TFA)-ACN]; B %: 42%-72%, 9 min) and lyophilized to give compound 38 as a white solid.

¹H NMR (400 MHz, MeOD-d₄) δ=7.91-7.88 (m, 4H), 7.40-7.29 (m, 6H), 4.92-4.88 (m, 1H), 3.03 (s, 3H), 2.70-2.63 (m, 2H), 2.30-2.20 (m, 2H), 2.13 (s, 3H) ppm.

LCMS (ESI) m/z: [M+H]⁺=505.3.

Example 76. Preparation of 3-(dimethylsulfamoyl)-N-2-[(4-isopropylthiazol-2-yl)amino]-2-oxoethyl]benzamide (compound 35)

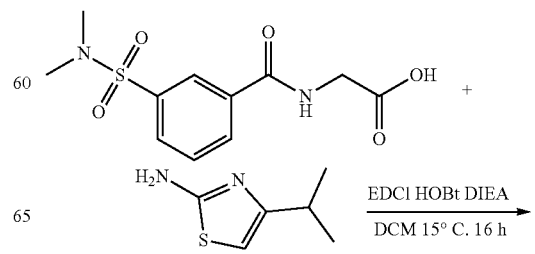

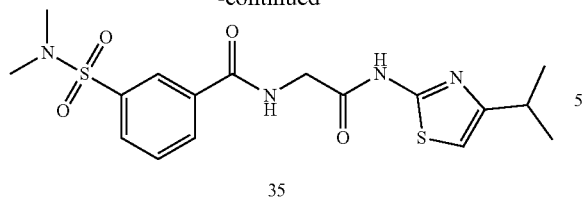

35

To a solution of 2-[[3-(dimethylsulfamoyl)benzoyl]amino]acetic acid (50.0 mg, 174.64 μmol), 4-isopropylthiazol-2-amine (24.84 mg, 174.64 μmol) in DCM (1.0 mL) were added DIEA (67.71 mg, 523.92 μmol, 91.26 μL), EDCI (50.22 mg, 261.96 μmol) and HOBt (35.40 mg, 261.96 μmol). The mixture was stirred at 15° C. for 16 hr. The reaction mixture was concentrated in vacuo to afford a residue. The residue was purified by prep-HPLC (FA conditions) to afford compound 35 as a white solid.

¹HNMR (400 MHz, DMSO-d6) δ=12.26 (br s, 1H), 9.26-9.24 (m, 1H), 8.26-8.22 (m, 2H), 7.94 (d, J=8.0 Hz, 1H), 7.81-7.78 (m, 1H), 6.75 (s, 1H), 4.17 (d, J=5.6 Hz, 2H), 2.96-2.90 (m, 1H), 2.65 (s, 6H), 1.22 (d, J=6.8 Hz, 6H) ppm. LCMS (ESI) m/z: [M+H]⁺=411.1.

Example 77. Preparation of N-[2-[(4-cyclohexylthiazol-2-yl)amino]-2-oxo-ethyl]-3-(dimethylsulfamoyl)benzamide (compound 34)

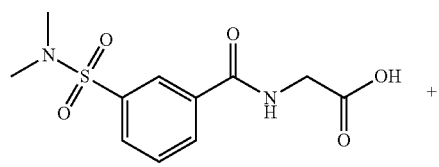 +

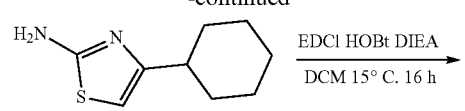

34

To a solution of 2-[[3-(dimethylsulfamoyl)benzoyl]amino]acetic acid (50 mg, 174.64 μmol), 4-cyclohexylthiazol-2-amine (31.83 mg, 174.64 μmol) in DCM (2.0 mL) were added DIEA (67.71 mg, 523.92 μmol, 91.26 μL), EDCI (50.22 mg, 261.96 μmol) and HOBt (35.40 mg, 261.96 μmol). The mixture was stirred at 15° C. for 16 hr. The reaction mixture was concentrated invacuo to afford a residue. The residue was purified by prep-HPLC (FA conditions) to afford compound 34 as a yellow solid.

1H NMR (400 MHz, DMSO-d6) δ=12.23 (br s, 1H), 9.26-9.24 (m, 1H), 8.25-8.21 (m, 2H), 7.94 (d, J=8.0 Hz, 1H), 7.81-7.77 (m, 1H), 6.72 (s, 1H), 4.17 (d, J=5.6 Hz, 2H), 2.64 (s, 6H), 2.59-2.56 (m, 1H), 1.94-1.92 (m, 2H), 1.76-1.73 (m, 3H), 1.39-1.31 (m, 4H), 1.18-1.15 (m, 1H) ppm.

LCMS (ESI) m/z: [M+H]⁺=451.0.

Example 78. Preparation of 3-[2-[[2-[[3-(dimethylsulfamoyl)benzoyl]amino]acetyl]amino]thiazol-4-yl]benzoic acid (compound 33)

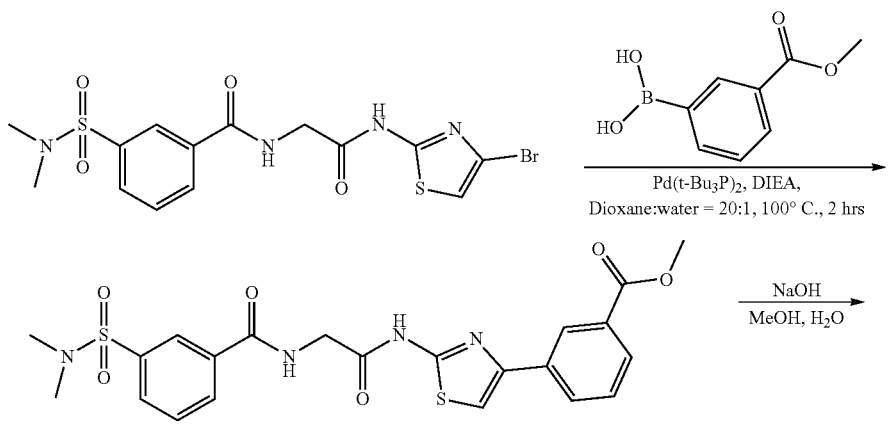

i-78a

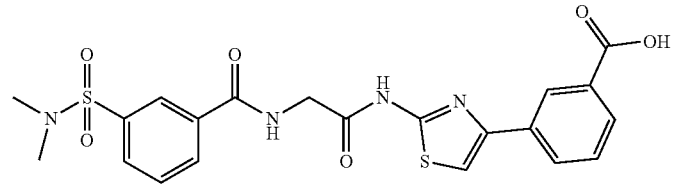

34

Step 1: Preparation of methyl 3-[2-[[2-[[3-(dimethylsulfamoyl)benzoyl]amino]acetyl]amino]thiazol-4-yl]benzoate (intermediate i-78a)

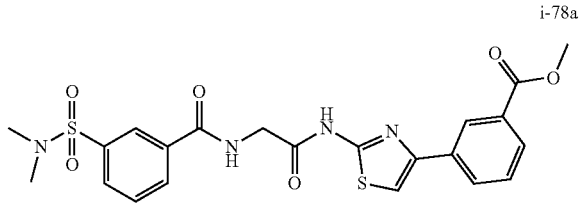

i-78a

To a solution of N-[2-[(4-bromothiazol-2-yl)amino]-2-oxo-ethyl]-3-(dimethylsulfamoyl) benzamide (30.0 mg, 67.07 μmol) and (3-methoxycarbonylphenyl)boronic acid (36.21 mg, 201.21 μmol) in dioxane (2.0 mL) and H$_2$O (0.1 mL) were added Pd(t-Bu$_3$P)$_2$ (17.14 mg, 33.53 μmol) and DIEA (43.34 mg, 335.35 μmol, 58.41 μL) under N$_2$. The mixture was stirred at 100° C. for 2 hrs. A solid was formed upon cooling to 30° C. The solid was filtered and triturated in EtOAc (3 mL), and then dried in vacuum to give intermediate i-78a as a light yellow solid which was used directly in the next step.

LCMS (ESI) m/z: [M+H]$^+$=503.2.

Step 2: Preparation of 3-[2-[[2-[[3-(dimethylsulfamoyl) benzoyl]amino]acetyl]amino]thiazol-4-yl] benzoic acid (compound 34)

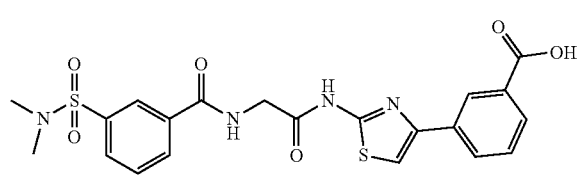

34

To a solution of intermediate i-78a (15.0 mg, 29.85 μmol) in MeOH (2.0 mL) and H$_2$O (1.0 mL) was added NaOH (1.19 mg, 29.85 μmol). The mixture was stirred at 30° C. for 12 hr then diluted with MeOH (10.0 mL) and treated with HCl (1M) to pH 5-6. The mixture was concentrated in vacuo to give a residue. The residue was purified through Pre-HPLC (column: Phenomenex Synergi C18 150*25*10 μm; mobile phase: [water (0.1% TFA)-ACN]; B %: 28%-58%, 9 min) and lyophilized to give compound 34 as an off-white solid.

$^1$H NMR (400 MHz, DMSO-d6) δ 13.02 (br s, 1H), 12.53 (s, 1H), 9.31-9.30 (m, 1H), 8.54 (s, 1H), 8.27-8.24 (m, 2H), 8.13 (d, J=8.0 Hz, 1H), 7.94 (d, J=7.6 Hz, 1H), 7.90 (d, J=7.60 Hz, 1H), 7.83-7.81 (m, 2H), 7.77-7.57 (m, 1H), 4.25 (d, J=5.6 Hz, 2H), 2.66 (s, 6H) ppm.

LCMS (ESI) m/z: [M+H]$^+$=488.9.

Example 79. Preparation of 3-(hydroxymethyl)-N-[(1S)-3-methylsulfanyl-1-[(4-phenylthiazol-2-yl)carbamoyl]propyl]benzamide (compound 84)

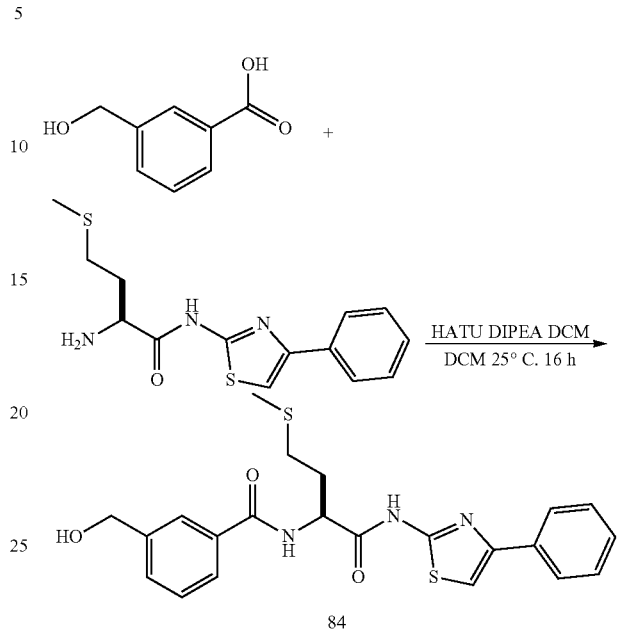

84

To a solution of 3-(hydroxymethyl)benzoic acid (14.85 mg, 97.58 μmol) and (2S)-2-amino-4-methylsulfanyl-N-(4-phenylthiazol-2-yl)butanamide (30.00 mg, 97.58 μmol) in DCM (0.5 mL) were added DIPEA (37.83 mg, 292.75 μmol) and HATU (55.66 mg, 146.37 μmol) at 25° C. The mixture was stirred at 25° C. for 16 hr. The reaction mixture was concentrated under reduced pressure to give a residue. The residue was purified by prep-HPLC (FA condition) to afford compound 84 as a white solid.

LCMS (ESI) m/z: [M+H]$^+$=442.1.

$^1$HNMR (400 MHz, METHANOL-d4): δ=7.90-7.88 (m, 3H), 7.80 (d, J=8.0 Hz, 1H), 7.56 (d, J=7.6 Hz, 1H), 7.48-7.46 (m, 1H), 7.40-7.36 (m, 3H), 7.29 (m, 1H), 4.94-4.90 (m, 1H), 4.68 (m, 2H), 2.71-2.64 (m, 2H), 2.28-2.22 (m, 2H), 2.13 (s, 3H) ppm.

Example 80. Preparation of 4-(hydroxymethyl)-N-[(1S)-3-methylsulfanyl-1-[(4-phenylthiazol-2-yl)carbamoyl]propyl]benzamide (compound 85)

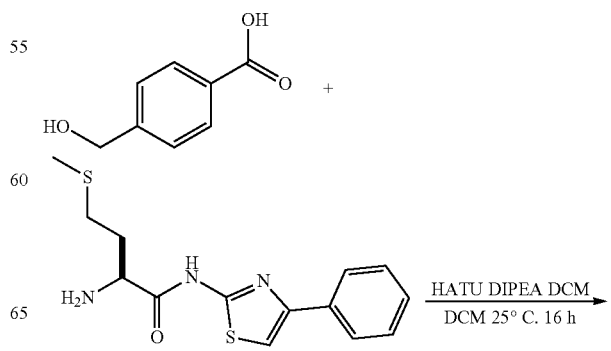

243
-continued

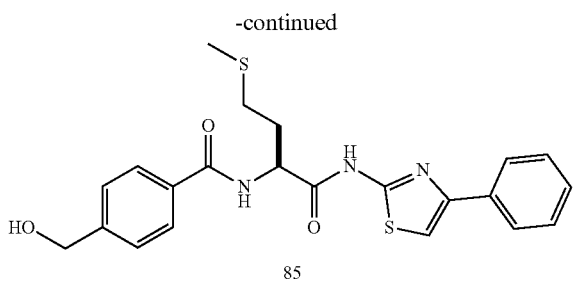

85

To a solution of 4-(hydroxymethyl)benzoic acid (14.85 mg, 97.58 μmol) and (2S)-2-amino-4-methylsulfanyl-N-(4-phenylthiazol-2-yl)butanamide (30.00 mg, 97.58 μmol) in DCM (0.5 mL) were added DIPEA (37.83 mg, 292.75 μmol) and HATU (55.66 mg, 146.37 μmol) at 25° C. The mixture was stirred at 25° C. for 16 hr. The reaction mixture was concentrated under reduced pressure to give a residue. The residue was purified by prep-HPLC (FA condition) to afford compound 85 as a white solid.

¹HNMR (DMSO-d6, 400 MHz): 5=12.37 (br s, 1H), 8.68 (d, J=7.2 Hz, 1H), 7.92-7.89 (m, 4H), 7.63 (s, 1H), 7.45-7.42 (m, 4H), 7.35-7.33 (m, 1H), 5.32 (br s, 1H), 4.79-4.73 (m, 1H), 4.57 (m, 2H), 2.59-2.50 (m, 3H), 2.15-2.10 (m, 5H) ppm.

LCMS (ESI) m/z: [M+H]⁺=441.9.

Example 81. Preparation of 4-amino-N-[(1S)-1-methyl-2-oxo-2-[(4-phenylthiazol-2-yl)amino]ethyl]benzamide (compound 82)

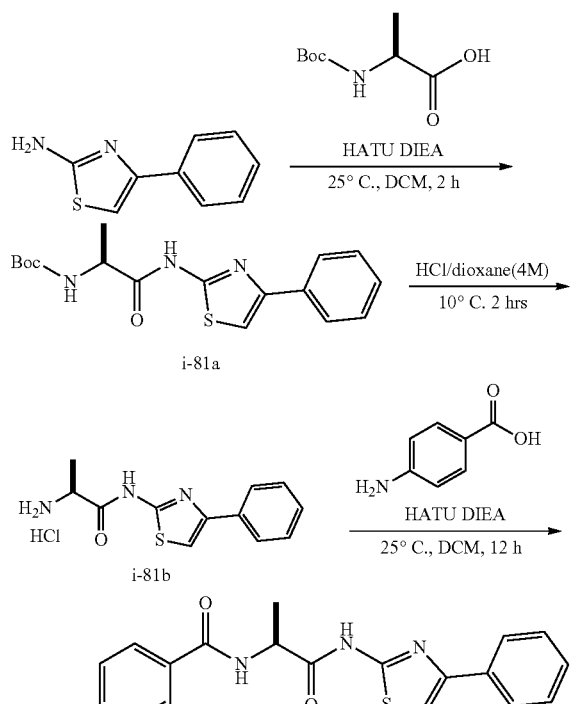

244

Step 1: Preparation of tert-butyl N-[(1S)-1-methyl-2-oxo-2-[(4-phenylthiazol-2-yl)amino]ethyl]carbamate (intermediate i-81a)

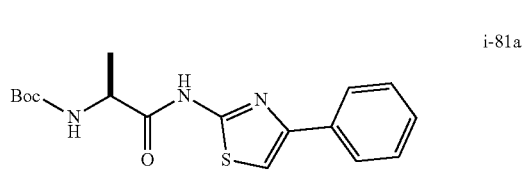 [SMILES: C[C@H](NC(=O)OC(C)(C)C)C(=O)Nc1nc(-c2ccccc2)cs1]

i-81a

To a mixture of 4-phenylthiazol-2-amine (200.0 mg, 1.13 mmol) and (2S)-2-(tert-butoxycarbonylamino)propanoic acid (214.72 mg, 1.13 mmol) in DCM (2.0 mL) were added DIPEA (440.00 mg, 3.40 mmol) and HATU (647.24 mg, 1.70 mmol) in one portion at 25° C. under N₂. The mixture was stirred at 25° C. for 2 hrs. The mixture was poured into water (10.0 mL) and stirred for 5 min. The aqueous phase was extracted with DCM (10.0 mL*2). The combined organic extracts were washed with brine (10.0 mL), dried over anhydrous Na₂SO₄, filtered and concentrated in vacuum to afford Intermediate i-81a as light yellow oil which was used in the next step without purification.

LCMS (ESI) m/z: [M+H]⁺=348.1.

Step 2: Preparation of (S)-2-amino-N-(4-phenylthiazol-2-yl)propanamide hydrochloride (intermediate i-81b)

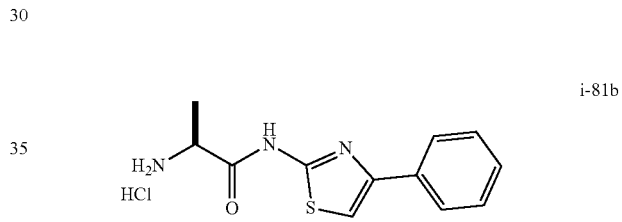

To a mixture of Intermediate i-81a (500 mg, 1.44 mmol) in dioxane (5.0 mL) was added HCl/dioxane (4 M, 1.80 mL) in one portion at 25° C. The mixture was stirred at 25° C. for 30 min and a solid precipitated. The mixture was filtered and the filter cake was washed with EtOAc (10 mL). Then the solid was dried in vacuum to give intermediate i-81b (HCl salt) as a white solid.

¹H NMR (400 MHz, D₂O) δ=7.84-7.79 (m, 1H), 7.49-7.43 (m, 1H), 4.39-4.35 (m, 1H), 2.80 (s, 1H), 1.67 (d, J=6.8 Hz, 3H).

Chiral HPLC: OD-3_5CM_MeOH (DEA)_5_40_3 ML_T35.

LCMS (ESI) m/z: [M+H]⁺=248.1.

Step 3: Preparation 4-amino-N-[(1S)-1-methyl-2-oxo-2-[(4-phenylthiazol-2-yl)amino]ethyl]benzamide (compound 82)

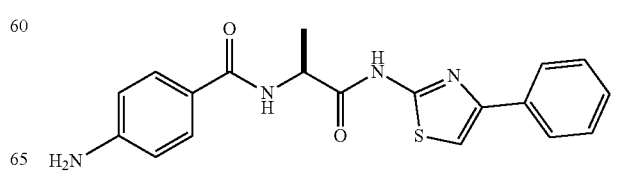

To a mixture of Intermediate i-81b (50 mg, 176.19 μmol) and 4-aminobenzoic acid (24.16 mg, 176.19 μmol) in DCM (1.0 mL) were added DIPEA (91.09 mg, 704.78 μmol) and HATU (100.49 mg, 264.29 μmol) in one portion at 25° C. The mixture was stirred at 25° C. for 12 hr. The mixture was concentrated in vacuum to afford a residue. The residue was purified by reverse phase column (FA conditions) to afford compound 82 as a white solid.

$^1$H NMR (400 MHz, METHANOL-d4) δ=7.88 (d, J=7.2 Hz, 2H), 7.69 (d, J=8.6 Hz, 2H), 7.40-7.37 (m, 3H), 7.31-7.27 (m, 1H), 6.68 (d, J=8.6 Hz, 2H), 4.77-4.72 (m, 1H), 1.56 (d, J=7.2 Hz, 3H) ppm.

LCMS (ESI) m/z: [M+H]$^+$=367.0.

Chiral HPLC: Amycoat_MeOH+CAN(DEA)_40_3 mL-35 T, 1.474 min.

Example 82. Preparation of 4-(methylamino)-N-[(1S)-3-methylsulfanyl-1-[(4-phenylthiazol-2-yl)carbamoyl]propyl]benzamide (compound 81)

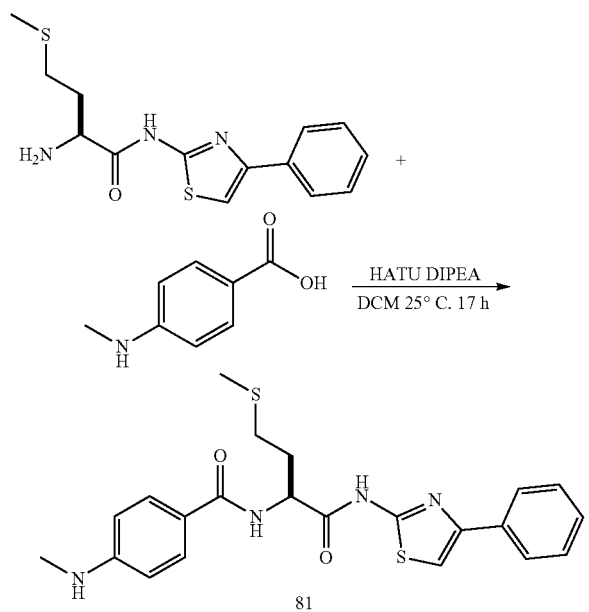

To a solution of 4-(methylamino)benzoic acid (10.76 mg, 71.18 μmol) in DCM (0.5 mL) were added DIPEA (27.60 mg, 213.55 μmol) and HATU (40.60 mg, 106.77 μmol) at 25° C. The mixture was stirred at 25° C. for 1 hr. To the reaction mixture was added (2S)-2-amino-4-methylsulfanyl-N-(4-phenylthiazol-2-yl)butanamide (30 mg, 71.18 μmol). The reaction mixture was stirred at 25° C. for 16 hr. Then the mixture was concentrated under reduced pressure to give a residue. The residue was purified through reverse phase-HPLC (FA condition) and followed by prep-TLC (PE/EA=1/1) to afford compound 81 as a white solid.

$^1$H NMR (400 MHz, METHANOL-d4) δ=7.89 (d, J=7.6 Hz, 2H), 7.74 (d, J=8.4 Hz, 2H), 7.40 (m, 3H), 7.30 (m, 1H), 6.61 (d, J=8.8 Hz, 2H), 4.89 (m, 1H), 2.81 (s, 3H), 2.69 (m, 2H), 2.26 (m, 2H), 2.12 (s, 3H) ppm.

LCMS (ESI) m/z: [M+H]+=441.0.

Chiral HPLC: Cellucoat-MeOH+ACN(DEA)-40-5 min-3 mL-35T, 1.895 min.

Example 83. Preparation of N-[(1S)-3-methylsulfanyl-1-[(4-phenylthiazol-2-yl)carbamoyl]propyl]indoline-5-carboxamide (compound 80)

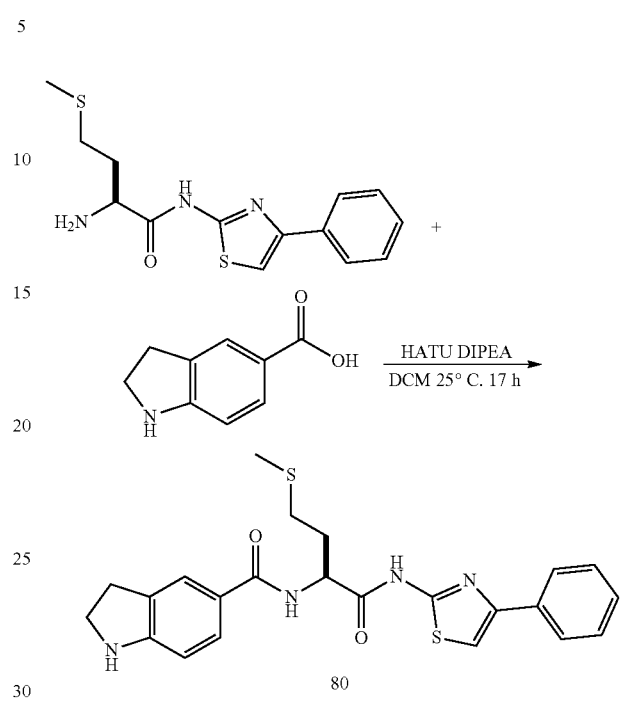

To a solution of indoline-5-carboxylic acid (11.61 mg, 71.18 μmol) in DCM (0.5 mL) were added DIPEA (27.60 mg, 213.55 μmol) and HATU (40.60 mg, 106.77 μmol) at 25° C. The mixture was stirred at 25° C. for 1 hr and then (2S)-2-amino-4-methylsulfanyl-N-(4-phenylthiazol-2-yl)butanamide (30.0 mg, 71.18 μmol) was added. The reaction mixture was stirred at 25° C. for 16 hr. The reaction mixture was concentrated in vacuum to give a residue. The residue was purified through reverse phase-HPLC (FA condition) and followed by prep-TLC (PE/EA=1/1) to afford compound 80 as a white solid.

$^1$HNMR (400 MHz, MeOD) δ=7.88-7.86 (m, 2H), 7.63-7.59 (m, 2H), 7.39-7.36 (m, 3H), 7.28-7.26 (m, 1H), 6.58-6.52 (m, 1H), 4.89-4.86 (m, 1H), 3.59-3.54 (m, 2H), 3.04-3.00 (m, 2H), 2.68-2.63 (m, 2H), 2.20-2.12 (m, 2H), 2.11 (s, 3H) ppm.

LCMS (ESI) m/z: [M+H]$^+$=453.0.

Chiral HPLC: Cellucoat-MeOH+ACN(DEA)-40-5 min-3 mL-35T, 1.444 min.

Example 84. Preparation of (S)—N-(4-(methylthio)-1-oxo-1-((4-phenylthiazol-2-yl)amino)butan-2-yl)-1H-indole-5-carboxamide (compound 83)

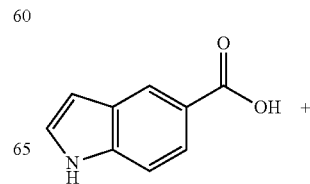

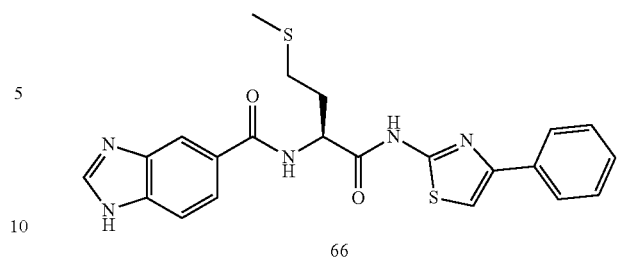

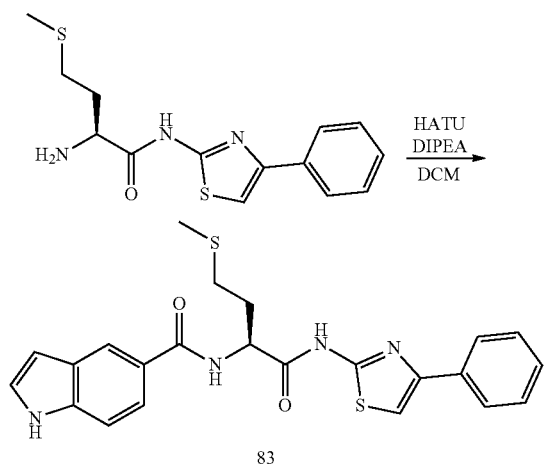

83

To a solution of 1H-indole-5-carboxylic acid (19.12 mg, 118.64 μmol) in DCM (1.0 mL) were added DIPEA (46.00 mg, 355.91 μmol), HATU (67.66 mg, 177.95 μmol) and followed by (2S)-2-amino-4-methylsulfanyl-N-(4-phenylthiazol-2-yl)butanamide (36.47 mg, 118.64 μmol). The reaction mixture was stirred at 30° C. for 2 hr. Then the reaction mixture was poured into water (5.0 mL) and extracted by EtOAc (5.0 mL×2). The combined organic layers were washed with brine, dried over anhydrous sodium sulfate, filtered and concentrated to give a residue. The residue was purified by prep-HPLC (FA condition) to afford compound 83 as a brown solid.

1H NMR (400 MHz, DMSO-d6) δ=12.43 (br s, 1H), 11.34 (s, 1H), 8.56 (d, J=7.2 Hz, 1H), 8.24 (s, 1H), 7.91-7.89 (m, 2H), 7.70-7.68 (m, 1H), 7.63 (s, 1H), 7.44-7.41 (m, 4H), 7.32-7.31 (m, 1H), 6.56 (s, 1H), 4.79-4.74 (m, 1H), 2.68-2.65 (m, 1H), 2.59-2.55 (m, 1H), 2.14-2.12 (m, 2H), 2.10 (s, 3H) ppm.

LCMS (ESI) m/z: [M+H]⁺=451.3.

Chiral SFC: OD-3_5 CM_MeOH (DEA)_40_3 ML_T35.M, 2.392 min.

Example 85. Preparation of (S)—N-(4-(methylthio)-1-oxo-1-((4-phenylthiazol-2-yl)amino)butan-2-yl)-1H-benzo[d]imidazole-5-carboxamide (compound 66)

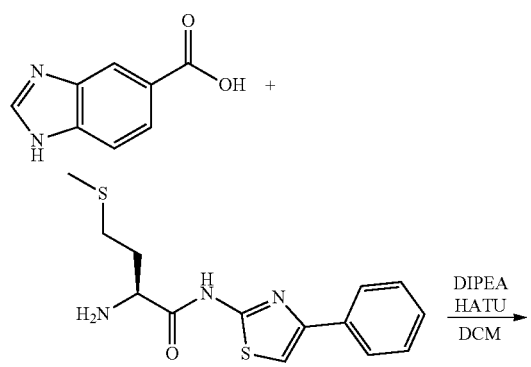

66

To a solution of 1H-benzimidazole-5-carboxylic acid (19.24 mg, 118.64 μmol) in DCM (1.0 mL) were added DIPEA (46.00 mg, 355.91 μmol), HATU (67.66 mg, 177.95 μmol) and then (2S)-2-amino-4-methylsulfanyl-N-(4-phenylthiazol-2-yl)butanamide (36.47 mg, 118.64 μmol) was added. The reaction mixture was stirred at 30° C. for 2 hrs. The reaction mixture was poured into water (5.0 mL) and extracted with EtOAc (5.0 mL×2). The combined organic extracts were washed with brine, dried over anhydrous sodium sulfate, filtered and concentrated to give a residue. The residue was purified by prep-HPLC (FA condition) to afford compound 66 as a yellow solid.

¹H NMR (400 MHz, DMSO-d6) δ=12.50 (br s, 1H), 8.73 (d, J=7.2 Hz, 1H), 8.34 (s, 1H), 8.25 (s, 1H), 7.91-7.81 (m, 2H), 7.80-7.79 (m, 1H), 7.62-7.61 (m, 2H), 7.44-7.40 (m, 2H), 7.32-7.31 (m, 1H), 4.80-4.75 (m, 1H), 2.68-2.65 (m, 1H), 2.59-2.56 (m, 1H), 2.17-2.14 (m, 2H), 2.10 (s, 3H) ppm.

LCMS (ESI) m/z: [M+H]⁺=452.3.

Chiral SFC: Cellucoat-MeOH (DEA)-40-3 mL-35 T, 0.942 min.

Example 86. Synthesis of Compound 87

Compound 87 was synthesized by the method illustrated in the below scheme:

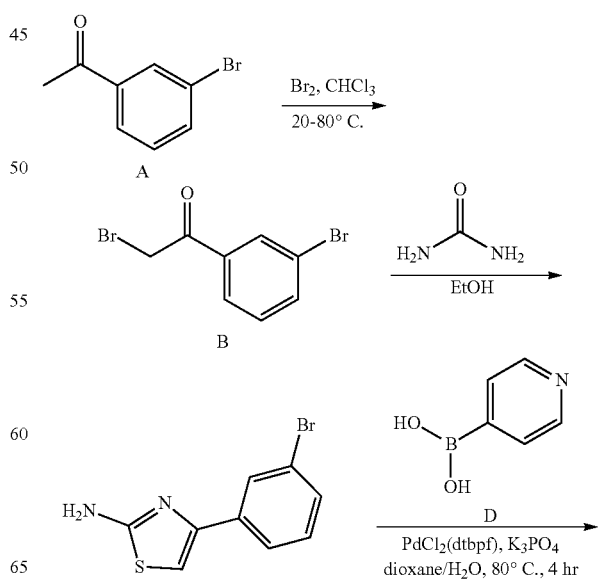

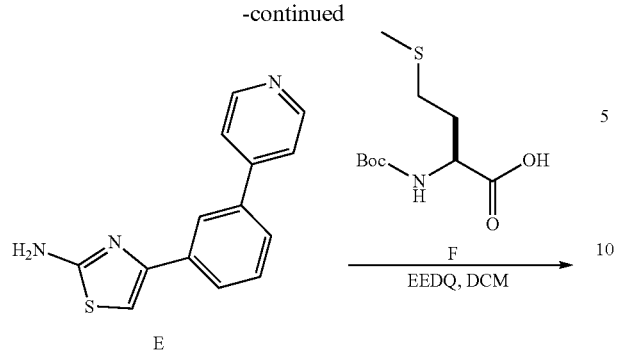
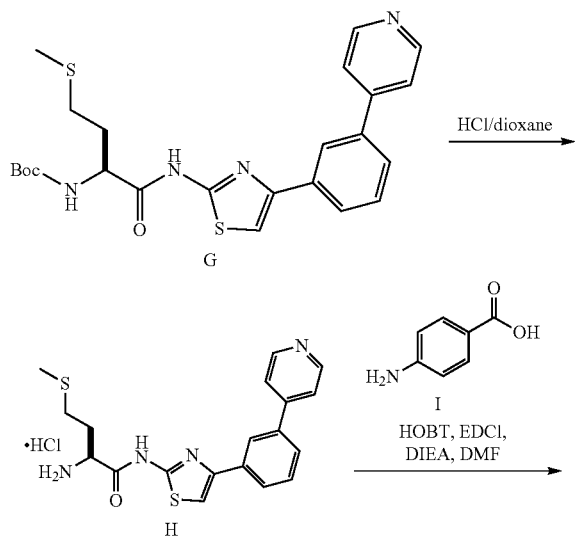
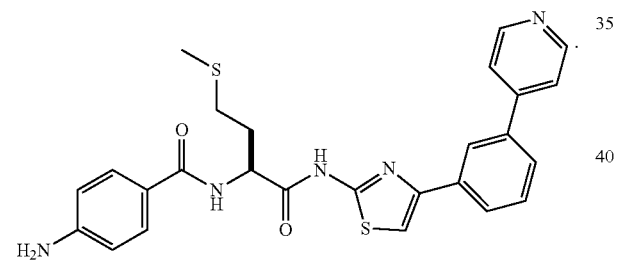
Preparation of (S)-4-amino-N-(4-(methylthio)-1-oxo-1-((4-(3-(pyridin-4-yl)phenyl)thiazol-2-yl)amino)butan-2-yl)benzamide (Compound 87)
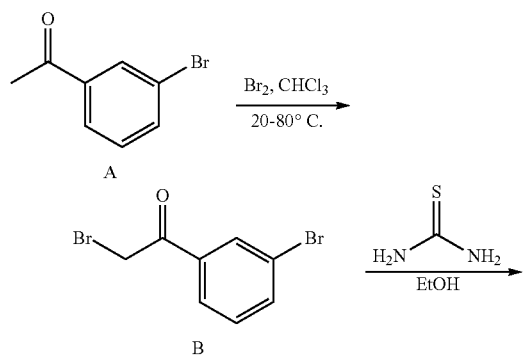
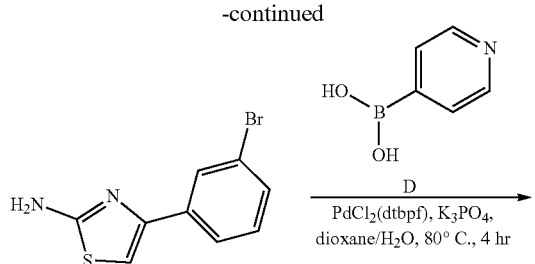
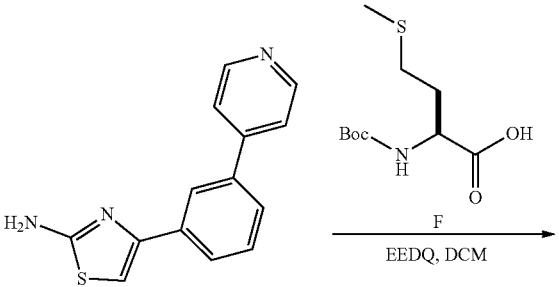
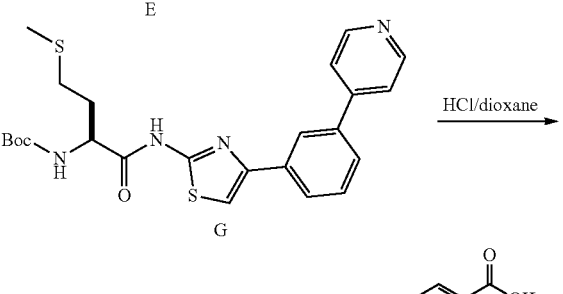
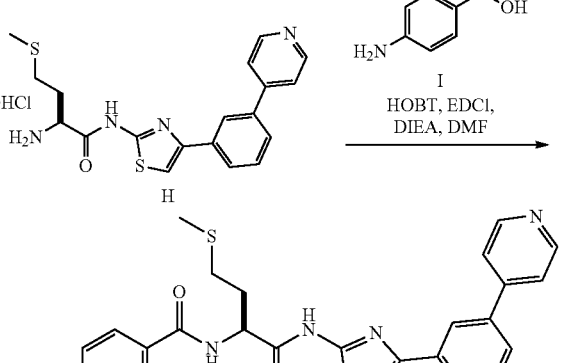
Compound 87
Step 1: Preparation of 2-bromo-1-(3-bromophenyl)ethenone (Intermediate B)
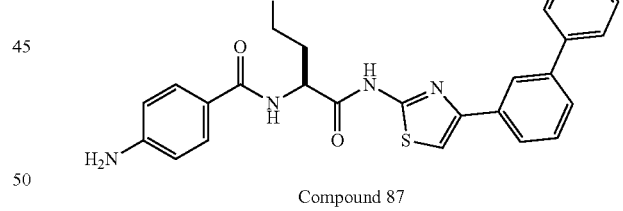
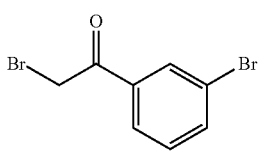
B To a solution of 1-(3-bromophenyl)ethanone (200 g, 1.00 mol, 132.45 mL) in CHCl₃ (250 mL) was added Br₂ (240.86 g, 1.51 mol, 77.70 mL) under N₂ dropwise at 20° C. The mixture was stirred at 80° C. for 1 hr. The reaction mixture was concentrated to give intermediate B (279.27 g, crude) as yellow oil, which was used for next step directly.

Step 2: Preparation of 4-(3-bromophenyl)thiazol-2-amine (Intermediate C)

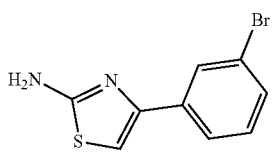

C

To a solution of thiourea (229.23 g, 3.01 mol) in EtOH (1.5 L) was added intermediate B (279 g, 1.00 mol). The mixture was stirred at 85° C. for 2 hr. Then the mixture was concentrated in vacuum to give a residue. The residue was poured into NaHCO₃ (2 L) solution to adjust pH to 8, then the solution was extracted with EA (2 L*3). The combined organic layers were washed with brine (4 L), dried over Na₂SO₄ and filtered. The filtrate was concentrated to give a residue. The residue was purified by column chromatography (SiO₂. PE:EA=5:1) to give intermediate C (130 g, 494.40 mmol, 49.25% yield) as a yellow solid. LCMS (ESI) m/z: [M+H]⁺=257.0. ¹H NMR (400 MHz, DMSO-d6) δ=7.98 (m, 1H), 7.79 (d, J=8.0 Hz, 1H), 7.44-7.42 (m, 1H), 7.33-7.29 (m, 1H), 7.14 (s, 1H), 7.09 (s, 2H) ppm.

Step 3: Preparation of 4-[3-(4-pyridyl)phenyl]thiazol-2-amine (Intermediate E)

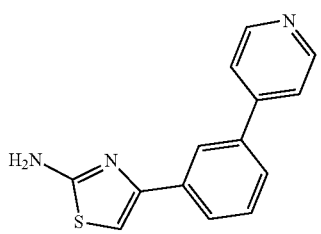

E 4-(3-bromophenyl)thiazol-2-amine (20 g, 78.40 mmol), 4-pyridylboronic acid (28.9 g, 239.18 mmol), ditert-butyl (cyclopentyl)phosphane;dichloropalladium;iron (2.56 g, 3.92 mmol) and K₃PO₄ (66.56 g, 313.56 mmol) were taken up in dioxane (240 mL) and H₂O (24 mL). The mixture was purged with N₂ three times and then stirred at 80° C. for 7 hr. Water (800 mL) was added and the mixture was extracted with EtOAc (800 mL*3). The combined organic layers were washed with brine, dried over anhydrous Na₂SO₄, filtered and concentrated under vacuum. The residue was added into DCM (30 mL) and MTBE (100 mL) and then stirred for 5 min. The precipitate was collected through filtration and washed with MTBE (10 mL) to give the intermediate E (16.2 g, 61.17 mmol, 78.03% of yield) as a yellow solid. LCMS (ESI) m/z: [M+H]⁺=254.0.

Step 4: Preparation of tert-butyl N-[(1S)-3-methylsulfanyl-1-[[4-[3-(4-pyridyl)phenyl]thiazol-2-yl]carbamoyl]propyl]carbamate (Intermediate G)

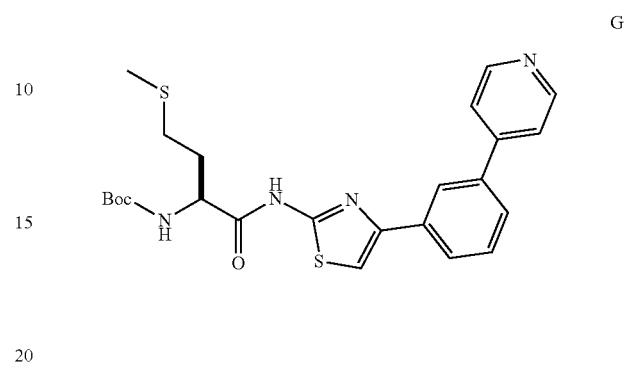

G

To a mixture of intermediate E (12.6 g, 49.74 mmol) and (2S)-2-(tert-butoxycarbonylamino)-4-methylsulfanyl-butanoic acid (18.6 g, 74.61 mmol) in DCM (900 mL) was added EEDQ (24.6 g, 99.48 mmol) and the mixture was stirred at 25° C. for 2 hr. The solvent was removed in vacuum. The residue was triturated with DCM (100 mL) followed by MeOH (200 mL) to give the intermediate G (11.7 g, 23.73 mmol, 47.71% yield, ee %=99.44%) as a white solid. LCMS (ESI) m/z: [M+H]⁺=485.1. ¹H NMR (400 MHz, DMSO) δ=12.39 (s, 1H), 8.68-8.66 (m, 2H), 8.30 (s, 1H), 8.02-7.99 (m, 1H), 7.83 (s, 1H), 7.76-7.74 (m, 3H), 7.61-7.57 (m, 1H), 7.28 (d, J=7.6 Hz, 1H), 4.31-4.30 (m, 1H), 2.65-2.44 (m, 2H), 2.06 (s, 3H) 2.01-1.85 (m, 2H), 1.38 (s, 9H) ppm. Note: The key point of this reaction is the concentration. (1 mmol E with 17-18 mL DCM was the best condition)

Step 5: Preparation of (2S)-2-amino-4-methylsulfanyl-N-[4-[3-(4-pyridyl)phenyl]thiazol-2-yl]butanamide (Intermediate H)

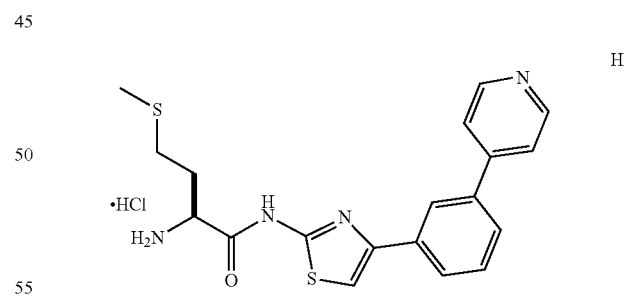

H

A mixture of intermediate G (11.5 g, 23.73 mmol) in MeOH (50 mL) was added HCl/dioxane (4 M, 100 mL) and the mixture was stirred at 25° C. for 1 hr. The mixture was poured into MTBE (1000 mL) and the precipitate was collected by filtration to give the intermediate H (9.99 g, 23.73 mmol, 100.00% yield, HCl salt) as a yellow solid. LCMS (ESI) m/z: [M+H]⁺=385.0

Step 6: Preparation of 4-amino-N-[(1S)-3-methyl-sulfanyl-1-[[4-[3-(4-pyridyl)phenyl]thiazol-2-yl]carbamoyl]propyl]benzamide (Intermediate E)

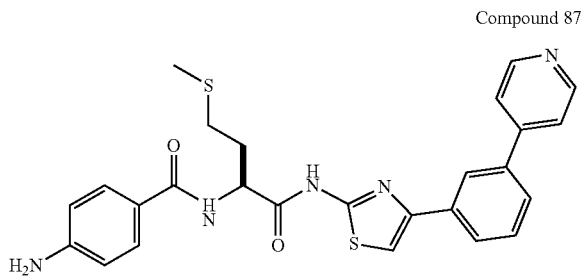 [SMILES: CSCC[C@H](NC(=O)c1ccc(N)cc1)C(=O)Nc1nc(-c2cccc(-c3ccncc3)c2)cs1]

Compound 87

To a mixture of intermediate H (4 g, 9.50 mmol) and 4-aminobenzoic acid (1.30 g, 9.50 mmol) in DMF (40 mL) was added DIEA (4.91 g, 38.01 mmol, 6.62 mL), EDCI (2.73 g, 14.25 mmol) and HOBt (1.93 g, 14.25 mmol). The solution was stirred at 25° C. for 14 hr and then poured into water (200 mL) and the precipitate was collected by filtration. The solid was triturated in MeOH (200 mL) (a gelatinous solid was formed). The precipitate was collected by filtration and the solid was further purified by column chromatography (SiO$_2$, DCM:MeOH=80:1-20:1) to give Compound 87 (2.13 g, 4.19 mmol, 44.11% yield, ee %=99.28%) as a white solid. LCMS (ESI) m/z: [M+H]$^+$ =504.0. $^1$H NMR (400 MHz, DMSO) δ=12.40 (s, 1H), 8.68-8.66 (m, 2H), 8.31-8.30 (m, 1H), 8.22 (d, J=7.2 Hz, 1H), 8.02-7.99 (m, 1H), 7.82 (s, 1H), 7.76-7.74 (m, 3H), 7.67-7.63 (m, 2H), 7.61-7.57 (m, 1H), 6.58-6.54 (m, 2H), 5.67 (s, 2H), 4.72-4.67 (m, 1H), 2.65-2.54 (m, 2H), 2.12-2.06 (in, 5H) ppm.

Example 87. Experimental Data for Compounds of the Invention

| # | Compound Name | LCMS m/z: M + H | HNMR |
|---|---|---|---|
| 88 | 3-(methylsulfonyl)-N-(2-oxo-2-((4-(1-oxo-1,2-dihydroisoquinolin-7-yl)thiazol-2-yl)amino)ethyl)benzamide | 483.1 | $^1$H NMR (400 MHz, DMSO-d6) δ = 12.57 (br s, 1H), 11.25 (br s, 1H), 9.29 (br s, 1H), 8.78 (br s, 1H), 8.46 (br s, 1H), 8.32-8.13 (m, 3H), 7.79-7.71 (m, 3H), 7.19 (br s, 1H), 6.56 (br s, 1H), 4.25 (br s, 2H), 3.29 (br s, 3H) ppm. |
| 89 | 3-(methylsulfonyl)-N-(2-oxo-2-((4-(3-(pyridin-4-yl)phenyl)thiazol-2-yl)amino)ethyl)benzamide | 493.0 | 1H NMR (400 MHz, DMSO-d6) δ = 12.50 (br s, 1H), 9.26 (br s, 1H), 8.68 (br s, 2H), 8.46 (br s, 1H), 8.31 (br s, 1H), 8.24 (br d, J = 8.4 Hz, 1H), 8.13 (br d, J = 6.8 Hz, 1H), 8.02 (br d, J = 7.6 Hz, 1H), 7.85-7.76 (m, 5H), 7.62-7.58 (m, 1H), 4.26 (br d, J = 4.8 Hz, 2H), 3.29 (br s, 3H) ppm. |
| 90 | 3-(methylsulfonyl)-N-(2-oxo-2-((4-(3-(pyrimidin-4-yl)phenyl)thiazol-2-yl)amino)ethyl)benzamide | 494.1 | 1H NMR (400 MHz, DMSO-d6) δ = 12.59 (br s, 1H), 9.29 (br s, 2H), 8.91-8.82 (m, 2H), 8.45 (br s, 1H), 8.25-8.09 (m, 5H), 7.82 (br s, 2H), 7.62 (br s, 1H), 4.25 (br s, 2H), 3.28 (br s, 3H) ppm |
| 91 | 3-(methylsulfonyl)-N-(2-oxo-2-((4-(3-(tetrahydro-2H-pyran-4-yl)phenyl)thiazol-2-yl)amino)ethyl)benzamide | 500.1 | 1H NMR (400 MHz, DMSO-d6) δ = 12.46 (br s, 1H), 9.27-9.24 (m, 1H), 8.45 (s, 1H), 8.23 (d, J = 8.0 Hz, 1H), 8.12 (d, J = 8.0 Hz, 1H), 7.82-7.78 (m, 2H), 7.73 (d, J = 8.0 Hz, 1H), 7.65 (s, 1H), 7.38-7.34 (m, 1H), 7.22 (d, J = 7.60 Hz, 1H), 4.24 (d, J = 6.0 Hz, 2H), 3.98-3.95 (m, 2H), 3.48-3.42 (m, 2H), 3.28 (s, 3H), 2.85-2.77 (m, 1H), 1.74-1.65 (m, 4H) ppm |
| 92 | N-(2-((4-(2,3-dihydrobenzo[b][1,4]dioxin-6-yl)thiazol-2-yl)amino)-2-oxoethyl)-3-(methylsulfonyl)benzamide | 474.3 | 1H NMR (400 MHz, DMSO-d6) δ = 12.40 (br s, 1H), 9.25-9.23 (m, 1H), 8.45-8.44 (m, 1H), 8.23 (d, J = 8.0 Hz, 1H), 8.15-8.10 (m, 1H), 7.82-7.80 (m, 1H), 7.47 (s, 1H), 7.40-7.34 (m, 2H), 6.89 (d, J = 8.2 Hz, 1H), 4.27 (s, 4H), 4.23 (d, J = 5.8 Hz, 2H), 3.28 (s, 3H) ppm |
| 93 | N-(2-((4-(3-methyl-4-oxo-3,4-dihydroquinazolin-6-yl)thiazol-2-yl)amino)-2-oxoethyl)-3-(methylsulfonyl)benzamide | 498.0 | 1H NMR (400 MHz, DMSO-d6) δ = 12.57 (s, 1H), 9.27-9.25 (m, 1H), 8.73 (d, J = 2.0 Hz, 1H), 8.46-8.45 (m, 1H), 8.37 (s, 1H), 8.34-7.32 (m, 1H), 8.24 (d, J = 7.6 Hz, 1H), 8.13 (d, J = 8.4 Hz, 1H), 7.85 (s, 1H), 7.82-7.79 (m, 1H), 7.72 (d, J = 8.4 Hz, 1H), 4.26 (d, J = 6.0 Hz, 2H), 3.51 (s, 3H), 3.28 (s, 3H) ppm |

-continued

| # | Compound Name | LCMS m/z: M + H | HNMR |
|---|---|---|---|
| 94 | N-(2-((4-(3-(methylsulfonamidomethyl)phenyl)thiazol-2-yl)amino)-2-oxoethyl)-3-(methylsulfonyl)benzamide | 523.3 | 1H NMR (400 MHz, DMSO) δ = 12.31 (br s, 1H), 9.25 (br s, 1H), 8.45 (s, 1H), 8.24 (d, J = 7.2 Hz, 1H), 8.12 (d, J = 7.2 Hz, 1H), 7.92 (s, 1H), 7.81 (d, J = 7.6 Hz, 2H), 7.62 (s, 1H), 7.58 (br s, 1H), 7.41-7.40 (m, 1H), 7.30 (d, J = 7.2 Hz, 1H), 4.23 (d, J = 5.2 Hz, 2H), 4.20 (d, J = 4.8 Hz, 2H), 3.28 (s, 3H), 2.89 (s, 3H) ppm |
| 95 | N-(2-oxo-2-((4-(3-(pyridin-4-yl)phenyl)thiazol-2-yl)amino)ethyl)indoline-5-carboxamide | 456.2 | 1H NMR (400 MHz, DMSO) δ = 12.39 (s, 1H), 8.88 (d, J = 6.4 Hz, 2H), 8.48-8.47 (m, 1H), 8.42 (s, 1H), 8.18 (br d, J = 6.0 Hz, 2H), 8.11 (d, J = 8.0 Hz, 1H), 7.94-7.84 (m, 2H), 7.68-7.67 (m, 1H), 7.63-7.53 (m, 2H), 6.53 (d, J = 8.0 Hz, 1H), 4.15-4.13 (m, 2H), 3.02-2.96 (m, 1H), 2.98 (m, 2H), 2.55 (br s, 2H) ppm |
| 96 | N-(2-oxo-2-((4-(3-(pyridin-4-yl)phenyl)thiazol-2-yl)amino)ethyl)-1H-indazole-5-carboxamide | 455.2 | 1H NMR (400 MHz, DMSO) δ = 13.37 (s, 1H), 12.54 (s, 1H), 9.00 (s, 1H), 8.75-8.74 (m, 2H), 8.47 (s, 1H), 8.37 (s, 1H), 8.31 (s, 1H), 8.09-8.07 (m, 1H), 7.91-7.90 (m, 1H), 7.85 (s, 1H), 7.83-7.82 (m, 3H), 7.69-7.66 (m, 2H), 4.30-4.28 (m, 2H) ppm |
| 97 | (S)-N-(4-(methylthio)-1-oxo-1-((4-(3-(pyridin-4-yl)phenyl)thiazol-2-yl)amino)butan-2-yl)benzamide | 489.2 | 1H NMR (400 MHz, DMSO) δ = 12.55 (s, 1H), 8.77 (d, J = 7.2 Hz, 1H), 8.71-8.65 (m, 2H), 8.32 (s, 1H), 8.02 (d, J = 8.0 Hz, 1H), 7.97-7.92 (m, 2H), 7.85 (s, 1H), 7.80-7.75 (m, 3H), 7.63-7.55 (m, 2H), 7.54-7.47 (m, 1H), 7.54-7.47 (m, 1H), 4.80-4.75 (m, 1H), 2.60-2.57 (m, 2H), 2.18-2.12 (m, 2H), 2.11 (s, 3H) ppm |
| 98 | 3-(methylsulfonyl)-N-(2-oxo-2-((4-(3-(thiazol-2-yl)phenyl)thiazol-2-yl)amino)ethyl)benzamide | 498.9 | 1H NMR (400 MHz, DMSO) δ = 12.57 (s, 1H), 9.28-9.25 (m, 1H), 8.55-8.54 (m, 1H), 8.45 (d, J = 1.6 Hz, 1H), 8.24 (d, J = 8.0 Hz, 1H), 8.12 (d, J = 8.4 Hz, 1H), 8.01 (d, J = 8.0 Hz, 1H), 7.96 (d, J = 3.2 Hz, 1H), 7.92-7.90 (m, 1H), 7.82-7.79 (m, 3H), 7.59-7.55 (m, 1H), 4.25 (d, J = 6.0 Hz, 2H), 3.28 (s, 3H) ppm |
| 99 | N-(2-oxo-2-((4-(3-(pyridin-4-yl)phenyl)thiazol-2-yl)amino)ethyl)-1,2,3,4-tetrahydroquinoline-6-carboxamide | 470.3 | 1H NMR (400 MHz, DMSO) δ = 12.36 (br s, 1H), 8.73-8.64 (m, 2H), 8.38 (s, 1H), 8.32-8.31 (m, 1H), 8.01 (d, J = 7.8 Hz, 1H), 7.82 (s, 1H), 7.79-7.73 (m, 3H), 7.60 (m, 1H), 7.49-7.40 (m, 2H), 6.44 (d, J = 9.0 Hz, 1H), 6.29 (s, 1H), 4.12 (d, J = 5.8 Hz, 2H), 3.23 (br s, 2H), 2.71-2.70 (m, 2H), 1.89-1.75 (m, 2H) ppm |
| 100 | 4-(aminomethyl)-N-(2-oxo-2-((4-(3-(pyridin-4-yl)phenyl)thiazol-2-yl)amino)ethyl)benzamide | 444 | 1H NMR (400 MHz, DEUTERIUM OXIDE) δ = 8.61 (d, J = 6.8 Hz, 2H), 8.08 (d, J = 6.8 Hz, 2H), 7.85 (d, J = 8.4 Hz, 2H), 7.81 (s, 1H), 7.71-7.69 (m, 1H), 7.59-7.57 (m, 1H), 7.56 (d, J = 8.4 Hz, 2H), 7.43-7.41 (m, 1H), 7.27 (s, 1H), 4.30 (s, 2H), 4.24 (s, 2H) ppm |
| 101 | N-(2-oxo-2-((4-(3-(pyridin-4-yl)phenyl)thiazol-2-yl)amino)ethyl)imidazo[1,5-a]pyridine-6-carboxamide | 455 | 1H NMR (400 MHz, DMSO) δ = 12.24 (br s, 1H), 9.03-8.95 (m, 2H), 8.71-8.65 (m, 2H), 8.55 (s, 1H), 8.31 (s, 1H), 8.02 (d, J = 7.8 Hz, 1H), 7.84 (s, 1H), 7.79-7.73 (m, 3H), 7.66-7.56 (m, 2H), 7.43 (s, 1H), 7.22-7.21 (m, 1H), 4.23 (d, J = 5.8 Hz, 2H) ppm |

-continued

| # | Compound Name | LCMS m/z: M + H | HNMR |
|---|---|---|---|
| 102 | N-(2-oxo-2-((4-(3-(pyridin-4-yl)phenyl)thiazol-2-yl)amino)ethyl)-5,6,7,8-tetrahydro-1,8-naphthyridine-3-carboxamide | 471.1 | 1H NMR (400 MHz, DMSO) δ = 8.63 (d, J = 5.8 Hz, 2H), 8.28-8.25 (m, 2H), 7.98 (d, J = 7.8 Hz, 1H), 7.75-7.72 (m, 4H), 7.60-7.58 (m, 2H), 4.11 (s, 2H), 3.30-3.27 (m, 2H), 2.68-2.67 (m, 2H), 1.77-1.74 (m, 2H) ppm |
| 103 | 4-(3-hydroxyazetidin-1-yl)-N-(2-oxo-2-((4-(3-(pyridin-4-yl)\phenyl)thiazol-2-yl)amino)ethyl)benzamide | 486.1 | 1H NMR (400 MHz, DMSO) δ = 12.36 (br s, 1H), 8.68 (d, J = 4.8 Hz, 2H), 8.53 (br s, 1H), 8.31 (s, 1H), 8.02 (d, J = 7.2 Hz, 1H), 7.80-7.74 (m, 6H), 7.64-7.56 (m, 1H), 6.45 (d, J = 8.0 Hz, 2H), 5.69 (d, J = 6.4 Hz, 1H), 4.60 (d, J = 6.0 Hz, 1H), 4.18-4.10 (m, 4H), 3.62-3.59 (m, 2H) ppm |
| 104 | 4-methylsulfonyl-N-[2-oxo-2-[[4-[3-(4-pyridyl)phenyl]thiazol-2-yl]amino]ethyl]pyridine-2-carboxamide | 494.1 | 1H NMR (400 MHz, DMSO) δ = 12.51 (s, 1H), 9.32-9.29 (m, 1H), 9.06 (d, J = 4.8 Hz, 1H), 8.80 (d, J = 5.6 Hz, 2H), 8.44 (s, 1H), 8.37 (s, 1H), 8.17-8.16 (m, 1H), 8.07-8.01 (m, 3H), 7.86-7.83 (m, 2H), 7.66-7.62 (m, 1H), 4.31 (d, J = 6.0 Hz, 2H), 3.41 (s, 3H) ppm |
| 105 | 3-hydroxy-N-[2-oxo-2-[[4-[3-(4-pyridyl)phenyl]thiazol-2-yl]amino]ethyl]-1,2,3,4-tetrahydroquinoline-6-carboxamide | 486.3 | 1H NMR (400 MHz, DMSO) δ = 8.87 (d, J = 4.8 Hz, 2H), 8.46-8.35 (m, 2H), 8.21-8.06 (m, 3H), 7.92-7.83 (m, 2H), 7.67-6.64 (m, 1H), 7.51-7.43 (m, 2H), 6.45 (d, J = 9.0 Hz, 1H), 4.13 (d, J = 5.7 Hz, 2H), 4.01-3.92 (m, 1H), 3.33-3.25 (m, 1H), 2.99-2.97 (m, 1H), 2.87 (d, J = 13.0 Hz, 1H), 2.69-2.65 (m, 1H), 2.61 (d, J = 7.6 Hz, 2H), 2.44-2.43 (m, 1H) ppm |
| 106 | 4-amino-N-(2-oxo-2-((4-phenylthiazol-2-yl)amino)ethyl)benzamide | 353.1 | 1H NMR (400 MHz, DMSO-d6) δ = 12.32 (br s, 1H), 8.42-8.39 (m, 1H), 7.90 (d, J = 7.6 Hz, 2H), 7.62-7.60 (m, 3H), 7.44-7.41 (m, 2H), 7.34-7.30 (m, 1H), 6.57 (d, J = 7.6 Hz, 2H), 5.65 (s, 2H), 4.12 (d, J = 5.2 Hz, 2H) ppm. |
| 107 | (S)-4-amino-N-(1-((4-(4-cyanophenyl)thiazol-2-yl)amino)-4-(methylthio)-1-oxobutan-2-yl)benzamide | 452.1 | 1H NMR (400 MHz, DMSO-d6) δ = 12.44 (s, 1H), 8.23 (d, J = 7.2 Hz, 1H), 8.08 (d, J = 8.4 Hz, 2H), 7.92-7.88 (m, 3H), 7.65 (d, J = 8.0 Hz, 2H), 6.58 (d, J = 8.4 Hz, 2H), 4.72-4.67 (m, 1H), 2.64-2.60 (m, 2H), 2.08 (s, 5H) ppm |
| 108 | 4-amino-N-(2-((4-(4-methoxyphenyl)thiazol-2-yl)amino)-2-oxoethyl)benzamide | 383.1 | 1HNMR (400 MHz, DMSO-d6) δ = 12.28 (br s, 1H), 8.44-8.43 (m, 1H), 7.84-7.82 (m, J = 8.8 Hz, 2H), 7.62-7.60 (m, 2H), 7.44 (s, 1H), 7.00-6.98 (m, 2H), 6.57-6.55 (m, 2H), 5.66 (s, 2H), 4.11 (d, J = 5.6 Hz, 2H), 3.79 (s, 3H) ppm |
| 109 | 4-amino-N-(2-((4-(2,3-dihydrobenzo[b][1,4]dioxin-6-yl)thiazol-2-yl)amino)-2-oxoethyl)benzamide | 411.3 | 1H NMR (400 MHz, DMSO-d6) δ = 12.27 (br s, 1H), 8.40-8.38 (m, 1H), 7.61 (d, J = 8.8 Hz, 2H), 7.45 (s, 1H), 7.41-7.34 (m, 2H), 6.89 (d, J = 8.0 Hz, 1H), 6.56 (d, J = 8.8 Hz, 2H), 5.65 (s, 2H), 4.26 (s, 4H), 4.10 (d, J = 6.0 Hz, 2H) ppm |
| 110 | methyl 3-(2-(2-(4-aminobenzamido)acetamido)thiazol-4-yl)-5,6-dihydropyridine-1(2H)-carboxylate | 416.1 | 1H NMR (400 MHz, MeOD) δ = 7.67 (d, J = 8.6 Hz, 2H), 6.92 (s, 1H), 6.69 (d, J = 8.6 Hz, 2H), 6.66 (s, 1H), 4.30 (s, 2H), 4.22 (s, 2H), 3.73 (s, 3H), 3.60-3.58 (m, 2H), 2.32-2.31 (m, 2H) ppm |
| 111 | 4-amino-N-(2-((4-(2,3-dihydrobenzofuran-5-yl)thiazol-2-yl)amino)-2-oxoethyl)benzamide | 395.3 | 1H NMR (400 MHz, DMSO-d6) δ = 12.24 (s, 1H), 8.40 (s, 1H), 7.75 (s, 1H), 7.69-7.56 (m, 3H), 7.38 (s, 1H), 6.80 (d, J = 8.4 Hz, 1H), 6.56 (d, J = 8.8 Hz, 2H), 5.65 (s, 2H), 4.56 (m, 2H), 4.10 (d, J = 5.6 Hz, 2H), 3.26-3.16 (m, 2H) ppm |
| 112 | 4-amino-N-(2-((4-(2,3-dihydrobenzofuran-6-yl)thiazol-2-yl)amino)-2-oxoethyl)benzamide | 395.2 | 1H NMR (400 MHz, DMSO-d6) δ = 12.47-11.92 (m, 1H), 8.30 (br s, 1H), 7.60 (d, J = 8.4 Hz, 2H), 7.46 (br s, 1H), 7.38 (s, 1H), 7.27 (s, 1H), 7.24 (d, J = 7.6 Hz, 1H), 6.56 (d, J = 8.4 Hz, 2H), 5.64 (s, 2H), 4.55 (m, 2H), 4.06 (d, J = 5.6 Hz, 2H), 3.18 (m, 2H) ppm |

| # | Compound Name | LCMS m/z: M + H | HNMR |
|---|---|---|---|
| 113 | 4-amino-N-(2-((4-(3-(5-methyl-1,3,4-oxadiazol-2-yl)phenyl)thiazol-2-yl)amino)-2-oxoethyl)benzamide | 435.1 | 1H NMR (400 MHz, DMSO-d6) δ = 12.47 (s, 1H), 8.54 (s, 1H), 8.46-8.43 (m, 1H), 8.13 (br d, J = 8.0 Hz, 1H), 7.93 (d, J = 8.0 Hz, 1H), 7.84-7.83 (m, 1H), 7.67-7.60 (m, 3H), 6.56 (d, J = 8.8 Hz, 2H), 5.68 (s, 2H), 4.12 (d, J = 5.6 Hz, 2H), 2.60 (s, 3H) ppm |
| 114 | 4-amino-N-(2-((4-(2-hydroxyphenyl)thiazol-2-yl)amino)-2-oxoethyl)benzamide | 369.3 | 1H NMR (400 MHz, DMSO-d6) δ = 12.40 (s, 1H), 10.90 (s, 1H), 8.47 (s, 1H), 7.92-7.91 ( m, 1H), 7.72 (s, 1H), 7.62 (d, J = 8.6 Hz, 2H), 7.22-7.13 (m, 1H), 6.96-6.85 (m, 2H), 6.57 (d, J = 8.6 Hz, 2H), 5.68 (br s, 2H), 4.13 (d, J = 5.8 Hz, 2H) ppm |
| 115 | 4-amino-N-(2-((4-(4-hydroxyphenyl)thiazol-2-yl)amino)-2-oxoethyl)benzamide | 369.1 | 1HNMR (400 MHz, DMSO-d6) δ = 12.22 (br s, 1H), 9.81-9.42 (m, 1H), 8.41 (br s, 1H), 7.78-7.51 (m, 4H), 7.34 (s, 1H), 6.81 (br d, J = 8.8 Hz, 2H), 6.57 (br d, J = 8.4 Hz, 2H), 5.66 (br s, 2H), 4.11 (br d, J = 5.2 Hz, 2H) ppm |
| 116 | (S)-4-amino-N-(1-((4-(5-cyano-[1,1'-biphenyl]-3-yl)thiazol-2-yl)amino)-4-(methylthio)-1-oxobutan-2-yl)benzamide | 528.3 | 1H NMR (400 MHz, CDCl3) δ = 11.10 (br s, 1H), 8.29 (s, 1H), 8.14 (s, 1H), 7.83-7.80 (m, 3H), 7.66-7.64 (m, 2H), 7.53-7.50 (m, 2H), 7.47-7.43 (m, 1H), 7.31 (s, 1H), 7.12 (d, J = 8.0 Hz, 1H), 6.72 (d, J = 8.0 Hz, 2H), 5.31-5.26 (m, 1H), 2.81-2.69 (m, 2H), 2.44-2.39 (m, 1H), 2.35-2.28 (m, 1H), 2.18 (s, 3H) ppm |
| 117 | 4-amino-N-(2-oxo-2-((4-(3-(pyridin-4-yl)phenyl)thiazol-2-yl)amino)ethyl)benzamide | 430.0 | 1H NMR (400 MHz, MeOD) δ = 8.89 (d, J = 6.8 Hz, 2H), 8.51 (s, 1H), 8.43 (d, J = 6.8 Hz, 2H), 8.21 (d, J = 7.6 Hz, 1H), 7.92 (br d, J = 8.0 Hz, 1H), 7.75 (d, J = 8.8 Hz, 2H), 7.71-7.67 (m, 1H), 7.64 (s, 1H), 6.81 (d, J = 8.8 Hz, 2H), 4.30 (s, 2H) ppm |
| 118 | (S)-4-amino-N-(1-((4-(4'-(aminomethyl)-[1,1'-biphenyl]-3-yl)thiazol-2-yl)amino)-4-(methylthio)-1-oxobutan-2-yl)benzamide | 532.4 | 1H NMR (400 MHz, MeOD) δ = 8.19 (s, 1H), 7.91 (d, J = 7.6 Hz, 1H), 7.79-7.75 (m, 4H), 7.59-7.54 (m, 3H), 7.51-7.48 (m, 2H), 6.84 (br d, J = 8.4 Hz, 2H), 4.89 (br s, 1H), 4.17 (s, 2H), 2.73-2.59 (m, 2H), 2.32-2.17 (m, 2H), 2.13 (br s, 3H) ppm |
| 119 | (S)-4-amino-N-(1-((4-(6-cyano-[1,1'-biphenyl]-3-yl)thiazol-2-yl)amino)-4-(methylthio)-1-oxobutan-2-yl)benzamide | 528.2 | 1H NMR (400 MHz, DMSO-d6) δ = 12.43 (s, 1H), 8.19 (s, 1H), 8.14 (s, 1H), 8.09 (d, J = 8.4 Hz, 1H), 8.04 (d, J = 8.0 Hz, 2H), 7.64 (d, J = 7.2 Hz, 4H), 7.58-7.51 (m, 3H), 6.55 (d, J = 8.8 Hz, 2H), 5.66 (s, 2H), 4.66 (s, 1H), 2.64-2.61 (m, 2H), 2.07 (m, 5H) ppm |
| 120 | (S)-N-(1-((4-(3-(acetamidomethyl)phenyl)thiazol-2-yl)amino)-4-(methylthio)-1-oxobutan-2-yl)-4-aminobenzamide | 498.1 | 1H NMR (400 MHz, DMSO-d6) δ = 12.31 (s, 1H), 8.38-8.34 (m, 1H), 8.21 (br d, J = 7.2 Hz, 1H), 7.79 (s, 1H), 7.76 (d, J = 7.6 Hz, 1H), 7.64 (d, J = 8.8 Hz, 2H), 7.59 (s, 1H), 7.39-7.35 (m, 1H), 7.20 (d, J = 7.2 Hz, 1H), 6.55 (d, J = 8.4 Hz, 2H), 5.67 (s, 2H), 4.67 (br d, J = 7.2 Hz, 1H), 4.28 (d, J = 6.0 Hz, 2H), 2.64-2.61 (m, 2H), 2.08-2.05 (m, 5H), 1.88 (s, 3H) ppm |
| 121 | (S)-N-(1-((4-(4-(acetamidomethyl)phenyl)thiazol-2-yl)amino)-4-(methylthio)-1-oxobutan-2-yl)-4-aminobenzamide | 498.1 | 1H NMR (400 MHz, DMSO) δ = 12.36 (s, 1H), 8.35-8.32 (m, 1H), 8.21 (d, J = 8.0 Hz, 1H), 7.83 (d, J = 8.4 Hz, 2H), 7.66-7.63 (m, 2H), 7.57 (s, 1H), 7.29 (d, J = 8.4 Hz, 2H), 6.57 (d, J = 8.4 Hz, 2H), 4.70-4.65 (m, 1H), 4.26 (d, J = 5.6 Hz, 2H), 2.64-2.50 (m, 2H), 2.08-2.04 (m, 5H), 1.87 (s, 3H) ppm |
| 122 | (S)-methyl 3-(2-(2-(4-aminobenzamido)acetamido)thiazol-4-yl)piperidine-1-carboxylate | 418.1 | 1H NMR (400 MHz, MeOD) δ = 7.67-7.65 (m, 2H), 6.76 (s, 1H), 6.69-6.67 (m, 2H), 4.25 (br d, J = 14.0 Hz, 1H), 4.21 (s, 2H), 4.03 (br d, J = 10.4 Hz, 1H), 3.68 (s, 3H), 2.98-2.92 (m, 2H), 2.78-2.76 (m, 1H), 2.10-2.07 (m, 1H), 1.77-1.74 (m, 2H), 1.71-1.56 (m, 1H) ppm |

| # | Compound Name | LCMS m/z: M + H | HNMR |
|---|---|---|---|
| 123 | N-(2-((4-(4'-(acetamidomethyl)-[1,1'-biphenyl]-3-yl)thiazol-2-yl) amino)-2-oxoethyl)-4-aminobenzamide | 500.1 | 1H NMR (400 MHz, DMSO δ = 12.36 (s, 1H), 8.42-8.35 (m, 2H), 8.18 (s, 1H), 7.89 (d, J = 7.6 Hz, 1H), 7.75 (s, 1H), 7.67 (d, J = 8.0 Hz, 2H), 7.62-7.59 (m, 3H), 7.53-7.49 (m, 1H), 7.38 (d, J = 8.0 Hz, 2H), 6.57 (d, J = 8.8 Hz, 2H), 5.66 (s, 2H), 4.31 (d, J = 6.0 Hz, 2H), 4.12 (d, J = 6.0 Hz, 2H), 1.90 (s, 3H) ppm |
| 124 | N-(2-((4-(3'-(acetamidomethyl)-[1,1'-biphenyl]-3-yl)thiazol-2-yl) amino)-2-oxoethyl)-4-aminobenzamide | 500.3 | 1H NMR (400 MHz, MeOD) δ = 8.20-8.19 (m, 1H), 7.90 (d, J = 7.6 Hz, 1H), 7.86-7.77 (m, 2H), 7.66-7.56 (m, 3H), 7.53-7.43 (m, 3H), 7.32 (d, J = 8.0 Hz,1H), 6.97 (d, J = 8.4 Hz, 2H), 4.46 (s, 2H), 4.31 (s, 2H), 2.03 (s, 3H) ppm |
| 125 | (S)-4-amino-N-(1-oxo-1-((4-(3-(pyridin-4-yl)phenyl) thiazol-2-yl)amino)propan-2-yl)benzamide | 444.1 | H NMR (400 MHz, DMSO-d6) δ = 12.33 (br s, 1H), 8.68-8.66 (m, 2H), 8.30 (s, 1H), 8.20 (br d, J = 6.4 Hz, 1H), 8.01 (br d, J = 8.0 Hz, 1H), 7.82 (s, 1H), 7.76-7.74 (m, 3H), 7.65 (d, J = 8.8 Hz, 2H), 7.61-7.57 (m, 1H), 6.56 (d, J = 8.4 Hz, 2H), 5.65 (s, 2H), 4.67-4.61 (m, 1H), 1.43 (d, J = 7.2 Hz, 3H) ppm |
| 126 | 4-(methylamino)-N-(2-oxo-2-((4-(3-(pyridin-4-yl)phenyl) thiazol-2-yl)amino)ethyl)benzamide | 444.3 | 1H NMR (400 MHz, DMSO-d6) δ = 12.24-12.23 (m, 1H), 8.67 (d, J = 6.4 Hz, 2H), 8.47-8.44 (m, 1H), 8.30 (s, 1H), 8.01 (br d, J = 7.6 Hz, 1H), 7.82 (s, 1H), 7.76 (br d, J = 6.0 Hz, 3H), 7.69 (d, J = 8.8 Hz, 2H), 7.61-7.57 (m, 1H), 6.55 (d, J = 8.8 Hz, 2H), 6.25-6.22 (m, 1H), 4.13 (br d, J = 6.0 Hz, 2H), 2.72 (d, J = 4.8 Hz, 3H) ppm |
| 127 | 4-amino-N-(2-((4-(3-(6-methoxypyridin-3-yl)phenyl) thiazol-2-yl)amino)-2-oxoethyl)benzamide | 460.0 | 1H NMR (400 MHz, DMSO) δ = 12.34 (br s, 1H), 8.54 (d, J = 2.4 Hz, 1H), 8.41 (br s, 1H), 8.16 (s, 1H), 8.07-8.05 (m, 1H), 7.90 (d, J = 8.0 Hz, 1H), 7.77 (s, 1H), 7.61 (d, J = 8.4 Hz, 3H), 7.54-7.50 (m, 1H), 6.95 (d, J = 8.4 Hz, 1H), 6.56 (d, J = 8.4 Hz, 2H), 5.65 (s, 2H), 4.12 (br d, J = 5.6 Hz, 2H), 3.91 (s, 3H) ppm |
| 128 | (S)-N-(1-((4-(3-(1,3,4-oxadiazol-2-yl)phenyl)thiazol-2-yl)amino)-4-(methylthio)-1-oxobutan-2-yl)-4-aminobenzamide | 495.3 | 1H NMR (400 MHz, DMSO-d6) δ = 12.46 (s, 1H), 9.37 (s, 1H), 8.61 (s, 1H), 8.21 (d, J = 6.8 Hz, 1H), 8.15 (d, J = 8.4 Hz, 1H), 7.98 (d, J = 7.6 Hz, 1H), 7.84 (s, 1H), 7.69-7.64 (m, 3H), 6.56 (d, J = 8.8 Hz, 2H), 5.66 (s, 2H), 4.71-4.67 (m, 1H), 2.64-2.54 (m, 2H), 2.12-2.09 (m, 5H) ppm |
| 129 | 4-amino-N-(2-((4-(3'-((N-methylacetamido)methyl)-[1,1'-biphenyl]-3-yl)thiazol-2-yl)amino)-2-oxoethyl)benzamide | 514.3 | 1H NMR (400 MHz, DMSO) δ = 12.37(br s, 1H), 8.43 (br s, 1H), 8.17 (br s, 1H), 7.91 (br d, J = 7.2 Hz, 1H), 7.76 (s, 1H), 7.65-7.32 (m, 7H), 7.28-7.19 (m, 1H), 6.57 (d, J = 8.4 Hz, 2H), 5.67 (s,2H), 4.69-4.54 (m, 2H), 4.13 (m, 2H), 3.02-2.82 (m, 3H), 2.12-2.03 (m, 3H) ppm |
| 130 | 3'-(2-(2-(4-aminobenzamido)acetamido)thiazol-4-yl)-N-methyl-[1,1'-biphenyl]-4-carboxamide | 486.1 | 1H NMR (400 MHz, DMSO) δ = 12.37 (s, 1H), 8.50-8.49 (m, 1H), 8.44-8.41 (m, 1H), 8.25 (s, 1H), 8.00-7.92 (m, 3H), 7.85-7.79 (m, 3H), 7.69 (d, J = 8.2 Hz, 1H), 7.62 (d, J = 8.6 Hz, 2H), 7.59-7.53 (m, 1H), 6.57 (d, J = 8.6 Hz, 2H), 5.67 (s, 2H), 4.13 (d, J = 5.6 Hz, 1H), 4.16-4.11 (m, 1H), 2.82 (d, J = 4.6 Hz, 3H) ppm |
| 131 | 3'-(2-(2-(4-aminobenzamido)acetamido)thiazol-4-yl)-N,N-dimethyl-[1,1'-biphenyl]-3-carboxamide | 500.3 | 1H NMR (400 MHz, DMSO) δ = 12.38 (s, 1H), 8.44-8.41 (m, 1H), 8.24 (s, 1H), 7.94 (d, J = 7.8 Hz, 1H), 7.83-7.78 (m, 2H), 7.72 (s, 1H), 7.67 (d, J = 7.8 Hz, 1H), 7.62 (d, J = 8.6 Hz, 2H), 7.59-7.53 (m, 2H), 7.42 (d, J = 7.6 Hz, 1H), 6.57 (d, J = 8.6 Hz, 2H), 5.67 (br s, 2H), 4.13 (d, J = 5.6 Hz, 2H), 3.08-2.91 (m, 6H) ppm |

| # | Compound Name | LCMS m/z: M + H | HNMR |
|---|---|---|---|
| 132 | 4-(dimethylamino)-N-(2-oxo-2-((4-(3-(pyridin-4-yl)phenyl)thiazol-2-yl)amino)ethyl)benzamide | 458.1 | 1H NMR (400 MHz, DMSO-d6) δ = 12.40 (s, 1H), 8.82 (d, J = 6.4 Hz, 2H), 8.56-8.53 (m, 1H), 8.38 (s, 1H), 8.07 (br d, J = 6.4 Hz, 3H), 7.85 (s, 2H), 7.76 (d, J = 8.8 Hz, 2H), 7.66-7.63 (m, 1H), 6.73 (d, J = 8.8 Hz, 2H), 4.15 (d, J = 5.6 Hz, 2H), 2.98 (s, 6H) ppm |
| 133 | 4-amino-N-(2-((4-(3-(2-aminopyridin-4-yl)phenyl)thiazol-2-yl)amino)-2-oxoethyl)benzamide | 445 | 1H NMR (400 MHz, DMSO) δ = 12.38 (br s, 1H), 8.44-8.43 (m, 1H), 8.23-8.13 (m, 2H), 8.04-7.92 (m, 2H), 7.76 (s, 1H), 7.68-7.51 (m, 4H), 6.82 (m, 1H), 6.75 (s, 1H), 6.57 (d, J = 8.8 Hz, 2H), 6.00 (s, 2H), 5.67 (br s, 1H), 4.13 (d, J = 5.6 Hz, 2H) ppm |
| 134 | 4-amino-N-(2-((4-(4'-(methylsulfonyl)-[1,1'-biphenyl]-3-yl)thiazol-2-yl)amino)-2-oxoethyl)benzamide | 507.2 | 1H NMR (400 MHz, DMSO) δ = 8.43 (s, 1H), 8.27 (s, 1H), 8.08-7.96 (m, 5H), 7.81 (s, 1H), 7.72 (br d, J = 7.6 Hz, 1H), 7.67-7.54 (m, 3H), 6.57 (d, J = 8.6 Hz, 2H), 5.71-5.63 (m, 1H), 5.67 (s, 1H), 4.13 (br d, J = 5.6 Hz, 2H), 3.28 (s, 3H) ppm |
| 135 | 4-amino-N-(2-((4-(3'-(aminomethyl)-[1,1'-biphenyl]-3-yl)thiazol-2-yl)amino)-2-oxoethyl)benzamide | 458.3 | 1H NMR (400 MHz, DMSO) δ = 12.35 (s, 1H), 8.47-8.46 (m, 1H), 8.21 (s, 4H), 7.94 (d, J = 7.6 Hz, 1H), 7.86 (s,1H), 7.79-7.73 (m, 2H), 7.42-7.69 (m, 7H), 6.59 (d, J = 8.8 Hz, 2H), 4.18-4.11 (m, 4H) ppm |
| 136 | 3'-(2-(2-(4-aminobenzamido)acetamido)thiazol-4-yl)-[1,1'-biphenyl]-3-carboxylic acid | 473.1 | 1H NMR (400 MHz, DMSO) δ = 13.12 (br s, 1 H), 12.40 (s, 1 H), 8.43 (br s, 1 H), 8.25 (br s, 2 H) 8.04-7.92 (m, 3 H), 7.80 (s, 1 H), 7.72-7.53 (m, 5 H), 6.57 (br d, J = 8.2 Hz, 2 H), 5.67 (br s, 2 H), 4.20-4.08 (m, 1 H), 4.13 (br d, J = 5.2 Hz, 1 H) ppm |
| 137 | 3'-(2-(2-(4-aminobenzamido)acetamido)thiazol-4-yl)-N,N-dimethyl-[1,1'-biphenyl]-4-carboxamide | 500.1 | 1H NMR (400 MHz, DMSO) δ = 12.37 (s, 1H), 8.44-8.41 (m, 1H), 8.24 (s, 1H), 7.96-7.92 (m, 1H), 7.79 (d, J = 6.6 Hz, 3H), 7.67 (d, J = 8.2 Hz, 1H), 7.62 (d, J = 8.6 Hz, 2H), 7.58 (s, 1H), 7.59-7.52 (m, 2H), 6.57 (d, J = 8.6 Hz, 2H), 5.67 (s, 2H), 4.13 (d, J = 5.8 Hz, 2H), 2.99 (br s, 6H) ppm |
| 138 | 4-amino-N-(2-((4-(4'-((N-methylacetamido)methyl)-[1,1'-biphenyl]-3-yl)thiazol-2-yl)amino)-2-oxoethyl)benzamide | 514.1 | 1H NMR (400 MHz, DMSO) δ = 12.38 (s, 1H), 8.47-8.44 (m, 1H), 8.19-8.17 (m, 1H), 7.90-7.88 (m, 1H), 7.77 (d, J = 2.4 Hz, 1H), 7.74-7.66 (m, 2H), 7.63-7.59 (m, 3H), 7.54-7.49 (m, 1H), 7.35-7.32 (m, 2H), 6.60 (d, J = 8.4 Hz, 2H), 4.61-4.54 (m, 2H), 4.13 (d, J = 5.6 Hz, 2H), 2.94-2.83 (m, 3H), 2.08-2.07 (m, 3H) ppm |
| 139 | 4-amino-N-(2-((4-(4'-hydroxy-[1,1'-biphenyl]-3-yl)thiazol-2-yl)amino)-2-oxoethyl)benzamide | 445.2 | 1H NMR (400 MHz, DMSO) δ = 12.35 (s, 1H), 9.57 (s, 1H), 8.43-8.41 (m, 1H), 8.10 (s, 1H), 7.80 (d, J = 7.6 Hz, 1H), 7.72 (s, 1H), 7.61 (d, J = 8.8 Hz, 2H), 7.54-7.51 (m, 3H), 7.47-7.43 (m, 1H), 6.88-6.86 (m, 2H), 6.55 (d, J = 8.4 Hz, 2H), 5.6 (s, 2H), 4.11 (d, J = 5.6 Hz, 2H) ppm |
| 140 | 4-amino-N-(2-((4-(3-(1-methyl-2-oxo-1,2-dihydropyridin-4-yl)phenyl)thiazol-2-yl)amino)-2-oxoethyl)benzamide | 460.2 | 1H NMR (400 MHz, DMSO) δ = 12.48-12.23 (m, 1H), 8.43 (br s, 1H), 8.24 (s, 1H), 8.00 (d, J = 8.2 Hz, 1H), 7.86-7.79 (m, 2H), 7.67 (d, J = 7.6 Hz, 1H), 7.62 (d, J = 8.6 Hz, 2H), 7.58-7.52 (m, 1H), 6.75 (d, J = 2.2 Hz, 1H), 6.63 (dd, J = 2.2, 7.2 Hz, 1H), 6.57 (d, J = 8.8 Hz, 2H), 5.68 (s, 2H), 4.12 (d, J = 5.8 Hz, 2H), 3.47 (s, 3H) ppm |
| 141 | 4-amino-N-(2-((4-(3'-hydroxy-[1,1'-biphenyl]-3-yl)thiazol-2-yl)amino)-2-oxoethyl)benzamide | 445.2 | 1H NMR (400 MHz, DMSO) δ = 12.37 (br s, 1H), 9.56 (s, 1H), 8.45-8.43 (m, 1H), 8.15 (s, 1H), 7.89 (d, J = 7.6 Hz, 1H), 7.75 (s, 1H), 7.62 (d, J = 8.4 Hz, 2H), 7.56-7.48 (m, 2H), 7.31-7.27 (m, 1H), 7.12 (d, J = 8.4 Hz, 1H), 7.08-7.06 (m, 1H), |

-continued

| # | Compound Name | LCMS m/z: M + H | HNMR |
|---|---|---|---|
| | | | 6.80 (dd, J = 2.0, 7.6 Hz, 1H), 6.57 (d, J = 8.8 Hz, 2H), 5.67 (s, 2H), 4.12 (d, J = 6.0 Hz, 2H) ppm |
| 142 | 4-amino-N-(2-((4-(2'-fluoro-[1,1'-biphenyl]-3-yl)thiazol-2-yl)\amino)-2-oxoethyl)benzamide | 446.9 | 1H NMR (400 MHz, DMSO) δ = 12.26 (br s, 1H), 8.43-8.42 (m, 1H), 8.10 (d, J = 1.2 Hz, 1H), 7.94-7.93 (m, 1H), 7.72 (s, 1H), 7.62-7.51 (m, 6H), 7.34-7.33 (m, 2H), 6.57 (d, J = 8.8 Hz, 2H), 5.65 (s, 2H), 4.12 (d, J = 6.0 Hz, 2H) ppm |
| 143 | 4-amino-N-(2-((4-(2-methyl-1-oxo-1,2-dihydroisoquinolin-7-yl)thiazol-2-yl)amino)-2-oxoethyl)benzamide | 434.1 | 1H NMR (400 MHz, DMSO-d6) δ = 12.43 (br s, 1H), 8.81 (s, 1H), 8.40 (br s, 1H), 8.21-8.19 (m, 1H), 7.74 (br s, 1H), 7.70 (d, J = 8.0 Hz, 1H), 7.61 (d, J = 8.4 Hz, 2H), 7.48 (d, J = 7.2 Hz, 1H), 6.63 (d, J = 7.2 Hz, 1H), 6.57 (d, J = 8.4 Hz, 2H), 5.65 (s, 2H), 4.12 (br d, J = 5.6 Hz, 2H), 3.52 (s, 3H) ppm |
| 144 | 3-[3-[2-12-1(4-aminobenzoyl)amino]acetyl]amino]thiazol-4-yl]phenyl]-N-methyl-benzamide | 486.4 | 1H NMR (400 MHz, DMSO) δ = 12.42 (s, 1 H), 8.58 (br d, J = 4.6 Hz, 1 H), 8.48-8.47 (m, 1 H), 8.26 (s, 1 H), 8.17 (s, 1 H), 7.94 (d, J = 7.8 Hz, 1 H), 7.90-7.84 (m, 2 H), 7.78 (s, 1 H), 7.70 (br d, J = 8.2 Hz, 1 H), 7.66 (d, J = 8.6 Hz, 2 H), 7.59-7.57 (m, 2 H), 6.64 (d, J = 8.7 Hz, 2 H), 4.14 (d, J = 5.6 Hz, 2 H), 2.84 (d, J = 4.6 Hz, 3 H) ppm |
| 145 | 4-amino-N-(2-((4-(4'-((dimethylamino)methyl)-[1,1'-biphenyl]-3-yl)thiazol-2-yl)amino)-2-oxoethyl)benzamide | 486.1 | 1H NMR (400 MHz, MeOD) δ = 8.18 (s, 1H), 7.87 (d, J = 8.0 Hz, 1H), 7.69-7.65 (m, 4H), 7.57 (d, J = 8.0 Hz, 1H), 7.49-7.40 (m, 4H), 6.70-6.68 (m, 2H), 4.27 (s, 2H), 3.54 (s, 2H), 2.28 (s, 6H) ppm |
| 146 | 4-amino-N-(2-((4-(3-(2-methoxypyridin-4-yl)phenyl)thiazol-2-yl)amino)-2-oxoethyl)benzamide | 460.2 | 1H NMR (400 MHz, DMSO) δ = 12.37 (s, 1H), 8.44 (br s, 1H), 8.28-8.26 (m, 2H), 8.00 (d, J = 7.6 Hz, 1H), 7.82 (s, 1H), 7.73 (d, J = 8.0 Hz, 1H), 7.63 (br d, J = 6.8 Hz, 2H), 7.59-7.55 (m, 1H), 7.37-7.35 (m, 1H), 7.16 (s, 1H), 6.59 (br d, J = 4.8 Hz, 2H), 4.12 (br d, J = 5.2 Hz, 2H), 3.91 (s, 3H) ppm |
| 147 | 4-amino-N-(2-oxo-2-((4-(1-oxo-1,2-dihydroisoquinolin-7-yl)thiazol-2-yl)amino)ethyl)benzamide | 420.1 | 1H NMR (400 MHz, DMSO) δ = 12.43 (br s, 1H), 11.24 (br d, J = 5.2 Hz, 1H), 8.78 (s, 1H), 8.43-8.42 ( m, 1H), 8.22-8.20 (m, 1H), 7.76 (s, 1H), 7.71 (d, J = 8.6 Hz, 1H), 7.63 (d, J = 8.6 Hz, 2H), 7.20-7.17 (m, 1H), 6.58-6.56 (m, 3H), 5.66 (s, 2H), 4.13 (d, J = 5.6 Hz, 2H) ppm |
| 148 | 4-amino-N-(2-((4-(3-methyl-4-oxo-3,4-dihydroquinazolin-6-yl)thiazol-2-yl)amino)-2-oxoethyl)benzamide | 435.3 | 1H NMR (400 MHz, DMSO-d6) δ = 12.31 (br s, 1H), 8.71 (s, 1H), 8.38-8.37 (m, 2H), 8.33-8.31 (m, 1H), 7.79 (s, 1H), 7.71 (d, J = 8.6 Hz, 1H), 7.61 (d, J = 8.6 Hz, 2H), 6.56 (d, J = 8.6 Hz, 2H), 5.65 (s, 2H), 4.11 (d, J = 5.6 Hz, 2H), 3.51 (s, 3H) ppm |
| 149 | 4-amino-N-(2-((4-(4'-cyano-[1,1'-biphenyl]-3-yl)thiazol-2-yl)amino)-2-oxoethyl)benzamide | 454 | 1H NMR (400 MHz, DMSO-d6) δ = 12.37 (br s, 1H), 8.42-8.26 (m, 1H), 7.99 (s, 1H), 7.97-7.93 (m, 5H), 7.81 (s, 1H), 7.62 (d, J = 8.8 Hz, 1H), 7.60-7.58 (m, 3H), 6.57 (d, J = 8.8 Hz, 2H), 5.66 (s, 2H), 4.12 (d, J = 5.6 Hz, 2H).ppm |
| 150 | 4-amino-N-(2-((4-(3-methyl-4-oxo-3,4-dihydrophthalazin-6-yl)thiazol-2-yl)amino)-2-oxoethyl)benzamide | 435.1 | 1H NMR (400 MHz, DMSO) δ = 12.53 (br s, 1H), 8.82 (s, 1H), 8.46-8.42 (m, 3H), 8.01-7.99 (m, 2H), 7.62 (d, J = 8.6 Hz, 2H), 6.57 (d, J = 8.6 Hz, 2H), 5.68 (s, 2H), 4.13 (d, J = 5.6 Hz, 2H), 3.74 (s, 3H) ppm |
| 151 | 4-amino-N-(2-oxo-2-((4-(3-(1-(2,2,2-trifluoroethyl)-1H-pyrazol-3-yl)phenyl)thiazol-2-yl)amino)ethyl)benzamide | 500.8 | 1H NMR (400 MHz, DMSO-d6) δ = 12.31 (br s, 1H), 8.57-8.32 (m, 2H), 7.93 (d, J = 2.3 Hz, 1H), 7.85 (d, J = 8.0 Hz, 1H), 7.76 (d, J = 7.6 Hz, 1H), 7.69 (s, 1H), 7.61 (d, J = 8.4 Hz, 2H), 7.49-7.48 (m, 1H), |

| # | Compound Name | LCMS m/z: M + H | HNMR |
|---|---|---|---|
| | | | 6.89 (d, J = 2.4 Hz, 1H), 6.56 (d, J = 8.4 Hz, 2H), 5.66 (s, 2H), 5.21-5.20 (m, 2H), 4.12 (d, J = 5.6 Hz, 2H).ppm |
| 152 | 4-amino-N-(2-((4-(3'-fluoro-[1,1'-biphenyl]-3-yl)thiazol-2-yl)amino)-2-oxoethyl)benzamide | 447.1 | 1H NMR (400 MHz, DMSO-d6) δ = 12.34 (br s, 1H), 8.42-8.41 (m, 1H), 8.22 (d, J = 1.6 Hz, 1H), 7.93-7.92 (m, 1H), 7.80 (s, 1H), 7.63-7.62 (m, 1H), 7.60-7.54 (m, 6H), 7.24-7.23 (m, 1H), 6.57 (d, J = 8.8 Hz, 2H), 5.65 (s, 2H), 4.12 (d, J = 6.0 Hz, 2H) ppm |
| 153 | 4-amino-N-(2-((4-(4'-(hydroxymethyl)-[1,1'-biphenyl]-3-yl)thiazol-2-yl)amino)-2-oxoethyl)benzamide | 458.8 | 1H NMR (400 MHz, DMSO-d6) δ = 8.49-8.38 (m, 2H), 8.20 (s, 1H), 7.89 (d, J = 7.8 Hz, 1H), 7.76 (s, 1H), 7.69 (d, J = 8.2 Hz, 2H), 7.62 (d, J = 8.4 Hz, 3H), 7.56-7.49 (m, 1H), 7.45 (d, J = 8.0 Hz, 2H), 6.57 (d, J = 8.6 Hz, 2H), 5.67 (s, 2H), 5.25 (br s, 1H), 4.57 (s, 2H), 4.13 (d, J = 5.6 Hz, 2H) ppm |
| 154 | 4-amino-N-(2-((4-(3'-(hydroxymethyl)-[1,1'-biphenyl]-3-yl)thiazol-2-yl)amino)-2-oxoethyl)benzamide | 459.1 | 1H NMR (400 MHz, DMSO-d6) δ = 12.37 (br s, 1H), 8.42 (s, 1H), 8.20 (s, 1H), 7.94-7.85 (m, 1H), 7.75 (s, 1H), 7.69-7.56 (m, 5H), 7.55-7.49 (m, 1H), 7.45 (m, 1H), 7.34 (br d, J = 7.6 Hz, 1H), 6.56 (d, J = 8.4 Hz, 2H), 5.66 (s, 2H), 5.28-5.27 (m, 1H), 4.59 (d, J = 6.0 Hz, 2H), 4.12 (br d, J = 5.6 Hz, 2H) ppm |
| 155 | (R)-4-amino-N-(4-(methylthio)-1-oxo-1-((4-(3-(pyridin-4-yl)phenyl)thiazol-2-yl)amino)butan-2-yl)benzamide | 504.3 | 1H NMR (400 MHz, DMSO-d6) δ = 12.38 (s, 1H), 8.67 (d, J = 6.0 Hz, 2H), 8.30 (s, 1H), 8.20 (d, J = 6.8 Hz, 1H), 8.01 (d, J = 7.6 Hz, 1H), 7.82 (s, 1H), 7.76-7.75 (m, 3H), 7.65 (d, J = 8.4 Hz, 2H), 7.61-7.57 (m, 1H), 6.56 (d, J = 8.8 Hz, 2H), 5.65-5.64 (m, 2H), 4.72-4.67 (m, 1H), 2.64-2.60 (m, 2H), 2.12-2.06 (m, 5H) ppm |
| 156 | 4-(3-(2-(2-(4-aminobenzamido)acetamido)thiazol-4-yl)phenyl)pyridine 1-oxide | 446.2 | 1H NMR (400 MHz, DMSO) δ = 12.36 (s, 1H), 8.42 (s, 1H), 8.31 (d, J = 7.6 Hz, 2H), 8.27 (s, 1H), 7.97 (s, 1H), 7.83-7.81 (m, 3H), 7.73 (d, J = 8.8 Hz, 1H), 7.61 (d, J = 8.4 Hz, 2H), 7.58-7.56 (m, 1H), 6.57 (d, J = 8.4 Hz, 2H), 4.12 (d, J = 5.6 Hz, 2H) ppm |
| 157 | 4-amino-N-(2-((4-(3'-cyano-[1,1'-biphenyl]-3-yl)thiazol-2-yl)amino)-2-oxoethyl)benzamide | 454.2 | 1H NMR (400 MHz, DMSO) δ = 12.36 (br s, 1H), 8.42 (br s, 1H), 8.25 (br d, J = 10.0 Hz, 2H), 8.15-7.94 (m, 2H), 7.89-7.55 (m, 7H), 6.57 (d, J = 3.8 Hz, 2H), 5.66 (s, 2H), 4.12 (s, 2H) ppm |
| 158 | 4-amino-N-(2-((4-(4'-(aminomethyl)-2',3',4',5'-tetrahydro-[1,1'-biphenyl]-3-yl)thiazol-2-yl)amino)-2-oxoethyl)benzamide | 462.3 | 1H NMR (400 MHz, DMSO) δ = 12.31-12.24 (m, 1H), 8.45-8.43 (m, 1H), 7.95 (s, 1H), 7.78-7.77 (m, 3H), 7.67 (s, 1H), 7.62 (d, J = 7.2 Hz, 1H), 7.39-7.38 (m, 2H), 6.58 (d, J = 8.8 Hz, 2H), 6.21 (br s, 1H), 4.12 (d, J = 5.6 Hz, 2H), 2.89-2.81 (m, 2H), 2.38 (br d, J = 17.2 Hz, 3H), 1.99-1.93 (m, 3H), 1.46-1.40 (m, 1H) ppm |
| 159 | 4-amino-N-(2-oxo-2-((4-(3-(2-(piperazin-1-yl)pyridin-4-yl)phenyl)thiazol-2-yl)amino)ethyl)benzamide | 514.3 | 1H NMR (400 MHz, DMSO) δ = 12.36 (s, 1H), 8.81 (br s, 2H), 8.47-8.44 (m, 1H), 8.26-8.24 (m, 2H), 7.98 (d, J = 8.0 Hz, 1H), 7.79 (s, 1H), 7.72 (d, J = 8.0 Hz, 1H), 7.63-7.58 (m, 3H), 7.24 (s, 1H), 7.12 (d, J = 6.4 Hz, 1H), 6.60 (d, J = 8.4 Hz, 2H), 4.13 (d, J = 5.6 Hz, 2H), 3.85-3.82 (m, 4H), 3.23-3.017 (m, 4H) ppm |

| # | Compound Name | LCMS m/z: M + H | HNMR |
|---|---|---|---|
| 160 | 4-amino-N-(2-((4-(3-(2-((2-aminoethyl)amino)pyridin-4-yl)phenyl)thiazol-2-yl)amino)-2-oxoethyl)benzamide | 488.2 | 1H NMR (400 MHz, MeOD) δ = 8.30 (s, 1H), 8.14-8.04 (m, 2H), 7.77-7.71 (m, 3H), 7.65-7.57 (m, 2H), 7.35-7.25 (m, 2H), 6.82-6.74 (m, 2H), 4.29 (s, 2H), 3.81-3.80 (m, 2H), 3.30-3.28 (m, 2H) ppm |
| 161 | 4-amino-N-(2-((4-(3-cyanophenyl)thiazol-2-yl)amino)-2-oxoethyl)benzamide | 378 | 1H NMR (400 MHz, DMSO-d6) δ = 12.38 (br s, 1H), 8.43-8.42 (m, 1H), 8.32 (s, 1H), 8.23-8.21 (m, 1H), 7.85 (s, 1H), 7.78 (d, J = 7.6 Hz, 1H), 7.69-7.64 (m, 1H), 7.64-7.57 (m, 2H), 6.56 (d, J = 8.8 Hz, 2H), 5.65 (s, 2H), 4.12 (d, J = 5.6 Hz, 2H) ppm |
| 162 | 4-amino-N-(2-oxo-2-((4-(3-(1-(tetrahydro-2H-pyran-4-yl)-1H-pyrazol-3-yl)phenyl)thiazol-2-yl)amino)ethyl)benzamide | 503.1 | 1H NMR (400 MHz, DMSO-d6) δ = 12.37 (br s, 1H), 8.43-8.42 (m, 1H), 8.37 (s, 1H), 7.87 (d, J = 2.0 Hz, 1H), 7.81 (br d, J = 7.6 Hz, 1H), 7.73 (br d, J = 7.6 Hz, 1H), 7.67 (s, 1H), 7.62 (br d, J = 8.4 Hz, 2H), 7.45-7.44 (m, 1H), 6.75 (d, J = 2.0 Hz, 1H), 6.57 (d, J = 8.4 Hz, 2H), 5.66 (s, 2H), 4.52-4.40 (m, 1H), 4.12 (br d, J = 5.6 Hz, 2H), 4.00-3.97 (m, 2H), 3.54-3.45 (m, 2H), 2.06-1.96 (m, 4H) ppm |
| 163 | 4-amino-N-(2-((4-(3-(2-(2-aminoethoxy)pyridin-4-yl)phenyl)thiazol-2-yl)amino)-2-oxoethyl)benzamide | 489 | 1H NMR (400 MHz, MeOD) δ = 8.28-8.21 (m, 2H), 8.02 (d, J = 7.8 Hz, 1H), 7.77-7.70 (m, 2H), 7.67 (d, J = 7.8 Hz, 1H), 7.60-7.51 (m, 2H), 7.39 (dd, J = 5.6Hz, 1.6 Hz, 1H), 7.22 (d, J = 1.2 Hz, 1H), 6.81-6.71 (m, 2H), 4.66-4.58 (m, 2H), 4.29 (s, 2H), 3.45-3.39 (m, 2H) ppm |
| 164 | 4-amino-N-(2-((4-(3-(2-(aminomethyl)pyridin-4-yl)phenyl)thiazol-2-yl)amino)-2-oxoethyl)benzamide | 459.2 | 1H NMR (400 MHz, DMSO) δ = 8.61 (d, J = 4.8 Hz, 1H), 8.44-8.41 (m, 1H), 8.32-8.30 (m, 2H), 8.01 (d, J = 8.0 Hz, 1H), 7.84 (s, 1H), 7.79 (s, 1H), 7.77-7.74 (m, 1H), 7.66-7.58 (m, 4H), 6.58-6.54 (m, 2H), 5.66 (s, 2H), 4.12 (d, J = 5.6 Hz, 2H), 4.01 (s, 2H) ppm |
| 165 | 4-amino-N-(2-((4-(3-(2-(hydroxymethyl)pyridin-4-yl)phenyl)thiazol-2-yl)amino)-2-oxoethyl)benzamide | 460.2 | 1H NMR (400 MHz, MeOD) δ = 8.74 (d, J = 6.2 Hz, 1H), 8.49 (s, 1H), 8.34 (s, 1H), 8.28 (br d, J = 6.2 Hz, 1H), 8.19 (d, J = 7.8 Hz, 1H), 7.91 (d, J = 8.6 Hz, 1H), 7.78-7.72 (m, 2H), 7.69-7.67 (m, 1H), 7.63 (s, 1H), 6.85-6.77 (m, 2H), 5.08 (s, 2H), 4.30 (s, 2H) ppm |
| 166 | 4-amino-N-(2-((4-(3-(1-(2-aminoethyl)-2-oxo-1,2-dihydropyridin-4-yl)phenyl)thiazol-2-yl)amino)-2-oxoethyl)benzamide | 489.2 | 1H NMR (400 MHz, MeOD) δ = 8.25 (s, 1H), 8.04 (d, J = 8.0 Hz, 1H), 7.81-7.69 (m, 3H), 7.66 (br d, J = 7.2 Hz, 1H), 7.60-7.53 (m, 2H), 6.92 (d, J = 2.0 Hz, 1H), 6.86 (dd, J = 7.2 Hz, 2.0 Hz, 1H), 6.80 (d, J = 8.8 Hz, 2H), 4.38-4.34 (m, 2H), 4.29 (s, 2H), 3.40 (m, 2H) ppm |
| 167 | 4-amino-N-(2-((4-(2-(2-(dimethylamino)ethyl)-1-oxo-1,2-dihydroisoquinolin-7-yl)thiazol-2-yl)amino)-2-oxoethyl)benzamide | 491 | 1H NMR (400 MHz, DMSO) δ = 12.42 (br s, 1H), 8.80 (d, J = 2.0 Hz, 1H), 8.43-8.40 (m, 1H), 8.21-8.19 (m, 1H), 8.15 (s, 1H), 7.76 (s, 1H), 7.69 (d, J = 8.4 Hz, 1H), 7.62 (d, J = 8.8 Hz, 2H), 7.45 (d, J = 7.2 Hz, 1H), 6.62 (d, J = 7.2 Hz, 1H), 6.57 (d, J = 8.8 Hz, 2H), 5.65 (s, 2H), 4.13 (d, J = 6.0 Hz, 2H), 4.08-4.05 (m, 2H), 2.58-2.55 (m, 2H), 2.20 (s, 6H) ppm |
| 168 | 4-amino-N-(2-((4-(3-(2-((dimethylamino)methyl)pyridin-4-yl)phenyl)thiazol-2-yl)amino)-2-oxoethyl)benzamide | 487 | 1H NMR (400 MHz, DMSO) δ = 12.37 (s, 1H), 10.01 (s, 1H), 8.78 (d, J = 5.2 Hz, 1H), 8.46-8.43 (m, 1H), 8.32 (s, 1H), 8.04 (d, J = 8.0 Hz, 1H), 7.94 (s, 1H), 7.88-7.86 (m, 1H), |

| # | Compound Name | LCMS m/z: M + H | HNMR |
|---|---|---|---|
| | | | 7.80-7.75 (m, 2H), 7.65-7.61 (m, 3H), 6.58 (d, J = 8.4 Hz, 2H), 4.53 (s, 2H), 4.13 (d, J = 5.6 Hz, 2H), 2.87 (s, 6H) ppm |
| 169 | 4-amino-N-(2-((4-(3-(4-(aminomethyl)cyclohexyl)phenyl) thiazol-2-yl)amino)-2-oxoethyl)benzamide | 464.2 | 1H NMR (400 MHz, MeOD) δ = 7.78 (br d, J = 13.2 Hz, 1H), 7.71-7.67 (m, 3H), 7.36-7.35 (m, 2H), 7.32-7.16 (m, 1H), 6.70 (d, J = 8.6 Hz, 2H), 4.25 (s, 2H), 3.08 (d, J = 7.6 Hz, 1H), 2.86 (d, J = 7.2 Hz, 1H), 2.72-2.55 (m, 1H), 1.80-1.89 (m, 2H), 1.95-1.75 (m, 5H), 1.61-1.58 (m, 1H), 1.29-1.23 (m, 1H) ppm |
| 170 | 4-amino-N-(2-((4-(3-(1-(2-(dimethylamino)ethyl)-6-oxo-1,6-dihydropyridin-3-yl) phenyl)thiazol-2-yl)amino)-2-oxoethyl)benzamide | 517.3 | 1H NMR (400 MHz, MeOD) δ = 8.40 (br s, 1H), 8.10-8.05 (m, 2H), 7.99 (d, J = 8.0 Hz, 1H), 7.90 (d, J = 8.0 Hz, 1H), 7.70 (d, J = 8.0 Hz, 2H), 7.51-7.47 (m, 3H), 8.73-8.70 (m, 3H), 4.39-4.36 (m, 2H), 4.28 (s, 2H), 3.22-3.19 (m, 2H), 2.72 (s, 6H) ppm |
| 171 | 4-amino-N-(2-((4-(2-(2-aminoethyl)-1-oxo-1,2-dihydroisoquinolin-7-yl) thiazol-2-yl)amino)-2-oxoethyl)benzamide | 463 | 1H NMR (400 MHz, DMSO) δ = 8.82 (d, J = 1.6 Hz, 1H), 8.46-8.43 (m, 1H), 8.31 (br s, 1H), 8.23-8.21 (m, 1H), 7.77 (s, 1H), 7.71 (d, J = 8.4 Hz, 1H), 7.62 (d, J = 8.8 Hz, 2H), 7.46 (d, J = 7.2 Hz, 1H), 6.65 (d, J = 7.2 Hz, 1H), 6.57 (d, J = 8.4 Hz, 2H), 5.66 (br s, 2H), 4.13 (d, J = 5.6 Hz, 2H), 4.06 (br s, 2H), 2.99 (br s, 2H) ppm |
| 172 | (S)-4-amino-N-(3-hydroxy-1-oxo-1-((4-(3-(pyridin-4-yl) phenyl)thiazol-2-yl)amino)propan-2-yl)benzamide | 460.2 | 1H NMR (400 MHz, DMSO-d6) δ = 12.35 (s, 1H), 8.92 (d, J = 6.4 Hz, 2H), 8.44 (s, 1H), 8.28 (d, J = 6.4 Hz, 2H), 8.12 (d, J = 8.0 Hz, 1H), 8.00 (d, J = 7.2 Hz, 1H), 7.92 (br d, J = 8.8 Hz, 1H), 7.87 (s, 1H), 7.69-7.64 (m, 3H), 6.61 (d, J = 8.8 Hz, 2H), 4.72-4.68 (m, 1H), 3.85-3.83 (m, 2H) ppm |
| 173 | 4-amino-N-(2-oxo-2-((4-(1-(pyridin-3-yl)piperidin-3-yl) thiazol-2-yl)amino)ethyl)benzamide | 437.4 | 1H NMR (400 MHz, DMSO) δ = 12.17 (s, 1H), 8.39-8.37 (m, 1H), 8.32 (d, J = 2.6 Hz, 1H), 7.96-7.95 (m, 1H), 7.60 (d, J = 8.6 Hz, 2H), 7.37-7.32 (m, 1H), 7.22-7.20 (m, 1H), 6.91 (s, 1H), 6.56 (d, J = 8.6 Hz, 2H), 5.65 (s, 2H), 4.07 (d, J = 5.8 Hz, 2H), 3.93 (d, J = 11.0 Hz, 1H), 3.78 (d, J = 11.4 Hz, 1H), 2.97-2.75 (m, 3H), 2.07 (d, J = 8.0 Hz, 1H), 1.84-1.78 (m, 1H), 1.68-1.66 (m, 2H) ppm |
| 174 | 4-amino-N-(2-((4-(3-((1r, 4r)-4-(aminomethyl)cyclohexyl)phenyl) thiazol-2-yl)amino)-2-oxoethyl)benzamide | 464.3 | 1H NMR (400 MHz, MeOD) δ = 7.78-7.67 (m, 4H), 7.37-7.27 (m, 2H), 7.17 (d, J = 7.6 Hz, 1H), 6.91-6.76 (m, 2H), 4.26 (s, 2H), 2.85 (d, J = 7.0 Hz, 2H), 2.62-2.53 (m, 1H), 2.03-1.92 (m, 4H), 1.74-1.72 (m, 1H), 1.65-1.52 (m, 2H), 1.31-1.17 (m, 2H) ppm |
| 175 | 4-amino-N-(2-((4-(3-((1s, 4s)-4-(aminomethyl)cyclohexyl)phenyl)thiazol-2-yl)amino)-2-oxoethyl)benzamide | 464.3 | 1H NMR (400 MHz, MeOD) δ = 7.85-7.75 (m, 3H), 7.71 (br d, J = 8.0 Hz, 1H), 7.41-7.30 (m, 2H), 7.24 (d, J = 7.8 Hz, 1H), 6.97 (br s, 2H), 4.29 (d, J = 2.6 Hz, 2H), 3.09 (d, J = 7.6 Hz, 2H), 2.73 (br s, 1H), 2.07 (br s, 1H), 1.80 (br s, 8H) ppm |
| 176 | 2-(4-(3-(2-(2-(4-aminobenzamido)acetamido)thiazol-4-yl) phenyl)-1H-pyrazol-1-yl)acetic acid | 477.2 | 1H NMR (400 MHz, DMSO-d6) δ = 13.13 (s, 1H), 12.35 (s, 1H), 8.43-8.40 (m, 1H), 8.18 (s, 1H), 8.09 (s, 1H), 7.94 (s, 1H), 7.74 (br d, J = 8.0 Hz, 1H), 7.71 (s, 1H), 7.61 (d, J = 8.8 Hz, 2H), 7.52 (br d, J = 8.0 Hz, 1H), 7.44-7.40 (m, 1H), 6.59-6.55 (m, 2H), 5.67 (br s, 2H), 4.99 (s, 2H), 4.12 (d, J = 6.0 Hz, 2H) ppm |

| # | Compound Name | LCMS m/z: M + H | HNMR |
|---|---|---|---|
| 177 | methyl 2-(4-(3-(2-(2-(4-aminobenzamido)acetamido)thiazol-4-yl)phenyl)pyridin-2-yl)acetate | 502.3 | 1H NMR (400 MHz, DMSO) δ = 12.37 (s, 1H), 8.58 (d, J = 5.2 Hz, 1H), 8.43-8.40 (m, 1H), 8.28 (s, 1H), 8.01 (br d, J = 8.0 Hz, 1H), 7.80 (s, 1H), 7.74-7.72 (m, 2H), 7.66-7.57 (m, 4H), 6.56 (d, J = 8.8 Hz, 2H), 5.65 (s, 2H), 4.12 (br d, J = 5.6 Hz, 2H), 3.94 (s, 2H), 3.64 (s, 3H) ppm |
| 178 | (S)-4-amino-N-(4-methoxy-1-oxo-1-((4-(3-(pyridin-4-yl)phenyl)thiazol-2-yl)amino)butan-2-yl)benzamide | 488.2 | 1H NMR (400 MHz, MeOD) δ = 8.88 (d, J = 7.2 Hz, 2H), 8.50 (s, 1H), 8.43 (d, J = 7.2 Hz, 2H), 8.20 (d, J = 8.0 Hz, 1H), 7.92 (d, J = 8.8 Hz, 1H), 7.72 (d, J = 8.4 Hz, 2H), 7.70-7.66 (m, 1H), 7.64 (s, 1H), 6.81-6.78 (m, 2H), 4.85-4.82 (m, 1H), 3.61-3.58 (m, 2H), 3.37 (s, 3H), 2.32-2.23 (m, 1H), 2.20-2.12 (m, 1H) ppm |
| 179 | 4-amino-N-(2-((4-(3-morpholinophenyl)thiazol-2-yl)amino)-2-oxoethyl)benzamide | 438.3 | 1H NMR (400 MHz, DMSO) δ = 12.29 (s, 1H), 8.41-8.38 (m, 1H), 7.63-7.57 (m, 3H), 7.46 (s, 1H), 7.38-7.32 (m, 1H), 7.31-7.24 (m, 1H), 6.92 (d, J = 8.0 Hz, 1H), 6.56 (d, J = 8.8 Hz, 2H), 5.65 (s, 2H), 4.10 (d, J = 5.6 Hz, 2H), 3.78-3.74 (m, 4H), 3.18-3.12 (m, 4H) ppm |
| 180 | methyl 2-(4-(3-(2-(2-(4-aminobenzamido)acetamido)thiazol-4-yl)phenyl)-1H-pyrazol-1-yl)acetate | 491.2 | 1H NMR (400 MHz, DMSO) δ = 12.25 (br s, 1H), 8.43-8.40 (m, 1H), 8.20 (s, 1H), 8.09 (s, 1H), 7.97 (s, 1H), 7.74 (d, J = 7.6 Hz, 1H), 7.70 (s, 1H), 7.61 (d, J = 8.8 Hz, 2H), 7.53 (d, J = 8.0 Hz, 1H), 7.44-7.40 (m, 1H), 6.56 (d, J = 8.8 Hz, 2H), 5.66 (s, 2H), 5.13 (s, 2H), 4.12 (d, J = 5.6 Hz, 2H), 3.71 (s, 3H) ppm |
| 181 | methyl 4-(3-(2-(2-(4-aminobenzamido)acetamido)thiazol-4-yl)phenyl)picolinate | 488.2 | 1H NMR (400 MHz, DMSO) δ = 12.36 (s, 1H), 8.81 (d, J = 5.2 Hz, 1H), 8.40-8.35 (m, 3H), 8.06-8.02 (m, 2H), 7.83-7.80 (m, 2H), 7.64-7.60 (m, 3H), 6.56 (d, J = 8.4 Hz, 2H), 5.65 (s, 2H), 4.11 (br d, J = 6.0 Hz, 2H), 3.93 (s, 3H) ppm |
| 182 | methyl 2-(4-(3-(2-(2-(4-aminobenzamido)acetamido)thiazol-4-yl)phenyl)pyridin-2-yl)-2-methylpropanoate | 530.1 | 1H NMR (400 MHz, DMSO) δ = 12.36 (s, 1H), 8.58 (d, J = 5.2 Hz, 1H), 8.44-8.41 (m, 1H), 8.25 (s, 1H), 8.01 (d, J = 8.0 Hz, 1H), 7.82 (s, 1H), 7.75 (d, J = 7.6 Hz, 1H), 7.68 (s, 1H), 7.62-7.57 (m, 4H), 6.56 (d, J = 8.4 Hz, 2H), 5.66 (s, 2H), 4.12 (d, J = 6.0 Hz, 2H), 3.60 (s, 3H), 1.60 (s, 6H) ppm |
| 183 | 4-amino-N-(2-((4-(3-(2-(N-methylacetamido)pyridin-4-yl)phenyl)thiazol-2-yl)amino)-2-oxoethyl)benzamide | 501.4 | 1H NMR (400 MHz, DMSO) δ = 12.38 (s, 1H), 8.57 (d, J = 5.2 Hz, 1H), 8.47-8.46 (m, 1H), 8.31 (s, 1H), 8.03 (d, J = 7.8 Hz, 1H), 7.89 (s, 1H), 7.83 (s, 1H), 7.79 (d, J = 7.6 Hz, 1H), 7.69-8.68 (m, 1H), 7.67-7.56 (m, 3H), 6.62 (d, J = 8.4 Hz, 2H), 4.18-4.10 (m, 2H), 3.34 (s, 3H), 2.08 (s, 3H) ppm |
| 184 | 5-amino-N-(2-oxo-2-((4-(3-(pyridin-4-yl)phenyl)thiazol-2-yl)amino)ethyl)picolinamide | 431.1 | 1H NMR (400 MHz, DMSO) δ = 8.69-8.67 (m, 2H), 8.65-8.62 (m, 1H), 8.30 (s, 1H), 8.02 (d, J = 8.0 Hz, 1H), 7.97 (d, J = 2.4 Hz, 1H), 7.83 (s, 1H), 7.77-7.61 (m, 3H), 7.72 (d, J = 8.4 Hz, 1H), 7.62-7.58 (m, 1H), 7.01-6.98 (m, 1H), 5.99 (s, 2H), 4.21 (d, J = 6.0 Hz, 2H) ppm |
| 185 | 4-amino-N-(2-((4-(3-(1,1-dioxidothiomorpholino)phenyl)thiazol-2-yl)amino)-2-oxoethyl)benzamide | 486.4 | 1H NMR (400 MHz, DMSO) δ = 12.31 (br s, 1H), 8.40 (s, 1H), 7.67-7.58 (m, 3H), 7.51 (s, 1H), 7.41-7.36 (m, 1H), 7.33-7.27 (m, 1H), 7.02-6.95 (m, 1H), 6.56 (d, J = 8.8 Hz, 2H), 5.66 (s, 2H), 4.10 (d, J = 5.6 Hz, 2H), 3.81 (br s, 4H), 3.16 (br s, 4H) ppm |

| # | Compound Name | LCMS m/z: M + H | HNMR |
|---|---|---|---|
| 186 | 4-amino-N-[2-[[4-[3-[2-[2-(dimethylamino)ethylamino]-2-oxo-ethyl]-4-pyridyl]phenyl]thiazol-2-yl]amino]-2-oxo-ethyl]benzamide | 558.3 | 1H NMR (400 MHz, DMSO) δ = 12.60 (s, 1H), 8.56 (d, J = 5.2 Hz, 1H), 8.43-8.40 (m, 1H), 8.27 (s, 1H), 8.18 (s, 1H), 8.07-8.06 (m, 1H), 8.00 (br d, J = 7.6 Hz, 1H), 7.79 (s, 1H), 7.72-7.69 (m, 2H), 7.62-7.57 (m, 4H), 6.56 (d, J = 8.4 Hz, 2H), 5.65 (s, 2H), 4.12 (br d, J = 6.0 Hz, 2H), 3.69 (s, 2H), 3.20-3.15 (m, 2H), 2.33-2.32 (m, 2H), 2.14 (s, 6H) ppm |
| 187 | 1-[3-[2-[[2-[(4-aminobenzoyl)amino]acetyl]amino]thiazol-4-yl]phenyl]piperidine-4-carboxylic acid | 480.1 | 1H NMR (400 MHz, MeOD) δ = 7.71-7.66 (m, 2H), 7.56 (s, 1H), 7.38-7.33 (m, 2H), 7.26-7.24 (m, 1H), 6.95-6.94 (m, 1H), 6.72-6.67 (m, 2H), 4.26 (s, 2H), 3.70 (d, J = 12.8 Hz, 2H), 2.89-2.77 (m, 1H), 2.46-2.45 (m, 1H), 2.09-1.99 (m, 2H), 1.92-1.78 (m, 2H) ppm |
| 188 | 4-amino-N-[2-[[4-[4-methyl-3-(4-pyridyl)phenyl]thiazol-2-yl]amino]-2-oxo-ethyl]benzamide | 444.1 | 1H NMR (400 MHz, DMSO) δ = 12.30 (br s, 1H), 8.66 (d, J = 5.6 Hz, 1H), 8.42-8.40 (m, 1H), 7.87 (br d, J = 8.0 Hz, 1H), 7.80 (s, 1H), 7.66 (s, 1H), 7.61 (br d, J = 8.8 Hz, 2H), 7.45 (d, J = 6.0 Hz, 2H), 7.41 (d, J = 8.0 Hz, 1H), 6.56 (d, J = 8.8 Hz, 2H), 5.66 (s, 2H), 4.10 (br d, J = 5.6 Hz, 2H), 2.28 (s, 3H) ppm |
| 189 | 4-amino-N-[2-[[4-[3-[2-[2-(dimethylamino)ethylamino]-4-pyridyl]phenyl]thiazol-2-yl]amino]-2-oxo-ethyl]benzamide | 516.4 | 1H NMR (400 MHz, DMSO) δ = 12.38 (br s, 1H), 8.42-8.44 (m, 1H), 8.32 (s, 1H), 8.19 (s, 1H), 8.06 (d, J = 5.8 Hz, 1H), 7.96 (br d, J = 7.6 Hz, 1H), 7.76 (s, 1H), 7.65-7.50 (m, 4H), 6.83-6.79 (m, 2H), 6.57 (d, J = 8.6 Hz, 2H), 6.42 (br s, 1H), 5.67 (br s, 2H), 4.13 (br d, J = 5.6 Hz, 2H), 3.41 (br s, 2H), 2.47 (br s, 2H), 2.22 (s, 6H) ppm |
| 190 | 4-amino-N-[2-[[4-[3-[2-(4-methylpiperazin-1-yl)-4-pyridyl]phenyl]thiazol-2-yl]amino]-2-oxo-ethyl]benzamide | 528.2 | 1H NMR (400 MHz, MeOD) δ = 8.27 (s, 1H), 8.22 (d, J = 5.6 Hz, 1H), 8.03 (d, J = 8.0 Hz, 1H), 7.79-7.77 (m, 2H), 7.72-7.70 (m, 1H), 7.58-7.54 (m, 1H), 7.41 (br d, J = 6.4 Hz, 1H), 7.30-7.27 (m, 1H), 6.91-6.88 (m, 2H), 4.28-3.99 (m, 6H), 3.47 (br s, 4H), 2.99 (s, 3H) ppm |
| 191 | 4-amino-N-[2-[[4-[3-[2-[2-(dimethylamino)ethyl-methyl-amino]-4-pyridyl]phenyl]thiazol-2-yl]amino]-2-oxo-ethyl]benzamide | 530.0 | 1H NMR (400 MHz, DMSO) δ = 12.35 (br s, 1H), 8.43-8.41 (m, 1H), 8.23-8.14 (m, 2H), 7.96 (d, J = 7.6 Hz, 1H), 7.78 (s, 1H), 7.67 (d, J = 8.0 Hz, 1H), 7.61 (d, J = 8.8 Hz, 2H), 7.58-7.51 (m, 1H), 6.94-6.71 (m, 2H), 6.56 (d, J = 8.4 Hz, 2H), 5.66 (br s, 2H), 4.12 (d, J = 6.0 Hz, 2H), 3.72-3.69 (m, 2H), 3.08 (s, 3H), 2.47-2.44 (m, 2H), 2.22 (s, 6H) ppm |
| 192 | 4-amino-N-[2-[[4-(1H-indazol-5-yl)thiazol-2-yl]amino]-2-oxo-ethyl]benzamide | 392.9 | 1H NMR (400 MHz, DMSO-d6) δ = 13.09 (s, 1H), 12.29 (s, 1H), 8.42-8.39 (m, 1H), 8.27 (s, 1H), 8.11 (s, 1H), 7.91-7.87 (m, 1H), 7.62-7.53 (m, 4H), 6.56 (d, J = 8.4 Hz, 2H), 5.65 (s, 2H), 4.12 (d, J = 5.6 Hz, 2H) ppm |
| 193 | 5-amino-N-[2-oxo-2-[[4-[3-(4-pyridyl)phenyl]thiazol-2-yl]amino]ethyl]pyrimidine-2-carboxamide | 432.2 | 1H NMR (400 MHz, DMSO) δ = 12.44 (s, 1H), 8.86-8.76 (m, 3H), 8.39 (s, 1H), 8.19 (s, 2H), 8.08 (d, J = 6.0 Hz, 3H), 7.89-7.83 (m, 2H), 7.66-7.64 (m, 1H), 4.21 (d, J = 6.0 Hz, 2H) ppm |
| 194 | 4-amino-N-[2-[[4-[3-(3-methyl-4-pyridyl)phenyl]thiazol-2-yl]amino]-2-oxo-ethyl]benzamide | 444.2 | 1H NMR (400 MHz, DMSO) δ = 12.33 (br s, 1H), 8.54 (s, 1H), 8.49 (d, J = 4.8 Hz, 1H), 8.43-8.40 (m, 1H), 7.98 (d, J = 8.4 Hz, 1H), 7.94 (d, J = 1.6 Hz, 1H), 7.75 (s, 1H), 7.62 (d, J = 8.8 Hz, 2H), 7.57-7.55 (m, 1H), 7.38 (d, J = 8.0 Hz, 1H), 7.30 (d, J = 4.8 Hz, 1H), 6.57 (d, J = 8.8 Hz, 2H), 5.66 (s, 2H), 4.12 (d, J = 6.0 Hz, 2H), 2.29 (s, 3H) ppm |
| 195 | 4-amino-N-[2-[[4-[3-(2-methyl-4-pyridyl)phenyl]thiazol-2-yl]amino]-2-oxo-ethyl]benzamide | 444.0 | 1H NMR (400 MHz, DMSO) δ = 12.36 (m, 1H), 8.53 (d, J = 5.2 Hz, 1H), 8.43-8.40 (m, 1H), 8.28 (s, 1H), 7.99 (d, J = 7.6 Hz, 1H), 7.81 (s, 1H), 7.73 (br d, J = 7.6 Hz, 1H), 7.62 (d, J = 2.4 Hz, 2H), 7.60-7.53 (m, 3H), 6.56 (d, J = 8.8 Hz, 2H), 5.66 (s, 2H), 4.12 (d, J = 5.6 Hz, 2H), 2.55 (s, 3H) ppm |

| # | Compound Name | LCMS m/z: M + H | HNMR |
|---|---|---|---|
| 196 | 4-amino-N-[2-[[4-[3-[2-(methylaminomethyl)-4-pyridyl]phenyl]thiazol-2-yl]amino]-2-oxo-ethyl]benzamide | 473.0 | 1H NMR (400 MHz, METHANOL-d4) δ = 8.72 (d, J = 5.2 Hz, 1H), 8.31 (s, 1H), 8.04 (d, J = 7.6 Hz, 1H), 7.81-7.77 (m, 4H), 7.73 (d, J = 8.0 Hz, 1H), 7.61-7.56 (m, 2H), 6.97-6.92 (m, 2H), 4.45 (s, 2H), 4.30 (s, 2H), 2.85 (s, 3H) ppm |
| 197 | 4-amino-N-[2-oxo-2-[[4-[3-(4-pyridyloxymethyl)phenyl]thiazol-2-yl]amino]ethyl]benzamide | 460.2 | 1H NMR (400 MHz, DMSO) δ = 12.33 (s, 1H), 8.41-8.39 (m, 3H), 8.13 (s, 1H), 8.00 (s, 1H), 7.88-7.84 (m, 1H), 7.64-7.59 (m, 3H), 7.48-7.40 (m, 2H), 7.06-7.05 (m, 2H), 6.56 (d, J = 8.4 Hz, 2H), 5.65 (br s, 2H), 5.24 (s, 1H), 5.25 (s, 1H), 4.11 (d, J = 5.6 Hz, 2H) ppm |
| 198 | 4-amino-N-[2-[[4-[3-(1-hydroxy-1-methyl-ethyl)phenyl]thiazol-2-yl]amino]-2-oxo-ethyl]benzamide | 411.2 | 1H NMR (400 MHz, DMSO) δ = 12.35 (s, 1H), 8.46-8.43 (m, 1H), 8.04 (s, 1H), 7.71 (br d, J = 7.6 Hz, 1H), 7.63 (d, J = 8.4 Hz, 2H), 7.57 (s, 1H), 7.42-7.40 (m, 1H), 7.36-7.32 (m, 1H), 6.62 (d, J = 8.8 Hz, 2H), 4.12 (br d, J = 5.6 Hz, 2H), 1.45 (s, 6H) ppm |
| 199 | 5-amino-N-[2-[[4-[3-(2-methoxy-4-pyridyl)phenyl]thiazol-2-yl]amino]-2-oxo-ethyl]pyridine-2-carboxamide | 461.2 | 1H NMR (400 MHz, DMSO) δ = 12.43 (br s, 1H), 8.64-8.62 (m, 1H), 8.27-8.23 (m, 2H), 8.04-7.92 (m, 2H), 7.83 (s, 1H), 7.75-7.67 (m, 2H), 7.62-7.52 (m, 1H), 7.36-7.35 (m, 1H), 7.17 (s, 1H), 7.0-6.97 (m, 1H), 5.99 (s, 2H), 4.20 (d, J = 6.0 Hz, 2H), 3.92 (s, 3H) ppm |
| 200 | 2-[[4-[3-[2-[[2-[(4-aminobenzoyl)amino]acetyl]amino]thiazol-4-yl]phenyl]-2-pyridyl]-methyl-amino]acetic acid | 517.3 | 1H NMR (400 MHz, DMSO) δ = 8.44-8.40 (m, 1H), 8.29 (s, 1H), 8.20 (s, 1H), 8.13 (d, J = 5.2 Hz, 1H), 7.97 (d, J = 7.6 Hz, 1H), 7.78 (s, 1H), 7.68 (d, J = 7.6 Hz, 1H), 7.61 (d, J = 8.8 Hz, 2H), 7.58-7.52 (m, 1H), 6.90 (d, J = 5.2 Hz, 1H), 6.85 (s, 1H), 6.56 (d, J = 8.8 Hz, 2H), 5.65 (br s, 2H), 4.25 (s, 2H), 4.12 (br d, J = 6.0 Hz, 2H), 3.12 (s, 3H) ppm |
| 201 | 4-amino-N-[2-oxo-2-[[4-[6-(4-pyridyl)-2-pyridyl]thiazol-2-yl]amino]ethyl]benzamide | 431.1 | 1H NMR (400 MHz, DMSO) δ = 12.44 (s, 1H), 8.87 (d, J = 4.8 Hz, 2H), 8.49-8.42 (m, 3H), 8.21-8.17 (m, 1H), 8.15-8.09 (m, 1H), 8.08-8.04 (m, 1H), 7.63 (d, J = 8.8 Hz, 2H), 6.59 (d, J = 8.8 Hz, 2H), 4.14 (d, J = 5.6 Hz, 2H) ppm 19F NMR (376 MHz, DMSO-d6) ä = −74.27 (s, 1F) |
| 202 | 4-amino-N-[2-[[4-[3-[2-[methyl-[2-(methylamino)-2-oxo-ethyl]amino]-4-pyridyl]phenyl]thiazol-2-yl]amino]-2-oxo-ethyl]benzamide | 530.2 | 1H NMR (400 MHz, DMSO) δ = 12.36 (br s, 1H), 8.44-8.41 (m, 1H), 8.21 (s, 1H), 8.15 (d, J = 5.2 Hz, 1H), 7.98 (d, J = 8.0 Hz, 1H), 7.81-7.74 (m, 2H), 7.68 (d, J = 7.6 Hz, 1H), 7.62 (d, J = 8.8 Hz, 2H), 7.58-7.54 (m, 1H), 6.97-6.91 (m, 1H), 6.87 (s, 1H), 6.57 (d, J = 8.8 Hz, 2H), 5.66 (s, 2H), 4.20 (s, 2H), 4.13 (d, J = 6.0 Hz, 2H), 3.13 (s, 3H), 2.60 (d, J = 4.4 Hz, 3H) ppm |
| 203 | 4-amino-N-[2-[[4-[3-[2-(1,1-dioxothiazinan-2-yl)-4-pyridyl]phenyl]thiazol-2-yl]amino]-2-oxo-ethyl]benzamide | 563.2 | 1H NMR (400 MHz, DMSO) δ = 12.38 (s, 1H), 8.53 (d, J = 5.2 Hz, 1H), 8.42-8.28 (m, 1H), 8.27 (s, 1H), 8.02 (d, J = 7.6 Hz, 1H), 7.81 (s, 1H), 7.72 (br d, J = 8.0 Hz, 1H), 7.64-7.60 (m, 5H), 6.57 (d, J = 8.4 Hz, 2H), 5.65 (s, 2H), 4.13 (d, J = 5.6 Hz, 2H), 4.01-3.98 (m, 2H), 3.33 (br s, 2H), 2.20-2.17 (m, 2H), 1.98-1.84 (m, 2H) ppm |
| 204 | 4-amino-N-[2-[[4-[3-(4-methyl-3-oxo-piperazin-1-yl)phenyl]thiazol-2-yl]amino]-2-oxo-ethyl]benzamide | 465.2 | 1H NMR (400 MHz, DMSO) δ = 12.33 (br s, 1H), 8.41 (m, 1H), 7.68-7.59 (m, 3H), 7.47 (s, 1H), 7.40-7.33 (m, 1H), 7.32-7.26 (m, 1H), 6.93 (m, 1H), 6.58 (d, J = 8.6 Hz, 2H), 5.67 (s, 2H), 4.11 (br d, J = 5.6 Hz, 2H), 3.82 (s, 2H), 3.56-3.52 (m, 2H), 3.47-3.44 (m, 2H), 2.92 (s, 3H) ppm |
| 205 | 4-amino-N-[2-[[4-[3-[2-[2-(methylamino)-2-oxo-ethyl]-4-pyridyl]phenyl]thiazol-2-yl]amino]-2-oxo-ethyl]benzamide | 501.2 | 1H NMR (400 MHz, DMSO) δ = 12.40 (br s, 1H), 8.57 (d, J = 5.4 Hz, 1H), 8.41 (br s, 1H), 8.28 (s, 1H), 8.01 (br d, J = 7.8 Hz, 2H), 7.79 (s, 1H), 7.75-7.68 (m, 2H), 7.67-7.56 (m, 4H), 6.57 (br d, J = 8.6 Hz, 2H), 5.66 (s, 2H), 4.13 (br d, J = 5.6 Hz, 2H), 3.69 (s, 2H), 2.62 (d, J = 4.6 Hz, 3H) ppm |

| # | Compound Name | LCMS m/z: M + H | HNMR |
|---|---|---|---|
| 206 | 4-amino-N-[2-[[4-[3-[[2-(dimethylamino)-2-oxo-ethyl]-methyl-amino]-4-pyridyl]phenyl]thiazol-2-yl]amino]-2-oxo-ethyl]benzamide | 544.2 | 1H NMR (400 MHz, DMSO) δ = 12.36 (s, 1H), 8.44-8.41 (m, 1H), 8.21 (s, 1H), 8.12 (d, J = 5.2 Hz, 1H), 7.98 (d, J = 7.6 Hz, 1H), 7.79 (s, 1H), 7.68 (d, J = 8.4 Hz, 1H), 7.62 (d, J = 8.4 Hz, 2H), 7.59-7.53 (m, 1H), 6.92-6.83 (m, 2H), 6.57 (d, J = 8.4 Hz, 2H), 5.66 (s, 2H), 4.52 (s, 2H), 4.13 (d, J = 5.6 Hz, 2H), 3.12-3.01 (m, 6H), 2.82 (s, 3H) ppm |
| 207 | 4-amino-N-[2-[[4-[3-(2-isopropyl-4-pyridyl)phenyl]thiazol-2-yl]amino]-2-oxo-ethyl]benzamide | 472.2 | 1H NMR (400 MHz, DMSO) δ = 12.37 (s, 1H), 8.57 (d, J = 4.8 Hz, 1H), 8.45-8.42 (m, 1H), 8.27 (s, 1H), 7.99 (d, J = 7.6 Hz, 1H), 7.82 (s, 1H), 7.74 (d, J = 8.4 Hz, 1H), 7.62-7.54 (m, 5H), 6.56 (d, J = 8.8 Hz, 2H), 5.67 (s, 2H), 4.12 (d, J = 5.6 Hz, 2H), 3.15-3.08 (m, 1H), 1.29 (d, J = 6.8 Hz, 6H) ppm |
| 208 | 4-amino-N-[2-oxo-2-[[4-[5-(4-pyridyl)-3-pyridyl]thiazol-2-yl]amino]ethyl]benzamide | 431.2 | 1H NMR (400 MHz, DMSO) δ = 12.68-12.28 (m, 1H), 9.20 (d, J = 2.0 Hz, 1H), 8.96 (d, J = 2.2 Hz, 1H), 8.74-8.70 (m, 2H), 8.62-8.61 (m, 1H), 8.44-8.42 (m, 1H), 7.99 (s, 1H), 7.87-7.84 (m, 2H), 7.62 (d, J = 8.6 Hz, 2H), 6.57 (d, J = 8.6 Hz, 2H), 5.66 (s, 2H), 4.13 (d, J = 5.6 Hz, 2H) ppm |
| 209 | methyl 2-[3-[3-[2-[[2-[(4-aminobenzoyl)amino]acetyl]amino]thiazol-4-yl]phenyl]pyrazol-1-yl]-2-methyl-propanoate | 519.2 | 1H NMR (400 MHz, DMSO) δ = 12.41 (s, 1H), 8.44 (s, 1H), 8.34 (s, 1H), 8.00 (s, 1H), 7.83 (d, J = 6.4 Hz, 1H), 7.77-7.68 (m, 2H), 7.63 (d, J = 7.2 Hz, 2H), 7.46 (s, 1H), 6.81 (s, 1H), 6.58 (d, J = 7.2 Hz, 2H), 5.68 (s, 2H), 4.13 (s, 2H), 3.65 (s, 3H), 1.84 (s, 6H) ppm |
| 210 | 2-[3-[3-[2-[[2-[(4-aminobenzoyl)amino]acetyl]amino]thiazol-4-yl]phenyl]pyrazol-1-yl]acetic acid | 477.1 | 1H NMR (400 MHz, DMSO) δ = 12.45 (s, 1H), 8.64-8.30 (m, 2H), 7.87-7.79 (m, 2H), 7.76-7.68 (m, 2H), 7.63 (d, J = 8.8 Hz, 2H), 7.46 (m, 1H), 6.78 (d, J = 2.2 Hz, 1H), 6.58 (d, J = 8.6 Hz, 2H), 5.01 (s, 2H), 4.13 (br d, J = 5.6 Hz, 2H) ppm |
| 211 | 4-amino-N-[2-[[4-[3-(1-amino-1-methyl-ethyl)-4-pyridyl]phenyl]thiazol-2-yl]amino]-2-oxo-ethyl]benzamide | 487.4 | 1H NMR (400 MHz, DMSO) δ = 8.61 (d, J = 5.2 Hz, 1H), 8.45-8.37 (m, 1H), 8.28 (s, 1H), 8.04-7.94 (m, 2H), 7.83-7.72 (m, 2H), 7.64-7.53 (m, 5H), 6.56 (d, J = 8.8 Hz, 2H), 5.66 (s, 2H), 4.12 (d, J = 5.6 Hz, 2H), 1.49 (s, 6H) ppm |
| 212 | 2-3-[3-12-1[2-1(4-aminobenzoyl)amino]acetyl]amino]thiazol-4-yl]phenyl]pyrazol-1-yl]-2-methyl-propanoic acid | 505.2 | 1H NMR (400 MHz, DMSO) δ = 12.42 (s, 1H), 8.42 (s, 1H), 8.36 (s, 1H), 7.96 (d, J = 2.4 Hz, 1H), 7.82 (br d, J = 8.0 Hz, 1H), 7.74 (br d, J = 7.6 Hz, 1H), 7.69 (s, 1H), 7.63 (d, J = 8.6 Hz, 2H), 7.46 (m, 1H), 6.79 (d, J = 2.4 Hz, 1H), 6.58 (d, J = 8.6 Hz, 2H), 4.14 (d, J = 5.6 Hz, 2H), 1.81 (s, 6H) ppm |
| 213 | 4-amino-N-[2-[[4-[3-[1-[1,1-dimethyl-2-(methylamino)-2-oxo-ethyl]pyrazol-3-yl]phenyl]thiazol-2-yl]amino]-2-oxo-ethyl]benzamide | 518.3 | 1H NMR (400 MHz, DMSO) δ = 12.43 (br s, 1H), 8.43 (m, 1H), 8.37 (s, 1H), 7.92 (d, J = 2.4 Hz, 1H), 7.83 (br d, J = 8.0 Hz, 1H), 7.76 (d, J = 7.8 Hz, 1H), 7.69 (s, 1H), 7.62 (d, J = 8.8 Hz, 2H), 7.46 (m, 1H), 7.34 (br d, J = 4.4 Hz, 1H), 6.81 (d, J = 2.4 Hz, 1H), 6.57 (d, J = 8.8 Hz, 2H), 5.68 (s, 2H), 4.13 (d, J = 5.6 Hz, 2H), 2.59 (d, J = 4.4 Hz, 3H), 1.76 (s, 6H) ppm |
| 214 | (S)-4-amino-N-(1-((4-(3-(2-methylpyridin-4-yl)phenyl)thiazol-2-yl)amino)-4-(methylthio)-1-oxobutan-2-yl)benzamide | 518.1 | 1H NMR (400 MHz, DMSO) δ = 12.44 (s, 1H), 8.92-8.79 (m, 1H), 8.46 (s, 1H), 8.36-8.09 (m, 4H), 7.94 (br d, J = 7.4 Hz, 1H), 7.89 (s, 1H), 7.74-7.59 (m, 3H), 6.59 (br dd, J = 8.6, 2.6 Hz, 2H), 4.75-4.65 (m, 1H), 2.76 (d, J = 2.4 Hz, 3H), 2.66-2.52 (m, 3H), 2.15-2.04 (m, 5H) ppm |
| 215 | N-[1-[4-[3-[2-[[2-[(4-aminobenzoyl)amino]acetyl]amino]thiazol-4-yl]phenyl]-2-pyridyl]-1-methyl-ethyl]-5-methyl-1,3,4-oxadiazole-2-carboxamide | 597.5 | 1H NMR (400 MHz, DMSO) δ = 12.46-12.29 (m, 1H), 9.59 (s, 1H), 8.65 (d, J = 5.2 Hz, 1H), 8.44-8.43 (m, 1H), 8.27 (s, 1H), 8.01 (d, J = 7.6 Hz, 1H), 7.89 (s, 1H), 7.81 (s, 1H), 7.75 (d, J = 7.6 Hz, 1H), 7.68-7.67 (m, 1H), 7.58 (s, 3H), 6.57 (d, J = 8.8 Hz, 2H), 5.67 (s, 2H), 4.12 (d, J = 5.6 Hz, 2H), 2.58 (s, 3H), 1.81 (s, 6H) ppm |

| # | Compound Name | LCMS m/z: M + H | HNMR |
|---|---|---|---|
| 216 | 4-amino-N-[2-[[4-[3-[1-[2-(methylamino)-2-oxo-ethyl]pyrazol-3-yl]phenyl]thiazol-2-yl]amino]-2-oxo-ethyl]benzamide | 490.2 | 1H NMR (400 MHz, DMSO) δ = 12.45 (br s, 1H), 8.52-8.34 (m, 2H), 8.04 (br d, J = 4.8 Hz, 1H), 7.82 (br d, J = 7.8 Hz, 1H), 7.79 (d, J = 2.4 Hz, 1H), 7.72 (br d, J = 7.8 Hz, 1H), 7.69 (s, 1H), 7.62 (d, J = 8.6 Hz, 2H), 7.46 (m, 1H), 6.77 (d, J = 2.4 Hz, 1H), 6.57 (d, J = 8.6 Hz, 2H), 5.68 (s, 2H), 4.84 (s, 2H), 4.13 (br d, J = 5.6 Hz, 2H), 2.65 (d, J = 4.6 Hz, 3H) ppm |
| 217 | 4-amino-N-[2-oxo-2-[[4-[2-(4-pyridyl)-4-pyridyl]thiazol-2-yl]amino]ethyl]benzamide | 431.2 | 1HNMR (400 MHz, DMSO) δ = 12.48 (m, 1H), 8.78 (d, J = 4.8 Hz, 1H), 8.74-8.72 (m, 2H), 8.52 (s, 1H), 8.45-8.42 (m, 1H), 8.18 (s, 1H), 8.10-8.09 (m, 2H), 7.61 (d, J = 8.8 Hz, 2H), 7.69-7.53 (m, 1H), 6.56 (d, J = 8.8 Hz, 2H), 5.66 (s, 2H), 4.13 (d, J = 5.6 Hz, 2H) ppm |
| 218 | 4-amino-N-[2-oxo-2-[[4-[3-[2-(4-pyridyl)ethyl]phenyl]thiazol-2-yl]amino]ethyl]benzamide | 458.2 | 1HNMR (400 MHz, MeOD) δ = 8.68 (d, J = 6.8 Hz, 2H), 7.91 (d, J = 6.8 Hz, 2H), 7.77-7.73 (m, 4H), 7.36 (s, 1H), 7.31-7.29 (m, 1H), 7.15 (d, J = 8.0 Hz, 1H), 6.86-6.84 (m, 2H), 4.27 (s, 2H), 3.36-3.34 (m, 2H), 3.16-3.12 (m, 2H) ppm |
| 219 | 1-[4-[3-[2-[[2-[(4-aminobenzoyl)amino]acetyl]amino]thiazol-4-yl]phenyl]-2-pyridyl]cyclopropanecarboxylic acid | 514.3 | 1H NMR (400 MHz, DMSO) δ = 13.40-12.88 (m, 1H), 12.53-12.29 (m, 1H), 8.60-8.52 (m, 1H), 8.48-8.38 (m, 1H), 8.31-8.25 (m, 1H), 8.05-7.97 (m, 1H), 7.89-7.80 (m, 2H), 7.78-7.71 (m, 1H), 7.66-7.55 (m, 4H), 6.63-6.53 (m, 2H), 5.72-5.61 (m, 2H), 4.17-4.09 (m, 2H), 1.61-1.44 (m, 4H) ppm |
| 220 | 4-amino-N-[2-[[4-[3-(l-methylimidazol-4-yl)phenyl]thiazol-2-yl]amino]-2-oxo-ethyl]benzamide | 433.1 | 1H NMR (400 MHz, DMSO) δ = 8.43-8.40 (m, 1H), 8.35 (s, 1H), 8.19 (s, 1H), 7.72-7.60 (m, 7H), 7.40-7.38 (m, 1H), 6.56 (d, J = 8.8 Hz, 2H), 5.66 (s, 2H), 4.12 (d, J = 6.0 Hz, 2H), 3.70 (s, 3H) ppm |
| 221 | 4-amino-N-[2-[[4-[3-[2-(3-amino-1-piperidyl)-4-pyridyl]phenyl]thiazol-2-yl]amino]-2-oxo-ethyl]benzamide | 528.3 | 1HNMR (400 MHz, DMSO) δ = 8.45-8.42 (m, 1H), 8.35-8.32 (m, 1H), 8.20 (s, 1H), 8.18 (d, J = 5.2 Hz, 1H), 7.97 (d, J = 7.6 Hz, 1H), 7.79 (s, 1H), 7.69 (br d, J = 8.0 Hz, 1H), 7.61 (d, J = 8.8 Hz, 2H), 7.57-7.53 (m, 1H), 7.08 (s, 1H), 6.95 (d, J = 5.2 Hz, 1H), 6.56 (d, J = 8.4 Hz, 2H), 5.67 (s, 2H), 4.36-4.33 (m, 1H), 4.15-4.11 (m, 3H), 3.03-2.78 (m, 4H), 2.00-1.88 (m, 1H), 1.77-1.67 (m, 2H), 1.57-1.34 (m, 2H) ppm |
| 222 | 4-amino-N-[2-[[4-[3-(1,2-dimethylimidazol-4-yl)phenyl]thiazol-2-yl]amino]-2-oxo-ethyl]benzamide | 447.2 | 1H NMR (400 MHz, DMSO) δ = 12.41 (s, 1H), 8.44-8.41 (m, 1H), 8.31-8.30 (m, 1H), 7.68-7.66 (m, 1H), 7.62-7.59 (m, 4H), 7.51 (s, 1H), 7.37-7.33 (m, 1H), 6.57-6.55 (m, 2H), 5.67 (s, 2H), 4.12 (d, J = 6.0 Hz, 2H), 3.58 (s, 3H), 2.32 (s, 3H) ppm |
| 223 | 4-amino-N-[2-[[4-[3-[2-[1-(methylcarbamoyl)cyclopropyl]-4-pyridyl]phenyl]thiazol-2-yl]amino]-2-oxo-ethyl]benzamide | 527.3 | 1H NMR (400 MHz, DMSO) δ = 12.49-12.20 (m, 1H), 8.61 (d, J = 5.4 Hz, 1H), 8.46-8.38 (m, 1H), 8.27 (s, 1H), 8.01 (d, J = 7.8 Hz, 1H), 7.82 (s, 1H), 7.74 (d, J = 7.8 Hz, 1H), 7.67-7.56 (m, 6H), 6.57 (d, J = 8.6 Hz, 2H), 5.67 (s, 2H), 4.13 (d, J = 5.8 Hz, 2H), 2.62 (d, J = 4.6 Hz, 3H), 1.43-1.37 (m, 2H), 1.30-1.24 (m, 2H) ppm |
| 224 | [2-[4-[3-[2-[[2-[(4-aminobenzoyl)amino]acetyl]amino]thiazol-4-yl]phenyl]-2-pyridyl]acetyl]oxysodium | 488.4 | 1H NMR (400 MHz, METHANOL-d4) δ = 8.46 (d, J = 5.2 Hz, 1H), 8.30 (s, 1H), 7.98 (d, J = 8.0 Hz, 1H), 7.77 (s, 1H), 7.72 (d, J = 8.8 Hz, 2H), 7.67 (d, J = 7.6 Hz, 1H), 7.60 (d, J = 5.2 Hz, 1H), 7.53-7.49 (m, 1H), 7.36 (s, 1H), 6.70 (d, J = 8.4 Hz, 2H), 4.20 (s, 2H), 3.80 (s, 2H) |
| 225 | 4-amino-N-[2-[[4-[3-[2-[3-(dimethylamino)-1-piperidyl]-4-pyridyl]phenyl]thiazol-2-yl]amino]-2-oxo-ethyl]benzamide | 556.2 | 1H NMR (400 MHz, MeOD) δ = 8.29-8.27 (m, 1H), 8.17 (d, J = 6.0 Hz, 1H), 8.07-8.05 (m, 1H), 7.78-7.73 (m, 3H), 7.59-7.56 (m, 2H), 7.46 (s, 1H), 7.31-7.30 (m, 1H), 6.87-6.83 (m, 2H), 4.50-4.47 (m, 1H), 4.27 (s, 2H), 4.09-4.05 (m, 1H), 3.68-3.63 (m, 1H), 3.54-3.47 (m, 1H), 3.39-3.34 (m, 1H), 3.00 (s, 6H), 2.30-2.26 (m, 1H), 2.08-1.77 (m, 3H) ppm |

| # | Compound Name | LCMS m/z: M + H | HNMR |
|---|---|---|---|
| 226 | 4-amino-N-[2-[[4-[3-[2-[1,1-dimethyl-2-(methylamino)-2-oxo-ethyl]-4-pyridyl]phenyl]thiazol-2-yl]amino]-2-oxo-ethyl]benzamide | 529.3 | 1H NMR (400 MHz, DMSO) δ = 12.48-12.23 (m, 1H), 8.61 (d, J = 5.4 Hz, 1H), 8.47-8.37 (m, 1H), 8.24 (s, 1H), 8.01 (d, J = 7.8 Hz, 1H), 7.82-7.68 (m, 2H), 7.66-7.55 (m, 5H), 7.40 (br d, J = 4.4 Hz, 1H), 6.57 (d, J = 8.8 Hz, 2H), 5.67 (s, 2H), 4.13 (br d, J = 5.4 Hz, 2H), 2.58 (d, J = 4.4 Hz, 3H), 1.56 (s, 6H) ppm |
| 227 | 4-amino-N-[2-oxo-2-[[4-(3-pyrimidin-4-yl)phenyl)thiazol-2-yl]amino]ethyl]benzamide | 431.2 | 1H NMR (400 MHz, DMSO) δ = 9.30 (s, 1H), 8.90 (d, J = 5.2 Hz, 1H), 8.82 (s, 1H), 8.45-8.43 (m, 1H), 8.20-8.04 (m, 3H), 7.80 (s, 1H), 7.62 (d, J = 8.8 Hz, 3H), 6.57 (d, J = 8.4 Hz, 2H), 5.67 (s, 2H), 4.13 (d, J = 6.0 Hz, 2H) ppm |
| 228 | 4-amino-N-[2-[[4-(1-methylindazol-6-yl)thiazol-2-yl]amino]-2-oxo-ethyl]benzamide | 407.0 | 1H NMR (400 MHz, DMSO-d6) δ = 12.39 (s, 1H), 8.45-8.43 (m, 1H), 8.11 (s, 1H), 8.04 (d, J = 0.8 Hz, 1H), 7.82-7.76 (m, 1H), 7.75-7.67 (m, 2H), 7.62 (d, J = 8.8 Hz, 2H), 6.57 (d, J = 8.4 Hz, 2H), 5.68 (s, 2H), 4.13 (d, J = 5.6 Hz, 2H), 4.07 (s, 3H) ppm |
| 229 | 4-amino-N-[2-[[4-[3-[1-(2-hydroxy-2-methyl-propyl)pyrazol-3-yl]phenyl]thiazol-2-yl]amino]-2-oxo-ethyl]benzamide | 491.4 | 1H NMR (400 MHz, DMSO-d6) δ = 12.37 (br s, 1H), 8.44-8.43 (m, 1H), 8.36 (s, 1H), 7.81 (d, J = 7.6 Hz, 1H), 7.75-7.72 (m, 2H), 7.67 (s, 1H), 7.63 (d, J = 8.6 Hz, 2H), 7.45-7.44 (m, 1H), 6.75 (d, J = 2.0 Hz, 1H), 6.57 (d, J = 8.6 Hz, 2H), 5.66 (s, 2H), 4.92-4.56 (m, 1H), 4.13 (d, J = 5.6 Hz, 2H), 4.09 (s, 2H), 1.12 (s, 6H). |
| 230 | 4-amino-N-[2-oxo-2-[[4-[3-(tetrahydropyran-4-yloxymethyl)phenyl]thiazol-2-yl]amino]ethyl]benzamide | 467.0 | 1H NMR (400 MHz, DMSO) δ (ppm) = 12.33 (br s, 1H), 8.43-8.40 (m, 1H), 7.88 (s, 1H), 7.81 (d, J = 7.6 Hz, 1H), 7.62-7.59 (m, 3H), 7.42-7.38 (m, 1H), 7.30 (d, J = 7.6 Hz, 1H), 6.57 (d, J = 8.4 Hz, 2H), 5.66 (s, 2H), 4.58 (s, 2H), 4.12 (d, J = 5.6 Hz, 2H), 3.85-3.80 (m, 2H), 3.63-3.56 (m, 1H), 3.40-3.35 (m, 2H), 1.99-1.85 (m, 2H), 1.55-1.41 (m, 2H) |
| 231 | 4-amino-N-[2-[[4-[3-(3-methylisoxazol-5-yl)phenyl]thiazol-2-yl]amino]-2-oxo-ethyl]benzamide | 434.2 | 1H NMR (400 MHz, DMSO-d6) δ = 12.36 (s, 1H), 8.43 (t, J = 6.0 Hz, 1H), 8.37 (s, 1H), 8.01 (d, J = 8.0 Hz, 1H), 7.80-7.77 (m, 2H), 7.64-7.59 (m, 3H), 6.92 (s, 1H), 6.57 (d, J = 8.4 Hz, 2H), 5.66 (s, 2H), 4.12 (d, J = 6.0 Hz, 2H), 2.31 (s, 3H) |
| 232 | 4-amino-N-[2-[[4-[3-[1-(2-methoxy-2-methyl-propyl)pyrazol-3-yl]phenyl]thiazol-2-yl]amino]-2-oxo-ethyl]benzamide | 505.1 | 1H NMR (400 MHz, DMSO) δ (ppm) = 12.48-12.30 (m, 1H), 8.43-8.40 (m, 1H), 8.34 (s, 1H), 7.83-7.78 (m, 1H), 7.73 (d, J = 8.0 Hz, 1H), 7.69 (d, J = 2.4 Hz, 1H), 7.67 (s, 1H), 7.61 (d, J = 8.7 Hz, 2H), 7.44 (t, J = 7.8 Hz, 1H), 6.74 (d, J = 2.3 Hz, 1H), 6.56 (d, J = 8.4 Hz, 2H), 5.66 (s, 2H), 4.18 (s, 2H), 4.12 (d, J = 6.0 Hz, 2H), 3.20 (s, 3H), 1.12 (s, 6H) |
| 233 | (S)-4-amino-N-(4-(dimethylamino)-1-oxo-1-((4-(3-(pyridin-4-yl)phenyl)thiazol-2-yl)amino)butan-2-yl)benzamide | 501.3 | 1H NMR (400 MHz, DMSO) δ = 8.73-8.64 (m, 2H), 8.52 (d, J = 7.0 Hz, 1H), 8.31 (s, 1H), 8.02 (d, J = 7.6 Hz, 1H), 7.82 (s, 1H), 7.79-7.72 (m, 3H), 7.65-7.56 (m, 3H), 6.57 (d, J = 8.8 Hz, 2H), 5.68 (s, 2H), 4.64 (br d, J = 5.6 Hz, 1H), 2.42-2.36 (m, 2H), 2.20 (s, 6H), 2.03-1.89 (m, 2H) ppm |
| 234 | 4-amino-N-[2-[[4-[3-[(3R)-3-hydroxy-1-piperidyl]phenyl]thiazol-2-yl]amino]-2-oxo-ethyl]benzamide | 452.0 | 1H NMR (400 MHz, DMSO-d6) δ = 12.35 (s, 1H) 8.48 (m, 1H), 7.58-7.67 (m, 4H), 7.40 (br s, 1H), 7.31 (m, 1H), 7.02 (m, 1H), 6.64 (d, J = 8.4 Hz, 2H), 4.12 (m, 2H), 3.58 (m, 3H), 2.83 (br s, 1H), 2.68-2.74 (m, 1H), 1.80-1.96 (m, 2H), 1.61 (m, 1 H), 1.36 (m, 1H) ppm |
| 235 | 4-amino-N-[2-oxo-2-[[4-[3-(1-tetrahydropyran-4-yloxyethyl)phenyl]thiazol-2-yl]amino]ethyl]benzamide | 481.1 | 1H NMR (400 MHz, DMSO-d6) δ = 12.32 (br s, 1H), 8.43 (m, 1H), 7.90 (s, 1H), 7.79 (d, J = 7.6 Hz, 1H), 7.66-7.57 (m, 3H), 7.40 (d, J = 7.6 Hz, 1H), 6.57 (d, J = 8.8 Hz, 2H), 5.68 (s, 2H), 4.70 (m, 1H), 4.12 (m, 2H), 3.86-3.68 (m, 2H), 3.41-3.39 (m, 1H), 3.30-3.24 (m, 2H), 1.92 (m, 1H), 1.71-1.61 (m, 1H), 1.50-1.31 (m, 5H) ppm |

-continued

| # | Compound Name | LCMS m/z: M + H | HNMR |
|---|---|---|---|
| 236 | 4-amino-N-[2-[[4-[3-[(3S)-3-hydroxy-1-piperidyl]phenyl]thiazol-2-yl]amino]-2-oxo-ethyl]benzamide | 452.1 | 1H NMR (400 MHz, DMSO-d6) δ = 12.33-12.32 (m, 1H), 8.42-8.39 (m, 1H), 7.62-7.58 (m, 3H), 7.47 (s, 1H), 7.28-7.21 (m, 2H), 6.88-6.86(m, 1H), 6.56 (d, J = 6.8 Hz, 2H), 5.66 (s, 2H), 4.85 (d, J = 2.0 Hz, 1H), 4.11 (d, J = 5.6 Hz, 2H), 3.62-3.51 (m, 2H), 2.68-2.66 (m, 1H), 2.71-2.66 (m, 2H), 1.93-1.89 (m, 1H), 1.79-1.74 (m, 1H), 1.59-1.50 (m, 1H), 1.33-1.24 (m, 1H) ppm |
| 237 | 4-amino-N-[(1S)-1-[[4-[3-[3-(aminomethyl)phenyl]phenyl]thiazol-2-yl]carbamoyl]-3-methylsulfanyl-propyl]benzamide | 532.3 | 1H NMR (400 MHz, METHANOL-d4) δ = 8.21 (s, 1H), 8.09 (d, J = 8.8 Hz, 2H), 7.92 (d, J = 7.6 Hz, 1H), 7.82 (s, 1H), 7.77 (d, J = 8.0 Hz, 1H), 7.64 (d, J = 8.0 Hz, 1H), 7.58-7.46 (m, 6H), 4.95-4.92 (m, 1H), 4.22 (s, 2H), 2.76-2.65 (m, 2H), 2.36-2.18 (m, 2H), 2.14 (s, 3H) ppm |
| 238 | 4-amino-N-[2-[[4-[3-[(3S)-3-methoxy-1-piperidyl]phenyl]thiazol-2-yl]amino]-2-oxo-ethyl]benzamide | 466.0 | 1H NMR (400 MHz, DMSO-d6) δ = 12.29 (s, 1H), 8.41-8.38 (s, 1H), 7.60 (d, J = 8.4, 3H), 7.46 (s, 1H), 7.30-7.22 (m, 2H), 6.92-6.89 (m, 1H), 6.56 (d, J = 8.4, 2H), 5.65 (s, 2H), 4.10 (d, J = 5.6, 2H), 3.69-3.65 (m, 1H), 3.47-3.43 (m, 1H), 3.37-3.35 (m, 1H), 3.29 (s, 3H), 2.84-2.77 (1H), 2.73-2.68 (m, 1H), 2.02-1.98 (m, 1H), 1.82-1.77 (m, 1H), 1.57-1.52 (s.1 H), 1.38-1.28 (m, 1H) ppm. |
| 239 | 4-amino-N-[2-oxo-2-[[4-(3-tetrahydropyran-2-ylphenyl)thiazol-2-yl]amino]ethyl]benzamide | 437.2 | 1H NMR (400 MHz, DMSO-d6) δ = 12.36 (br s, 1H), 8.46 (br s, 1H), 7.91 (br s, 1H), 7.76 (d, J = 7.2 Hz, 1H), 7.65 (s, 2H), 7.59 (s, 1H), 7.36 (m, 1H), 7.24 (d, J = 6.8 Hz, 1H), 6.71-6.51 (m, 2H), 4.34 (d, J = 10.8 Hz, 1H), 4.13 (s, 2H), 4.08-3.98 (m, 2H), 1.96-1.75 (m, 2H), 1.71-1.32 (m, 4H) 1H NMR (400 MHz, DMSO + D2O) δ = 7.88 (br s, 1H), 7.74 (d, J = 7.6 Hz, 1H), 7.65 (d, J = 8.0 Hz, 2H), 7.55 (s, 1H), 7.41-7.30 (m, 1H), 7.23 (d, J = 7.6 Hz, 1H), 6.70 (d, J = 8.4 Hz, 2H), 4.32 (d, J = 10.8 Hz, 1H), 4.12 (s, 2H), 4.01 (d, J = 11.2 Hz, 1H), 3.59-3.42 (m, 1H), 1.90-1.75 (m, 2H), 1.70-1.35 (m, 4H) 19F NMR (376 MHz, DMSO + D2O) δ = −74.24 (s) |
| 240 | 4-amino-N-[2-oxo-2-[(4-quinazolin-7-ylthiazol-2-yl)amino]ethyl]benzamide | 405.3 | 1H NMR (400 MHz, DMSO-d6) δ = 9.58 (s, 1H), 9.29 (s, 1H), 8.50 (s, 1H), 8.45 (t, J = 6.0 Hz, 1H), 8.33-8.31 (m, 1H), 8.21 (d, J = 8.4 Hz, 1H), 8.10 (s, 1H), 7.62 (d, J = 8.4 Hz, 2H), 6.56 (d, J = 8.4 Hz, 2H), 5.67 (s, 2H), 4.14 (d, J = 6.0 Hz, 2H) |
| 241 | 4-amino-N-[2-[[4-[3-[1-(2-amino-2-methyl-propyl)pyrazol-3-yl]phenyl]thiazol-2-yl]amino]-2-oxo-ethyl]benzamide | 490.1 | 1H NMR (400 MHz, DMSO-d6) δ = 12.34 (s, 1H), 8.44-8.43(m, 1H), 8.33 (s, 1H), 8.00 (br s, 3H), 7.88-7.79 (m, 3H), 7.69-7.64 (m, 1H), 7.61 (d, J = 8.6 Hz, 2H), 7.50-7.48 (m, 1H), 6.85 (d, J = 2.2 Hz, 1H), 6.56 (d, J = 8.7 Hz, 2H), 5.66 (br s, 2H), 4.33 (s, 2H), 4.12 (br d, J = 5.7 Hz, 2H), 1.26 (s, 6H) |

Example 88. Assay for ATPase Catalytic Activity of BRM and BRG-1

The ATPase catalytic activity of BRM or BRG-1 was measured by the in vitro biochemical assay using ADP-Glo™ (Promega, V9102). The ADP-Glo™ kinase assay is performed in two steps once the reaction is complete. The first step is to deplete any unconsumed ATP in the reaction. The second step is to convert the reaction product ADP to ATP, which will be utilized by the luciferase to generate luminesce and be detected by a luminescence reader, such as Envision.

The assay reaction mixture (10 µL) contains 30 nM of BRM or BRG-1, 20 nM salmon sperm DNA (from Invitrogen, UltraPure™ Salmon Sperm DNA Solution, cat #15632011), and 400 µM of ATP in the ATPase assay buffer, which comprises of 20 mM Tris, pH 8, 20 mM MgCl$_2$, 50 mM NaCl, 0.1% Tween-20, and 1 mM fresh DTT (Pierce™ DTT (Dithiothreitol), cat #20290). The reaction is initiated by the addition of the 2.5 µL ATPase solution to 2.5 µL ATP/DNA solution on low volume white Proxiplate-384 plus plate (Perkin Elmer, cat #6008280) and incubates at room temperature for 1 hour. Then following addition of 5 µL of ADP-Glo™ Reagent provided in the kit, the reaction incubates at room temperature for 40 minutes. Then 10 µL of Kinase Detection Reagent provided in the kit is added to convert ADP to ATP, and the reaction incubates at room temperature for 60 minutes. Finally, luminescence measurement is collected with a plate-reading luminometer, such as Envision.

BRM and BRG-1 were synthesized from high five insect cell lines with a purity of greater than 90%. $IP_{50}$ data for compounds 1-241 from the ATPase catalytic activity assay described herein are shown in Tables 5 and 6 below.

TABLE 5

| Compound No. | BRM $IP_{50}$ (μM)* | BRM Max % Inhibition | BRG1 $IP_{50}$ (μM)* | BRG1 Max % Inhibition |
|---|---|---|---|---|
| 1 | ++ | >95% | ++ | >70% |
| 2 | +++ | >95% | ++ | >95% |
| 3 | ++ | >95% | ++ | >90% |
| 4 | ++ | >90% | + | >70% |
| 5 | + | >90% | + | >70% |
| 6 | ++ | >90% | + | >60% |
| 7 | ++ | >90% | ++ | >60% |
| 8 | ++ | >90% | + | >70% |
| 9 | +++ | >90% | +++ | >60% |
| 10 | + | >90% | + | >90% |
| 11 | ++ | >80% | + | >70% |
| 12 | ++ | >80% | + | >60% |
| 13 | ++ | >80% | ++ | >30% |
| 14 | ++ | >80% | + | >60% |
| 15 | ++ | >80% | ++ | >60% |
| 16 | ++ | >80% | + | >60% |
| 17 | ++ | >80% | + | >60% |
| 18 | + | >80% | + | >60% |
| 19 | +++ | >70% | + | >30% |
| 20 | + | >70% | + | >60% |
| 21 | + | >70% | + | >60% |
| 22 | + | >70% | + | >60% |
| 23 | ++ | >70% | ++ | >50% |
| 24 | ++ | >70% | NT | >99% |
| 25 | + | >70% | + | >50% |
| 26 | + | >60% | + | <30% |
| 27 | + | >60% | + | >30% |
| 28 | ++ | >50% | ++ | >30% |
| 29 | + | >50% | + | >60% |
| 30 | NT | >70% | NT | >50% |
| 31 | ++ | >30% | ++ | <30% |
| 32 | + | >30% | + | <30% |
| 33 | + | >80% | + | >80% |
| 34 | + | >90% | + | >60% |
| 35 | + | >95% | + | >90% |
| 36 | +++ | >95% | ++ | >90% |
| 37 | + | >50% | + | >30% |
| 38 | + | >80% | + | >80% |
| 39 | + | >30% | + | <30% |
| 40 | NT | >50% | NT | <30% |
| 41 | ++ | >90% | ++ | >80% |
| 42 | ++ | >90% | ++ | >80% |
| 43 | + | >80% | + | >70% |
| 44 | + | >70% | + | >70% |
| 45 | + | NT | + | NT |
| 46 | ++ | >60% | ++ | >70% |
| 47 | + | >70% | + | >70% |
| 48 | + | >50% | + | >30% |
| 49 | ++ | >50% | ++ | >30% |
| 50 | + | >30% | + | >30% |
| 51 | ++ | >90% | + | >80% |
| 52 | +++ | >95% | +++ | >95% |
| 53 | ++ | >95% | ++ | >90% |
| 54 | ++ | >90% | ++ | >90% |
| 55 | ++ | >90% | ++ | >80% |
| 56 | + | >90% | + | >80% |
| 57 | + | >90% | + | >90% |
| 58 | ++ | >90% | ++ | >90% |
| 59 | + | >90% | + | >90% |
| 60 | + | >90% | + | >80% |
| 61 | ++ | >80% | ++ | >50% |
| 62 | ++ | >80% | ++ | >70% |
| 63 | + | >80% | + | >80% |
| 64 | ++ | >70% | ++ | >60% |
| 65 | ++ | >70% | ++ | >30% |
| 66 | + | >70% | + | >50% |
| 67 | + | >70% | + | >70% |
| 68 | + | >60% | + | >60% |
| 69 | + | >60% | + | >60% |
| 70 | + | >60% | + | >50% |
| 71 | ++ | >60% | + | >50% |
| 72 | + | >60% | + | >50% |
| 73 | +++ | >50% | ++ | >30% |
| 74 | + | >50% | + | >30% |
| 75 | + | >50% | + | >60% |
| 76 | + | >30% | + | >30% |
| 77 | + | >30% | + | >30% |
| 78 | + | NT | + | NT |
| 79 | +++ | >30% | ++ | >30% |
| 80 | +++ | >95% | +++ | >95% |
| 81 | +++ | >95% | +++ | >95% |
| 82 | ++ | >95% | ++ | >95% |
| 83 | ++ | >90% | + | >80% |
| 84 | + | >80% | + | >80% |
| 85 | ++ | >95% | ++ | >90% |
| 86 | + | >70% | + | >70% |

"+" indicates inhibitory effect of >10 uM;
"++" indicates inhibitory effect of 1-10 uM;
"+++" indicates inhibitory effect of <1 uM;
"NT" indicates not tested

TABLE 6

| Compound No. | BRM $IP_{50}$ (μM)* | BRM Max % Inhibition | BRG1 $IP_{50}$ (μM)* | BRG1 Max % Inhibition |
|---|---|---|---|---|
| 87 | ++++ | >95% | ++++ | >95% |
| 88 | +++ | >95% | ++ | >95% |
| 89 | ++++ | >80% | +++ | >80% |
| 90 | ++++ | >70% | ++++ | >50% |
| 91 | +++ | >95% | ++ | >90% |
| 92 | +++ | >90% | +++ | >80% |
| 93 | +++ | >90% | +++ | >90% |
| 94 | +++ | >95% | ++ | >90% |
| 95 | ++++ | >95% | ++++ | >95% |
| 96 | +++ | >70% | ++ | >70% |
| 97 | +++ | >70% | +++ | >70% |
| 98 | +++ | >90% | +++ | >70% |
| 99 | ++++ | >90% | ++++ | >95% |
| 100 | +++ | >80% | ++ | >80% |
| 101 | +++ | >95% | +++ | >95% |
| 102 | +++ | >80% | +++ | >80% |
| 103 | +++ | >70% | ++ | >80% |
| 104 | ++++ | >70% | ++++ | >60% |
| 105 | +++ | >80% | +++ | >50% |
| 106 | +++ | >70% | +++ | >60% |
| 107 | +++ | >95% | ++ | >95% |
| 108 | +++ | >80% | +++ | >90% |
| 109 | +++ | >90% | +++ | >90% |
| 110 | +++ | >80% | ++ | >80% |
| 111 | +++ | >90% | +++ | >90% |
| 112 | +++ | >90% | +++ | >80% |
| 113 | +++ | >95% | +++ | >95% |
| 114 | +++ | >80% | ++ | >80% |
| 115 | +++ | >90% | +++ | >90% |
| 116 | +++ | >95% | +++ | >95% |
| 117 | ++++ | >95% | ++++ | >95% |
| 118 | +++ | >90% | ++ | >90% |
| 119 | +++ | >95% | ++ | >95% |
| 120 | +++ | >90% | +++ | >90% |
| 121 | +++ | >95% | +++ | >95% |
| 122 | +++ | >95% | ++ | >90% |
| 123 | +++ | >80% | +++ | >80% |
| 124 | +++ | >95% | +++ | >95% |
| 125 | ++++ | >95% | ++++ | >95% |
| 126 | +++ | >80% | ++++ | >80% |
| 127 | +++ | >90% | +++ | >80% |
| 128 | ++++ | >95% | ++++ | >95% |
| 129 | +++ | >95% | +++ | >95% |
| 130 | +++ | >70% | ++ | >70% |
| 131 | ++++ | >95% | ++++ | >95% |

TABLE 6-continued

| Compound No. | BRM IP$_{50}$ (μM)* | BRM Max % Inhibition | BRG1 IP$_{50}$ (μM)* | BRG1 Max % Inhibition |
|---|---|---|---|---|
| 132 | ++++ | >80% | ++++ | >70% |
| 133 | ++++ | >95% | ++++ | >95% |
| 134 | +++ | >50% | +++ | >50% |
| 135 | ++++ | >95% | ++++ | >95% |
| 136 | +++ | >95% | +++ | >95% |
| 137 | +++ | >90% | +++ | >95% |
| 138 | +++ | >90% | +++ | >90% |
| 139 | ++++ | >95% | ++++ | >95% |
| 140 | +++ | >95% | +++ | >90% |
| 141 | ++++ | >95% | +++ | >95% |
| 142 | +++ | >90% | +++ | >90% |
| 143 | ++++ | >95% | ++++ | >95% |
| 144 | +++ | >95% | +++ | >95% |
| 145 | +++ | >90% | +++ | >90% |
| 146 | ++++ | >95% | ++++ | >95% |
| 147 | ++++ | >95% | ++++ | >95% |
| 148 | ++++ | >95% | ++++ | >95% |
| 149 | ++++ | >80% | ++++ | >80% |
| 150 | ++++ | >95% | ++++ | >90% |
| 151 | +++ | >80% | +++ | >80% |
| 152 | +++ | >90% | +++ | >80% |
| 153 | ++++ | >90% | ++++ | >80% |
| 154 | ++++ | >95% | ++++ | >95% |
| 155 | +++ | >80% | +++ | >80% |
| 156 | +++ | >95% | +++ | >90% |
| 157 | ++++ | >95% | ++++ | >90% |
| 158 | +++ | >90% | +++ | >95% |
| 159 | +++ | >90% | +++ | >95% |
| 160 | +++ | >95% | +++ | >95% |
| 161 | +++ | >70% | +++ | >50% |
| 162 | ++++ | >95% | ++++ | >95% |
| 163 | ++++ | >95% | +++ | >95% |
| 164 | ++++ | >95% | ++++ | >95% |
| 165 | ++++ | >95% | ++++ | >95% |
| 166 | +++ | >95% | +++ | >95% |
| 167 | +++ | >95% | +++ | >95% |
| 168 | ++++ | >95% | ++++ | >95% |
| 169 | +++ | >95% | +++ | >95% |
| 170 | +++ | >95% | +++ | >95% |
| 171 | +++ | >95% | +++ | >95% |
| 172 | +++ | >95% | +++ | >90% |
| 173 | +++ | >90% | +++ | >90% |
| 174 | +++ | >80% | +++ | >80% |
| 175 | +++ | >90% | +++ | >80% |
| 176 | +++ | >90% | +++ | >80% |
| 177 | ++++ | >95% | ++++ | >95% |
| 178 | ++++ | >95% | ++++ | >95% |
| 179 | +++ | >90% | +++ | >95% |
| 180 | +++ | >90% | +++ | >95% |
| 181 | ++++ | >95% | ++++ | >95% |
| 182 | ++++ | >95% | +++ | >90% |
| 183 | ++++ | >95% | ++++ | >95% |
| 184 | ++++ | >80% | ++++ | >70% |
| 185 | +++ | >80% | +++ | >70% |
| 186 | +++ | >95% | +++ | >95% |
| 187 | +++ | >70% | +++ | >60% |
| 188 | ++++ | >95% | ++++ | >80% |
| 189 | +++ | >90% | +++ | >90% |
| 190 | +++ | >80% | +++ | >80% |
| 191 | ++++ | >95% | +++ | >95% |
| 192 | +++ | >90% | +++ | >90% |
| 193 | +++ | >80% | +++ | >90% |
| 194 | +++ | >90% | +++ | >80% |
| 195 | ++++ | >95% | ++++ | >95% |
| 196 | +++ | >95% | +++ | >90% |
| 197 | ++++ | >90% | ++++ | >80% |
| 198 | +++ | >80% | +++ | >60% |
| 199 | +++ | >95% | +++ | >95% |
| 200 | ++++ | >95% | ++++ | >95% |
| 201 | ++++ | >95% | ++++ | >90% |
| 202 | ++++ | >95% | ++++ | >95% |
| 203 | +++ | >80% | +++ | >80% |
| 204 | +++ | >80% | +++ | >70% |
| 205 | ++++ | >95% | ++++ | >95% |
| 206 | +++ | >95% | +++ | >95% |
| 207 | ++++ | >95% | ++++ | >95% |
| 208 | +++ | >90% | +++ | >80% |
| 209 | ++++ | >95% | ++++ | >95% |
| 210 | +++ | >95% | +++ | >80% |
| 211 | +++ | >95% | +++ | >90% |
| 212 | +++ | >95% | +++ | >95% |
| 213 | ++++ | >95% | ++++ | >95% |
| 214 | ++++ | >95% | ++++ | >95% |
| 215 | +++ | >90% | +++ | >90% |
| 216 | ++++ | >90% | +++ | >95% |
| 217 | ++++ | >90% | ++++ | >90% |
| 218 | ++++ | >95% | +++ | >90% |
| 219 | ++++ | >95% | ++++ | >95% |
| 220 | +++ | >95% | ++ | >80% |
| 221 | +++ | >95% | +++ | >80% |
| 222 | +++ | >95% | +++ | >80% |
| 223 | ++++ | >95% | ++++ | >90% |
| 224 | ++++ | >95% | ++++ | >90% |
| 225 | +++ | >80% | +++ | >90% |
| 226 | ++++ | >95% | ++++ | >95% |
| 227 | ++++ | >95% | ++++ | >95% |
| 228 | +++ | >90% | +++ | >90% |
| 229 | +++ | >95% | +++ | >95% |
| 230 | +++ | >95% | +++ | >90% |
| 231 | +++ | >90% | +++ | >90% |
| 232 | +++ | >80% | +++ | >80% |
| 233 | +++ | >90% | +++ | >80% |
| 234 | +++ | >90% | +++ | >90% |
| 235 | +++ | >90% | +++ | >70% |
| 236 | +++ | >90% | +++ | >90% |
| 237 | +++ | >90% | +++ | >90% |
| 238 | +++ | >90% | +++ | >95% |
| 239 | +++ | >90% | +++ | >80% |
| 240 | +++ | >80% | +++ | >80% |
| 241 | +++ | >90% | +++ | >90% |

"+" indicates inhibitory effect of >10 uM;
"++" indicates inhibitory effect of 1-10 uM;
"+++" indicates inhibitory effect of 0.1-1 uM,
"++++" indicates inhibitory effect of <0.1 uM Example 89. Effects of BRG1/BRM ATPase Inhibition on the Growth of Uveal Melanoma and Hematological Cancer Cell Lines Procedure: Uveal melanoma cell lines (92-1, MP41, MP38, MP46), prostate cancer cell lines (LNCAP), lung cancer cell lines (NCIH1299), and immortalized embryonic kidney lines (HEK293T) were plated into 96 well plates with growth media (See Table 7). BRG1/BRM ATPase inhibitor, Compound 87, was dissolved in DMSO and added to the cells in a concentration gradient from 0 to 10 micromolar at the time of plating. Cells were incubated at 37 degrees Celsius for 3 days. After three days of treatment, the media was removed from the cells, and 30 microliters of TrypLE (Gibco) was added to cells for 10 minutes. Cells were detached from the plates, and resuspended with the addition of 170 microliters of growth media. Cells from two DMSO-treated control wells were counted, and the initial number of cells plated at the start of the experiment, were re-plated into fresh-compound containing plates for an additional four days at 37 degrees Celsius. At day 7, cells were harvested as described above. On day 3 and day 7, relative cell growth was measured by the addition of Cell-titer glo (Promega), and luminescence was measured on an Envision plate reader (Perkin Elmer). The concentration of compound at which each cell line's growth was inhibited by 50% (GI$_{50}$), was calculated using Graphpad Prism, and is plotted below. For multiple myeloma cell lines (OPM2, MM1 S, LP1), ALL cell lines (TALL1, JURKAT, RS411), DLBCL cell lines (SUDHL6, SUDHL4, DB, WSUDLCL2, PFEIFFER), AML cell lines (OCIAML5), MDS cell lines (SKM1), ovarian cancer cell lines (OV7, TYKNU), esophageal cancer cell lines (KYSE150), rhabdoid tumor lines (RD, G402, G401, HS729, A204), liver cancer cell lines (HLF, HLE, PLCRPF5), and lung cancer cell lines (SW1573, NCIH2444), the above methods were performed with the following modifications: Cells were plated in 96 well plates, and the next day, BRG1/BRM ATPase inhibitor, Compound 87, was dissolved in DMSO and added to the cells in a concentration gradient from 0 to 10 micromolar. At the time of cell splitting on days 3 and 7, cells were split into new 96 well plates, and fresh compound was added four hours after re-plating.

Table 7 lists the tested cell lines and growth media used.

TABLE 7

| Cell Lines and Growth Media | | |
|---|---|---|
| Cell Line | Source | Growth Media |
| 92-1 | SIGMA | RPMI1640 + 20% FBS |
| A204 | ATCC | McCoy's 5A + 10% FBS |
| DB | ATCC | RPMI1640 + 10% FBS |
| G401 | ATCC | McCoy's 5A + 10% FBS |
| G402 | ATCC | McCoy's 5A + 10% FBS |
| HEK293T | ATCC | DMEM + 10%FBS |
| HLE | JCRB | DMEM + 10%FBS |
| HLF | JCRB | DMEM + 10%FBS |
| HS729 | ATCC | DMEM + 10%FBS |
| JURKAT | ATCC | RPMI1640 + 10% FBS |
| KYSE150 | DSMZ | RPMI1640/Ham's F12 + 10% FBS |
| LNCAP | ATCC | RPMI1640 + 10% FBS |
| LP1 | DSMZ | IMDM + 20% FBS |
| MM1S | ATCC | RPMI1640 + 10% FBS |
| MP38 | ATCC | RPMI1640 + 20% FBS |
| MP41 | ATCC | RPMI1640 + 20% FBS |
| MP46 | ATCC | RPMI1640 + 20% FBS |
| NCIH1299 | ATCC | RPMI1640 + 10% FBS |
| NCIH2444 | ATCC | RPMI1640 + 20% FBS |
| OCIAML5 | DSMZ | alpha-MEM + 20% FBS +10 ng/ml GM-CSF |
| OPM2 | DSMZ | RPMI1640 + 10% FBS |
| OV7 | ECACC | DMEM/Ham's F12 (1:1) + 2 mM Glutamine + 10% FBS + 0.5 ug/ml hydrocortisone + 10 ug/ml insulin |
| PFEIFFER | ATCC | RPMI1640 + 10% FBS |
| PLCPRF5 | ATCC | EMEM + 10% FBS |
| RD | ATCC | DMEM + 10%FBS |
| RS411 | ATCC | RPMI1640 + 10% FBS |
| SKM1 | JCRB | RPMI1640 + 10% FBS |
| SUDHL4 | DSMZ | RPMI1640 + 10% FBS |
| SUDHL6 | ATCC | RPMI1640 + 20% FBS |
| SW1573 | ATCC | DMEM + 10%FBS |
| TALL1 | JCRB | RPMI1640 + 10% FBS |

TABLE 7-continued

| Cell Lines and Growth Media | | |
|---|---|---|
| Cell Line | Source | Growth Media |
| TYKNU | JCRB | EMEM + 20% FBS |
| WSUDLCL2 | DSMZ | RPMI1640 + 10% FBS |

Results: As shown in FIG. 1, the uveal melanoma and hematologic cancer cell lines were more sensitive to BRG1/BRM inhibition than the other tested cell lines. Inhibition of the uveal melanoma and hematologic cancer cell lines was maintained through day 7.

Example 90. Comparison of BRG1/BRM Inhibitors to Clinical PKC and MEK Inhibitors in Uveal Melanoma Cell Lines Procedure: Uveal melanoma cell lines, 92-1 or MP41, were plated in 96 well plates in the presence of growth media (See Table 7). BAF ATPase inhibitors (Compound 87), PKC inhibitor (LXS196; MedChemExpress), or MEK inhibitor (Selumetinib; Selleck Chemicals) were dissolved in DMSO and added to the cells in a concentration gradient from 0 to 10 micromolar at the time of plating. Cells were incubated at 37 degrees Celsius for 3 days. After three days of treatment, cell growth was measured with Cell-titer glow (Promega), and luminescence was read on an Envision plate reader (Perkin Elmer).

Figure 2:
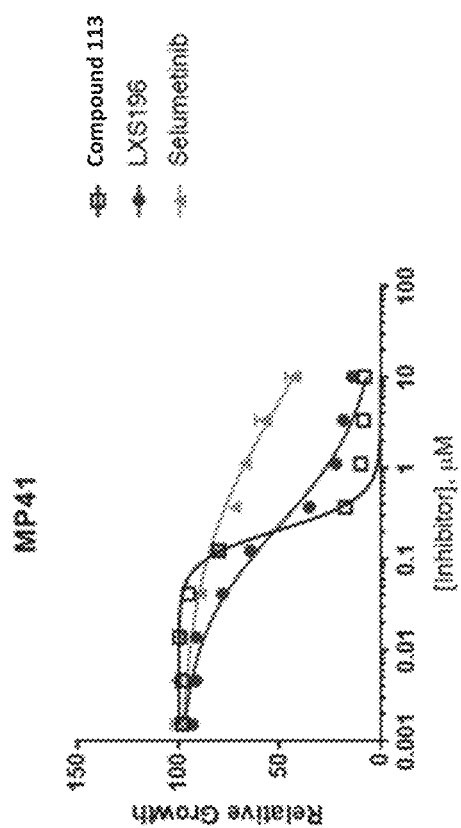
FIG. 2 is a graph illustrating inhibition of cell proliferation of uveal melanoma cells by a BRG1/BRM inhibitor (Compound 87), a MEK inhibitor (Selumetinib), and a PKC inhibitor (LXS196).
Figure 2:
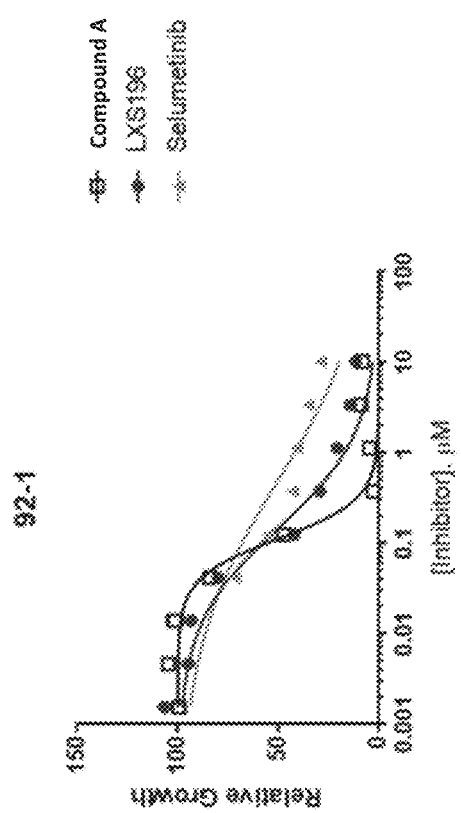

Results: As shown in FIG. 2, Compound 87 showed comparable growth inhibition of uveal melanoma cells as the clinical PKC and MEK inhibitors. Further, compound 87 was found to result in a faster onset of inhibition than the clinical PKC and MEK inhibitors.

Example 91. Synthesis of Compound B

BRG1/BRM Inhibitor Compound B has the structure:

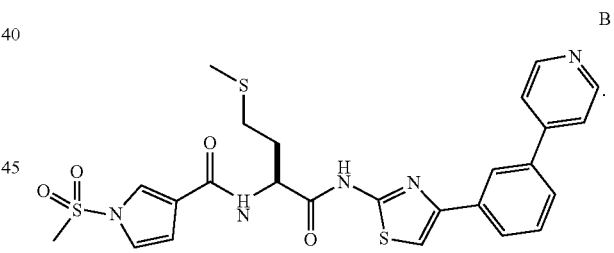

B

Compound B was synthesized as shown in Scheme 2 below.

Scheme 2. Synthesis of Compound B

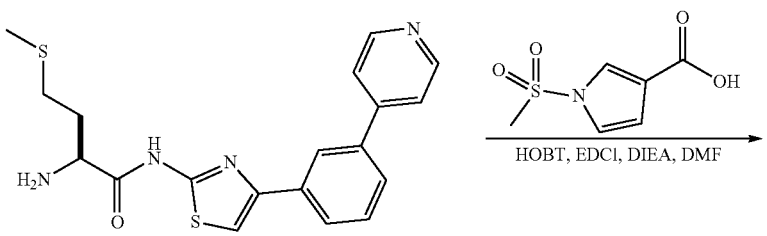

HOBT, EDCl, DIEA, DMF

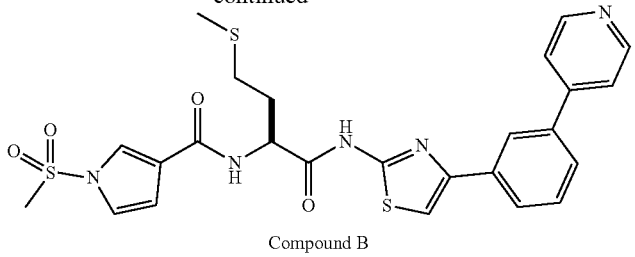

Compound B

Step 1: Preparation of (S)-1-(methylsulfonyl)-N-(4-(methylthio)-1-oxo-1-((4-(3-(pyridin-4-yl)phenyl)thiazol-2-yl)amino)butan-2-yl)-1H-pyrrole-3-carboxamide (Compound B)

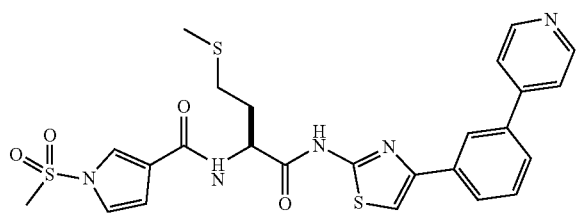

Compound B

To a mixture of (2S)-2-amino-4-methylsulfanyl-N-[4-[3-(4-pyridyl)phenyl]thiazol-2-yl]butanamide (2 g, 4.75 mmol, HCl salt) and 1-methylsulfonylpyrrole-3-carboxylic acid (898.81 mg, 4.75 mmol) in DMF (20 mL) was added EDCI (1.37 g, 7.13 mmol), HOBt (962.92 mg, 7.13 mmol) and DIEA (2.46 g, 19.00 mmol, 3.31 mL) and the mixture was stirred at 25° C. for 3 hours. The mixture was poured into H$_2$O (100 mL) and the precipitate was collected by filtration. The solid was triturated in MeOH (20 mL) and the precipitate was collected by filtration. The solid was dissolved in DMSO (10 mL) and then the mixture was poured into MeOH (50 mL) and the formed precipitate was collected by filtration and lyophilized to give Compound B (2.05 g, 3.66 mmol, 77.01% yield) as a white solid. LCMS (ESI) m/z [M+H]$^+$=555.9. $^1$H NMR (400 MHz, DMSO) δ 12.49 (s, 1H), 8.68-8.66 (m, 2H), 8.46 (d, J=7.2 Hz, 1H), 8.31-8.30 (m, 1H), 8.02-8.00 (m, 1H), 7.94-7.96 (m, 1H), 7.83 (s, 1H), 7.73-7.74 (m, 3H), 7.61-7.57 (m, 1H), 7.31-7.29 (m, 1H), 6.79-6.77 (m, 1H), 4.74-4.69 (m, 1H), 3.57 (s, 3H), 2.67-2.53 (m, 2H), 2.13-2.01 (m, 5H). SFC: AS-3-MeOH (DEA)-40-3 mL-35T.Icm, t=0.932 min, ee %=100%.

Example 92. Effects of BRG1/BRM ATPase Inhibition on the Growth of Uveal Melanoma, Hematological Cancer, Prostate Cancer, Breast Cancer, and Ewing's Sarcoma Cell Lines Procedure: All cell lines described above in Example 89 were also tested as described above with Compound B. In addition, the following cell lines were also tested as follows. Briefly, for Ewing's sarcoma cell lines (CADOES1, RDES, SKES1), retinoblastoma cell lines (WERIRB1), ALL cell lines (REH), AML cell lines (KASUMI1), prostate cancer cell lines (PC3, DU145, 22RV1), melanoma cell lines (SH4, SKMEL28, WM115, COLO829, SKMEL3, A375), breast cancer cell lines (MDAMB415, CAMA1, MCF7, BT474, HCC1419, DU4475, BT549), B-ALL cell lines (SUPB15), CML cell lines (K562, MEG01), Burkitt's lymphoma cell lines (RAMOS2G64C10, DAUDI), mantle cell lymphoma cell lines (JEKO1, REC1), bladder cancer cell lines (HT1197), and lung cancer cell lines (SBC5), the above methods were performed with the following modifications: Cells were plated in 96 well plates, and the next day, BRG1/BRM ATPase inhibitor, Compound B, was dissolved in DM10 and added to the cells in a concentration gradient from 0 to 10 micromolar. At the time of cell splitting on days 3 and 7, cells were split into new 96 well plates, and fresh compound was added four hours after re-plating.

Table 8 lists the tested cell lines and growth media used.

| Cell Line | Source | Growth Media |
| --- | --- | --- |
| 22RV1 | ATCC | RPMI1640 + 10% FBS |
| A375 | ATCC | DMEM + 10% FBS |
| BT474 | ATCC | Hybricare medium + 1.5 g/L sodium bicarbonate + 10% FBS |
| BT549 | ATCC | RPMI1640 + 0.023 IU/ml insulin + 10% FBS |
| CADOES1 | DSMZ | RPMI1640 + 10% FBS |
| CAMA1 | ATCC | EMEM + 10% FBS |
| COLO829 | ATCC | RPMI1640 + 10% FBS |
| DAUDI | ATCC | RPMI1640 + 10% FBS |
| DU145 | ATCC | EMEM + 10% FBS |
| DU4475 | ATCC | RPMI1640 + 10% FBS |
| HCC1419 | ATCC | RPMI1640 + 10% FBS |
| HT1197 | ATCC | EMEM + 10% FBS |
| JEKO1 | ATCC | RPMI1640 + 20% FBS |
| K562 | ATCC | IMDM + 10% FBS |
| KASUMI1 | ATCC | RPMI1640 + 10% FBS |
| MCF7 | ATCC | EMEM + 0.01 mg/ml bovine insulin + 10% FBS |
| MDAMB415 | ATCC | Leibovitz's L-15 + 2 mM L-glutamine + 10 mcg/ml insulin + 10 mcg/ml glutathione + 15% FBS |
| MEG01 | ATCC | RPMI1640 + 10% FBS |
| PC3 | ATCC | F-12K + 10% FBS |
| RAMOS2G64C10 | ATCC | RPMI1640 + 10% FBS |
| RDES | ATCC | RPMI1640 + 15% FBS |
| REC1 | ATCC | RPMI1640 + 10% FBS |
| REH | ATCC | RPMI1640 + 10% FBS |
| SBC5 | JCRB | EMEM + 10% FBS |
| SH4 | ATCC | DMEM + 10% FBS |
| SKES1 | ATCC | McCoy's 5A + 15% FBS |
| SKMEL28 | ATCC | EMEM + 10% FBS |
| SKMEL3 | ATCC | McCoy's 5A + 15% FBS |
| SUPB15 | ATCC | IMDM + 4 mM L-glutamine + 1.5 g/L sodium bicarbonate + 0.05 mM 2-mercaptoethanol + 20% FBS |
| WERIRB1 | ATCC | RPMI1640 + 10% FBS |
| WM115 | ATCC | EMEM + 10% FBS |

Figure 3:
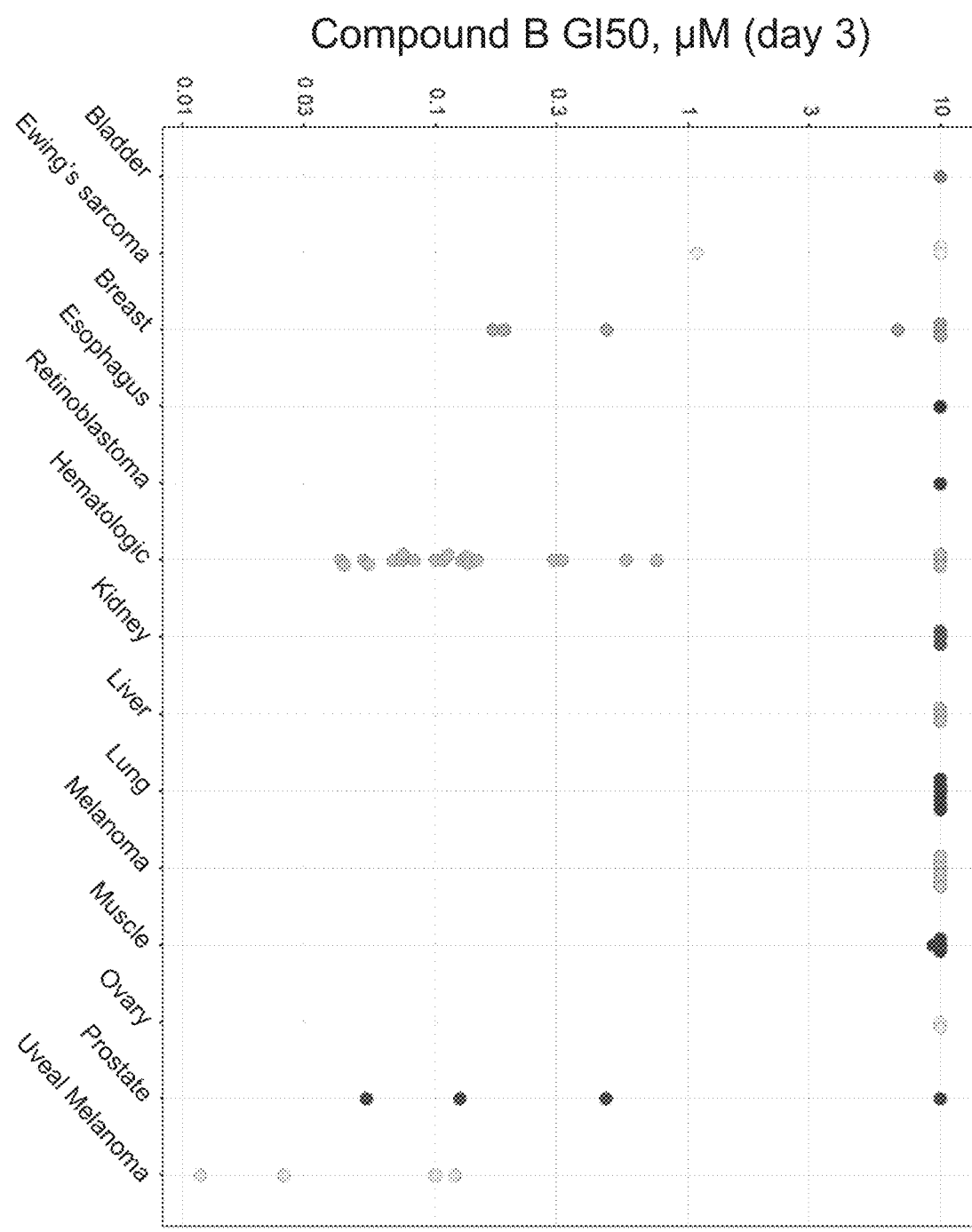
FIG. 3 is a graph illustrating inhibition of cell proliferation of several cancer cell lines by a BRG1/BRM inhibitor (Compound B).

Results: As shown in FIG. 3, the uveal melanoma, hematologic cancer, prostate cancer, breast cancer, and Ewing's sarcoma cell lines were more sensitive to BRG1/BRM inhibition than the other tested cell lines. Inhibition of the uveal melanoma, hematologic cancer, prostate cancer, breast cancer, and Ewing's sarcoma cell lines was maintained through day 7.

Other Embodiments

While the invention has been described in connection with specific embodiments thereof, it will be understood that invention is capable of further modifications and this application is intended to cover any variations, uses, or adaptations of the invention following, in general, the principles of the invention and including such departures from the present disclosure that come within known or customary practice within the art to which the invention pertains and may be applied to the essential features hereinbefore set forth, and follows in the scope of the claims.

Other embodiments are in the claims.

The invention claimed is:
1. A compound having the structure of Formula I:

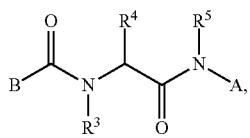

Formula I wherein
B is

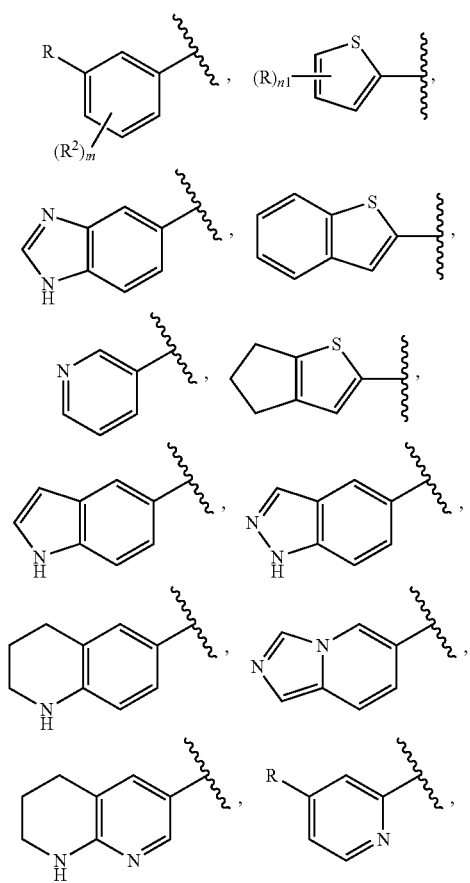

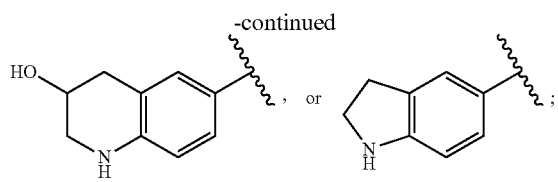

each R is

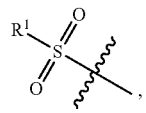

wherein $R^1$ is optionally substituted $C_6$-$C_{10}$ aryl, optionally substituted $C_2$-$C_9$ heteroaryl, hydroxy, optionally substituted $C_1$-$C_6$ alkoxy, or $-NR^{1a}R^{1b}$, wherein each $R^{1a}$ and $R^{1b}$ is, independently, H or $CH_3$;

m is 0, 1, 2, 3, or 4;

each $R^3$ and $R^5$ is, independently, selected from the group consisting of H, optionally substituted $C_1$-$C_6$ alkyl, or optionally substituted $C_1$-$C_6$ heteroalkyl;

$R^4$ is hydrogen, optionally substituted $C_1$-$C_6$ alkyl, optionally substituted $C_1$-$C_6$ heteroalkyl, optionally substituted $C_3$-$C_{10}$ carbocyclyl, optionally substituted $C_1$-$C_6$ alkyl $C_3$-$C_{10}$ carbocyclyl, optionally substituted $C_1$-$C_6$ heteroalkyl $C_3$-$C_{10}$ carbocyclyl, optionally substituted $C_2$-$C_9$ heterocyclyl, optionally substituted $C_1$-$C_6$ alkyl $C_2$-$C_9$ heterocyclyl, optionally substituted $C_1$-$C_6$ heteroalkyl $C_2$-$C_9$ heterocyclyl, optionally substituted $C_6$-$C_{10}$ aryl, optionally substituted $C_1$-$C_6$ alkyl $C_6$-$C_{10}$ aryl, optionally substituted $C_1$-$C_6$ heteroalkyl $C_6$-$C_{10}$ aryl, optionally substituted $C_2$-$C_9$ heteroaryl, optionally substituted $C_1$-$C_6$ alkyl $C_2$-$C_9$ heteroaryl, or optionally substituted $C_1$-$C_6$ heteroalkyl $C_2$-$C_9$ heteroaryl; and A is

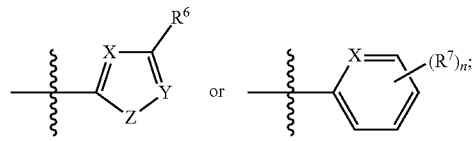

wherein X is N or $CR^X$, wherein $R^X$ is H, halo, optionally substituted $C_1$-$C_6$ alkyl, optionally substituted $C_1$-$C_6$ heteroalkyl, optionally substituted $C_3$-$C_{10}$ carbocyclyl, optionally substituted $C_2$-$C_9$ heterocyclyl, optionally substituted $C_6$-$C_{10}$ aryl, optionally substituted $C_2$-$C_9$ heteroaryl, optionally substituted $C_2$-$C_6$ alkenyl, or optionally substituted $C_2$-$C_6$ heteroalkenyl;

Y is N or $CR^Y$, wherein $R^Y$ is H, halo, optionally substituted $C_1$-$C_6$ alkyl, optionally substituted $C_1$-$C_6$ heteroalkyl, optionally substituted $C_3$-$C_{10}$ carbocyclyl, optionally substituted $C_2$-$C_9$ heterocyclyl, optionally substituted $C_6$-$C_{10}$ aryl, optionally substituted $C_2$-$C_9$ heteroaryl, optionally substituted $C_2$-$C_6$ alkenyl, or optionally substituted $C_2$-$C_6$ heteroalkenyl;

Z is S, O, or $NR^Z$, wherein $R^Z$ is H, optionally substituted $C_1$-$C_6$ alkyl, or optionally substituted $C_1$-$C_6$ heteroalkyl;

R⁶ and R⁷ are, independently, halo, optionally substituted $C_1$-$C_6$ alkyl, optionally substituted $C_1$-$C_6$ heteroalkyl, optionally substituted $C_3$-$C_{10}$ carbocyclyl, optionally substituted $C_2$-$C_9$ heterocyclyl, optionally substituted $C_6$-$C_{10}$ aryl, optionally substituted $C_1$-$C_6$ alkyl optionally substituted $C_6$-$C_{10}$ aryl, optionally substituted $C_2$-$C_9$ heteroaryl, optionally substituted $C_2$-$C_6$ alkenyl, optionally substituted $C_2$-$C_6$ heteroalkenyl, or optionally substituted amino, or two R⁷ combine with the carbons to which they are attached to form a 5- or 6-membered ring; and n is 1, 2, 3, or 4, n1 is 1;

or a pharmaceutically acceptable salt thereof.

2. The compound of claim 1, wherein A is

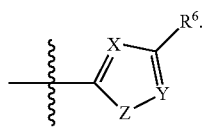

3. The compound of claim 1, wherein both R³ and R⁵ are H.

4. The compound of claim 1, wherein R⁴ is H,

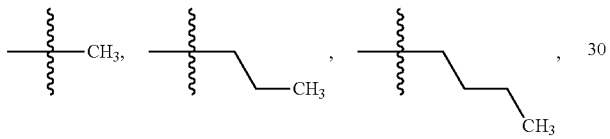

-continued

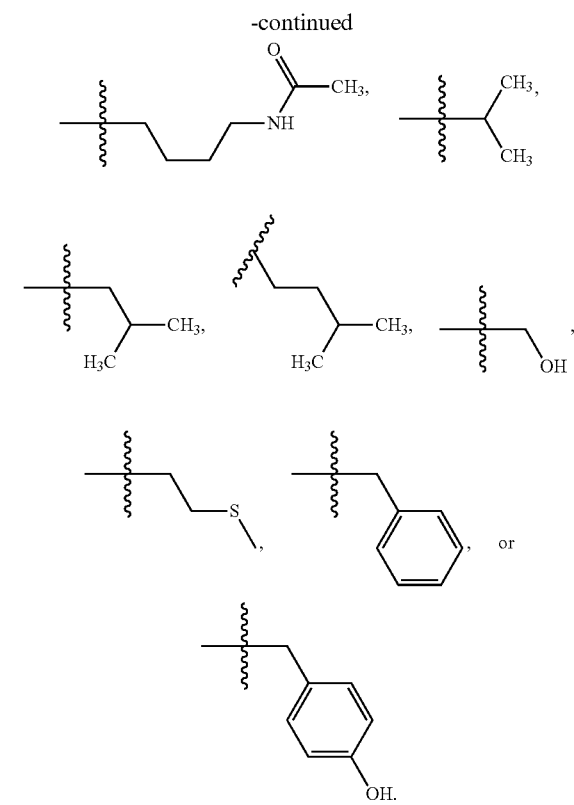

5. A compound having the structure of any one of compounds:

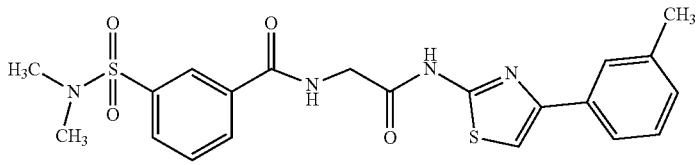

1

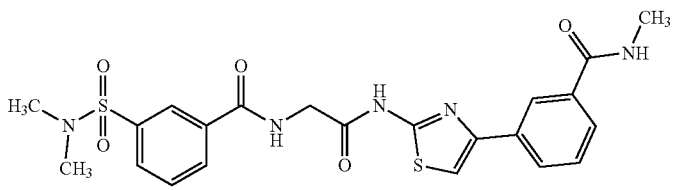

4

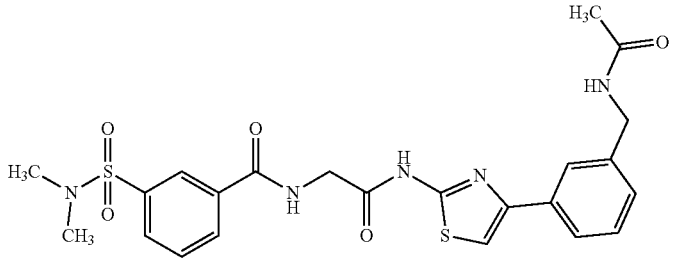

5

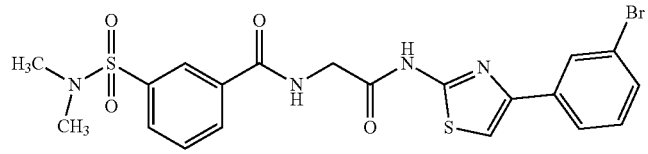
7
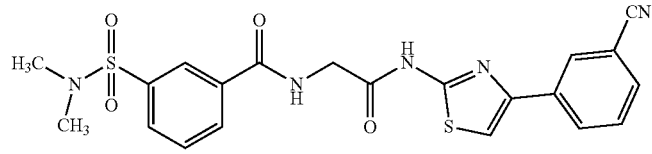
8
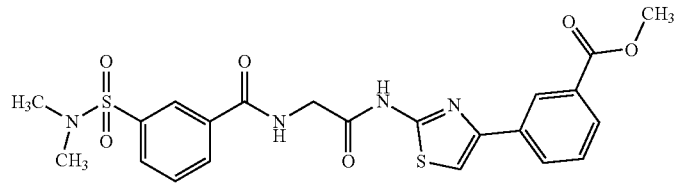
9
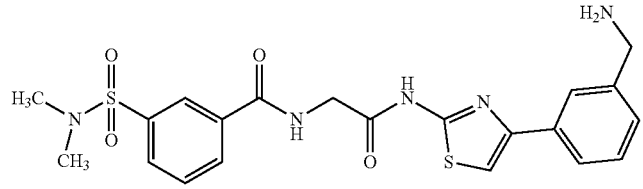
10
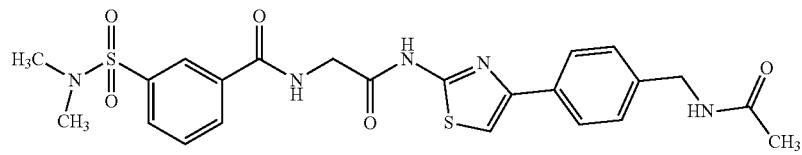
11
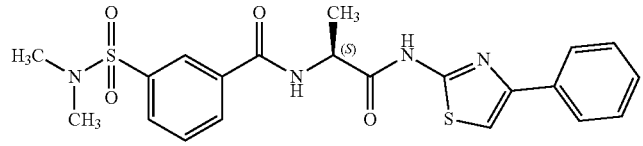
12
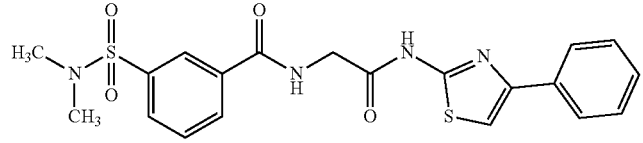
13
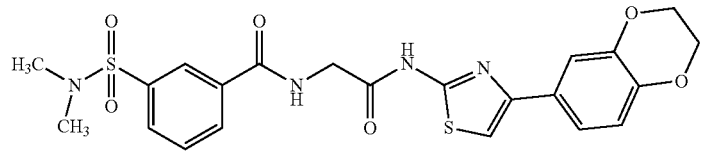
15
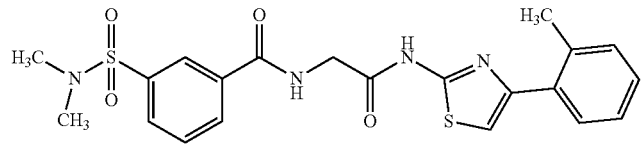
16

-continued
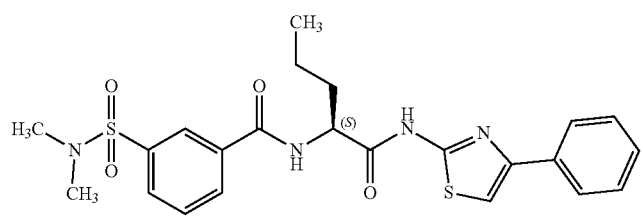
17
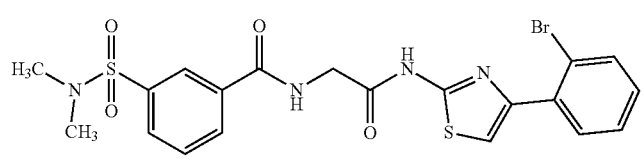
18
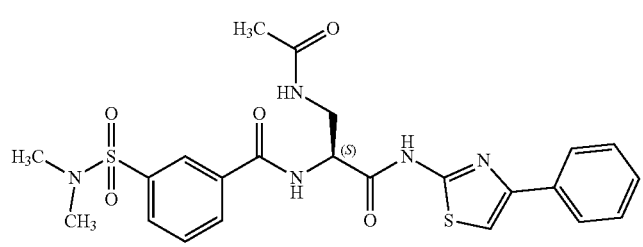
21
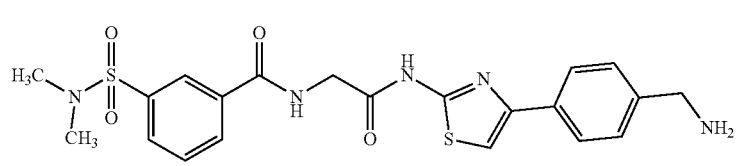
22
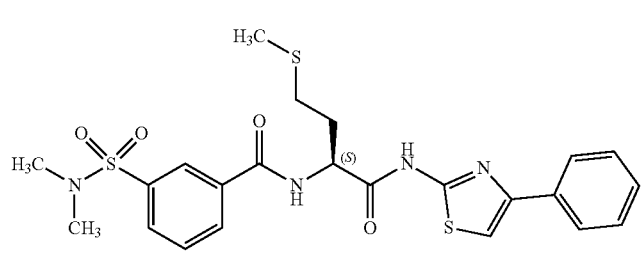
24
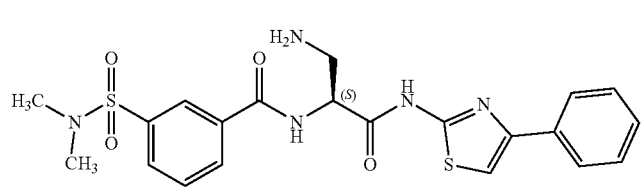
25
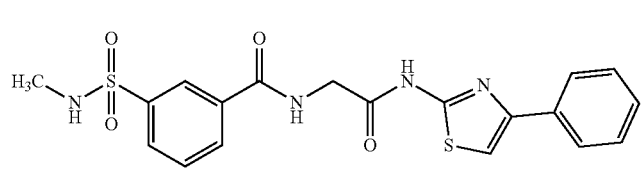
26
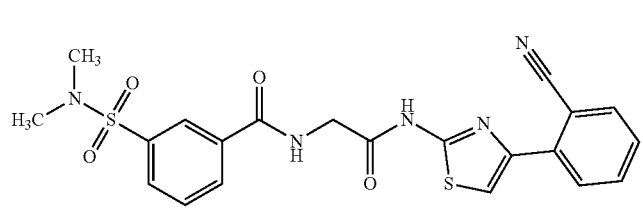
27

-continued
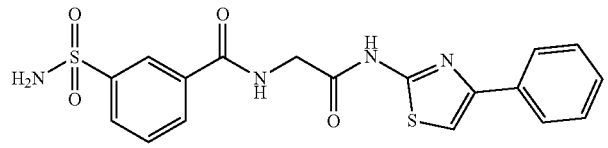
28
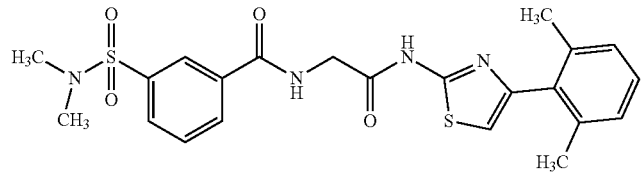
29
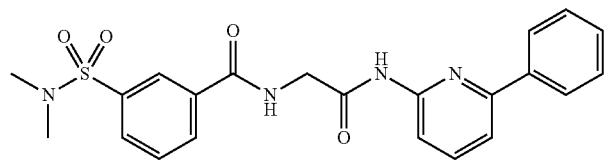
30
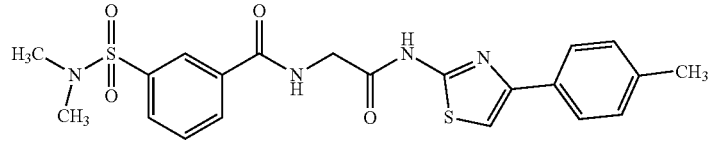
31
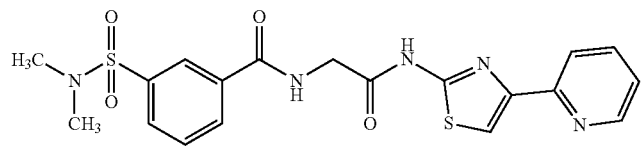
32
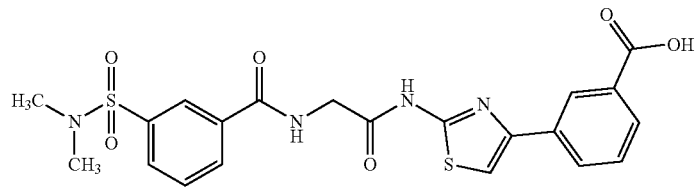
33
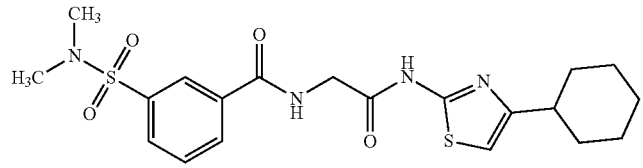
34
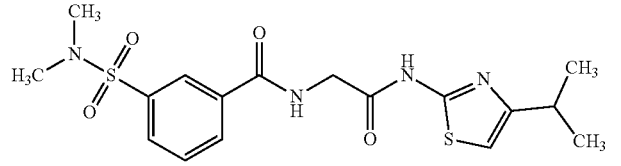
35
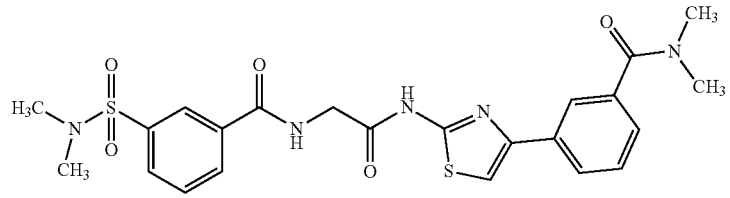
37

-continued
71
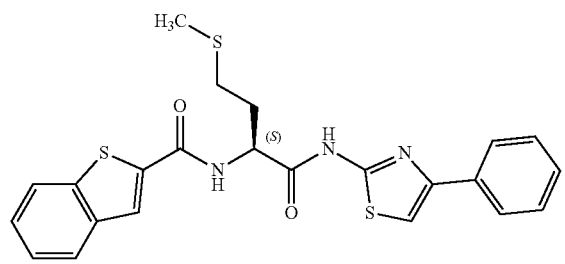
40
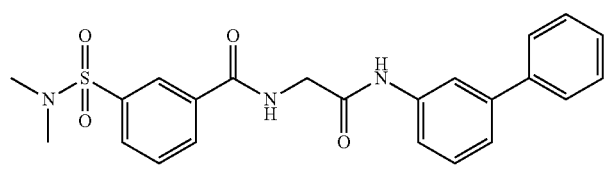
79
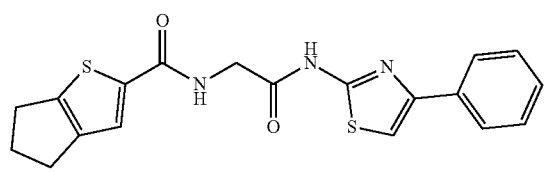
58
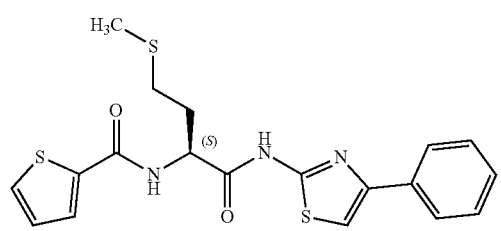
83
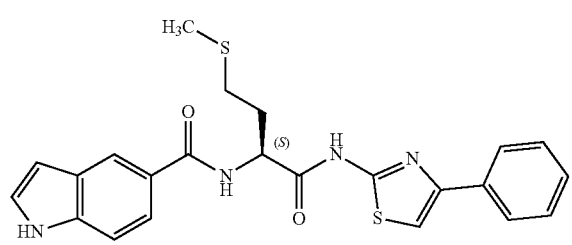
62
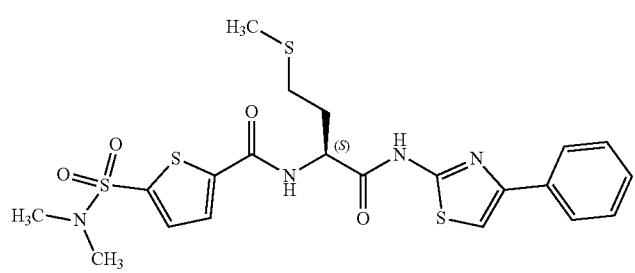
96
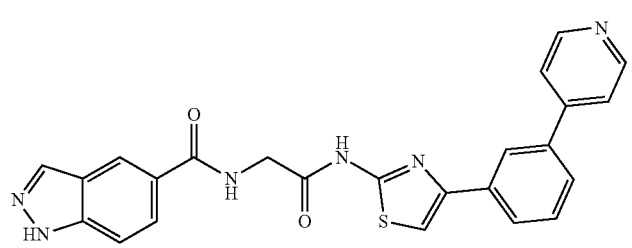

64
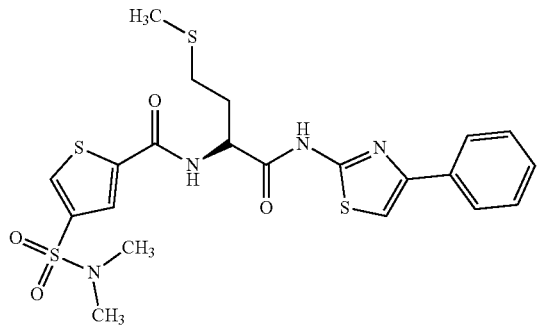
99
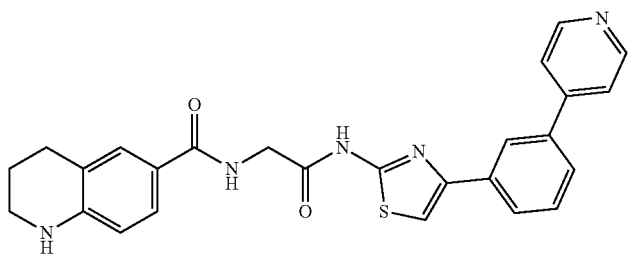
66
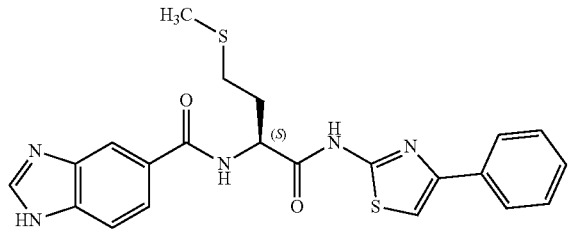
199
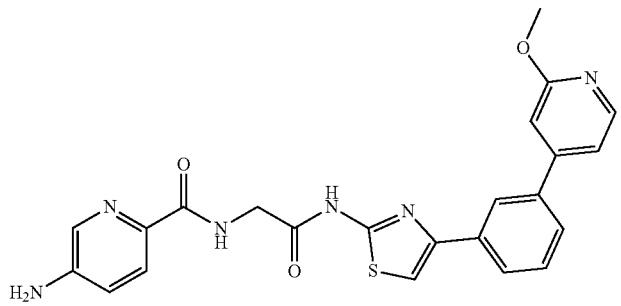
70
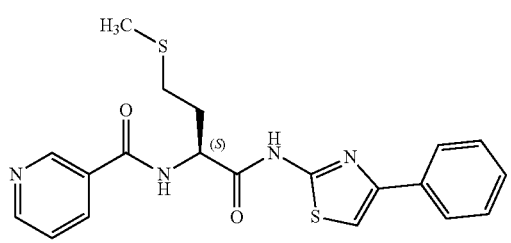
80
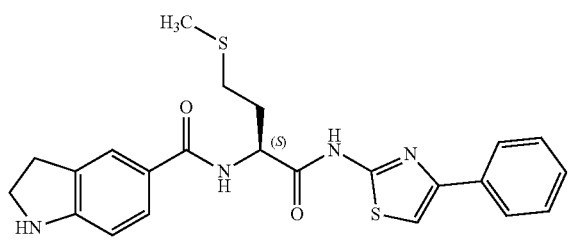

-continued

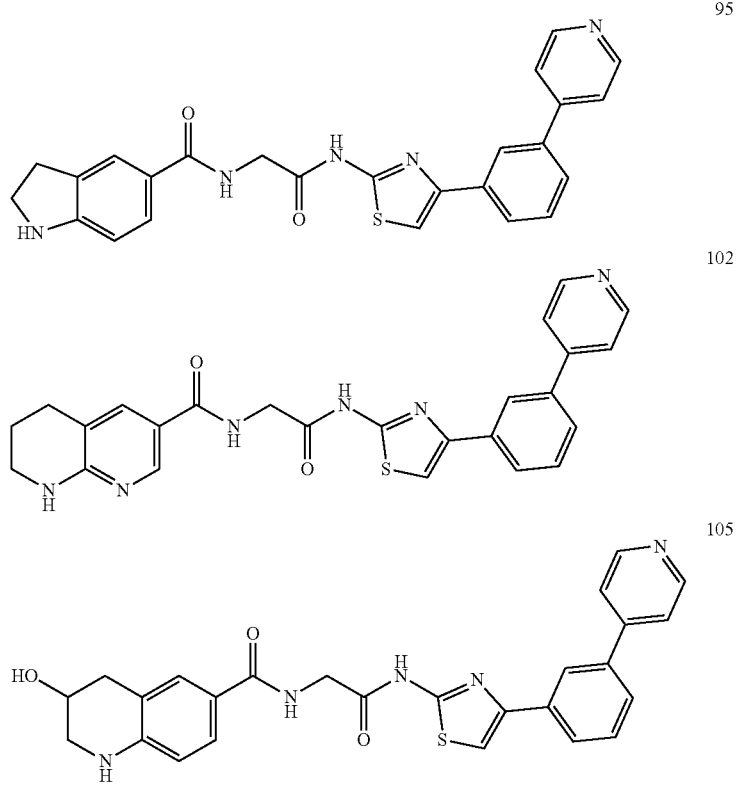

or a pharmaceutically acceptable salt thereof.

6. A pharmaceutical composition comprising the compound of claim 1 and a pharmaceutically acceptable excipient.

7. A method of treating cancer in a subject in need thereof, the method comprising administering to the subject an effective amount of a compound of claim 1.

8. The method of claim 7, wherein the compound is a BRM-selective compound.

9. The method of claim 8, wherein the BRM-selective compound inhibits the level and/or activity of BRM at least 10-fold greater than the compound inhibits the level and/or activity of BRG1 and/or the compound binds to BRM at least 10-fold greater than the compound binds to BRG1.

10. The method of claim 7, wherein the compound is a BRM/BRG1 dual inhibitor compound.

* * * * *